(12) United States Patent
Muller et al.

(10) Patent No.: US 8,481,568 B2
(45) Date of Patent: Jul. 9, 2013

(54) ISOINDOLE-IMIDE COMPOUNDS AND COMPOSITIONS COMPRISING AND METHODS OF USING THE SAME

(75) Inventors: George Muller, Rancho Santa Fe, CA (US); Roger Shen-Chu Chen, Edison, NJ (US); Hon-Wah Man, Princeton, NJ (US); Alexander L. Ruchelman, Cream Ridge, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 13/030,075

(22) Filed: Feb. 17, 2011

(65) Prior Publication Data

US 2011/0144158 A1 Jun. 16, 2011

Related U.S. Application Data

(63) Continuation of application No. 11/513,563, filed on Aug. 30, 2006, now abandoned.

(60) Provisional application No. 60/712,387, filed on Aug. 31, 2005.

(51) Int. Cl.
*A61K 31/454* (2006.01)
*C07D 401/04* (2006.01)

(52) U.S. Cl.
USPC .......................................... 514/323; 546/201

(58) Field of Classification Search
USPC .......................................... 514/323; 546/201
See application file for complete search history.

(56) References Cited

U.S. PATENT DOCUMENTS

| 7,091,353 | B2 | 8/2006 | Robarge et al. |
| 8,012,997 | B2 * | 9/2011 | Robarge et al. ............... 514/323 |
| 2003/0096841 | A1 | 5/2003 | Robarge et al. |
| 2007/0049618 | A1 | 3/2007 | Muller et al. |

FOREIGN PATENT DOCUMENTS

WO        WO 99/47512        9/1999

* cited by examiner

*Primary Examiner* — Charanjit Aulakh
(74) *Attorney, Agent, or Firm* — Jones Day

(57) ABSTRACT

This invention relates to isoindole-imide compounds, and pharmaceutically acceptable salts, solvates, stereoisomers, and prodrugs thereof. Methods of use, and pharmaceutical compositions of these compounds are disclosed.

5 Claims, No Drawings

ISOINDOLE-IMIDE COMPOUNDS AND COMPOSITIONS COMPRISING AND METHODS OF USING THE SAME

This application is a continuation of U.S. application Ser. No. 11/513,563, filed Aug. 30, 2006, now abandoned which claims priority to U.S. provisional No. 60/712,387, filed Aug. 31, 2005, the entirety of both of which is incorporated herein by reference.

1. FIELD OF THE INVENTION

This invention relates to isoindole-imide compounds. Pharmaceutical compositions comprising the compounds and methods for treating, preventing and managing various disorders are also disclosed.

2. BACKGROUND OF THE INVENTION

2.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993). There is an enormous variety of cancers which are described in detail in the medical literature. Examples includes cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, bFGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; and proliferative vitreoretinopathy.

Accordingly, compounds that can control angiogenesis or inhibit the production of certain cytokines, including TNF-α, may be useful in the treatment and prevention of various diseases and conditions.

2.2 Methods of Treating Cancer

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient.

Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, N.Y.).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for safe and effective methods of treating, preventing and managing cancer and other diseases and conditions, particularly for diseases that are refractory to standard treatments, such as surgery, radiation therapy, chemotherapy and hormonal therapy, while reducing or avoiding the toxicities and/or side effects associated with the conventional therapies.

3. SUMMARY OF THE INVENTION

This invention is directed, in part, to isoindole-imide compounds, and pharmaceutically acceptable salts, solvates (e.g., hydrates), prodrugs, or stereoisomers thereof.

This invention also encompasses methods of treating and managing various diseases or disorders. The methods comprise administering to a patient in need of such treatment or management a therapeutically effective amount of a compound of this invention, or a pharmaceutically acceptable salt, solvate, stereoisomer, or prodrug thereof.

The invention also encompasses methods of preventing various diseases and disorders, which comprise administering to a patient in need of such prevention a prophylactically effective amount of a compound of this invention, or a pharmaceutically acceptable salt, solvate, hydrate, stereoisomer, or prodrug thereof.

This invention also encompasses pharmaceutical compositions, single unit dosage forms, dosing regimens and kits which comprise a compound of this invention, or a pharmaceutically acceptable salt, solvate, hydrate, stereoisomer, clathrate, or prodrug thereof.

4. DETAILED DESCRIPTION OF THE INVENTION

In one embodiment, this invention encompasses isoindole-imide compounds, and pharmaceutically acceptable salts, solvates, stereoisomers and prodrugs thereof. In another embodiment, this invention encompasses methods of treating, managing, and preventing various diseases and disorders, which comprises administering to a patient in need of such treatment or prevention a therapeutically or prophylactically effective amount of a compound of this invention, or a pharmaceutically acceptable salt, solvate, stereoisomer or prodrug thereof. Examples of diseases and disorders are described herein.

In particular embodiments, a compound of this invention, or a pharmaceutically acceptable salt, solvate, stereoisomer, or prodrug thereof, is administered in combination with another drug ("second active agent") or treatment. Second active agents include small molecules and large molecules (e.g., proteins and antibodies), examples of which are provided herein, as well as stem cells. Methods, or therapies, that can be used in combination with the administration of compounds of this invention include, but are not limited to, surgery, blood transfusions, immunotherapy, biological therapy, radiation therapy, and other non-drug based therapies presently used to treat, prevent or manage various disorders described herein.

This invention also encompasses pharmaceutical compositions (e.g., single unit dosage forms) that can be used in methods disclosed herein. Particular pharmaceutical compositions comprise a compound of this invention, or a pharmaceutically acceptable salt, solvate, stereoisomer, or prodrug thereof, and optionally a second active agent.

4.1 Compounds

In one embodiment, this invention encompasses compounds of formula (I):

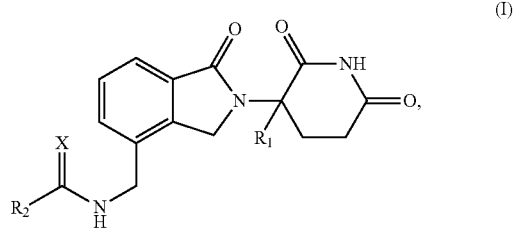

and pharmaceutically acceptable salts, solvates, stereoisomers, and prodrugs thereof, wherein:

X is O or S;

$R_1$ is H or methyl;

$R_2$ is: $(C_2-C_6)$alkyl, excluding cycloalkyl; $(C_4-C_6)$cycloalkyl; $(C_1-C_4)$alkoxy;
  $(C_1-C_6)$alkyl, substituted with $(C_1-C_4)$alkoxy;
  $(C_0-C_1)$alkyl-phenyl, wherein the phenyl is optionally substituted with one or more of halogen, $(C_1-C_4)$alkoxy, $(C_1-C_4)$alkyl, or cyano;
  $(C_0-C_1)$alkyl-(5 to 6 membered heteroaryl), wherein the heteroaryl is optionally substituted with one or more of $(C_1-C_4)$alkyl or halogen; or
  $(C_0-C_3)$alkyl-$NR_3R_4$;

$R_3$ and $R_4$ are each independently:
  H; $(C_1-C_6)$alkyl; $(C_3-C_6)$cycloalkyl;
  $(C_0-C_1)$alkyl-$(C_6-C_{10})$aryl, wherein the aryl is optionally substituted with one or more of $(C_1-C_4)$alkoxy, halogen, methyl, cyano, or —O—$CH_2$—O—;
  $(C_0-C_1)$alkyl-(5 to 10 membered heteroaryl), wherein the heteroaryl is substituted with one or more of $(C_1-C_4)$ alkoxy, halogen, or methyl; or $C(O)R_5$; and $R_5$ is $(C_1-C_4)$alkoxy or $(C_1-C_2)$alkyl-O—$(C_1-C_2)$alkyl;
with the proviso that if one of $R_3$ and $R_4$ is H, then the other is not ethyl.

In one embodiment, X is O. In another embodiment, X is S. In another embodiment, $R_2$ is phenyl, optionally substituted with one or more halogen.

In another embodiment, $R_2$ is $NHR_4$. In a specific embodiment, $R_4$ is $(C_6-C_{10})$aryl or 5 to 10 membered heteroaryl, both optionally substituted with one or more of $(C_1-C_4)$alkoxy, halogen, and methyl. In particular, the aryl or heteroaryl is phenyl, pyridyl, or naphthyl.

Examples of compounds of formula (I) include, but are not limited to, those listed in Table 1, below:

TABLE 1

Compounds of Formula I

| No. | Structure | Name |
|---|---|---|
| 1 | 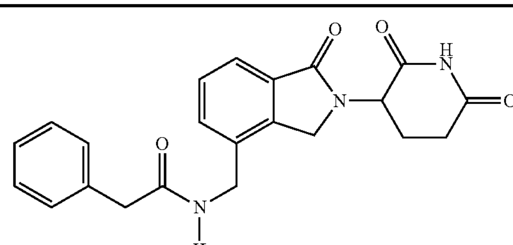 | N-[2-(2,6-Dioxo-piperidin-3-yl)-1-oxo2,3-dihydro-1H-isoindol-4-ylmethyl]-2-phenyl-acetamide |

TABLE 1-continued

Compounds of Formula I

| No. | Structure | Name |
|---|---|---|
| 2 | 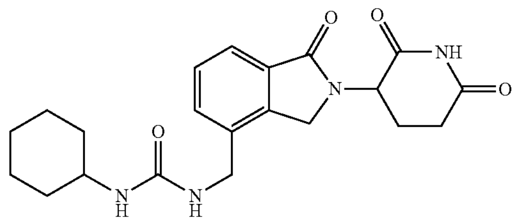 [SMILES: O=C1CCC(N2Cc3c(CNC(=O)NC4CCCCC4)cccc3C2=O)C(=O)N1] | 1-Cyclohexyl-3-[2-(2,6-dioxo-piperidin-3-yl)-1-oxo-2,3-dihydro-1H-isoindol-4-ylmethyl]-urea |
| 3 | 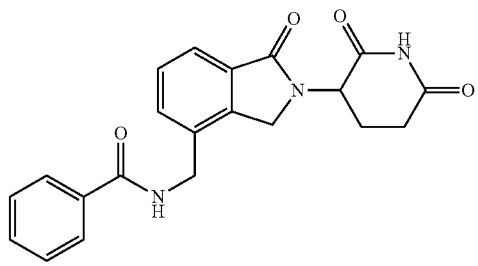 [SMILES: O=C1CCC(N2Cc3c(CNC(=O)c4ccccc4)cccc3C2=O)C(=O)N1] | N-[2-(2,6-Dioxo-piperidin-3-yl)-1-oxo-2,3-dihydro-1H-isoindol-4-ylmethyl]-benzamide |
| 4 | 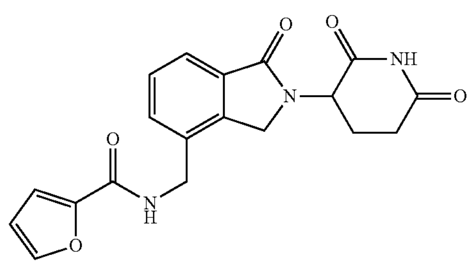 [SMILES: O=C1CCC(N2Cc3c(CNC(=O)c4ccco4)cccc3C2=O)C(=O)N1] | Furan-2-carboxylic acid [2-(2,6-dioxo-piperidin-3-yl)-1-oxo-2,3-dihydro-1H-isoindol-4-ylmethyl]-amide |
| 5 | 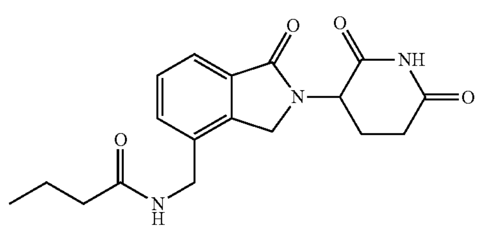 [SMILES: CCCC(=O)NCc1cccc2c1CN(C1CCC(=O)NC1=O)C2=O] | N-[2-(2,6-Dioxo-piperidin-3-yl)-1-oxo-2,3-dihydro-1H-isoindol-4-ylmethyl]-butyramide |
| 6 | 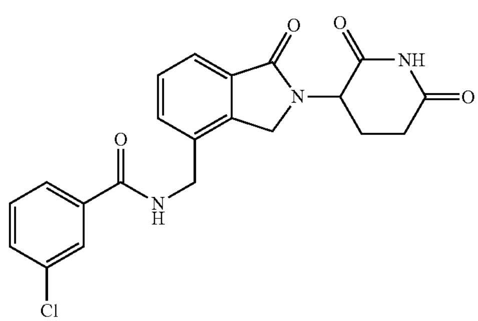 | 3-Chloro-N-[2-(2,6-dioxo-piperidin-3-yl)-1-oxo-2,3-dihydro-1H-sioindol-4-ylmethyl]-benzamide |
| 7 | 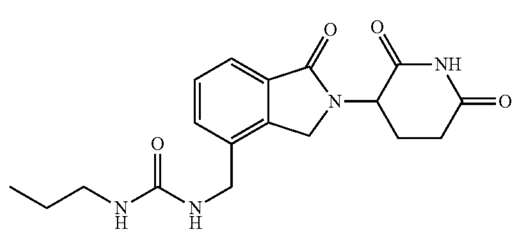 [SMILES: CCCNC(=O)NCc1cccc2c1CN(C1CCC(=O)NC1=O)C2=O] | 1-[2-(2,6-Dioxo-piperidin-3-yl)-1-oxo-2,3-dihydro-1H-isoindol-4-ylmethyl]-3-propyl-urea |

TABLE 1-continued

Compounds of Formula I

| No. | Structure | Name |
|---|---|---|
| 8 | 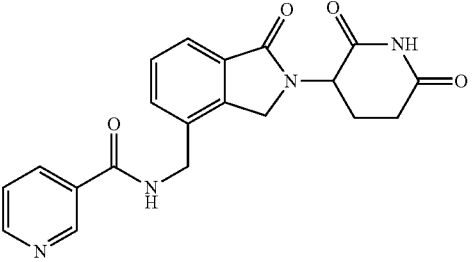 [SMILES: O=C1CCC(N2Cc3c(CNC(=O)c4cccnc4)cccc3C2=O)C(=O)N1] | N-[2-(2,6-Dioxo-piperidin-3-yl)-1-oxo-2,3-dihydro-1H-isoindol-4-ylmethyl]-nicotinamide |
| 9 | 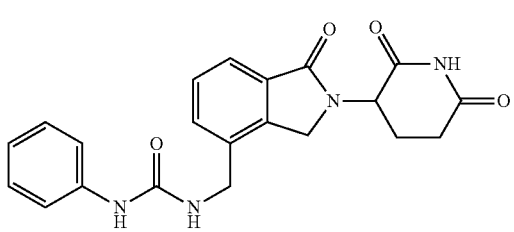 [SMILES: O=C1CCC(N2Cc3c(CNC(=O)Nc4ccccc4)cccc3C2=O)C(=O)N1] | 1-[2-(2,6-Dioxo-piperidin-3-yl)-1-oxo-2,3-dihydro-1H-isoindol-4-ylmethyl]-3-phenyl-urea |
| 10 | 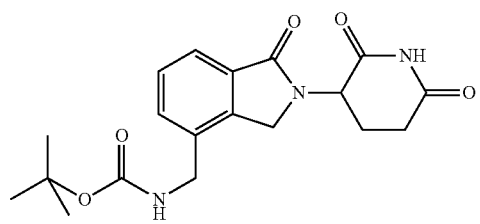 [SMILES: CC(C)(C)OC(=O)NCc1cccc2c1CN(C1CCC(=O)NC1=O)C2=O] | [2-(2,6-Dioxo-piperidin-3-yl)-1-oxo-2,3-dihydro-1H-isoindol-4-ylmethyl]-carbamic acid tert-butyl ester |
| 11 | 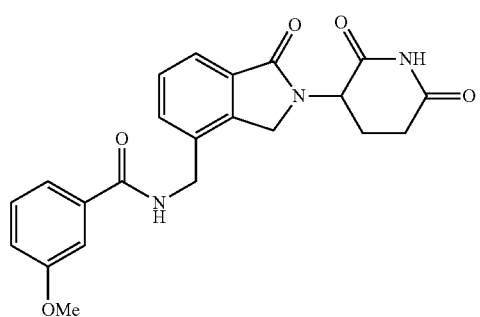 [SMILES: COc1cccc(C(=O)NCc2cccc3c2CN(C2CCC(=O)NC2=O)C3=O)c1] | N-[2-(2,6-Dioxo-piperidin-3-yl)-1-oxo-2,3-dihydro-1H-isoindol-4-ylmethyl]-3-methoxy-benzamide |
| 12 | 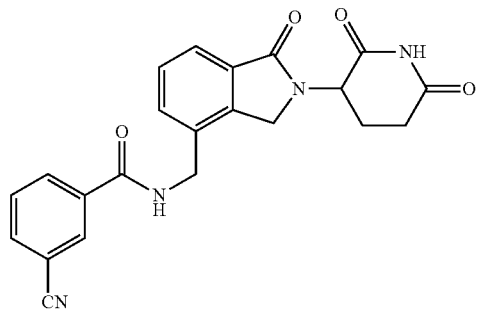 [SMILES: N#Cc1cccc(C(=O)NCc2cccc3c2CN(C2CCC(=O)NC2=O)C3=O)c1] | 3-Cyano-N-[2-(2,6-dioxo-piperidin-3-yl)-1-oxo-2,3-dihydro-1H-isoindol-4-ylmethyl]-benzamide |

TABLE 1-continued

Compounds of Formula I

| No. | Structure | Name |
|---|---|---|
| 13 | 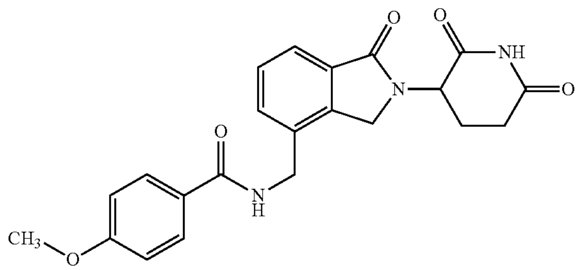 [SMILES: COc1ccc(C(=O)NCc2cccc3c2CN(C2CCC(=O)NC2=O)C3=O)cc1] | N-[2-(2,6-Dioxo-piperidin-3-yl)-1-oxo-2,3-dihydro-1H-isoindol-4-ylmethyl]-4-methoxy-benzamide |
| 14 | 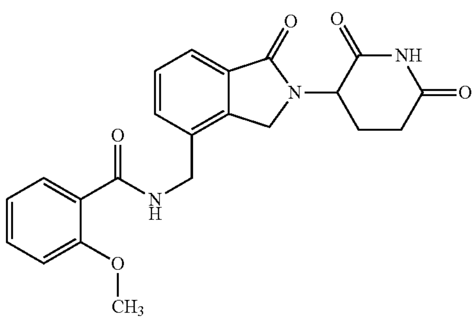 [SMILES: COc1ccccc1C(=O)NCc1cccc2c1CN(C1CCC(=O)NC1=O)C2=O] | N-[2-(2,6-Dioxo-piperidin-3-yl)-1-oxo-2,3-dihydro-1H-isoindol-4-ylmethyl]-2-methoxy-benzamide |
| 15 | 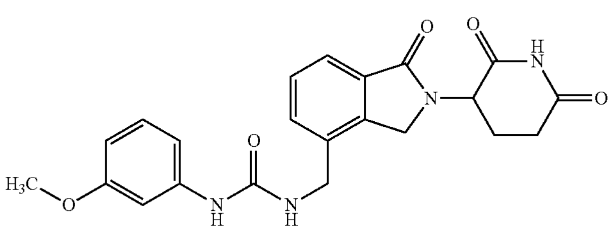 [SMILES: COc1cccc(NC(=O)NCc2cccc3c2CN(C2CCC(=O)NC2=O)C3=O)c1] | 1-[2-(2,6-Dioxo-pipderidin-3-yl)-1-oxo-2,3-dihydro-1H-isoindol-4-ylmethyl]-3-(3-methoxy-phenyl)-urea |
| 16 | 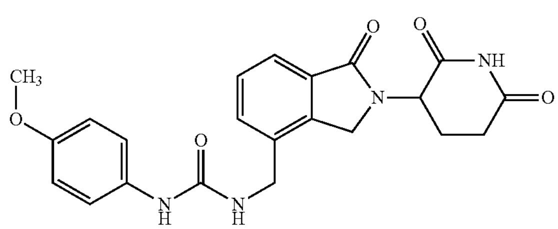 [SMILES: COc1ccc(NC(=O)NCc2cccc3c2CN(C2CCC(=O)NC2=O)C3=O)cc1] | 1-[2-(2,6-Dioxo-piperidin-3-yl)-1-oxo-2,3-dihydro-1H-isoindol-4-ylmethyl]-3-(4-methoxy-phenyl)-urea |
| 17 | 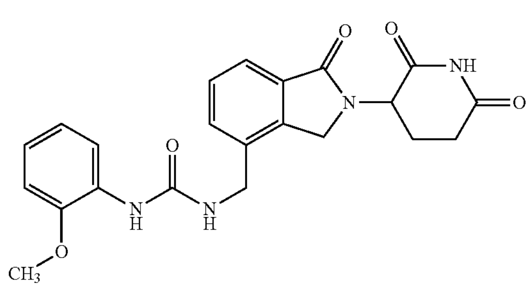 [SMILES: COc1ccccc1NC(=O)NCc1cccc2c1CN(C1CCC(=O)NC1=O)C2=O] | 1-[2-(2,6-Dioxo-piperidin-3-yl)-1-oxo-2,3-dihydro-1H-isoindol-4-ylmethyl]-3-(2-methoxy-phenyl)-urea |

TABLE 1-continued

Compounds of Formula I

| No. | Structure | Name |
|---|---|---|
| 18 | 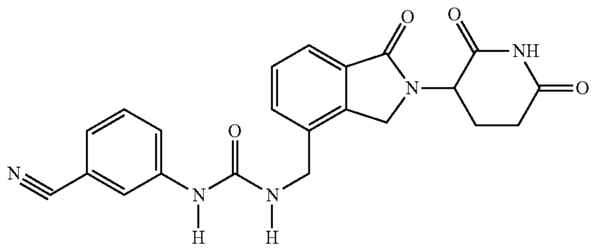 [SMILES: N#Cc1cccc(NC(=O)NCc2cccc3c2CN(C2CCC(=O)NC2=O)C3=O)c1] | 1-(3-Cyano-phenyl)-3-[2-(2,6-dioxo-piperidin-3-yl)-1-oxo-2,3-dihydro-1H-isoindol-4-ylmethyl]-urea |
| 19 | 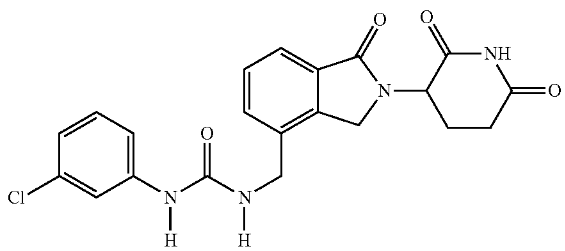 [SMILES: O=C1CCC(N2Cc3c(CNC(=O)Nc4cccc(Cl)c4)cccc3C2=O)C(=O)N1] | 1-(3-Chloro-phenyl)-3-[2-(2,6-dioxo-piperidin-3-yl)-1-oxo-2,3-dihydro-1H-isoindol-4-ylmethyl]-urea |
| 20 | 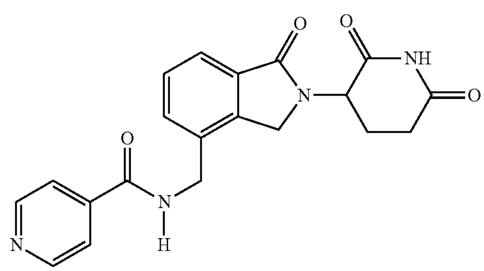 [SMILES: O=C1CCC(N2Cc3c(CNC(=O)c4ccncc4)cccc3C2=O)C(=O)N1] | N-[2-(2,6-Dioxo-piperidin-3-yl)-1-oxo-2,3-dihydro-1H-isoindol-4-ylmethyl]-isonicotinamide |
| 21 | 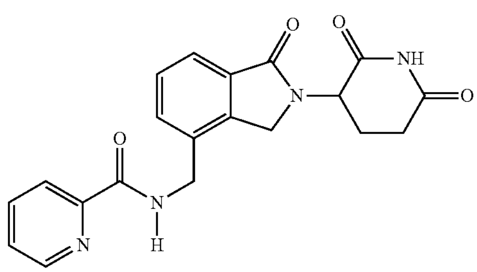 [SMILES: O=C1CCC(N2Cc3c(CNC(=O)c4ccccn4)cccc3C2=O)C(=O)N1] | Pyridine-2-carboxylic acid [2-(2,6-dioxo-piperidin-3-yl)-1-oxo-2,3-dihydro-1H-isoindol-4-ylmethyl]-amide |
| 22 | 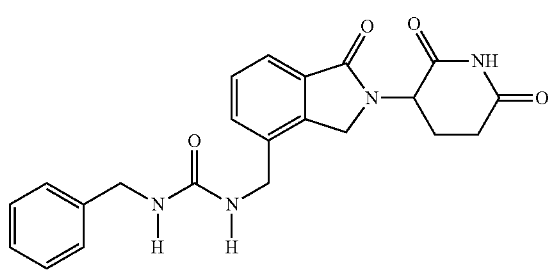 [SMILES: O=C1CCC(N2Cc3c(CNC(=O)NCc4ccccc4)cccc3C2=O)C(=O)N1] | 1-Benzyl-3-[2-(2,6-dioxo-piperidin-3-yl)-1-oxo-2,3-dihydro-1H-isoindol-4-ylmethyl]-urea |
| 23 | 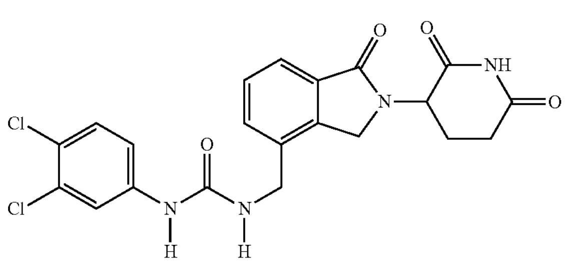 [SMILES: O=C1CCC(N2Cc3c(CNC(=O)Nc4ccc(Cl)c(Cl)c4)cccc3C2=O)C(=O)N1] | 1-(3,4-Dichloro-phenyl)-3-[2-(2,6-dioxo-piperidin-3-yl)-1-oxo-2,3-dihydro-1H-isoindol-4-ylmethyl]-urea |

TABLE 1-continued

Compounds of Formula I

| No. | Structure | Name |
|---|---|---|
| 24 | 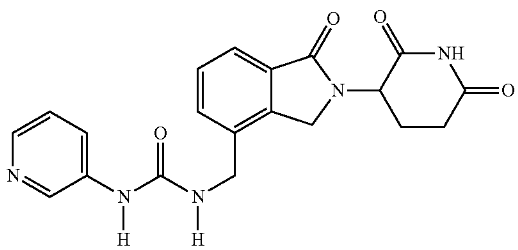 [SMILES: O=C1CCC(N2Cc3c(CNC(=O)Nc4cccnc4)cccc3C2=O)C(=O)N1] | 1-[2-(2,6-Dioxo-piperidin-3-yl)-1-oxo-2,3-dihydro-1H-isoindol-4-ylmethyl]-3-pyridin-3-yl-urea |
| 25 | 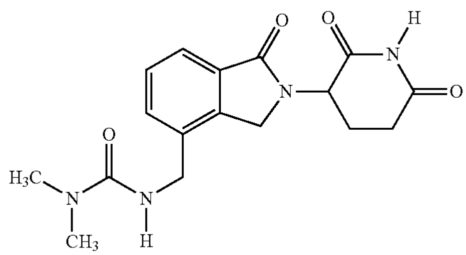 [SMILES: CN(C)C(=O)NCc1cccc2c1CN(C1CCC(=O)NC1=O)C2=O] | 3-[2-(2,6-Dioxo-piperidin-3-yl)-1-oxo-2,3-dihydro-1H-isoindol-4-ylmethyl]-1,1-dimethyl-urea |
| 26 | 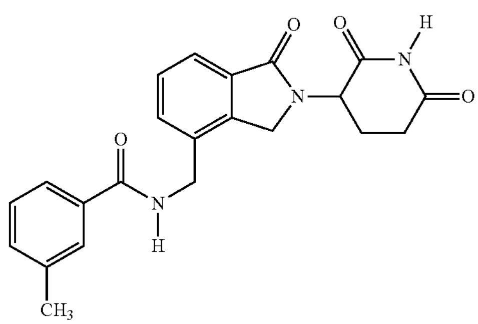 [SMILES: Cc1cccc(C(=O)NCc2cccc3c2CN(C2CCC(=O)NC2=O)C3=O)c1] | N-[2-(2,6-Dioxo-piperidin-3-yl)-1-oxo-2,3-dihydro-1H-isoindol-4-ylmethyl]-3-methyl-benzamide |
| 27 | 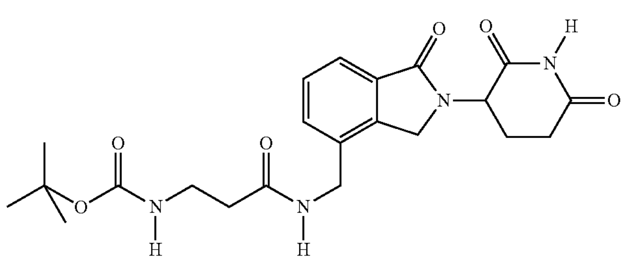 [SMILES: CC(C)(C)OC(=O)NCCC(=O)NCc1cccc2c1CN(C1CCC(=O)NC1=O)C2=O] | (2-{[2-(2,6-Dioxo-piperidin-3-yl)-1-oxo-2,3-dihydro-1H-isoindol-4-ylmethyl]-carbamoyl}-ethyl)-carbamic acid t-butyl ester |
| 28 | 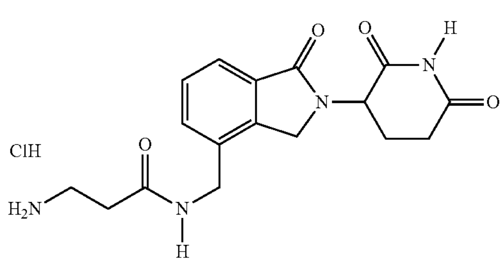 [SMILES: Cl ; NCCC(=O)NCc1cccc2c1CN(C1CCC(=O)NC1=O)C2=O] | 3-Amino-N-[2-(2,6-dioxo-piperidin-3-yl)-1-oxo-2,3-dihydro-1H-isoindol-4-ylmethyl]-propionamide Hydrochloride |

TABLE 1-continued

Compounds of Formula I

| No. | Structure | Name |
|---|---|---|
| 29 | 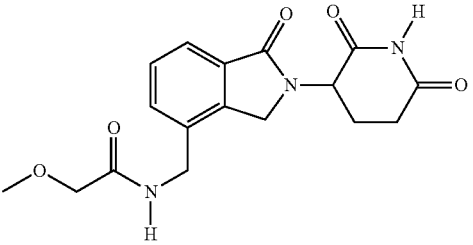 [SMILES: COCC(=O)NCc1cccc2c1CN(C1CCC(=O)NC1=O)C2=O] | N-[2-(2,6-Dioxo-piperidin-3-yl)-1-oxo-2,3-dihydro-1H-isoindol-4-ylmethyl]-2-methoxy-acetamide |
| 30 | 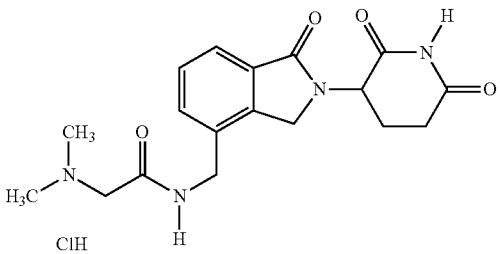 [SMILES: CN(C)CC(=O)NCc1cccc2c1CN(C1CCC(=O)NC1=O)C2=O ; Cl] | 2-Dimethylamino-N-[2-(2,6-dioxo-piperidin-3-yl)-1-oxo-2,3-dihydro-1H-isoindol-4-ylmethyl]-acetamide Hydrochloride |
| 31 | 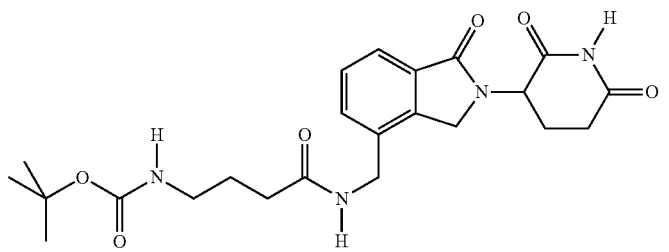 [SMILES: CC(C)(C)OC(=O)NCCCC(=O)NCc1cccc2c1CN(C1CCC(=O)NC1=O)C2=O] | (3-{[2-(2,6-Dioxo-piperidin-3-yl)-1-oxo-2,3-dihydro-1H-isoindol-4-ylmethyl]-carbamoyl}-propyl)-carbamic acid t-butyl ester |
| 32 | 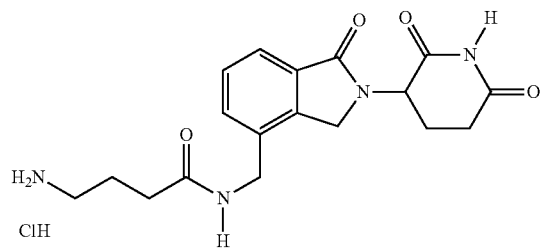 [SMILES: Cl ; NCCCC(=O)NCc1cccc2c1CN(C1CCC(=O)NC1=O)C2=O] | 4-Amino-[2-(2,6-dioxo-piperidin-3-yl)-1-oxo-2,3-dihydro-1H-isoindol-4-ylmethyl]-butyramide hydrochloride |
| 33 | 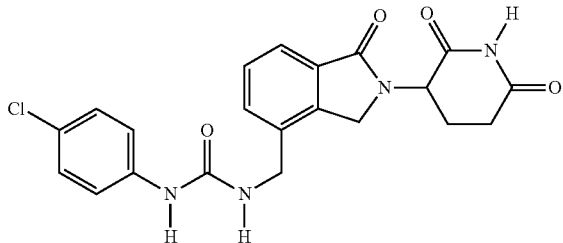 [SMILES: O=C1CCC(N2Cc3c(CNC(=O)Nc4ccc(Cl)cc4)cccc3C2=O)C(=O)N1] | 1-(4-Chloro-phenyl)-3-[2-(2,6-dioxo-piperidin-3-yl)-1-oxo-2,3-dihydro-1H-isoindol-4-ylmethyl]-urea |
| 34 | 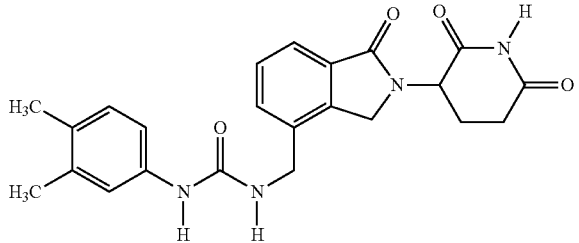 [SMILES: Cc1ccc(NC(=O)NCc2cccc3c2CN(C2CCC(=O)NC2=O)C3=O)cc1C] | 1-(3,4-Dimethyl-phenyl)-3-[2-(2,6-dioxo-piperidin-3-yl)-1-oxo-2,3-dihydro-1H-isoindol-4-ylmethyl]-urea |

TABLE 1-continued

Compounds of Formula I

| No. | Structure | Name |
|---|---|---|
| 35 | 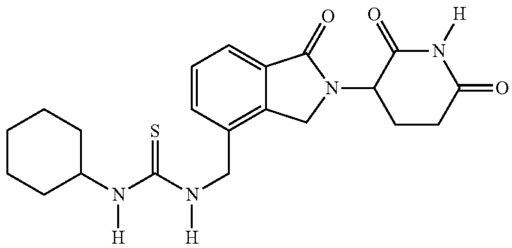 [SMILES: O=C1CCC(N2Cc3c(CNC(=S)NC4CCCCC4)cccc3C2=O)C(=O)N1] | 1-Cyclohexyl-3-[2-(2,6-dioxo-piperidin-3-yl)-1-oxo-2,3-dihydro-1H-isoindol-4-ylmethyl]-thiourea |
| 36 | 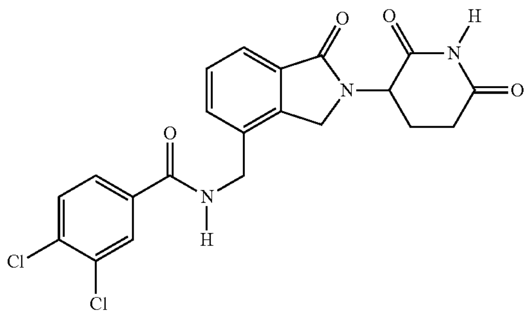 [SMILES: O=C1CCC(N2Cc3c(CNC(=O)c4ccc(Cl)c(Cl)c4)cccc3C2=O)C(=O)N1] | 3,4-Dichloro-N-[2-(2,6-dioxo-piperidin-3-yl)-1-oxo-2,3-dihydro-1H-isoindol-4-ylmethyl]-benzamide |
| 37 | 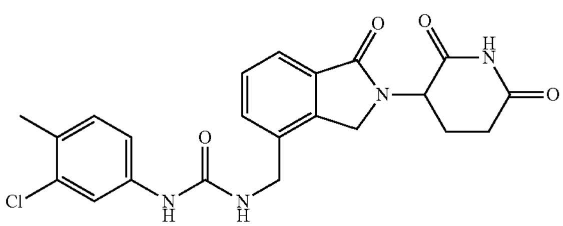 [SMILES: Cc1ccc(NC(=O)NCc2cccc3c2CN(C2CCC(=O)NC2=O)C3=O)cc1Cl] | 1-(3-Chloro-4-methylphenyl)-3-[2-(2,6-dioxo-piperidin-3-yl)-1-oxo-2,3-dihydro-1H-isoindol-4-ylmethyl]urea |
| 38 | 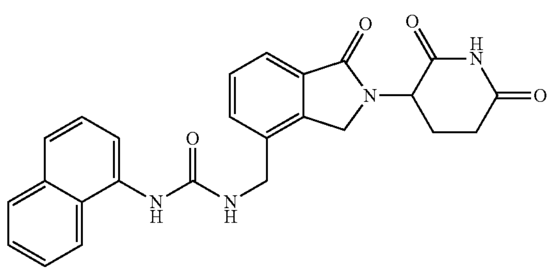 [SMILES: O=C1CCC(N2Cc3c(CNC(=O)Nc4cccc5ccccc45)cccc3C2=O)C(=O)N1] | 1-[2-(2,6-Dioxopiperidin-3-yl)-1-oxo-2,3-dihydro-1H-isoindol-4-ylmethyl]-3-naphthalen-1-yl-urea |
| 39 | 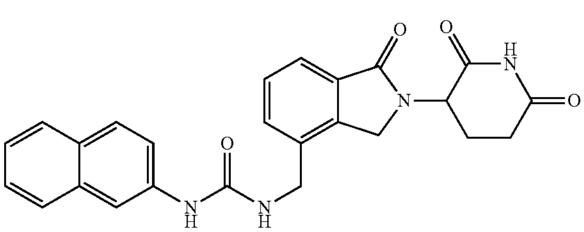 [SMILES: O=C1CCC(N2Cc3c(CNC(=O)Nc4ccc5ccccc5c4)cccc3C2=O)C(=O)N1] | 1-[2-(2,6-Dioxopiperidin-3-yl)-1-oxo-2,3-dihydro-1H-isoindol-4-ylmethyl]-3-naphthalen-2-yl-urea |

In another embodiment, this invention encompasses compounds of formula (II):

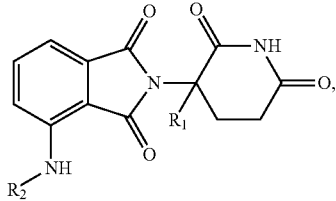

and pharmaceutically acceptable salts, solvates, stereoisomers, and prodrugs thereof, wherein:
$R_1$ is H or methyl; and
$R_2$ is: $(C_6\text{-}C_{10})$aryl, optionally substituted with one or more of: $(C_1\text{-}C_8)$alkyl, optionally substituted with $NH_2$, $NH(CH_3)$, or $N(CH_3)_2$; $(C_1\text{-}C_4)$alkoxy, optionally substituted with $NH_2$, $NH(CH_3)$, $N(CH_3)_2$, or 3 to 6 membered heterocycloalkyl; $(C_3\text{-}C_6)$cycloalkyl; $(C_5\text{-}C_{10})$aryloxy; hydroxy; $NH_2$; $NH(CH_3)$; $N(CH_3)_2$; —$CH_2$—$CH_2$—$CH_2$—; halogen; or —O—$CH_2$—O—;
$(C_3\text{-}C_6)$alkyl, optionally substituted with one or more of $(C_1\text{-}C_4)$alkoxy;
$(C_1\text{-}C_2)$alkyl, optionally substituted with carboxyl;
$(C_1\text{-}C_6)$alkyl-$(C_3\text{-}C_6)$cycloalkyl; or
5 to 10 membered heterocycle;
with the proviso that if $R_2$ is pentyl, then $R_1$ is methyl.

In one embodiment, $R_2$ is phenyl, optionally substituted with one or more of $(C_1\text{-}C_4)$alkoxy or —O—$CH_2$—O—. In another embodiment, $R_2$ is phenyl substituted with one or more $(C_1\text{-}C_4)$alkoxy, substituted with $N(CH_3)_2$. In another embodiment, $R_2$ is $(C_3\text{-}C_6)$alkyl, optionally substituted with one or more of $(C_1\text{-}C_4)$alkoxy.

Examples of compounds of formula (II) include, but are not limited to, those listed in Table 2, below:

TABLE 2

Compounds of Formula II

| No. | Structure | Name |
|---|---|---|
| 40 | 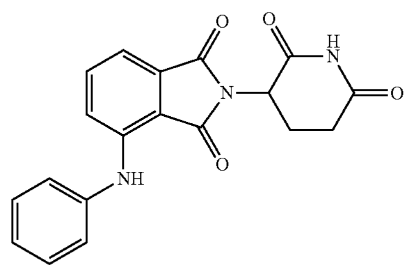 [SMILES: O=C1CCC(N2C(=O)c3cccc(Nc4ccccc4)c3C2=O)C(=O)N1] | 2-(2,6-Dioxopiperidin-3-yl)-4-phenylaminoisoindole-1,3-dione |
| 41 | 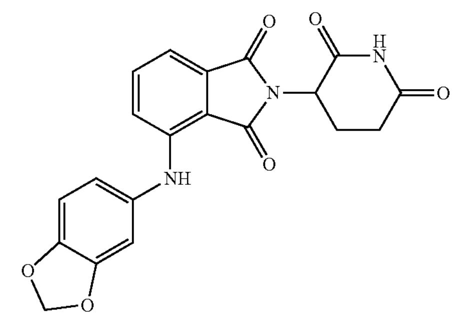 [SMILES: O=C1CCC(N2C(=O)c3cccc(Nc4ccc5c(c4)OCO5)c3C2=O)C(=O)N1] | 2-(2,6-Dioxopiperidin-3-yl)-4-(3,4-methylenedioxyphenylamino)isoindole-1,3-dione |
| 42 | 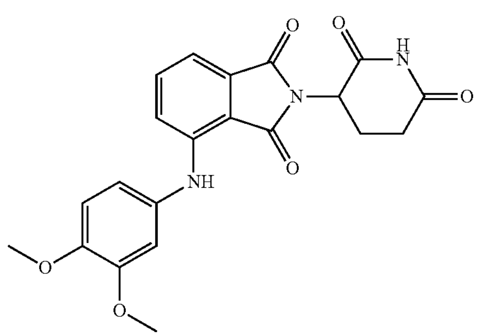 [SMILES: COc1ccc(Nc2cccc3c2C(=O)N(C2CCC(=O)NC2=O)C3=O)cc1OC] | 2-(2,6-Dioxopiperidin-3-yl)-4-(3,4-dimethoxyphenylamino)isoindole-1,3-dione |

TABLE 2-continued

Compounds of Formula II

| No. | Structure | Name |
|---|---|---|
| 43 | 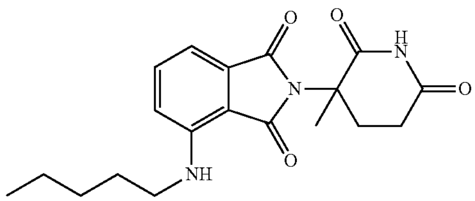 [SMILES: CCCCCNc1cccc2c1C(=O)N(C1(C)CCC(=O)NC1=O)C2=O] | 2-(3-Methyl-2,6-dioxopiperidin-3-yl)-4-pentylaminoisoindole-1,3-dione |
| 44 | 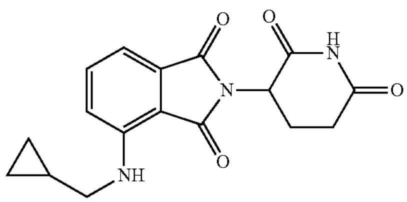 [SMILES: O=C1CCC(N2C(=O)c3cccc(NCC4CC4)c3C2=O)C(=O)N1] | 4-(Cyclopropylmethylamino)-2-(2,6-dioxopiperidin-3-yl)isoindole-1,3-dione |
| 45 | 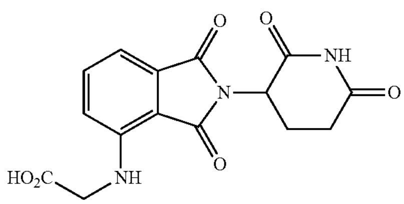 [SMILES: O=C(O)CNc1cccc2c1C(=O)N(C1CCC(=O)NC1=O)C2=O] | [2-(2,6-Dioxopiperidin-3-yl)-1,3-dioxo-2,3-dihydro-1H-isoindol-4-yl-amino]acetic acid |
| 46 | 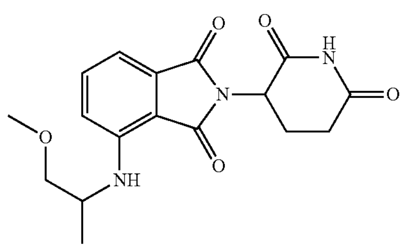 [SMILES: COCC(C)Nc1cccc2c1C(=O)N(C1CCC(=O)NC1=O)C2=O] | 2-(2,6-Dioxopiperidin-3-yl)-4-(2-methoxy-1-methylethylamino)isoindole-1,3-dione |
| 47 | 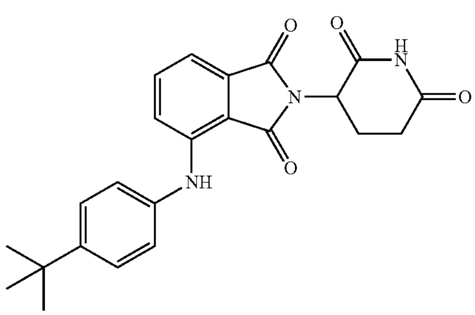 [SMILES: CC(C)(C)c1ccc(Nc2cccc3c2C(=O)N(C2CCC(=O)NC2=O)C3=O)cc1] | 4-(4-tert-Butylphenylamino)-2-(2,6-dioxopiperidin-3-yl)isoindole-1,3-dione |
| 48 | 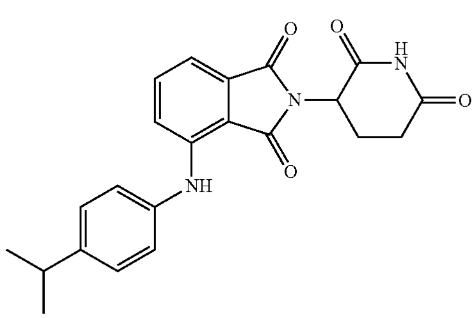 [SMILES: CC(C)c1ccc(Nc2cccc3c2C(=O)N(C2CCC(=O)NC2=O)C3=O)cc1] | 4-(4-Isopropylphenylamino)-2-(2,6-dioxopiperidin-3-yl)isoindole-1,3-dione |

TABLE 2-continued
Compounds of Formula II
| No. | Structure | Name |
|---|---|---|
| 49 | 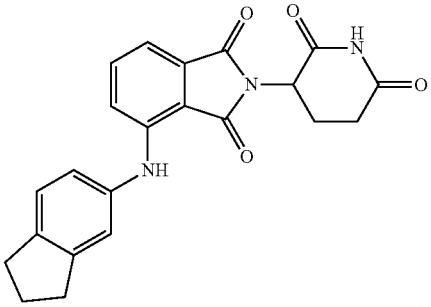 [SMILES: O=C1CCC(N2C(=O)c3cccc(Nc4ccc5c(c4)CCC5)c3C2=O)C(=O)N1] | 2-(2,6-Dioxo-piperidin-3-yl)-4-(indan-5-ylamino)-isoindole-1,3-dione |
| 50 | 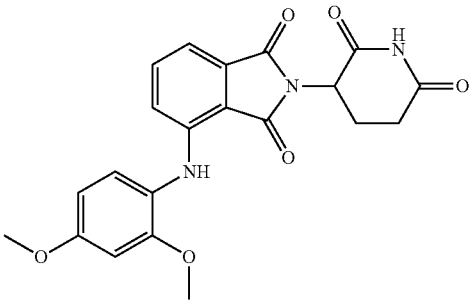 [SMILES: COc1ccc(Nc2cccc3c2C(=O)N(C2CCC(=O)NC2=O)C3=O)c(OC)c1] | 4-(2,4-Dimethoxyphenylamino)-2-(2,6-dioxopiperidin-3-yl)isoindole-1,3-dione |
| 51 | 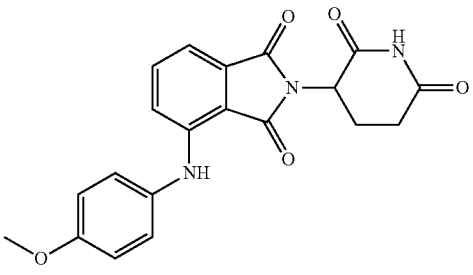 [SMILES: COc1ccc(Nc2cccc3c2C(=O)N(C2CCC(=O)NC2=O)C3=O)cc1] | 2-(2,6-Dioxopiperidin-3-yl)-4-(4-methoxyphenylamino)isoindole-1,3-dione |
| 52 | 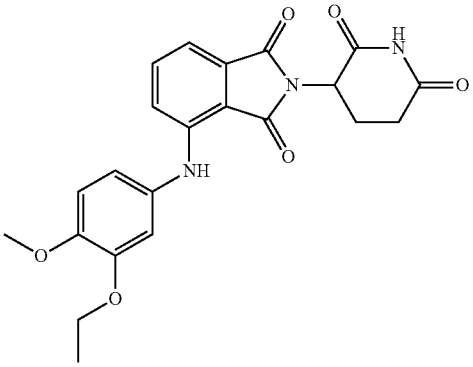 [SMILES: CCOc1cc(Nc2cccc3c2C(=O)N(C2CCC(=O)NC2=O)C3=O)ccc1OC] | 2-(2,6-Dioxopiperidin-3-yl)-4-(3-ethoxy-4-methoxyphenylamino)-isoindole-1,3-dione |

TABLE 2-continued
Compounds of Formula II
| No. | Structure | Name |
|---|---|---|
| 53 | 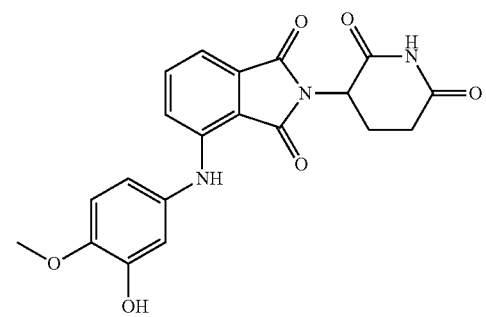 [SMILES: COc1ccc(Nc2cccc3c2C(=O)N(C2CCC(=O)NC2=O)C3=O)cc1O] | 2-(2,6-Dioxopiperidin-3-yl)-4-(3-hydroxy-4-methoxyphenylamino)-isoindole-1,3-dione |
| 54 | 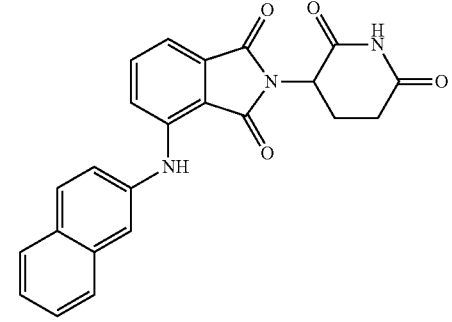 [SMILES: O=C1CCC(N2C(=O)c3cccc(Nc4ccc5ccccc5c4)c3C2=O)C(=O)N1] | 2-(2,6-Dioxopiperidin-3-yl)-4-(naphthalen-2-ylamino)isoindole-1,3-dione |
| 55 | 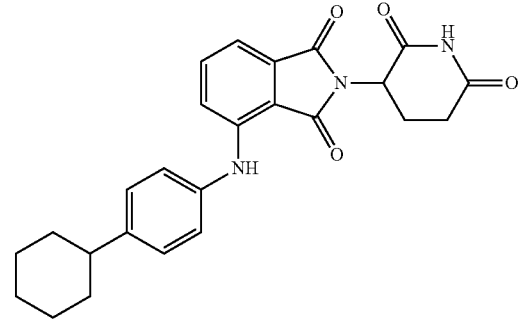 [SMILES: O=C1CCC(N2C(=O)c3cccc(Nc4ccc(C5CCCCC5)cc4)c3C2=O)C(=O)N1] | 4-(4-Cyclohexylphenylamino)-2-(2,6-dioxopiperidin-3-yl)isoindole-1,3-dione |
| 56 | 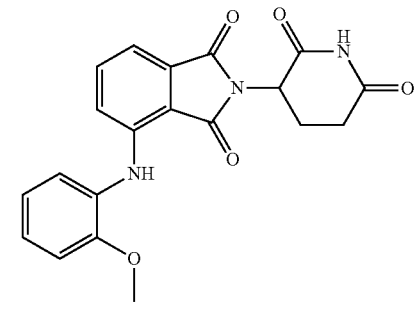 [SMILES: COc1ccccc1Nc1cccc2c1C(=O)N(C1CCC(=O)NC1=O)C2=O] | 4-(2-Methoxyphenylamino)-2-(2,6-dioxopiperidin-3-yl)isoindole-1,3-dione |

TABLE 2-continued

Compounds of Formula II

| No. | Structure | Name |
|---|---|---|
| 57 | 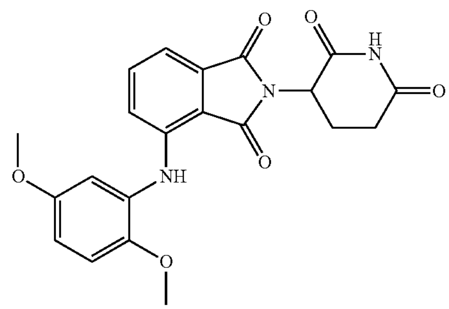 [SMILES: COc1ccc(OC)c(Nc2cccc3c2C(=O)N(C2CCC(=O)NC2=O)C3=O)c1] | 4-(2,5-Dimethoxyphenylamino)-2-(2,6-dioxopiperidin-3-yl)isoindole-1,3-dione |
| 58 | 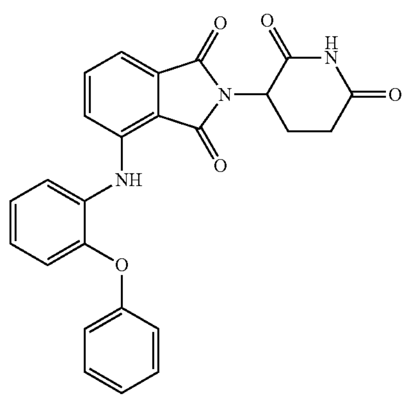 [SMILES: O=C1CCC(N2C(=O)c3cccc(Nc4ccccc4Oc4ccccc4)c3C2=O)C(=O)N1] | 4-(2-Phenoxyphenylamino)-2-(2,6-dioxopiperidin-3-yl)isoindole-1,3-dione |
| 59 | 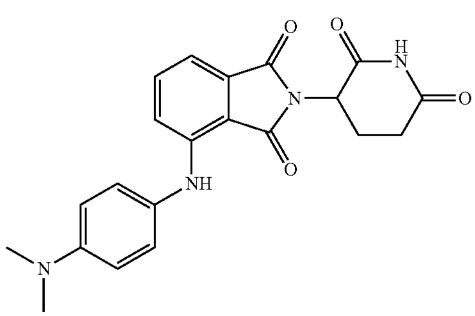 | 4-(4-Dimethylaminophenylamino)-2-(2,6-dioxopiperidin-3-yl)isoindole-1,3-dione |
| 60 | 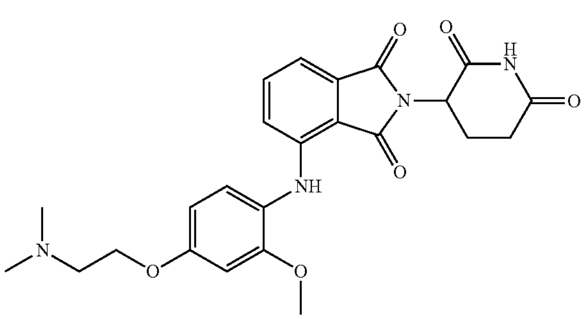 [SMILES: COc1cc(OCCN(C)C)ccc1Nc1cccc2c1C(=O)N(C1CCC(=O)NC1=O)C2=O] | 4-[4-(2-Dimethylaminoethoxy)-2-methoxyphenylamino]-2-(2,6-dioxo-piperidin-3-yl)-isoindole-1,3-dione |

TABLE 2-continued

Compounds of Formula II

| No. | Structure | Name |
|---|---|---|
| 61 | 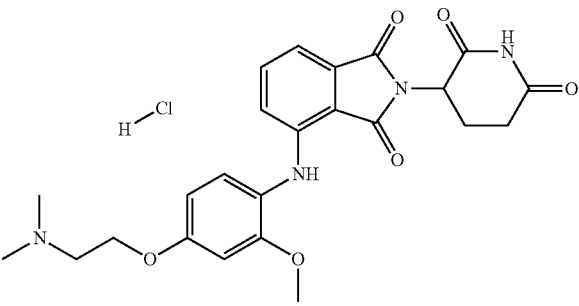 [SMILES: COc1cc(OCCN(C)C)ccc1Nc1cccc2c1C(=O)N(C1CCC(=O)NC1=O)C2=O ; Cl] | 4-[4-(2-Dimethylaminoethoxy)-2-methoxyphenylamino]-2-(2,6-dioxo-piperidin-3-yl)-isoindole-1,3-dione hydrochloride |
| 62 | 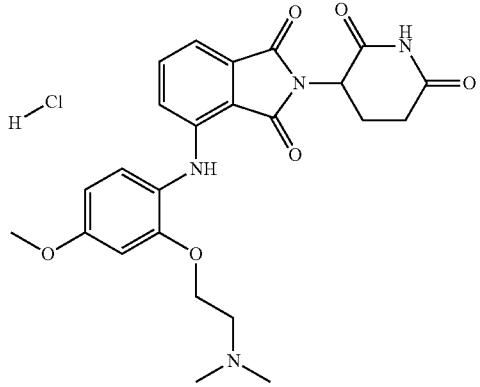 [SMILES: COc1ccc(Nc2cccc3c2C(=O)N(C2CCC(=O)NC2=O)C3=O)c(OCCN(C)C)c1 ; Cl] | 4-[2-(2-Dimethylaminoethoxy)-4-methoxyphenylamino]-2-(2,6-dioxopiperidin-3-yl)isoindole-1,3-dione hydrochloride |
| 63 | 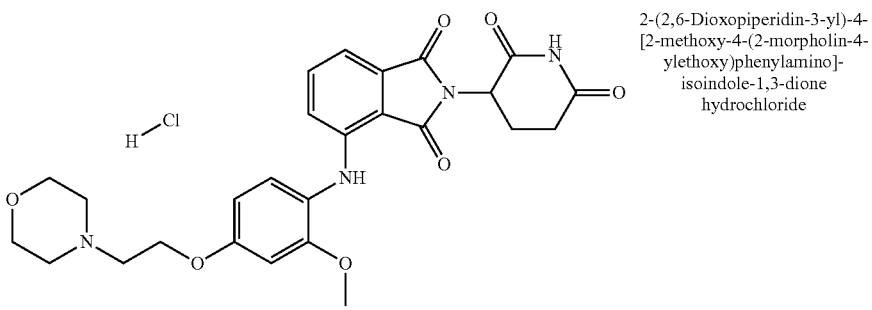 | 2-(2,6-Dioxopiperidin-3-yl)-4-[2-methoxy-4-(2-morpholin-4-ylethoxy)phenylamino]-isoindole-1,3-dione hydrochloride |
| 64 | 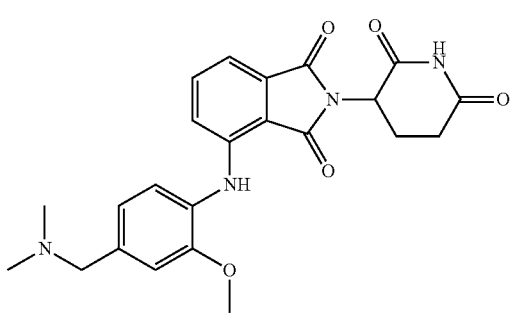 [SMILES: COc1cc(CN(C)C)ccc1Nc1cccc2c1C(=O)N(C1CCC(=O)NC1=O)C2=O] | 4-(4-Dimethylaminomethyl-2-methoxyphenylamino)-2-(2,6-dioxopiperidin-3-yl)isoindole-1,3-dione |

TABLE 2-continued

Compounds of Formula II

| No. | Structure | Name |
|---|---|---|
| 65 | 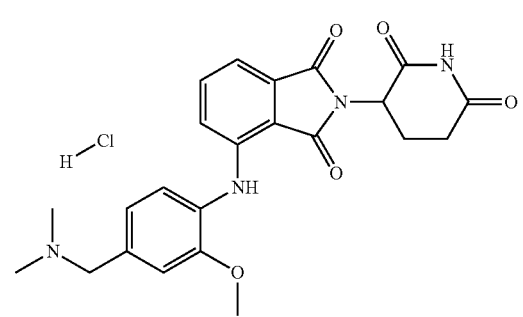 | 4-(4-Dimethylaminomethyl-2-methoxyphenylamino)-2-(2,6-dioxopiperidin-3-yl)isoindole-1,3-dione hydrochloride |
| 66 | 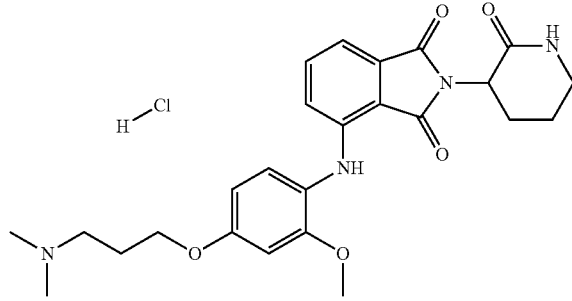 | 4-[4-(3-Dimethylaminopropoxy)-2-methoxyphenylamino]-2-(2,6-dioxopiperidin-3-yl)isoindole-1,3-dione hydrochloride |
| 67 | 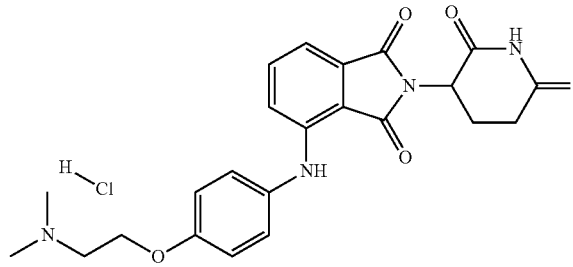 | 4-[4-(2-Dimethylamino-ethoxy)-phenylamino]-2-(2,6-dioxo-piperidin-3-yl)-isoindole-1,3-dione |
| 68 | 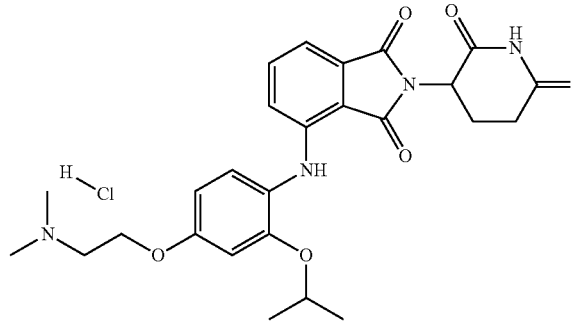 | 4-[4-(2-Dimethylamino-ethoxy)-2-isopropoxy-phenylamino]-2-(2,6-dioxo-piperidin-3-yl)-isoindole-1,3-dione |

TABLE 2-continued
Compounds of Formula II
| No. | Structure | Name |
|---|---|---|
| 69 | 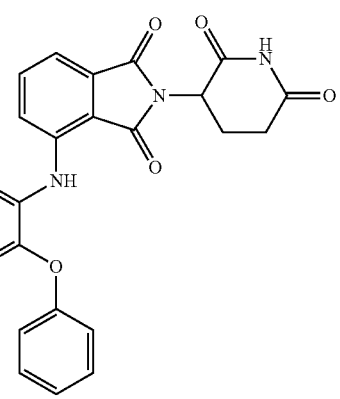 | 2-(2,6-Dioxo-piperidin-3-yl)-4-(4-methoxy-2-phenoxy-phenylamino)-isoindole-1,3-dione |
| 70 | 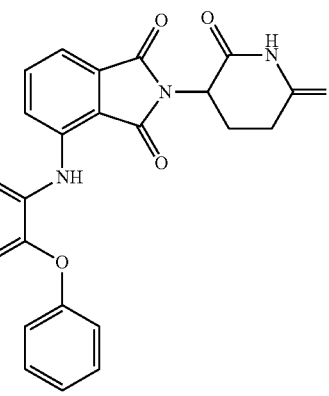 | 4-[4-(2-Dimethylamino-ethoxy)-2-phenoxy-phenylamino]-2-(2,6-dioxo-piperidin-3-yl)-isoindole-1,3-dione |
| 71 | 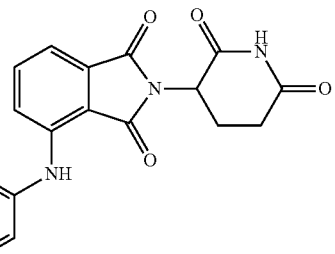 | 2-(2,6-Dioxo-piperidin-3-yl)-4-[4-(2-morpholin-4-yl-ethoxy)-phenylamino]-isoindole-1,3-dione |
| 72 | 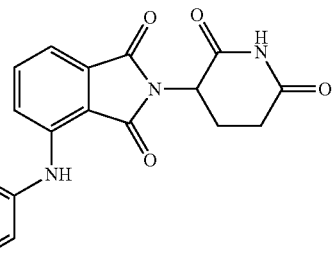 | 2-(2,6-Dioxo-piperidin-3-yl)-4-[3-(2-morpholin-4-yl-ethoxy)-phenylamino]-isoindole-1,3-dione |

TABLE 2-continued

Compounds of Formula II

| No. | Structure | Name |
|---|---|---|
| 73 | 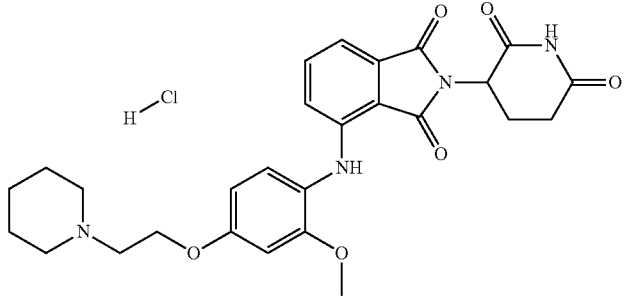 [SMILES: COc1cc(OCCN2CCCCC2)ccc1Nc1cccc2c1C(=O)N(C1CCC(=O)NC1=O)C2=O ; Cl] | 2-(2,6-Dioxo-piperidin-3-yl)-4-[2-methoxy-4-(2-piperidin-1-yl-ethoxy)-phenylamino]-isoindole-1,3-dione |
| 74 | 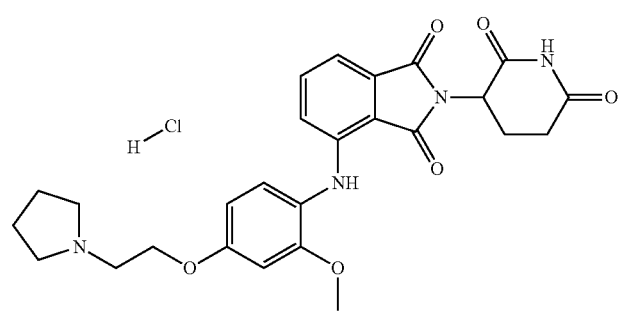 [SMILES: COc1cc(OCCN2CCCC2)ccc1Nc1cccc2c1C(=O)N(C1CCC(=O)NC1=O)C2=O ; Cl] | 2-(2,6-Dioxo-piperidin-3-yl)-4-[2-methoxy-4-(2-pyrrolidin-1-yl-ethoxy)-phenylamino]-isoindole-1,3-dione |
| 75 | 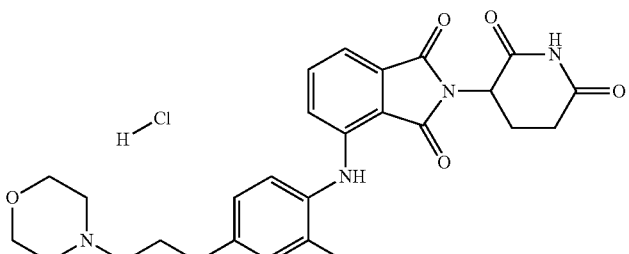 | 2-(2,6-Dioxo-piperidin-3-yl)-4-[2-fluoro-4-(2-morpholin-4-yl-ethoxy)-phenylamino]-isoindole-1,3-dione |
| 76 | 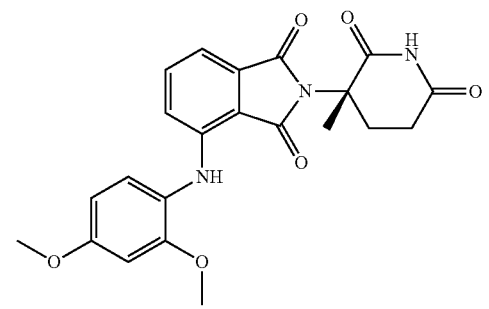 [SMILES: COc1ccc(Nc2cccc3c2C(=O)N([C@@]2(C)CCC(=O)NC2=O)C3=O)c(OC)c1] | 4-(2,4-Dimethoxy-phenylamino)-2-[(3S)-3-methyl-2,6-dioxo-piperidin-3-yl]-isoindole-1,3-dione |
| 77 | 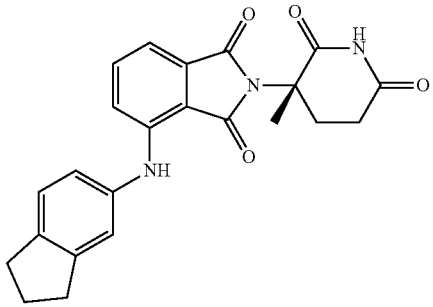 [SMILES: C[C@]1(N2C(=O)c3cccc(Nc4ccc5c(c4)CCC5)c3C2=O)CCC(=O)NC1=O] | 4-(Indan-5-ylamino)-2-[(3S)-3-methyl-2,6-dioxo-piperidin-3-yl]-isoindole-1,3-dione |

TABLE 2-continued

Compounds of Formula II

| No. | Structure | Name |
|---|---|---|
| 78 | 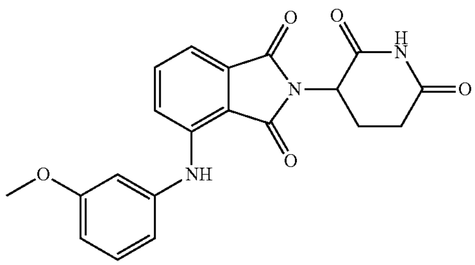 [SMILES: COc1cccc(Nc2cccc3c2C(=O)N(C2CCC(=O)NC2=O)C3=O)c1] | 2-(2,6-Dioxo-piperidin-3-yl)-4-(3-methoxy-phenylamino)-isoindole-1,3-dione |

In another embodiment, this invention encompasses compounds of formula (III):

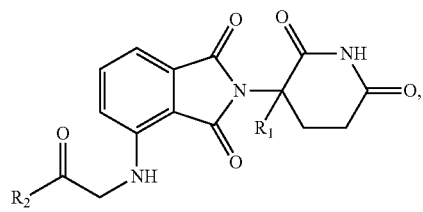

(III)

and pharmaceutically acceptable salts, solvates, stereoisomers, and prodrugs thereof, wherein:

$R_1$ is H or methyl; and $R_2$ is: amino, optionally substituted with one or more of ($C_1$-$C_6$)alkyl, ($C_3$-$C_6$)cycloalkyl, or phenyl; 3 to 6 membered heterocycloalkyl; or ($C_1$-$C_4$)alkoxy.

In one specific embodiment, $R_2$ is —NH(CH$_3$) or —N(CH$_3$)$_2$. In another embodiment, $R_2$ is ($C_3$-$C_6$)cycloalkyl.

Examples of compounds of formula (III) include, but are not limited to, those listed in Table 3, below:

TABLE 3

Compounds of Formula III

| No. | Structure | Name |
|---|---|---|
| 79 | 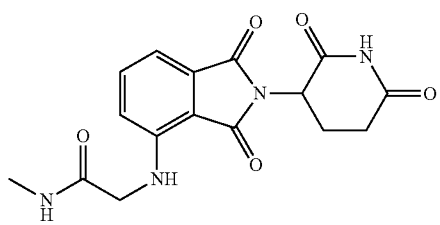 [SMILES: CNC(=O)CNc1cccc2c1C(=O)N(C1CCC(=O)NC1=O)C2=O] | 2-[2-(2,6-Dioxopiperidin-3-yl)-1,3-dioxo-2,3-dihydro-1H-isoindol-4-ylamino]-N-methylacetamide |
| 80 | 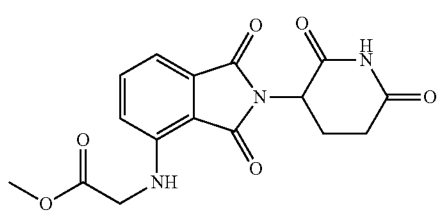 [SMILES: COC(=O)CNc1cccc2c1C(=O)N(C1CCC(=O)NC1=O)C2=O] | [2-(2,6-Dioxopiperidin-3-yl)-1,3-dioxo-2,3-dihydro-1H-isoindol-4-ylamino]acetic acid methyl ester |
| 81 | 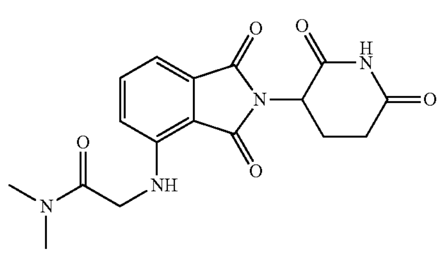 [SMILES: CN(C)C(=O)CNc1cccc2c1C(=O)N(C1CCC(=O)NC1=O)C2=O] | 2-[2-(2,6-Dioxopiperidin-3-yl)-1,3-dioxo-2,3-dihydro-1H-isoindol-4-ylamino]-N-methylacetamide |

TABLE 3-continued

Compounds of Formula III

| No. | Structure | Name |
|---|---|---|
| 82 | 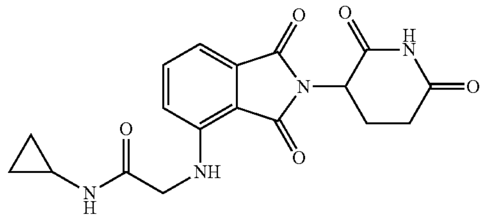 [SMILES: O=C1CCC(N2C(=O)c3cccc(NCC(=O)NC4CC4)c3C2=O)C(=O)N1] | N-Cyclopropyl-2-[2-(2,6-dioxopiperidin-3-yl)-1,3-dioxo-2,3-dihydro-1H-isoindol-4-ylamino]acetamide |
| 83 | 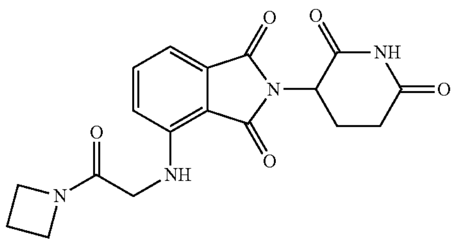 [SMILES: O=C1CCC(N2C(=O)c3cccc(NCC(=O)N4CCC4)c3C2=O)C(=O)N1] | 4-(2-(Azetidin-1-yl)-2-oxoethylamino)-2-(2,6-dioxo piperidin-3-yl)isoindoline-1,3-dione |
| 84 | 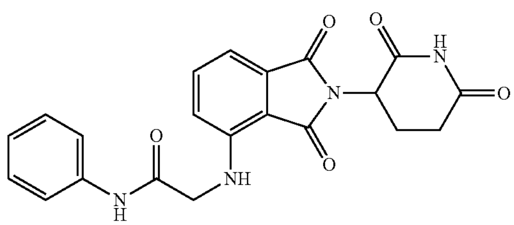 [SMILES: O=C1CCC(N2C(=O)c3cccc(NCC(=O)Nc4ccccc4)c3C2=O)C(=O)N1] | 2-[2-(2,6-Dioxopiperidin-3-yl)-1,3-dioxo-2,3-dihydro-1H-isoindol-4-ylamino]-N-phenyl-acetamide |

In another embodiment, this invention encompasses compounds of formula (IV): or a pharmaceutically acceptable salt, solvate, stereoisomer, or prodrug thereof:

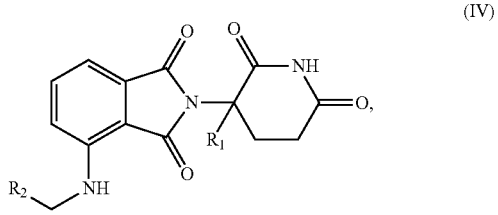

(IV)

and pharmaceutically acceptable salts, solvates, stereoisomers, and prodrugs thereof, wherein $R_1$ is H or methyl; and $R_2$ is 5 to 6 membered heteroaryl;

with the proviso that if $R_2$ is furan or thiophene, then $R_1$ is methyl; and with the proviso that if $R_2$ is pyridine, then the pyridine is not connected to the core at the 3 position.

In one specific embodiment, $R_2$ is not pyridine.

Examples of compounds of formula IV include, but are not limited to, those listed in Table 4, below:

TABLE 4

Compounds of Formula IV

| No. | Structure | Name |
|---|---|---|
| 85 | 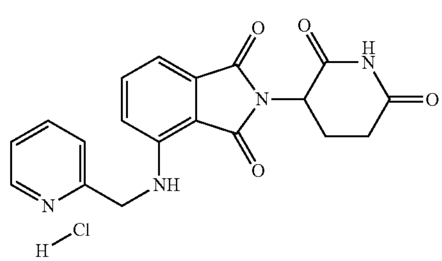 | 2-(2,6-Dioxopiperidin-3-yl)-4-[(pyridin-2-yl-methyl)amino]isoindole-1,3-dione hydrochloride |

TABLE 4-continued

Compounds of Formula IV

| No. | Structure | Name |
|---|---|---|
| 86 | 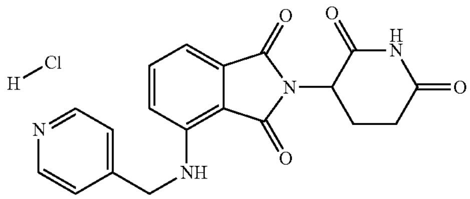 | 2-(2,6-Dioxopiperidin-3-yl)-4-[(pyridin-4-yl-methyl)amino]isoindole-1,3-dione hydrochloride |
| 87 | 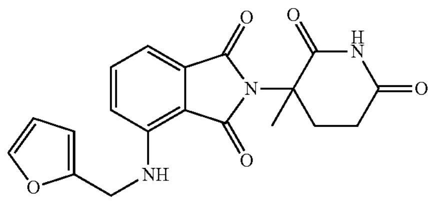 [SMILES: CC1(N2C(=O)c3cccc(NCc4ccco4)c3C2=O)CCC(=O)NC1=O] | 4-[(Furan-2-ylmethyl)amino]-2-(3-methyl-2,6-dioxopiperidin-3-yl)isoindole-1,3-dione |

In another embodiment, this invention encompasses compounds of formula (V):

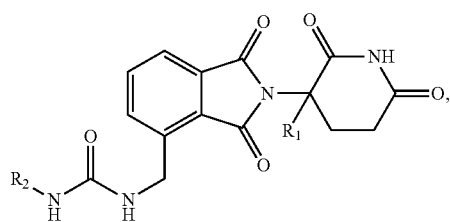

(V)

and pharmaceutically acceptable salts, solvates, stereoisomers, and prodrugs thereof:
wherein:
$R_1$ is H or methyl; and
$R_2$ is: H; methyl; ethyl;
phenyl, substituted with one or more of $(C_1$-$C_6)$alkyl, halogen, $(C_1$-$C_4)$alkoxy, cyano, or —O—$CH_2$—O—;
naphthyl, optionally substituted with one or more of $(C_1$-$C_6)$alkyl, halogen, $(C_1$-$C_4)$alkoxy, or cyano; or
5 to 10 membered heteroaryl, optionally substituted with one or more of $(C_1$-$C_6)$alkyl, halogen, $(C_1$-$C_4)$alkoxy, or cyano;
with the proviso that if $R_2$ is ethyl, then $R_1$ is methyl; and
with the proviso that if $R_2$ is pyridine, then the pyridine is not connected to the core at the 3 position.

In one specific embodiment, $R_2$ is phenyl, optionally substituted with one or more of methyl, halogen, $(C_1$-$C_4)$alkoxy, cyano, and —O—$CH_2$—O—. In another embodiment, $R_2$ is naphthyl. In another embodiment, $R_2$ is not pyridine.

Examples of compounds of formula (V) include, but are not limited to, those listed in Table 5, below:

TABLE 5

Compounds of Formula V

| No. | Structure | Name |
|---|---|---|
| 88 | 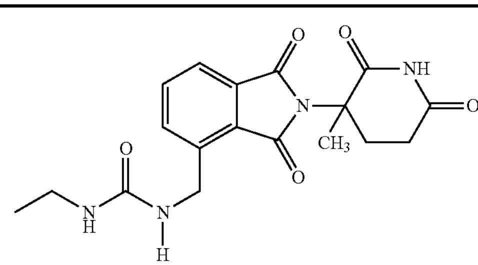 | 1-Ethyl-3-[2-(3-methyl-2,6-dioxo-piperidin-3-yl)-1,3-dioxo-2,3-dihydro-1H-isoindol-4-ylmethyl]-urea |
| 89 | 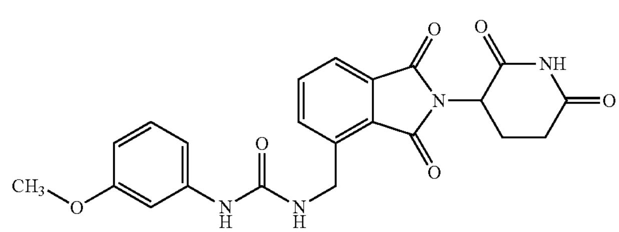 [SMILES: COc1cccc(NC(=O)NCc2cccc3c2C(=O)N(C2CCC(=O)NC2=O)C3=O)c1] | 1-[2-(2,6-Dioxo-piperidin-3-yl)-1,3-dioxo-2,3-dihydro-1H-isoindol-4-ylmethyl]-3-(3-methoxy-phenyl)-urea |

TABLE 5-continued

Compounds of Formula V

| No. | Structure | Name |
|---|---|---|
| 90 | 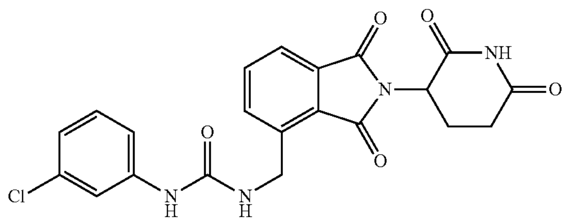 [SMILES: O=C1CCC(N2C(=O)c3cccc(CNC(=O)Nc4cccc(Cl)c4)c3C2=O)C(=O)N1] | 1-(3-Chloro-phenyl)-3-[2-(2,6-dioxo-piperidin-3-yl)-1,3-dioxo-2,3-dihydro-1H-isoindol-4-ylmethyl]-urea |
| 91 | 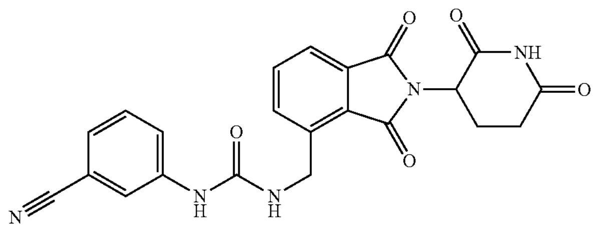 [SMILES: N#Cc1cccc(NC(=O)NCc2cccc3c2C(=O)N(C2CCC(=O)NC2=O)C3=O)c1] | 1-(3-Cyano-phenyl)-3-[2-(2,6-dioxo-piperidin-3-yl)-1,3-dioxo-2,3-dihydro-1H-isoindol-4-ylmethyl]-urea |
| 92 | 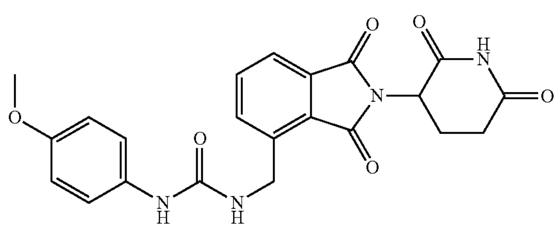 | 1-[2-(2,6-Dioxo-piperidin-3-yl)-1,3-dioxo-2,3-dihydro-1H-isoindol-4-ylmethyl]-3-(4-methoxy-phenyl)-urea |
| 93 | 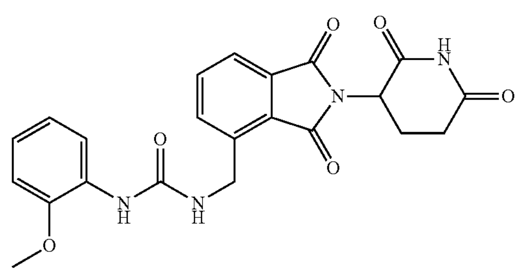 [SMILES: COc1ccccc1NC(=O)NCc1cccc2c1C(=O)N(C1CCC(=O)NC1=O)C2=O] | 1-[2-(2,6-Dioxo-piperidin-3-yl)-1,3-dioxo-2,3-dihydro-1H-isoindol-4-ylmethyl]-3-(2-methoxy-phenyl)-urea |
| 94 | 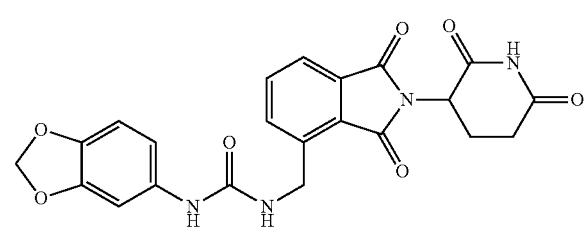 [SMILES: O=C1CCC(N2C(=O)c3cccc(CNC(=O)Nc4ccc5c(c4)OCO5)c3C2=O)C(=O)N1] | 1-(3,4-Methylenedioxyphenyl)-3-[2-(2,6-dioxopiperidin-3-yl)-1,3-dioxo-2,3-dihydro-1H-isoindol-4-ylmethyl]urea |
| 95 | 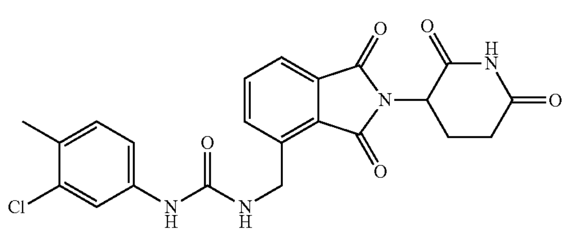 | 1-(3-Chloro-4-methylphenyl)-3-[2-(2,6-dioxopiperidin-3-yl)-1,3-dioxo-2,3-dihydro-1H-isoindol-4-ylmethyl]urea |

TABLE 5-continued

Compounds of Formula V

| No. | Structure | Name |
| --- | --- | --- |
| 96 | 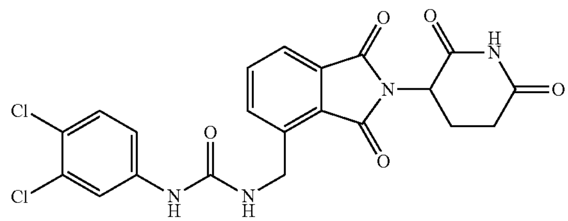 [SMILES: O=C1CCC(N2C(=O)c3cccc(CNC(=O)Nc4ccc(Cl)c(Cl)c4)c3C2=O)C(=O)N1] | 1-(3,4-dichlorophenyl)-3-[2-(2,6-dioxopiperidin-3-yl)-1,3-dioxo-2,3-dihydro-1H-isoindol-4-ylmethyl]urea |
| 97 | 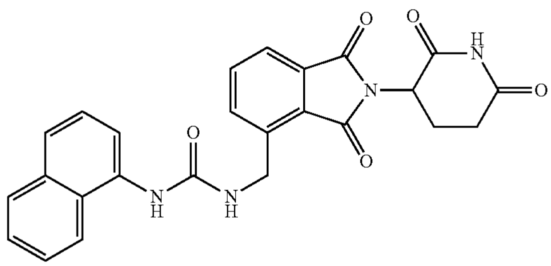 [SMILES: O=C1CCC(N2C(=O)c3cccc(CNC(=O)Nc4cccc5ccccc45)c3C2=O)C(=O)N1] | 1-[2-(2,6-Dioxopiperidin-3-yl)-1,3-dioxo-2,3-dihydro-1H-isoindol-4-ylmethyl]-3-naphthalen-1-yl-urea |
| 98 | 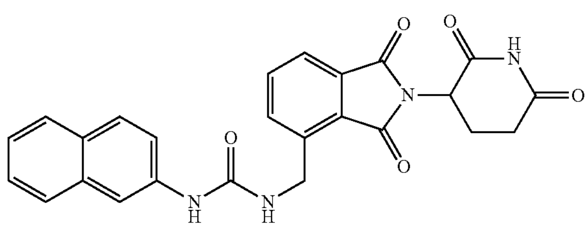 [SMILES: O=C1CCC(N2C(=O)c3cccc(CNC(=O)Nc4ccc5ccccc5c4)c3C2=O)C(=O)N1] | 1-[2-(2,6-Dioxopiperidin-3-yl)-1,3-dioxo-2,3-dihydro-1H-isoindol-4-ylmethyl]-3-naphthalen-2-yl-urea |
| 99 | 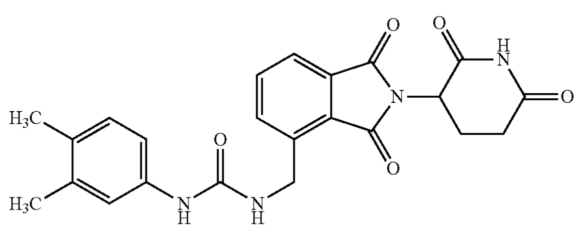 [SMILES: Cc1ccc(NC(=O)NCc2cccc3c2C(=O)N(C2CCC(=O)NC2=O)C3=O)cc1C] | 1-(3,4-Dimethyl-phenyl)-3-[2-(2,6-dioxo-piperidin-3-yl)-1,3-dioxo-2,3-dihydro-1H-isoindol-4-ylmethyl]-urea |
| 100 | 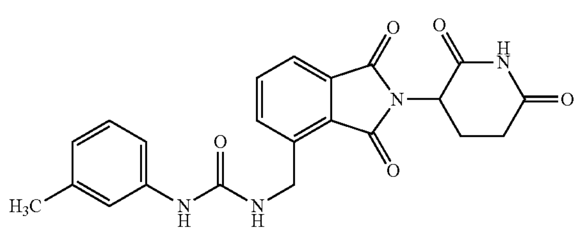 [SMILES: Cc1cccc(NC(=O)NCc2cccc3c2C(=O)N(C2CCC(=O)NC2=O)C3=O)c1] | 1-(2-(2,6-Dioxo-piperidin-3-yl)-1,3-dioxo-2,3-dihydro-1H-isoindol-4-ylmethyl]-3-m-tolyl-urea |

TABLE 5-continued

Compounds of Formula V

| No. | Structure | Name |
|---|---|---|
| 101 | 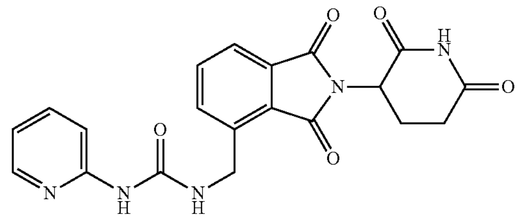 [SMILES: O=C1CCC(N2C(=O)c3cccc(CNC(=O)Nc4ccccn4)c3C2=O)C(=O)N1] | 1-[2-(2,6-Dioxo-piperidin-3-yl)-1,3-dioxo-2,3-dihydro-1H-isoindol-4-ylmethyl]-3-pyridin-2-yl-urea |
| 102 | 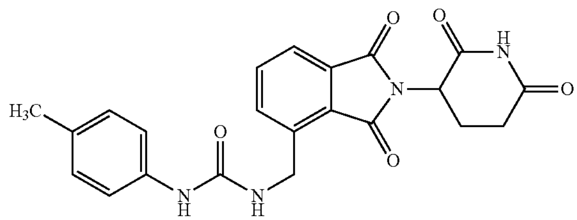 [SMILES: Cc1ccc(NC(=O)NCc2cccc3c2C(=O)N(C2CCC(=O)NC2=O)C3=O)cc1] | 1-[2-(2,6-Dioxo-piperidin-3-yl)-1,3-dioxo-2,3-dihydro-1H-isoindol-4-ylmethyl]-3-p-tolyl-urea |
| 103 | 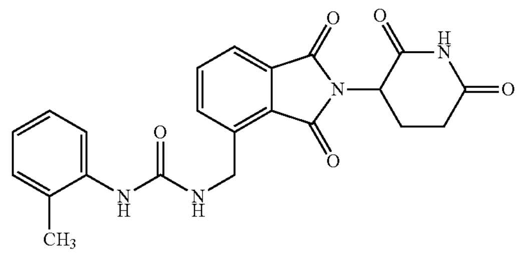 [SMILES: Cc1ccccc1NC(=O)NCc1cccc2c1C(=O)N(C1CCC(=O)NC1=O)C2=O] | 1-[2-(2,6-Dioxo-piperidin-3-yl)-1,3-dioxo-2,3-dihydro-1H-isoindol-4-ylmethyl]-3-o-tolyl-urea |
| 104 | 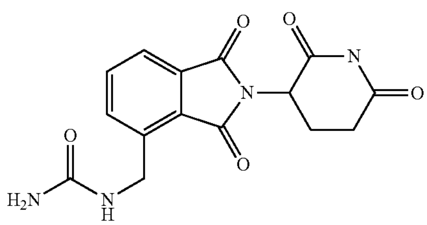 [SMILES: NC(=O)NCc1cccc2c1C(=O)N(C1CCC(=O)NC1=O)C2=O] | [2-(2,6-Dioxo-piperidin-3-yl)-1,3-dioxo-2,3-dihydro-1H-isoindol-4-ylmethyl]-urea |

In another embodiment, this invention encompasses compounds of formula (VI):

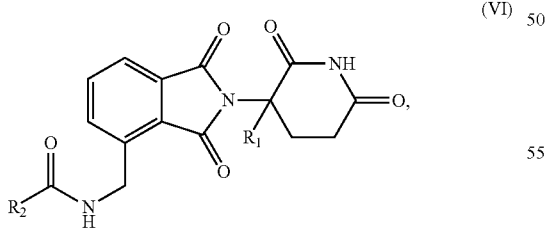

(VI)

and pharmaceutically acceptable salts, solvates, stereoisomers, and prodrugs thereof, wherein:

$R_1$ is H or methyl; and $R_2$ is: $N(CH_3)_2$;

($C_0$-$C_1$)alkyl-($C_6$-$C_{10}$)aryl, substituted with one or more of: methyl, itself optionally substituted with one or more halogen; ($C_1$-$C_4$)alkoxy, itself optionally substituted with one or more halogen; or halogen;

($C_0$-$C_1$)alkyl-(5 to 10 membered heteroaryl), optionally substituted with one or more of ($C_1$-$C_4$)alkyl, ($C_1$-$C_4$)alkoxy, or halogen; or (5 to 6 membered heteroaryl)-phenyl, wherein the heteroaryl and phenyl are each independently optionally substituted with one or more of ($C_1$-$C_4$)alkyl or ($C_1$-$C_4$)alkoxy;

with the proviso that $R_2$ is not unsubstituted pyridine, furan, or thiophene.

In one specific embodiment, $R_2$ is phenyl, substituted with one or more of methyl, ($C_1$-$C_4$)alkoxy, and halogen. In another embodiment, $R_2$ is pyrazine, pyrimidine, quinoxaline, or isoquinoline, optionally substituted with one or more of ($C_1$-$C_4$)alkyl and halogen. In another embodiment, $R_2$ is 5 membered heteroaryl, substituted with one of more ($C_1$-$C_4$) alkyl.

Examples of compounds of formula (VI) include, but are not limited to, those listed in Table 6, below:

TABLE 6

| | Compounds of Formula VI | |
|---|---|---|
| No. | Structure | Name |
| 105 | | 3-[2-(2,6-Dioxo-piperidin-3-yl)-1,3-dioxo-2,3-dihydro-1H-isoindol-4-ylmethyl]-1,1-dimethyl-urea |
| 106 | | N-[2-(2,6-Dioxo-piperidin-3-yl)-1,3-dioxo-2,3-dihydro-1H-isoindol-4-ylmethyl]-4-methoxy-benzamide |
| 107 | | N-[2-(2,6-Dioxo-piperidin-3-yl)-1,3-dioxo-2,3-dihydro-1H-isoindol-4-ylmethyl]-3-methyl-benzamide |
| 108 | | 3,4-Dichloro-N-[2-(2,6-dioxopiperidin-3-yl)-1,3-dioxo-2,3-dihydro-1H-isoindol-4-yl-methyl]benzamide |
| 109 | | Isoquinoline-3-carboxylic acid [2-(2,6-dioxopiperidin-3-yl)-1,3-dioxo-2,3-dihydro-1H-isoindol-4-ylmethyl]amide |

TABLE 6-continued

Compounds of Formula VI

| No. | Structure | Name |
|-----|-----------|------|
| 110 | 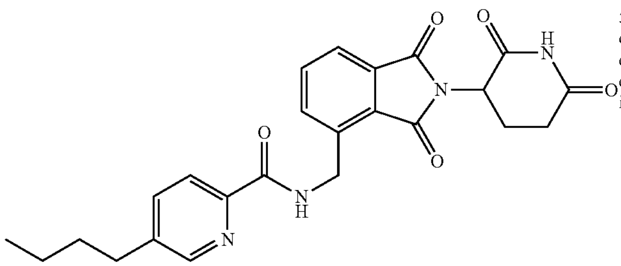 [SMILES: CCCCc1ccc(C(=O)NCc2cccc3c2C(=O)N(C2CCC(=O)NC2=O)C3=O)nc1] | 5-Butylpyridine-2-carboxylic acid [2-(2,6-dioxopiperidin-3-yl)-1,3-dioxo-2,3-dihydro-1H-isoindol-4-ylmethyl]amide |
| 111 | 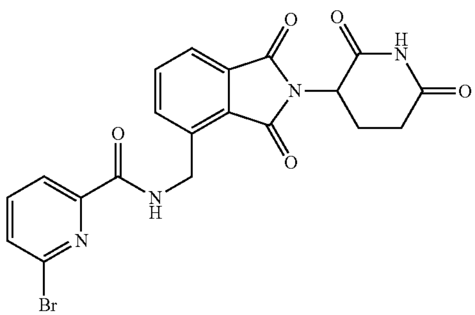 [SMILES: O=C1CCC(N2C(=O)c3cccc(CNC(=O)c4cccc(Br)n4)c3C2=O)C(=O)N1] | 6-Bromopyridine-2-carboxylic acid [2-(2,6-dioxopiperidin-3-yl)-1,3-dioxo-2,3-dihydro-1H-isoindol-4-ylmethyl]amide |
| 112 | 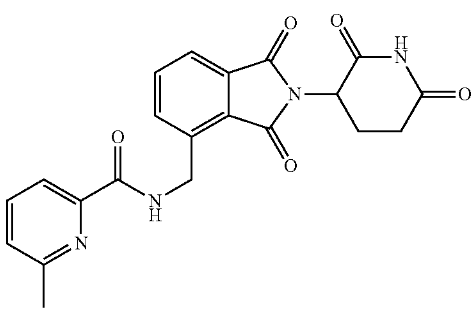 [SMILES: Cc1cccc(C(=O)NCc2cccc3c2C(=O)N(C2CCC(=O)NC2=O)C3=O)n1] | 6-Methylpyridine-2-carboxylic acid [2-(2,6-dioxopiperidin-3-yl)-1,3-dioxo-2,3-dihydro-1H-isoindol-4-ylmethyl]amide |
| 113 | 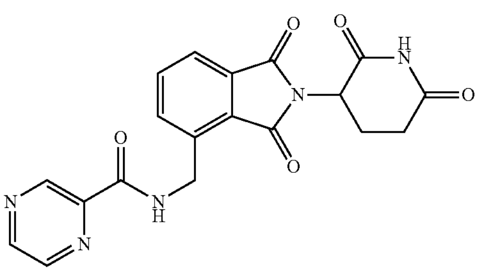 [SMILES: O=C1CCC(N2C(=O)c3cccc(CNC(=O)c4cnccn4)c3C2=O)C(=O)N1] | Pyrazine-2-carboxylic acid [2-(2,6-dioxopiperidin-3-yl)-1,3-dioxo-2,3-dihydro-1H-isoindol-4-yl-methyl]amide |
| 114 | 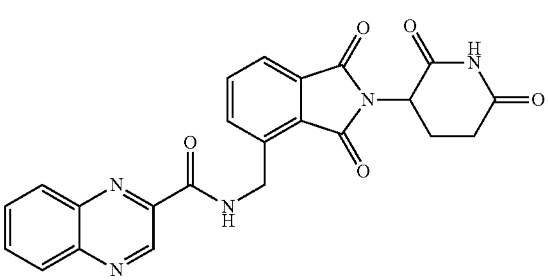 [SMILES: O=C1CCC(N2C(=O)c3cccc(CNC(=O)c4cnc5ccccc5n4)c3C2=O)C(=O)N1] | Quinoxaline-2-carboxylic acid [2-(2,6-dioxopiperidin-3-yl)-1,3-dioxo-2,3-dihydro-1H-isoindol-4-ylmethyl]amide |

TABLE 6-continued

Compounds of Formula VI

| No. | Structure | Name |
|---|---|---|
| 115 | 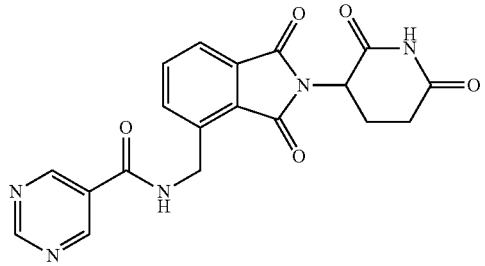 [SMILES: O=C1CCC(N2C(=O)c3cccc(CNC(=O)c4cncnc4)c3C2=O)C(=O)N1] | Pyrimidine-5-carboxylic acid [2-(2,6-dioxopiperidin-3-yl)-1,3-dioxo-2,3-dihydro-1H-isoindol-4-ylmethyl]amide |
| 116 | 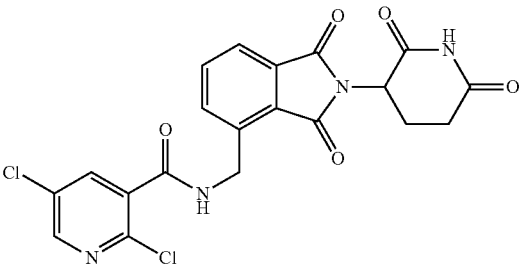 [SMILES: O=C1CCC(N2C(=O)c3cccc(CNC(=O)c4cc(Cl)cnc4Cl)c3C2=O)C(=O)N1] | 2,5-Dichloro-N-[2-(2,6-dioxopiperidin-3-yl)-1,3-dioxo-2,3-dihydro-1H-isoindol-4-yl-methyl]nicotinamide |
| 117 | 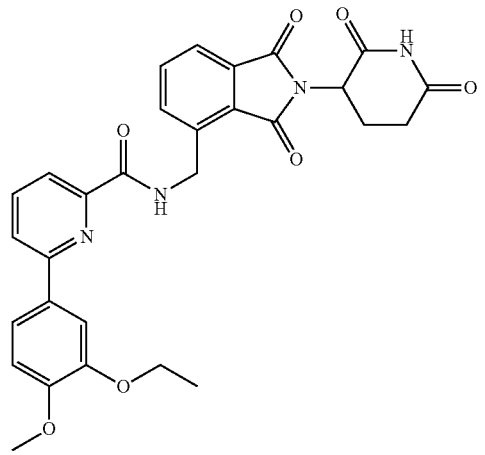 [SMILES: CCOc1cc(-c2cccc(C(=O)NCc3cccc4c3C(=O)N(C3CCC(=O)NC3=O)C4=O)n2)ccc1OC] | 6-(3-Ethoxy-4-methoxyphenyl)pyridine-2-carboxylic acid [2-(2,6-dioxopiperidin-3-yl)-1,3-dioxo-2,3-dihydro-1H-isoindol-4-ylmethyl]amide |
| 118 | 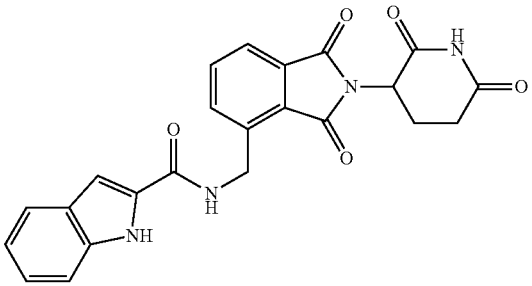 [SMILES: O=C1CCC(N2C(=O)c3cccc(CNC(=O)c4cc5ccccc5[nH]4)c3C2=O)C(=O)N1] | 1H-Indole-2-carboxylic acid [2-(2,6-dioxo-piperidin-3-yl)-1,3-dioxo-2,3-dihydro-1H-isoindol-4-ylmethyl]-amide |

TABLE 6-continued

Compounds of Formula VI

| No. | Structure | Name |
|-----|-----------|------|
| 119 | 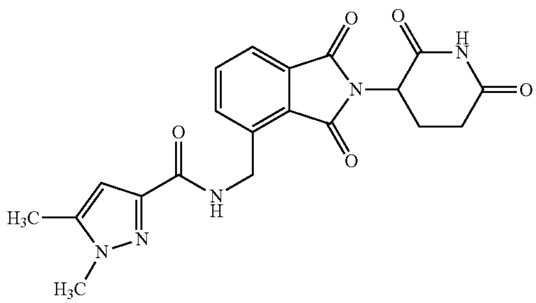 [SMILES: Cc1cc(C(=O)NCc2cccc3c2C(=O)N(C2CCC(=O)NC2=O)C3=O)nn1C] | 1,5-Dimethyl-1H-pyrazole-3-carboxylic acid [2-(2,6-dioxo-piperidin-3-yl)-1,3-dioxo-2,3-dihydro-1H-isoindol-4-ylmethyl]-amide |
| 120 | 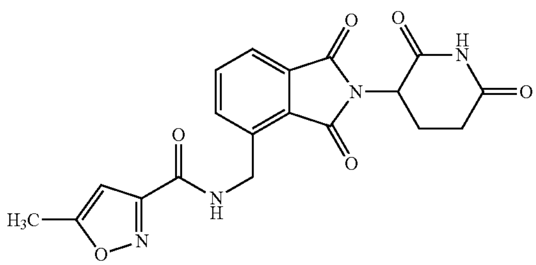 [SMILES: Cc1cc(C(=O)NCc2cccc3c2C(=O)N(C2CCC(=O)NC2=O)C3=O)no1] | 5-Methyl-isoxazole-3-carboxylic acid [2-(2,6-dioxo-piperidin-3-yl)-1,3-dioxo-2,3-dihydro-1H-isoindol-4-ylmethyl]-amide |
| 121 | 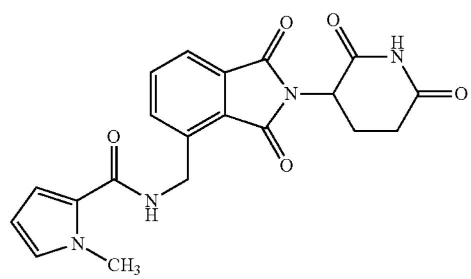 [SMILES: Cn1cccc1C(=O)NCc1cccc2c1C(=O)N(C1CCC(=O)NC1=O)C2=O] | 1-Methyl-1H-pyrrole-2-carboxylic acid [2-(2,6-dioxo-piperidin-3-yl)-1,3-dioxo-2,3-dihydro-1H-isoindol-4-ylmethyl]-amide |
| 122 | 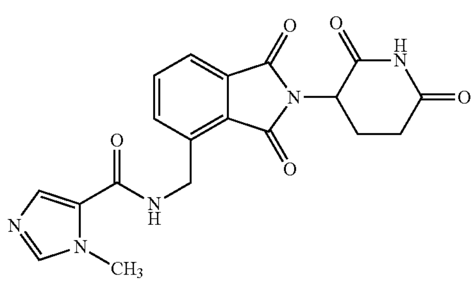 [SMILES: Cn1cncc1C(=O)NCc1cccc2c1C(=O)N(C1CCC(=O)NC1=O)C2=O] | 3-Methyl-3H-imidazole-4-carboxylic acid [2-(2,6-dioxo-piperidin-3-yl)-1,3-dioxo-2,3-dihydro-1H-isoindol-4-ylmethyl]-amide |
| 123 | 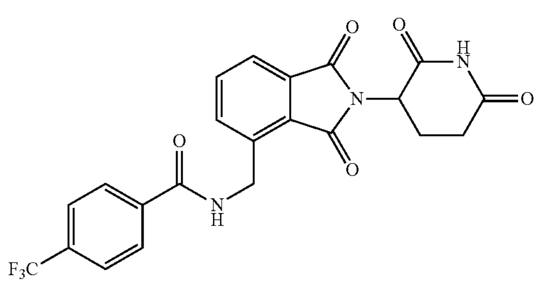 [SMILES: O=C1CCC(N2C(=O)c3cccc(CNC(=O)c4ccc(C(F)(F)F)cc4)c3C2=O)C(=O)N1] | N-[2-(2,6-dioxo-piperidin-3-yl)-1,3-dioxo-2,3-dihydro-1H-isoindol-4-ylmethyl]-4-trifluoromethyl-benzamide |

TABLE 6-continued

| Compounds of Formula VI | | |
|---|---|---|
| No. | Structure | Name |
| 124 | | 5-Phenyl-[1,3,4]oxadiazole-2-carboxylic acid [2-(2,6-dioxo-piperidin-3-yl)-1,3-dioxo-2,3-dihydro-1H-isoindol-4-ylmethylamide |
| 125 | | N-[2-(2,6-Dioxo-piperidin-3-yl)-1,3-dioxo-2,3-dihydro-1H-isoindol-4-ylmethyl]-3-trifluoromethyl-benzamide |
| 126 | | N-[2-(2,6-Dioxo-piperidin-3-yl)-1,3-dioxo-2,3-dihydro-1H-isoindol-4-ylmethyl]-3,4-difluoro-benzamide |
| 127 | | N-[2-(2,6-Dioxo-piperidin-3-yl)-1,3-dioxo-2,3-dihydro-1H-isoindol-4-ylmethyl]-3-fluoro-benzamide |
| 128 | | N-[2-(2,6-Dioxo-piperidin-3-yl)-1,3-dioxo-2,3-dihydro-1H-isoindol-4-ylmethyl]-4-methyl-benzamide |

TABLE 6-continued

Compounds of Formula VI

| No. | Structure | Name |
|---|---|---|
| 129 | 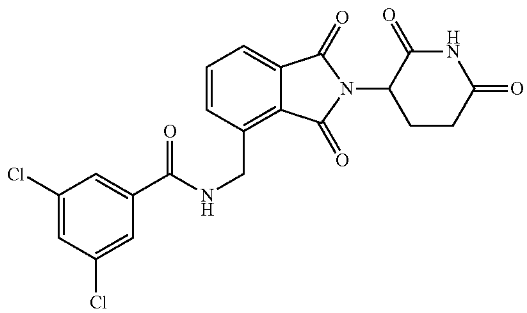 [SMILES: O=C1CCC(N2C(=O)c3cccc(CNC(=O)c4cc(Cl)cc(Cl)c4)c3C2=O)C(=O)N1] | 3,5-Dichloro-N-[2-(2,6-dioxo-piperidin-3-yl)-1,3-dioxo-2,3-dihydro-1H-isoindol-4-ylmethyl]-benzamide |
| 130 | 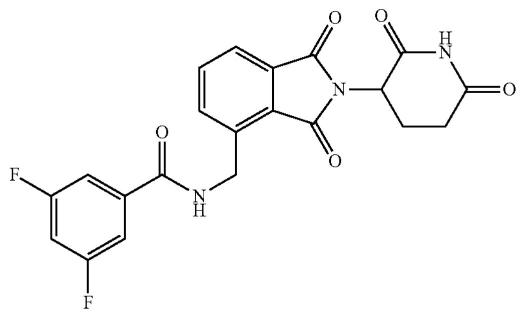 [SMILES: O=C1CCC(N2C(=O)c3cccc(CNC(=O)c4cc(F)cc(F)c4)c3C2=O)C(=O)N1] | N-[2-(2,6-Dioxo-piperidin-3-yl)-1,3-dioxo-2,3-dihydro-1H-isoindol-4-ylmethyl]-3,5-difluoro-benzamide |
| 131 | 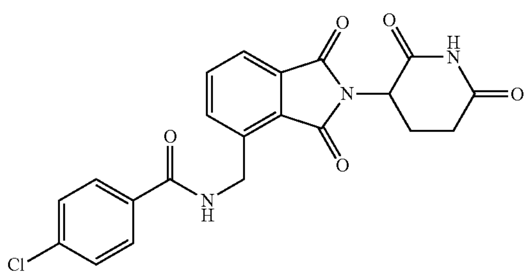 [SMILES: O=C1CCC(N2C(=O)c3cccc(CNC(=O)c4ccc(Cl)cc4)c3C2=O)C(=O)N1] | 4-Chloro-N-[2-(2,6-dioxo-piperidin-3-yl)-1,3-dioxo-2,3-dihydro-1H-isoindol-4-ylmethyl]-benzamide |
| 132 | 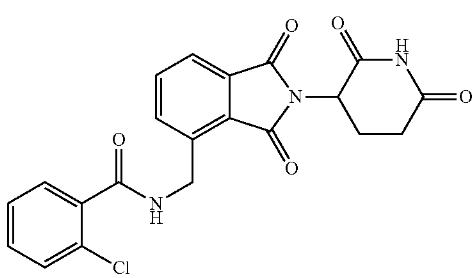 [SMILES: O=C1CCC(N2C(=O)c3cccc(CNC(=O)c4ccccc4Cl)c3C2=O)C(=O)N1] | 2-Chloro-N-[2-(2,6-dioxo-piperidin-3-yl)-1,3-dioxo-2,3-dihydro-1H-isoindol-4-ylmethyl]-benzamide |
| 133 | 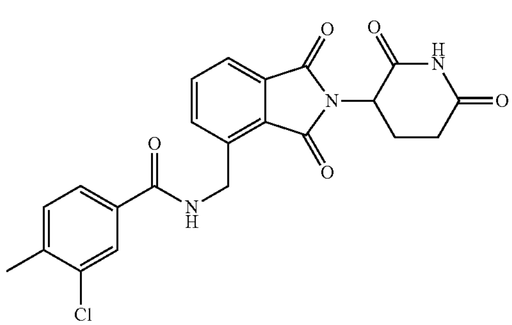 [SMILES: Cc1ccc(C(=O)NCc2cccc3c2C(=O)N(C2CCC(=O)NC2=O)C3=O)cc1Cl] | 3-Chloro-N-[2-(2,6-dioxo-piperidin-3-yl)-1,3-dioxo-2,3-dihydro-1H-isoindol-4-ylmethyl]-4-methyl-benzamide |

TABLE 6-continued

| | Compounds of Formula VI | |
|---|---|---|
| No. | Structure | Name |
| 134 | | Benzofuran-2-carboxylic acid [2-(2,6-dioxo-piperidin-3-yl)-1,3-dioxo-2,3-dihydro-1H-isoindol-4-ylmethyl]-amide |
| 135 | | 2-(3,4-Dichloro-phenyl)-N-[2-(2,6-dioxo-piperidin-3-yl)-1,3-dioxo-2,3-dihydro-1H-isoindol-4-ylmethyl]-acetamide |
| 136 | | 2-(3-Chloro-phenyl)-N-[2-(2,6-dioxo-piperidin-3-yl)-1,3-dioxo-2,3-dihydro-1H-isoindol-4-ylmethyl]-acetamide |
| 137 | | Benzo[1,3]dioxole-5-carboxylic acid [2-(2,6-dioxo-piperidin-3-yl)-1,3-dioxo-2,3-dihydro-1H-isoindol-4-ylmethyl]-amide |
| 138 | | N-[2-(2,6-Dioxo-piperidin-3-yl)-1,3-dioxo-2,3-dihydro-1H-isoindol-4-ylmethyl]-3,4-dimethoxy-benzamide |

TABLE 6-continued

Compounds of Formula VI

| No. | Structure | Name |
|---|---|---|
| 139 | 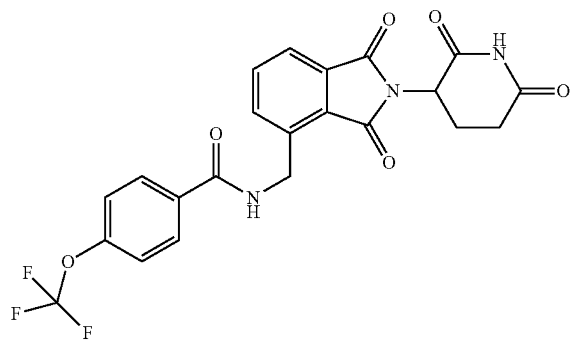 [SMILES: O=C1CCC(N2C(=O)c3cccc(CNC(=O)c4ccc(OC(F)(F)F)cc4)c3C2=O)C(=O)N1] | N-[2-(2,6-Dioxo-piperidin-3-yl)-1,3-dioxo-2,3-dihydro-1H-isoindol-4-ylmethyl]-4-trifluoromethoxy-benzamide |
| 140 | 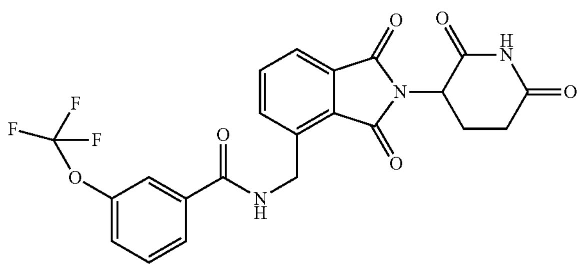 [SMILES: O=C1CCC(N2C(=O)c3cccc(CNC(=O)c4cccc(OC(F)(F)F)c4)c3C2=O)C(=O)N1] | N-[2-(2,6-Dioxo-piperidin-3-yl)-1,3-dioxo-2,3-dihydro-1H-isoindol-4-ylmethyl]-3-trifluoromethoxy-benzamide |
| 141 | 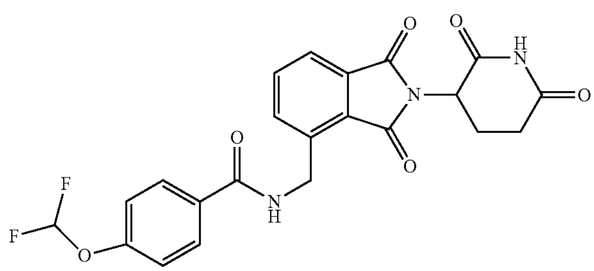 [SMILES: O=C1CCC(N2C(=O)c3cccc(CNC(=O)c4ccc(OC(F)F)cc4)c3C2=O)C(=O)N1] | 4-Difluoromethoxy-N-[2-(2,6-dioxo-piperidin-3-yl)-1,3-dioxo-2,3-dihydro-1H-isoindol-4-ylmethyl]-benzamide |
| 142 | 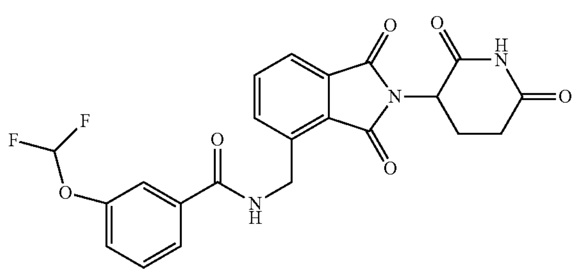 [SMILES: O=C1CCC(N2C(=O)c3cccc(CNC(=O)c4cccc(OC(F)F)c4)c3C2=O)C(=O)N1] | 3-Difluoromethoxy-N-[2-(2,6-dioxo-piperidin-3-yl)-1,3-dioxo-2,3-dihydro-1H-isoindol-4-ylmethyl]-benzamide |
| 143 | 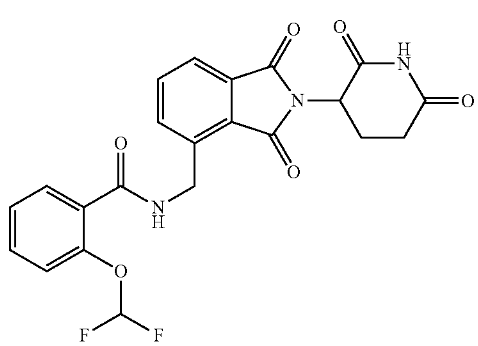 [SMILES: O=C1CCC(N2C(=O)c3cccc(CNC(=O)c4ccccc4OC(F)F)c3C2=O)C(=O)N1] | 2-Difluoromethoxy-N-[2-(2,6-dioxo-piperidin-3-yl)-1,3-dioxo-2,3-dihydro-1H-isoindol-4-ylmethyl]-benzamide |

TABLE 6-continued

Compounds of Formula VI

| No. | Structure | Name |
|---|---|---|
| 144 | 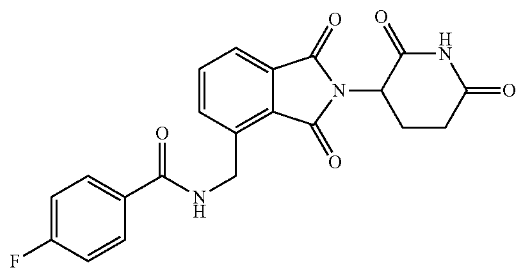 | N-[2-(2,6-Dioxo-piperidin-3-yl)-1,3-dioxo-2,3-dihydro-1H-isoindol-4-ylmethyl]-4-fluoro-benzamide |
| 145 | 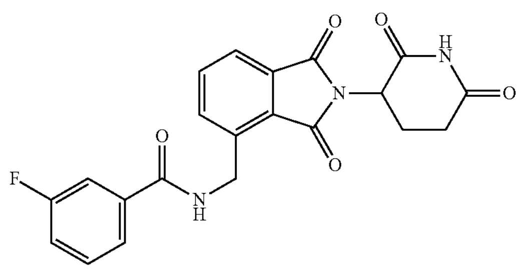 [SMILES: O=C1CCC(N2C(=O)c3cccc(CNC(=O)c4cccc(F)c4)c3C2=O)C(=O)N1] | N-[2-(2,6-Dioxo-piperidin-3-yl)-1,3-dioxo-2,3-dihydro-1H-isoindol-4-ylmethyl]-2-(4-fluoro-phenyl)-acetamide |
| 146 | 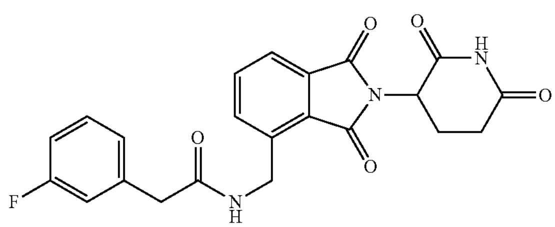 [SMILES: O=C(Cc1cccc(F)c1)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-(3-fluoro-phenyl)-acetamide |
| 147 | 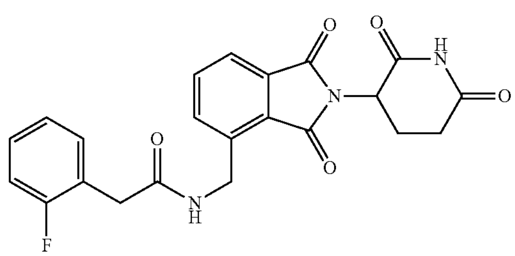 [SMILES: O=C(Cc1ccccc1F)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-(2-fluoro-phenyl)-acetamide |
| 148 | 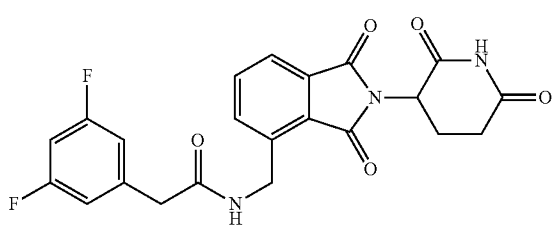 [SMILES: O=C(Cc1cc(F)cc(F)c1)NCc1cccc2c1C(=O)N(C1CCC(=O)NC1=O)C2=O] | 2-(3,5-Difluoro-phenyl)-N-[2-(2,6-dioxo-piperidin-3-yl)-1,3-dioxo-2,3-dihydro-1H-isindol-4-ylmethyl]-acetamide |
| 149 | 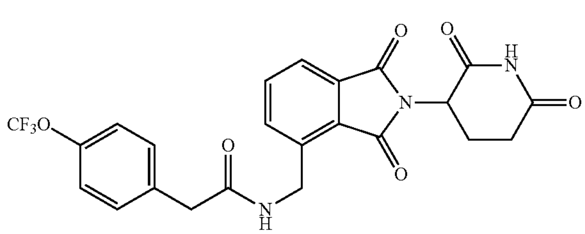 | N-[2-(2,6-Dioxo-piperidin-3-yl)-1,3-dioxo-2,3-dihydro-1H-isoindol-4-ylmethyl]-2-(4-trifluoromethoxy-phenyl)-acetamide |

TABLE 6-continued

Compounds of Formula VI

| No. | Structure | Name |
|---|---|---|
| 150 | 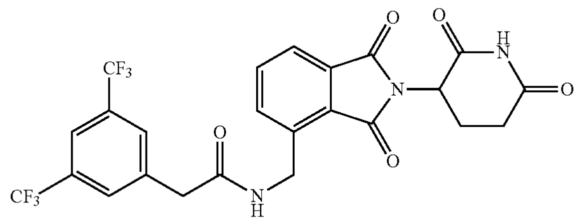 [SMILES: O=C(Cc1cc(C(F)(F)F)cc(C(F)(F)F)c1)NCc1cccc2c1C(=O)N(C1CCC(=O)NC1=O)C2=O] | 2-(3,5-Bis-trifluoromethyl-phenyl)-N-[2-(2,6-dioxo-piperidin-3-yl)-1,3-dioxo-2,3-dihydro-1H-isoindol-4-ylmethyl]-acetamide |
| 151 | 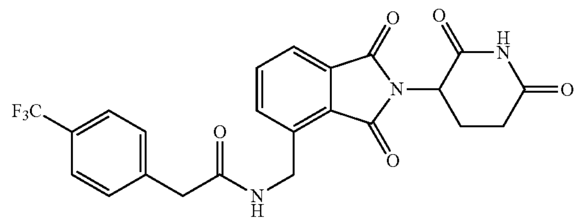 [SMILES: O=C(Cc1ccc(C(F)(F)F)cc1)NCc1cccc2c1C(=O)N(C1CCC(=O)NC1=O)C2=O] | (N-[2-(2,6-Dioxo-piperidin-3-yl)-1,3-dioxo-2,3-dihydro-1H-isoindol-4-ylmethyl]-2-(4-trifluoromethyl-phenyl)-acetamide |
| 152 | 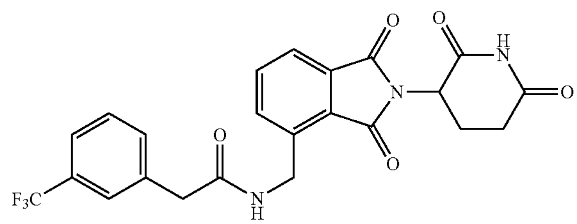 [SMILES: O=C(Cc1cccc(C(F)(F)F)c1)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-(3-trifluoromethyl-phenyl)-acetamide |
| 153 | 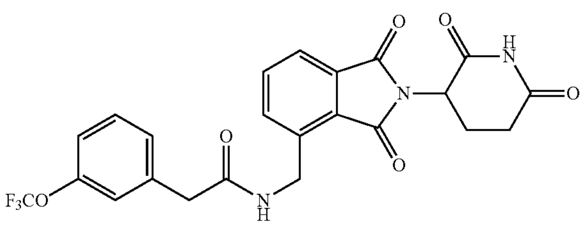 [SMILES: O=C(Cc1cccc(OC(F)(F)F)c1)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-(3-trifluoromethoxy-phenyl)-acetamide |
| 154 | 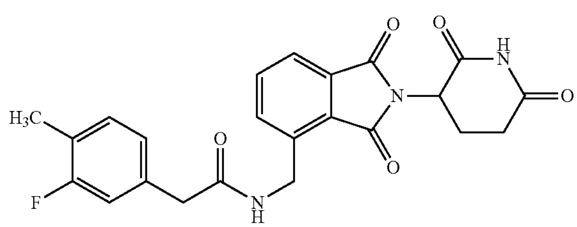 [SMILES: Cc1ccc(CC(=O)NCc2cccc3c2C(=O)N(C2CCC(=O)NC2=O)C3=O)cc1F] | N-[2-(2,6-Dioxo-piperidin-3-yl)-1,3-dioxo-2,3-dihydro-1H-isoindol-4-ylmethyl]-2-(3-fluoro-4-methyl-phenyl)-acetamide |
| 155 | 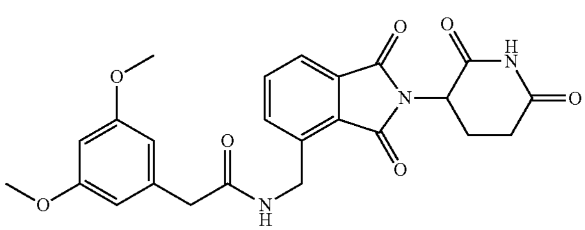 [SMILES: COc1cc(CC(=O)NCc2cccc3c2C(=O)N(C2CCC(=O)NC2=O)C3=O)cc(OC)c1] | 2-(3,5-Dimethoxy-phenyl)-N-[2-(2,6-dioxo-piperidin-3-yl)-1,3-dioxo-2,3-dihydro-1H-isoindol-4-ylmethyl]-acetamide |

TABLE 6-continued

Comounds of Formula VI

| No. | Structure | Name |
|---|---|---|
| 156 | 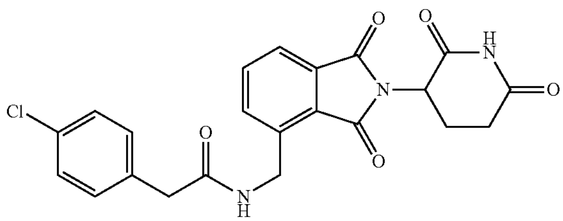 [SMILES: O=C(Cc1ccc(Cl)cc1)NCc1cccc2c1C(=O)N(C1CCC(=O)NC1=O)C2=O] | 2-(4-Chloro-phenyl)-N-[2-(2,6-dioxo-piperidin-3-yl)-1,3-dioxo-2,3-dihydro-1H-isoindol-4-ylmethyl]-acetamide |
| 157 | 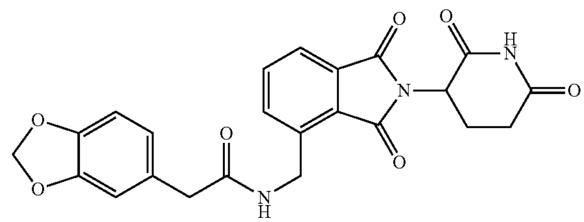 [SMILES: O=C(Cc1ccc2c(c1)OCO2)NCc1cccc2c1C(=O)N(C1CCC(=O)NC1=O)C2=O] | 2-Benzo[1,3]dioxo-5-yl-N-[2-(2,6-dioxo-piperidin-3-yl)-1,3-dioxo-2,3-dihydro-1H-isoindol-4-ylmethyl]-acetamide |
| 158 | 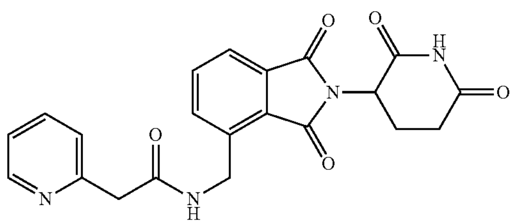 [SMILES: O=C(Cc1ccccn1)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-pyridinyl-2-yl-acetamide |
| 159 | 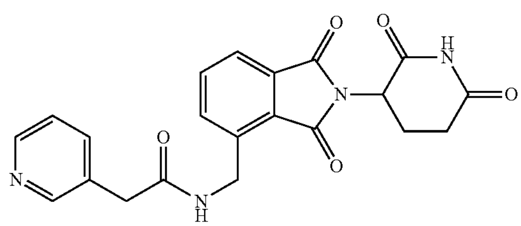 [SMILES: O=C(Cc1cccnc1)NCc1cccc2c1C(=O)N(C1CCC(=O)NC1=O)C2=O] | N-[2-(2,6-dioxo-piperidin-3-yl)-1,3-dioxo-2,3-dihydro-1H-isoindol-4-ylmethyl]-2-pyridinyl-3-yl-acetamide |
| 160 | 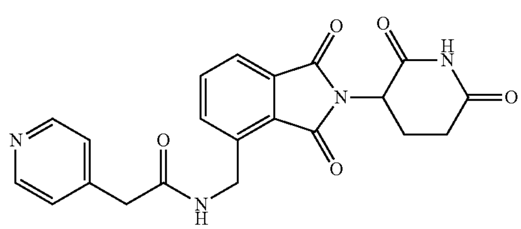 [SMILES: O=C(Cc1ccncc1)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-pyridin-4-yl-acetamide |
| 161 | 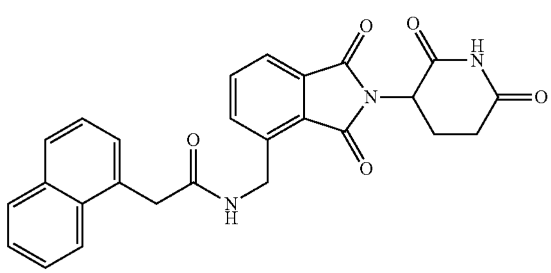 [SMILES: O=C(Cc1cccc2ccccc12)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-naphthalen-1-yl-acetamide |

TABLE 6-continued

Compounds of Formula VI

| No. | Structure | Name |
| --- | --- | --- |
| 162 | 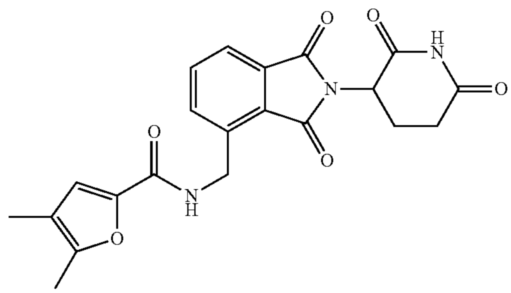 [SMILES: Cc1cc(C(=O)NCc2cccc3c2C(=O)N(C2CCC(=O)NC2=O)C3=O)oc1C] | 2-(4,5-Dimethyl-furan-2-yl)-N-[2-(2,6-dioxo-piperidin-3-yl)-1,3-dioxo-2,3-dihydro-1H-isoindol-4-ylmethyl]-acetamide |
| 163 | 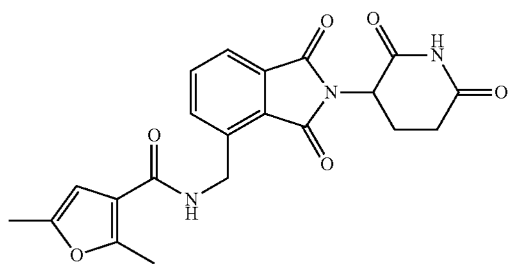 [SMILES: Cc1cc(C(=O)NCc2cccc3c2C(=O)N(C2CCC(=O)NC2=O)C3=O)c(C)o1] | 2-(2,5-Dimethyl-furan-3-yl)-N-[2-(2,6-dioxo-piperidin-3-yl)-1,3-dioxo-2,3-dihydro-1H-isoindol-4-ylmethyl]-acetamide |
| 164 | 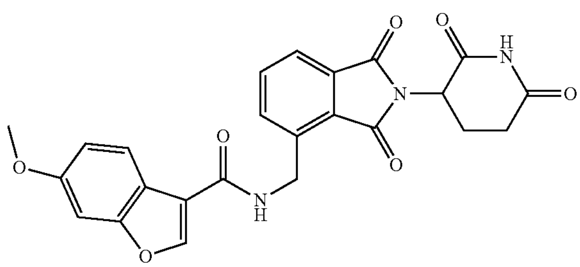 [SMILES: COc1ccc2c(C(=O)NCc3cccc4c3C(=O)N(C3CCC(=O)NC3=O)C4=O)coc2c1] | N-[2-(2,6-Dioxo-piperidin-3-yl)-1,3-dioxo-2,3-dihydro-1H-isoindol-4-ylmethyl]2-(6-methoxy-benzofuran-3-yl)-acetamide |
| 165 | 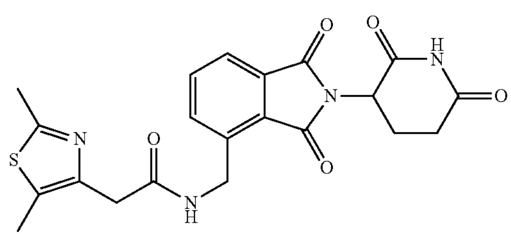 [SMILES: Cc1nc(CC(=O)NCc2cccc3c2C(=O)N(C2CCC(=O)NC2=O)C3=O)c(C)s1] | 2-{2,5-Dimethyl-1,3-thiazol-4-yl)-N-[2-(2,6-dioxo-piperidin-3-yl)-1,3-dioxo-2,3-dihydro-1H-isoindol-4-ylmethyl]-acetamide |
| 166 | 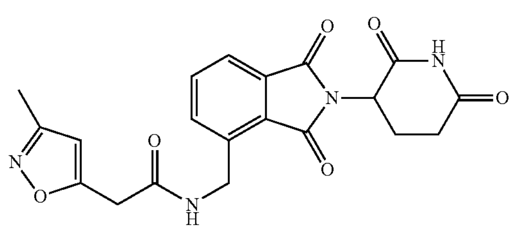 [SMILES: Cc1cc(CC(=O)NCc2cccc3c2C(=O)N(C2CCC(=O)NC2=O)C3=O)on1] | N-[2-(2,6-Dioxo-piperidin-3-yl)-1,3-dioxo-2,3-dihydro-1H-isoindol-4-ylmethyl]-2-(3-methyl-isoxazol-5-yl)-acetamide |
| 167 | 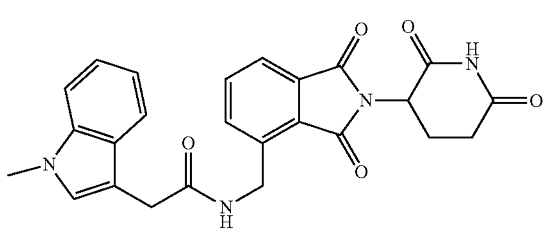 [SMILES: Cn1cc(CC(=O)NCc2cccc3c2C(=O)N(C2CCC(=O)NC2=O)C3=O)c2ccccc21] | N-[2-(2,6-Dioxo-piperidin-3-yl)-1,3-dioxo-2,3-dihydro-1H-isoindol-4-ylmethyl]-2-(1-methyl-1H-indol-3-yl)-acetamide |

TABLE 6-continued

Compounds of Formula VI

| No. | Structure | Name |
|-----|-----------|------|
| 168 | 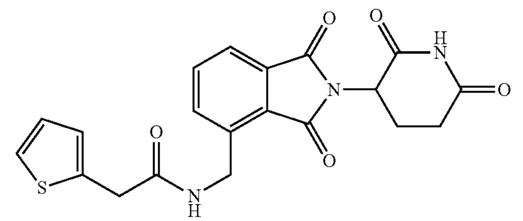 [SMILES: O=C(Cc1cccs1)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-thiophen-2-yl-acetamide |
| 169 | 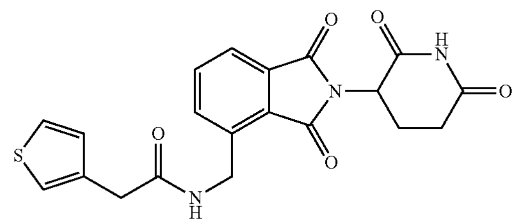 [SMILES: O=C(Cc1ccsc1)NCc1cccc2c1C(=O)N(C1CCC(=O)NC1=O)C2=O] | N-[2-(2,6-Dioxo-piperidin-3-yl)-1,3-dioxo-2,3-dihydro-1H-isoindol-4-ylmethyl]-2-thiophen-2-yl-acetamide |
| 170 | 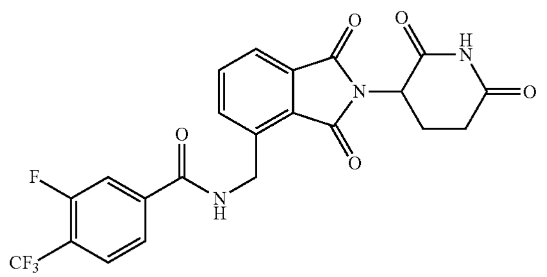 | N-[2-(2,6-Dioxo-piperidin-3-yl)-1,3-dioxo-2,3-dihydro-1H-isoindol-4-ylmethyl]-3-fluoro-4-trifluoromethyl-benzamide |
| 171 | 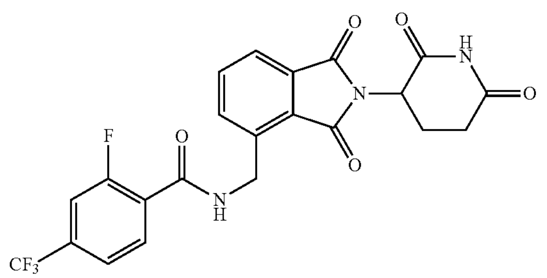 | N-[2-(2,6-Dioxo-piperidin-3-yl)-1,3-dioxo-2,3-dihydro-1H-isoindol-4-ylmethyl]-2-fluoro-4-trifluoromethyl-benzamide |
| 172 | 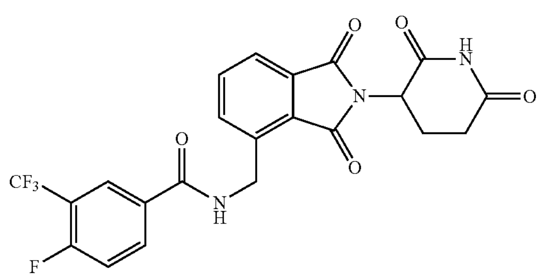 [SMILES: O=C1CCC(N2C(=O)c3cccc(CNC(=O)c4ccc(F)c(C(F)(F)F)c4)c3C2=O)C(=O)N1] | N-[2-(2,6-Dioxo-piperidin-3-yl)-1,3-dioxo-2,3-dihydro-1H-isoindol-4-ylmethyl]-4-fluoro-3-trifluoromethyl-benzamide |
| 173 | 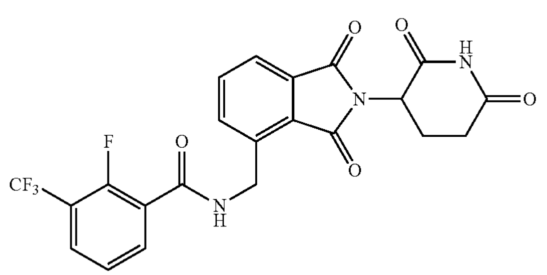 [SMILES: O=C1CCC(N2C(=O)c3cccc(CNC(=O)c4cccc(C(F)(F)F)c4F)c3C2=O)C(=O)N1] | N-[2-(2,6-Dioxo-piperidin-3-yl)-1,3-dioxo-2,3-dihydro-1H-isoindol-4-ylmethyl]-2-fluoro-3-trifluoromethyl-benzamide |

TABLE 6-continued

Compounds of Formula VI

| No. | Structure | Name |
|---|---|---|
| 174 | 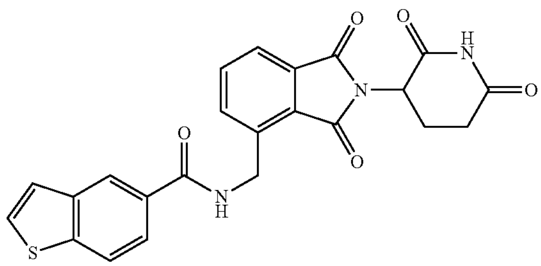 [SMILES: O=C1CCC(N2C(=O)c3cccc(CNC(=O)c4ccc5sccc5c4)c3C2=O)C(=O)N1] | Benzo[b]thiophene-5-carboxylic acid [2-(2,6-dioxo-piperidin-3-yl)-1,3-dioxo-2,3-dihydro-1H-isoindol-4-ylmethyl]-amide |
| 175 | 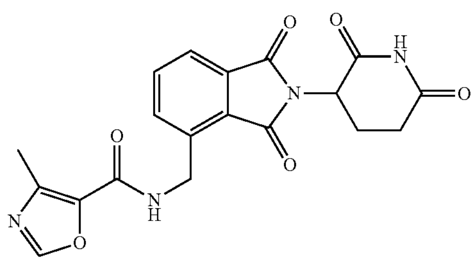 [SMILES: Cc1ncoc1C(=O)NCc1cccc2c1C(=O)N(C1CCC(=O)NC1=O)C2=O] | 4-Methyl-oxazole-5-carboxylic acid [2-(2,6-dioxo-piperidin-3-yl)-1,3-dioxo-2,3-dihydro-1H-isoindol-4-ylmethyl]-amide |
| 176 | 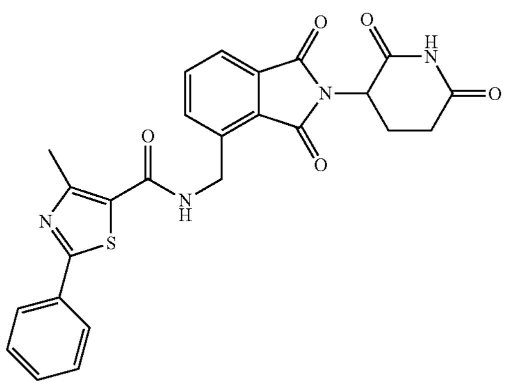 [SMILES: Cc1nc(-c2ccccc2)sc1C(=O)NCc1cccc2c1C(=O)N(C1CCC(=O)NC1=O)C2=O] | 4-Methyl-2-phenyl-thiazole-5-carboxylic acid [2-(2,6-dioxo-piperidin-3-yl)-1,3-dioxo-2,3-dihydro-1H-isoindol-4-ylmethylamide |
| 177 | 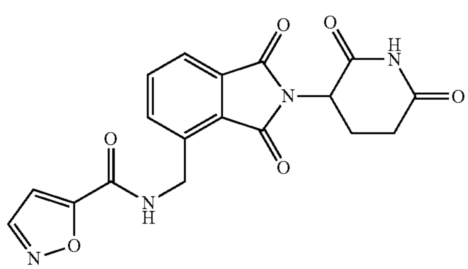 [SMILES: O=C1CCC(N2C(=O)c3cccc(CNC(=O)c4ccno4)c3C2=O)C(=O)N1] | Isoxazole-5-carboxylic acid [2-(2,6-dioxo-piperidin-3-yl)-1,3-dioxo-2,3-dihydro-1H-isoindol-4-ylmethyl]-amide |
| 178 | 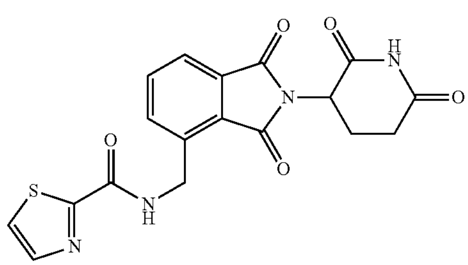 [SMILES: O=C1CCC(N2C(=O)c3cccc(CNC(=O)c4nccs4)c3C2=O)C(=O)N1] | Thiazole-2-carboxylic acid [2-(2,6-dioxo-piperidin-3-yl)-1,3-dioxo-2,3-dihydro-1H-isoindol-4-ylmethyl]-amide |

TABLE 6-continued

Compounds of Formula VI

| No. | Structure | Name |
|---|---|---|
| 179 | 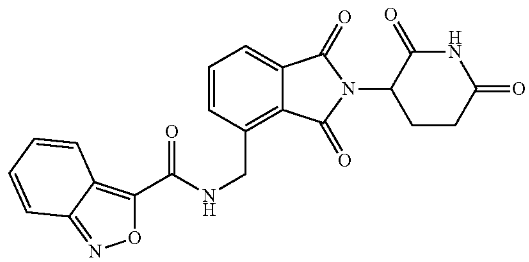 [SMILES: O=C1CCC(N2C(=O)c3cccc(CNC(=O)c4onc5ccccc45)c3C2=O)C(=O)N1] | Benzo[c]isoxazole-3-carboxylic acid [2-(2,6-dioxo-piperidin-3-yl)-1,3-dioxo-2,3-dihydro-1H-isoindol-4-ylmethyl]-amide |

This invention also encompasses the compounds of the following formula, and pharmaceutically acceptable salts, solvates, stereoisomers, and prodrugs thereof.

TABLE 7

| No. | Structure | Name |
|---|---|---|
| 180 | 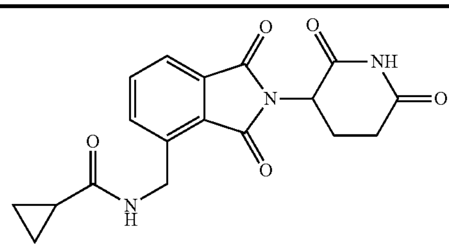 | cyclopropanecarboxylic acid [2-(2,6-dioxo-piperidin-3-yl)-1,3-dioxo-2,3-dihydro-1H-isoindol-4-ylmethyl]-amide |
| 181 | 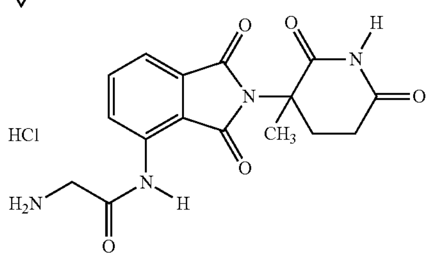 | 2-amino-N-[2-(3-methyl-2,6-dioxo-piperidin-3-yl)-1,3-dioxo-2,3-dihydro-1H-isoindol-4-yl]-acetamide |
| 182 | 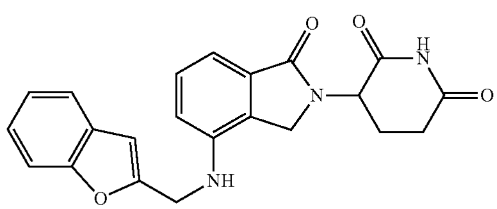 [SMILES: O=C1CCC(N2Cc3c(NCc4cc5ccccc5o4)cccc3C2=O)C(=O)N1] | 3-{4-[(Benzofuran-2-ylmethyl)-amino]-1-oxo-1,3-dihydro-isoindol-2-yl}-piperidine-2,6-dione |
| 183 | 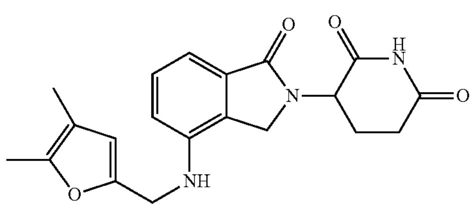 [SMILES: Cc1cc(CNc2cccc3c2CN(C2CCC(=O)NC2=O)C3=O)oc1C] | 3-{4-[(4,5-Dimethyl-furan-2-ylmethyl)-amino]-1-oxo-1,3-dihydro-isoindol-2-yl}-piperidine-2,6-dione |
| 184 | 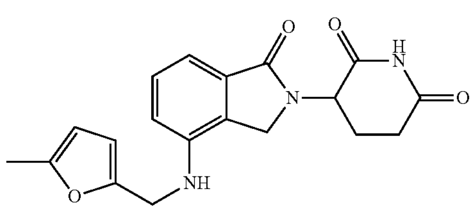 [SMILES: Cc1ccc(CNc2cccc3c2CN(C2CCC(=O)NC2=O)C3=O)o1] | 3-{4-[(5-Methyl-furan-2-ylmethyl)-amino]-1-oxo-1,3-dihydro-isoindol-2-yl}-piperidine-2,6-dione |

In specific embodiments, this invention encompasses a stereomerically pure (R) isomer and a stereomerically pure (S) isomer of the compounds listed above.

This invention also encompasses, which has the following structure:
and pharmaceutically acceptable salts, solvates, stereoisomers, and prodrugs thereof.

In specific embodiments, this invention encompasses a stereomerically pure (R) isomer and a stereomerically pure (S) isomer of 2-amino-N-[2-(3-methyl-2,6-dioxo-piperidin-3-yl)-1,3-dioxo-2,3-dihydro-1H-isoindol-4-yl]-acetamide, and a racemic mixture thereof.

As used herein, and unless otherwise specified, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. Suitable are hydrochloric, hydrobromic, phosphoric, and sulfuric acids.

As used herein, and unless otherwise specified, the term "solvate" means a compound of the present invention or a salt thereof, that further includes a stoichiometric or non-stoichiometric amount of solvent bound by non-covalent intermolecular forces. Where the solvent is water, the solvate is a hydrate.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein, and unless otherwise specified, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise specified, the term "stereoisomer" encompasses all enantiomerically/stereomerically pure and enantiomerically/stereomerically enriched compounds of this invention.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, preferably greater than about 70% by weight, more preferably greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

As used herein, and unless otherwise indicated, the term "alkyl" refers to a saturated straight chain or branched hydrocarbon having number of carbon atoms as specified herein. Representative saturated straight chain alkyls include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like.

As used herein, and unless otherwise specified, the term "alkoxy" refers to —O-(alkyl), wherein alkyl is defined herein. Examples of alkoxy include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O—(CH$_2$)$_5$CH$_3$.

As used herein, the term "aryl" means a carbocyclic aromatic ring containing from 6 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Specifically, the aryl group is a monocyclic ring or bicyclic ring. Representative aryl groups include phenyl, anthracenyl, fluorenyl, indenyl, azulenyl, phenanthrenyl and naphthyl.

As used herein, and unless otherwise specified, the term "heteroaryl" means an aromatic ring containing from 5 to 14 ring atoms, of which at least one (e.g., one, two, or three) is a heteroatom (e.g., nitrogen, oxygen, or sulfur). Heteroaryl ring structures include compounds having one or more ring structures such as mono-, bi-, or tricyclic compounds, as well as fused heterocyclic moieties. Examples of heteroaryls include, but are not limited to, triazolyl, tetrazolyl, oxadiazolyl, pyridyl, furyl, benzofuranyl, thiophenyl, thiazolyl, benzothiophenyl, benzoisoxazolyl, benzoisothiazolyl, quinolinyl, isoquinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, quinoxalinyl, acridinyl, pyrimidyl, oxazolyl, benzo[1,3]dioxole and 2,3-dihydro-benzo[1,4]dioxine.

The term "heterocycle" means a monocyclic or polycyclic ring comprising carbon and hydrogen atoms, optionally having 1 or 2 multiple bonds, and the ring atoms contain at least one heteroatom, specifically 1 to 3 heteroatoms, independently selected from nitrogen, oxygen, and sulfur. Heterocycle ring structures include, but are not limited to compounds having one or more ring structures such as mono-, bi-, or tri-cyclic compounds. Specific heterocycles are monocyclic or bicyclic. Representative heterocycles include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl and tetrahydrothiopyranyl. A heterocyclic ring can be unsubstituted or substituted.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Methods of Treatment, Prevention and Management

This invention encompasses methods of treating, preventing, and/or managing various diseases or disorders using a compound of this invention, or a pharmaceutically acceptable salt, solvate, stereoisomer or prodrug thereof.

Examples of diseases or disorders include, but are not limited to, cancer, disorders associated with angiogenesis, pain including Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNFα related disorders, and other various diseases and disorders.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder.

As used herein, and unless otherwise specified, the terms "prevent," "preventing" and "prevention" refer to the prevention of the onset, recurrence or spread of a disease or disorder, or of one or more symptoms thereof.

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic or therapeutic agent do not result in a cure of the disease or disorder.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Examples of cancer and precancerous conditions include, but are not limited to, those described in U.S. Pat. Nos. 6,281,230 and 5,635,517 to Muller et al., in various U.S. patent applications to Zeldis, including application Ser. Nos. 10/411,649, filed Apr. 11, 2003 (Treatment of Myelodysplastic Syndrome); 10/438,213 filed May 15, 2003 (Treatment of Various Types of Cancer); and 10/411,656, filed Apr. 11, 2003 (Treatment of Myeloproliferative Diseases). Examples also include those described in PCT/US04/14004, filed May 5, 2004. All of these references are incorporated herein in their entireties by reference.

Specific examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are particularly useful for treating cancers of the blood and bone marrow, such as multiple myeloma and acute and chronic leukemias, for example, lymphoblastic, myelogenous, lymphocytic, and myelocytic leukemias. The compounds of the invention can be used for treating, preventing or managing either primary or metastatic tumors.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In one specific embodiment, this invention encompasses methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another specific embodiment, this invention encompasses methods of treating, preventing or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma, MCL, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, and any type of the mantle cell lymphomas that can be seen under the microscope (nodular, diffuse, blastic and mentle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent application Ser. No. 10/693,794, filed Oct. 23, 2003, which is incorporated herein by reference. Specific types of pain include, but are not limited to, nociceptive pain, neuropathic pain, mixed pain of nociceptive and neuropathic pain, visceral pain, migraine, headache and postoperative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. application Ser. No. 11/085,905, filed Mar. 22, 2005, which is incorporated herein by reference. Specific examples include, but are not limited to, keratoses and related symptoms, skin diseases or disorders characterized with overgrowths of the epidermis, acne, and wrinkles.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trélat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. provisional application No. 60/565,172, filed Apr. 23, 2004, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vasular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. provisional application No. 60/626,975, filed Nov. 12, 2004, which is incorporated herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, C. panvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovis, Babesia canis, Banesia Gibsoni, Besnoitia darlingi, Cytauxzoon felis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. provisional application No. 60/631,870, filed Dec. 1, 2004. Specific examples include, but are not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. provisional application No. 60/533,862, filed Dec. 30, 2003, and the co-pending U.S. application Ser. No. 11/022,075, filed Dec. 23, 2004, both of which are incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. provisional application No. 60/630,599, filed Nov. 23, 2004, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but not limited to, viral, genetic, allergic, and autoimmune diseases. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury.

Examples of atherosclerosis and related conditions include, but are not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated by the invention including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated by the invention:

| Artery | Body Area |
| --- | --- |
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |
| Splenic | Stomach, pancreas, and spleen |
| Subclavian | Shoulder |
| Superior mesenteric | Pancreas, small intestine, ascending and transverse colon |
| Testicular | Testes |
| Ulnar | Forearm |

Examples of dysfunctional sleep and related syndromes include, but are not limited to, those disclosed in U.S. provisional application No. 60/559,261, filed Apr. 1, 2004, and U.S. application Ser. No. 11/093,848, filed Mar. 30, 2005, both of which are incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. application Ser. No. 11/004,736, filed Dec. 2, 2004, which is incorporated herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; NFκB related disorders such as rheumatoid arthritis, rheumatoid spondylitis, osteoarthritis and other arthritic conditions, septic shock, septis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; cAMP related disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In other embodiments, the use of compounds of this invention in various immunological applications, in particular, as vaccine adjuvants, particularly anticancer vaccine adjuvants, as disclosed in U.S. Provisional Application No. 60/712,823, filed Sep. 1, 2005, which is incorporated herein in its entirety by reference, is also encompassed. This aspect of the invention also relates to the uses of compounds of this invention in combination with vaccines to treat or prevent cancer or infectious diseases, and other various uses of immunomodulatory compounds such as reduction or desensitization of allergic reactions.

Doses of a compound of this invention, or a pharmaceutically acceptable salt, solvate, stereoisomer or prodrug thereof, vary depending on factors such as: specific indication to be treated, prevented, or managed; age and condition of a patient; and amount of second active agent used, if any. Generally, a compound of this invention, or a pharmaceutically acceptable salt, solvate, stereoisomer or prodrug thereof, may be used in an amount of from about 0.1 mg to about 500 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management.

In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

4.3 Second Active Agents

A compound of this invention, or a pharmaceutically acceptable salt, solvate, stereoisomer or prodrug thereof, can be combined with other pharmacologically active compounds ("second active agents") in methods and compositions of the invention. It is believed that certain combinations may work synergistically in the treatment of particular types diseases or disorders, and conditions and symptoms associated with such diseases or disorders. A compound of this invention, or a pharmaceutically acceptable salt, solvate, stereoisomer or prodrug thereof, can also work to alleviate adverse effects associated with certain second active agents, and vice versa.

One or more second active ingredients or agents can be used in the methods and compositions of the invention. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, small molecule anti-cancer agents and antibiotics (e.g., clarithromycin).

Specific second active compounds that can be combined with compounds of this invention vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; metureedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine;

cecropin B; cetrorelix; chlorins; chloroquinoxaline sulfonamide; cicaprost; cis-porphyrin; cladribine; clathromycin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), bortezomib, statins, semaxanib, cyclosporin, etanercept, doxycycline, bortezomib, oblimersen)(Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate) (Emcyt®), sulindac, and etoposide.

Similarly, examples of specific second agents according to the indications to be treated, prevented, or managed can be found in the following references, all of which are incorporated herein in their entireties: U.S. Pat. Nos. 6,281,230 and 5,635,517; U.S. application Ser. Nos. 10/411,649, 10/483,213, 10/411,656, 10/693,794, 10/699,154, and 10/981,189; and U.S. provisional application Nos. 60/554,923, 60/565,172, 60/626,975, 60/630,599, 60/631,870, and 60/533,862.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenyloin (Dilantin®), carbamazepine)(Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

Examples of second active agents that may be used for the treatment, prevention and/or management of MD and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin lutetium, 9-fluoro-11,21-dihydroxy-16,17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited above are incorporated herein in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hepertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin 12 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stibogluconate), interfereon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises l-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a compound of this invention, or a pharmaceutically acceptable salt, solvate, stereoisomer or prodrug thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for compounds of this invention is oral. Preferred routes of administration for the second active agents or ingredients of the invention are known to those of ordinary skill in the art. See, e.g., *Physicians' Desk Reference,* 1755-1760 (56th ed., 2002).

In one embodiment of the invention, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds of the invention and any optional additional active agents concurrently administered to the patient.

As discussed elsewhere herein, the invention encompasses a method of reducing, treating and/or preventing adverse or undesired effects associated with conventional therapy including, but not limited to, surgery, chemotherapy, radiation therapy, hormonal therapy, biological therapy and immunotherapy. Compounds of the invention and other active ingredients can be administered to a patient prior to, during, or after the occurrence of the adverse effect associated with conventional therapy.

4.4 Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, a compound of the invention is administered daily in a single or divided doses in a four to six week cycle with a rest period of about a week or two weeks. The invention further allows the frequency, number, and length of dosing cycles to be increased. Thus, another specific embodiment of the invention encompasses the administration of a compound of the invention for more cycles than are typical when it is administered alone. In yet another specific embodiment of the invention, a compound of the invention is administered for a greater number of cycles that would typically cause dose-limiting toxicity in a patient to whom a second active ingredient is not also being administered.

In one embodiment, a compound of the invention is administered daily and continuously for three or four weeks at a dose of from about 0.1 mg to about 500 mg per day, followed by a break of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a break.

In one embodiment of the invention, a compound of the invention and a second active ingredient are administered orally, with administration of the compound of the invention occurring 30 to 60 minutes prior to the second active ingredient, during a cycle of four to six weeks. In another embodiment of the invention, the combination of a compound of the invention and a second active ingredient is administered by intravenous infusion over about 90 minutes every cycle.

Typically, the number of cycles during which the combinatorial treatment is administered to a patient will be from about one to about 24 cycles, more typically from about two to about 16 cycles, and even more typically from about four to about three cycles.

4.5 Pharmaceutical Compositions and Dosage Forms

Pharmaceutical compositions can be used in the preparation of individual, single unit dosage forms. Pharmaceutical compositions and dosage forms of the invention comprise a compound of the invention, or a pharmaceutically acceptable salt, solvate, stereoisomer, or prodrug thereof. Pharmaceutical compositions and dosage forms of the invention can further comprise one or more excipients.

Pharmaceutical compositions and dosage forms of the invention can also comprise one or more additional active ingredients. Examples of optional second, or additional, active ingredients are disclosed in Section 4.3, above.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers. Like the amounts and types of excipients, the amounts and specific types of active ingredients in a dosage form may differ depending on factors such as, but not limited to, the route by which it is to be administered to patients. However, typical dosage forms of the invention comprise a compound of the invention in an amount of from about 0.10 to about 500 mg. Typical dosage forms comprise a compound of the invention in an amount of about 0.1, 1, 2, 5, 7.5, 10, 12.5, 15, 17.5, 20, 25, 50, 100, 150, 200, 250, 300, 350, 400, 450, or 500 mg.

Typical dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the type of cancer being treated or managed, and the amount(s) of a compound of the invention and any optional additional active agents concurrently administered to the patient.

4.5.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents. Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581.

Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form. Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof. Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises a compound of the invention, anhydrous lactose, microcrystalline cellulose, polyvinylpyrrolidone, stearic acid, colloidal anhydrous silica, and gelatin.

4.5.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.5.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention and its derivatives. See, e.g., U.S. Pat. No. 5,134,127, which is incorporated herein by reference.

4.5.4 Topical and Mucosal Dosage Forms

Topical and mucosal dosage forms of the invention include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.6 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of a compound of the invention. Kits encompassed by this invention can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 4.3).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples.

5.1 N-[2-(2,6-DIOXO-PIPERIDIN-3-YL)-1-OXO-2,3-DIHYDRO-1H-ISOINDOL-4-YLMETHYL]-2-PHENYL-ACETAMIDE

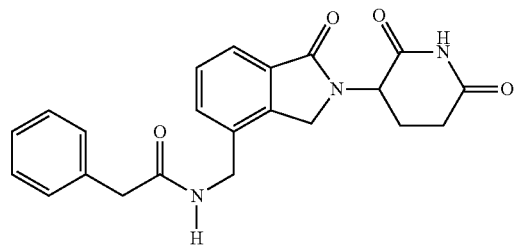 [SMILES: O=C(Cc1ccccc1)NCc1cccc2c1CN(C1CCC(=O)NC1=O)C2=O]

1,8-Diazabicyclo[5,4,0]undec-7-ene (0.7 g, 4.3 mmol) was added to a stirred suspension of 3-[4-(aminomethyl)-1-oxo-1,3-dihydro-isoindol-2-yl]piperidine-2,6-dione hydrochloride (0.6 g, 1.9 mmol) in acetonitrile (50 mL). After stirring for 30 minutes, phenylacetyl chloride (0.4 g, 2.3 mmol) was added. The mixture was stirred at room temperature for 17 hours. Solvent was removed and the residue was stirred with water (40 mL) to give N-[2-(2,6-dioxo-piperidin-3-yl)-1-oxo-2,3-dihydro-1H-isoindol-4-ylmethyl]-2-phenyl-acetamide (0.41 g, 54%) as a white solid: mp 236-238° C.; $^1$H NMR (DMSO-$d_6$) δ 1.94-1.98 (m, 1H, CH$_2$), 2.15-2.19 (m, 1H, CH$_2$), 2.49-2.63 (m, 1H, CH$_2$), 2.85-2.99 (m, 1H, CH$_2$), 3.47 (s, 2H, CH$_2$), 4.23-4.43 (m, 4H, 2CH$_2$), 5.07-5.14 (dd, J=5.1 and 13.2 Hz, 1H, CH), 7.18-7.33 (m, 5H, Ar), 7.46-7.64 (m, 3H, Ar), 8.61 (t, J=5.6 Hz, 1H, NH), 11.03 (s, 1H, NH); $^{13}$C NMR (DMSO-$d_6$) δ 22.51, 31.14, 42.23, 46.08, 51.47, 121.70, 126.34, 128.22, 128.95, 130.73, 131.69, 134.49, 136.16, 140.09, 167.99, 170.18, 170.87, 172.81; Anal. calcd. for $C_{22}H_{21}N_3O_4$+0.07H$_2$O: C, 67.29; H, 5.43; N, 10.70. Found: C, 66.94; H, 5.22; N, 10.63.

5.2 1-CYCLOHEXYL-3-[2-(2,6-DIOXO-PIPERIDIN-3-YL)-1-OXO-2,3-DIHYDRO-1H-ISOINDOL-4-YLMETHYL]-UREA

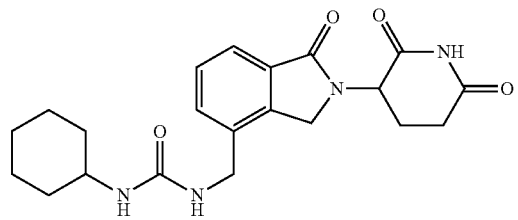 [SMILES: O=C1CCC(N2Cc3c(CNC(=O)NC4CCCCC4)cccc3C2=O)C(=O)N1]

1,8-Diazabicyclo[5,4,0]undec-7-ene (0.4 g, 2.9 mmol) was added to a stirred suspension of 3-(4-aminomethyl-1-oxo-1,3-dihydro-isoindol-2-yl)-piperidine-2,6-dione hydrochloride (0.6 g, 1.9 mmol) in acetonitrile (100 mL). The mixture was heated for 30 minutes, then cooled to room temperature. Cyclohexyl isocyanate (0.4 g, 2.9 mmol) was added and the mixture was stirred at room temperature overnight. The mixture was filtered and the solid was stirred with water (25 mL) to give 0.9 g of crude product. The crude product was recrystallized from methanol to give 1-cyclohexyl-3-[2-(2,6-dioxo-piperidin-3-yl)-1-oxo-2,3-dihydro-1H-isoindol-4-ylmethyl]-urea (0.12 g, 16%) as a white solid: mp 309-311° C.; $^1$H NMR (DMSO-d$_6$) δ 0.97-1.75 (m, 10H), 1.99-2.04 (m, 1H), 2.32-2.64 (m, 3H), 2.86-2.98 (m, 1H), 4.27-4.51 (m, 4H), 5.11-5.18 (dd, J=4.9 and 13.1 Hz, 1H, CH), 5.86 (d, J=7.9 Hz, 1H), 6.26 (t, J=5.5 Hz, 1H, NH), 7.47-7.62 (m, 3H, Ar), 11.01 (s, 1H, NH); $^{13}$C NMR (DMSO-d$_6$) δ 22.64, 24.44, 25.29, 31.16, 33.32, 46.09, 47.50, 47.85, 51.47, 121.36, 128.18, 130.26, 131.61, 136.28, 139.77, 157.20, 168.09, 170.97, 172.82; Anal. calcd. for C$_{21}$H$_{26}$N$_4$O$_4$: C, 63.30; H, 6.58; N, 14.06. Found: C, 63.18; N, 6.58; N, 13.99.

5.3 N-[2-(2,6-DIOXO-PIPERIDIN-3-YL)-1-OXO-2,3-DIHYDRO-1H-ISOINDOL-4-YLMETHYL]-BENZAMIDE

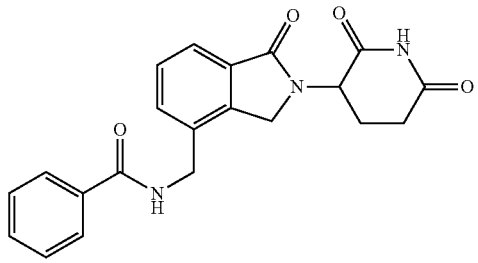 [SMILES: O=C1CCC(N2Cc3c(CNC(=O)c4ccccc4)cccc3C2=O)C(=O)N1]

1,8-Diazabicyclo[5,4,0]-undec-7-ene (0.8 g, 5.3 mmol) was added to a stirred suspension of 3-(4-aminomethyl-1-oxo-1,3-dihydro-isoindol-2-yl)-piperidine-2,6-dione hydrochloride (0.7 g, 2.1 mmol) in acetonitrile (100 mL). The mixture was stirred for 30 minutes, and benzoyl chloride (0.4 g, 3.2 mmol) was added. The mixture was stirred at room temperature overnight. The mixture was concentrated and the residue was stirred with 2N HCl (30 mL) and CH$_2$Cl$_2$ (80 mL). The solid was collected to give N-[2-(2,6-dioxo-piperidin-3-yl)-1-oxo-2,3-dihydro-1H-isoindol-4-ylmethyl]-benzamide (0.5 g, 68%) as a white solid: mp 228-230° C.; $^1$H NMR (DMSO-d$_6$) δ 2.01-2.05 (m, 1H), 2.33-2.65 (m, 2H), 2.86-3.00 (m, 1H), 4.48 (d, J=17.3 Hz, 1H), 4.53 (d, J=22.1 Hz, 1H), 4.55 (s, 2H), 5.12-5.19 (dd, J=5.0 and 13.2 Hz, 1H, CH), 7.44-7.65 (m, 6H, Ar), 7.87 (d, J=7.1 Hz, 2H, Ar), 9.11 (t, J=5.7 Hz, 1H, NH), 11.03 (s, 1H, NH); $^{13}$C NMR (DMSO-d$_6$) δ 22.61, 31.20, 46.30, 51.60, 121.67, 127.25, 128.35, 130.67, 131.36, 131.63, 134.07, 134.74, 140.16, 166.37, 168.10, 171.04, 172.88; Anal. calcd. for C$_{21}$H$_{19}$N$_3$O$_4$: C, 66.83; H, 5.07; N, 11.13. Found: C, 66.58; H, 5.08; N, 11.12.

5.4 FURAN-2-CARBOXYLIC ACID [2-(2,6-DIOXO-PIPERIDIN-3-YL)-1-OXO-2,3-DIHYDRO-1H-ISOINDOL-4-YLMETHYL]-AMIDE

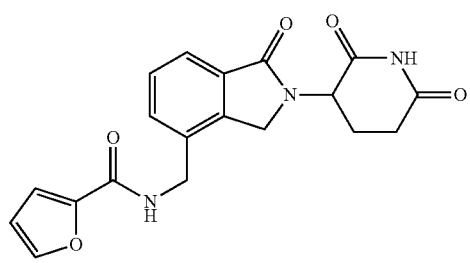 [SMILES: O=C1CCC(N2Cc3c(CNC(=O)c4ccco4)cccc3C2=O)C(=O)N1]

1,8-Diazabicyclo[5,4,0]-undec-7-ene (0.8 g, 5.3 mmol) was added to a stirred suspension of 3-(4-aminomethyl-1-oxo-1,3-dihydro-isoindol-2-yl)-piperidine-2,6-dione hydrochloride (0.7 g, 2.1 mmol) in acetonitrile (100 mL). The mixture was stirred for 30 minutes. 2-Furoyl chloride (0.4 g, 3.2 mmol) was added and the mixture was stirred at room temperature overnight. The mixture was concentrated, and the residue was stirred with CH$_2$Cl$_2$ (60 mL) and 2N HCl (30 mL). The mixture was filtered, and the solid was slurried with ethanol (20 mL) to give furan-2-carboxylic acid [2-(2,6-dioxo-piperidin-3-yl)-1-oxo-2,3-dihydro-1H-isoindol-4-ylmethyl]-amide (0.5 g, 58%) as a white solid: mp 219-221° C.; $^1$H NMR (DMSO-d$_6$) δ 2.00-2.05 (m, 1H), 2.30-2.65 (m, 2H), 2.86-3.00 (m, 1H), 4.39-4.49 (m, 3H), 4.53 (d, J=17.3 Hz, 1H), 5.11-5.18 (dd, J=5.0 and 13.1 Hz, 1H, CH), 6.62-6.63 9m, 1H), 7.14 (d, J=3.4 Hz, 1H), 7.47-7.65 (m, 3H, Ar), 7.84 (s, 1H), 8.00 (t, J=5.8 Hz, 1H, NH), 11.01 (s, 1H, NH); $^{13}$C NMR (DMSO-d$_6$) δ 22.59, 31.18, 38.72, 46.24, 51.58, 111.87, 113.69, 121.70, 128.32, 130.74, 131.61, 134.55, 140.11, 145.15, 147.61, 157.84, 168.05, 171.01, 172.85; Anal. calcd. for C$_{19}$H$_{17}$N$_3$O$_5$: C, 62.12; H, 4.66; N, 11.44. Found: C, 61.91; H, 4.64; N, 11.38.

5.5 N-[2-(2,6-DIOXO-PIPERIDIN-3-YL)-1-OXO-2,3-DIHYDRO-1H-ISOINDOL-4-YLMETHYL]-BUTYRAMIDE

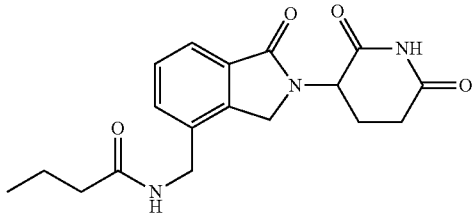 [SMILES: CCCC(=O)NCc1cccc2c1CN(C1CCC(=O)NC1=O)C2=O]

1,8-Diazabicyclo[5,4,0]-undec-7-ene (0.8 g, 5.3 mmol) was added to a stirred suspension of 3-(4-aminomethyl-1-oxo-1,3-dihydro-isoindol-2-yl)-piperidine-2,6-dione hydrochloride (0.7 g, 2.1 mmol) in acetonitrile (100 mL). The mixture was stirred for 30 minutes. n-Butyryl chloride (0.3 g, 3.2 mmol) was added, and the mixture was stirred at room temperature overnight. The mixture was concentrated, and the residue was stirred with CH$_2$Cl$_2$ (60 mL) and 2NHCl (30 mL). Solid was collected and slurried with ethanol (20 mL) to give N-[2-(2,6-dioxo-piperidin-3-yl)-1-oxo-2,3-dihydro-1H-isoindol-4-ylmethyl]-butyramide (0.5 g, 67%) as a white solid: mp 244-246° C.; $^1$H NMR (DMSO-d$_6$) δ 0.85 (t, J=7.4 Hz, 3H, CH$_3$), 1.40-1.60 (m, 2H), 1.99-2.14 (m, 3H), 2.34-2.65 (m, 2H), 2.86-2.98 (m, 1H), 4.32-4.53 (m, 4H), 5.11-5.18 (dd, J=4.9 and 13.2 Hz, 1H, CH), 7.48-7.64 (m, 3H, Ar), 8.13 (t, J=5.1 Hz, 1H, NH), 11.02 (s, 1H, NH); $^{13}$C NMR (DMSO-d$_6$) δ 13.67; 18.65, 22.61, 31.19, 37.16, 38.93, 46.15, 51.54, 121.62, 128.29, 130.60, 131.63, 134.82, 140.08, 168.08, 171.02, 172.01, 172.88; Anal. calcd. for C$_{18}$H$_{21}$N$_3$O$_4$: C, 62.96; H, 6.16; N, 12.24. Found: C, 63.08; H, 6.06; N, 12.08.

5.6 3-CHLORO-N-[2-(2,6-DIOXO-PIPERIDIN-3-YL)-1-OXO-2,3-DIHYDRO-1H-SIOINDOL-4-YL-METHYL]-BENZAMIDE

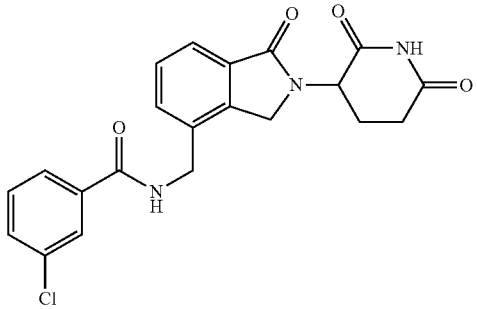 [SMILES: O=C1CCC(N2Cc3c(CNC(=O)c4cccc(Cl)c4)cccc3C2=O)C(=O)N1]

1,8 Diazabicyclo[5,4,0]-undec-7-ene (0.8 g, 5.3 mmol) was added to a stirred suspension of 3-(4-aminomethyl-1-oxo-1,3-dihydro-isoindol-2-yl)-piperidine-2,6-dione hydrochloride in acetonitrile (100 mL). The mixture was stirred for 30 minutes. 3-Chlorobenzoyl chloride (0.6 g, 3.2 mmol) was added, and the mixture was stirred at room temperature overnight. The mixture was concentrated and the residue was stirred with CH$_2$Cl$_2$ (60 mL) and 2N HCl (30 mL). The mixture was filtered and the solid was slurried with ethanol (20 mL) to give 3-chloro-N-[2-(2,6-dioxo-piperidin-3-yl)-1-oxo-2,3-dihydro-1H-isoindol-4-ylmethyl]-benzamide (0.8 g, 96%) as a white solid: mp 266-268° C.; $^1$H NMR (DMSO-d$_6$) δ 2.01-2.06 (m, 1H), 2.37-2.66 (m, 2H), 2.86-2.99 (m, 1H), 4.48 (d, J=17.3 Hz, 1H), 4.53 (d, J=21.1 Hz, 1H), 4.55 (s, 2H), 5.12-5.20 (dd, J=5.0 and 13.2 Hz, 1H, CH), 7.48-7.66 (m, 5H, Ar), 7.87 (d, J=7.7 Hz, 1H, Ar), 7.93 (d, J=1.3 Hz, 1H, Ar), 9.23 (t, J=5.6 Hz, 1H, NH), 11.03 (s, 1H, NH); $^{13}$C NMR (DMSO-d$_6$) δ 22.60, 31.20, 39.66, 46.28, 51.60, 121.76, 126.07, 127.08, 128.38, 130.40, 130.77, 131.22, 131.65, 133.23, 134.37, 136.01, 140.21, 164.94, 168.07, 171.04, 172.88; Anal. calcd. for C$_{21}$H$_{18}$N$_3$O$_4$Cl: C, 61.24; H, 4.41; N, 10.20; Cl, 8.61. Found: C, 60.92; H, 4.21; N, 10.01; Cl, 8.92.

5.7 1-[2-(2,6-DIOXO-PIPERIDIN-3-YL)-1-OXO-2,3-DIHYDRO-1H-ISOINDOL-4-YLMETHYL]-3-PROPYL-UREA

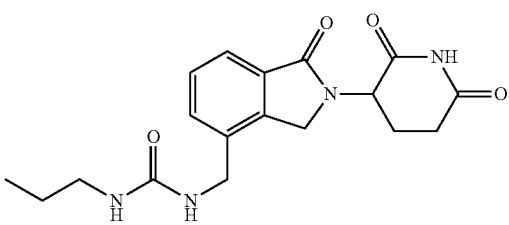 [SMILES: CCCNC(=O)NCc1cccc2c1CN(C1CCC(=O)NC1=O)C2=O]

1,8-Diazabicyclo[5,4,0]-unded-7-ene (0.8 g, 5.3 mmol) was added to a stirred suspension of 3-(4-aminomethyl-1-oxo-1,3-dihydro-isoindol-2-yl)-piperidine-2,6-dione hydrochloride (0.7 g, 2.1 mmol) in acetonitrile (100 mL). The mixture was stirred for 30 minutes. Propyl isocyanate (0.3 g, 3.2 mmol) was added, and the mixture was stirred at room temperature overnight. The mixture was concentrated, and the residue was stirred with CH$_2$Cl$_2$ (60 mL) and 2N HCl (30 mL). The mixture was filtered and the solid was slurried with methanol (40 mL) to give 1-[2-(2,6-dioxo-piperidin-3-yl)-1-oxo-2,3-dihydro-1H-isoindol-4-ylmethyl]-3-propyl-urea (0.3 g, 31%) as a white solid: mp 298-300° C.; $^1$H NMR (DMSO-d$_6$) δ 0.82 (t, J=7.3 Hz, 3H, CH$_3$), 1.32-1.41 (m, 2H), 1.99-2.04 (m, 1H), 2.37-2.65 (m, 2H), 2.86-2.99 (m, 3H), 4.29 (d, J=6.0 Hz, 2H), 4.37 (d, J=17.3 Hz, 1H), 4.45 (d, J=17.3 Hz, 1H), 5.11-5.18 (dd, J=5.1 and 13.2 Hz, 1H, CH), 6.00 (t, J=5.5 Hz, 1H, NH), 6.38 (t, J=5.9 Hz, 1H, NH), 7.47-7.62 (m, 3H, Ar), 11.03 (s, 1H, NH); $^{13}$C NMR (DMSO-d$_6$) δ 11.31, 22.62, 23.24, 31.18, 41.16, 46.13, 51.50, 121.36, 128.19, 130.24, 131.58, 136.29, 139.80, 157.97, 168.13, 171.01, 172.87; Anal. calcd. for C$_{18}$H$_{22}$N$_4$O$_4$: C, 60.32; H, 6.19; N, 15.63. Found: C, 59.93; H, 6.27; N, 15.40.

5.8 N-[2-(2,6-DIOXO-PIPERIDIN-3-YL)-1-OXO-2,3-DIHYDRO-1H-ISOINDOL-4-YLMETHYL]-NICOTINAMIDE

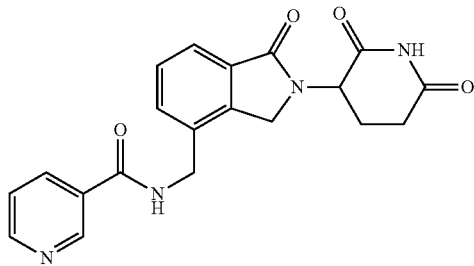 [SMILES: O=C1CCC(N2Cc3c(CNC(=O)c4cccnc4)cccc3C2=O)C(=O)N1]

1,8-Diazabicyclo[5,4,0]-undec-7-ene (1.1 g, 7.3 mmol) was added to a stirred suspension of 3-(4-aminomethyl-1-oxo-1,3-dihydro-isoindol-2-yl)-piperidine-2,6-dione hydrochloride (0.7 g, 2.1 mmol) in acetonitrile (100 mL). The mixture was stirred for 30 minutes. 3-Nicotinoyl chloride (0.5 g, 2.5 mmol) was added, and the mixture was stirred at room temperature overnight. The mixture was concentrated, and the residue was stirred with water (40 mL). The mixture was filtered and the solid was slurried with hot methanol (25 mL) to give N-[2-(2,6-dioxo-piperidin-3-yl)-1-oxo-2,3 dihydro-1H-idoindol-4-ylmethyl]-nicotinamide (0.4 g, 51%): mp 259-261° C.; $^1$H NMR (DMSO-d$_6$) δ 2.01-2.06 (m, 1H), 2.34-2.65 (m, 2H), 2.86-3.01 (m, 1H), 4.41-4.62 (m, 4H, 2CH$_2$), 5.13-5.20 (dd, J=4.8 and 13.1 Hz, 1H, CH), 7.50-7.67 (m, 4H, Ar), 8.21 (d, J=7.9 Hz, 1H, Ar), 8.73 (d, J=4.2 Hz, 1H, Ar), 9.05 (s, 1H, Ar), 9.30 (t, J=5.1 Hz, 1H, NH), 11.04 (s, 1H, NH); $^{13}$C NMR (DMSO-d$_6$) δ 22.58, 31.19, 46.27, 51.60, 121.77, 123.48, 128.37, 129.56, 130.77, 131.67, 134.30, 135.02, 140.22, 148.41, 151.99, 164.97, 168.05, 171.02, 172.37; Anal. calcd. for C$_{20}$H$_{18}$N$_4$O$_4$: C, 63.49; H, 4.79; N, 14.81. Found: C, 63.19; H, 4.75; N, 14.68.

5.9 1-[2-(2,6-DIOXO-PIPERIDIN-3-YL)-1-OXO-2,3-DIHYDRO-1H-ISOINDOL-4-YLMETHYL]-3-PHENYL-UREA

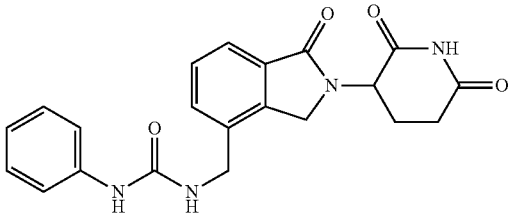 [SMILES: O=C1CCC(N2Cc3c(CNC(=O)Nc4ccccc4)cccc3C2=O)C(=O)N1]

A suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.7 mmol) in THF (30 mL) was cooled to 4° C. Phenyl isocyanate (0.3 g, 2.7 mmol) was added, and the mixture was stirred at room temperature for 5 hours. The mixture was concentrated, and the residue was stirred with 1N HCl (30 mL). The solid was collected and slurried with ethanol (10 mL) to give 1-[2-(2,6-dioxo-piperidin-3-yl)-1-oxo-2,3-dihydro-1H-isoindol-4-ylmethyl]-3-phenyl-urea (0.7 g, 89%) as a white solid: mp 328-330° C.; $^1$H NMR (DMSO-$d_6$) δ 2.00-2.04 (m, 1H), 2.36-2.64 (m, 2H), 2.86-2.98 (m, 1H), 4.37-4.58 (m, 4H, 2CH$_2$), 5.12-5.19 (dd, J=5.0 and 13.2 Hz, 1H, CH), 6.71 (t, J=5.7 Hz, 1H, NH), 6.89 (t, J=7.3 Hz, 1H, Ar), 7.21 (t, J=7.6 Hz, 2H, Ar), 7.38 (d, J=7.6 Hz, 2H, Ar), 7.48-7.65 (m, 3H, Ar), 8.61 (s, 1H, NH), 11.03 (s, 1H, NH); $^{13}$C NMR (DMSO-$d_6$) δ 22.57, 31.18, 39.67, 46.20, 51.58, 117.80, 121.20, 121.54, 128.29, 128.62, 130.33, 131.64, 135.59, 139.90, 140.29, 155.22, 168.09, 171.01, 172.84; Anal. calcd. for $C_{21}H_{20}N_4O_4$: C, 64.28; H, 5.14; N, 14.28. Found: C, 64.36; H, 4.96; N, 14.17.

5.10 [2-(2,6-DIOXO-PIPERIDIN-3-YL)-1-OXO-2,3-DIHYDRO-1H-ISOINDOL-4-YLMETHYL]-CARBAMIC ACID TERT-BUTYL ESTER

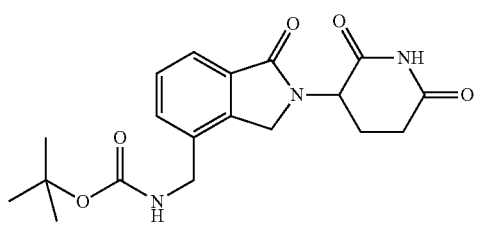 [SMILES: CC(C)(C)OC(=O)NCc1cccc2c1CN(C1CCC(=O)NC1=O)C2=O]

Di-tert-butyl dicarbonate (0.6 g, 2.7 mmol) was added to a stirred suspension of 3-(4-aminomethyl-1-oxo-1,3-dihydro-isoindol-2-yl)-piperidine-2,6-dione hydrochloride (0.7 g, 2.1 mmol) and triethylamine (0.5 g, 5.3 mmol) in THF (30 mL). The mixture was stirred at room temperature overnight. The mixture was concentrated, and the residue was stirred with water (40 mL). The mixture was filtered, and the solid was slurried with hot ethanol (20 mL) to give [2-(2,6-dioxo-piperidin-3-yl)-1-oxo-2,3-dihydro-1H-isoindol-4-ylmethyl]-carbamic acid tert-butyl ester (0.7 g, 91%) as a white solid: mp 239-241° C.; $^1$H NMR (DMSO-$d_6$) δ 1.38 (s, 9H, 3CH$_3$), 2.00-2.05 (m, 1H), 2.31-2.65 (m, 2H), 2.86-3.00 (m, 1H), 4.21 (d, J=5.5 Hz, 2H, CH$_2$), 4.37 (d, J=17.3 Hz, 1H), 4.45 (d, J=17.3 Hz, 1H), 5.11-5.18 (dd, J=4.8 and 13.0 Hz, 1H, CH), 7.48-7.62 (m, 4H, Ar and NH), 11.01 (s, 1H, NH); $^{13}$C NMR (DMSO-$d_6$) δ 22.64, 28.17, 31.15, 40.36, 46.02, 51.48, 78.01, 121.56, 128.23, 130.37, 131.60, 135.25, 139.84, 155.69, 168.05, 170.98, 172.81; Anal. calcd. for $C_{19}H_{23}N_3O_5$: C, 61.12; H, 6.21; N, 11.25. Found: C, 60.90; H, 6.19; N, 11.21.

5.11 N-[2-(2,6-DIOXO-PIPERIDIN-3-YL)-1-OXO-2,3-DIHYDRO-1H-ISOINDOL-4-YLMETHYL]-3-METHOXY-BENZAMIDE

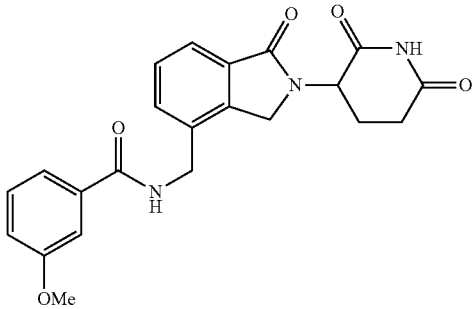

A suspension of 3-(4-aminomethyl-1-oxo-1,3-dihydro-isoindol-2-yl)-piperidine-2,6-dione hydrochloride (0.7 g, 2.1 mmol) and m-anisoyl chloride (0.4 g, 2.5 mmol) in THF 30 mL) was cooled to 5° C. Triethylamine (0.5 g, 4.8 mmol) was added, and the mixture was stirred at room temperature for 5 hours. The mixture was concentrated, and the residue was stirred with 1N HCl (40 mL). The mixture was filtered, and the solid was slurried with hot ethanol (20 mL) to give N-[2-(2,6-dioxo-piperidin-3-yl)-1-oxo-2,3-dihydro-1H-isoindol-4-ylmethyl]-3-methoxy-benzamide (0.8 g, 93%) as a white solid: mp 244-246° C.; $^1$H NMR (DMSO-$d_6$) δ 2.01-2.07 (m, 1H), 2.36-2.65 (m, 2H), 2.86-3.00 (m, 1H), 3.80 (s, 3H, CH$_3$), 4.41-4.61 (m, 4H, 2CH$_2$), 5.12-5.19 (dd, J=5.1 and 13.2 Hz, 1H, CH), 7.08-7.12 (m, 1H, Ar), 7.35-7.65 (m, 6H, Ar), 9.09 (t, J=5.6 Hz, 1H, NH), 11.02 (s, 1H, NH); $^{13}$C NMR (DMSO-$d_6$) δ 22.59, 31.17, 46.29, 51.59, 55.24, 112.41, 117.19, 119.44, 121.65, 128.31, 129.46, 130.67, 131.61, 134.68, 135.46, 140.12, 159.18, 166.08, 168.06, 171.00, 172.82; Anal. calcd. for $C_{22}H_{21}N_3O_5$: C, 64.86; H, 5.20; N, 10.31. Found: C, 64.62; H, 5.06; N, 10.23.

5.12 3-CYANO-N-[2-(2,6-DIOXO-PIPERIDIN-3-YL)-1-OXO-2,3-DIHYDRO-1H-ISOINDOL-4-YL-METHYL]-BENZAMIDE

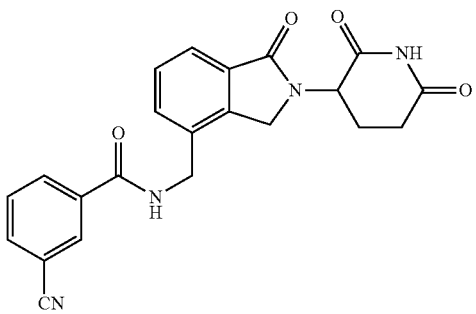 [SMILES: N#Cc1cccc(C(=O)NCc2cccc3c2CN(C2CCC(=O)NC2=O)C3=O)c1]

A suspension of 3-(4-aminomethyl-1-oxo-1,3-dihydro-isoindol-2-yl)-piperidine-2,6-dione hydrochloride (0.7 g, 2.1 mmol) and m-cyanobenzoyl chloride (0.4 g, 2.5 mmol) in THF (30 mL) was cooled to 5° C. Triethylamine (0.5 g, 4.8 mmol) was added, and the mixture was stirred at room temperature for 5 hours. The mixture was concentrated, and the residue was stirred with 1N HCl (40 mL). The mixture was filtered, and the solid was slurried with warmed ethanol (20 mL) to give 3-cyano-N-[2-(2,6-dioxo-piperidin-3-yl)-1-oxo-2,3-dihydro-1H-isoindol-4-ylmethyl]-benzamide (0.8 g, 92%) as a white solid: mp 282-284° C.; $^1$H NMR (DMSO-$d_6$) δ 2.01-2.06 (m, 1H), 2.34-2.65 (m, 2H), 2.86-3.00 (m, 1H), 4.41-4.62 (m, 4H, 2CH$_2$), 5.11-5.18 (dd, J=4.8 and 13 Hz, 1H, CH), 7.48-7.74 (m, 4H, Ar), 8.01 (d, J=7.7 Ha, 1H, Ar), 8.17 (d, J=7.9 Hz, 1H, Ar), 8.31 (s, 1H, Ar), 9.28 (t, J=5.0 Hz, 1H, NH), 11.01 (s, 1H, NH); $^{13}$C NMR (DMSO-$d_6$) δ 22.69, 31.17, 46.26, 51.60, 111.50, 118.26, 121.79, 128.35, 129.80, 130.82, 130.89, 131.65, 132.08, 134.14, 134.79, 135.00, 140.25, 164.54, 168.02, 170.98, 172.81; Anal. calcd. for $C_{22}H_{18}N_4O_4$: C, 65.67; H, 4.51; N, 13.92. Found: C, 65.38; H, 4.42; N, 13.77.

5.13 N-[2-(2,6-DIOXO-PIPERIDIN-3-YL)-1-OXO-2,3-DIHYDRO-1H-ISOINDOL-4-YLMETHYL]-4-METHOXY-BENZAMIDE

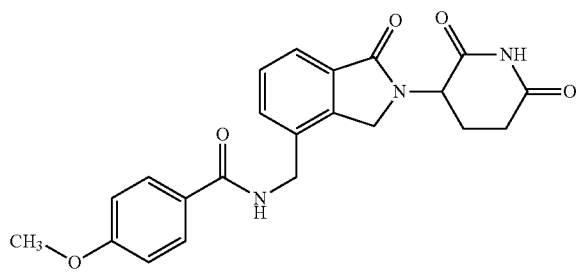 [SMILES: COc1ccc(C(=O)NCc2cccc3c2CN(C2CCC(=O)NC2=O)C3=O)cc1]

A suspension of 3-(4-aminomethyl-1-oxo-1,3-dihydro-isoindol-2-yl)-piperidine-2,6-dione hydrochloride (0.7 g, 2.1 mmol) and p-anisoyl chloride (0.4 g, 2.5 mmol) in THF (30 mL) was cooled to 5° C. Triethylamine (0.5 g, 4.8 mmol) was added, and the mixture was stirred at room temperature for 5 hours. The mixture was concentrated, and the residue was stirred with 1N HCl (30 mL). The mixture was filtered, and the solid was slurried with ethanol (15 mL) to give N-[2-(2,6-dioxo-piperidin-3-yl)-1-oxo-2,3-dihydro-1H-isoindol-4-ylmethyl]-4-methoxy-benzamide (0.8 g, 90%) as a white solid: mp 289-291° C.; $^1$H NMR (DMSO-$d_6$) δ 2.01-2.05 (m, 1H), 2.32-2.65 (m, 2H), 2.86-3.00 (m, 1H), 3.81 (s, 3H, OCH$_3$), 4.40-4.60 (m, 4H, 2CH$_2$), 5.11-5.18 (dd, J=4.9 and 13.1 Hz, 1H, CH), 7.02 (d, J=8.6 Hz, 2H, Ar), 7.46-7.64 (m, 3H, Ar), 7.85 (d, J=8.7 Hz, 2H, Ar), 8.93 (t, J=5.3 Hz, 1H, NH), 11.00 (s, 1H, NH); $^{13}$C NMR (DMSO-$d_6$) δ 22.58, 31.17, 46.28, 51.59, 55.32, 113.51, 121.57, 126.25, 128.27, 129.06, 130.64, 131.58, 134.93, 140.07, 161.63, 165.81, 168.07, 170.98, 172.81; Anal. calcd. for $C_{22}H_{21}N_3O_5$: C, 64.86; H, 5.20; N, 10.31. Found: C, 64.51; H, 5.04; N, 10.09.

5.14 N-[2-(2,6-DIOXO-PIPERIDIN-3-YL)-1-OXO-2,3-DIHYDRO-1H-ISOINDOL-4-YLMETHYL]-2-METHOXY-BENZAMIDE

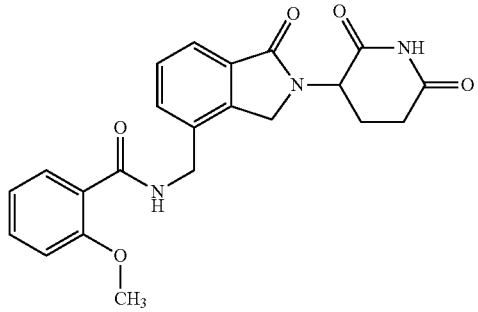

A suspension of 3-(4-aminomethyl-1-oxo-1,3-dihydro-isoindol-2-yl)-piperidine-2,6-dione hydrochloride (0.7 g, 2.1 mmol) and o-anisoyl chloride (0.4 g, 2.5 mmol) in THF (30 mL) was cooled to 5° C. Triethylamine (0.5 g, 4.8 mmol) was added, and the mixture was stirred at room temperature overnight. The reaction was quenched with methanol (1 mL), and the mixture was concentrated. The residue was stirred with 1N HCl (30 mL) and filtered. The solid was slurried with ethanol (15 mL) to give N-[2-(2,6-dioxo-piperidin-3-yl)-1-oxo-2,3-dihydro-1H-isoindol-4-ylmethyl]-2-methoxy-benzamide (0.8 g, 94%) as a white solid: mp 236-238° C.; $^1$H NMR (DMSO-$d_6$) δ 2.01-2.06 (m, 1H), 2.32-2.66 (m, 2H), 2.86-3.01 (m, 1H), 3.88 (s, 3H, OCH$_3$), 4.39-4.61 (m, 4H, 2CH$_2$), 5.12-5.19 (dd, J=4.9 and 13.1 Hz, 1H, CH), 7.02 (t, J=7.4 Hz, 1H, Ar), 7.16 (d, J=8.3 Hz, 1H, Ar), 7.44-7.72 (m, 5H, Ar), 8.77 (t, J=5.6 Hz, 1H, NH), 11.02 (s, 1H, NH); $^{13}$C NMR (DMSO-$d_6$) δ 22.60, 31.17, 46.20, 51.55, 55.82, 111.93, 120.41, 121.51, 123.10, 128.24, 130.22, 130.43, 131.57, 132.17, 134.89, 139.94, 156.87, 165.34, 168.09, 171.00, 172.83; Anal. calcd. for $C_{22}H_{21}N_3O_5$: C, 64.86; H, 5.20; N, 10.31. Found: C, 64.59; H, 5.01; N, 10.17.

5.15 1-[2-(2,6-DIOXO-PIPDERIDIN-3-YL)-1-OXO-2,3-DIHYDRO-1H-ISOINDOL-4-YLMETHYL]-3-(3-METHOXY-PHENYL)-UREA

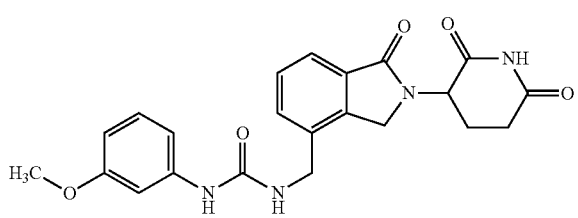 [SMILES: COc1cccc(NC(=O)NCc2cccc3c2CN(C2CCC(=O)NC2=O)C3=O)c1]

A stirred suspension of 3-(4-aminomethyl-1-oxo-1,3-dihydro-isoineol-2-yl)-piperidine-2,6-dione hydrochloride (0.7 g, 2.1 mmol) and triethylamine (0.3 g, 2.7 mmol) in THF (30 mL) was cooled to 5° C. 3-Methoxyphenyl isocyanate (0.4 g, 2.7 mmol) was added, and the mixture was stirred at room temperature overnight. The mixture was concentrated, and the residue was stirred with 1N HCl (30 mL). The mixture was filtered, and the solid was slurried with warmed methanol (15 mL) to give 1-[2-(2,6-dioxo-piperidin-3-yl)-1-oxo-2,3-dihydro-1H-isoindol-4-ylmethyl]-3-(3-methoxy-phenyl)-urea (0.8 g, 95%) as a white solid: mp 340-342° C.; $^1$H NMR (DMSO-$d_6$) δ 2.00-2.04 (m, 1H), 2.33-2.64 (m, 2H), 2.86-

3.00 (m, 1H), 3.69 (s, 3H, OCH$_3$), 4.36-4.57 (m, 4H, 2CH$_2$), 5.11-5.18 (dd, J=5.0 and 13.2 Hz, 1H, CH), 6.45-6.50 (m, 1H, Ar), 6.70 (t, J=5.7 Hz, 1H, NH), 6.89 (d, J=8.3 Hz, 1H, Ar), 7.08-7.14 (m, 2H, Ar), 7.48-7.64 (m, 3H, Ar), 8.63 (s, 1H, NH), 11.02 (s, 1H, NH); $^{13}$C NMR (DMSO-d$_6$) δ 22.56, 31.17, 39.65, 46.19, 51.57, 54.81, 103.57, 106.63, 110.14, 121.52, 128.28, 129.34, 130.29, 131.62, 135.55, 139.87, 141.50, 155.12, 159.60, 168.07, 170.99, 172.81; Anal. calcd. for C$_{22}$H$_{22}$N$_4$O$_5$: C, 62.55; H, 5.25; N, 13.26. Found: C, 62.41; H, 5.04; N, 13.25.

5.16 1-[2-(2,6-DIOXO-PIPERIDIN-3-YL)-1-OXO-2,3-DIHYDRO-1H-ISOINDOL-4-YLMETHYL]-3-(4-METHOXY-PHENYL)-UREA

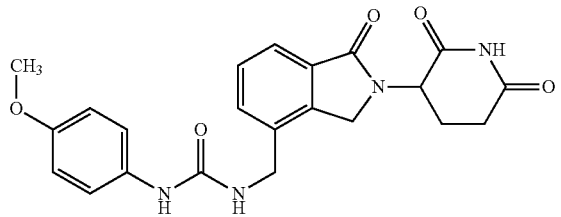 [SMILES: COc1ccc(NC(=O)NCc2cccc3c2CN(C2CCC(=O)NC2=O)C3=O)cc1]

A stirred suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.7 mmol) in THF (30 mL) was cooled to 5° C. 4-Methoxyphenyl isocyanate (0.4 g, 2.7 mmol) was added, and the mixture was stirred at room temperature overnight. The reaction was quenched with methanol (1 mL), and then concentrated. The residue was stirred with 1N HCl (30 mL) for one hour then filtered. The solid was slurried with hot methanol (20 mL) to give 1-[2-(2,6-dioxo-piperidin-3-yl)-1-oxo-2,3-dihydro-1H-isoindol-4-ylmethyl]-3-(4-methoxy-phenyl)-urea (0.8 g, 93%) as a white solid: mp 320-322° C.; $^1$H NMR (DMSO-d$_6$) δ 2.00-2.04 (m, 1H), 2.36-2.64 (m, 2H), 2.86-3.00 (m, 1H), 3.68 (s, 3H, OCH$_3$), 4.35-4.57 (m, 4H, 2CH$_2$), 5.12-5.19 (dd, J=4.6 and 13.0 Hz, 1H, CH), 6.61 (t, J=5.5 Hz, 1H, NH), 6.83 (d, J=8.9 Hz, 2H, Ar), 7.27 (d, J=8.9 Hz, 2H, Ar), 7.47-7.64 (m, 3H, Ar), 8.40 (s, 1H, NH), 11.03 (s, 1H); $^{13}$C NMR (DMSO-d$_6$) δ 22.58, 31.18, 46.20, 51.58, 55.11, 113.86, 119.70, 121.49, 128.27, 130.34, 131.62, 133.36, 135.76, 139.88, 154.08, 155.47, 168.10, 171.00, 172.84; Anal. calcd. for C$_{22}$H$_{22}$N$_4$O$_5$: C, 62.55; H, 5.25; N, 13.26. Found: C, 62.61; H, 4.95; N, 13.59.

5.17 1-[2-(2,6-DIOXO-PIPERIDIN-3-YL)-1-OXO-2,3-DIHYDRO-1H-ISOINDOL-4-YLMETHYL]-3-(2-METHOXY-PHENYL)-UREA

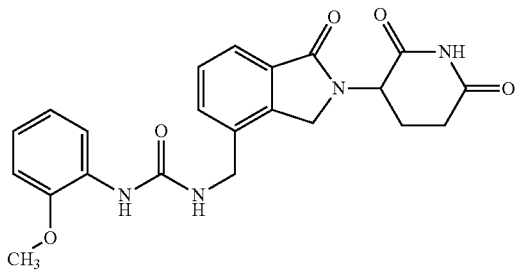 [SMILES: COc1ccccc1NC(=O)NCc1cccc2c1CN(C1CCC(=O)NC1=O)C2=O]

A stirred suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.7 mmol) in THF (30 mL) was cooled to 5° C. 2-Methoxyphenyl isocycnate (0.4 g, 2.7 mmol) was added, and the mixture was stirred at room temperature overnight. The reaction was quenched with methanol (1 mL), and then concentrated. The residue was stirred with 1N HCl (30 mL) for 1 hour and then filtered. The solid was slurried with hot methanol (20 mL) to give 1-[2-(2,6-dioxo-piperidin-3-yl)-1-oxo-2,3-dihydro-1H-isoindol-4-ylmethyl]-3-(2-methoxy-phenyl)-urea (0.8 g, 89%) as a white solid: mp 187-189° C.; $^1$H NMR (DMSO-d$_6$) δ 2.00-2.04 (m, 1H), 2.31-2.64 (m, 2H), 2.86-3.00 (m, 1H), 3.82 (s, 3H, OCH$_3$), 4.36-4.58 (m, 4H, 2CH$_2$), 5.11-5.18 (dd, J=5.0 and 13.2 Hz, 1H, CH), 6.98-6.82 (m, 3H, Ar), 7.38 (t, J=5.6 Hz, 1H, NH), 7.48-7.66 (m, 3H, Ar), 8.04-8.08 (m, 2H), 11.03 (s, 1H, NH); $^{13}$C NMR (DMSO-d$_6$) δ 22.56, 31.18, 39.63, 46.18, 51.60, 55.64, 110.58, 118.07, 120.44, 121.19, 128.35, 129.21, 130.40, 131.69, 135.36, 139.99, 147.36, 155.14, 168.07, 171.00, 172.84; Anal. calcd. for C$_{22}$H$_{22}$N$_4$O$_5$+0.35H$_2$O: C, 61.63; H, 5.34; N, 13.07. Found: C, 61.34; H, 5.15; N, 12.78.

5.18 1-(3-CYANO-PHENYL)-3-[2-(2,6-DIOXO-PIPERIDIN-3-YL)-1-OXO-2,3-DIHYDRO-1H-ISOINDOL-4-YLMETHYL]-UREA

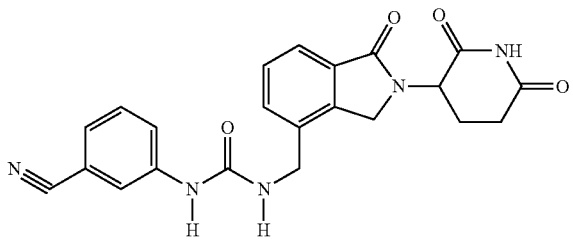 [SMILES: N#Cc1cccc(NC(=O)NCc2cccc3c2CN(C2CCC(=O)NC2=O)C3=O)c1]

3-Cyanophenyl isocyanate (0.4 g, 2.7 mmol) was added to a stirred suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.9 mmol) in THF (30 mL) at 5-10° C. After stirring at 5° C. for 10 min, the mixture was warmed to room temperature and stirred overnight. The reaction was quenched with methanol (1 mL) and concentrated. The residue was stirred with 1N HCl (30 mL) for 30 minutes and filtered. The solid was slurried with hot methanol (15 mL) to give 1-(3-cyano-phenyl)-3-[2-(2,6-dioxo-piperidin-3-yl)-1-oxo-2,3-dihydro-1H-isoindol-4-ylmethyl]-urea (0.33 g, 38%) as a white solid: mp 330-333° C.; $^1$H NMR (DMSO-d$_6$) δ 2.01-2.05 (m, 1H), 2.37-2.65 (m, 2H), 2.86-3.00 (m, 1H), 4.37-4.58 (m, 4H, 2CH$_2$), 5.11-5.18 (dd, J=4.9 and 13.1 Hz, 1H, CH), 6.92 (t, J=5.5 Hz, 1H, NH), 7.32-7.65 (m, 6H, Ar), 7.93 (s, 1H, Ar), 9.00 (s, 1H, NH), 11.01 (s, 1H, NH); $^{13}$C NMR (DMSO-d$_6$) δ 22.55, 31.17, 39.67, 46.18, 51.57, 111.41, 118.91, 120.24, 121.59, 122.36, 124.64, 128.30, 130.02, 130.35, 131.63, 135.27, 139.92, 141.21, 154.98, 168.05, 171.00, 172.82; Anal. calcd. for C$_{22}$H$_{19}$N$_5$O$_4$+0.1H$_2$O: C, 63.03; H, 4.62; N, 16.71. Found: C, 62.69, H, 4.48; N, 16.41.

5.19 1-(3-CHLORO-PHENYL)-3-[2-(2,6-DIOXO-PIPERIDIN-3-YL)-1-OXO-2,3-DIHYDRO-1H-ISOINDOL-4-YLMETHYL]-UREA

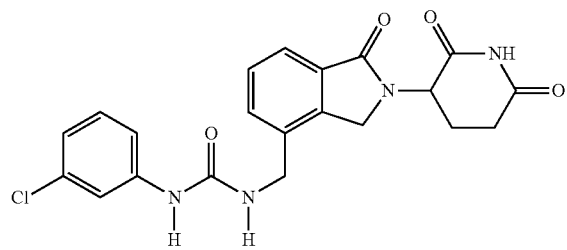 [SMILES: O=C1CCC(N2Cc3c(CNC(=O)Nc4cccc(Cl)c4)cccc3C2=O)C(=O)N1]

3-Chlorophenyl isocyanate (0.4 g, 2.7 mmol) was added to a stirred suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.9 mmol) in THF (30 mL) at 5-10° C. After stirring at 5° C. for 10 minutes, the mixture was stirred at room temperature overnight. The reaction was quenched with methanol (1 mL) and then concentrated. The residue was stirred with 1N HCl (30 mL) for 1 hour and filtered. The solid was slurried with hot methanol (15 mL) to give 1-(3-chloro-phenyl)-3-[2-(2,6-dioxo-piperidin-3-yl)-1-oxo-2,3-dihydro-1H-isoindol-4-ylmethyl]-urea (0.8 g, 91%): mp 250-252° C.; $^1$H NMR (DMSO-$d_6$) δ 2.00-2.05 (m, 1H), 2.37-2.65 (m, 2H), 2.86-2.98 (m, 1H), 4.37 (d, J=5.3 Hz, 2H, CH$_2$), 4.44 (d, J=17.2 Hz, 1H), 4.51 (d, J=17.3 Hz, 1H), 5.11-5.18 (dd, J=4.9 and 13.1 Hz, 1H, CH), 6.82 (t, J=5.4 Hz, 1H, NH), 6.92-6.95 (m, 1H, Ar), 7.18-7.27 (m, 2H, Ar), 7.48-7.65 (m, 4H, Ar), 8.84 (s, 1H, NH), 11.01 (s, 1H, NH); $^{13}$C NMR (DMSO-$d_6$) δ 22.57, 31.18, 39.68, 46.20, 51.59, 116.15, 117.13, 120.78, 121.57, 128.30, 130.21, 130.35, 131.64, 133.06, 135.37, 139.90, 141.86, 154.99, 168.07, 171.00, 172.82; Anal. calcd. for $C_{21}H_{19}N_4O_4Cl$: C, 59.09; H, 4.49; N, 13.13; Cl, 8.31. Found: C, 59.06; H, 4.39; N, 13.24; Cl, 7.95.

5.20 N-[2-(2,6-DIOXO-PIPERIDIN-3-YL)-1-OXO-2,3-DIHYDRO-1H-ISOINDOL-4-YLMETHYL]-ISONICOTINAMIDE

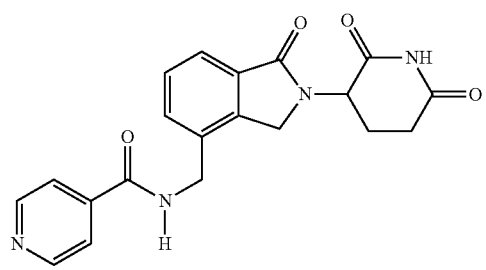 [SMILES: O=C1CCC(N2Cc3c(CNC(=O)c4ccncc4)cccc3C2=O)C(=O)N1]

Triethylamine (0.7 g, 7.4 mmol) was added to a stirred suspension of 3-(4-aminomethyl-1-oxo-1,3-dihydro-isoindol-2-yl)-piperidine-2,6-dione hydrochloride (0.7 g, 2.1 mmol) and isonicotinoyl chloride hydrochloride (0.5 g, 2.5 mmol) in THF (30 mL) at 5-10° C. After stirring for 10 minutes at 5° C., the mixture was stirred at room temperature overnight. The mixture was filtered, and the solid was slurried with hot methanol (30 mL) to give N-[2-(2,6-dioxo-piperidin-3-yl)-1-oxo-2,3-dihydro-1H-isoindol-4-ylmethyl]-isonicotinamide (0.5 g, 63%): mp 282-284° C.; $^1$H NMR (DMSO-$d_6$) δ 2.01-2.06 (m, 1H), 2.38-2.66 (m, 2H), 2.86-2.98 (m, 1H), 4.41-4.64 (m, 4H, 2CH$_2$), 5.12-5.19 (dd, J=4.6 and 13.0 Hz, 1H, CH), 7.48-7.67 (m, 3H, Ar), 7.78-7.80 (d, J=4.8 Hz, 2H, Ar), 8.73-8.75 (m, d, J=4.8 Hz, 2H, Ar), 9.39 (s, 1H, NH), 11.03 (s, 1H, NH); $^{13}$C NMR (DMSO-$d_6$) δ 22.59, 31.18, 39.67, 46.27, 51.61, 121.25, 121.83, 128.38, 130.76, 131.68, 134.11, 140.24, 140.98, 150.27, 164.87, 168.03, 171.00, 172.84; Anal. calcd. for $C_{20}H_{18}N_4O_4$: C, 63.49; H, 4.79; N, 14.81. Found: C, 63.22; H, 4.73; N, 14.62.

5.21 PYRIDINE-2-CARBOXYLIC ACID [2-(2,6-DIOXO-PIPERIDIN-3-YL)-1-OXO-2,3-DIHYDRO-1H-ISOINDOL-4-YLMETHYL]-AMIDE

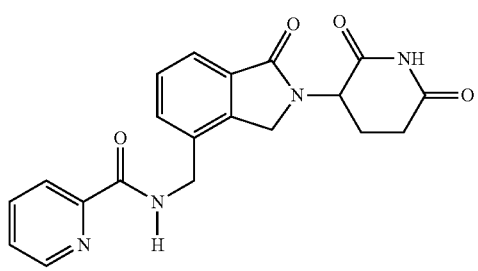 [SMILES: O=C1CCC(N2Cc3c(CNC(=O)c4ccccn4)cccc3C2=O)C(=O)N1]

Triethylamine (0.7 g, 7.4 mmol) was added to a stirred suspension of 3-(4-aminomethyl-1-oxo-1,3-dihydro-isoindol-2-yl)-piperidine-2,6-dione hydrochloride (0.7 g, 2.1 mmol) and picolinoyl chloride hydrchloride (0.5 g, 2.5 mmol) in THF (30 mL) at 5-10° C. After stirring at 5° C. for 10 minutes, the mixture was stirred at room temperature overnight. The mixture was concentrated, and the residue was stirred with H$_2$O (30 mL). The mixture was filtered, and the solid was slurried with hot methanol (15 mL) to give pyridine-2-carboxylic acid [2-(2,6-dioxo-piperidin-3-yl)-1-oxo-2,3-dihydro-1H-isoindol-4-ylmethyl]-amide (0.6 g, 78%): mp 254-256° C.; $^1$H NMR (DMSO-$d^6$) δ 2.01-2.06 (m, 1H), 2.32-2.66 (m, 2H), 2.86-3.01 (m, 1H), 4.43-4.65 (m, 4H, 2CH$_2$), 5.12-5.19 (dd, J=4.7 and 13.0 Hz, 1H, CH), 7.45-7.64 (m, 4H, Ar), 7.97-8.07 (m, 2H, Ar), 8.65 (d, J=4.2 Hz, 1H, Ar), 9.51 (t, J=5.8 Hz, 1H, NH), 11.03 (s, 1H, NH); $^{13}$C NMR (DMSO-$d_6$) δ 22.59, 31.17, 46.30, 51.57, 121.63, 122.02, 126.60, 128.28, 130.77, 131.58, 134.73, 137.79, 140.08, 148.44, 149.80, 164.16, 168.06, 170.99, 172.82; Anal. calcd. for $C_{20}H_{18}N_4O_4$: C, 63.49; H, 4.79; N, 14.81. Found: C, 63.32; H, 4.66; N, 14.80.

5.22 1-BENZYL-3-[2-(2,6-DIOXO-PIPERIDIN-3-YL)-1-OXO-2,3-DIHYDRO-1H-ISOINDOL-4-YL-METHYL]-UREA

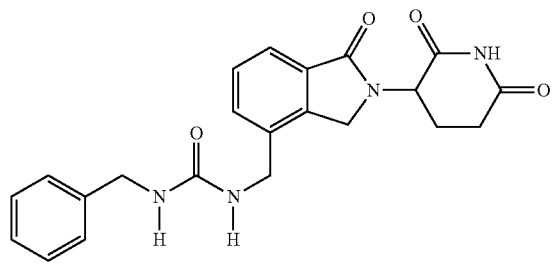 [SMILES: O=C1CCC(N2Cc3c(CNC(=O)NCc4ccccc4)cccc3C2=O)C(=O)N1]

Benzyl isocyanate (0.4 g, 2.7 mmol) was added to a stirred suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.9 mmol) in THF (30 mL). The mixture was stirred at room temperature overnight. The mixture was concentrated, and the residue was stirred with 1N HCl (30 mL). The mixture was filtered, and the solid was slurried with hot methanol (15 mL) to give 1-benzyl-3-[2-(2,6-dioxo-piperidin-3-yl)-1-oxo-2,3-dihydro-1H-isoindol-4-ylmethyl]-urea (0.8 g, 88%) as a white solid: mp 304-306° C., $^1$H NMR (DMSO-d$_6$) δ 1.97-2.02 (m, 1H), 2.30-2.34 (m, 1H), 2.50-2.65 (m, 1H), 2.85-2.98 (m, 1H), 4.21-4.52 (m, 6H), 5.09-5.16 (dd, J=4.5 and 13.0 Hz, 1H, CH), 6.51-6.53 (m, 2H), 7.23-7.61 (m, 8H), 11.01 (s, 1H), $^{13}$C NMR (DMSO-d$_6$) δ 22.56, 31.18, 40.01, 42.96, 46.14, 51.52, 121.38, 126.52, 126.95, 128.17, 130.23, 131.60, 136.11, 139.80, 140.78, 157.95, 168.09, 170.95, 172.82; Anal. calcd. for C$_{22}$H$_{22}$N$_4$O$_4$: C, 65.01; H, 5.46; N, 13.78. Found: C, 64.90; H, 5.53; N, 13.46.

5.23 1-(3,4-DICHLORO-PHENYL)-3-[2-(2,6-DI-OXO-PIPERIDIN-3-YL)-1-OXO-2,3-DIHYDRO-1H-ISOINDOL-4-YLMETHYL]-UREA

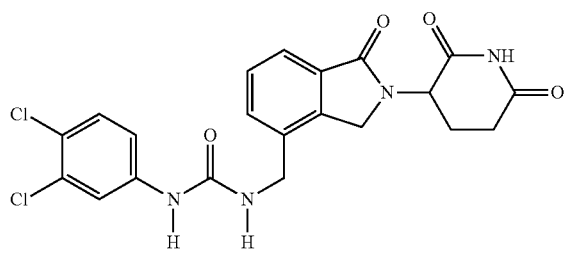 [SMILES: O=C1CCC(N2Cc3c(CNC(=O)Nc4ccc(Cl)c(Cl)c4)cccc3C2=O)C(=O)N1]

3,4-Dichlorophenyl isocyanate (0.5 g, 2.7 mmol) was added to a stirred suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.9 mmol) in THF (30 mL). The mixture was stirred at room temperature overnight. The mixture was concentrated, and the residue was stirred with 1N HCl (30 mL). The mixture was filtered, and the solid was slurried with hot methanol (20 mL) to give 1-(3,4-dichloro-phenyl)-3-[2-(2,6-dioxo-piperidin-3-yl)-1-oxo-2,3-dihydro-1H-isoindol-4-ylmethyl]-urea (0.6 g, 67%) as a white solid: mp 253-255° C.; $^1$H NMR (DMSO-d$_6$) δ 2.00-2.05 (m, 1H), 2.37-2.65 (m, 2H), 2.86-3.00 (m, 1H), 4.36-4.58 (m, 4H, 2CH$_2$), 5.11-5.18 (dd, J=4.9 and 13.1 Hz, 1H, CH), 6.89 (t, J=5.6 Hz, 1H, NH), 7.24-7.84 (m, 6H, Ar), 8.96 (s, 1H, NH), 11.01 (s, 1H, NH); $^{13}$C NMR (DMSO-d$_6$) δ 22.56, 31.17, 39.69, 46.19, 51.58, 117.86, 118.83, 121.58, 122.37, 128.29, 130.38, 130.86, 131.64, 135.27, 139.91, 140.56, 154.87, 168.05, 170.98, 172.81; Anal. calcd. for C$_{21}$H$_{18}$N$_4$O$_4$Cl$_2$: C, 54.68; H, 3.93; N, 12.15; Cl, 15.37. Found: C, 54.52; H, 3.78; N, 11.89; Cl, 15.28.

5.24 1-[2-(2,6-DIOXO-PIPERIDIN-3-YL)-1-OXO-2,3-DIHYDRO-1H-ISOINDOL-4-YLMEHYL]-3-PYRIDIN-3-YL-UREA

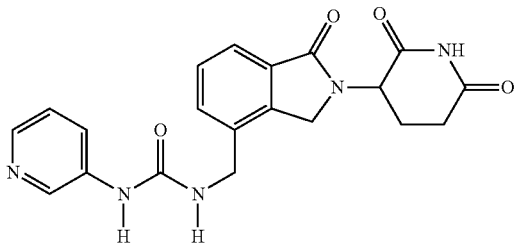 [SMILES: O=C1CCC(N2Cc3c(CNC(=O)Nc4cccnc4)cccc3C2=O)C(=O)N1]

Step 1:

A solution of 3-aminopyridine (1.5 g, 15.5 mmol) in acetonitrile (20 mL) was added to a stirred solution of N,N'-disuccinimidyl carbomate (4.0 g, 15.5 mmol) in acetonitrile (150 mL). The mixture was stirred at room temperature overnight. The mixture was concentrated, and the residue was dissolved in CH$_2$Cl$_2$ (120 mL). The CH$_2$Cl$_2$ solution was washed with saturated NaHCO$_3$ (40 mL), H$_2$O (40 mL), brine (40 mL), and dried (MgSO$_4$). Solvent was removed to give pyridin-3-yl-carbamic acid 2,5-dioxo-pyrrolidin-1-yl ester (1.3 g, 36%), which was used in next step without purification.

Step 2:

Pyridin-3-yl-carbamic acid 2,5-dioxo-pyrroidin-1-yl ester (0.5 g, 2.1 mmol) was added to a stirred suspension of 3-(4-aminomethyl-1-oxo-1,3-dihydro-isoindol-2-yl)-piperidine-2,6-dione hydrochloride (0.7 g, 2.1 mmol) and 1,8-diazabicyclo[5,4,0]undec-7-ene (0.4 g, 2.3 mmol) in acetonitrile (100 mL). The mixture was stirred at room temperature overnight. The mixture was concentrated, and the residue was stirred with water (30 mL). The mixture was filtered, and the solid was slurried with hot methanol (15 mL) to give 1-[2-(2,6-dioxo-phenyl-3-yl)-1-oxo-2,3-dihydro-1H-isoindol-4-ylmethyl]-3-pyridin-3-yl-urea (0.5 g, 60%) as a white solid: mp 273-275° C.; $^1$H NMR (DMSO-d$_6$) δ 2.00-2.05 (m, 1H), 2.33-2.65 (m, 2H), 2.85-3.00 (m, 1H), 4.38-4.58 (m, 4H, 2CH$_2$), 5.11-5.18 (dd, J=4.9 and 13.1 Hz, 1H, CH), 6.87 (t, J=5.4 Hz, 1H, NH), 7.22-7.27 (w, 1H, Ar), 7.48-7.65 (m, 3H, Ar), 7.86 (d, J=8.3 Hz, 1H, Ar), 8.11 (d, J=2.9 Hz, 1H, Ar), 8.54 (s, 1H, Ar), 8.80 (s, 1H, NH), 11.00 (s, 1H, NH); $^{13}$C NMR (DSMO-d$_6$) δ 22.56, 31.17, 46.19, 51.57, 121.57, 123.43, 124.62, 128.29, 130.34, 131.64, 135.37, 136.96, 139.69, 139.90, 142.25, 155.16, 168.06, 170.99, 172.81; Anal. calcd. for C$_{20}$H$_{19}$N$_5$O$_4$: C, 61.06; H, 4.87; N, 17.80. Found: C, 60.74, 4.75; N, 17.66.

5.25 3-[2-(2,6-DIOXO-PIPERIDIN-3-YL)-1-OXO-2,3-DIHYDRO-1H-ISOINDOL-4-YLMETHYL]-1,1-DIMETHYL-UREA

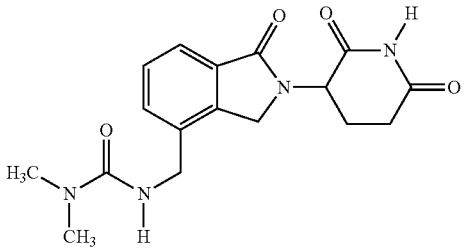 [SMILES: CN(C)C(=O)NCc1cccc2c1CN(C1CCC(=O)NC1=O)C2=O]

Triethylamine (0.6 g, 5.9 mmol) was added slowly to a stirred suspension of 3-(4-aminomethyl-1-oxo-1,3-dihydro-isoindol-2-yl)-piperidine-2,6-dione hydrochloride (0.7 g, 2.1 mmol) and dimethylcarbamoyl chloride (0.3 g, 3.2 mmol) in THF (100 mL). The mixture was stirred at room temperature overnight. Another portion of dimethylcarbamoyl chloride (0.3 g) and 1,8-diazabicyclo[5,4,0]-undec-7-ene (0.6 g) was added and stirred for another day. The mixture was concentrated, and the residue was stirred with 1N HCl (15 mL). The mixture was filtered, and the solid was slurried with hot methanol (10 mL) to give 3-[2-(2,6-dioxo-piperidin-3-yl)-1-oxo-2,3-dihydro-1H-isoindol-4-ylmethyl]-1,1-dimethyl-urea (0.3 g, 46%) as a white solid: mp 169-171° C.; $^1$H NMR (DMSO-$d_6$) δ 1.99-2.04 (m, 1H), 2.32-2.64 (m, 2H), 2.80 (s, 6H, 2CH$_3$), 2.85-3.00 (m, 1H), 4.27 (d, J=5.6 Hz, 2H, CH$_2$), 4.40 (d, J=17.3 Hz, 1H), 4.47 (d, J=17.3 Hz, 1H), 5.10-5.17 (dd, J=5.0 and 13.2 Hz, 1H, CH), 6.94 (t, J=5.6 Hz, 1H, NH), 7.44-7.64 (m, 3H, Ar), 11.02 (s, 1H); $^{13}$C NMR (DMSO-$d_6$) δ 22.58, 31.18, 35.88, 46.20, 51.55, 121.20, 128.08, 130.38, 131.39, 136.35, 139.77, 158.08, 168.15, 171.00, 172.83; Anal. calcd. for $C_{17}H_{20}N_4O_4$: C, 59.29; H, 5.85; N, 16.27. Found: C, 59.05; H, 5.91; N, 15.92.

5.26 N-[2-(2,6-DIOXO-PIPERIDIN-3-YL)-1-OXO-2,3-DIHYDRO-1H-ISOINDOL-4-YLMETHYL]-3-METHYL-BENZAMIDE

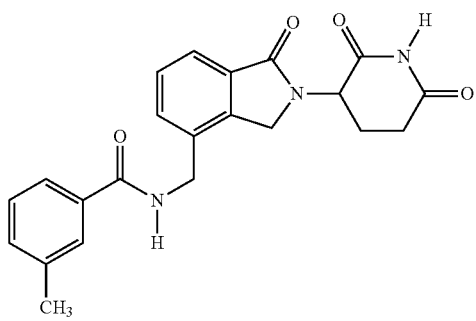 [SMILES: Cc1cccc(C(=O)NCc2cccc3c2CN(C2CCC(=O)NC2=O)C3=O)c1]

Teiethylamine (0.5 g, 5.2 mmol) was added to a stirred suspension of 3-(4-aminomethyl-1-oxo-1,3-dihydro-isoindol-2-yl)-piperidine-2,6-dione hydrochloride (0.7 g, 2.1 mmol) and m-toluoyl chloride (0.5 g, 2.9 mmol) in THF (30 mL) at 5-10° C. After stirring at 5° C. for 10 minutes, the mixture was stirred at room temperature overnight. The mixture was concentrated, and the residue was stirred with 1N HCl (20 mL). The mixture was filtered, and the solid was slurried with hot methanol (15 mL) to give N-[2-(2,6-dioxo-piperidin-3-yl)-1-oxo-2,3-dihydro-1H-isoindol-4-ylmethyl]-3-methyl-benzamide (0.7 g, 86%) as a white solid: mp 253-255° C.; $^1$H NMR (DMSO-$d_6$) δ 2.01-2.05 (m, 1H), 2.35 (s, 3H, CH3), 2.35-2.65 (m, 2H), 2.86-3.00 (m, 1H), 4.40-4.61 (m, 4H, 2CH$_2$), 5.12-5.19 (dd, J=5.0 and 13.2 Hz, 1H, CH), 7.34-7.70 (m, 7H, Ar), 9.05 (t, J=5.6 Hz, 1H, NH), 11.03 (s, 1H, NH); $^{13}$C NMR (DMSO-$d_6$) δ 20.90, 22.59, 31.17, 46.28, 51.58, 121.62, 124.36, 127.76, 128.20, 128.30, 130.66, 131.60, 131.86, 134.07, 134.75, 137.59, 140.11, 166.45, 168.06, 170.99, 172.82; Anal. calcd. for $C_{22}H_{21}N_3O_4$: C, 67.51; H, 5.41; N, 10.74. Found: C, 67.52; H, 5.35; N, 10.71.

5.27 (2-{[2-(2,6-DIOXO-PIPERIDIN-3-YL)-1-OXO-2,3-DIHYDRO-1H-ISOINDOL-4-YLMETHYL]-CARBAMOYL}-ETHYL)-CARBAMIC ACID T-BUTYL ESTER

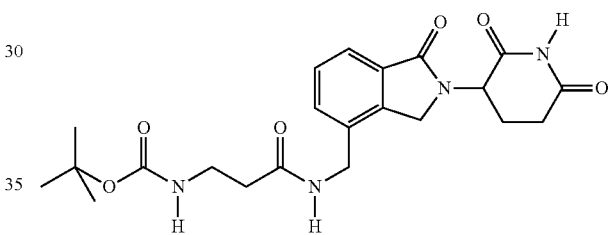

1,8-Diazabicyclo[5,4,0]-undec-7-ene (2.6 g, 16.8 mmol) was added to a stirred solution of 3-(4-aminomethyl-1-oxo-1,3-dihydro-isoindol-2-yl)-piperidine-2,6 dione hydrochloride (2.0 g, 6.5 mmol) in DMF (100 mL). After stirring for 10 minutes, 1-hydrocybenztriazole (1.1 g, 7.8 mmol) and N—BOC-β-alanine (1.4 g, 7.1 mmol) were added. The reaction was initiated by addition of 1-[3-(dimethylamino0propyl]-3-ethylcarbodiimide hydrochloride (1.9 g, 9.7 mmol). The mixture was stirred at room temperature overnight. The mixture was concentrated, and the residue was stirred with H$_2$O (40 mL) and CH$_2$Cl$_2$ (120 mL). The solid was collected to give (2-{[2-(2,6-dioxo-piperidin-3-yl)-1-oxo-2,3-dihydro-1H-isoindol-4-ylmethyl]-carbamoyl}-ethyl)-carbamic acid t-butyl ester (2.1 g, 73%) as a white solid: mp 203-205° C.; $^1$H NMR (DMSO-$d_6$) δ 1.36 (s, 9H, 3CH$_3$), 1.99-2.04 (m, 1H), 2.27-2.64 (m, 2H), 2.85-2.98 (m, 1H), 3.00-3.18 (m, 2H), 4.31 (d, J=5.3 Hz, 2H, CH$_2$), 4.33-4.53 (dd, J=17.3 and 37.3 Hz, 2H, CH$_2$), 5.10-5.17 (dd, J=4.8 and 13.1 Hz, 1H, CH), 6.79 (t, 1H, NH), 7.47-7.52 (m, 2H, Ar), 7.61-7.64 (m, 1H, Ar), 8.43 (t, J=5.3 Hz, 1H, NH), 11.01 (s, 1H, NH); $^{13}$C NMR (DMSO-$d_6$) δ 22.54, 28.19, 31.17, 35.60, 36.67, 46.15, 51.55, 77.77, 121.60, 128.24, 130.56, 131.61, 134.56, 140.04, 155.43, 168.02, 170.43, 170.95, 172.80; Anal. calcd. for $C_{22}H_{28}N_4O_6$: C, 59.45; H, 6.35; N, 12.60. Found: C, 59.16; H, 6.31; N, 12.50.

5.28 3-AMINO-N-[2-(2,6-DIOXO-PIPERIDIN-3-YL)-1-OXO-2,3-DIHYDRO-1H-ISOINDOL-4-YL-METHYL]-PROPIONAMIDE HYDROCHLORIDE

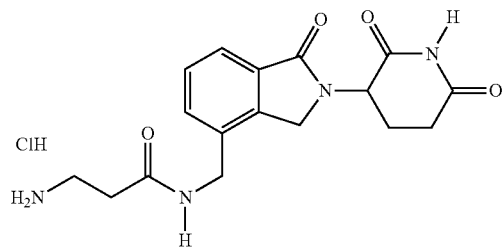 [SMILES: Cl ; NCCC(=O)NCc1cccc2c1CN(C1CCC(=O)NC1=O)C2=O]

4N HCl/dioxane (3.4 mL) was added to a stirred solution of (2-{[2-(2,6-dioxo-piperidin-3-yl)-1-oxo-2,3-dihydro-1H-isoindol-4-ylmethyl]-carbamoyl}-ethyl)-carbamic acid t-butyl ester (1.5 g, 3.4 mmol) in $CH_2Cl_2$ (50 mL) and DMF (25 mL). The mixture was stirred at room temperature for 7 days. The mixture was filtered to give 3-amino-N-[2-(2,6-dioxo-piperidin-3-yl)-1-oxo-2,3-dihydro-1H-isoindol-4-ylmethyl]-propionamide hydrochloride (1.0 g, 74%) as a white solid: mp 249-251° C.; $^1$H NMR (DMSO-$d_6$) δ 2.00-2.04 (m, 1H), 2.37-2.65 (m, 4H, 2CH$_2$), 2.86-2.99 (m, 3H), 4.34-4.57 (m, 4H, 2CH$_2$), 5.11-5.18 (dd, J=4.8 and 13.1 Hz, 1H, CH), 7.46-7.64 (m, 3H, Ar), 8.02 (s, 3H, NH$_3$), 8.78 (t, J=5.3 Hz, 1H, NH), 11.01 (s, 1H, NH); $^{13}$C NMR (DMSO-$d_6$) δ 22.57, 31.17, 31.94, 35.09, 39.02, 46.21, 51.57, 121.71, 128.27, 130.81, 131.65, 134.28, 140.14, 167.99, 169.47, 170.96, 172.83; Anal. calcd. for $C_{17}H_{21}N_4O_4Cl$: C, 52.38; H, 5.69; N, 14.37; Cl, 9.09. Found: C, 52.31; H, 5.56; N, 14.19; Cl, 9.01.

5.29 N-[2-(2,6-DIOXO-PIPERIDIN-3-YL)-1-OXO-2,3-DIHYDRO-1H-ISOINDOL-4-YLMETHYL]-2-METHOXY-ACETAMIDE

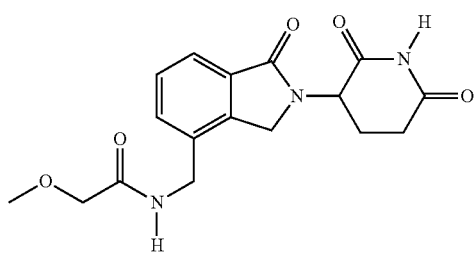 [SMILES: COCC(=O)NCc1cccc2c1CN(C1CCC(=O)NC1=O)C2=O]

Triethylamine (0.5 g, 5.0 mmol) was added to a stirred suspension of 3-(4-aminomethyl-1-oxo-1,3-dihydro-isoindol-2-yl)-piperidine-2,6-dione hydrochloride (0.7 g, 2.1 mmol) and methoxyacetyl chloride (0.3 g, 2.7 mmol) in THF (30 mL) at room temperature. The mixture was stirred at room temperature overnight. Reaction mixture was quenched with methanol (1 mL) and then concentrated. The residue was stirred with 1N HCl (30 mL) for 30 minutes and filtered. The solid was slurried with ethanol (15 mL) to give N-[2-(2,6-dioxo-piperidin-3-yl)-1-oxo-2,3-dihydro-1H-isoindol-4-ylmethyl]-2-methoxy-acetamide (0.4 g, 57%) as a white solid: mp 232-234° C.; $^1$H NMR (DMSO-$d_6$) δ 2.00-2.04 (m, 1H), 2.32-2.64 (m, 2H), 2.85-3.00 (m, 1H), 3.31 (s, 3H, CH$_3$), 3.87 (s, 2H, CH$_2$), 4.35 (d, J=6.2 Hz, 2H, CH$_2$), 4.41 (d, J=17.3 Hz, 1H), 4.49 (d, J=17.3 Hz, 1H), 5.10-5.17 (dd, J=5.0 and 13.2 Hz, 1H, CH), 7.45-7.64 (m, 3H, Ar), 8.46 (t, J=5.8 Hz, 1H, NH), 11.00 (s, 1H, NH); $^{13}$C NMR (DMSO-$d_6$) δ 22.57, 31.16, 38.42, 46.18, 51.54, 58.61, 71.46, 121.60, 128.23, 130.69, 131.56, 134.65, 140.01, 168.03, 169.20, 170.97, 172.82, Anal. calcd. for $C_{17}H_{19}N_3O_5$: C, 59.12; H, 5.55; N, 12.17. Found: C, 59.10; H, 5.51; N, 12.05.

5.30 2-DIMETHYLAMINO-N-[2-(2,6-DIOXO-PIPERIDIN-3-YL)-1-OXO-2,3-DIHYDRO-1H-ISOINDOL-4-YLMETHYL]-ACETAMIDE HYDROCHLORIDE

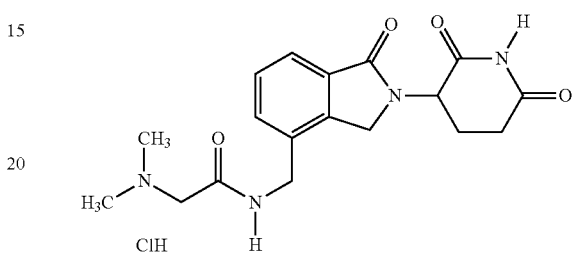

Step 1:

Triethylamine (0.7 g, 6.5 mmol) was added to a stirred suspension of 3-(4-aminomethyl-1-oxo-1,3-dihydro-isoindol-2-yl)-piperidine-2,6-dione hydrochloride (0.8 g, 2.6 mmol) in THF (50 mL). After stirring for 5 minutes, chloroacetyl chloride (0.4 g, 3.6 mmol) was added slowly. The resulting brown suspension was refluxed overnight. The mixture was cooled and quenched with methanol (1 mL). The mixture was concentrated, and the solid was stirred with 0.5N HCl (30 mL). The mixture was filtered, and the solid was slurried with ethanol (15 mL) to give 2-chloro-N-[2-(2,6-dioxo-piperidin-3-yl)-1-oxo-2,3-dihydro-1H-isoindol-4-ylmethyl]-acetamide (0.7 g, 76%): $^1$H NMR (DMSO-$d_6$) δ 1.99-2.04 (m, 1H), 2.35-2.65 (m, 2H), 2.85-2.94 (m, 1H), 4.19 (s, 2H, CH$_2$), 5.10-5.18 (dd, J=5.1 and 13.3 Hz, 1H, CH), 7.50-7.66 (m, 3H), 8.80 (t, J=5.7 Hz, 1H, NH), 11.01 (s, 1H, NH).

Step 2:

Dimethylamine/THF (2M, 6.1 mL, 12.3 mmol) was added to a stirred solution of 2-chloro-N-[2-(2,6-dioxo-piperidin-3-yl)-1-oxo-2,3-dihydro-1H-isoindol-4-ylmethyl]-acetamide (1.0 g, 3.1 mmol) in DMF (30 mL). The resulting solution was stirred at room temperature overnight. The mixture was concentrated, and the residue was stirred with $CH_2Cl_2$ (15 mL). The mixture was filtered, and the solid was dissolved in $H_2O$ (10 mL). 4N HCl (1.5 mL) was added and stirred for 30 minutes. The resulting solution was concentrated, and the residue was evaporated with ethanol (3×10 mL). The residue was slurried with ether (15 mL) and ethanol (5 mL). The mixture was filtered to give 2-dimethylamino-N-[2-(2,6-dioxo-piperidin-3-yl)-1-oxo-2,3-dihydro-1H-isoindol-4-ylmethyl]-acetamide hydrochloride (0.7 g, 54%) as a white solid: mp 273-275° C.; $^1$H NMR (DMSO-$d_6$) δ 2.00-2.04 (m, 1H), 2.33-2.65 (m, 2H), 2.81 (s, 6H, 2CH$_3$), 2.87-3.01 (m, 1H), 4.02 (s, 2H, CH$_2$), 4.36 (d, J=17.4 Hz, 1H), 4.43 (d, J=4.6 Hz, 2H, CH$_2$), 4.55 (d, J=17.4 Hz, 1H), 5.12-5.19 (dd, J=5.0 and 13.1 Hz, 1H, CH), 7.48-7.67 (m, 3H, Ar), 9.41 (t, J=5.7 Hz, 1H, NH), 10.08 (s, 1H, NH), 11.04 (s, 1H, NH); $^{13}$C NMR (DMSO-$d_6$) δ 22.60, 31.16, 39.06, 43.05, 46.19, 51.55, 57.07, 121.95, 128.32, 130.87, 131.72, 133.59, 140.25, 164.43, 167.93, 170.94, 172.84; Anal. calcd. for $C_{18}H_{23}N_4O_4Cl+$ 0.34H₂O: C, 53.92; H, 5.95; N, 13.94; Cl, 8.84. Found: C, 54.06; H, 6.08; N, 13.72; Cl, 9.06.

5.31 (3-{[2-(2,6-DIOXO-PIPERIDIN-3-YL)-1-OXO-2,3-DIHYDRO-1H-ISOINDOL-4-YLM-ETHYL]-CARBAMOYL}-PROPYL)-CARBAMIC ACID T-BUTYL ESTER

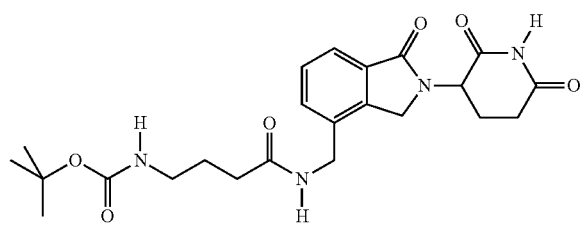 [SMILES: CC(C)(C)OC(=O)NCCCC(=O)NCc1cccc2c1CN(C1CCC(=O)NC1=O)C2=O]

1,8-Diazabicyclo[5,4,0]-undec-7-ene (1.8 g, 11.8 mmol) was added to a stirred suspension of 3-(4-aminomethyl-1-oxo-1,3-dihydro-isoindol-2-yl)-piperidine-2,6-dione hydrochloride (1.4 g, 4.5 mmol) in DMF (50 mL). After stirring for 10 minutes, 1-hydroxbenzotriazole (0.7 g, 5.4 mmol) and N—BOC-γ-aminobutyric acid (1.1 g, 5.4 mmol) were added. The reaction was initiated by addition of 1-[3-(dimethylamino)propyl]-3-ethylcarbodiimide hydrochloride (1.3 g, 6.8 mmol). The mixture was stirred at room temperature overnight. The mixture was concentrated, and the residue was stirred with EtOAc (50 mL) and H₂O (40 mL) for 30 minutes. The mixture was filtered, and dried to give (3-{[2-(2,6-dioxo-piperidin-3-yl)-1-oxo-2,3-dihydro-1H-isoindol-4-ylmethyl]-carbamoyl}-propyl-carbamic acid t-butyl ester (1.6 g, 77%) as a white solid: mp 199-201° C.; $^1$H NMR (DMSO-d₆) δ 1.37 (s, 9H, 3CH₃), 1.58-1.66 (m, 2H, CH₂), 1.99-2.16 (m, 3H), 2.36-2.49 (m, 1H), 2.58-2.64 (m, 1H), 2.86-2.94 (m, 3H), 4.31 (d, J=5.6 Hz, 2H, CH₂), 4.38 (d, J=17.3 Hz, 1H), 4.46 (d, J=17.3 Hz, 1H), 5.10-5.18 (dd, J=5.0 and 13.1 Hz, 1H, CH), 6.81 (t, J=5.4 Hz, 1H, NH), 7.48-7.64 (m, 3H, Ar), 8.37 (t, J=5.7 Hz, 1H, NH), 11.02 (s, 1H, NH); $^{13}$C NMR (DMSO-d₆) δ 22.56, 25.72, 28.23, 31.18, 32.63, 38.95, 46.15, 51.56, 77.04, 121.60, 128.27, 130.55, 131.61, 134.70, 140.06, 155.55, 168.04, 170.97, 171.90, 172.82; Anal. calcd. for C₂₃H₃₀N₄O₆: C, 60.25; H, 6.59; N, 12.22. Found: C, 60.12; H, 6.55; N, 12.15.

5.32 4-AMINO-[2-(2,6-DIOXO-PIPERIDIN-3-YL)-1-OXO-2,3-DIHYDRO-1H-ISOINDOL-4-YLM-ETHYL]-BUTYRAMIDE HYDROCHLORIDE

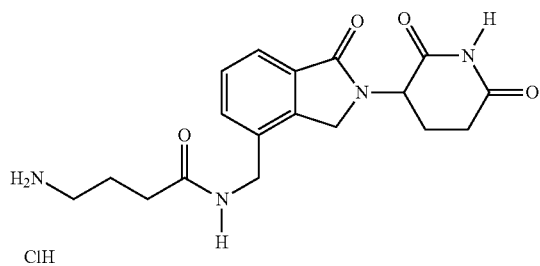 [SMILES: NCCCC(=O)NCc1cccc2c1CN(C1CCC(=O)NC1=O)C2=O ; Cl]

2N HCl/ether (4 mL) was added to a stirred solution of (3-{[2-(2,6-dioxo-piperidin-3-yl)-1-oxo-2,3-dihydro-1H-isoindol-4-ylmethyl]-carbamoyl}-propyl)-carbamic acid t-butyl ester (1 g, 2.2 mmol) in DMF (20 mL). The mixture was stirred at room temperature for 7 days. The mixture was diluted with CH₂Cl₂ (20 mL) and filtered to give 4-amino-N-[2-(2,6-dioxo-piperidin-3-yl)-1-oxo-2,3-dihydro-1H-isoindol-4-ylmethyl]-butyramide hydrochloride (0.8 g, 87%) as a white solid: mp 268-270° C.; $^1$H NMR (DMSO-d₆) δ 1.74-1.86 (m, 2H, CH₂), 2.00-2.04 (m, 1H), 2.24-2.79 (m, 6H), 2.86-2.98 (m, 1H), 4.32-4.39 (m, 3H), 4.49 (d, J=17.5 Hz, 1H), 5.10-5.18 (dd, J=5.0 and 12.5 Hz, 1H, CH), 7.49-7.64 (m, 3H, Ar), 8.01 (b, 3H, NH₃), 8.61 (t, J=5.0 Hz, 1H, NH), 11.01 (s, 1H, NH); $^{13}$C NMR (DMSO-d₆) δ 22.59, 23.10, 31.18, 31.87, 38.40, 38.98, 46.20, 51.57, 121.64, 128.28, 130.64, 131.63, 134.61, 140.09, 168.03, 170.99, 171.37, 172.85; Anal. calcd. for C₁₈H₂₃N₄O₄Cl: C, 54.75; H, 5.87; N, 14.19; Cl, 8.98. Found: C, 54.50; H, 5.81; N, 13.90; Cl, 8.92.

5.33 1-(4-CHLORO-PHENYL)-3-[2-(2,6-DIOXO-PIPERIDIN-3-YL)-1-OXO-2,3-DIHYDRO-1H-ISOINDOL-4-YLMETHYL]-UREA

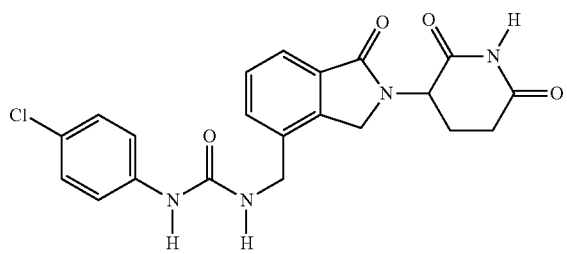 [SMILES: O=C1CCC(N2Cc3c(CNC(=O)Nc4ccc(Cl)cc4)cccc3C2=O)C(=O)N1]

4-Chlorophenyl isocyanate (0.4 g, 2.7 mmol) was added to a stirred suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.9 mmol) in THF (30 mL) at 5-10° C. After stirring at 5° C. for 10 minutes, the mixture was stirred at room temperature overnight. The reaction was quenched with methanol (1 mL) and concentrated. The residue was stirred with 1N HCl (30 mL) for 30 minutes. The mixture was filtered, and the solid was slurried with hot acetone (10 mL) to give 1-(4-chloro-phenyl)-3-[2-(2,6-dioxo-piperidin-3-yl)-1-oxo-2,3-dihydro-1H-isoindol-4-ylmethyl]-urea (0.7 g, 73%) as a white solid: mp>260° C.; $^1$H NMR (DMSO-d₆) δ 2.00-2.04 (m, 1H), 2.33-2.65 (m, 2H), 2.86-3.00 (m, 1H), 4.36-4.58 (m, 4H, 2CH₂), 5.11-5.18 (dd, J=5.0 and 12.5 Hz, 1H, CH), 6.77 (t, J=5.0 Hz, 1H, NH), 7.27 (d, J=10.0 Hz, 2H, Ar), 7.40 (d, J=10 Hz, 2H, Ar), 7.47-7.64 (m, 3H, Ar), 8.77 (s, 1H, NH), 11.02 (s, 1H, NH); $^{13}$C NMR (DMSO-d₆) δ 22.57, 31.18, 39.68, 45.19, 51.58, 119.29, 121.56, 124.66, 128.30, 128.44, 130.35, 131.64, 135.46, 139.31, 139.92, 155.08, 168.07, 171.00, 172.84; Anal. calcd. for C₂₁H₁₉N₄O₄Cl: C, 59.09; H, 4.49; N, 13.13; Cl, 8.31. Found: C, 58.85; H, 4.35; N, 12.97; Cl, 8.19.

5.34 1-(3,4-DIMETHYL-PHENYL)-3-[2-(2,6-DI-OXO-PIPERIDIN-3-YL)-1-OXO-2,3-DIHYDRO-1H-ISOINDOL-4-YLMETHYL]-UREA

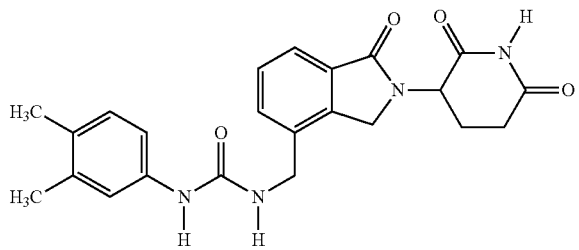 [SMILES: Cc1ccc(NC(=O)NCc2cccc3c2CN(C2CCC(=O)NC2=O)C3=O)cc1C]

3,4-Dimethylphenyl isocyanate (0.4 g, 2.7 mmol) was added to a stirred suspension of 3-(4-aminomethyl-1-oxo-1,3-dihydro-isondol-2-yl)-piperidine-2,6-dione hydrochloride (0.7 g, 2.1 mmol) and triethylamine (0.3 g, 2.9 mmol) in THF (30 mL) at 5-10° C. After stirring at 5° C. for 10 minutes, the mixture was stirred at room temperature overnight. The reaction was quenched with methanol (1 mL) and then concentrated. The residue was stirred with 1N HCl (30 mL) for 1 hour then filtered. The solid was slurried with hot acetone (10 mL) for 30 minutes to give 1-(3,4-dimethyl-phenyl)-3-[2-(2,6-dioxo-piperidin-3-yl)-1-oxo-2,3-dihydro-1H-isoindol-4-ylmethyl]-urea (0.8 g, 91%) as a white solid: mp>260° C.; $^1$H NMR (DMSO-$d_6$) δ 2.00-2.04 (m, 1H), 2.11 (s, 3H, CH$_3$), 2.14 (s, 3H, CH$_3$), 2.32-2.64 (m, 2H), 2.85-3.00 (m, 1H), 4.34-4.57 (m, 4H, 2CH$_2$), 5.11-5.18 (dd, J=5.0 and 12.5 Hz, 1H, CH), 6.64 (t, J=5.0 Hz, 1H, NH), 6.94-7.15 (m, 3H, Ar), 7.47-7.64 (m, 3H, Ar), 8.39 (s, 1H, NH), 11.02 (s, 1H, NH); $^{13}$C NMR (DMSO-$d_6$) δ 18.59, 19.60, 22.57, 31.18, 39.69, 46.19, 51.57, 115.45, 119.25, 121.51, 128.28, 128.76, 129.49, 130.34, 131.63, 135.71, 136.09, 137.95, 139.88, 155.29, 168.09, 171.00, 172.84; Anal. calcd. for C$_{23}$H$_{24}$N$_4$O$_4$: C, 65.70; H, 5.75; N, 13.32. Found: C, 65.36; H, 5.61; N, 13.10.

5.35 1-CYCLOHEXYL-3-[2-(2,6-DIOXO-PIPERIDIN-3-YL)-1-OXO-2,3-DIHYDRO-1H-ISOINDOL-4-YLMETHYL]-THIOUREA

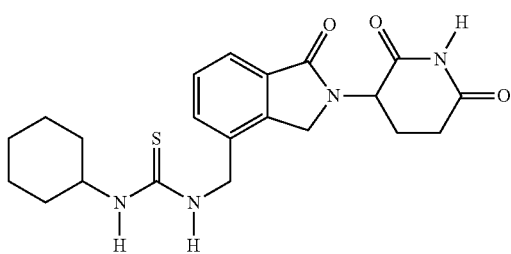 [SMILES: O=C1CCC(N2Cc3c(CNC(=S)NC4CCCCC4)cccc3C2=O)C(=O)N1]

Cyclohexyl isothiocycnate (0.4 g, 2.5 mmol) was added to a stirred suspension of 3-(4-aminomethyl-1-oxo-1,3-dihydro-isoindol-2-yl)-piperidine-2,6-dione hydrochloride (0.7 g, 2.1 mmol) and triethylamine (0.3 g, 2.9 mmol) in THF (30 mL) at 5-10° C. After stirring at 5° C. for 10 minutes, the mixture was stirred at room temperature for 6 days. The mixture was concentrated, and the residue was stirred with 1N HCl (30 mL) for 1 hour. The mixture was filtered, and the solid was slurried with hot methanol (20 mL) to give 0.5 g of crude product. The crude product was purified by prep. HPLC to give 1-cyclohexyl-3-[2-(2,6-dioxo-piperidin-3-yl)-1-oxo-2,3-dihydro-1H-isoindol-4-ylmethyl]-thiourea (0.3 g, 29%) as a white solid: mp>260° C.; $^1$H NMR (DMSO-$d_6$) δ 1.10-1.34 (m, 5H), 1.52-1.63 (m, 3H), 1.82-1.85 (m, 2H), 2.00-2.05 (m, 1H), 2.32-2.39 (m, 1H), 2.58-2.65 (m, 1H), 2.86-3.00 (m, 1H), 4.31 (b, 1H), 4.38 (d, J=17.3 Hz, 1H), 4.47 (d, J=17.4 Hz, 1H), 4.77 (d, J=5.0 Hz, 2H), 5.11-5.19 (dd, J=5.0 and 13.2 Hz, 1H), 7.49-7.73 (m, 5H), 11.02 (s, 1H), $^{13}$C NMR (DMSO-$d_6$) δ 22.65, 24.44, 25.12, 31.15, 32.24, 43.89, 46.21, 51.48, 51.91, 121.55, 128.20, 130.35, 131.68, 134.92, 139.74, 168.02, 170.97, 172.82; Anal. calcd. for C$_{21}$H$_{26}$N$_4$O$_3$S: C, 60.85; H, 6.32; N, 13.52; S, 7.74. Found: C, 60.51; H, 6.05; N, 13.33; S, 7.79.

5.36 3,4-DICHLORO-N-[2-(2,6-DIOXO-PIPERIDIN-3-YL)-1-OXO-2,3-DIHYDRO-1H-ISOINDOL-4-YLMETHYL]-BENZAMIDE

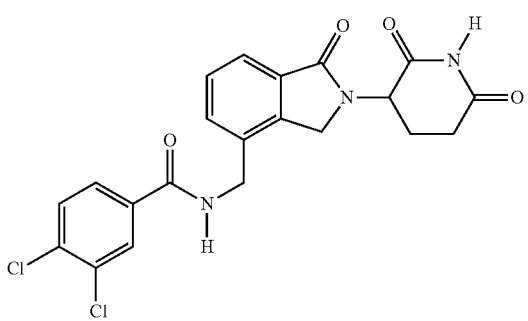 [SMILES: O=C1CCC(N2Cc3c(CNC(=O)c4ccc(Cl)c(Cl)c4)cccc3C2=O)C(=O)N1]

Triethylamine (0.5 g, 5.3 mmol) was added to a stirred suspension of 3-(4-aminomethyl-1-oxo-1,3-dihydro-isoindol-2-yl)-piperidine-2,6-dione hydrochloride (0.7 g, 2.1 mmol) and 3,4-dichlorobenzoyl chloride (0.6 g, 2.9 mmol) in THF (30 mL) at 5-10° C. After stirring at 5° C. for 10 minutes, the mixture was stirred at room temperature overnight. The reaction was quenched with methanol (1 mL) and concentrated. The residue was stirred with 1N HCl (40 mL) for 1 hour then filtered. The solid was slurried with hot acetone (25 mL) to give 3,4-dichloro-N-[2-(2,6-dioxo-piperidin-3-yl)-1-oxo-2,3-dihydro-1H-isoindol-4-ylmethyl]-benzamide (0.6 g, 62%) as a white solid: mp>260° C.; $^1$H NMR (DMSO-$d_6$) δ 2.01-2.08 (m, 1H), 2.33-2.65 (m, 2H), 2.86-3.00 (m, 1H), 4.40-4.61 (m, 4H, 2CH$_2$), 5.11-5.19 (dd, J=5.0 and 13.2 Hz, 1H, CH), 7.47-7.88 (m, 5H, Ar), 8.12 (d, J=1.9 Hz, 1H, Ar), 9.26 (t, J=5.6 Hz, 1H, NH), 11.02 (s, 1H, NH); $^{13}$C NMR (DMSO-$d_6$) δ 22.56, 31.16, 39.73, 46.25, 51.58, 121.78, 127.60, 128.34, 129.22, 130.73, 130.81, 131.27, 131.65, 134.16, 134.33, 140.23, 164.09, 168.01, 170.98, 172.81; Anal. calcd. for C$_{21}$H$_{17}$N$_3$O$_4$Cl$_2$: C, 56.52; H, 3.84; N, 9.42; Cl, 15.89. Found: C, 56.42; H, 3.79; N, 9.21; Cl, 15.85.

5.37 1-(3-CHLORO-4-METHYLPHENYL)-3-[2-(2,6-DIOXO-PIPERIDIN-3-YL)-1-OXO-2,3-DIHYDRO-1H-ISOINDOL-4-YLMETHYL]UREA

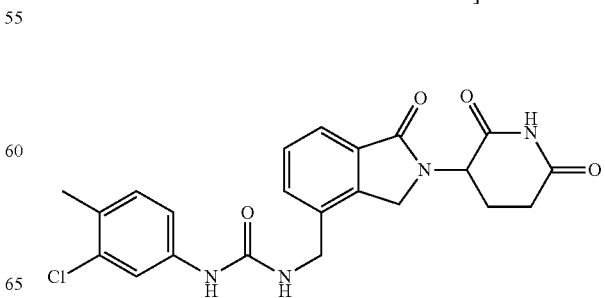

A mixture of 3-(4-aminomethyl-1-oxo-1,3-dihydroisoindol-2-yl)-piperidine-2,6-dione hydrochloride (0.50 g, 1.6 mmol), 3-chloro-4-methylphenyl isocyanate (0.26 g, 1.6 mmol) and diisopropylethylamine (0.40 g, 3.1 mmol) in 10 mL pyridine was warmed to 40° C. with stirring under $N_2$, and the resulting solution was stirred at this temperature for 2 hours. The mixture was cooled, and the solvent was evaporated under vacuum. The residue was chromatographed, eluting with 95:5 methylene chloride-methanol, to provide 0.35 g of the product in 50% yield: mp>260° C.; $^1$H NMR (DMSO-$d_6$) δ 2.00-2.04 (m, 1H), 2.22 (s, 3H), 2.36-2.43 (m, 1H), 2.57-2.64 (m, 1H), 2.86-2.98 (m, 1H), 4.36 (d, J=5.6 Hz, 2H), 4.40 (d, J=17.3 Hz, 1H), 4.54 (d, J=17.3 Hz, 1H), 5.15 (dd, J=13.1 Hz, J=5.0 Hz, 1H), 6.77 (t, J=5.6 Hz, 1H), 7.09-7.19 (m, 2H), 7.48-7.57 (m, 2H), 7.61-7.64 (m, 2H), 8.72 (s, 1H), 11.01 (s, 1H); $^{13}$C NMR (DMSO-$d_6$) δ 18.7, 22.6, 31.2, 39.7, 46.2, 51.6, 116.5, 117.7, 121.6, 127.5, 128.3, 130.4, 131.0, 131.7, 133.0, 135.5, 139.5, 139.9, 155.1, 168.1, 171.0, 172.8; Anal. calcd for $C_{22}H_{21}ClN_4O_4 \cdot 0.2H_2O$: C, 59.45; H, 4.85; N, 12.60. Found: C, 59.28; H, 4.83; N, 12.39.

5.38 1-[2-(2,6-DIOXOPIPERIDIN-3-YL)-1-OXO-2,3-DIHYDRO-1H-ISOINDOL-4-YLMETHYL]-3-NAPHTHALEN-1-YL-UREA

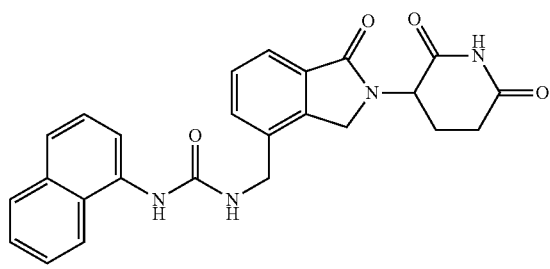 [SMILES: O=C1CCC(N2Cc3c(CNC(=O)Nc4cccc5ccccc45)cccc3C2=O)C(=O)N1]

A heterogeneous mixture of 3-(4-aminomethyl-1-oxo-1,3-dihydroisoindol-2-yl)-piperidine-2,6-dione hydrochloride (0.50 g, 1.6 mmol), 1-naphthyl isocyanate (0.26 g, 1.6 mmol), and triethylamine (4.9 g, 4.9 mmol) in 25 mL THF was stirred under nitrogen at ambient temperature for 18 hours. The solvent was removed under vacuum. The residue was triturated with 3% aqueous HCl (100 mL) for 1 hour and then filtered, and the filter was washed with additional 3% HCl. The resulting solid was dried, triturated with 30 mL refluxing acetone for 1 hour and filtered, and the filter was washed with additional hot acetone. The resulting solid was dried and then triturated with 30 mL refluxing acetonitrile, filtered, and dried, to provide 0.40 g of the product in 56% yield: $^1$H NMR (DMSO-$d_6$) δ 2.00-2.09 (m, 1H), 2.35-2.42 (m, 1H), 2.57-2.63 (m, 1H), 2.86-2.98 (m, 1H), 4.44 (d, J=17.2 Hz, 1H), 4.46 (d, J=5.8 Hz, 2H), 4.58 (d, J=17.2 Hz, 1H), 5.16 (dd, J=13.1 Hz, J=5.1 Hz, 1H), 7.11 (t, J=5.8 Hz, 1H), 7.09-7.67 (m, 7H), 7.90 (dd, J=6.6 Hz, J=2.9 Hz, 1H), 7.95 (d, J=7.4 Hz, 1H), 8.09 (t, J=9.0 Hz, 1H), 8.66 (s, 1H), 11.03 (s, 1H); $^{13}$C NMR (DMSO-$d_6$) δ 22.6, 31.2, 40.0, 46.2, 51.6, 117.0, 121.4, 121.6, 122.4, 125.5, 125.8, 125.9, 128.3, 128.4, 130.4, 131.7, 133.7, 134.9, 135.5, 140.0, 155.7, 168.1, 171.0, 172.8; Anal. calcd for $C_{25}H_{22}N_4O_4$: C, 67.86; H, 5.01; N, 12.66. Found: C, 67.64; H, 4.99; N, 12.28.

5.39 1-[2-(2,6-DIOXOPIPERIDIN-3-YL)-1-OXO-2,3-DIHYDRO-1H-ISOINDOL-4-YLMETHYL]-3-NAPHTHALEN-2-YL-UREA

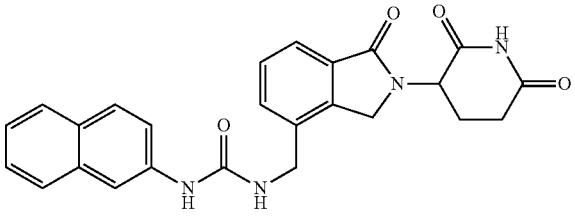 [SMILES: O=C1CCC(N2Cc3c(CNC(=O)Nc4ccc5ccccc5c4)cccc3C2=O)C(=O)N1]

A heterogeneous mixture of 3-(4-aminomethyl-1-oxo-1,3-dihydroisoindol-2-yl)-piperidine-2,6-dione hydrochloride (0.50 g, 1.6 mmol), 2-naphthyl isocyanate (0.26 g, 1.6 mmol), and triethylamine (4.9 g, 4.9 mmol) in 25 mL THF was stirred under nitrogen at ambient temperature for 18 hours. The solvent was removed under vacuum. The residue was triturated with 3% aqueous HCl (100 mL) for 1 hour and then filtered, and the filter was washed with additional 3% HCl. The resulting solid was dried, triturated with 30 mL refluxing acetone for 1 hour, and filtered, and the filter was washed with additional hot acetone. The resulting solid was dried and then triturated with 30 mL refluxing acetonitrile, filtered, and dried, to provide 0.45 g of the product in 63% yield: $^1$H NMR (DMSO-$d_6$) δ 2.01-2.08 (m, 1H), 2.38-2.45 (m, 1H), 2.57-2.65 (m, 1H), 2.86-2.93 (m, 1H), 4.41 (d, J=5.0 Hz, 2H), 4.43 (d, J=17.4 Hz, 1H), 4.57 (d, J=17.4 Hz, 1H), 5.16 (dd, J=13.2 Hz, J=5.1 Hz, 1H), 6.83 (t, J=5.8 Hz, 1H), 7.28-7.79 (m, 9H), 8.02 (d, J=1.8 Hz, 1H), 8.85 (s, 1H), 11.03 (s, 1H); $^{13}$C NMR (DMSO-$d_6$) δ 22.6, 31.2, 39.8, 46.2, 51.6, 112.8, 119.6, 121.6, 123.6, 126.2, 126.8, 127.4, 128.2, 128.3, 128.8, 130.4, 131.7, 133.8, 135.6, 138.0, 139.9, 155.3, 168.1, 171.0, 172.8; Anal. calcd for $C_{25}H_{22}N_4O_4 \cdot 0.2H_2O$: C, 67.31; H, 5.06; N, 12.56. Found: C, 67.37; H, 4.90; N, 12.53.

5.40 2-(2,6-DIOXOPIPERIDIN-3-YL)-4-PHENYLAMINOISOINDOLE-1,3-DIONE

50.40.1 3-Nitrophthalic Acid Dimethyl Ester

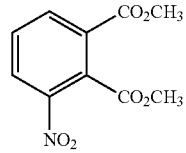

Methyl iodide (30.2 g, 213 mmol) was added to a stirred mixture of 3-nitrophthalic acid (15.0 g, 71.0 mmol) and sodium bicarbonate (23.9 g, 284 mmol) in DMF (150 mL) at room temperature, and the mixture was then heated in an oil bath set to 60° C. for 4 hours. The mixture was then poured into 700 mL of ice water. After the ice melted, the mixture was extracted with ethyl acetate (3×150 mL) and the organic phases were washed with water (7×500 mL), dried (MgSO$_4$) and evaporated, providing 16.2 g of the product as a pale yellow solid in 95% yield: $^1$H NMR (CDCl$_3$) δ 3.95 (s, 3H), 4.02 (s, 3H), 7.69 (t, J=8.1 Hz, 1H), 8.36 (m, 2H).

5.40.2 3-Aminophthalic Acid Dimethyl Ester

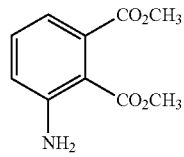 [SMILES: COC(=O)c1cccc(N)c1C(=O)OC]

A mixture of 3:1 ethanol-conc. HCl (200 mL) was cooled to 0° C. and then 3-nitrophthalic acid dimethyl ester (15.0 g, 62.8 mmol) was added. Maintaining the cooling, tin chloride (70.8 g, 314 mmol) was added portionwise, over a period of 15 minutes. Following completion of the addition, the cooling bath was removed, and stirring proceeded at room temperature. After 2 hours, the mixture was neutralized by the addition of solid sodium bicarbonate, and the resulting mixture was extracted with ethyl acetate (3×150 mL) and the combined extracts were washed with water (5×250 mL), were dried (MgSO$_4$) and evaporated, providing 11.3 g of the product as a yellow oil in 86% yield: $^1$H NMR (CDCl$_3$) δ 3.84 (s, 3H), 3.86 (s, 3H), 5.20 (br, 2H), 6.78 (dd, J=8.5 Hz, J=1.0 Hz, 1H), 6.90 (dd, 1H, J=7.3 Hz, J=1.0 Hz, 1H), 7.24 (t, J=7.8 Hz, 1H).

5.40.3 3-Iodophthalic Acid Dimethyl Ester

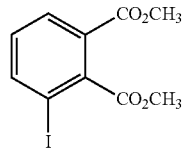 [SMILES: COC(=O)c1cccc(I)c1C(=O)OC]

A solution of 3-aminophthalic acid dimethyl ester (9.5 g, 45.4 mmol) in 1:1 water-conc. HCl (300 mL) was cooled to 0° C., during which a precicipitate formed. A solution of NaNO$_2$ (3.5 g, 50.0 mmol) in 10 mL water was then added slowly, maintaining the temperature between 0-5° C. throughout the addition. Following completion of the addition, the mixture was stirred at the same temperature for 10 minutes, before adding a solution of KI (11.3 g, 68.3 mmol) in 30 mL of 1:1 water-conc. HCl. This solution was added all at once, and then the reaction flask was transferred immediately to an oil bath preheated to 65° C. The mixture was stirred with heating for 10 minutes, and was then cooled in an ice bath. The mixture was extracted with CH$_2$Cl$_2$ (3×150 mL), and the combined organic extracts were washed with water (3×150 mL), dried (MgSO$_4$), and evaporated, and the residue was chromatographed using hexanes-ethyl acetate gradient. The product, which eluted at 17:3 hexanes-ethyl acetate, was a light purple solid, and was then triturated with hexanes to give 9.7 g (67%) of the final product after drying, as a colorless solid: $^1$H NMR (CDCl$_3$) δ 3.90 (s, 3H), 3.99 (s, 3H), 7.19 (t, J=7.9 Hz, 1H), 8.02 (d, J=7.9 Hz, 2H).

5.40.4 3-Phenylaminophthalic Acid Dimethyl Ester

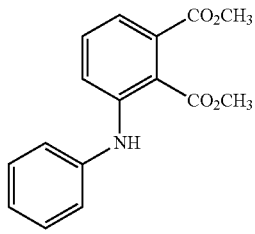 [SMILES: COC(=O)c1cccc(Nc2ccccc2)c1C(=O)OC]

A mixture of 3-iodophthalic acid dimethyl ester (1.0 g, 3.1 mmol), aniline (0.31 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and then filtered through Celite, and the filter was washed with additional CH$_2$Cl$_2$ (30 mL). The filtrate was evaporated, and the residue was chromatographed using a hexanes-ethyl acetate gradient, eluting 0.60 g of the product at 4:1 hexanes-ethyl acetate, in 83% yield: $^1$H NMR (CDCl$_3$) δ 3.87 (s, 3H), 3.89 (s, 3H), 7.03-7.16 (m, 4H), 7.29-7.40 (m, 4H), 8.06 (br, 1H).

5.40.5 3-Phenylaminophthalic Acid

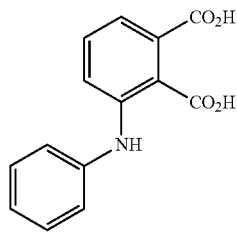 [SMILES: O=C(O)c1cccc(Nc2ccccc2)c1C(=O)O]

A mixture of 3-phenylaminophthalic acid dimethyl ester (0.60 g, 2.1 mmol) and 3N NaOH (50 mL) in ethanol (100 mL) was heated to reflux for 2.5 hours. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.52 g of the product in 97% yield: $^1$H NMR (DMSO-d$_6$) δ 6.92 (t, J=7.3 Hz, 1H), 7.06-7.09 (m, 2H), 7.18-7.29 (m, 3H), 7.33-7.42 (m, 2H), 7.98 (s, 1H).

5.40.6 2-(2,6-Dioxopiperidin-3-yl)-4-Phenylaminoisoindole-1,3-Dione

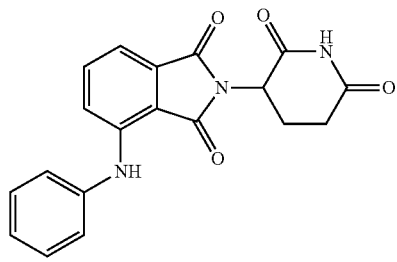 [SMILES: O=C1CCC(N2C(=O)c3cccc(Nc4ccccc4)c3C2=O)C(=O)N1]

A mixture of 3-phenylaminophthalic acid (0.52 g, 2.0 mmol) and rac-α-aminoglutarimide hydrochloride (0.33 g, 2.0 mmol) in pyridine (10 mL) was heated to reflux for 16 hours. The mixture was cooled and evaporated under vacuum. The residue was chromatographed using a hexanes-ethyl acetate gradient, eluting 0.60 g of the product at 4:6 hexanes-ethyl acetate, in 83% yield: mp 214-216° C.; $^1$H NMR (DMSO-$d_6$) δ 1.99-2.09 (m, 1H), 2.53-2.64 (m, 2H), 2.84-2.97 (m, 1H), 5.13 (dd, J=12.6 Hz, J=5.4 Hz, 1H), 7.11-7.16 (m, 1H), 7.25 (d, J=7.0 Hz, 1H), 7.31-7.45 (m, 5H), 7.61 (t, J=7.8 Hz, 1H), 8.45 (s, 1H), 11.14 (s, 1H); $^{13}$C NMR (DMSO-$d_6$) δ 22.1, 31.0, 48.7, 112.0, 113.4, 119.4, 121.9, 124.0, 129.4, 132.5, 136.2, 139.4, 142.8, 167.0, 168.3, 170.0, 172.8; Anal. calcd for $C_{19}H_{15}N_3O_4$: C, 65.32; H, 4.33; N, 12.03. Found: C, 64.93; H, 4.33; N, 11.79.

5.41 2-(2,6-DIOXOPIPERIDIN-3-YL)-4-(3,4-METHYLENE DIOXYPHENYLAMINO)ISOINDOLE-1,3-DIONE

5.41.1 3-(3,4-Methylenedioxyphenylamino)phthalic Acid Dimethyl Ester

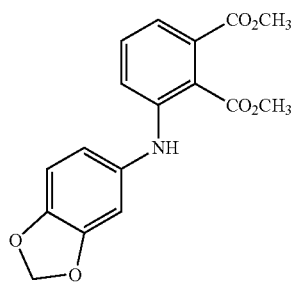 [SMILES: COC(=O)c1cccc(Nc2ccc3c(c2)OCO3)c1C(=O)OC]

A mixture of 3-iodophthalic acid dimethyl ester (1.0 g, 3.1 mmol), 3,4-methylenedioxyaniline (0.43 g, 3.1 mmol), $Pd_2(dba)_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with $CH_2Cl_2$ (10 mL), and then filtered through Celite, and the filter was washed with additional $CH_2Cl_2$ (30 mL). The filtrate was evaporated, and the residue was chromatographed using a hexanes-ethyl acetate gradient, eluting 0.69 g of the product at 85:15 hexanes-ethyl acetate, in 67% yield: $^1$H NMR (CDCl$_3$) δ 3.87 (s, 3H), 3.88 (s, 3H), 5.97 (s, 2H), 6.63 (dd, J=8.2 Hz, J=2.1 Hz, 1H), 6.70 (d, J=2.1 Hz, 1H), 6.78 (d, J=8.2 Hz, 1H), 6.98 (dd, J=7.3 Hz, J=1.1 Hz, 1H), 7.13 (dd, J=7.3 Hz, J=1.1 Hz, 1H), 7.25 (t, J=7.9 Hz, 1H), 8.06 (br, 1H).

5.41.2 3-(3,4-Methylenedioxyphenylamino)phthalic Acid

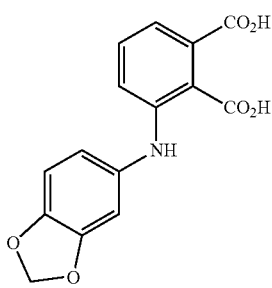 [SMILES: O=C(O)c1cccc(Nc2ccc3c(c2)OCO3)c1C(=O)O]

A mixture of 3-(3,4-methylenedioxyphenylamino)phthalic acid dimethyl ester (0.63 g, 1.9 mmol) and 3N NaOH (50 mL) in ethanol (100 mL) was heated to reflux for 2 hours. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.50 g of the product in 88% yield: $^1$H NMR (DMSO-$d_6$) δ 5.99 (s, 2H), 6.59 (dd, J=8.7 Hz, J=2.1 Hz, 1H), 6.77 (d, J=2.1 Hz, 1H), 6.85 (d, J=8.7 Hz, 1H), 7.04 (dd, J=7.3 Hz, J=0.9 Hz, 1H), 7.13 (dd, J=8.5 Hz, J=0.9 Hz, 1H), 7.31 (t, J=7.9 Hz, 1H), 7.95 (s, 1H).

5.41.3 2-(2,6-Dioxopiperidin-3-yl)-4-(3,4-Methylene dioxyphenylamino)Isoindole-1,3-Dione

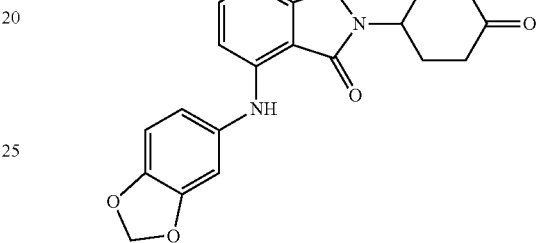

A mixture of 3-(3,4-methylenedioxyphenylamino)phthalic acid (0.50 g, 1.7 mmol) and rac-α-aminoglutarimide hydrochloride (0.29 g, 1.7 mmol) in pyridine (10 mL) was heated to reflux for 16 hours. The mixture was cooled and evaporated under vacuum. The residue was chromatographed using a methylene chloride-methanol gradient, eluting 0.52 g of the product at 95:5 methylene chloride-methanol, in 80% yield: mp>260° C.; $^1$H NMR (DMSO-$d_6$) δ 2.03-2.08 (m, 1H), 2.57-2.63 (m, 2H), 2.83-2.96 (m, 1H), 5.11 (dd, J=12.6 Hz, J=5.3 Hz, 1H), 6.04 (s, 2H), 6.80 (dd, J=8.3 Hz, J=1.9 Hz, 1H), 6.92-6.95 (m, 2H), 7.16-7.22 (m, 2H), 7.56 (t, J=7.8 Hz, 1H), 8.25 (s, 1H), 11.12 (s, 1H); $^{13}$C NMR (DMSO-$d_6$) δ 22.1, 31.0, 48.7, 101.3, 105.5, 108.6, 110.9, 112.7, 116.7, 118.9, 132.3, 133.2, 136.2, 144.1, 144.5, 147.9, 167.1, 168.3, 170.0, 172.8; Anal. calcd for $C_{20}H_{15}N_3O_6 \cdot 0.2H_2O$: C, 60.51; H, 3.91; N, 10.58. Found: C, 60.49; H, 3.62; N, 10.50.

5.42 2-(2,6-DIOXOPIPERIDIN-3-YL)-4-(3,4-DIMETHOXYPHENYL AMINO)ISOINDOLE-1,3-DIONE

5.42.1 3-(3,4-Dimethoxyphenylamino)Phthalic Acid Dimethyl Ester

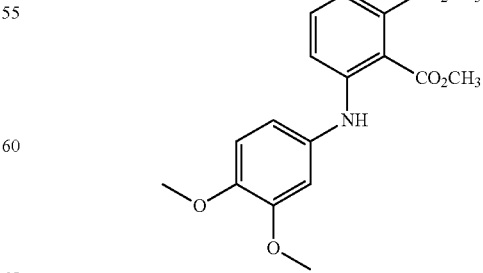

A mixture of 3-iodophthalic acid dimethyl ester (1.0 g, 3.1 mmol), 3,4-dimethoxyaniline (0.48 g, 3.1 mmol), $Pd_2(dba)_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with $CH_2Cl_2$ (10 mL), and then filtered through Celite, and the filter was washed with additional $CH_2Cl_2$ (30 mL). The filtrate was evaporated, and the residue was chromatographed using a hexanes-ethyl acetate gradient, eluting 0.80 g of the product at 65:35 hexanes-ethyl acetate, in 74% yield: $^1$H NMR (CDCl$_3$) δ 3.84 (s, 3H), 3.87 (s, 3H), 3.89 (s, 6H), 6.71-6.77 (m, 2H), 6.85 (d, J=8.3 Hz, 1H), 6.98 (d, J=6.9 Hz, 1H), 7.14 (d, J=7.7 Hz, 1H), 7.25 (t, J=7.9 Hz, 1H), 8.08 (br, 1H).

5.42.2 3-(3,4-Dimethoxyphenylamino)Phthalic Acid

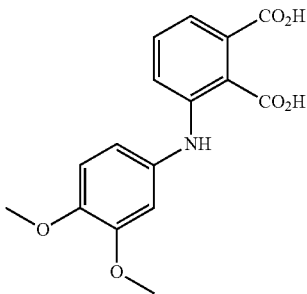 [SMILES: COc1ccc(Nc2cccc(C(=O)O)c2C(=O)O)cc1OC]

A mixture of 3-(3,4-dimethoxyphenylamino)phthalic acid dimethyl ester (0.80 g, 2.3 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.59 g of the product in 81% yield: $^1$H NMR (DMSO-d$_6$) δ 3.72 (s, 6H), 6.68 (dd, J=8.6 Hz, J=2.4 Hz, 1H), 6.81 (d, J=2.4 Hz, 1H), 6.90 (d, J=8.6 Hz, 1H), 7.00 (d, J=7.3 Hz, 1H), 7.16 (d, J=8.4 Hz, 1H), 7.30 (t, J=7.9 Hz, 1H), 7.98 (br, 1H).

5.42.3 2-(2,6-Dioxopiperidin-3-yl)-4-(3,4-Dimethoxyphenyl amino)Isoindole-1,3-Dione

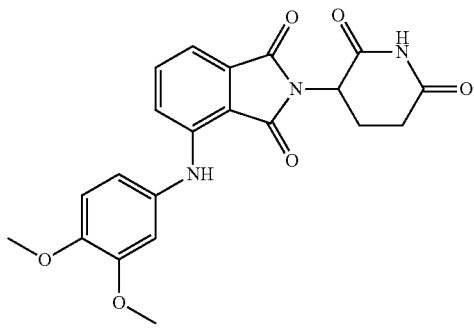 [SMILES: COc1ccc(Nc2cccc3c2C(=O)N(C2CCC(=O)NC2=O)C3=O)cc1OC]

A mixture of 3-(3,4-dimethoxyphenylamino)phthalic acid (0.59 g, 1.9 mmol) and rac-α-aminoglutarimide hydrochloride (0.32 g, 1.9 mmol) in pyridine (10 mL) was heated to reflux for 16 hours. The mixture was cooled and evaporated under vacuum. The residue was chromatographed using a methylene chloride-methanol gradient, eluting 0.64 g of the product at 96:4 methylene chloride-methanol, in 85% yield: mp>215-217° C.; $^1$H NMR (CDCl$_3$) δ 2.15-2.19 (m, 1H), 2.74-2.96 (m, 3H), 3.88 (s, 3H), 3.91 (s, 3H), 4.97 (dd, J=11.8 Hz, J=5.1 Hz, 1H), 6.78-6.81 (m, 1H), 6.85-6.91 (m, 2H), 7.16-7.21 (m, 2H), 7.45 (t, J=7.8 Hz, 1H), 7.87 (s, 1H), 8.07 (s, 1H); $^{13}$C NMR (CDCl$_3$) δ 22.8, 31.4, 49.0, 56.0, 56.2, 108.6, 110.9, 111.8, 113.2, 116.5, 118.5, 131.7, 132.4, 135.9, 145.2, 147.1, 149.8, 167.4, 168.2, 169.4, 170.8; Anal. calcd for $C_{21}H_{19}N_3O_6$: C, 61.61; H, 4.68; N, 10.26. Found: C, 61.47; H, 4.52; N, 10.12.

5.43 2-(3-METHYL-2,6-DIOXOPIPERIDIN-3-YL)-4-PENTYLAMINO ISOINDOLE-1,3-DIONE

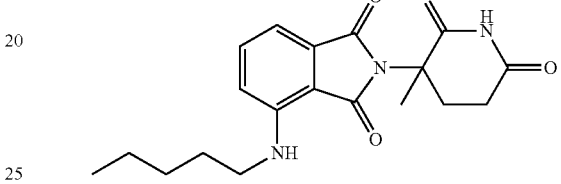

Step 1:
To a stirred solution of dimethyl 3-aminophthalate (0.84 g, 4.0 mmol) in $CH_2Cl_2$ (40 mL), was added pentanal (0.67 g, 8.0 mmol) and acetic acid (1.4 mL). The mixture was stirred for 5 minutes, followed by addition of sodium triacetoxyborohydride (2.5 g, 12 mmol). The mixture was stirred at ambient temperature overnight under an atmosphere of nitrogen. The reaction mixture was diluted with 60 mL of $CH_2Cl_2$, washed with water (2×100 mL), saturated aqueous sodium bicarbonate (2×100 mL) and brine (100 mL), and dried (MgSO$_4$). The solvent was evaporated, providing 1.1 g of a light yellow oil.

Step 2:
A mixture of the product from step 1 and 5N NaOH (8 mL) in methanol (20 mL) was stirred overnight. The solvent was evaporated, and the resulting white solid was dissolved in water (50 mL), washed with diethyl ether (2×100 mL), and acidified to pH 2-3 (conc. HCl). The aqueous mixture was then extracted with ethyl acetate (3×75 mL). The combined organic extracts were washed with water (100 mL) and brine (100 mL), and dried (MgSO$_4$) and evaporated, providing a yellow oil.

Step 3:
The product from step 2 and α-methyl-α-aminoglutarimide hydrochloride (0.71 g, 4.0 mmol) were dissolved in pyridine (40 mL), and the resulting mixture was heated to reflux for 4 hours. The mixture was cooled to ambient temperature, and the solvent was evaporated in vacuo. The residue was dissolved in $CH_2Cl_2$ (120 mL), washed with water (2×100 mL), 0.1N HCl (2×100 mL), brine (100 mL), and was dried (MgSO$_4$). The solvent was evaporated in vacuo, and the resulting yellow solid was triturated in diethyl ether (10 mL), providing 0.63 g of product in 44% overall yield (3 steps): mp 96-98° C.; $^1$H NMR (DMSO-d$_6$) δ 0.87 (t, J=5.9 Hz, 3H), 1.32 (m, 4H), 1.57 (m, 2H), 1.88 (s, 3H), 1.96-2.07 (m, 1H), 2.48-2.79 (m, 3H), 3.26 (q, J=6.4 Hz, 2H), 6.56 (t, J=5.5 Hz, 1H), 6.94 (d, J=7.0 Hz, 1H), 7.04 (d, J=8.5 Hz, 1H), 7.55 (t, J=7.8 Hz, 1H), 11.00 (s, 1H); $^{13}$C NMR (DMSO-d$_6$) δ 13.90, 20.97, 21.87, 28.35, 28.52, 28.63, 29.26, 41.77, 58.39, 108.72, 109.91, 116.89, 131.99, 136.18, 146.24, 167.98,

5.44 4-(CYCLOPROPYLMETHYLAMINO)-2-(2,6-DIOXOPIPERIDIN-3-YL)ISOINDOLE-1,3-DIONE

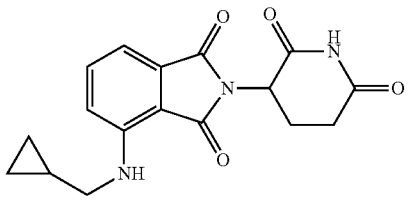 [SMILES: O=C1CCC(N2C(=O)c3cccc(NCC4CC4)c3C2=O)C(=O)N1]

Step 1:

To a stirred solution of dimethyl 3-aminophthalate (1.1 g, 5.0 mmol) in $CH_2Cl_2$ (40 mL) was added cyclopropanecarboxaldehyde (0.70 g, 10.0 mmol) and acetic acid (1.7 mL). The mixture was stirred for 5 minutes, followed by addition of sodium triacetoxyborohydride (3.2 g, 15 mmol). The mixture was stirred at ambient temperature overnight under an atmosphere of nitrogen. The reaction mixture was diluted with 50 mL of $CH_2Cl_2$, washed with water (2×100 mL), saturated aqueous sodium bicarbonate (100 mL), and brine (100 mL), and dried ($MgSO_4$). Upon evaporation of the solvent, 1.2 g of a yellow oil was obtained.

Step 2:

A mixture of the product from step 1 and 5N KOH (10 mL) in methanol (15 mL) was stirred overnight. The solvent was evaporated, and the resulting white solid was dissolved in water (30 mL), washed with diethyl ether (2×50 mL), acidified to pH 2-3 (conc. HCl), and extracted with ethyl acetate (3×100 mL). The combined organic extracts were washed with brine (100 mL), dried ($MgSO_4$), and evaporated, providing a yellow solid, which was dried under high vacuum to afford 0.81 g of a yellow solid.

Step 3:

The product from step 2 and rac-α-aminoglutarimide hydrochloride (0.73 g, 4.5 mmol) were dissolved in pyridine (20 mL), and the resulting mixture was heated to reflux for 18 hours. The mixture was cooled to ambient temperature, and the solvent was evaporated in vacuo. The residue was dissolved in $CH_2Cl_2$ (100 mL), washed with water (3×100 mL) and brine (100 mL), and dried ($MgSO_4$). The solution was treated with Norite (~2 g), stirred for 15 minutes, and filtered through Celite. The yellow filtrate was evaporated in vacuo to give a yellow solid, which was chromatographed eluting with 9:1 methylene chloride-ethyl acetate. The resulting material was further purified by preparative HPLC, eluting with 3:2 water-acetonitrile and providing 0.59 g of the product as a yellow solid, in 36% overall yield (3 steps): mp 162-164° C.; $^1H$ NMR (DMSO-$d_6$) δ 0.25-0.35 (m, 2H), 0.46-0.53 (m, 2H), 1.06-1.16 (m, 1H), 2.02-2.09 (m, 1H), 2.50-2.63 (m, 2H), 2.82-2.97 (m, 1H), 3.18 (t, J=6.3 Hz, 2H), 5.06 (dd, J=12.5 Hz, J=5.4 Hz, 1H), 6.58 (t, J=5.6 Hz, 1H), 7.03 (d, J=7.0 Hz, 1H), 7.13 (d, J=8.6 Hz, 1H), 7.58 (t, J=7.9 Hz, 1H), 11.11 (s, 1H); $^{13}C$ NMR (DMSO-$d_6$) δ 3.21, 10.61, 22.13, 30.95, 46.22, 48.54, 108.97, 110.47, 117.36, 132.10, 136.23, 146.38, 167.26, 168.97, 170.04, 172.76; Anal. calcd for $C_{17}H_{17}N_3O_4 \cdot 0.97H_2O$: C, 61.77; H, 5.29; N, 12.71. Found: C, 61.39; H, 5.24; N, 12.55.

169.91, 172.17, 172.46; Anal. calcd for $C_{19}H_{23}N_3O_4$: C, 63.85; H, 6.49; N, 11.76. Found: C, 63.63; H, 6.27; N, 11.68.

5.45 [2-(2,6-DIOXOPIPERIDIN-3-YL)-1,3-DIOXO-2,3-DIHYDRO-1H-ISOINDOL-4-YLAMINO]ACETIC ACID

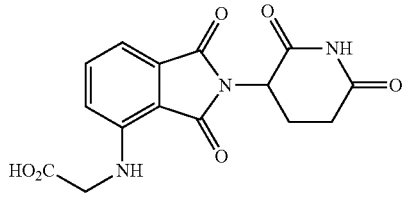 [SMILES: O=C(O)CNc1cccc2c1C(=O)N(C1CCC(=O)NC1=O)C2=O]

Step 1:

To a stirred solution of dimethyl 3-aminophthalate (4.2 g, 20 mmol) in $CH_2Cl_2$ (100 mL), were added glyoxylic acid (3.7 g, 40 mmol) and acetic acid (6.9 mL). The mixture was stirred for 5 minutes, followed by addition of sodium triacetoxyborohydride (12 g, 60 mmol). The mixture was stirred at ambient temperature overnight under an atmosphere of nitrogen. The reaction mixture was washed with 0.1N HCl (3×100 mL) and brine (100 mL), and dried ($MgSO_4$). The solvent was evaporated leaving an oily residue, which was dissolved in sat. aq. sodium bicarbonate (50 mL). This aqueous solution was washed with ethyl acetate (3×50 mL) and then acidified to pH 2-3 (conc. HCl). This mixture was extracted with ethyl acetate (3×100 mL), and the combined extracts were washed with brine (100 mL), and dried ($MgSO_4$). Evaporation provided 3.4 g of an off-white solid (63%).

Step 2:

A mixture of the product from step 1 and 5N KOH (30 mL) was stirred overnight at room temperature. The mixture was then acidified to pH 2-3 (conc. HCl). The solvent was evaporated in vacuo to give a yellow solid residue that was used without further purification.

Step 3:

The product from step 2 and rac-α-aminoglutarimide hydrochloride (2.1 g, 13 mmol) were dissolved in pyridine (60 mL), and the resulting mixture was heated to reflux for 6 hours. The mixture was cooled to ambient temperature, and the solvent was evaporated in vacuo. The residue was dissolved in sat. aq. sodium bicarbonate (100 mL) and washed with ethyl acetate (3×100 mL). The aqueous phase was acidified to pH 2-3 (conc. HCl), and the resulting precipitate was isolated by filtration and washed with additional water (30 mL), and then ethyl acetate (50 mL). The solid was triturated with 50 mL of ethyl acetate overnight, filtered and dried under high vacuum, providing 3.6 g of the product in 84% yield (final 2 steps): $^1H$ NMR (DMSO-$d_6$) δ 1.98-2.07 (m, 1H), 2.47-2.62 (m, 2H), 2.83-2.95 (m, 1H), 4.11 (d, J=5.4 Hz, 2H), 5.08 (dd, J=12.3 Hz, J=5.1 Hz, 1H), 6.84 (br, 1H), 6.99 (d, J=8.5 Hz, 1H), 7.07 (d, J=7.0 Hz, 1H), 7.58 (t, J=8.4 Hz, 1H), 11.12 (s, 1H), 12.93 (br, 1H).

5.46 2-(2,6-DIOXOPIPERIDIN-3-YL)-4-(2-METHOXY-1-METHYLETHYL AMINO)ISOINDOLE-1,3-DIONE

5.46.1 3-Bromophthalic Acid

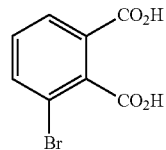

3-Bromo-2-methylbenzoic acid (2.15 g, 10.0 mmol) was dissolved in 100 mL of 0.5N KOH. To this clear solution, was added KMnO$_4$. The resulting mixture was heated to 70° C. for 16 hours. To the reaction mixture was added ethanol (30 mL), resulting in formation of a black precipitate of MnO$_2$. NaHSO$_3$ (3.0 g, 29 mmol) was added, followed by the slow addition of conc. HCl, until a clear, colorless, homogeneous solution was obtained. The solution was acidified further to pH 2-3 to give a white precipitate. The mixture was extracted with ethyl acetate (3×100 mL), and the combined extracts were washed with brine (150 mL), and dried (MgSO$_4$). The solvent was evaporated, providing 2.5 g of the product as a white solid (100%): $^1$H NMR (DMSO-d$_6$) δ 7.47 (t, J=7.9 Hz, 1H), 7.92 (t, J=7.3 Hz, 2H), 13.49 (br, 2H).

5.46.2 3-Bromophthalic Acid Dimethyl Ester

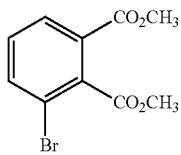 [SMILES: COC(=O)c1cccc(Br)c1C(=O)OC]

To a stirred solution of 3-bromophthalic acid (2.5 g, 10 mmol) in DMF (20 mL), were added iodomethane (3.1 g, 22 mmol) and sodium bicarbonate (1.8 g, 22 mmol). The mixture was heated to 70° C. with stirring for 26 hours. The solvent was evaporated in vacuo, and the residue was partitioned between diethyl ether (100 mL) and water (100 mL). The organic phase was washed with sat. sodium bicarbonate (100 mL) and brine (100 mL), and dried (MgSO$_4$). The solvent was evaporated in vacuo, and dried under high vacuum to afford 2.4 g (86%) of the product as a white solid: $^1$H NMR (DMSO-d$_6$) δ 3.84 (s, 3H), 3.86 (s, 3H), 7.57 (t, J=8.0 Hz, 1H), 8.01 (d, J=8.1 Hz, 2H).

5.46.3 3-(2-Methoxy-1-Methylethylamino)Phthalic Acid Dimethyl Ester

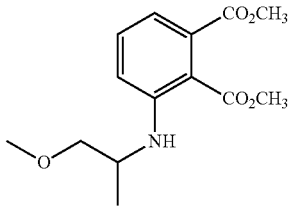 [SMILES: COCC(C)Nc1cccc(C(=O)OC)c1C(=O)OC]

To a stirred solution of 3-Bromophthalic acid dimethyl ester (0.82 g, 3.0 mmol) in toluene (20 mL), were added S-BINAP (56 mg, 0.09 mmol), Pd$_2$(dba)$_3$ (55 mg, 0.06 mmol), Cs$_2$CO$_3$ (1.37 g, 4.2 mmol), and 1-methoxy-2-propanamine (0.32 g, 3.6 mmol), and the resulting mixture was heated to reflux with stirring under nitrogen for 24 hours. The mixture was allowed to cool to room temperature, and diethyl ether was added (70 mL). The mixture was filtered, and the filtrate was evaporated in vacuo. The residue was chromatographed eluting with 17:3 hexanes-ethyl acetate. The resulting material was further purified by preparative HPLC, eluting with 11:9 water-acetonitrile, and providing 0.32 g of the product in 38% yield: $^1$H NMR (DMSO-d$_6$) δ1.14 (d, J=6.4 Hz, 3H), 3.29 (s, 3H), 3.37 (d, J=4.8 Hz, 2H), 3.74 (s, 3H), 3.77 (s, 3H), 3.74-3.80 (m, 1H), 6.53 (d, J=7.8 Hz, 1H), 6.76 (d, J=7.3 Hz, 1H), 6.99 (d, J=8.6 Hz, 1H), 7.38 (t, J=7.8 Hz, 1H).

5.46.4 2-(2,6-Dioxopiperidin-3-yl)-4-(2-Methoxy-1-Methylethylamino)Isoindole-1,3-Dione

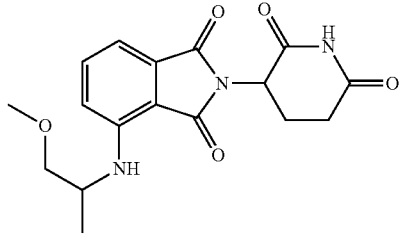 [SMILES: COCC(C)Nc1cccc2c1C(=O)N(C1CCC(=O)NC1=O)C2=O]

Step 1:
A mixture of 3-(2-methoxy-1-methylethylamino)phthalic acid dimethyl ester (0.47 g, 1.7 mmol) and 5N KOH (4 mL) in methanol (10 mL) was stirred at room temperature for 26 hours. The solvent was removed under vacuum, and water (30 mL) was added. The mixture was washed with diethyl ether (2×50 mL), and the aqueous phase was acidified to pH 2 (conc. HCl) and extracted with ethyl acetate (3×75 mL). The combined ethyl acetate extracts were washed with brine (100 mL), dried (MgSO$_4$), and the solvent was evaporated.

Step 2:
The product from Step 1 and rac-α-aminoglutarimide hydrochloride (0.32 g, 2.0 mmol) were dissolved in pyridine (20 mL), and the resulting mixture was heated to reflux for 8 hours. The mixture was cooled to ambient temperature, and the solvent was evaporated in vacuo. The residue was dissolved in CH$_2$Cl$_2$ (100 mL), washed with water (3×100 mL) and brine (100 mL), and dried (MgSO$_4$), and the solvent was evaporated in vacuo. Following trituration with diethyl ether (30 mL), 350 mg of the product was obtained as a yellow solid (64% yield, two steps): mp 193-195° C.; $^1$H NMR (DMSO-d$_6$) δ 1.19 (d, J=6.3 Hz, 3H), 2.01-2.06 (m, 1H), 2.62-2.45 (m, 2H), 2.82-2.94 (m, 1H), 3.30 (s, 3H), 3.43 (d, J=4.2 Hz, 2H), 3.97 (m, 1H), 5.06 (dd, J=12.4 Hz, J=5.0 Hz, 1H), 6.39 (d, J=8.4 Hz, 1H), 7.04 (d, J=7.0 Hz, 1H), 7.16 (d, J=8.6 Hz, 1H), 7.59 (t, 7.8 Hz, 1H), 11.12 (s, 1H); $^{13}$C NMR (DMSO-d$_6$) δ 17.45, 22.12, 30.96, 46.87, 48.55, 58.52, 75.18, 109.14, 110.66, 117.55, 132.11, 136.31, 145.74, 167.19, 169.11, 170.05, 172.77; Anal. calcd for C$_{17}$H$_{19}$N$_3$O$_5$: C, 59.12; H, 5.55; N, 12.17. Found: C, 58.83; H, 5.44; N, 12.01.

5.47 4-(4-tert-BUTYLPHENYLAMINO)-2-(2,6-DIOXOPIPERIDIN-3-YL)ISOINDOLE-1,3-DIONE

5.47.1 3-(4-tert-Butylphenylamino)phthalic acid dimethyl ester

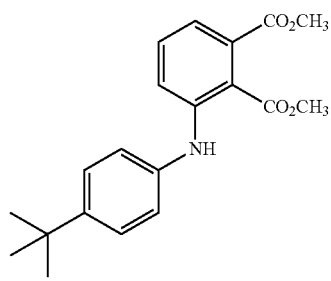 [SMILES: COC(=O)c1cccc(Nc2ccc(C(C)(C)C)cc2)c1C(=O)OC]

A mixture of 3-iodophthalic acid dimethyl ester (1.0 g, 3.1 mmol), 4-tert-butylaniline (0.46 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with $CH_2Cl_2$ (10 mL), and filtered through Celite, and the filter was washed with additional $CH_2Cl_2$ (30 mL). The filtrate was evaporated, and the residue was chromatographed using a hexanes-ethyl acetate gradient, eluting 0.78 g of the product at 85:15 hexanes-ethyl acetate, in 74% yield: $^1$H NMR ($CDCl_3$) δ 1.32 (s, 9H), 3.86 (s, 3H), 3.88 (s, 3H), 7.01-7.11 (m, 3H), 7.27-7.36 (m, 4H), 8.07 (br, 1H).

5.47.2 3-(4-tert-Butylphenylamino)phthalic acid

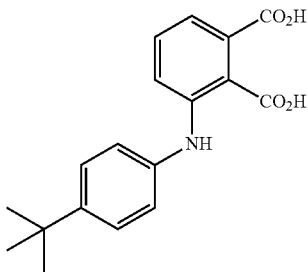 [SMILES: CC(C)(C)c1ccc(Nc2cccc(C(=O)O)c2C(=O)O)cc1]

A mixture of 3-(4-tert-butylphenylamino)phthalic acid dimethyl ester (0.70 g, 2.1 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried ($MgSO_4$), and evaporated. The brown residue was dissolved in 15 mL of 1:1 hexanes-ether. Addition of 35 mL hexanes resulted in precipitation of the product as a bright yellow solid, providing 0.50 g in 78% yield: $^1$H NMR ($CDCl_3$) δ 1.33 (s, 9H), 7.11-7.15 (m, 3H), 7.33-7.39 (m, 4H).

5.47.3 4-(4-tert-Butylphenylamino)-2-(2,6-dioxopiperidin-3-yl)isoindole-1,3-dione

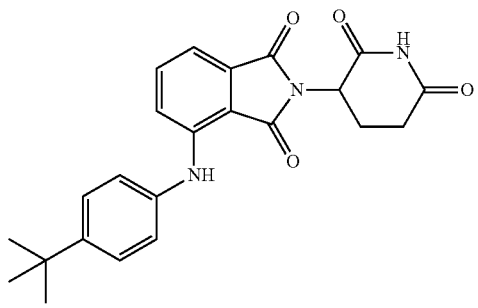 [SMILES: CC(C)(C)c1ccc(Nc2cccc3c2C(=O)N(C2CCC(=O)NC2=O)C3=O)cc1]

A mixture of 3-(4-tert-butylphenylamino)phthalic acid (0.50 g, 1.6 mmol) and rac-α-aminoglutarimide hydrochloride (0.26 g, 1.6 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 1:1 hexanes-ethyl acetate, eluting 0.60 g of the product, in 92% yield: mp 228-230° C.; $^1$H NMR ($CDCl_3$) δ 1.34 (s, 9H), 2.14-2.19 (m, 1H), 2.73-2.96 (m, 3H), 4.96 (dd, J=11.9 Hz, J=5.1 Hz, 1H), 7.16-7.22 (m, 3H), 7.33-7.49 (m, 4H), 7.98 (s, 1H), 8.07 (s, 1H); $^{13}$C NMR ($CDCl_3$) δ 22.8, 31.3, 31.4, 34.5, 49.0, 111.2, 113.4, 118.6, 122.7, 126.5, 132.5, 135.8, 136.1, 144.4, 148.1, 167.4, 168.4, 169.3, 171.1; Anal. calcd for $C_{23}H_{23}N_3O_4 \cdot 0.25H_2O$: C, 67.39; H, 5.78; N, 10.25. Found: C, 67.42; H, 5.65; N, 10.15.

5.48 4-(4-ISOPROPYLPHENYLAMINO)-2-(2,6-DIOXOPIPERIDIN-3-YL)ISOINDOLE-1,3-DIONE

5.48.1 3-(4-Isopropylphenylamino)phthalic acid dimethyl ester

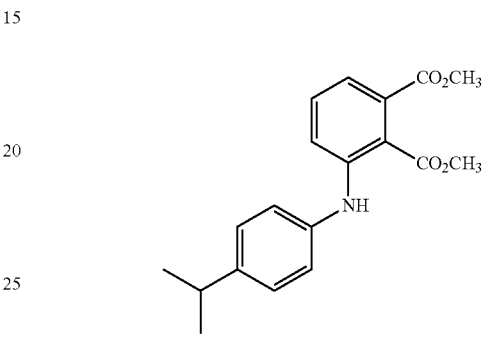

A mixture of 3-iodophthalic acid dimethyl ester (1.0 g, 3.1 mmol), 4-isopropylaniline (0.42 g, 3.1 mmol), $Pd_2(dba)_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with $CH_2Cl_2$ (10 mL), and filtered through Celite, and the filter was washed with additional $CH_2Cl_2$ (30 mL). The filtrate was evaporated, and the residue was chromatographed using a hexanes-ethyl acetate gradient, eluting 0.70 g of the product at 85:15 hexanes-ethyl acetate, in 70% yield: $^1$H NMR ($CDCl_3$) δ 1.25 (s, J=6.8 Hz, 6H), 2.90 (m, 1H), 3.86 (s, 3H), 3.88 (s, 3H), 7.01-7.13 (m, 3H), 7.27-7.34 (m, 4H), 8.07 (br, 1H).

5.48.2 3-(4-Isopropylphenylamino)phthalic acid

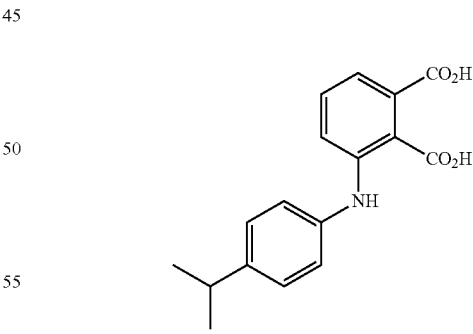

A mixture of 3-(4-isopropylphenylamino)phthalic acid dimethyl ester (0.70 g, 2.1 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried ($MgSO_4$), and evaporated, providing 0.64 g in quantitative yield: ¹H NMR (DMSO-d₆) δ 1.18 (d, J=6.9 Hz, 6H), 2.84 (m, 1H), 7.02-7.06 (m, 2H), 7.08-7.18 (m, 3H), 7.26-7.37 (m, 2H), 7.99 (br, 1H).

5.48.3 4-(4-Isopropylphenylamino)-2-(2,6-dioxopiperidin-3-yl)isoindole-1,3-dione

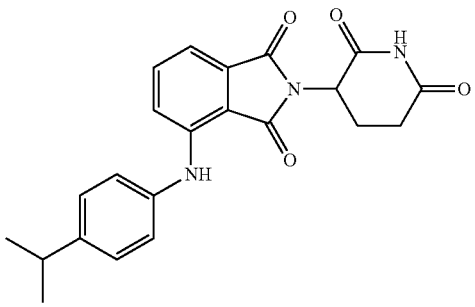

A mixture of 3-(4-isopropylphenylamino)phthalic acid (0.64 g, 2.1 mmol) and rac-α-aminoglutarimide hydrochloride (0.35 g, 2.1 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 1:1 hexanes-ethyl acetate, eluting 0.74 g of the product, in 89% yield: mp 138-140° C.; ¹H NMR (DMSO-d₆) δ 1.21 (d, J=6.9 Hz, 6H), 2.04-2.08 (m, 1H), 2.52-2.64 (m, 2H), 2.84-2.94 (m, 2H), 5.13 (dd, J=12.6 Hz, J=5.3 Hz, 1H), 7.19-7.30 (m, 5H), 7.35 (d, J=8.5 Hz, 1H), 7.58 (t, J=7.8 Hz, 1H), 8.35 (s, 1H), 11.15 (s, 1H); ¹³C NMR (DMSO-d₆) δ 22.1, 23.9, 31.0, 32.9, 48.7, 111.3, 113.0, 119.0, 122.5, 127.2, 132.4, 136.2, 136.9, 143.3, 144.5, 167.1, 168.4, 170.0, 172.8; Anal. calcd for $C_{22}H_{21}N_3O_4$: C, 67.51; H, 5.41; N, 10.74. Found: C, 67.27; H, 5.36; N, 10.64.

5.49 2-(2,6-DIOXOPIPERIDIN-3-YL)-4-(INDAN-5-YLAMINO)-ISOINDOLE-1,3-DIONE

5.49.1 3-(Indan-5-ylamino)phthalic acid dimethyl ester

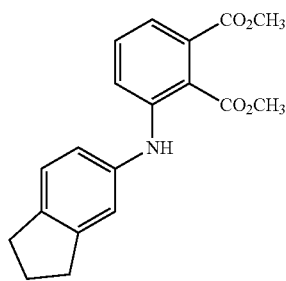 [SMILES: COC(=O)c1cccc(Nc2ccc3c(c2)CCC3)c1C(=O)OC]

A mixture of 3-iodophthalic acid dimethyl ester (1.0 g, 3.1 mmol), 5-aminoindan (0.42 g, 3.1 mmol), Pd₂(dba)₃ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH₂Cl₂ (10 mL), and filtered through Celite, and the filter was washed with additional CH₂Cl₂ (30 mL). The filtrate was evaporated, and the residue was chromatographed using a hexanes-ethyl acetate gradient, eluting 0.82 g of the product at 85:15 hexanes-ethyl acetate, in 82% yield: ¹H NMR (CDCl₃) δ 2.09 (m, 2H), 2.88 (t, J=7.4 Hz, 4H), 3.86 (s, 3H), 3.88 (s, 3H), 6.93 (dd, J=7.9 Hz, J=1.8 Hz, 1H), 6.99-7.06 (m, 2H), 7.12-7.21 (m, 1H), 7.25-7.29 (m, 1H), 7.40-7.71 (m, 1H), 8.07 (br, 1H).

5.49.2 2-(2,6-Dioxo-piperidin-3-yl)-4-(indan-5-ylamino)-isoindole-1,3-dione

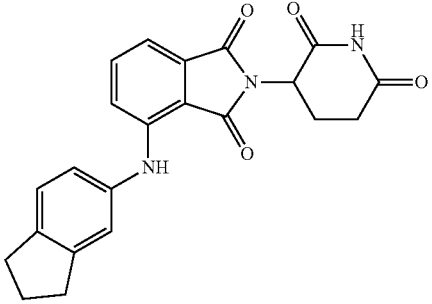 [SMILES: O=C1CCC(N2C(=O)c3cccc(Nc4ccc5c(c4)CCC5)c3C2=O)C(=O)N1]

Step 1:

A mixture of 3-(indan-5-ylamino)phthalic acid dimethyl ester (0.80 g, 2.5 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO₄), and evaporated, providing 0.14 g.

Step 2:

The product from Step 1 and rac-α-aminoglutarimide hydrochloride (0.082 g, 0.5 mmol) in pyridine (5 mL) were heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 1:1 hexanes-ethyl acetate, eluting 0.14 g of the product, in 15% yield for the final two steps: mp 230-232° C.; ¹H NMR (CDCl₃) δ 2.05-2.19 (m, 3H), 2.72-2.95 (m, 7H), 4.96 (dd, J=12.0 Hz, J=5.1 Hz, 1H), 7.02 (d, J=7.9 Hz, 1H), 7.11 (s, 1H), 7.19 (d, J=7.2 Hz, 1H), 7.23 (d, J=7.9 Hz, 1H), 7.30 (d, J=8.5 Hz, 1H), 7.45 (dd, J=8.5 Hz, J=7.2 Hz, 1H), 7.96 (s, 1H), 8.02 (s, 1H); ¹³C NMR (CDCl₃) δ 22.8, 25.7, 31.4, 32.4, 33.0, 49.0, 110.1, 113.2, 118.6, 119.6, 121.4, 125.2, 132.4, 135.8, 136.8, 141.4, 144.8, 146.0, 167.4, 168.4, 169.3, 170.8; Anal. calcd for $C_{23}H_{19}N_3O_4$: C, 67.86; H, 4.92; N, 10.79. Found: C, 67.69; H, 4.91; N, 10.61.

5.50 4-(2,4-DIMETHOXYPHENYLAMINO)-2-(2,6-DIOXOPIPERIDIN-3-YL)ISOINDOLE-1,3-DIONE

5.50.1 3-(2,4-Dimethoxyphenylamino)phthalic acid dimethyl ester

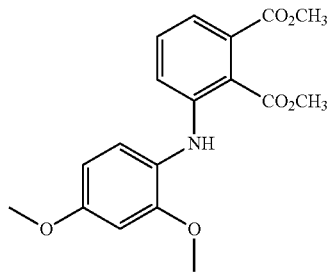 [SMILES: COC(=O)c1cccc(Nc2ccc(OC)cc2OC)c1C(=O)OC]

A mixture of 3-iodophthalic acid dimethyl ester (1.0 g, 3.1 mmol), 2,4-dimethoxyaniline (0.48 g, 3.1 mmol), $Pd_2(dba)_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with $CH_2Cl_2$ (10 mL), and filtered through Celite, and the filter was washed with additional $CH_2Cl_2$ (30 mL). The filtrate was evaporated, and the residue was chromatographed using a hexanes-ethyl acetate gradient, eluting 0.87 g of the product at 70:30 hexanes-ethyl acetate, in 81% yield: $^1H$ NMR ($CDCl_3$) δ 3.81 (s, 6H), 3.87 (s, 6H), 6.46 (dd, J=8.6 Hz, J=2.6 Hz, 1H), 6.54 (d, J=2.6 Hz, 1H), 6.98 (dd, J=7.3 Hz, J=0.9 Hz, 1H), 7.09 (dd, J=8.0 Hz, J=0.9 Hz, 1H), 7.16 (d, J=8.6 Hz, 1H), 7.23 (t, J=7.3 Hz, 1H), 7.92 (br, 1H).

5.50.2 3-(2,4-Dimethoxyphenylamino)phthalic acid

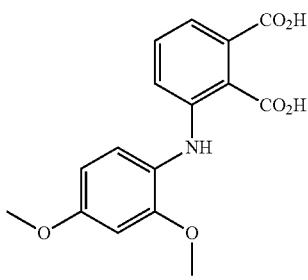 [SMILES: COc1ccc(Nc2cccc(C(=O)O)c2C(=O)O)c(OC)c1]

A mixture of 3-(2,4-dimethoxyphenylamino)phthalic acid dimethyl ester (0.85 g, 2.5 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried ($MgSO_4$), and evaporated, providing 0.76 g in 97% yield: $^1H$ NMR ($CDCl_3$) δ 3.82 (s, 3H), 3.84 (s, 3H), 6.52 (dd, J=8.6 Hz, J=2.5 Hz, 1H), 6.57 (d, J=2.5 Hz, 1H), 7.11 (d, J=8.6 Hz, 1H), 7.22-7.26 (m, 2H), 7.52 (t, J=7.8 Hz, 1H), 7.61 (br, 1H).

5.50.3 4-(2,4-Dimethoxyphenylamino)-2-(2,6-dioxopiperidin-3-yl)isoindole-1,3-dione

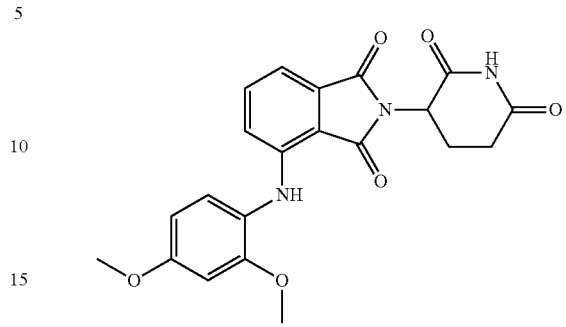

A mixture of 3-(2,4-dimethoxyphenylamino)phthalic acid (0.75 g, 2.4 mmol) and rac-α-aminoglutarimide hydrochloride (0.40 g, 2.4 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed using a hexanes-ethyl acetate gradient, eluting 0.64 g of the product at 25:75 hexanes-ethyl acetate, in 67% yield: mp 208-210° C.; $^1H$ NMR (DMSO-$d_6$) δ 2.04-2.09 (m, 1H), 2.54-2.64 (m, 2H), 2.83-2.92 (m, 1H), 3.78 (s, 3H), 3.79 (s, 3H), 5.12 (dd, J=12.7 Hz, J=5.4 Hz, 1H), 6.57 (dd, J=8.6 Hz, J=2.6 Hz, 1H), 6.71 (d, J=2.6 Hz, 1H), 7.00 (d, J=8.6 Hz, 1H), 7.15 (d, J=7.0 Hz, 1H), 7.29 (d, J=8.7 Hz, 1H), 7.54 (t, J=7.9 Hz, 1H), 7.95 (s, 1H), 11.15 (s, 1H); $^{13}C$ NMR (DMSO-$d_6$) δ 22.1, 31.0, 48.7, 55.4, 55.7, 99.5, 104.7, 110.4, 112.2, 118.3, 120.1, 125.2, 132.1, 136.1, 144.2, 153.7, 157.9, 167.2, 168.9, 170.1, 172.8; Anal. calcd for $C_{21}H_{19}N_3O_6 \cdot 0.3H_2O$: C, 60.81; H, 4.76; N, 10.13. Found: C, 60.87; H, 4.64; N, 10.00.

5.51 2-(2,6-DIOXOPIPERIDIN-3-YL)-4-(4-METHOXYPHENYLAMINO)ISOINDOLE-1,3-DIONE

5.51.1 3-(4-Methoxyphenylamino)phthalic acid dimethyl ester

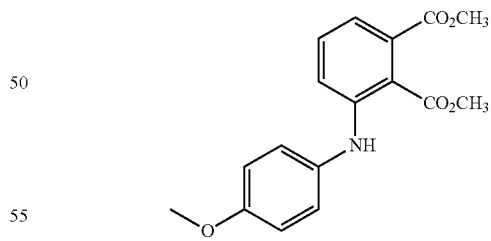

A mixture of 3-iodophthalic acid dimethyl ester (1.0 g, 3.1 mmol), p-anisidine (0.38 g, 3.1 mmol), $Pd_2(dba)_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with $CH_2Cl_2$ (10 mL), and filtered through Celite, and the filter was washed with additional $CH_2Cl_2$ (30 mL). The filtrate was evaporated, and the residue was chromatographed using a hexanes-ethyl acetate gradient, eluting 0.80 g of the product at 70:30 hexanes-ethyl acetate, in 82% yield: $^1$H NMR (CDCl$_3$) δ 3.81 (s, 3H), 3.87 (s, 3H), 3.88 (s, 3H), 6.86-6.96 (m, 3H), 7.05-7.12 (m, 3H), 7.23 (t, J=7.6 Hz, 1H), 8.11 (br, 1H).

5.51.2 3-(4-Methoxyphenylamino)phthalic acid

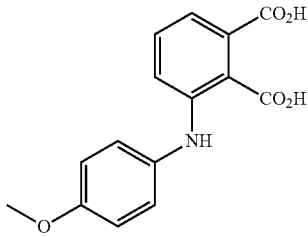 [SMILES: COc1ccc(Nc2cccc(C(=O)O)c2C(=O)O)cc1]

A mixture of 3-(4-methoxyphenylamino)phthalic acid dimethyl ester (0.80 g, 2.5 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.61 g in 85% yield: $^1$H NMR (DMSO-d$_6$) δ 3.74 (s, 3H), 6.89-6.99 (m, 3H), 7.03-7.12 (m, 3H), 7.29 (t, J=8.0 Hz, 1H), 8.01 (br, 1H).

5.51.3 2-(2,6-Dioxopiperidin-3-yl)-4-(4-methoxyphenylamino)isoindole-1,3-dione

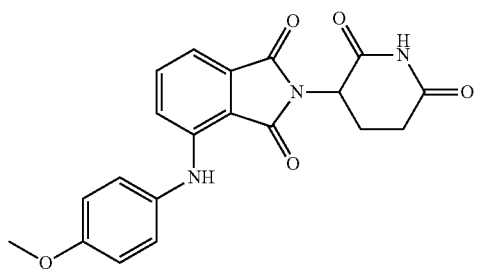 [SMILES: COc1ccc(Nc2cccc3c2C(=O)N(C2CCC(=O)NC2=O)C3=O)cc1]

A mixture of 3-(4-methoxyphenylamino)phthalic acid (0.52 g, 1.8 mmol) and rac-α-aminoglutarimide hydrochloride (0.30 g, 1.8 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 95:5 methylene chloride-methanol, eluting 0.58 g of the product, in 84% yield: mp 228-230° C.; $^1$H NMR (DMSO-d$_6$) δ 2.04-2.09 (m, 1H), 2.52-2.64 (m, 2H), 2.83-2.96 (m, 1H), 3.77 (s, 3H), 5.12 (dd, J=12.6 Hz, J=5.4 Hz, 1H), 6.96-7.00 (m, 2H), 7.12-7.17 (m, 2H), 7.24-7.28 (m, 2H), 7.54 (t, J=7.9 Hz, 1H), 8.24 (s, 1H), 11.13 (s, 1H); $^{13}$C NMR (DMSO-d$_6$) δ 22.1, 31.0, 48.7, 55.3, 110.6, 112.4, 114.7, 118.5, 125.3, 131.8, 132.4, 136.1, 144.3, 156.6, 167.1, 168.4, 170.0, 172.8; Anal. calcd for C$_{20}$H$_{17}$N$_3$O$_5$: C, 63.32; H, 4.52; N, 11.08. Found: C, 63.31; H, 4.47; N, 10.83.

5.52 2-(2,6-DIOXOPIPERIDIN-3-YL)-4-(3-ETHOXY-4-METHOXYPHENYLAMINO)-ISOINDOLE-1,3-DIONE

5.52.1 2-Ethoxy-1-methoxy-4-nitrobenzene

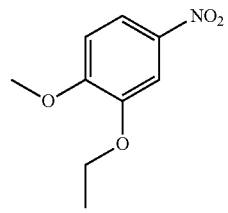

A mixture of 2-methoxy-5-nitrophenol (5.3 g, 31.3 mmol), iodoethane (14.6 g, 93.9 mmol), and potassium carbonate (43.2 g, 310 mmol) in acetone (100 mL) was heated to reflux for 4 hours. The reaction mixture was cooled, and the solvent was evaporated in vacuo. The residue was dissolved in water (250 mL) and extracted with ethyl acetate (3×75 mL). The combined organic extracts were washed with water (3×75 mL) and dried (MgSO$_4$), and the solvent was evaporated under vacuum, providing 5.8 g of the product, in 99% yield: $^1$H NMR (CDCl$_3$) δ 1.51 (t, J=7.0 Hz, 3H), 3.97 (s, 3H), 4.18 (q, J=7.0 Hz, 2H), 6.22 (dd, J=8.4 Hz, J=2.4 Hz, 1H), 6.31 (d, J=2.4 Hz, 1H), 6.70 (d, J=8.4 Hz, 1H).

5.52.2 3-Ethoxy-4-methoxy-phenylamine

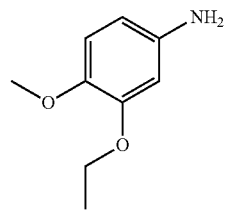

A mixture of 2-ethoxy-1-methoxy-4-nitrobenzene (1.5 g, 7.6 mmol) and 5% Pd—C (0.3 g) in 30 mL of ethyl acetate was hydrogenated under 50 psi of hydrogen gas for 14 hours. The mixture was filtered through Celite and the filtrate was evaporated, providing 1.25 g of the product, in 98% yield: $^1$H NMR (CDCl$_3$) δ 1.44 (t, J=7.0 Hz, 3H), 3.27 (br, 2H), 3.79 (s, 3H), 4.04 (q, J=7.0 Hz, 2H), 6.90 (d, J=8.9 Hz, 1H), 7.74 (d, J=2.5 Hz, 1H), 7.90 (dd, J=8.9 Hz, J=2.5 Hz, 1H).

5.52.3 3-(3-Ethoxy-4-methoxyphenylamino)phthalic acid dimethyl ester

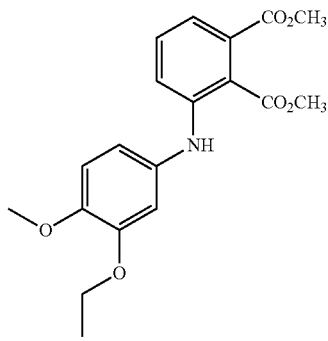 [SMILES: CCOc1cc(Nc2cccc(C(=O)OC)c2C(=O)OC)ccc1OC]

A mixture of 3-iodophthalic acid dimethyl ester (1.0 g, 3.1 mmol), 3-ethoxy-4-methoxyaniline (0.51 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with $CH_2Cl_2$ (10 mL), and filtered through Celite, and the filter was washed with additional $CH_2Cl_2$ (30 mL). The filtrate was evaporated, and the residue was chromatographed using a hexanes-ethyl acetate gradient, eluting 0.90 g of the product at 70:30 hexanes-ethyl acetate, in 80% yield: $^1$H NMR (CDCl$_3$) δ 1.45 (t, J=7.0 Hz, 1H), 3.86 (s, 3H), 3.87 (s, 3H), 3.88 (s, 3H), 4.05 (q, J=7.0 Hz, 2H), 6.71-6.74 (m, 2H), 6.84 (d, J=7.4 Hz, 1H), 6.96 (dd, J=7.3 Hz, J=1.0 Hz, 1H), 7.13 (dd, J=8.5 Hz, J=1.0 Hz, 1H), 7.24 (t, J=7.4 Hz, 1H), 8.07 (s, 1H).

5.52.4 3-(3-Ethoxy-4-methoxyphenylamino)phthalic acid

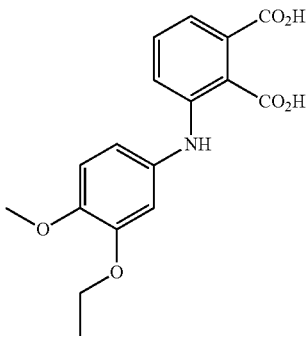 [SMILES: CCOc1cc(Nc2cccc(C(=O)O)c2C(=O)O)ccc1OC]

A mixture of 3-(3-ethoxy-4-methoxyphenylamino)phthalic acid dimethyl ester (0.85 g, 2.4 mmol) and 3N NaOH (50 mL) in ethanol (100 mL) was heated to reflux for 3 hours. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.68 g of the product, in 87% yield: $^1$H NMR (DMSO-d$_6$) δ 1.31 (t, J=6.9 Hz, 3H), 3.73 (s, 3H), 3.96 (q, J=6.9, 2H), 6.69 (dd, J=8.6 Hz, J=2.4 Hz, 1H), 6.78 (d, J=2.4 Hz, 1H), 6.90 (d, J=8.6 Hz, 1H), 7.00 (d, J=7.2 Hz, 1H), 7.15 (d, J=8.0 Hz, 1H), 7.30 (t, J=7.9 Hz, 1H), 7.97 (s, 1H).

5.52.5 2-(2,6-Dioxopiperidin-3-yl)-4-(3-ethoxy-4-methoxyphenylamino)-isoindole-1,3-dione

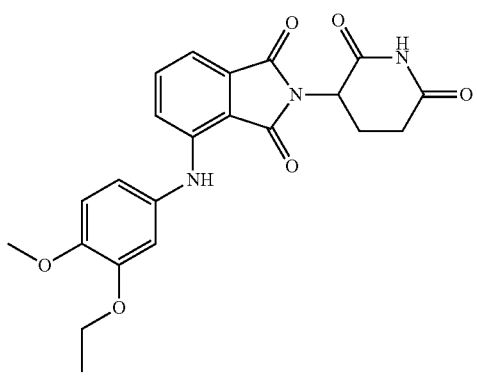 [SMILES: CCOc1cc(Nc2cccc3c2C(=O)N(C2CCC(=O)NC2=O)C3=O)ccc1OC]

A mixture of 3-(3-ethoxy-4-methoxyphenylamino)phthalic acid (0.85 g, 2.6 mmol) and rac-α-aminoglutarimide hydrochloride (0.43 g, 2.6 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 95:5 methylene chloride-methanol, eluting 0.72 g of the product, in 67% yield: mp 162-164° C.; $^1$H NMR (CDCl$_3$) δ 1.46 (t, J=7.0 Hz, 3H), 2.11-2.18 (m, 1H), 2.72-2.94 (m, 3H), 3.89 (s, 3H), 4.06 (q, J=7.0 Hz, 3H), 4.96 (dd, J=12.0 Hz, J=5.0 Hz, 1H), 6.76-6.89 (m, 3H), 7.14-7.19 (m, 2H), 7.43 (t, J=7.8 Hz, 1H), 7.86 (s, 1H), 8.43 (s, 1H); $^{13}$C NMR (CDCl$_3$) δ 14.7, 22.8, 31.4, 49.0, 56.2, 64.5, 109.9, 110.8, 112.1, 113.1, 116.4, 118.5, 131.7, 132.4, 135.9, 145.2, 147.4, 149.1, 167.5, 168.4, 169.4, 171.1; Anal. calcd for $C_{22}H_{21}N_3O_6$: C, 62.41; H, 5.00; N, 9.92. Found: C, 62.16; H, 4.89; N, 9.72.

5.53 2-(2,6-DIOXOPIPERIDIN-3-YL)-4-(3-HYDROXY-4-METHOXYPHENYL-AMINO)—ISOINDOLE-1,3-DIONE

5.53.1 tert-Butyl-(2-methoxy-5-nitrophenoxy)dimethylsilane

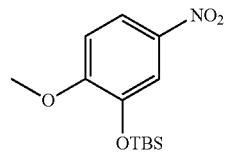

A mixture of 2-methoxy-5-nitrophenol (3.0 g, 17.8 mmol), tert-butyldimethylsilyl chloride (3.2 g, 21.4 mmol), and ethyldiisopropylamine (5.8 g, 44.5 mmol) in DMF (50 mL) was stirred at room temperature for 3 hours. The mixture was poured into water (100 mL) and extracted with methylene chloride (3×100 mL). The combined organic extracts were washed with water (5×100 mL) and dried (MgSO$_4$), and the solvent was evaporated under vacuum. The residue was recrystallized from ethanol-water, providing 3.2 g of the product as white crystals, in 64% yield: $^1$H NMR (CDCl$_3$) δ 0.19 (s, 6H), 1.01 (s, 9H), 3.91 (s, 3H), 6.89 (d, J=8.9 Hz, 1H), 7.71 (d, J=2.8 Hz, 1H), 7.89 (dd, J=8.9 Hz, J=2.8 Hz, 1H).

5.53.2 3-(tert-Butyldimethylsilanyloxy)-4-methoxyphenylamine

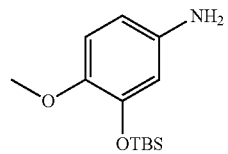 [SMILES: COc1ccc(N)cc1O[Si](C)(C)C(C)(C)C]

A mixture of tert-butyl-(2-methoxy-5-nitrophenoxy)dimethylsilane (3.0 g, 10.6 mmol) and 5% Pd—C (0.3 g) in 30 mL of ethyl acetate was hydrogenated under 50 psi of hydrogen gas for 14 hours. The mixture was filtered through Celite and the filtrate was evaporated. The residue was chromatographed using a hexanes-ethyl acetate gradient, eluting 2.0 g of the product at 85:15 hexanes-ethyl acetate, in 74% yield: $^1$H NMR (CDCl₃) δ 0.15 (s, 6H), 0.99 (s, 9H), 3.37 (br, 2H), 3.72 (s, 3H), 6.23-6.29 (m, 2H), 6.68 (d, J=8.1 Hz, 1H).

5.53.3 3-[3-(tert-Butyldimethylsilanyloxy)-4-methoxyphenylamino]phthalic acid dimethyl ester

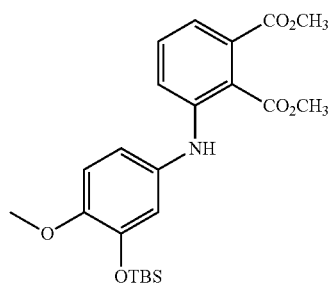 [SMILES: COC(=O)c1cccc(Nc2ccc(OC)c(O[Si](C)(C)C(C)(C)C)c2)c1C(=O)OC]

A mixture of 3-iodophthalic acid dimethyl ester (1.0 g, 3.1 mmol), 3-(tert-butyldimethylsilanyloxy)-4-methoxyphenylamine (0.79 g, 3.1 mmol), Pd₂(dba)₃ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH₂Cl₂ (10 mL), and filtered through Celite, and the filter was washed with additional CH₂Cl₂ (30 mL). The filtrate was evaporated, and the residue was chromatographed using a hexanes-ethyl acetate gradient, eluting 1.0 g of the product at 90:10 hexanes-ethyl acetate, in 71% yield: ¹H NMR (CDCl₃) δ 0.16 (s, 6H), 0.98 (s, 9H), 3.81 (s, 3H), 3.87 (s, 3H), 3.88 (s, 3H), 6.69-6.75 (m, 2H), 6.82 (d, J=8.2 Hz, 1H), 6.95 (dd, J=7.3 Hz, J=1.1 Hz, 1H), 7.12 (dd, J=7.0 Hz, J=1.1 Hz, 1H), 7.24 (t, J=7.8 Hz, 1H), 8.04 (s, 1H).

5.53.4 3-(3-Hydroxy-4-methoxyphenylamino)phthalic acid

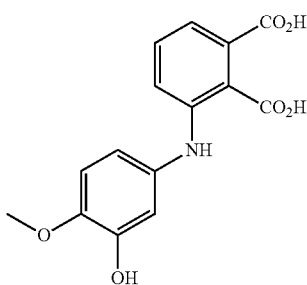 [SMILES: COc1ccc(Nc2cccc(C(=O)O)c2C(=O)O)cc1O]

A mixture of 3-[3-(tert-butyldimethylsilanyloxy)-4-methoxyphenyl-amino]phthalic acid dimethyl ester (1.0 g, 2.2 mmol) and 3N NaOH (50 mL) in ethanol (100 mL) was heated to reflux for 2 hours. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO₄), and evaporated, providing 0.65 g of the product, in 96% yield: ¹H NMR (DMSO-d₆) δ 3.73 (s, 3H), 6.54 (dd, J=8.5 Hz, J=2.5 Hz, 1H), 6.60 (d, J=2.5 Hz, 1H), 6.86 (d, J=8.5 Hz, 1H), 6.98 (d, J=7.3 Hz, 1H), 7.13 (d, J=7.7 Hz, 1H), 7.30 (t, J=7.9 Hz, 1H), 7.93 (s, 1H).

5.53.5 2-(2,6-Dioxopiperidin-3-yl)-4-(3-hydroxy-4-methoxyphenylamino)-isoindole-1,3-dione

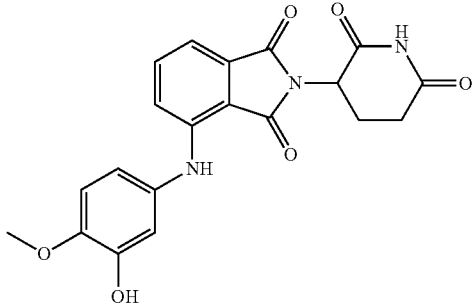 [SMILES: COc1ccc(Nc2cccc3c2C(=O)N(C2CCC(=O)NC2=O)C3=O)cc1O]

A mixture of 3-(3-hydroxy-4-methoxyphenylamino)phthalic acid (0.60 g, 2.0 mmol) and rac-α-aminoglutarimide hydrochloride (0.33 g, 2.0 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), was dried (MgSO₄) and evaporated. The residue was triturated in 1:1 acetonitrile-water (15 mL) and filtered, and the resulting solid was washed with additional 1:1 acetonitrile-water and dried under high vacuum, providing 0.45 g of the product, in 58% yield: mp 225-227° C.; ¹H NMR (DMSO-d₆) δ 2.03-2.08 (m, 1H), 2.52-2.63 (m, 2H), 2.83-2.92 (m, 1H), 3.77 (s, 3H), 5.11 (dd, J=12.5 Hz, J=5.4 Hz, 1H), 6.69-6.76 (m, 2H), 6.94 (d, J=8.5 Hz, 1H), 7.14-7.23 (m, 2H), 7.56 (t, J=7.8 Hz, 1H), 8.15 (s, 1H), 9.21 (s, 1H), 11.13 (s, 1H); ¹³C NMR (DMSO-d₆) δ 22.1, 31.0, 48.6, 55.9, 110.7, 111.5, 112.5, 113.0, 114.2, 118.8, 132.1, 132.3, 136.1, 144.2, 145.2, 147.2, 167.1, 168.4, 170.0, 172.8; Anal. calcd for C₂₀H₁₇N₃O₆: C, 60.76; H, 4.33; N, 10.63. Found: C, 60.76; H, 4.11; N, 10.42.

5.54 2-(2,6-DIOXOPIPERIDIN-3-YL)-4-(NAPHTHALEN-2-YLAMINO)ISOINDOLE-1,3-DIONE

5.54.1 3-(Naphthalen-2-ylamino)phthalic acid dimethyl ester

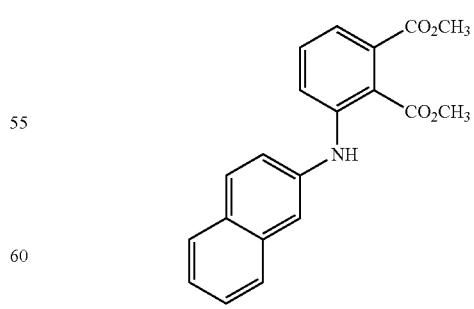

A mixture of 3-iodophthalic acid dimethyl ester (1.0 g, 3.1 mmol), 2-aminonaphthalene (0.44 g, 3.1 mmol), Pd₂(dba)₃ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a hexanes-ethyl acetate gradient, eluting 0.78 g of the product at 85:15 hexanes-ethyl acetate, in 75% yield: $^1$H NMR (CDCl$_3$) δ 3.89 (s, 3H), 3.90 (s, 3H), 7.14 (dd, J=7.3 Hz, J=1.0 Hz, 1H), 7.27-7.50 (m, 5H), 7.55 (d, J=1.8 Hz, 1H), 7.71 (d, J=8.0 Hz, 1H), 7.77-7.82 (m, 2H), 8.20 (br, 1H).

5.54.2 3-(Naphthalen-2-ylamino)phthalic acid

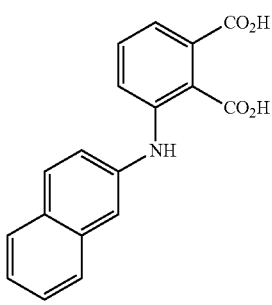 [SMILES: O=C(O)c1cccc(Nc2ccc3ccccc3c2)c1C(=O)O]

A mixture of 3-(naphthalen-2-ylamino)phthalic acid dimethyl ester (0.75 g, 2.2 mmol) and 3N NaOH (50 mL) in ethanol (100 mL) was heated to reflux for 3 hours. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.64 g in 93% yield: $^1$H NMR (DMSO-d$_6$) δ 7.29-7.54 (m, 7H), 7.68 (d, J=8.1 Hz, 1H), 7.76-7.81 (m, 2H), 8.16 (br, 1H).

5.54.3 2-(2,6-Dioxopiperidin-3-yl)-4-(naphthalen-2-ylamino)isoindole-1,3-dione

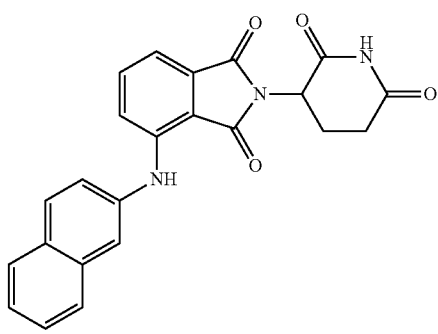 [SMILES: O=C1CCC(N2C(=O)c3cccc(Nc4ccc5ccccc5c4)c3C2=O)C(=O)N1]

A mixture of 3-(naphthalen-2-ylamino)phthalic acid (0.62 g, 1.8 mmol) and rac-α-aminoglutarimide hydrochloride (0.33 g, 2.0 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 95:5 methylene chloride-methanol, eluting 0.74 g of the product, in 92% yield: mp 235-237° C.; $^1$H NMR (DMSO-d$_6$) δ 2.06-2.11 (m, 1H), 2.54-2.64 (m, 2H), 2.85-3.00 (m, 1H), 3.77 (s, 3H), 5.15 (dd, J=12.7 Hz, J=5.3 Hz, 1H), 7.29 (d, J=6.3 Hz, 1H), 7.39-7.52 (m, 3H), 7.57-7.69 (m, 2H), 7.80-7.95 (m, 4H), 8.66 (s, 1H), 11.16 (s, 1H); $^{13}$C NMR (DMSO-d$_6$) δ 22.1, 31.0, 48.8, 112.5, 113.8, 117.0, 120.0, 122.1, 124.8, 126.6, 127.0, 127.6, 129.2, 130.0, 132.5, 133.7, 136.2, 137.3, 142.5, 167.0, 168.2, 170.0, 172.8; Anal. calcd for C$_{23}$H$_{17}$N$_3$O$_4$.0.1H$_2$O: C, 68.86; H, 4.32; N, 10.47. Found: C, 68.73; H, 4.01; N, 10.36.

5.55 4-(4-CYCLOHEXYLPHENYLAMINO)-2-(2,6-DIOXOPIPERIDIN-3-YL)ISOINDOLE-1,3-DIONE 5.55.1 3-(4-Cyclohexylphenylamino)phthalic acid dimethyl ester

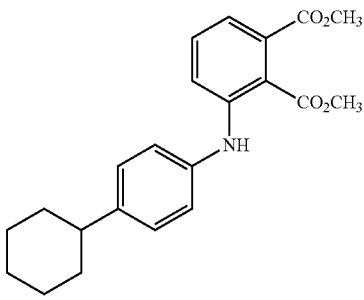 [SMILES: COC(=O)c1cccc(Nc2ccc(C3CCCCC3)cc2)c1C(=O)OC]

A mixture of 3-iodophthalic acid dimethyl ester (1.0 g, 3.1 mmol), 4-cyclohexylaniline (0.54 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a hexanes-ethyl acetate gradient, eluting 0.90 g of the product at 90:10 hexanes-ethyl acetate, in 78% yield: $^1$H NMR (CDCl$_3$) δ 1.27-1.44 (m, 6H), 1.73-1.85 (m, 4H), 2.45-2.55 (m, 1H), 3.86 (s, 3H), 3.88 (s, 3H), 7.00-7.10 (m, 3H), 7.15-7.18 (m, 2H), 7.23-7.34 (m, 2H), 8.07 (br, 1H).

5.55.2 3-(4-Cyclohexylphenylamino)phthalic acid

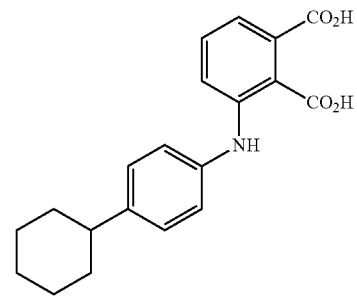 [SMILES: O=C(O)c1cccc(Nc2ccc(C3CCCCC3)cc2)c1C(=O)O]

A mixture of 3-(4-cyclohexylphenylamino)phthalic acid dimethyl ester (0.85 g, 2.3 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.70 g in 90% yield: $^1$H NMR (DMSO-d$_6$) δ 1.14-1.44 (s, 5H), 1.67-1.78 (m, 5H), 2.35-2.45 (m, 1H), 7.00-7.04 (m, 2H), 7.08-7.14 (m, 3H), 7.26-7.37 (m, 2H), 7.98 (s, 1H).

5.55.3 4-(4-Cyclohexylphenylamino)-2-(2,6-dioxopiperidin-3-yl)isoindole-1,3-dione

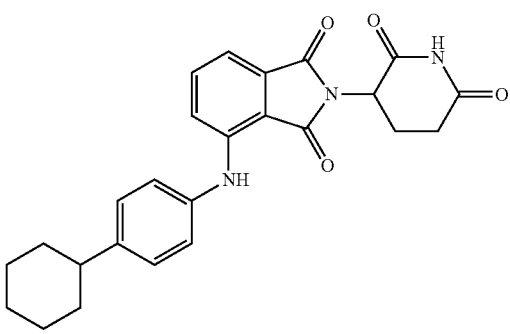 [SMILES: O=C1CCC(N2C(=O)c3cccc(Nc4ccc(C5CCCCC5)cc4)c3C2=O)C(=O)N1]

A mixture of 3-(4-cyclohexylphenylamino)phthalic acid (0.80 g, 2.4 mmol) and rac-α-aminoglutarimide hydrochloride (0.39 g, 2.4 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 1:1 hexanes-ethyl acetate, eluting 0.86 g of the product, in 86% yield: mp 219-221° C.; $^1$H NMR (DMSO-d$_6$) δ 1.10-1.46 (m, 5H), 1.67-1.80 (m, 5H), 2.04-2.07 (m, 1H), 2.40-2.50 (m, 1H), 2.53-2.64 (m, 2H), 2.83-2.90 (m, 1H), 5.12 (dd, J=12.6 Hz, J=5.3 Hz, 1H), 7.19-7.24 (m, 5H), 7.35 (d, J=8.6 Hz, 1H), 7.58 (t, J=7.9 Hz, 1H), 8.34 (s, 1H), 11.14 (s, 1H); $^{13}$C NMR (DMSO-d$_6$) δ 22.1, 25.6, 26.4, 31.0, 34.0, 43.2, 48.7, 111.3, 113.0, 119.0, 122.4, 127.6, 132.4, 136.2, 136.9, 143.3, 143.7, 167.1, 168.4, 170.0, 172.8; Anal. calcd for C$_{25}$H$_{25}$N$_3$O$_4$: C, 69.59; H, 5.84; N, 9.74. Found: C, 69.38; H, 5.85; N, 9.41.

5.56 4-(2-METHOXYPHENYLAMINO)-2-(2,6-DIOXOPIPERIDIN-3-YL)ISOINDOLE-1,3-DIONE

5.56.1 3-(2-Methoxyphenylamino)phthalic acid dimethyl ester

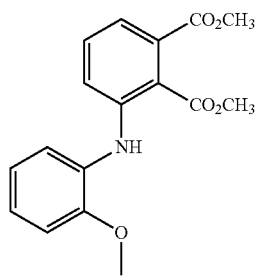 [SMILES: COC(=O)c1cccc(Nc2ccccc2OC)c1C(=O)OC]

A mixture of 3-iodophthalic acid dimethyl ester (1.0 g, 3.1 mmol), 2-methoxyaniline (0.38 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a hexanes-ethyl acetate gradient, eluting 0.75 g of the product at 75:25 hexanes-ethyl acetate, in 77% yield: $^1$H NMR (CDCl$_3$) δ 3.88 (s, 9H), 6.89-7.00 (m, 3H), 7.14 (d, J=7.0 Hz, 1H), 7.27-7.34 (m, 2H), 7.46 (d, J=8.1 Hz, 1H), 7.99 (br, 1H).

5.56.2 3-(2-Methoxyphenylamino)phthalic acid

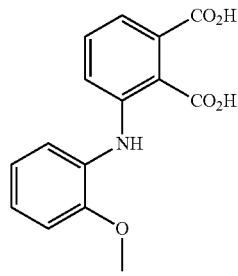 [SMILES: COc1ccccc1Nc1cccc(C(=O)O)c1C(=O)O]

A mixture of 3-(2-methoxyphenylamino)phthalic acid dimethyl ester (0.74 g, 2.4 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.61 g in 91% yield: $^1$H NMR (DMSO-d$_6$) δ 3.83 (s, 3H), 6.89-7.11 (m, 4H), 7.24 (dd, J=7.5 Hz, J=1.5 Hz, 1H), 7.33-7.41 (m, 2H), 7.96 (s, 1H).

5.56.3 4-(2-Methoxyphenylamino)-2-(2,6-dioxopiperidin-3-yl)isoindole-1,3-dione

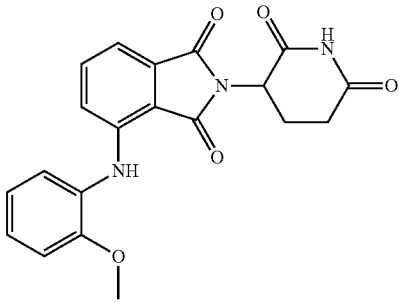 [SMILES: COc1ccccc1Nc1cccc2c1C(=O)N(C1CCC(=O)NC1=O)C2=O]

A mixture of 3-(2-methoxyphenylamino)phthalic acid (0.55 g, 1.9 mmol) and rac-α-aminoglutarimide hydrochloride (0.31 g, 1.9 mmol) in pyridine (10 mL) was heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 95:5 methylene chloride-methanol, eluting 0.66 g of the product, in 92% yield: mp 223-225° C.; $^1$H NMR (CDCl$_3$) δ 2.13-2.20 (m, 1H), 2.73-2.95 (m, 3H), 3.88 (s, 3H), 4.97 (dd, J=11.9 Hz, J=5.0 Hz, 1H), 6.94-7.00 (m, 2H), 7.09-7.15 (m, 1H), 7.21-7.26 (m, 1H), 7.38-7.52 (m, 3H), 8.08 (s, 1H), 8.15 (s, 1H); $^{13}$C NMR (CDCl$_3$) δ 22.8, 31.4, 49.0, 55.7, 111.4, 112.1, 113.6, 118.8, 120.6, 121.1, 124.8, 128.2, 132.5, 135.7, 143.6, 151.4, 167.4, 168.1, 169.1, 170.8; Anal. calcd for C$_{20}$H$_{17}$N$_3$O$_5$.0.1H$_2$O: C, 63.02; H, 4.55; N, 11.02. Found: C, 62.91; H, 4.42; N, 10.71.

5.57 4-(2,5-DIMETHOXYPHENYLAMINO)-2-(2,6-DIOXOPIPERIDIN-3-YL)ISOINDOLE-1,3-DIONE

5.57.1 3-(2,5-Dimethoxyphenylamino)phthalic acid dimethyl ester

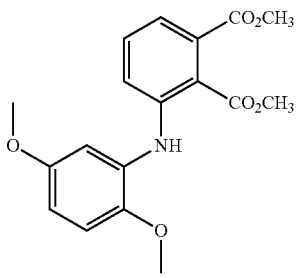 [SMILES: COC(=O)c1cccc(Nc2cc(OC)ccc2OC)c1C(=O)OC]

A mixture of 3-iodophthalic acid dimethyl ester (1.0 g, 3.1 mmol), 2,5-dimethoxyaniline (0.48 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a hexanes-ethyl acetate gradient, eluting 0.73 g of the product at 80:20 hexanes-ethyl acetate, in 68% yield: $^1$H NMR (CDCl$_3$) δ 3.74 (s, 3H), 3.85 (s, 3H), 3.88 (s, 3H), 3.89 (s, 3H), 6.48 (dd, J=8.8 Hz, J=2.9 Hz, 1H), 6.83 (d, J=8.8 Hz, 1H), 6.87 (d, J=2.9 Hz, 1H), 7.19 (dd, J=7.7 Hz, J=0.9 Hz, 1H), 7.34 (t, J=7.9 Hz, 1H), 7.55 (dd, J=8.5 Hz, J=0.9 Hz, 1H), 7.95 (br, 1H).

5.57.2 4-(2,5-Dimethoxyphenylamino)-2-(2,6-dioxopiperidin-3-yl)isoindole-1,3-dione

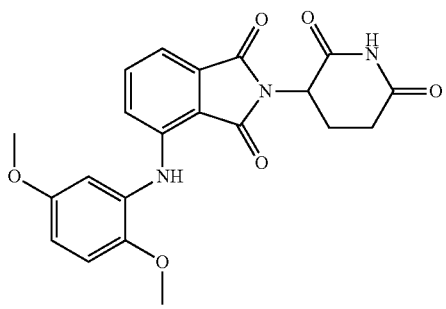 [SMILES: COc1ccc(OC)c(Nc2cccc3c2C(=O)N(C2CCC(=O)NC2=O)C3=O)c1]

Step 1:
A mixture of 3-(2,5-dimethoxyphenylamino)phthalic acid dimethyl ester (0.71 g, 2.1 mmol) and 3N NaOH (50 mL) in ethanol (100 mL) was heated to reflux for 3 hours. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.48 g.

Step 2:
The product from Step 1 and rac-α-aminoglutarimide hydrochloride (0.26 g, 1.6 mmol) in pyridine (10 mL) were heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 95:5 methylene chloride-methanol, providing 0.42 g of the product, in 68% yield: mp 231-233° C.; $^1$H NMR (DMSO-d$_6$) δ 2.04-2.09 (m, 1H), 2.53-2.64 (m, 2H), 2.82-2.92 (m, 1H), 3.78 (s, 3H), 3.79 (s, 3H), 5.13 (dd, J=12.6 Hz, J=5.3 Hz, 1H), 6.70 (dd, J=8.9 Hz, J=2.6 Hz, 1H), 7.03-7.07 (m, 2H), 7.26 (d, J=7.0 Hz, 1H), 7.45 (d, J=8.5 Hz, 1H), 7.65 (t, J=7.8 Hz, 1H), 8.31 (s, 1H), 11.14 (s, 1H); $^{13}$C NMR (DMSO-d$_6$) δ 22.1, 31.0, 48.7, 55.4, 56.2, 107.3, 108.4, 111.9, 112.6, 113.4, 119.2, 128.6, 132.2, 136.4, 142.2, 144.9, 153.3, 167.0, 168.8, 170.0, 172.8; Anal. calcd for C$_{21}$H$_{19}$N$_3$O$_6$: C, 61.61; H, 4.68; N, 10.26. Found: C, 61.46; H, 4.50; N, 10.23.

5.58 4-(2-PHENOXYPHENYLAMINO)-2-(2,6-DIOXOPIPERIDIN-3-YL)ISOINDOLE-1,3-DIONE

5.58.1 3-(2-Phenoxyphenylamino)phthalic acid dimethyl ester

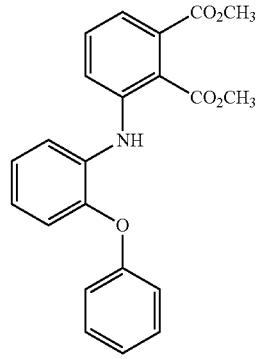 [SMILES: COC(=O)c1cccc(Nc2ccccc2Oc2ccccc2)c1C(=O)OC]

A mixture of 3-iodophthalic acid dimethyl ester (1.0 g, 3.1 mmol), 2-phenoxyaniline (0.57 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a hexanes-ethyl acetate gradient, eluting 0.86 g of the product at 80:20 hexanes-ethyl acetate, in 73% yield: $^1$H NMR (CDCl$_3$) δ 3.75 (s, 3H), 3.86 (s, 3H), 6.93-7.03 (m, 4H), 7.06-7.12 (m, 2H), 7.17 (dd, J=7.3 Hz, J=1.0 Hz, 1H), 7.29-7.38 (m, 4H), 7.46 (d, J=8.4 Hz, 1H), 7.89 (s, 1H).

5.58.2 4-(2-Phenoxyphenylamino)-2-(2,6-dioxopiperidin-3-yl)isoindole-1,3-dione

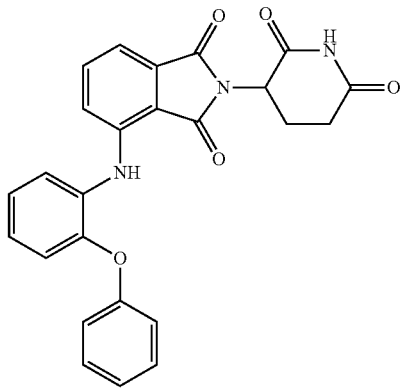 [SMILES: O=C1CCC(N2C(=O)c3cccc(Nc4ccccc4Oc4ccccc4)c3C2=O)C(=O)N1]

Step 1:

A mixture of 3-(2-phenoxyphenylamino)phthalic acid dimethyl ester (0.85 g, 2.3 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified (HCl) and extracted with ethyl acetate (3×75 mL). The combined organic extracts were washed with water (3×75 mL), dried (MgSO$_4$), and evaporated, providing 0.72 g.

Step 2:

The product from Step 1 and rac-α-aminoglutarimide hydrochloride (0.32 g, 2.0 mmol) in pyridine (10 mL) were heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed using a methylene chloride-methanol gradient, eluting 0.85 g of the product at 98:2 methylene chloride-methanol, in 93% yield: mp 219-221° C.; $^1$H NMR (CDCl$_3$) δ 2.07-2.17 (m, 1H), 2.63-2.92 (m, 3H), 4.92 (dd, J=12.0 Hz, J=5.4 Hz, 1H), 6.95-7.01 (m, 3H), 7.07-7.15 (m, 2H), 7.22-7.33 (m, 4H), 7.40-7.52 (m, 3H), 8.07 (s, 1H), 8.13 (s, 1H); $^{13}$C NMR (CDCl$_3$) δ 22.7, 31.4, 48.9, 112.3, 113.9, 118.4, 119.0, 119.7, 122.6, 123.6, 123.9, 125.2, 129.8, 130.5, 132.5, 135.7, 143.4, 149.2, 156.6, 167.3, 168.0, 168.9, 170.8; Anal. calcd for C$_{25}$H$_{19}$N$_3$O$_5$: C, 68.02; H, 4.34; N, 9.52. Found: C, 68.00; H, 4.13; N, 9.43.

5.59 4-(4-DIMETHYLAMINOPHENYLAMINO)-2-(2,6-DIOXOPIPERIDIN-3-YL)ISOINDOLE-1,3-DIONE

5.59.1 3-(4-Dimethylaminophenylamino)phthalic acid dimethyl ester

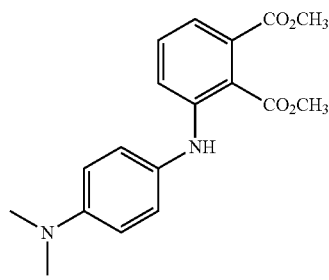 [SMILES: COC(=O)c1cccc(Nc2ccc(N(C)C)cc2)c1C(=O)OC]

A mixture of 3-iodophthalic acid dimethyl ester (1.0 g, 3.1 mmol), N,N-dimethyl-1,4-phenylenediamine (0.42 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a hexanes-ethyl acetate gradient, eluting 0.73 g of the product at 70:30 hexanes-ethyl acetate, in 71% yield: $^1$H NMR (CDCl$_3$) δ 2.95 (s, 6H), 3.86 (s, 3H), 3.88 (s, 3H), 6.71-6.76 (m, 2H), 6.88 (d, J=7.4 Hz, 1H), 7.00-7.09 (m, 3H), 7.20 (t, J=7.9 Hz, 1H), 8.10 (br, 1H).

5.59.2 4-(4-Dimethylaminophenylamino)-2-(2,6-dioxopiperidin-3-yl)isoindole-1,3-dione

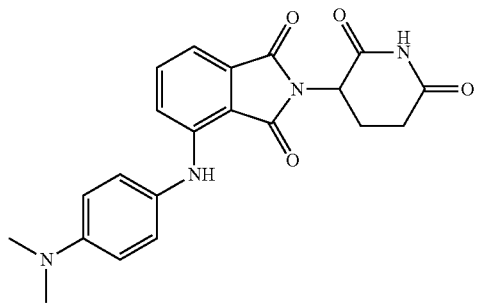 [SMILES: CN(C)c1ccc(Nc2cccc3c2C(=O)N(C2CCC(=O)NC2=O)C3=O)cc1]

Step 1:

A mixture of 3-(4-dimethylaminophenylamino)phthalic acid dimethyl ester (0.70 g, 2.1 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.35 g, 2.1 mmol) in pyridine (10 mL) were heated to reflux for 16 hours. The mixture was cooled and evaporated under vacuum. The residue was dissolved in ethyl acetate (150 mL), washed with dilute aqueous HCl (2×100 mL) and water (2×100 mL), and evaporated. The residue was chromatographed in 95:5 methylene chloride-methanol, eluting 0.50 g. This material was purified further by reverse phase preparative HPLC, eluting with 1:1 acetonitrile-water, and providing 90 mg (11% yield for the final two steps): mp>260° C.; $^1$H NMR (DMSO-d$_6$) δ 2.03-2.08 (m, 1H), 2.53-2.63 (m, 2H), 2.83-3.00 (m, 7H), 5.11 (dd, J=12.6 Hz, J=5.5 Hz, 1H), 6.76-6.79 (m, 2H), 7.04-7.17 (m, 4H), 7.52 (t, J=7.8 Hz, 1H), 8.11 (s, 1H), 11.13 (s, 1H); $^{13}$C NMR (DMSO-d$_6$) δ 22.1, 31.0, 40.3, 48.6, 110.0, 111.9, 113.1, 118.3, 125.5, 127.6, 132.3, 136.1, 145.0, 148.4, 167.2, 168.6, 170.1, 172.8; Anal. calcd for C$_{21}$H$_{20}$N$_4$O$_4$·0.2H$_2$O: C, 62.65; H, 5.13; N, 13.85. Found: C, 62.85; H, 4.78; N, 13.67.

5.60 4-[4-(2-DIMETHYLAMINOETHOXY)-2-METHOXYPHENYL AMINO]-2-(2,6-DIOXOPIPERIDIN-3-YL)ISOINDOLE-1,3-DIONE

5.60.1 4-Fluoro-2-methoxy-1-nitrobenzene

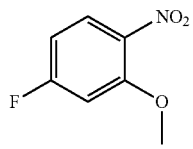

A mixture of 5-fluoro-2-nitrophenol (5.0 g, 31.8 mmol), iodomethane (13.5 g, 95.4 mmol), and potassium carbonate (16.7 g, 159 mmol) in acetone (80 mL) was heated to reflux for 4 hours. The mixture was cooled and evaporated under vacuum, and the residue was dissolved in ethyl acetate (200 mL) and washed with water (3×250 mL), dried (MgSO$_4$), and evaporated, providing 5.25 g, in 97% yield: $^1$H NMR (CDCl$_3$) δ 3.97 (s, 3H), 6.69-6.82 (m, 2H), 7.97 (dd, J=8.9 Hz, J=6.0 Hz, 1H).

5.60.2 [2-(3-Methoxy-4-nitrophenoxy)ethyl]dimethylamine

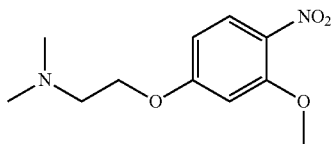 [SMILES: COc1cc(OCCN(C)C)ccc1[N+](=O)[O-]]

N,N-Dimethylethanolamine (0.80 g, 9.0 mmol) was added to a mixture of powdered KOH (0.50 g, 9.0 mmol) and Aliquat 336 (0.36 g, 0.9 mmol) and the resulting mixture was stirred for 5 minutes at 80° C. Then 4-fluoro-2-methoxy-1-nitrobenzene (1.28 g, 7.5 mmol) was added, and stirring proceeded at this temperature for 30 minutes. The mixture was cooled and partitioned between methylene chloride (80 mL) and dilute aqueous HCl (50 mL), and the organic layer was extracted with dilute aqueous HCl (2×50 mL). The combined aqueous phases were washed with methylene chloride (3×75 mL), basified (3N NaOH), and extracted with methylene chloride (3×75 mL). The combined organic extracts were washed with water (3×100 mL), dried (MgSO$_4$), and evaporated, providing 1.1 g as a yellow oil, in 62% yield: $^1$H NMR (CDCl$_3$) δ 2.34 (s, 6H), 2.75 (t, J=5.5 Hz, 2H), 3.93 (s, 3H), 4.12 (t, J=5.5 Hz, 2H), 6.51 (dd, J=9.1 Hz, J=2.5 Hz, 1H), 6.60 (d, J=2.5 Hz, 1H), 8.00 (d, J=9.1 Hz, 1H).

5.60.3 4-(2-Dimethylaminoethoxy)-2-methoxyphenylamine

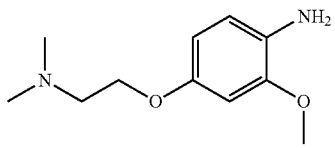

A mixture of [2-(3-Methoxy-4-nitrophenoxy)ethyl]dimethylamine (1.0 g, 4.2 mmol) and 5% Pd—C (0.2 g) in ethyl acetate (75 mL) was shaken under 50 psi of hydrogen for 24 hours. The mixture was filtered through Celite and evaporated, providing 0.80 g of the product as a light gold oil, in 91% yield: $^1$H NMR (CDCl$_3$) δ 2.33 (s, 6H), 2.69 (t, J=5.8 Hz, 2H), 3.82 (s, 3H), 4.00 (t, J=5.8 Hz, 2H), 6.35 (dd, J=8.3 Hz, J=2.6 Hz, 1H), 6.50 (d, J=2.6 Hz, 1H), 6.63 (d, J=8.3 Hz, 1H).

5.60.4 3-[4-(2-Dimethylaminoethoxy)-2-methoxyphenylamino]phthalic acid dimethyl ester

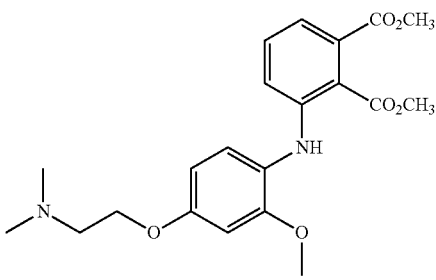 [SMILES: COC(=O)c1cccc(Nc2ccc(OCCN(C)C)cc2OC)c1C(=O)OC]

A mixture of 3-iodophthalic acid dimethyl ester (1.0 g, 3.1 mmol), 4-(2-dimethylaminoethoxy)-2-methoxyphenylamine (0.65 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a methylene chloride-methanol gradient, eluting 0.75 g of the product at 96:4 methylene chloride-methanol, in 60% yield: $^1$H NMR (CDCl$_3$) δ 2.35 (s, 6H), 2.73 (t, J=5.7 Hz, 2H), 3.80 (s, 3H), 3.87 (s, 3H), 3.88 (s, 3H), 4.06 (t, J=5.7 Hz, 2H), 6.46 (dd, J=8.6 Hz, J=2.7 Hz, 1H), 6.59 (d, J=2.7 Hz, 1H), 6.98 (dd, J=7.3 Hz, J=1.0 Hz, 1H), 7.08-7.16 (m, 2H), 7.22 (t, J=7.5 Hz, 1H), 7.93 (br, 1H).

5.60.5 4-[4-(2-Dimethylaminoethoxy)-2-methoxyphenylamino]-2-(2,6-dioxo-piperidin-3-yl)-isoindole-1,3-dione

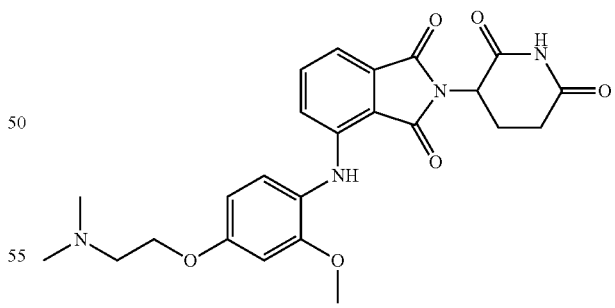

Step 1:
A mixture of 3-[4-(2-dimethylaminoethoxy)-2-methoxyphenylamino]phthalic acid dimethyl ester (0.72 g, 1.8 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.30 g, 1.8 mmol) in pyridine (20 mL) were heated to reflux for 16 hours. The mixture was cooled and evaporated under vacuum. The residue was partitioned between methylene chloride (100 mL) and water (150 mL). The aqueous phase was washed with methylene chloride (2×100 mL), basified (saturated $Na_2CO_3$), and extracted with methylene chloride (3×100 mL). The combined organic layers were washed with water (3×100 mL), dried ($MgSO_4$), and evaporated. The residue was triturated with ether and filtered, providing 0.45 g of the product, in 52% yield for the final 2 steps: $^1$H NMR (DMSO-$d_6$) δ 2.00-2.08 (m, 1H), 2.22 (s, 6H), 2.53-2.65 (m, 4H), 2.83-2.90 (m, 1H), 3.79 (s, 3H), 4.07 (t, J=5.8 Hz, 2H), 5.11 (dd, J=12.6 Hz, J=5.4 Hz, 1H), 6.58 (dd, J=8.6 Hz, J=2.4 Hz, 1H), 6.72 (d, J=2.4 Hz, 1H), 7.01 (d, J=8.6 Hz, 1H), 7.15 (d, J=7.0 Hz, 1H), 7.28 (d, J=8.6 Hz, 1H), 7.55 (t, J=7.8 Hz, 1H), 7.95 (s, 1H), 11.15 (s, 1H).

5.61 4-[4-(2-DIMETHYLAMINOETHOXY)-2-METHOXYPHENYL AMINO]-2-(2,6-DIOXOPIPERIDIN-3-YL)ISOINDOLE-1,3-DIONE HYDROCHLORIDE

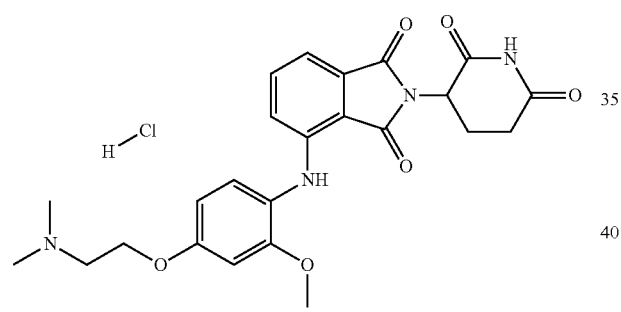

4-[4-(2-Dimethylaminoethoxy)-2-methoxyphenylamino]-2-(2,6-dioxo-piperidin-3-yl)-isoindole-1,3-dione (0.45 g, 1.0 mmol) was dissolved in 9:1 methylene chloride-methanol (30 mL) and a 2 M solution of hydrogen chloride in ether (2.0 mL) was added. The mixture was stirred at room temperature for 1 hour, and was evaporated under vacuum. The residue was triturated with ether and filtered, providing 0.49 g, in quantitative yield: mp>260° C.; $^1$H NMR (DMSO-$d_6$) δ 2.04-2.09 (m, 1H), 2.57-2.64 (m, 2H), 2.84-2.91 (m, 7H), 3.50 (t, J=4.6 Hz, 2H), 3.81 (s, 3H), 4.39 (t, J=4.6 Hz, 2H), 5.11 (dd, J=13.4 Hz, J=5.2 Hz, 1H), 6.65 (dd, J=8.6 Hz, J=2.0 Hz, 1H), 6.80 (d, J=2.0 Hz, 1H), 7.04 (d, J=8.4 Hz, 1H), 7.17 (d, J=7.0 Hz, 1H), 7.34 (d, J=8.6 Hz, 1H), 7.56 (t, J=7.8 Hz, 1H), 8.00 (s, 1H), 10.57 (br, 1H), 11.14 (s, 1H); $^{13}$C NMR (DMSO-$d_6$) δ 22.1, 31.0, 42.7, 48.7, 55.2, 55.9, 62.7, 100.4, 105.7, 110.6, 112.4, 118.3, 121.1, 124.8, 132.1, 136.2, 144.0, 153.4, 155.9, 167.1, 168.8, 170.0, 172.8; Anal. calcd for $C_{24}H_{27}ClN_4O_6 \cdot 0.1Et_2O \cdot 0.8H_2O$: C, 55.85; H, 5.69; N, 10.68. Found: C, 55.80; H, 5.32; N, 10.38.

5.62 4-[2-(2-DIMETHYLAMINOETHOXY)-4-METHOXYPHENYL AMINO]-2-(2,6-DIOXOPIPERIDIN-3-YL)ISOINDOLE-1,3-DIONE HYDROCHLORIDE

5.62.1 2-Fluoro-4-methoxy-1-nitrobenzene

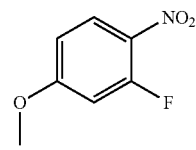

A mixture of 3-fluoro-4-nitrophenol (5.0 g, 31.8 mmol), iodomethane (13.5 g, 95.4 mmol), and potassium carbonate (16.7 g, 159 mmol) in acetone (80 mL) was heated to reflux for 16 hours. The mixture was cooled and evaporated under vacuum, and the partitioned between water (75 mL) and methylene chloride (75 mL) and the aqueous phase was extracted with methylene chloride (2×75 mL). The combined organic phases were washed with water (3×75 mL), dried ($MgSO_4$), and evaporated, providing 5.30 g, in 97% yield: $^1$H NMR (CDCl$_3$) δ 3.90 (s, 3H), 6.70-6.79 (m, 2H), 8.09 (t, J=9.1 Hz, 1H).

5.62.2 [2-(5-Methoxy-2-nitrophenoxy)ethyl]dimethylamine

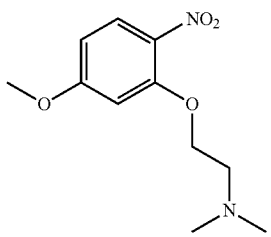

N,N-Dimethylethanolamine (0.80 g, 9.0 mmol) was added to a mixture of powdered KOH (0.50 g, 9.0 mmol) and Aliquat 336 (0.36 g, 0.9 mmol) and the resulting mixture was stirred for 5 minutes at 80° C. Then 2-fluoro-4-methoxy-1-nitrobenzene (1.28 g, 7.5 mmol) was added, and stirring proceeded at this temperature for 30 minutes. The mixture was cooled and partitioned between methylene chloride (80 mL) and dilute aqueous HCl (50 mL), and the organic layer was extracted with dilute aqueous HCl (2×50 mL). The combined aqueous phases were washed with methylene chloride (3×75 mL), basified (3N NaOH), and extracted with methylene chloride (3×75 mL). The combined organic extracts were washed with water (3×100 mL), dried ($MgSO_4$), and evaporated, providing 1.3 g as a yellow oil, in 74% yield: $^1$H NMR (CDCl$_3$) δ 2.36 (s, 6H), 2.81 (t, J=5.8 Hz, 2H), 3.86 (s, 3H), 4.17 (t, J=5.8 Hz, 2H), 6.47-6.54 (m, 2H), 6.97 (d, J=9.0 Hz, 1H).

5.62.3 2-(2-Dimethylaminoethoxy)-4-methoxyphenylamine

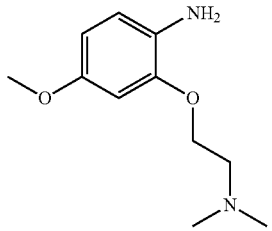

A mixture of [2-(5-methoxy-2-nitrophenoxy)ethyl]dimethylamine (1.2 g, 5.0 mmol) and 5% Pd—C (0.3 g) in ethyl acetate (75 mL) was shaken under 50 psi of hydrogen for 24 hours. The mixture was filtered through Celite and evaporated, providing 0.94 g of the product, in 90% yield: $^1$H NMR (CDCl$_3$) δ 2.34 (s, 6H), 2.75 (t, J=5.8 Hz, 2H), 3.74 (s, 3H), 4.08 (t, J=5.8 Hz, 2H), 6.36 (dd, J=8.4 Hz, J=2.5 Hz, 1H), 6.47 (d, J=2.5 Hz, 1H), 6.65 (d, J=8.4 Hz, 1H).

6.62.4 3-[2-(2-Dimethylaminoethoxy)-4-methoxyphenylamino]phthalic acid dimethyl ester

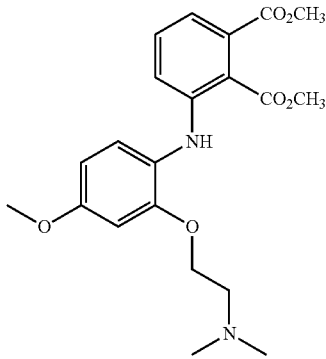 [SMILES: COC(=O)c1cccc(Nc2ccc(OC)cc2OCCN(C)C)c1C(=O)OC]

A mixture of 3-iodophthalic acid dimethyl ester (1.0 g, 3.1 mmol), 2-(2-dimethylaminoethoxy)-4-methoxyphenylamine (0.65 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a methylene chloride-methanol gradient, eluting 0.82 g of the product at 95:5 methylene chloride-methanol. This material was dissolved in methylene chloride (100 mL) and extracted with dilute aqueous HCl (3×75 mL). The combined aqueous extracts were washed with methylene chloride (3×75 mL), made basic (Na$_2$CO$_3$), and extracted into methylene chloride (3×75 mL). The organic phases were dried (MgSO$_4$) and evaporated, providing 0.25 g, in 20% yield: $^1$H NMR (CDCl$_3$) δ 2.28 (s, 6H), 2.70 (t, J=5.8 Hz, 2H), 3.80 (s, 3H), 3.87 (s, 3H), 3.88 (s, 3H), 4.06 (t, J=5.8 Hz, 2H), 6.46 (dd, J=8.6 Hz, J=2.5 Hz, 1H), 6.54 (d, J=2.7 Hz, 1H), 7.00 (dd, J=7.3 Hz, J=1.1 Hz, 1H), 7.09-7.23 (m, 3H), 7.87 (br, 1H).

5.62.5 4-[2-(2-Dimethylaminoethoxy)-4-methoxyphenylamino]-2-(2,6-dioxopiperidin-3-yl)isoindole-1,3-dione hydrochloride

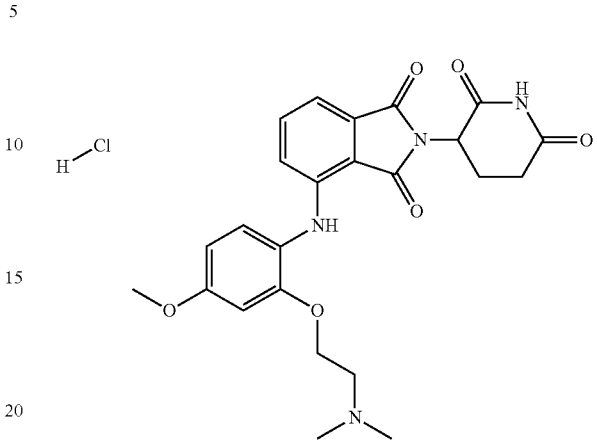

Step 1:

A mixture of 3-[2-(2-dimethylaminoethoxy)-4-methoxyphenylamino]phthalic acid dimethyl ester (0.20 g, 0.5 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.10 g, 0.6 mmol) in pyridine (20 mL) were heated to reflux for 16 hours. The mixture was cooled and evaporated under vacuum. The residue was partitioned between methylene chloride (100 mL) and water (150 mL). The aqueous phase was washed with methylene chloride (2×100 mL), basified (sat. Na$_2$CO$_3$), and extracted with methylene chloride (3×100 mL). The combined organic layers were washed with water (3×100 mL), dried (MgSO$_4$), and evaporated. The residue was triturated with ether and filtered, providing 0.10 g of the product, in 44% yield for the final 2 steps.

Step 3: 4-[4-(2-Dimethylaminoethoxy)-2-methoxyphenylamino]-2-(2,6-dioxo-piperidin-3-yl)-isoindole-1,3-dione (0.10 g, 0.2 mmol) was dissolved in methylene chloride (30 mL) and a 2M solution of hydrogen chloride in ether (0.4 mL) was added. The mixture was stirred at room temperature for 1 hour, and was evaporated under vacuum. The residue was triturated with ether and filtered, providing 0.10 g, in quantitative yield: mp 210-212° C.; $^1$H NMR (DMSO-d$_6$) δ 2.04-2.08 (m, 1H), 2.57-2.71 (m, 8H), 2.83-2.91 (m, 1H), 3.38 (m, 2H), 3.80 (s, 3H), 4.41 (m, 2H), 5.11 (dd, J=15.4 Hz, J=5.3 Hz, 1H), 6.64 (dd, J=8.7 Hz, J=2.4 Hz, 1H), 6.19 (d, J=2.4 Hz, 1H), 7.06 (d, J=8.5 Hz, 1H), 7.17 (d, J=7.0 Hz, 1H), 7.35 (d, J=8.6 Hz, 1H), 7.56 (t, J=7.8 Hz, 1H), 8.01 (s, 1H), 10.43 (br, 1H), 11.14 (s, 1H); $^{13}$C NMR (DMSO-d$_6$) δ 22.1, 31.0, 43.0, 48.7, 55.5, 55.6, 63.4, 100.7, 105.6, 110.6, 112.4, 118.5, 120.7, 125.8, 132.1, 136.2, 144.4, 152.1, 157.8, 167.1, 168.8, 170.0, 172.8; Anal. calcd for C$_{24}$H$_{27}$ClN$_4$O$_6$·0.5H$_2$O: C, 56.31; H, 5.51; N, 10.94. Found: C, 56.24; H, 5.34; N, 10.72.

5.63 2-(2,6-DIOXOPIPERIDIN-3-YL)-4-[2-METH-OXY-4-(2-MORPHOLIN-4-YLETHOXY)PHENY-LAMINO]ISOINDOLE-1,3-DIONE HYDROCHLORIDE

5.63.1
4-[2-(3-Methoxy-4-nitrophenoxy)ethyl]morpholine

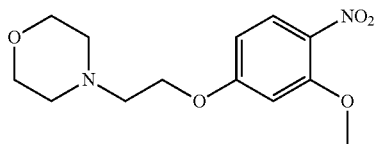 [SMILES: COc1cc(OCCN2CCOCC2)ccc1[N+](=O)[O-]]

4-(2-Hydroxyethyl)morpholine (0.98 g, 9.0 mmol) was added to a mixture of powdered KOH (0.50 g, 9.0 mmol) and Aliquat 336 (0.36 g, 0.9 mmol) and the resulting mixture was stirred for 5 minutes at 80° C. Then 4-fluoro-2-methoxy-1-nitrobenzene (1.28 g, 7.5 mmol) was added, and stirring proceeded at this temperature for 30 minutes. The mixture was cooled and partitioned between methylene chloride (80 mL) and dilute aqueous HCl (50 mL), and the organic layer was extracted with dilute aqueous HCl (2×50 mL). The combined aqueous phases were washed with methylene chloride (3×75 mL), basified (3N NaOH), and extracted with methylene chloride (3×75 mL). The combined organic extracts were washed with water (3×100 mL), dried (MgSO$_4$), and evaporated, providing 1.2 g as a yellow oil, in 57% yield: $^1$H NMR (CDCl$_3$) δ 2.58 (t, J=4.6 Hz, 6H), 2.83 (t, J=5.6 Hz, 2H), 3.74 (t, J=4.6 Hz, 4H), 3.94 (s, 3H), 4.17 (t, J=5.6 Hz, 2H), 6.51 (dd, J=9.1 Hz, J=2.4 Hz, 1H), 6.56 (d, J=2.4 Hz, 1H), 8.00 (d, J=9.1 Hz, 1H).

5.63.2
2-Methoxy-4-(2-morpholin-4-ylethoxy)phenylamine

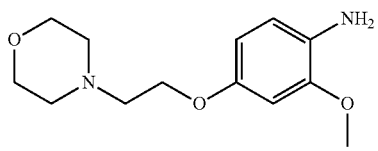

A mixture of 4-[2-(3-methoxy-4-nitrophenoxy)ethyl]morpholine (1.2 g, 4.3 mmol) and 5% Pd—C (0.2 g) in ethyl acetate (75 mL) was shaken under 50 psi of hydrogen for 24 hours. The mixture was filtered through Celite and evaporated, providing 0.95 g of the product as a light grey oil, in 87% yield: $^1$H NMR (CDCl$_3$) δ 2.57 (t, J=4.6 Hz, 4H), 2.77 (t, J=5.7 Hz, 2H), 3.74 (t, J=4.6 Hz, 4H), 3.82 (s, 3H), 4.05 (t, J=5.7 Hz, 2H), 6.34 (dd, J=8.4 Hz, J=2.5 Hz, 1H), 6.47 (d, J=2.5 Hz, 1H), 6.63 (d, J=8.4 Hz, 1H).

5.63.3 3-[2-Methoxy-4-(2-morpholin-4-ylethoxy)phenylamino]phthalic acid dimethyl ester

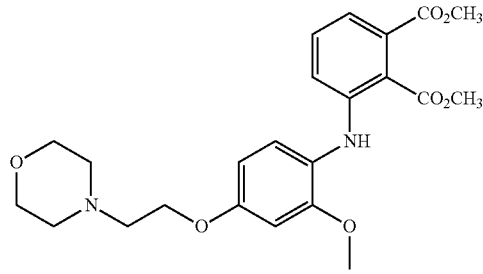 [SMILES: COC(=O)c1cccc(Nc2ccc(OCCN3CCOCC3)cc2OC)c1C(=O)OC]

A mixture of 3-iodophthalic acid dimethyl ester (1.0 g, 3.1 mmol), 2-methoxy-4-(2-morpholin-4-ylethoxy)phenylamine (0.78 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a methylene chloride-methanol gradient, eluting 1.0 g of the product at 95:5 methylene chloride-methanol, in 72% yield: $^1$H NMR (CDCl$_3$) δ 2.59 (t, J=4.6 Hz, 4H), 2.81 (t, J=5.7 Hz, 2H), 3.75 (t, J=4.6 Hz, 4H), 3.81 (s, 3H), 3.87 (s, 3H), 3.88 (s, 3H), 4.11 (t, J=5.7 Hz, 2H), 6.45 (dd, J=8.6 Hz, J=2.6 Hz, 1H), 6.56 (d, J=2.6 Hz, 1H), 6.98 (dd, J=7.3 Hz, J=1.0 Hz, 1H), 7.08-7.17 (m, 2H), 7.22 (t, J=7.5 Hz, 1H), 7.93 (br, 1H).

5.63.4 2-(2,6-Dioxopiperidin-3-yl)-4-[2-methoxy-4-(2-morpholin-4-ylethoxy)phenylamino]-isoindole-1,3-dione hydrochloride

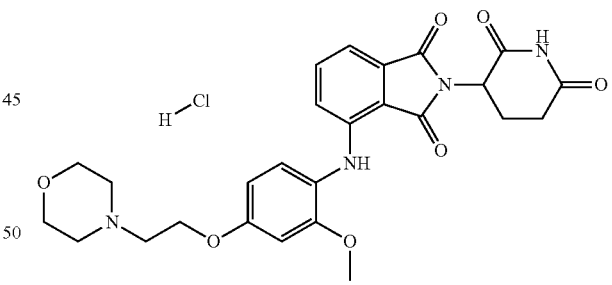

Step 1:

A mixture of 3-[2-methoxy-4-(2-morpholin-4-ylethoxy)phenylamino]phthalic acid dimethyl ester (1.0 g, 2.2 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.36 g, 2.2 mmol) in pyridine (20 mL) were heated to reflux for 16 hours. The mixture was cooled and evaporated under vacuum. The residue was partitioned between methylene chloride (100 mL) and water (150 mL). The aqueous phase was washed with methylene chloride (2×100 mL), basified (saturated $Na_2CO_3$), and extracted with methylene chloride (3×100 mL). The combined organic layers were washed with water (3×100 mL), dried ($MgSO_4$), and evaporated. The residue was chromatographed in 95:5 methylene chloride-methanol, providing 0.3 g of the product, in 27% yield over 2 steps.

Step 3:

The product from Step 2 was dissolved in 9:1 methylene chloride-methanol (30 mL) and a 2M solution of hydrogen chloride in ether (1.0 mL) was added. The mixture was stirred at room temperature for 1 hour, and was evaporated under vacuum. The residue was triturated with ether and filtered, providing 0.3 g, in quantitative yield: mp>260° C.; $^1$H NMR (DMSO-$d_6$) δ 2.03-2.13 (m, 1H), 2.57-2.71 (m, 2H), 2.84-2.95 (m, 1H), 3.38 (t, J=7.0 Hz, 2H), 3.42-3.55 (m, 4H), 3.80-3.92 (m, 7H), 4.47 (s, 2H), 5.10 (d, J=8.4 Hz, 1H), 6.64 (d, J=7.6 Hz, 1H), 6.79 (s, 1H), 7.03 (d, J=7.9 Hz, 1H), 7.16 (d, J=6.1 Hz, 1H), 7.33 (d, J=8.0 Hz, 1H), 7.55 (t, J=6.9 Hz, 1H), 7.98 (s, 1H), 11.13 (s, 1H), 11.62 (br, 1H); $^{13}$C NMR (DMSO-$d_6$) δ 22.1, 31.0, 48.7, 51.7, 54.8, 55.9, 62.7, 63.2, 100.4, 105.7, 110.6, 112.4, 118.3, 121.0, 124.8, 132.1, 136.2, 144.0, 153.5, 155.9, 167.1, 168.8, 170.0, 172.8; Anal. calcd for $C_{26}H_{29}ClN_4O_7 \cdot H_2O$: C, 55.47; H, 5.55; N, 9.95. Found: C, 55.40; H, 5.24; N, 9.66.

5.64 4-(4-DIMETHYLAMINOMETHYL-2-METHOXYPHENYLAMINO)-2-(2,6-DIOXOPIPERIDIN-3-YL)ISOINDOLE-1,3-DIONE

5.64.1 (3-Methoxy-4-nitrobenzyl)dimethylamine

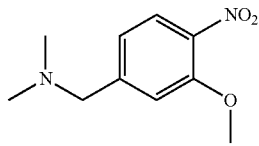

Triethylamine (5 mL) was added to a solution of 3-methoxy-4-nitrobenzyl alcohol (2.5 g, 13.6 mmol) in 50 mL of methylene chloride, and the mixture was cooled to 0° C. under nitrogen. Methanesulfonyl chloride (1.9 g, 16.3 mmol) was added dropwise and the mixture stirred at this temperature for 1 hour. Triethylamine (5 mL) was added, followed by dimethylamine hydrochloride (1.6 g, 20.4 mmol). After 5 minutes, the cooling bath was removed, and the mixture stirred at ambient temperature for 2.5 hours. The mixture was diluted with methylene chloride (75 mL) and washed with water (3×75 mL), and extracted into dilute aqueous HCl (3×75 mL). The combined aqueous extracts were washed with methylene chloride (3×75 mL), basified (3N NaOH), and extracted into methylene chloride (3×75 mL). The combined organic extracts were washed with water (3×75 mL), dried ($MgSO_4$), and evaporated, providing 1.8 g of the product, in 65% yield: $^1$H NMR (CDCl$_3$) δ 2.26 (s, 6H), 3.45 (s, 2H), 3.97 (s, 3H), 6.95 (d, J=8.2 Hz, 1H), 7.12 (s, 1H), 7.82 (d, J=8.2 Hz, 1H).

5.64.2 4-Dimethylaminomethyl-2-methoxyphenylamine

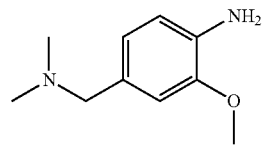

A mixture of (3-methoxy-4-nitrobenzyl)dimethylamine (1.5 g, 7.1 mmol) and 5% Pd—C (0.2 g) in ethyl acetate (75 mL) was shaken under 50 psi of hydrogen for 24 hours. The mixture was filtered through Celite and evaporated, providing 1.2 g of the product as a light grey oil, in 93% yield: $^1$H NMR (CDCl$_3$) δ 2.22 (s, 6H), 3.32 (s, 2H), 3.74 (br, 2H), 3.86 (s, 3H), 6.62-6.67 (m, 2H), 6.78 (s, 1H).

5.64.3 3-(4-Dimethylaminomethyl-2-methoxyphenylamino)phthalic acid dimethyl ester

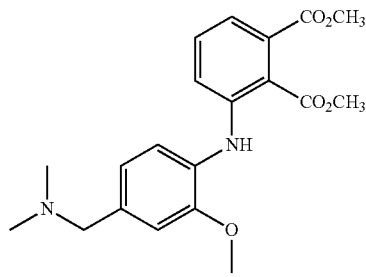 [SMILES: COC(=O)c1cccc(Nc2ccc(CN(C)C)cc2OC)c1C(=O)OC]

A mixture of 3-iodophthalic acid dimethyl ester (1.0 g, 3.1 mmol), 4-dimethylaminomethyl-2-methoxyphenylamine (0.56 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with $CH_2Cl_2$ (10 mL), and filtered through Celite, and the filter was washed with additional $CH_2Cl_2$ (30 mL). The filtrate was evaporated, and the residue was chromatographed using a methylene chloride-methanol gradient, eluting 0.9 g of the product at 92:8 methylene chloride-methanol, in 78% yield: $^1$H NMR (CDCl$_3$) δ 2.31 (s, 6H), 3.47 (s, 2H), 3.87 (s, 3H), 3.88 (s, 3H), 3.90 (s, 3H), 6.80 (dd, J=8.0 Hz, J=1.4 Hz, 1H), 6.99 (s, 1H), 7.14 (dd, J=7.3 Hz, J=0.9 Hz, 1H), 7.20 (d, J=8.0 Hz, 1H), 7.31 (t, J=7.9 Hz, 1H), 7.45 (dd, J=8.5 Hz, J=0.9 Hz, 1H), 7.99 (br, 1H).

5.64.4 4-(4-Dimethylaminomethyl-2-methoxyphenylamino)-2-(2,6-dioxopiperidin-3-yl)isoindole-1,3-dione

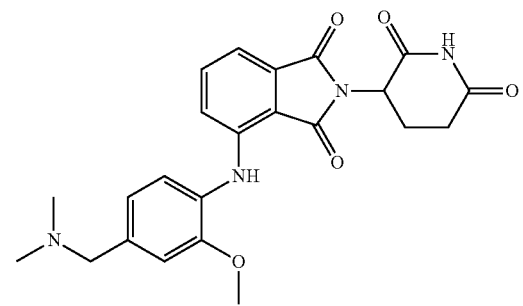 [SMILES: COc1cc(CN(C)C)ccc1Nc1cccc2c1C(=O)N(C1CCC(=O)NC1=O)C2=O]

Step 1:

A mixture of 3-(4-dimethylaminomethyl-2-methoxyphenylamino)phthalic acid dimethyl ester (0.9 g, 2.4 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.39 g, 2.4 mmol) in pyridine (20 mL) were heated to reflux for 16 hours. The mixture was cooled and evaporated under vacuum. The residue was partitioned between methylene chloride (100 mL) and water (150 mL). The aqueous phase was washed with methylene chloride (2×100 mL), basified (saturated $Na_2CO_3$), and extracted with methylene chloride (3×100 mL). The combined organic layers were washed with water (3×100 mL), dried ($MgSO_4$), and evaporated. The residue was triturated in diethyl ether and filtered, providing 0.45 g of the product, in 43% yield over 2 steps: $^1H$ NMR (DMSO-$d_6$) δ 2.05-2.09 (m, 1H), 2.11 (s, 6H), 2.53-2.64 (m, 2H), 2.82-2.92 (m, 1H), 3.38 (s, 2H), 3.84 (s, 3H), 5.12 (dd, J=12.6 Hz, J=5.3 Hz, 1H), 6.91 (d, J=8.8 Hz, 1H), 7.05 (s, 1H), 7.22 (d, J=7.1 Hz, 1H), 7.34-7.41 (m, 2H), 7.62 (t, J=7.9 Hz, 1H), 8.24 (s, 1H), 11.14 (s, 1H).

5.65 4-(4-DIMETHYLAMINOMETHYL-2-METHOXYPHENYLAMINO)-2-(2,6-DIOXOPIPERIDIN-3-YL)ISOINDOLE-1,3-DIONE HYDROCHLORIDE

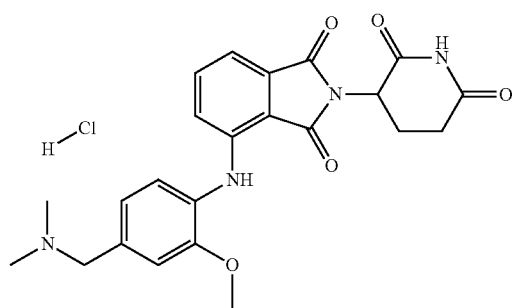

4-(4-Dimethylaminomethyl-2-methoxyphenylamino)-2-(2,6-dioxopiperidin-3-yl)isoindole-1,3-dione (0.42 g, 1.0 mmol) was dissolved in 9:1 methylene chloride-methanol (75 mL) and a 2 M solution of hydrogen chloride in ether (1.0 mL) was added. The mixture was stirred at room temperature for 1 hour, and was evaporated under vacuum. The residue was triturated with ether and filtered, providing 0.44 g, in quantitative yield: mp>260° C.; $^1H$ NMR (DMSO-$d_6$) δ 1.96-2.14 (m, 1H), 2.53-2.68 (m, 8H), 2.84-2.95 (m, 1H), 3.90 (s, 3H), 4.24 (s, 2H), 5.13 (d, J=7.8 Hz, 1H), 7.13 (d, J=7.1 Hz, 1H), 7.28 (d, J=5.7 Hz, 1H), 7.25-7.66 (m, 4H), 8.41 (s, 1H), 11.11 (br, 1H), 11.14 (s, 1H); $^{13}C$ NMR (DMSO-$d_6$) δ 22.1, 31.0, 41.4, 48.8, 56.1, 59.4, 112.3, 113.7, 114.3, 119.3, 123.5, 126.1, 129.0, 132.2, 136.4, 141.7, 150.0, 167.0, 168.8, 170.0, 172.8; Anal. calcd for $C_{23}H_{25}ClN_4O_5 \cdot 0.5H_2O \cdot 0.1Et_2O$: C, 57.44; H, 5.56; N, 11.45. Found: C, 57.44; H, 5.48; N, 11.08.

5.66 4-[4-(3-DIMETHYLAMINOPROPOXY)-2-METHOXYPHENYL AMINO]-2-(2,6-DIOXOPIPERIDIN-3-YL)ISOINDOLE-1,3-DIONE HYDROCHLORIDE

5.66.1
[3-(3-Methoxy-4-nitrophenoxy)propyl]dimethylamine

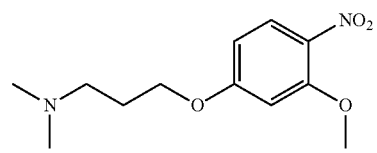 [SMILES: COc1cc(OCCCN(C)C)ccc1[N+](=O)[O-]]

3-Dimethylaminopropanol (1.45 g, 14.0 mmol) was added to a mixture of powdered KOH (0.79 g, 14.0 mmol) and Aliquat 336 (0.57 g, 1.4 mmol) and the resulting mixture was stirred for 5 minutes at 80° C. Then 4-fluoro-2-methoxy-1-nitrobenzene (2.0 g, 11.7 mmol) was added, and stirring proceeded at this temperature for 30 minutes. The mixture was cooled and partitioned between methylene chloride (80 mL) and dilute aqueous HCl (80 mL), and the organic layer was extracted with dilute aqueous HCl (2×50 mL). The combined aqueous phases were washed with methylene chloride (3×75 mL), basified (3N NaOH), and extracted with methylene chloride (3×75 mL). The combined organic extracts were washed with water (3×100 mL), dried ($MgSO_4$), and evaporated, providing 2.1 g as a yellow oil, in 71% yield: $^1H$ NMR ($CDCl_3$) δ 1.98 (q, J=6.8 Hz, 6H), 2.25 (s, 6H), 2.45 (t, J=7.0 Hz, 2H), 3.74 (t, J=4.6 Hz, 4H), 3.94 (s, 3H), 4.10 (t, J=6.4 Hz, 2H), 6.48-6.53 (m, 2H), 7.99 (d, J=8.8 Hz, 1H).

5.66.2
4-(3-Dimethylaminopropoxy)-2-methoxyphenylamine

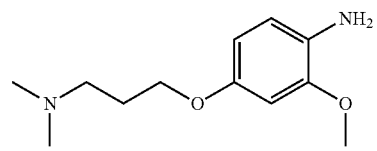 [SMILES: COc1cc(OCCCN(C)C)ccc1N]

A mixture of [3-(3-methoxy-4-nitrophenoxy)propyl]dimethylamine (2.0 g, 7.7 mmol) and 5% Pd—C (0.4 g) in ethyl acetate (75 mL) was shaken under 50 psi of hydrogen for 24 hours. The mixture was filtered through Celite and evaporated, providing 1.7 g of the product as a light grey oil, in 97% yield: $^1H$ NMR ($CDCl_3$) δ 1.86-1.98 (m, 2H), 2.25 (s, 6H), 2.44 (t, J=7.3 Hz, 2H), 3.44 (br, 2H), 3.82 (s, 3H), 3.94 (t, J=6.5 Hz, 2H), 6.35 (dd, J=8.4 Hz, J=2.6 Hz, 1H), 6.46 (d, J=2.6 Hz, 1H), 6.62 (d, J=8.4 Hz, 1H).

5.66.3 3-[4-(3-Dimethylaminopropoxy)-2-methoxyphenylamino]phthalic acid dimethyl ester

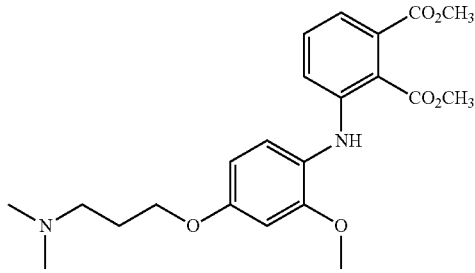 [SMILES: COC(=O)c1cccc(Nc2ccc(OCCCN(C)C)cc2OC)c1C(=O)OC]

A mixture of 3-iodophthalic acid dimethyl ester (1.0 g, 3.1 mmol), 4-(3-dimethylaminopropoxy)-2-methoxyphenylamine (0.70 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 24 hours. The reaction mixture was cooled, diluted with CH$_2$Cl$_2$ (10 mL), and filtered through Celite, and the filter was washed with additional CH$_2$Cl$_2$ (30 mL). The filtrate was evaporated, and the residue was chromatographed using a methylene chloride-methanol gradient, eluting 0.6 g of the product at 94:6 methylene chloride-methanol, in 46% yield: $^1$H NMR (CDCl$_3$) δ 1.98 (p, J=6.8 Hz, 2H), 2.30 (s, 6H), 2.51 (t, J=7.3 Hz, 2H), 3.81 (s, 3H), 3.87 (s, 6H), 4.02 (t, J=6.4 Hz, 2H), 6.45 (dd, J=8.6 Hz, J=2.6 Hz, 1H), 6.54 (d, J=2.6 Hz, 1H), 6.97 (dd, J=7.3 Hz, J=1.0 Hz, 1H), 7.09 (dd, J=8.5 Hz, J=1.0 Hz, 1H), 7.14 (d, J=8.6 Hz, 1H), 7.21 (t, J=7.5 Hz, 1H), 7.92 (br, 1H).

5.66.4 4-[4-(3-Dimethylaminopropoxy)-2-methoxyphenylamino]-2-(2,6-dioxopiperidin-3-yl)isoindole-1,3-dione hydrochloride

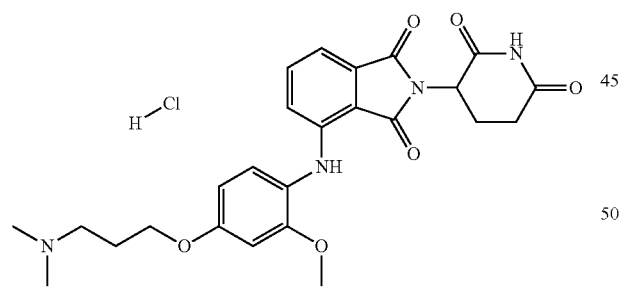

Step 1:
A mixture of 3-[4-(3-dimethylaminopropoxy)-2-methoxyphenylamino]phthalic acid dimethyl ester (0.6 g, 1.4 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:
The product from Step 1 and rac-α-aminoglutarimide hydrochloride (0.23 g, 1.4 mmol) in pyridine (20 mL) were heated to reflux for 16 hours. The mixture was cooled and evaporated under vacuum. The residue was partitioned between methylene chloride (100 mL) and water (150 mL). The aqueous phase was washed with methylene chloride (2×100 mL), basified (saturated Na$_2$CO$_3$), and extracted with methylene chloride (3×100 mL). The combined organic layers were washed with water (3×100 mL), dried (MgSO$_4$), and evaporated. The residue was triturated in diethyl ether and filtered, providing 0.2 g of the product, in 29% yield over 2 steps.

Step 3:
The product from Step 2 was dissolved in 9:1 methylene chloride-methanol (25 mL) and a 2M solution of hydrogen chloride in ether (0.8 mL) was added. The mixture was stirred at room temperature for 1 hour, and was evaporated under vacuum. The residue was triturated with ether and filtered, providing 0.2 g, in quantitative yield: mp 225-227° C.; $^1$H NMR (DMSO-d$_6$) δ 1.94-2.22 (m, 3H), 2.56-2.62 (m, 2H), 2.77 (s, 6H), 2.82-2.92 (m, 1H), 3.21 (t, J=7.0 Hz, 2H), 3.79 (s, 3H), 4.09 (t, J=7.0 Hz, 2H), 5.11 (dd, J=12.3 Hz, J=4.6 Hz, 1H), 6.59 (d, J=7.9 Hz, 1H), 6.72 (s, 1H), 7.01 (d, J=8.4 Hz, 1H), 7.15 (d, J=6.8 Hz, 1H), 7.30 (d, J=8.5 Hz, 1H), 7.55 (t, J=7.5 Hz, 1H), 7.96 (s, 1H), 10.70 (br, 1H), 11.13 (s, 1H); $^{13}$C NMR (DMSO-d$_6$) δ 22.1, 23.9, 31.0, 42.1, 48.7, 54.0, 55.8, 65.3, 100.1, 105.4, 110.5, 112.3, 118.3, 120.4, 125.0, 132.1, 136.1, 144.1, 153.5, 156.8, 167.1, 168.8, 170.0, 172.8; Anal. calcd for C$_{25}$H$_{29}$ClN$_4$O$_6$.H$_2$O: C, 56.13; H, 5.84; N, 10.47. Found: C, 55.91; H, 5.62; N, 10.31.

5.67 4-[4-(2-DIMETHYLAMINO-ETHOXY)-PHENYLAMINO]-2-(2,6-DIOXO-PIPERIDIN-3-YL)-ISOINDOLE-1,3-DIONE HYDROCHLORIDE

5.67.1 Dimethyl-[2-(4-nitro-phenoxy)-ethyl]-amine

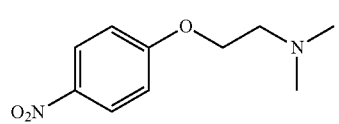

A mixture of 4-nitrophenol (3.5 g, 25 mmol), 2-(dimethylamino)ethyl chloride hydrochloride (3.6 g, 25 mmol), and potassium carbonate (13.2 g, 125 mmol) in acetone (100 mL) was heated to reflux for 30 hours. The solvent was removed under vacuum. The residue was partitioned between water (150 mL) and ethyl acetate (150 mL), and the aqueous phase was extracted with ethyl acetate (100 mL). The combined organic layers were washed with water (3×150 mL) and extracted with dilute aqueous HCl (2×125 mL). These extracts were washed with CH$_2$Cl$_2$ (2×150 mL), made basic (NaOH) and extracted into ethyl acetate (3×75 mL). These organic extracts were washed with water (3×75 mL), dried (MgSO$_4$), and evaporated, providing 3.0 g as a pale yellow solid, in 57% yield; $^1$H NMR (CDCl$_3$) δ 2.35 (s, 6H), 2.76 (t, J=5.6 Hz, 2H), 4.15 (t, J=5.6 Hz, 2H), 6.96-7.00 (m, 2H), 8.17-8.22 (m, 2H).

5.67.2 4-(2-Dimethylamino-ethoxy)-phenylamine

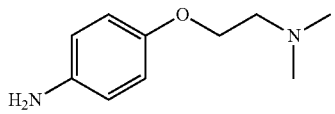

A mixture of dimethyl-[2-(4-nitro-phenoxy)-ethyl]-amine (3.0 g, 14 mmol) and 5% Pd—C (0.4 g) in ethyl acetate (70 mL) was hydrogenated under 50 psi hydrogen for 20 hours. The mixture was filtered through Celite and the filtrate was evaporated in vacuo, providing 2.6 g, in quantitative yield; $^1$H NMR (CDCl$_3$) δ 2.32 (s, 6H), 2.69 (t, J=5.8 Hz, 2H), 3.99 (t, J=5.8 Hz, 2H), 6.00-6.66 (m, 2H), 6.73-6.78 (m, 2H).

5.67.3 3-[4-(2-Dimethylamino-ethoxy)-phenylamino]-phthalic acid dimethyl ester

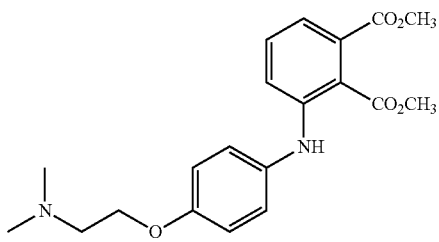 [SMILES: COC(=O)c1cccc(Nc2ccc(OCCN(C)C)cc2)c1C(=O)OC]

A mixture of 4-(2-dimethylamino-ethoxy)-phenylamine (0.56 g, 3.1 mmol), 3-iodophthalic acid dimethyl ester (1.0 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 16 hours. The reaction mixture was cooled, diluted with CH$_2$Cl$_2$ (10 mL), and filtered through Celite, and the filter was washed with additional CH$_2$Cl$_2$ (30 mL). The filtrate was evaporated in vacuo, and the residue was purified by ISCO silica gel flash chromatography using a methylene chloride-methanol gradient, eluting 0.53 g of the product at 95:5 methylene chloride-methanol, in 46% yield, as a pale yellow solid; $^1$H NMR (CDCl$_3$) δ 2.34 (s, 3H), 2.73 (t, J=5.7 Hz, 2H), 3.86 (s, 3H), 3.88 (s, 3H), 4.06 (t, J=5.7 Hz, 2H), 6.89-6.96 (m, 3H), 7.06-7.23 (m, 3H), 7.33-7.50 (m, 1H), 8.09 (s, 1H).

5.67.4 4-[4-(2-Dimethylamino-ethoxy)-phenylamino]-2-(2,6-dioxo-piperidin-3-yl)-isoindole-1,3-dione hydrochloride

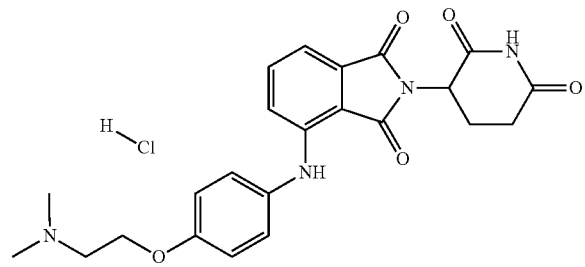 [SMILES: CN(C)CCOc1ccc(Nc2cccc3c2C(=O)N(C2CCC(=O)NC2=O)C3=O)cc1 ; Cl]

Step 1:
A mixture of 3-[4-(2-dimethylamino-ethoxy)-phenylamino]-phthalic acid dimethyl ester (0.50 g, 1.3 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:
The product from Step 1 and rac-α-aminoglutarimide hydrochloride (0.21 g, 1.3 mmol) in pyridine (20 mL) were heated to reflux for 16 hours. The mixture was cooled and evaporated under vacuum. The residue was partitioned between water (150 mL) and ethyl acetate (75 mL). The aqueous phase was washed with CH$_2$Cl$_2$ (3×75 mL), and was basified (sat. Na$_2$CO$_3$) and then extracted into ethyl acetate (3×75 mL). The combined organic extracts were washed with water (3×75 mL), dried (MgSO$_4$) and evaporated, and the residue was triturated with ethyl ether and filtered, providing 130 mg as an orange solid.

Step 3:
The product from Step 2 was dissolved in 9:1 methylene chloride-methanol (20 mL), and a 2N solution of HCl in ethyl ether (0.6 mL) was added dropwise. The mixture stirred at room temperature for 1 hour and was then evaporated, providing 0.13 g as an orange solid, in 21% yield over 3 steps: mp>260° C.; HPLC, Waters Xterra RP18, 3.9×150 mm, 5 µm, 1 mL/min, 240 nm, 40/60 (CH$_3$CN/0.1% HCO$_2$NH$_4$): t$_R$=2.50 (95.99%); $^1$H NMR (DMSO-d$_6$) δ 2.04-2.12 (m, 1H), 2.53-2.64 (m, 2H), 2.84-2.97 (m, 7H), 3.39 (t, J=4.8 Hz, 2H), 4.37 (t, J=4.8 Hz, 2H), 5.12 (dd, J=12.5 Hz, J=5.3 Hz, 1H), 7.06 (d, J=8.8 Hz, 2H), 7.16-7.20 (m, 2H), 7.30 (d, J=8.8 Hz, 2H), 7.57 (t, J=7.8 Hz, 1H), 8.30 (s, 1H), 10.53 (br, 1H), 11.14 (s, 1H); $^{13}$C NMR (DMSO-d$_6$) δ 22.1, 31.0, 42.7, 48.7, 55.3, 62.6, 110.9, 112.7, 115.6, 118.6, 125.0, 132.4, 132.7, 136.2, 144.0, 154.7, 167.1, 168.4, 170.0, 172.8; Anal. calcd For C$_{23}$H$_{25}$ClN$_4$O$_5$·0.7H$_2$O: C, 56.89; H, 5.48; N, 11.54. Found: C, 57.02; H, 5.28; N, 11.15.

5.68 4-[4-(2-DIMETHYLAMINO-ETHOXY)-2-ISOPROPOXY-PHENYLAMINO]-2-(2,6-DIOXO-PIPERIDIN-3-YL)-ISOINDOLE-1,3-DIONE HYDROCHLORIDE

5.68.1 4-Fluoro-2-isopropoxy-1-nitro-benzene

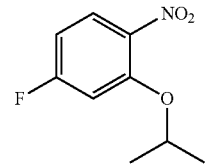

A mixture of 5-fluoro-2-nitrophenol (2.5 g, 15.9 mmol), 2-iodopropane (5.4 g, 31.8 mmol), and potassium carbonate (4.2 g, 39.8 mmol) in acetone (40 mL) was heated to reflux for 16 hours. The mixture was cooled and evaporated under vacuum, and the residue was partitioned between ethyl acetate (100 mL) and water (150 mL), and the aqueous phase was extracted with ethyl acetate (100 mL). The combined organic layers were washed with water (3×150 mL), dried (MgSO$_4$), and evaporated, providing 3.2 g, in quantitative yield; $^1$H NMR (CDCl$_3$) δ 1.42 (d, J=6.0 Hz, 6H), 4.63 (septet, J=6.0 Hz, 6H), 6.64-6.72 (m, 1H), 6.76 (dd, J=9.8 Hz, J=2.5 Hz, 1H), 7.88 (dd, J=8.9 Hz, J=6.1 Hz, 1H).

5.68.2 [2-(3-Isopropoxy-4-nitro-phenoxy)-ethyl]-dimethyl-amine

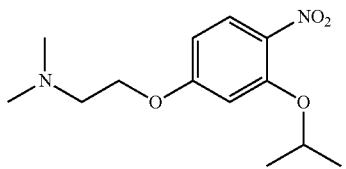 [SMILES: CC(C)Oc1cc(OCCN(C)C)ccc1[N+](=O)[O-]]

N,N-Dimethylethanolamine (1.6 g, 18 mmol) was added to a mixture of powdered KOH (1.0 g, 18 mmol) and Aliquat 336 (0.72 g, 1.8 mmol), and the resulting mixture was stirred for 5 minutes at 80° C. Then 4-fluoro-2-isopropoxy-1-nitrobenzene (3.0 g, 15 mmol) was added, and stirring proceeded at this temperature for 30 minutes. The mixture was cooled and partitioned between methylene chloride (100 mL) and dilute aqueous HCl (100 mL), and the organic layer was extracted with dilute aqueous HCl (2×100 mL). The combined aqueous phases were washed with methylene chloride (3×150 mL), basified (3N NaOH), and extracted with methylene chloride (3×100 mL). The combined organic extracts were washed with water (3×100 mL), dried ($MgSO_4$), and evaporated, providing 2.2 g as a yellow oil, in 55% yield; $^1$H NMR ($CDCl_3$) δ 1.40 (d, J=6.1 Hz, 6H), 2.34 (s, 6H), 2.74 (t, J=5.6 Hz, 2H), 4.10 (t, J=5.6 Hz, 2H), 4.61 (septet, J=6.1 Hz, 1H), 6.48 (dd, J=9.1 Hz, J=2.5 Hz, 1H), 6.57 (d, J=2.5 Hz, 1H), 7.91 (d, J=9.1 Hz, 1H).

5.68.3 4-(2-Dimethylamino-ethoxy)-2-isopropoxy-phenylamine

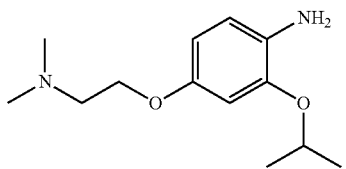 [SMILES: CC(C)Oc1cc(OCCN(C)C)ccc1N]

A mixture of [2-(3-isopropoxy-4-nitrophenoxy)ethyl]dimethylamine (2.0 g, 7.5 mmol) and 5% Pd—C (0.3 g) in ethyl acetate (70 mL) was shaken under 50 psi of hydrogen for 24 hours. The mixture was filtered through Celite and evaporated, providing 1.7 g of the product as a light gold oil, in 98% yield; $^1$H NMR ($CDCl_3$) δ 1.34 (d, J=6.0 Hz, 6H), 2.32 (s, 6H), 2.68 (t, J=5.8 Hz, 2H), 3.48 (br, 2H), 3.98 (t, J=5.8 Hz, 2H), 4.48 (septet, J=6.0 Hz, 1H), 6.35 (dd, J=8.4 Hz, J=2.5 Hz, 1H), 6.50 (d, J=2.5 Hz, 1H), 6.63 (d, J=8.4 Hz, 1H).

5.68.4 3-[4-(2-Dimethylamino-ethoxy)-2-isopropoxy-phenylamino]-phthalic acid dimethyl ester

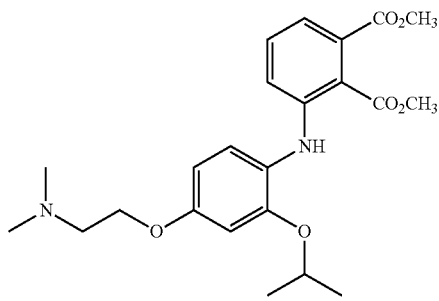 [SMILES: COC(=O)c1cccc(Nc2ccc(OCCN(C)C)cc2OC(C)C)c1C(=O)OC]

A mixture of 3-iodophthalic acid dimethyl ester (2.0 g, 6.2 mmol), 4-(2-dimethylaminoethoxy)-2-isopropoxyphenylamine (1.5 g, 6.2 mmol), $Pd_2(dba)_3$ (0.26 g, 0.28 mmol), rac-BINAP (0.12 g, 0.19 mmol), and cesium carbonate (2.8 g, 8.6 mmol), in 12 mL toluene was heated to reflux under nitrogen for 24 hours. The reaction mixture was cooled, diluted with $CH_2Cl_2$ (20 mL), and filtered through Celite, and the filter was washed with additional $CH_2Cl_2$ (60 mL). The filtrate was evaporated in vacuo, and the residue was purified by ISCO silica gel flash chromatography using a methylene chloride-methanol gradient, eluting 1.3 g of the product at 96:4 methylene chloride-methanol, in 47% yield; $^1$H NMR ($CDCl_3$) δ 1.31 (d, J=6.1 Hz, 6H), 2.96 (d, J=4.8 Hz, 6H), 3.41-3.47 (m, 2H), 3.87 (s, 6H), 4.47-4.51 (m, 3H), 6.45 (dd, J=8.7 Hz, J=2.6 Hz, 1H), 6.56 (d, J=2.6 Hz, 1H), 7.07 (dd, J=6.0 Hz, J=2.5 Hz, 1H), 7.18 (d, J=8.7 Hz, 1H), 7.20-7.18 (m, 2H), 7.90 (s, 1H).

5.68.5 4-[4-(2-Dimethylamino-ethoxy)-2-isopropoxy-phenylamino]-2-(2,6-dioxo-piperidin-3-yl)-isoindole-1,3-dione hydrochloride

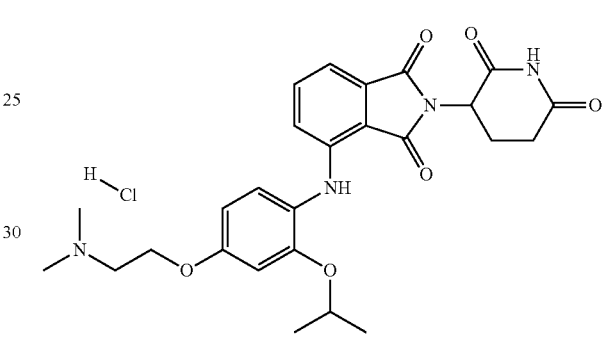

Step 1:

A mixture of 3-[4-(2-dimethylamino-ethoxy)-2-isopropoxy-phenylamino]-phthalic acid dimethyl ester (1.1 g, 2.7 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.45 g, 2.7 mmol) in pyridine (20 mL) were heated to reflux for 16 hours. The mixture was cooled and evaporated under vacuum. The residue was partitioned between water (150 mL) and ethyl acetate (75 mL). The aqueous phase was washed with $CH_2Cl_2$ (3×75 mL), and was basified (sat. $Na_2CO_3$) and then extracted into ethyl acetate (3×75 mL). The combined organic extracts were washed with water (3×75 mL), dried ($MgSO_4$) and evaporated, and the residue was triturated with ethyl ether and filtered, providing 260 mg as an orange solid.

Step 3:

The product from Step 2 was dissolved in 9:1 methylene chloride-methanol (20 mL), and a 2N solution of HCl in ethyl ether (0.3 mL) was added dropwise. The mixture stirred at room temperature for 1 hour and was then evaporated, providing 0.16 g as an orange solid, in 12% yield over 3 steps: mp 247-249° C.; HPLC, Waters Xterra RP18, 3.9×150 mm, 5 μm, 1 mL/min, 240 nm, 40/60 ($CH_3CN$/0.1% $HCO_2NH_4$): $t_R$=4.02 (96.99%); $^1$H NMR (DMSO-$d_6$) δ 1.25 (d, J=5.9 Hz, 1H), 2.05-2.10 (m, 1H), 2.51-2.63 (m, 2H), 2.84-2.91 (m, 7H), 3.49 (t, J=4.8 Hz, 2H), 4.38 (t, J=4.8 Hz, 2H), 4.65

(septet, J=5.9 Hz, 1H), 5.13 (dd, J=12.4 Hz, J=5.2 Hz, 1H), 6.64 (dd, J=8.7 Hz, J=2.2 Hz, 1H), 6.82 (d, J=2.2 Hz, 1H), 7.17-7.25 (m, 2H), 7.38 (d, J=8.7 Hz, 1H), 7.60 (t, J=7.8 Hz, 1H), 8.13 (s, 1H), 10.54 (br, 1H), 11.14 (s, 1H); $^{13}$C NMR (DMSO-$d_6$) δ 21.8, 22.1, 31.0, 42.7, 48.7, 55.2, 62.7, 71.0, 102.8, 106.2, 110.9, 112.6, 118.5, 122.7, 123.2, 132.1, 136.2, 143.4, 150.7, 155.2, 167.1, 168.9, 170.0, 172.8; Anal. calcd For $C_{26}H_{31}ClN_4O_6 \cdot 0.6H_2O$: C, 57.64; H, 5.99; N, 10.34. Found: C, 57.62; H, 5.87; N, 10.25.

5.69 2-(2,6-DIOXO-PIPERIDIN-3-YL)-4-(4-METHOXY-2-PHENOXY-PHENYLAMINO)-ISOINDOLE-1,3-DIONE

5.69.1 4-Methoxy-1-nitro-2-phenoxy-benzene

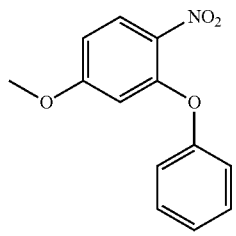 [SMILES: COc1ccc([N+](=O)[O-])c(Oc2ccccc2)c1]

A 60% dispersion of sodium hydride (0.86 g, 22 mmol) was added to a mixture of copper bromide (2.6 g, 17.9 mmol) and phenol (1.7 g, 17.9 mmol) in pyridine (300 mL). After the effervescence subsided, the mixture was heated to reflux for 30 minutes. 3-Iodo-4-nitroanisole (5.0 g, 17.9 mmol) was added and stirring proceeded under nitrogen for 20 hours. The mixture was cooled and the reaction was quenched with saturated ammonium chloride (1 mL). The mixture was evaporated in vacuo. The residue was dissolved in ethyl acetate (250 mL) and washed with dilute aqueous HCl (2×200 mL), saturated sodium carbonate (2×200 mL) and water (200 mL), and was evaporated in vacuo. The residue was purified by ISCO silica gel flash chromatography in hexanes-ethyl acetate gradient, eluting 2.8 g of the product at 7:3 hexanes-ethyl acetate, in 64% yield; $^1$H NMR (CDCl$_3$) δ 3.78 (s, 3H), 6.43 (d, J=2.3 Hz, 1H), 6.68 (dd, J=9.2, J=2.3 Hz, 1H), 7.03-7.07 (m, 2H), 7.19 (t, J=7.3 Hz, 1H), 7.37-7.41 (m, 2H), 8.07 (d, J=9.2 Hz, 1H).

5.69.2 4-Methoxy-2-phenoxy-phenylamine

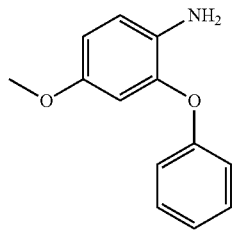

A mixture 4-methoxy-1-nitro-2-phenoxy-benzene (1.3 g, 5.3 mmol) and 5% Pd—C (0.3 g) in ethyl acetate (100 mL) was shaken under 50 psi of hydrogen for 20 hours. The mixture was filtered through Celite and evaporated, providing 1.1 g of the product as a light gold oil; $^1$H NMR (CDCl$_3$) δ 3.70 (s, 3H), 6.49 (d, J=2.6 Hz, 1H), 6.59 (dd, J=8.6 Hz, J=2.6 Hz, 1H), 6.78 (d, J=8.6 Hz, 1H), 6.96-7.00 (m, 2H), 7.07 (t, J=7.3 Hz, 1H), 7.28-7.35 (m, 2H).

5.69.3 3-(4-Methoxy-2-phenoxy-phenylamino)-phthalic acid dimethyl ester

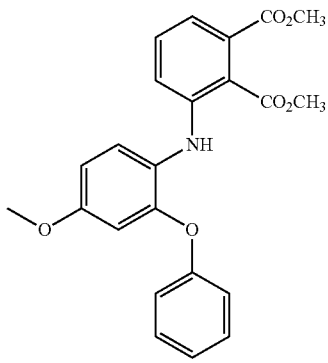 [SMILES: COC(=O)c1cccc(Nc2ccc(OC)cc2Oc2ccccc2)c1C(=O)OC]

A mixture of 3-iodophthalic acid dimethyl ester (1.0 g, 3.1 mmol), 4-methoxy-2-phenoxy-phenylamine (0.67 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 16 hours. The reaction mixture was cooled, diluted with CH$_2$Cl$_2$ (10 mL), and filtered through Celite, and the filter was washed with additional CH$_2$Cl$_2$ (30 mL). The filtrate was evaporated in vacuo, and the residue was purified by ISCO silica gel flash chromatography using a hexanes-ethyl acetate gradient, eluting 0.9 g of the product at 8:2 hexanes-ethyl acetate, in 71% yield; $^1$H NMR (CDCl$_3$) δ 3.74 (s, 3H), 3.76 (s, 3H), 3.84 (s, 3H), 6.60 (d, J=2.9 Hz, 1H), 6.69 (dd, J=8.7 Hz, J=2.9 Hz, 1H), 6.85-6.89 (m, 2H), 6.97-7.07 (m, 2H), 7.09 (dd, J=8.5 Hz, J=1.0 Hz, 1H), 7.22-7.29 (m, 4H), 7.84 (s, 1H).

5.69.4 3-(4-Methoxy-2-phenoxy-phenylamino)-phthalic acid

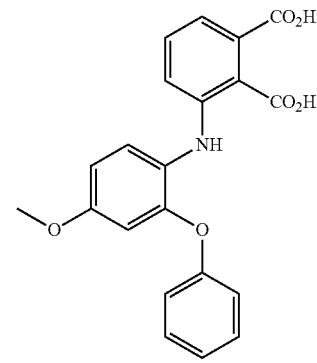 [SMILES: COc1ccc(Nc2cccc(C(=O)O)c2C(=O)O)c(Oc2ccccc2)c1]

A mixture of 3-(4-methoxy-2-phenoxy-phenylamino)-phthalic acid dimethyl ester (0.80 g, 2.0 mmol) and 3N NaOH (50 mL) in ethanol (100 mL) was heated to reflux for 90 minutes. The mixture was cooled, and the solvent was removed under vacuum. The residue was dissolved in water (100 mL), washed with CH$_2$Cl$_2$ (2×100 mL), and acidified (HCl). The resulting mixture was extracted with ethyl acetate (4×50 mL) and the combined extracts were washed with water (3×100 mL), dried (MgSO$_4$) and evaporated, providing 0.69 g, in 93% yield; $^1$H NMR (DMSO-d$_6$) δ 3.71 (s, 3H), 6.58 (d, J=2.7, 1H), 6.80 (dd, J=8.8 Hz, J=2.7 Hz, 1H), 6.88-6.94 (m, 3H), 7.03-7.10 (m, 2H), 7.27-7.36 (m, 4H), 8.07 (s, 1H).

5.69.5 2-(2,6-Dioxo-piperidin-3-yl)-4-(4-methoxy-2-phenoxy-phenylamino)-isoindole-1,3-dione

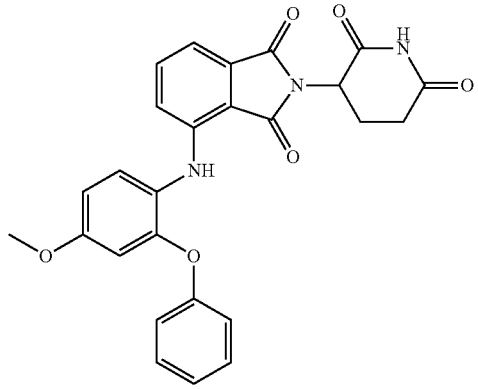 [SMILES: COc1ccc(Nc2cccc3c2C(=O)N(C2CCC(=O)NC2=O)C3=O)c(Oc2ccccc2)c1]

A mixture of 3-(4-methoxy-2-phenoxy-phenylamino)-phthalic acid (0.60 g, 1.6 mmol) and rac-α-aminoglutarimide hydrochloride (0.26 g, 1.6 mmol) in pyridine (10 mL) were heated to reflux for 20 hours. The mixture was cooled and evaporated under vacuum. The residue was dissolved in ethyl acetate (100 mL) and washed with dilute aqueous HCl (3×100 mL) and water (100 mL), and then evaporated under vacuum. The residue was purified by ISCO silica gel flash chromatography using a methylene chloride-methanol gradient, eluting 0.66 g of the product, an orange solid, at 95:5 methylene chloride-methanol, in 89% yield: mp 142-144° C.; HPLC, Waters Symmetry C-18, 3.9×150 mm, 5 µm, 1 mL/min, 240 nm, 60/40 CH$_3$CN/0.1% H$_3$PO$_4$, 4.71 min (96.79%); $^1$H NMR (DMSO-d$_6$) δ 1.98-2.04 (m, 1H), 2.49-2.61 (m, 2H), 2.81-2.90 (m, 1H), 3.73 (s, 3H), 5.06 (dd, J=12.8 Hz, J=5.3 Hz, 1H), 6.58 (d, J=2.8 Hz, 1H), 6.84 (dd, J=8.8, J=2.8 Hz, 1H), 6.90-6.94 (m, 2H), 7.04-7.10 (m, 2H), 7.16 (d, J=7.0 Hz, 1H), 7.27-7.34 (m, 2H), 7.45 (d, J=8.7 Hz, 1H), 7.57 (dd, J=8.3 Hz, J=7.4 Hz, 1H), 7.95 (s, 1H), 11.10 (s, 1H); $^{13}$C NMR (DMSO-d$_6$) δ 22.1, 30.9, 48.6, 55.5, 105.9, 109.6, 110.7, 112.6, 117.9, 118.7, 122.8, 123.5, 127.2, 129.9, 132.0, 136.0, 144.0, 151.1, 156.2, 157.8, 167.1, 168.5, 169.9, 172.8; Anal. calcd For C$_{26}$H$_{21}$N$_3$O$_6$·0.3H$_2$O: C, 65.49; H, 4.55; N, 8.84. Found: C, 65.43; H, 4.29; N, 8.73.

5.70 4-[4-(2-DIMETHYLAMINO-ETHOXY)-2-PHENOXY-PHENYLAMINO]-2-(2,6-DIOXO-PIPERIDIN-3-YL)-ISOINDOLE-1,3-DIONE HYDROCHLORIDE

5.70.1 [2-(3-Fluoro-4-nitro-phenoxy)-ethyl]-dimethyl-amine

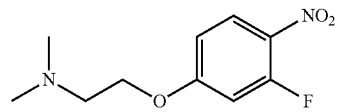 [SMILES: CN(C)CCOc1ccc([N+](=O)[O-])c(F)c1]

A mixture of 3-fluoro-4-nitrophenol (3.0 g, 19 mmol), 2-(dimethylamino)ethyl chloride hydrochloride (3.0 g, 21 mmol) and potassium carbonate (5.4 g, 39 mmol) in 2-butanone (75 mL) was heated to reflux for 20 hours. An additional portion of 2-(dimethylamino)ethyl chloride hydrochloride (2.0 g, 14 mmol) was added, and stirring at reflux proceeded for 24 hours. The mixture was cooled and evaporated under vacuum, and the residue was partitioned between ethyl acetate (100 mL) and water (150 mL), and the aqueous phase was extracted with ethyl acetate (100 mL). The combined organic layers were washed with water (3×150 mL) and extracted into dilute aqueous HCl (3×75 mL). The combined aqueous extracts were washed with ethyl acetate (2×100 mL) and basified (NaOH), and the resulting mixture was extracted with ethyl acetate (3×100 mL). The combined extracts were washed with water (3×100 mL), dried (MgSO$_4$), and evaporated, providing 2.9 g as a yellow oil, in 67% yield; $^1$H NMR (CDCl$_3$) δ 2.34 (s, 6H), 2.76 (t, J=5.5 Hz, 2H), 4.13 (t, J=5.5 Hz, 2H), 6.72-6.81 (m, 2H), 8.09 (t, J=9.1 Hz, 1H).

5.70.2 Dimethyl-[2-(4-nitro-3-phenoxy-phenoxy)-ethyl]-amine

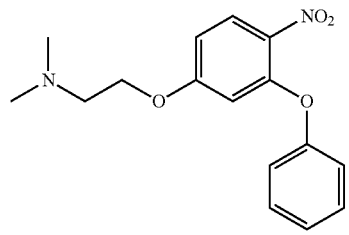 [SMILES: CN(C)CCOc1ccc([N+](=O)[O-])c(Oc2ccccc2)c1]

A mixture of [2-(3-fluoro-4-nitro-phenoxy)-ethyl]-dimethyl-amine (2.8 g, 12 mmol) and phenol (1.4 g, 15 mmol) in DMF (100 mL) was treated with potassium carbonate (3.4 g, 25 mmol) and the mixture heated at 110° C. under N$_2$ with stirring. After 4 hours, the mixture was cooled to ambient temperature. The mixture was evaporated in vacuo, and the residue was partitioned between ethyl acetate (100 mL) and water (100 mL), and the aqueous phase was extracted with ethyl acetate (100 mL). The combined organic phases were washed with 10% potassium carbonate (2×100 mL) and water (2×100 mL), and were then extracted with dilute aqueous HCl (3×75 mL). The combined aqueous extracts were washed with CH$_2$Cl$_2$ (2×100 mL), basified (NaOH), and extracted into ethyl acetate (3×75 mL). The combined organic phases were washed with water (2×100 mL), dried (MgSO$_4$) and evaporated, providing 3.1 g, in 84% yield; $^1$H NMR (CDCl$_3$) δ 2.29 (s, 6H), 2.67 (t, J=5.8 Hz, 2H), 4.00 (t, J=5.8 Hz, 2H), 6.46 (d, J=2.6 Hz, 1H), 6.68 (dd, J=9.2 Hz, J=2.6 Hz, 1H), 7.03-7.07 (m, 2H), 7.18-7.22 (m, 1H), 7.35-7.42 (m, 2H), 8.06 (d, J=9.2 Hz, 1H).

5.70.3 4-(2-Dimethylamino-ethoxy)-2-phenoxy-phenylamine

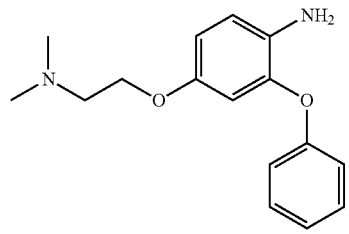

A mixture dimethyl-[2-(4-nitro-3-phenoxy-phenoxy)-ethyl]-amine (3.0 g, 9.9 mmol) and 5% Pd—C (0.6 g) in ethyl acetate (100 mL) was shaken under 50 psi of hydrogen for 20 hours. The mixture was filtered through Celite and evaporated, providing 2.7 g of the product, in quantitative yield; $^1$H NMR (CDCl$_3$) δ 2.30 (s, 6H), 2.65 (t, J=5.7 Hz, 2H), 3.93 (t, J=5.7 Hz, 2H), 6.51 (d, J=2.6 Hz, 1H), 6.60 (dd, J=8.6 Hz, J=2.9 Hz, 1H), 6.74 (d, J=8.6 Hz, 1H), 6.95-7.00 (m, 2H), 7.06 (t, J=7.3 Hz, 1H), 7.28-7.34 (m, 2H).

5.70.4 3-[4-(2-Dimethylamino-ethoxy)-2-phenoxy-phenylamino]-phthalic acid dimethyl ester

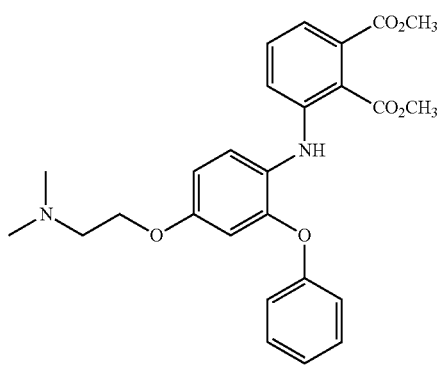 [SMILES: COC(=O)c1cccc(Nc2ccc(OCCN(C)C)cc2Oc2ccccc2)c1C(=O)OC]

A mixture of 3-iodophthalic acid dimethyl ester (2.0 g, 6.2 mmol), 4-(2-dimethylamino-ethoxy)-2-phenoxy-phenylamine (1.9 g, 6.2 mmol), Pd$_2$(dba)$_3$ (0.26 g, 0.28 mmol), rac-BINAP (0.12 g, 0.19 mmol), and cesium carbonate (2.8 g, 8.6 mmol), in 12 mL toluene was heated to reflux under nitrogen for 16 hours. The reaction mixture was cooled, diluted with CH$_2$Cl$_2$ (20 mL), and filtered through Celite, and the filter was washed with additional CH$_2$Cl$_2$ (60 mL). The filtrate was evaporated in vacuo, and the residue was purified by ISCO silica gel flash chromatography using a methylene chloride-methanol gradient, eluting 2.2 g of the product, an orange solid, at 95:5 methylene chloride-methanol, in 76% yield; $^1$H NMR (CDCl$_3$) δ 2.31 (s, 6H), 2.69 (t, J=5.6 Hz, 2H), 3.74 (s, 3H), 3.84 (s, 3H), 3.99 (t, J=5.6 Hz, 2H), 6.61 (d, J=2.6 Hz, 1H), 6.69 (dd, J=8.5 Hz, J=2.8 Hz, 1H), 6.86-6.90 (m, 2H), 6.98 (dd, J=7.3 Hz, J=1.1 Hz, 1H), 7.01-7.07 (m, 1H), 7.11 (dd, J=8.6 Hz, J=1.1 Hz, 1H), 7.22-7.30 (m, 4H), 7.85 (s, 1H).

5.70.5 4-[4-(2-Dimethylamino-ethoxy)-2-phenoxy-phenylamino]-2-(2,6-dioxo-piperidin-3-yl)-isoindole-1,3-dione hydrochloride

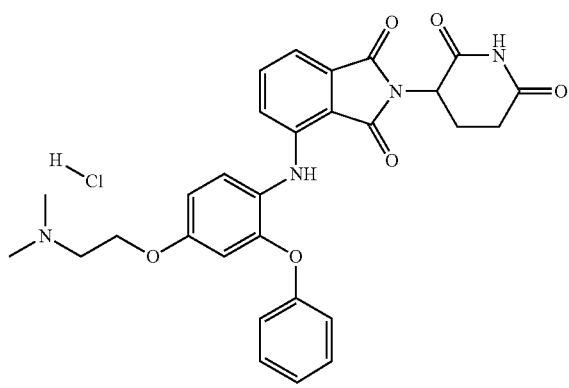

Step 1:
A mixture of 3-[4-(2-dimethylamino-ethoxy)-2-phenoxy-phenylamino]-phthalic acid dimethyl ester (2.0 g, 4.3 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:
The product from Step 1 and rac-α-aminoglutarimide hydrochloride (0.70 g, 4.3 mmol) in pyridine (20 mL) were heated to reflux for 16 hours. The mixture was cooled and evaporated under vacuum. The residue was partitioned between water (150 mL) and ethyl acetate (75 mL). The aqueous phase was washed with CH$_2$Cl$_2$ (3×75 mL), and was basified (sat. Na$_2$CO$_3$) and then extracted into ethyl acetate (3×75 mL). The combined organic extracts were washed with water (3×75 mL), dried (MgSO$_4$) and evaporated, and the residue was triturated with ethyl ether and filtered, providing 260 mg as an orange solid.

Step 3:
The product from Step 2 was dissolved in 9:1 methylene chloride-methanol (20 mL), and a 2N solution of HCl in ethyl ether (4.3 mL) was added dropwise. The mixture stirred at room temperature for 1 hour and was then evaporated, providing 0.98 g of the product as an orange solid, in 41% yield over 3 steps: mp>400° C.; HPLC, Waters Xterra RP18, 3.9× 150 mm, 5 μm, 1 mL/min, 240 nm, 40/60 (CH$_3$CN/0.1% HCO$_2$NH$_4$): t$_R$=5.50 (96.24%); $^1$H NMR (DMSO-d$_6$) δ 1.99-2.04 (m, 1H), 2.51-2.61 (m, 2H), 2.80-2.94 (m, 7H), 3.46-3.56 (m, 2H), 4.33 (t, J=4.7 Hz, 2H), 5.07 (dd, J=12.6 Hz, J=5.1 Hz, 1H), 6.64 (d, J=2.6 Hz, 1H), 6.90 (dd, J=8.8 Hz, J=2.6 Hz, 1H), 6.93-6.97 (m, 2H), 7.07-7.14 (m, 2H), 7.18 (d, J=7.0 Hz, 1H), 7.30-7.37 (m, 2H), 7.50 (d, J=8.8 Hz, 1H), 7.59 (t, J=7.8 Hz, 1H), 8.04 (s, 1H), 10.50 (br, 1H), 11.11 (s, 1H); $^{13}$C NMR (DMSO-d$_6$) δ 22.1, 30.9, 42.7, 48.6, 55.1, 62.7, 106.7, 110.0, 110.9, 112.7, 118.2, 118.7, 123.6, 123.8, 126.8, 130.0, 132.0, 136.1, 143.8, 151.0, 155.9, 156.0, 167.0, 168.6, 169.9, 172.8; Anal. calcd. For C$_{29}$H$_{29}$ClN$_4$O$_6$·0.85H$_2$O: C, 60.02; H, 5.33; N, 9.65. Found: C, 60.02; H, 5.30; N, 9.30.

5.71 2-(2,6-DIOXO-PIPERIDIN-3-YL)-4-[4-(2-MORPHOLIN-4-YL-ETHOXY)-PHENYLAMINO]-ISOINDOLE-1,3-DIONE HYDROCHLORIDE

5.71.1 4-[2-(4-Nitro-phenoxy)-ethyl]-morpholine

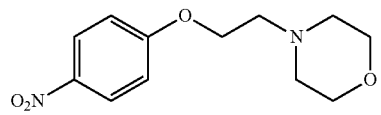

A mixture of 4-nitrophenol (3.5 g, 25 mmol), N-(2-chloroethyl)morpholine hydrochloride (4.7 g, 25 mmol), and potassium carbonate (13.2 g, 125 mmol) in acetone (100 mL) was heated to reflux for 18 hours. The solvent was removed under vacuum. The residue was partitioned between water (150 mL) and ethyl acetate (150 mL), and the aqueous phase was extracted with ethyl acetate (100 mL). The combined organic layers were washed with water (3×100 mL) and extracted with dilute aqueous HCl (2×125 mL). These extracts were washed with $CH_2Cl_2$ (2×125 mL), made basic (NaOH), and extracted into ethyl acetate (3×75 mL). These organic extracts were washed with water (3×75 mL), dried ($MgSO_4$), and evaporated, providing 3.4 g as a pale yellow solid, in 54% yield; $^1H$ NMR ($CDCl_3$) δ 2.59 (t, J=4.7 Hz, 4H), 2.84 (t, J=5.7 Hz, 2H), 3.74 (t, J=4.7 Hz, 4H), 4.20 (t, J=5.7 Hz, 2H), 6.97 (d, J=9.0 Hz, 2H), 8.20 (d, J=9.0 Hz, 2H).

5.71.2 4-(2-Morpholin-4-yl-ethoxy)-phenylamine

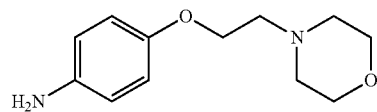 [SMILES: O=[N+]([O-])c1ccc(OCCN2CCOCC2)cc1]

A mixture of 4-[2-(4-nitro-phenoxy)-ethyl]-morpholine (3.2 g, 13 mmol) and 5% Pd—C (0.3 g) in ethyl acetate (70 mL) was hydrogenated under 50 psi hydrogen for 20 hours. The mixture was filtered through Celite, and the filtrate was evaporated in vacuo, providing 2.0 g, in 72% yield; $^1H$ NMR ($CDCl_3$) δ 2.57 (t, J=4.6 Hz, 4H), 2.77 (t, J=5.8 Hz, 2H), 3.74 (t, J=4.6 Hz, 4H), 4.04 (t, J=5.8 Hz, 2H), 6.63 (d, J=8.8 Hz, 2H), 6.75 (d, J=8.8 Hz, 2H).

5.71.3 3-[4-(2-Morpholin-4-yl-ethoxy)-phenylamino]-phthalic acid dimethyl ester

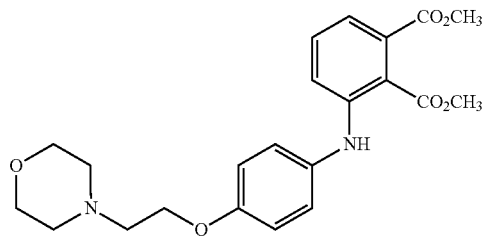 [SMILES: COC(=O)c1cccc(Nc2ccc(OCCN3CCOCC3)cc2)c1C(=O)OC]

A mixture of 4-(2-morpholin-4-yl-ethoxy)-phenylamine (1.4 g, 6.2 mmol), 3-iodophthalic acid dimethyl ester (2.0 g, 6.2 mmol), $Pd_2(dba)_3$ (0.26 g, 0.28 mmol), rac-BINAP (0.12 g, 0.19 mmol), and cesium carbonate (2.8 g, 8.6 mmol), in 12 mL toluene was heated to reflux under nitrogen for 16 hours. The reaction mixture was cooled, diluted with $CH_2Cl_2$ (20 mL), and filtered through Celite, and the filter was washed with additional $CH_2Cl_2$ (60 mL). The filtrate was evaporated in vacuo, and the residue was purified by ISCO silica gel flash chromatography using a methylene chloride-methanol gradient, eluting 1.8 g of the product at 95:5 methylene chloride-methanol, in 70% yield, as a pale yellow solid; $^1H$ NMR ($CDCl_3$) δ 3.00-3.51 (m, 6H), 3.87 (s, 3H), 3.88 (s, 3H), 4.08-4.34 (m, 4H), 4.52-4.62 (m, 2H), 6.89 (d, J=8.7 Hz, 2H), 6.99 (d, J=7.1 Hz, 1H), 7.09-7.12 (m, 3H), 7.23-7.28 (m, 1H), 8.08 (s, 1H).

5.71.4 2-(2,6-Dioxo-piperidin-3-yl)-4-[4-(2-morpholin-4-yl-ethoxy)-phenylamino]-isoindole-1,3-dione hydrochloride

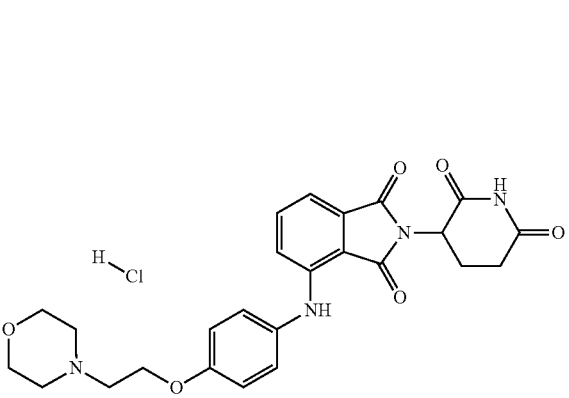 [SMILES: O=C1CCC(N2C(=O)c3cccc(Nc4ccc(OCCN5CCOCC5)cc4)c3C2=O)C(=O)N1 ; Cl]

Step 1:

A mixture of 3-[4-(2-morpholin-4-yl-ethoxy)-phenylamino]-phthalic acid dimethyl ester (1.5 g, 3.6 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.59 g, 3.6 mmol) in pyridine (20 mL) were heated to reflux for 16 hours. The mixture was cooled and evaporated under vacuum. The residue was purified by ISCO silica gel flash chromatography in methylene chloride-methanol gradient, eluting 0.76 g at 93:7 methylene chloride-methanol, as an orange solid.

Step 3:

The product from Step 2 was dissolved in 9:1 methylene chloride-methanol (20 mL), and a 4N solution of HCl in dioxane (1.5 mL) was added dropwise. The mixture stirred at room temperature for 1 hour and was then evaporated, providing 0.75 g as an orange solid, in 38% yield over 3 steps: mp 206-208° C.; HPLC, Waters Xterra RP18, 3.9×150 mm, 5 μm, 1 mL/min, 240 nm, 40/60 ($CH_3CN$/0.1% $HCO_2NH_4$): $t_R$=4.09 (97.99%); $^1H$ NMR (DMSO-$d_6$) δ 2.05-2.08 (m, 1H), 2.49-2.64 (m, 2H), 2.85-2.97 (m, 1H), 3.07-3.27 (m, 2H), 3.39-3.54 (m, 4H), 3.85-3.94 (m, 4H), 4.36-4.45 (m, 2H), 5.11 (dd, J=12.5 Hz, J=5.3 Hz, 1H), 7.05 (d, J=8.7 Hz, 2H), 7.16-7.20 (m, 2H), 7.30 (d, J=8.7 Hz, 2H), 7.56 (t, J=7.8 Hz, 1H), 8.29 (s, 1H), 11.13 (s, 1H), 11.45 (br, 1H); $^{13}C$ NMR (DMSO-$d_6$) δ 22.1, 31.0, 48.6, 51.7, 54.9, 62.5, 63.1, 110.9, 112.1, 115.6, 118.6, 125.0, 132.4, 132.6, 136.1, 144.0, 154.7, 167.1, 168.4, 170.0, 172.8; Anal. calcd For $C_{25}H_{27}ClN_4O_6$·0.65$H_2O$: C, 57.01; H, 5.42; N, 10.64. Found: C, 57.32; H, 5.30; N, 10.26.

5.72 2-(2,6-DIOXO-PIPERIDIN-3-YL)-4-[3-(2-MORPHOLIN-4-YL-ETHOXY)-PHENY-LAMINO]-ISOINDOLE-1,3-DIONE HYDROCHLORIDE

5.72.1 4-[2-(3-Nitro-phenoxy)-ethyl]-morpholine

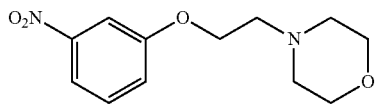 [SMILES: O=[N+]([O-])c1cccc(OCCN2CCOCC2)c1]

A mixture of 3-nitrophenol (3.5 g, 25 mmol), N-(2-chloroethyl)morpholine hydrochloride (4.7 g, 25 mmol), and potassium carbonate (13.2 g, 125 mmol) in acetone (100 mL) was heated to reflux for 20 hours. The solvent was removed under vacuum. The residue was partitioned between water (150 mL) and ethyl acetate (150 mL) and the aqueous phase was extracted with ethyl acetate (100 mL). The combined organic layers were washed with water (3×100 mL) and extracted with dilute aqueous HCl (2×125 mL). These extracts were washed with $CH_2Cl_2$ (2×125 mL), made basic (NaOH) and extracted into ethyl acetate (3×75 mL). These organic extracts were washed with water (3×75 mL), dried ($MgSO_4$), and evaporated, providing 4.4 g, in 70% yield; $^1H$ NMR ($CDCl_3$) δ 2.59 (t, J=4.7 Hz, 4H), 2.84 (t, J=5.6 Hz, 2H), 3.75 (t, J=4.7 Hz, 4H), 4.19 (t, J=5.6 Hz, 2H), 7.22-7.25 (m, 1H), 7.43 (t, J=8.1 Hz, 1H), 7.76 (t, J=2.3 Hz, 1H), 7.82-7.85 (m, 1H).

5.72.2 3-(2-Morpholin-4-yl-ethoxy)-phenylamine

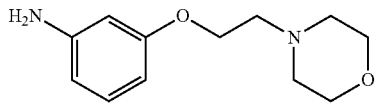

A mixture of 4-[2-(3-nitro-phenoxy)-ethyl]-morpholine (4.0 g, 13 mmol) and 5% Pd—C (0.3 g) in ethyl acetate (100 mL) was hydrogenated under 50 psi hydrogen for 23 hours. The mixture was filtered through Celite, and the filtrate was evaporated in vacuo, providing 3.0 g, in 86% yield; $^1H$ NMR ($CDCl_3$) δ 2.58 (t, J=4.7 Hz, 4H), 2.78 (t, J=5.8 Hz, 2H), 3.65 (br, 2H), 3.73 (t, J=4.7 Hz, 4H), 4.07 (t, J=5.8 Hz, 2H), 6.24-6.34 (m, 3H), 7.05 (t, J=8.1 Hz, 1H).

5.72.3 3-[3-(2-Morpholin-4-yl-ethoxy)-phenylamino]-phthalic acid dimethyl ester

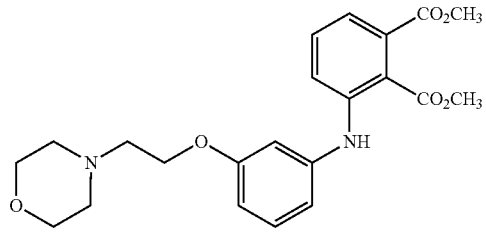 [SMILES: COC(=O)c1cccc(Nc2cccc(OCCN3CCOCC3)c2)c1C(=O)OC]

A mixture of 3-(2-morpholin-4-yl-ethoxy)-phenylamine (1.4 g, 6.1 mmol), 3-iodophthalic acid dimethyl ester (2.0 g, 6.2 mmol), $Pd_2(dba)_3$ (0.26 g, 0.28 mmol), rac-BINAP (0.12 g, 0.19 mmol), and cesium carbonate (2.8 g, 8.6 mmol), in 12 mL toluene was heated to reflux under nitrogen for 16 hours. The reaction mixture was cooled, diluted with $CH_2Cl_2$ (20 mL), and filtered through Celite, and the filter was washed with additional $CH_2Cl_2$ (60 mL). The filtrate was evaporated in vacuo, and the residue was purified by ISCO silica gel flash chromatography using a methylene chloride-methanol gradient, eluting 1.9 g of the product at 95:5 methylene chloride-methanol, in 73% yield; $^1H$ NMR ($CDCl_3$) δ 2.57 (t, J=4.6 Hz, 4H), 2.79 (t, J=5.7 Hz, 2H), 3.73 (t, J=4.6 Hz, 4H), 3.87 (s, 3H), 3.89 (s, 3H), 4.09 (t, J=5.7 Hz, 2H), 6.60 (dd, J=8.0 Hz, J=2.0 Hz, 1H), 6.70 (t, J=2.1 Hz, 1H), 6.74 (dd, J=7.8 Hz, J=1.8 Hz, 1H), 7.11 (dd, J=7.4 Hz, J=1.0 Hz, 1H), 7.21 (t, J=8.1 Hz, 1H), 7.31 (t, J=8.0 Hz, 1H), 7.43 (dd, J=8.4 Hz, J=0.9 Hz, 1H), 7.98 (s, 1H).

5.72.4 2-(2,6-Dioxo-piperidin-3-yl)-4-[3-(2-morpholin-4-yl-ethoxy)-phenylamino]-isoindole-1,3-dione hydrochloride

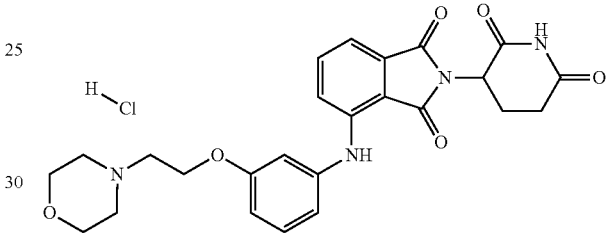

Step 1:
A mixture of 3-[3-(2-morpholin-4-yl-ethoxy)-phenylamino]-phthalic acid dimethyl ester (1.6 g, 3.9 mmol) and 3N NaOH (50 mL) in ethanol (100 mL) was heated to reflux for 2 hours. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:
The product from Step 1 and rac-α-aminoglutarimide hydrochloride (0.64 g, 3.9 mmol) in pyridine (20 mL) were heated to reflux for 16 hours. The mixture was cooled and evaporated under vacuum. The residue chromatographed in methylene chloride-methanol gradient, eluting 1.0 g at 93:7 methylene chloride-methanol, as an orange solid.

Step 3:
The product from Step 2 was dissolved in 9:1 methylene chloride-methanol (20 mL), and a 4N solution of HCl in dioxane (2.0 mL) was added dropwise. The mixture stirred at room temperature for 1 hour and was then evaporated, providing 0.96 g as an orange solid, in 48% yield over 3 steps: mp 249-251° C.; HPLC, Waters Xterra RP18, 3.9×150 mm, 5 μm, 1 mL/min, 240 nm, 40/60 ($CH_3CN$/0.1% $HCO_2NH_4$): $t_R$=4.45 (99.53%); $^1H$ NMR (DMSO-$d_6$) δ 1.97-2.04 (m, 1H), 2.42-2.27 (m, 2H), 2.79-2.91 (m, 1H), 3.07-3.18 (m, 2H), 3.40-3.57 (m, 4H), 3.77-3.86 (m, 4H), 4.33-4.42 (m, 2H), 5.06 (dd, J=12.8 Hz, J=5.3 Hz, 1H), 6.69 (d, J=1.8 Hz, 1H), 6.89-6.92 (m, 2H), 7.20-7.28 (m, 2H), 7.46 (d, J=8.4 Hz, 1H), 7.58 (dd, J=8.6 Hz, J=7.1 Hz, 1H), 8.40 (s, 1H), 11.07 (s, 1H), 11.36 (br, 1H); $^{13}C$ NMR (DMSO-$d_6$) δ 22.1, 30.9, 48.7, 51.6, 54.8, 63.1, 66.3, 107.8, 110.1, 112.4, 113.7, 114.2, 119.9, 130.3, 132.4, 136.2, 140.9, 142.4, 158.4, 167.0, 168.2, 170.0, 172.8; Anal. calcd For $C_{25}H_{27}ClN_4O_6 \cdot 0.65H_2O$: C, 57.01; H, 5.42; N, 10.64. Found: C, 57.33; H, 5.42; N, 10.26.

5.73 2-(2,6-DIOXO-PIPERIDIN-3-YL)-4-[2-METHOXY-4-(2-PIPERIDIN-1-YL-ETHOXY)-PHENYLAMINO]-ISOINDOLE-1,3-DIONE HYDROCHLORIDE

5.73.1 1-[2-(3-Methoxy-4-nitro-phenoxy)-ethyl]-piperidine

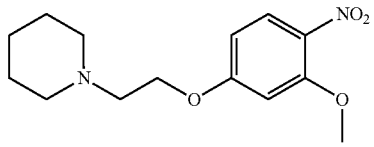 [SMILES: COc1cc(OCCN2CCCCC2)ccc1[N+](=O)[O-]]

1-Piperidineethanol (1.8 g, 14 mmol) was added to a mixture of powdered KOH (0.78 g, 14 mmol) and Aliquat 336 (0.56 g, 1.4 mmol), and the resulting mixture was stirred for 5 minutes at 80° C. Then 4-fluoro-2-methoxy-1-nitrobenzene (2.0 g, 12 mmol) was added, and stirring proceeded at this temperature for 30 minutes. The mixture was cooled and partitioned between methylene chloride (75 mL) and water (75 mL), and the organic phase was washed with water (75 mL) and extracted with dilute aqueous HCl (3×60 mL). The combined aqueous phases were washed with methylene chloride (3×75 mL), basified (3N NaOH), and extracted with methylene chloride (3×75 mL). The combined organic extracts were washed with water (3×100 mL), dried (MgSO$_4$), and evaporated, providing 1.6 g, in 49% yield; $^1$H NMR (DMSO-d$_6$) δ 1.48-1.53 (m, 6H), 2.40-2.44 (m, 4H), 2.67 (t, J=5.8 Hz, 2H), 3.93 (s, 3H), 4.21 (t, J=5.8 Hz, 2H), 6.67 (dd, J=9.3 Hz, J=1.5 Hz, 1H), 6.81 (d, J=1.5 Hz, 1H), 7.95 (d, J=9.3 Hz, 1H).

5.73.2 2-Methoxy-4-(2-piperidin-1-yl-ethoxy)-phenylamine

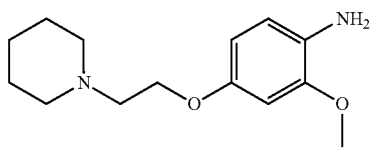 [SMILES: COc1cc(OCCN2CCCCC2)ccc1N]

A mixture of 1-[2-(3-methoxy-4-nitro-phenoxy)-ethyl]-piperidine (1.5 g, 5.4 mmol) and 5% Pd—C (0.5 g) in ethyl acetate (70 mL) was shaken under 50 psi of hydrogen for 18 hours. The mixture was filtered through Celite and evaporated, providing 1.1 g of the product, in 81% yield: $^1$H NMR (DMSO-d$_6$) δ 1.45-1.53 (m, 6H), 2.35-2.41 (m, 4H), 2.59 (t, J=6.0 Hz, 2H), 3.74 (s, 3H), 3.93 (t, J=6.0 Hz, 2H), 6.28 (dd, J=8.3 Hz, J=2.6 Hz, 1H), 6.45 (d, J=2.6 Hz, 1H), 6.63 (d, J=8.3 Hz, 1H).

5.73.3 3-[2-Methoxy-4-(2-piperidin-1-yl-ethoxy)-phenylamino]-phthalic acid dimethyl ester

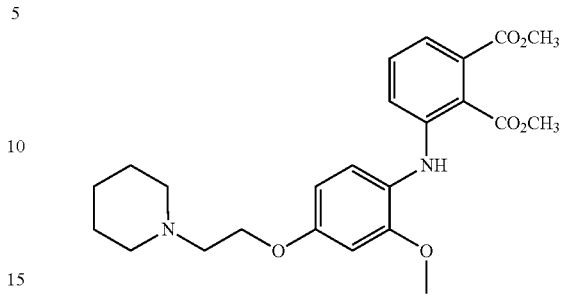

A mixture of 3-iodophthalic acid dimethyl ester (1.0 g, 3.1 mmol), 2-methoxy-4-(2-piperidin-1-yl-ethoxy)-phenylamine (0.78 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 20 hours. The reaction mixture was cooled, diluted with CH$_2$Cl$_2$ (15 mL), and filtered through Celite, and the filter was washed with additional CH$_2$Cl$_2$ (25 mL). The filtrate was evaporated in vacuo, and the residue was purified by ISCO silica gel flash chromatography using a methylene chloride-methanol gradient, eluting 1.1 g of the product at 95:5 methylene chloride-methanol, in 78% yield; $^1$H NMR (DMSO-d$_6$) δ 1.47-1.49 (m, 2H), 1.57-1.64 (m, 4H), 2.50-2.53 (m, 4H), 2.78 (t, J=6.2 Hz, 2H), 3.81 (s, 3H), 3.87 (s, 3H), 3.88 (s, 3H), 4.10 (t, J=6.2 Hz, 2H), 6.46 (dd, J=8.7 Hz, J=2.7 Hz, 1H), 6.56 (d, J=2.7 Hz, 1H), 6.98 (dd, J=7.2 Hz, J=1.2 Hz, 1H), 7.09-7.16 (m, 2H), 7.21-7.23 (m, 1H), 7.92 (br, 1H).

5.73.4 2-(2,6-Dioxo-piperidin-3-yl)-4-[2-methoxy-4-(2-piperidin-1-yl-ethoxy)-phenylamino]-isoindole-1,3-dione hydrochloride

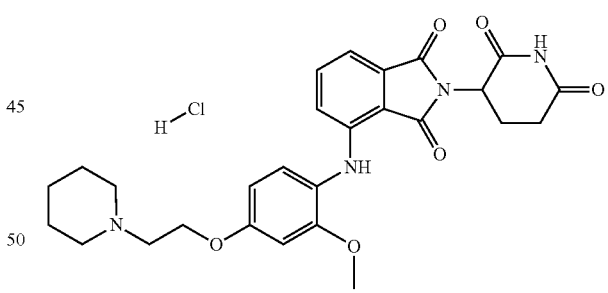

Step 1:
A mixture of 3-[2-methoxy-4-(2-piperidin-1-yl-ethoxy)-phenylamino]-phthalic acid dimethyl ester (1.0 g, 2.2 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:
The product from Step 1 and rac-α-aminoglutarimide hydrochloride (0.36 g, 2.2 mmol) in pyridine (20 mL) were heated to reflux for 16 hours. The mixture was cooled and evaporated under vacuum. The residue chromatographed in methylene chloride-methanol gradient, eluting the product at 93:7 methylene chloride-methanol.

Step 3:

The product from Step 2 was dissolved in 9:1 methylene chloride-methanol (20 mL) and a 4N solution of hydrogen chloride in dioxane (1.0 mL) was added. The mixture was stirred at room temperature for 1 hour, and was evaporated in vacuo. The residue was triturated with ether and filtered, providing 0.63 g as an orange solid, in 53% yield over three steps: mp 210-212° C.; HPLC, Waters Xterra RP18, 3.9×150 mm, 5 μm, 1 mL/min, 240 nm, 40/60 ($CH_3CN$/0.1% $HCO_2NH_4$): $t_R$=4.22 (96.21%); $^1$H NMR (DMSO-$d_6$) δ 1.37-1.91 (m, 6H), 2.05-2.09 (m, 1H), 2.53-2.64 (m, 2H), 2.85-3.02 (m, 3H), 3.46-3.53 (m, 4H), 3.82 (s, 3H), 4.48 (t, J=4.7 Hz, 2H), 5.12 (dd, J=12.5 Hz, J=5.3 Hz, 1H), 6.65 (dd, J=8.6 Hz, J=2.3 Hz, 1H), 6.80 (d, J=2.1 Hz, 1H), 7.05 (d, J=8.7 Hz, 1H), 7.17 (d, J=6.9 Hz, 1H), 7.34 (d, J=8.4 Hz, 1H), 7.57 (t, J=8.0 Hz, 1H), 8.00 (s, 1H), 10.85 (br, 1H), 11.14 (s, 1H); $^{13}$C NMR (DMSO-$d_6$) δ 21.1, 22.0, 22.2, 30.9, 48.6, 52.5, 54.5, 55.8, 62.6, 100.2, 105.6, 110.5, 112.3, 118.2, 120.9, 124.8, 132.0, 136.1, 143.9, 153.4, 155.9, 167.0, 168.8, 170.0, 172.7; Anal. calcd for $C_{27}H_{31}ClN_4O_6$·0.5$H_2O$: C, 58.75; H, 5.84; N, 10.15. Found: C, 58.72; H, 5.90; N, 9.78.

5.74 2-(2,6-DIOXO-PIPERIDIN-3-YL)-4-[2-METHOXY-4-(2-PYRROLIDIN-1-YL-ETHOXY)-PHENYLAMINO]-ISOINDOLE-1,3-DIONE HYDROCHLORIDE

5.74.1 1-[2-(3-Methoxy-4-nitro-phenoxy)-ethyl]-pyrrolidine

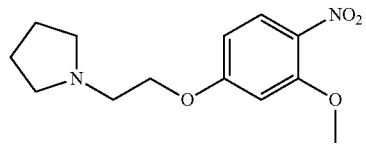 [SMILES: COc1cc(OCCN2CCCC2)ccc1[N+](=O)[O-]]

1-(2-Hydroxyethyl)pyrrolidine (1.6 g, 14 mmol) was added to a mixture of powdered KOH (0.78 g, 14 mmol) and Aliquat 336 (0.56 g, 1.4 mmol) and the resulting mixture was stirred for 5 minutes at 80° C. Then 4-fluoro-2-methoxy-1-nitrobenzene (2.0 g, 12 mmol) was added, and stirring proceeded at this temperature for 30 minutes. The mixture was cooled and partitioned between methylene chloride (75 mL) and water (75 mL), and the organic phase was washed with water (75 mL) and extracted with dilute aqueous HCl (3×60 mL). The combined aqueous phases were washed with methylene chloride (3×75 mL), basified (3N NaOH), and extracted with methylene chloride (3×75 mL). The combined organic extracts were washed with water (3×100 mL), dried (MgSO$_4$), and evaporated, providing 2.4 g, in 76% yield; $^1$H NMR of the HCl salt (DMSO-$d_6$) δ 1.83-2.01 (m, 4H), 3.04-3.19 (m, 4H), 3.58 (t, J=5.0 Hz, 2H), 3.94 (s, 3H), 4.51 (t, J=5.0 Hz, 2H), 6.74 (dd, J=9.0 Hz, J=2.4 Hz, 1H), 6.90 (d, J=2.4 Hz, 1H), 7.99 (d, J=9.0 Hz, 1H), 10.97 (br, 1H).

5.74.2 2-Methoxy-4-(2-pyrrolidin-1-yl-ethoxy)-phenylamine

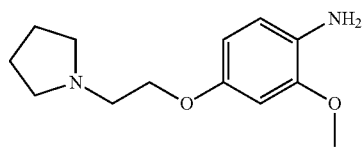

A mixture of 1-[2-(3-methoxy-4-nitro-phenoxy)-ethyl]-pyrrolidine (2.2 g, 8.3 mmol) and 5% Pd—C (0.4 g) in ethyl acetate (70 mL) was shaken under 50 psi of hydrogen for 22 hours. The mixture was filtered through Celite and evaporated, providing 1.8 g of the product, in 89% yield; $^1$H NMR (DMSO-$d_6$) δ 1.78-1.83 (m, 4H), 2.58-2.63 (m, 4H), 2.86 (t, J=6.0 Hz, 2H), 3.53 (by, 2H), 3.81 (s, 3H), 4.04 (t, J=6.0 Hz, 2H), 6.35 (dd, J=8.4 Hz, J=2.7 Hz, 1H), 6.49 (d, J=2.7 Hz, 1H), 6.61 (d, J=8.4 Hz, 1H).

5.74.3 3-[2-Methoxy-4-(2-pyrrolidin-1-yl-ethoxy)-phenylamino]-phthalic acid dimethyl ester

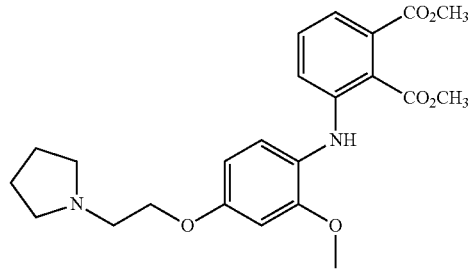 [SMILES: COC(=O)c1cccc(Nc2ccc(OCCN3CCCC3)cc2OC)c1C(=O)OC]

A mixture of 3-iodophthalic acid dimethyl ester (1.0 g, 3.1 mmol), 2-methoxy-4-(2-pyrrolidin-1-yl-ethoxy)-phenylamine (0.73 g, 3.1 mmol), Pd$_2$(dba)$_3$ (0.13 g, 0.14 mmol), rac-BINAP (0.058 g, 0.093 mmol), and cesium carbonate (1.4 g, 4.3 mmol), in 6 mL toluene was heated to reflux under nitrogen for 20 hours. The reaction mixture was cooled, diluted with CH$_2$Cl$_2$ (15 mL), and filtered through Celite, and the filter was washed with additional CH$_2$Cl$_2$ (25 mL). The filtrate was evaporated in vacuo, and the residue was purified by ISCO silica gel flash chromatography using a methylene chloride-methanol gradient, eluting 0.9 g of the product at 95:5 methylene chloride-methanol, in 69% yield; $^1$H NMR (DMSO-$d_6$) δ 1.68-1.71 (m, 4H), 2.49-2.53 (m, 4H), 2.79 (t, J=5.9 Hz, 2H), 3.78 (s, 3H), 3.79 (s, 3H), 3.80 (s, 3H), 4.07 (t, J=5.9 Hz, 2H), 6.53 (dd, J=8.7 Hz, J=2.6 Hz, 1H), 6.69 (d, J=2.6 Hz, 1H), 6.92-6.98 (m, 2H), 7.14 (d, J=8.7 Hz, 1H), 7.33 (t, J=8.0 Hz, 1H), 7.73 (s, 1H).

5.74.4 2-(2,6-Dioxo-piperidin-3-yl)-4-[2-methoxy-4-(2-pyrrolidin-1-yl-ethoxy)-phenylamino]-isoindole-1,3-dione hydrochloride

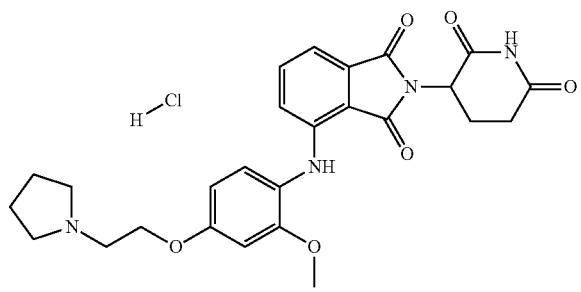 [SMILES: COc1cc(OCCN2CCCC2)ccc1Nc1cccc2c1C(=O)N(C1CCC(=O)NC1=O)C2=O ; Cl]

Step 1:

A mixture of 3-[2-methoxy-4-(2-pyrrolidin-1-yl-ethoxy)-phenylamino]-phthalic acid dimethyl ester (0.6 g, 1.4 mmol) and 3N NaOH (50 mL) in ethanol (100 mL) was heated to reflux for 3 hours. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.23 g, 1.4 mmol) in pyridine (20 mL) were heated to reflux for 16 hours. The mixture was cooled and evaporated under vacuum. The residue chromatographed in methylene chloride-methanol gradient, eluting the product at 93:7 methylene chloride-methanol.

Step 3:

The product from Step 2 was dissolved in 9:1 methylene chloride-methanol (20 mL) and a 4N solution of hydrogen chloride in dioxane (1.0 mL) was added. The mixture was stirred at room temperature for 1 hour, and was evaporated in vacuo. The residue was triturated with ether and filtered, providing 0.23 g as an orange solid, in 31% yield over three steps: mp 185-187° C.; HPLC, Waters Xterra RP18, 3.9×150 mm, 5 μm, 1 mL/min, 240 nm, 40/60 ($CH_3CN$/0.1% $HCO_2NH_4$): $t_R$=2.52 (95.82%); $^1$H NMR (DMSO-$d_6$) δ 1.91-2.09 (m, 5H), 2.53-2.64 (m, 2H), 2.85-2.97 (m, 1H), 3.12 (t, J=5.0 Hz, 2H), 3.57-3.59 (m, 4H), 3.82 (s, 3H), 4.40 (t, J=5.0 Hz, 2H), 5.12 (dd, J=12.6 Hz, J=5.4 Hz, 1H), 6.66 (dd, J=8.7 Hz, J=2.7 Hz, 1H), 6.82 (d, J=2.7 Hz, 1H), 7.05 (d, J=8.7 Hz, 1H), 7.17 (d, J=6.9 Hz, 1H), 7.34 (d, J=8.7 Hz, 1H), 7.57 (dd, J=8.4 Hz, J=7.2 Hz, 1H), 8.00 (s, 1H), 10.91 (br, 1H), 11.14 (s, 1H); $^{13}$C NMR (DMSO-$d_6$) δ 22.0, 22.5, 30.9, 48.6, 52.5, 53.6, 55.8, 63.6, 100.3, 105.6, 110.5, 112.3, 118.2, 120.9, 124.7, 132.0, 136.1, 143.9, 153.4, 155.9, 167.0, 168.8, 170.0, 172.7; Anal. calcd for $C_{26}H_{29}ClN_4O_6 \cdot 0.75H_2O$: C, 57.56; H, 5.67; N, 10.33. Found: C, 57.33; H, 5.67; N, 10.04.

5.75 2-(2,6-DIOXO-PIPERIDIN-3-YL)-4-[2-FLUORO-4-(2-MORPHOLIN-4-YL-ETHOXY)-PHENYLAMINO]-ISOINDOLE-1,3-DIONE HYDROCHLORIDE

5.75.1 4-[2-(3-Fluoro-4-nitro-phenoxy)-ethyl]-morpholine

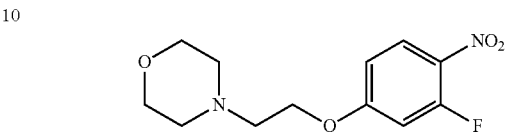

A mixture of 3-fluoro-4-nitrophenol (1.6 g, 10 mmol), 4-(2-chloroethyl)morpholine hydrochloride (1.9 g, 10 mmol), and potassium carbonate (5.5 g, 52 mmol) in acetone (50 mL) was heated to reflux with stirring for 16 hours. The mixture was cooled and evaporated under vacuum. The residue was partitioned between water (100 mL) and ethyl acetate (100 mL), and the organic phase was washed with water (100 mL) and brine (100 mL), was dried ($MgSO_4$), and evaporated, providing 2.6 g, in 93% yield; $^1$H NMR (DMSO-$d_6$) δ 2.47 (t, 4H, J=4.6), 2.71 (t, J=5.6 Hz, 2H), 3.57 (t, J=4.6, 4H), 4.25 (t, J=5.6 Hz, 2H), 6.99 (dd, J=9.3 Hz, J=2.7 Hz, 1H), 7.19-7.24 (m, 1H), 8.14 (t, J=9.3 Hz, 1H).

5.75.2 2-Fluoro-4-(2-morpholin-4-yl-ethoxy)-phenylamine

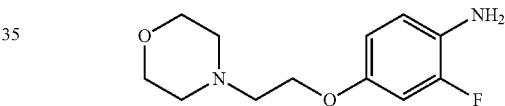

A mixture of 4-[2-(3-fluoro-4-nitro-phenoxy)-ethyl]-morpholine (2.4 g, 8.9 mmol) and 5% Pd—C (0.3 g) in ethyl acetate (70 mL) was shaken under 50 psi of hydrogen for 20 hours. The mixture was filtered through Celite and evaporated, providing 2.0 g of the product, in 94% yield; $^1$H NMR (DMSO-$d_6$) δ 2.44 (t, J=4.5, 4H), 2.62 (t, J=5.8 Hz, 2H), 3.57 (t, J=4.5, 4H), 3.95 (t, J=5.8 Hz, 2H), 6.50-6.55 (m, 1H), 6.52-6.72 (m, 2H).

5.75.3 3-[2-Fluoro-4-(2-morpholin-4-yl-ethoxy)-phenylamino]-phthalic acid dimethyl ester

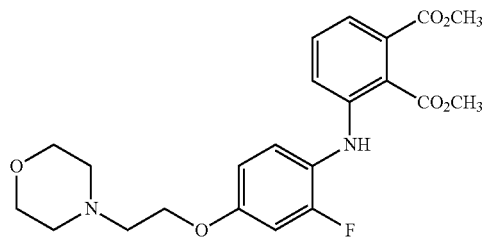 [SMILES: COC(=O)c1cccc(Nc2ccc(OCCN3CCOCC3)cc2F)c1C(=O)OC]

A mixture of 3-iodophthalic acid dimethyl ester (2.0 g, 6.2 mmol), 2-fluoro-4-(2-morpholin-4-yl-ethoxy)-phenylamine (1.5 g, 6.2 mmol), $Pd_2(dba)_3$ (0.26 g, 0.28 mmol), rac-BINAP (0.12 g, 0.19 mmol), and cesium carbonate (2.8 g, 8.6 mmol), in 12 mL toluene was heated to reflux under nitrogen for 18 hours. The reaction mixture was cooled, diluted with $CH_2Cl_2$ (15 mL), and filtered through Celite, and the filter was washed with additional $CH_2Cl_2$ (25 mL). The filtrate was evaporated in vacuo, and the residue was purified by ISCO silica gel flash chromatography using a methylene chloride-methanol gradient, eluting 2.5 g of the product at 95:5 methylene chloride-methanol, in 93% yield; $^1$H NMR (DMSO-$d_6$) δ 2.47 (t, J=4.7, 4H), 2.69 (t, J=5.6 Hz, 2H), 3.58 (t, J=4.7, 4H), 3.80 (s, 6H), 4.10 (t, J=5.6 Hz, 2H), 6.76-6.83 (m, 2H), 6.97 (dd, J=12.6 Hz, J=2.7 Hz, 1H), 7.06 (dd, J=7.5 Hz, J=0.9 Hz, 1H), 7.23 (t, J=9.2 Hz, 1H), 7.34 (t, J=8.0 Hz, 1H), 7.69 (s, 1H).

5.75.4 2-(2,6-Dioxo-piperidin-3-yl)-4-[2-fluoro-4-(2-morpholin-4-yl-ethoxy)-phenylamino]-isoindole-1,3-dione hydrochloride

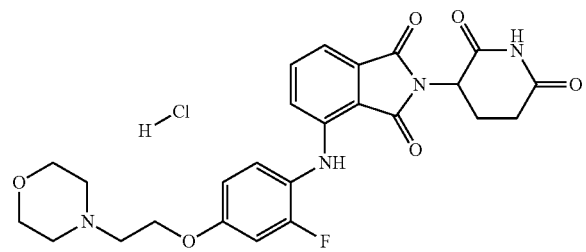 [SMILES: O=C1CCC(N2C(=O)c3cccc(Nc4ccc(OCCN5CCOCC5)cc4F)c3C2=O)C(=O)N1 ; Cl]

Step 1:

A mixture of 3-[2-fluoro-4-(2-morpholin-4-yl-ethoxy)-phenylamino]-phthalic acid dimethyl ester (2.3 g, 5.3 mmol) and 3N NaOH (50 mL) in ethanol (100 mL) was heated to reflux for 90 minutes. The mixture was cooled, and the solvent was removed under vacuum. The residue was dissolved in water (100 mL), washed with ethyl acetate (3×75 mL), acidified to pH 2-3 (HCl) and evaporated, providing a crude product that was used directly in the next step.

Step 2:

The product from Step 1 and rac-α-aminoglutarimide hydrochloride (0.87 g, 5.3 mmol) in pyridine (20 mL) were heated to reflux for 16 hours. The mixture was cooled and evaporated under vacuum. The residue was purified by ISCO silica gel flash chromatography in methylene chloride-methanol gradient, eluting the product at 92:8 methylene chloride-methanol. The appropriate fractions were pooled and treated with a 2N solution of hydrogen chloride in ethyl ether (10 mL). The mixture was stirred at room temperature for 1 hour, and was evaporated in vacuo. The residue was triturated with ether and filtered, providing 1.8 g as an orange solid, in 65% yield over two steps: mp 219-221° C.; HPLC, Waters Xterra RP18, 3.9×150 mm, 5 μm, 1 mL/min, 240 nm, 40/60 ($CH_3CN$/0.1% $HCO_2NH_4$): $t_R$=4.56 (98.82%); $^1$H NMR (DMSO-$d_6$) δ 2.06-2.09 (m, 1H), 2.54-2.64 (m, 2H), 2.86-2.97 (m, 1H), 3.18-3.24 (m, 2H), 3.50-3.60 (m, 4H), 3.84-3.95 (m, 4H), 4.44-4.52 (m, 2H), 5.12 (dd, J=12.5 Hz, J=5.3 Hz, 1H), 6.85 (dd, J=8.4 Hz, J=1.8 Hz, 1H), 6.93 (d, J=9.0 Hz, 1H), 7.11 (dd, J=12.3 Hz, J=1.8 Hz, 1H), 7.21 (d, J=7.2 Hz, 1H), 7.43 (t, J=9.2 Hz, 1H), 7.58 (t, J=7.8 Hz, 1H), 8.18 (s, 1H), 11.14 (s, 1H), 11.39 (br, 1H); $^{13}$C NMR (DMSO-$d_6$) δ 22.1, 31.0, 48.7, 51.6, 54.7, 62.9, 63.1, 103.5 (d, J=23.4 Hz), 110.9, 111.5, 112.8, 118.6, 119.7, 130.3 (d, J=278 Hz), 136.2, 144.0, 155.5, 156.3, 158.8, 167.0, 168.4, 170.0, 172.8; Anal. calcd for $C_{25}H_{26}ClFN_4O_6$·1.6$H_2O$: C, 59.25; H, 4.50; N, 10.91. Found: C, 59.06; H, 4.20; N, 10.80.

5.76 4-(2,4-DIMETHOXY-PHENYLAMINO)-2-[(3S)-3-METHYL-2,6-DIOXO-PIPERIDIN-3-YL]-ISOINDOLE-1,3-DIONE

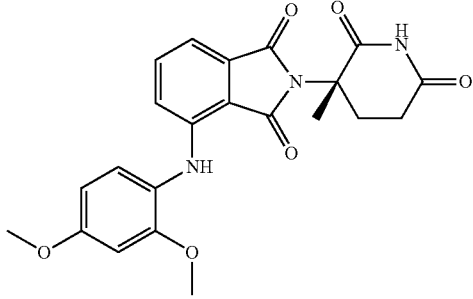 [SMILES: COc1ccc(Nc2cccc3c2C(=O)N([C@@]2(C)CCC(=O)NC2=O)C3=O)c(OC)c1]

A mixture of 3-(2,4-dimethoxyphenylamino)phthalic acid (0.37 g, 1.2 mmol) and (3S)-3-amino-3-methyl-piperidine-2,6-dione hydrobromide (0.28 g, 1.2 mmol) in pyridine (10 mL) was heated to reflux for 24 hours. The mixture was cooled and evaporated under vacuum. The residue was dissolved in ethyl acetate (100 mL), washed with dilute aqueous HCl (2×100 mL) and water (2×100 mL), and evaporated. The residue was purified by ISCO silica gel flash chromatography using a hexanes-ethyl acetate gradient, eluting 0.20 g of the product, an orange solid, at 50:50 hexanes-ethyl acetate, in 41% yield: mp 255-257° C.; HPLC, Waters Symmetry C-18, 3.9×150 mm, 5 μm, 1 mL/min, 240 nm, 65/35 ($CH_3CN$/0.1% $H_3PO_4$): $t_R$=2.72 (97.30%); $^1$H NMR (DMSO-$d_6$) δ 1.91 (s, 3H), 2.05-2.08 (m, 1H), 2.59-2.73 (m, 3H), 3.79 (s, 6H), 6.57 (d, J=7.5 Hz, 1H), 6.71 (s, 1H), 6.97-7.08 (m, 2H), 7.27 (d, J=8.1 Hz, 1H), 7.52 (m, 1H), 7.94 (s, 1H), 11.01 (s, 1H); $^{13}$C NMR (DMSO-$d_6$) δ 21.0, 28.6, 29.2, 55.4, 55.7, 58.5, 99.5, 104.7, 110.2, 111.8, 118.1, 120.1, 125.0, 131.9, 136.0, 144.0, 153.6, 157.9, 167.8, 169.8, 172.1, 172.4; Anal. calcd for $C_{22}H_{21}N_3O_6$·0.2$H_2O$: C, 61.88; H, 5.05; N, 9.84. Found: C, 61.91; H, 5.01; N, 8.52.

5.77 4-(INDAN-5-YLAMINO)-2-[(3S)-3-METHYL-2,6-DIOXO-PIPERIDIN-3-YL]-ISOINDOLE-1,3-DIONE

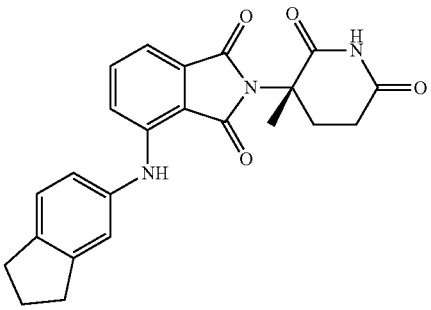 [SMILES: C[C@]1(N2C(=O)c3cccc(Nc4ccc5c(c4)CCC5)c3C2=O)CCC(=O)NC1=O]

A mixture of 3-(indan-5-ylamino)-phthalic acid (0.62 g, 3.1 mmol) and (3S)-3-amino-3-methyl-piperidine-2,6-dione hydrobromide (0.50 g, 2.1 mmol) in pyridine (10 mL) was heated to reflux for 17 hours. The mixture was cooled and evaporated under vacuum. The residue was dissolved in ethyl acetate (100 mL), washed with dilute aqueous HCl (2×100 mL) and water (2×100 mL), and evaporated. The residue was purified by ISCO silica gel flash chromatography using a hexanes-ethyl acetate gradient, eluting 0.37 g of the product, an orange solid, at 70:30 hexanes-ethyl acetate, in 45% yield: mp 200-202° C.; HPLC, Waters Symmetry C-18, 3.9×150 mm, 5 μm, 1 mL/min, 240 nm, 65/35 (CH$_3$CN/0.1% H$_3$PO$_4$): t$_R$=5.40 (99.54%); $^1$H NMR (DMSO-d$_6$) δ 1.91 (s, 3H), 2.00-2.08 (m, 3H), 2.54-2.75 (m, 3H), 2.82-2.88 (m, 4H), 7.04-7.31 (m, 5H), 7.55 (t, J=7.8 Hz, 1H), 8.30 (s, 1H), 11.00 (s, 1H); $^{13}$C NMR (DMSO-d$_6$) δ 21.0, 25.2, 28.6, 29.2, 31.8, 32.4, 58.5, 110.9, 112.4, 118.7, 120.7, 124.9, 132.2, 136.0, 137.2, 139.9, 143.4, 145.1, 167.8, 169.4, 172.2, 172.3; Anal. calcd for C$_{23}$H$_{21}$N$_3$O$_4$: C, 68.47; H, 5.25; N, 10.42. Found: C, 68.25; H, 5.12; N, 10.30.

5.78 2-(2,6-DIOXO-PIPERIDIN-3-YL)-4-(3-METHOXY-PHENYLAMINO)-ISOINDOLE-1,3-DIONE

5.78.1 3-(3-Methoxy-phenylamino)-phthalic acid dimethyl ester

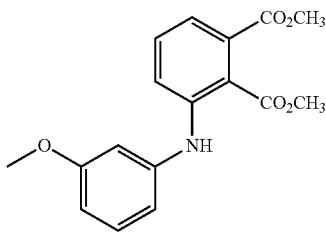 [SMILES: COC(=O)c1cccc(Nc2cccc(OC)c2)c1C(=O)OC]

A mixture of 3-iodo-phthalic acid dimethyl ester (1.0 g, 3.1 mmol), cesium carbonate (1.4 g, 4.3 mmol), Pd$_2$(dba) (0.13 g, 0.14 mmol) and rac-BINAP (0.058 g, 0.093 mmol) in toluene (6 mL) was stirred at room temperature for 5 minutes. m-Anisidine (0.38 g, 3.1 mmol) was then added, and the reaction mixture was refluxed for 48 hours. The reaction mixture was diluted with methylene chloride (20 mL) and filtered through celite. The filter was washed with additional methylene chloride (25 mL). The combined filtrates were evaporated, and the residue was purified by ISCO silica gel flash chromatography using a hexanes-ethyl acetate gradient, eluting the product at 7:3 hexanes-ethyl acetate. It was then purified by preparative HPLC using an acetonitrile-water gradient, eluting the product at 6:4 acetonitrile:water to give the title product, 0.46 g in 47% yield; $^1$H NMR (CDCl$_3$) δ 3.79 (s, 3H), 3.87 (s, 3H), 3.89 (s, 3H), 6.59-6.75 (m, 3H), 7.09-7.46 (m, 4H), 8.00 (s, 1H).

5.78.2 3-(3-Methoxy-phenylamino)-phthalic acid

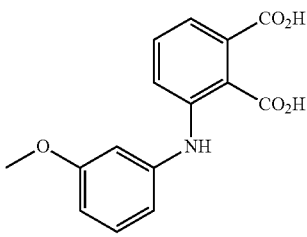 [SMILES: COc1cccc(Nc2cccc(C(=O)O)c2C(=O)O)c1]

A mixture of 3-(3-methoxy-phenylamino)-phthalic acid dimethyl ester (0.43 g, 1.4 mmol) and 3N NaOH (25 mL) in ethanol (50 mL) was heated to reflux for 2 hours and cooled to room temperature. The solvent was removed under vacuum and the residue was dissolved in water (50 mL), washed with CH$_2$Cl$_2$ (2×50 mL), and acidified with 6N HCl to pH 1-2. The resulting mixture was extracted with ethyl acetate (2×50 mL). The organic extracts were washed with water (2×50 mL) and dried (MgSO$_4$). After filtration of the MgSO$_4$, the solvent was evaporated in vacuo to give the product, 0.32 g, 82% yield; $^1$H NMR (DMSO-d$_6$) δ 3.70 (s, 3H), 6.48 (dd, J=7.9 Hz, J=1.7 Hz, 1H), 6.62-6.64 (m, 2H), 7.11-7.44 (m, 4H), 7.92 (s, 1H), 13.12 (br, 2H).

5.78.3 2-(2,6-Dioxo-piperidin-3-yl)-4-(3-methoxy-phenylamino)-isoindole-1,3-dione

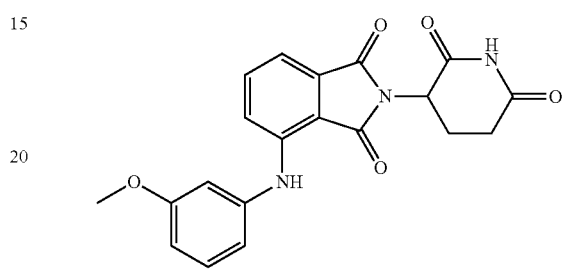

A mixture of 3-(3-methoxy-phenylamino)-phthalic acid (0.32 g, 1.1 mmol) and rac-α-aminoglutarimide hydrochloride (0.18 g, 1.1 mmol) in pyridine (10 mL) was heated to reflux for 15 hours. The reaction mixture was cooled, and the solvent was evaporated in vacuo. The residue was suspended in ethyl acetate (100 mL) and washed with dilute aqueous HCl (2×100 mL) and water (2×100 mL). Solvent was evaporated in vacuo. The residue was purified by ISCO silica gel flash chromatography using a methanol-methylene chloride gradient, eluting the product at 5:95 methanol-methylene chloride to give the title product (0.32 g, 76% yield): mp 210-212° C.; HPLC, Waters Symmetry C-18, 3.9×150 mm, 5 μm, 1 mL/min, 240 nm, 60/40 CH$_3$CN/0.1% H$_3$PO$_4$, 2.70 (97.39%); $^1$H NMR (DMSO-d$_6$) δ 2.04-2.08 (m, 1H), 2.49-2.64 (m, 2H), 2.84-2.94 (m, 1H), 3.75 (s, 3H), 5.13 (dd, J=12.6 Hz, J=5.4 Hz, 1H), 6.71 (dd, J=8.4 Hz, J=2.2 Hz, 1H), 6.90-6.92 (m, 2H), 7.25-7.32 (m, 2H), 7.50 (d, J=8.4 Hz, 1H), 7.60-7.66 (m, 1H), 8.42 (s, 1H), 11.14 (s, 1H); $^{13}$C NMR (DMSO-d$_6$) δ 22.1, 31.0, 48.7, 55.1, 107.3, 109.6, 112.2, 113.6, 119.9, 130.2, 132.5, 136.2, 140.7, 142.6, 160.2, 167.0, 168.2, 170.0, 172.8; Anal. calcd for C$_{20}$H$_{17}$N$_3$O$_5$: C, 63.32; H, 4.52; N, 11.08. Found: C, 63.22; H, 4.51; N, 10.78.

5.79 2-[2-(2,6-DIOXOPIPERIDIN-3-YL)-1,3-DIOXO-2,3-DIHYDRO-1H-ISOINDOL-4-YLAMINO]-N-METHYLACETAMIDE

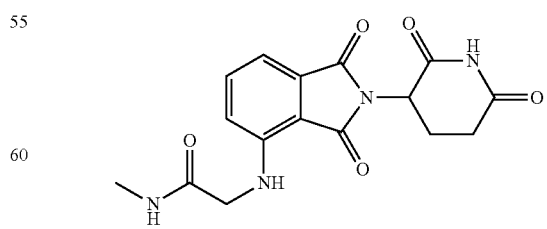

To a stirred solution of [2-(2,6-dioxopiperidin-3-yl)-1,3-dioxo-2,3-dihydro-1H-isoindol-4-ylamino]acetic acid (0.73 g, 2.2 mmol) in DMF (20 mL), were successively added HOBt (0.32 g, 2.4 mmol), DBU (0.38 g, 2.5 mmol), methylamine (0.062 g, 2.0 mmol) and EDC-Cl (0.58 g, 3.0 mmol). The solution was stirred overnight at room temperature. The solvent was evaporated in vacuo, giving a yellow oil. The oil was dissolved in $CH_2Cl_2$ (100 mL), washed with water (3×50 mL) and brine (100 mL), and dried ($MgSO_4$). The solvent was evaporated in vacuo to give a yellow solid. This material was triturated with diethyl ether for 1 hour and then filtered, and the resulting solid was recrystallized from ethanol, and the recrystallized solid was rinsed with diethyl ether, providing 0.45 g (65%) of the product as a yellow solid: mp 239-241° C.; $^1H$ NMR (DMSO-$d_6$) δ 2.01-2.05 (m, 1H), 2.47-2.56 (m, 2H), 2.62 (d, J=4.5 Hz, 3H), 2.97-2.82 (m, 1H), 3.91 (d, J=5.6 Hz, 2H), 5.07 (dd, J=12.5 Hz, J=5.4 Hz, 1H), 6.86 (d, J=8.5 Hz, 1H), 6.95 (t, J=5.5 Hz, 1H), 7.07 (d, J=7.1 Hz, 1H), 7.60 (t, J=7.6 Hz, 1H), 8.00 (d, J=4.5 Hz, 1H), 11.10 (s, 1H); $^{13}C$ NMR (DMSO-$d_6$) δ 22.14, 25.53, 30.95, 45.16, 48.53, 109.87, 110.92, 117.38, 132.02, 136.19, 145.80, 167.28, 168.65, 168.87, 169.99, 172.76; Anal. calcd. for $C_{16}H_{16}N_4O_5 \cdot 0.15H_2O \cdot 0.03Et_2O$: C, 55.44; H, 4.79; N, 16.04. Found: C, 55.31; H, 4.56; N, 15.65.

5.80 [2-(2,6-DIOXOPIPERIDIN-3-YL)-1,3-DIOXO-2,3-DIHYDRO-1H-ISOINDOL-4-YLAMINO]ACETIC ACID METHYL ESTER

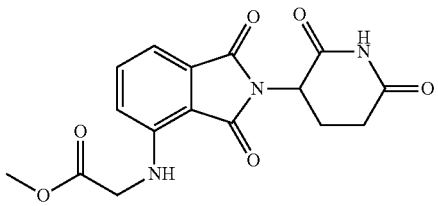 [SMILES: COC(=O)CNc1cccc2c1C(=O)N(C1CCC(=O)NC1=O)C2=O]

To a stirred solution of [2-(2,6-dioxopiperidin-3-yl)-1,3-dioxo-2,3-dihydro-1H-isoindol-4-ylamino]acetic acid (0.66 g, 2.0 mmol) in DMF (20 mL), were added methyl iodide (0.34 g, 2.4 mmol) and potassium carbonate (0.33 g, 2.4 mmol). The mixture was stirred overnight at room temperature. The solvent was evaporated in vacuo, giving a yellow oil. The oil was dissolved in $CH_2Cl_2$ (100 mL), washed with sat. aq. sodium bicarbonate (100 mL), water (100 mL) and brine (100 mL), and dried ($MgSO_4$). The solvent was evaporated in vacuo to give a yellow solid. This material was triturated with diethyl ether and then filtered, and the resulting solid was chromatographed, eluting with 9:1 methylene chloride-ethyl acetate. The resulting solid was triturated in 1:1 ethyl ether-water, filtered, and dried under high vacuum, providing 0.42 g (61%) of the product as a yellow solid: mp 210-212° C.; $^1H$ NMR (DMSO-$d_6$) δ 2.03-2.07 (m, 1H), 2.47-2.63 (m, 2H), 2.96-2.83 (m, 1H), 3.69 (s, 3H), 4.23 (d, J=6.0 Hz, 2H), 5.08 (dd, J=12.4 Hz, J=5.2 Hz, 1H), 6.91-7.11 (m, 3H), 7.61 (t, J=7.7 Hz, 1H), 11.12 (s, 1H); $^{13}C$ NMR (DMSO-$d_6$) δ 22.10, 30.96, 43.62, 48.51, 51.90, 109.76, 111.22, 117.65, 132.01, 136.09, 145.76, 167.21, 168.70, 170.12, 170.65, 172.77; Anal. calcd. for $C_{16}H_{15}N_3O_6$: C, 55.65; H, 4.38; N, 12.17. Found: C, 55.64; H, 4.28; N, 11.98.

5.81 2-[2-(2,6-DIOXOPIPERIDIN-3-YL)-1,3-DIOXO-2,3-DIHYDRO-1H-ISOINDOL-4-YLAMINO]-N-METHYLACETAMIDE

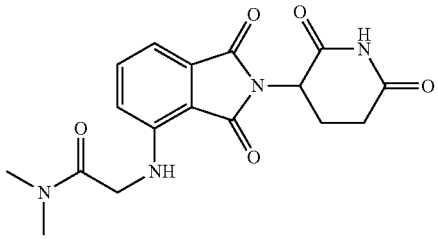 [SMILES: CN(C)C(=O)CNc1cccc2c1C(=O)N(C1CCC(=O)NC1=O)C2=O]

To a stirred solution of [2-(2,6-dioxopiperidin-3-yl)-1,3-dioxo-2,3-dihydro-1H-isoindol-4-ylamino]acetic acid (0.73 g, 2.2 mmol) in DMF (20 mL), were successively added HOBt (0.32 g, 2.4 mmol), DBU (0.38 g, 2.5 mmol), dimethylamine (90 mg, 2 mmol) and EDC-Cl (0.58 g, 3.0 mmol). The solution was stirred overnight at room temperature. The solvent was evaporated in vacuo, giving a yellow oil. The oil was dissolved in $CH_2Cl_2$ (200 mL), washed with water (3×100 mL) and brine (100 mL), and dried ($MgSO_4$). The solvent was evaporated in vacuo to give a yellow solid. Following an ethanol trituration, the resulting solid was purified by preparative HPLC, giving 0.52 g of the product in 73% yield: mp 239-241° C.; $^1H$ NMR (DMSO-$d_6$) δ 2.02-2.06 (m, 1H), 2.47-2.63 (m, 2H), 2.83-3.01 (m, 7H), 4.15 (d, J=3.9 Hz, 2H), 5.08 (dd, J=12.6 Hz, J=5.3 Hz, 1H), 7.05-7.10 (m, 3H), 7.60 (t, J=8.1 Hz, 1H), 11.12 (s, 1H); $^{13}C$ NMR (DMSO-$d_6$) δ 22.12, 30.96, 35.04, 35.34, 45.53, 48.55, 109.48, 110.72, 118.13, 131.98, 136.12, 145.36, 167.31, 167.59, 168.75, 170.02, 172.76; Anal. calcd. for $C_{17}H_{18}N_4O_5 \cdot 0.3H_2O$: C, 56.13; H, 5.15; N, 15.40. Found: C, 56.17; H, 5.15; N, 15.26.

5.82 N-CYCLOPROPYL-2-[2-(2,6-DIOXOPIPERIDIN-3-YL)-1,3-DIOXO-2,3-DIHYDRO-1H-ISOINDOL-4-YLAMINO]ACETAMIDE

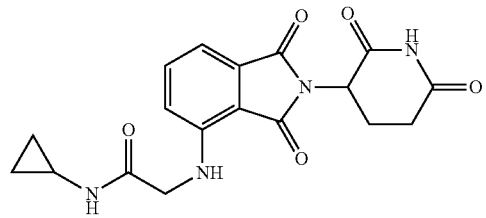 [SMILES: O=C1CCC(N2C(=O)c3cccc(NCC(=O)NC4CC4)c3C2=O)C(=O)N1]

N-Methylmorpholine (0.15 g, 1.5 mmol) was added to a stirred suspension of [2-(2,6-dioxopiperidin-3-yl)-1,3-dioxo-2,3-dihydro-1H-isoindol-4-ylamino]acetic acid (0.50 g, 1.5 mmol) in 50 mL THF under nitrogen at room temperature. Ethyl chloroformate (0.16 g, 1.5 mmol) was then added. Following 30 minutes stirring at room temperature, cyclopropylamine (0.086 g, 1.5 mmol) was added, and stirring proceeded for 21 hours. The solvent was evaporated in vacuo, and the dark yellow residue was dissolved in ethyl acetate (200 mL) and washed with sat. sodium bicarbonate (2×100 mL), water (100 mL), 1N citric acid (2×100 mL), water (100 mL) and brine (100 mL). The organic phase was dried ($MgSO_4$) and evaporated to provide 0.15 g (27%) of the product as a yellow solid: mp 240-242° C.; $^1H$ NMR (DMSO-$d_6$) δ 0.39-0.45 (m, 2H), 0.59-0.73 (m, 2H), 2.02-2.06 (m, 1H), 2.45-2.70 (m, 3H), 2.96-2.83 (m, 1H), 3.88 (d, J=5.3 Hz, 2H), 5.07 (dd, J=12.5 Hz, J=5.3 Hz, 1H), 6.83-6.92 (m, 2H), 7.07 (d, J=7.0 Hz, 1H), 7.60 (t, J=7.9 Hz, 1H), 11.11 (s, 1H); $^{13}$C NMR (DMSO-d$_6$) δ 5.57, 22.13, 22.26, 30.96, 44.92, 48.59, 109.77, 110.88, 117.42, 132.02, 136.17, 145.80, 167.28, 168.68, 169.46, 170.07, 172.77; Anal. calcd. for $C_{18}H_{18}N_4O_5$: C, 58.37; H, 4.90; N, 15.13. Found: C, 58.16; H, 4.64; N, 14.84.

5.83 4-(2-(AZETIDIN-1-YL)-2-OXOETHY-LAMINO)-2-(2,6-DIOXOPIPERIDIN-3-YL)ISOIN-DOLINE-1,3-DIONE

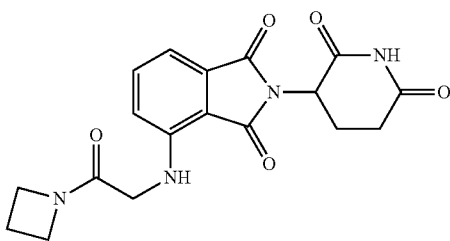 [SMILES: O=C1CCC(N2C(=O)c3cccc(NCC(=O)N4CCC4)c3C2=O)C(=O)N1]

To a stirred solution of [2-(2,6-dioxopiperidin-3-yl)-1,3-dioxo-2,3-dihydro-1H-isoindol-4-ylamino]acetic acid (0.50 g, 1.5 mmol) in DMF (20 mL), were successively added HOBt (0.22 g, 1.7 mmol), DBU (0.63 g, 4.1 mmol), trimethylamine (0.15 g, 1.7 mmol) and EDC-Cl (0.38 g, 2.0 mmol). The solution was stirred overnight at room temperature. The solvent was evaporated in vacuo, and the residue was dissolved in ethyl acetate (200 mL), washed with water (100 mL), 0.1N HCl (100 mL), water (100 mL), and brine (100 mL), and was dried (MgSO$_4$). The solvent was evaporated in vacuo, and the residue was chromatographed eluting with 3:2 ethyl acetate-methylene chloride, providing 0.15 g of the product in 27% yield: mp 272-274° C.; $^1$H NMR (DMSO-d$_6$) δ 1.09-1.99 (m, 1H), 2.20-2.32 (m, 2H), 2.47-2.63 (m, 2H), 2.97-2.82 (m, 1H), 4.04-3.90 (m, 4H), 4.19 (t, J=7.5 Hz, 2H), 5.07 (dd, J=12.5 Hz, J=5.3 Hz, 1H), 6.86 (t, J=4.6 Hz, 1H), 6.99 (d, J=8.5 Hz, 1H), 7.07 (d, J=7.1 Hz, 1H), 7.60 (t, J=7.8 Hz, 1H), 11.12 (s, 1H); $^{13}$C NMR (DMSO-d$_6$) δ 15.45, 22.11, 30.96, 41.82, 47.99, 48.56, 49.28, 109.58, 110.88, 117.90, 131.99, 136.13, 145.57, 167.28, 167.66, 168.75, 170.02, 172.77; Anal. calcd. for $C_{19}H_{20}N_4O_5$·0.15EtOAc: C, 58.24; H, 5.05; N, 14.61. Found: C, 57.88; H, 4.81; N, 14.72.

5.84 2-[2-(2,6-DIOXOPIPERIDIN-3-YL)-1,3-DI-OXO-2,3-DIHYDRO-1H-ISOINDOL-4-YLAMINO]-N-PHENYL-ACETAMIDE

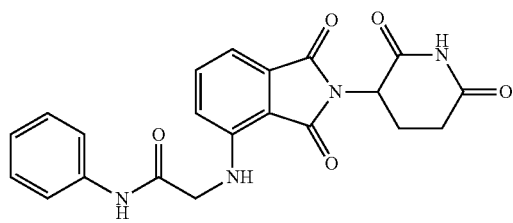 [SMILES: O=C1CCC(N2C(=O)c3cccc(NCC(=O)Nc4ccccc4)c3C2=O)C(=O)N1]

Step 1:
To a stirred solution of dimethyl 3-aminophthalate (4.2 g, 20 mmol) in CH$_2$Cl$_2$ (100 mL), were added glyoxylic acid (3.7 g, 40 mmol) and acetic acid (6.9 mL). The mixture was stirred for 5 minutes followed by addition of sodium triacetoxyborohydride (13 g, 60 mmol). The mixture was stirred at ambient temperature overnight under an atmosphere of nitrogen. The reaction mixture was washed with 0.1N HCl (3×100 mL) and brine (100 mL), and dried (MgSO$_4$). The solvent was evaporated leaving an oily residue, which was dissolved in sat. aq. sodium bicarbonate (50 mL). This aqueous solution was washed with ethyl acetate (3×50 mL) and then acidified to pH 2-3 (conc. HCl). This mixture was extracted with ethyl acetate (3×100 mL). The combined extracts were washed with brine (100 mL), and dried (MgSO$_4$). Evaporation provided 3.4 g of an off-white solid (63%).

Step 2:
A sample of the product from step 1 (0.53 g, 2.0 mmol) was suspended in THF and cooled to 0° C. under nitrogen. N-Methylmorpholine (0.20 g, 2.0 mmol) was added, followed by ethyl chloroformate (0.22 g, 2.0 mmol). The mixture was stirred for 10 minutes, and then aniline (0.19 g, 2.0 mmol) was added. The mixture was stirred at room temperature for 2 hours and then at reflux for 1 hour. The solvent was evaporated in vacuo, and the residue was partitioned between ethyl acetate (100 mL) and water (100 mL). The organic layer was washed with water (3×100 mL), 0.1 N HCl (50 mL), sat. sodium bicarbonate (100 mL) and brine (100 mL), and dried (MgSO$_4$) and evaporated. The residue was chromatographed eluting with 7:3 hexanes-ethyl acetate, providing 0.51 g of the sample.

Step 3:
The product from step 2 was added to a mixture of 5N KOH (3 mL) and methanol (20 mL), and the resulting mixture was stirred at room temperature for 18 hours. The solvent was evaporated, and the residue was dissolved in water (50 mL) and washed with ethyl acetate (50 mL). The aqueous phase was then acidified to pH 2-3 (conc. HCl) and then extracted with ethyl acetate (3×75 mL). The combined ethyl acetate extracts were washed with brine (100 mL) and dried (MgSO$_4$). The solvent was evaporated in vacuo, affording 0.41 g of the sample.

Step 4:
The product from step 3 and rac-α-aminoglutarimide hydrochloride (0.26 g, 1.6 mmol) were dissolved in pyridine (20 mL), and the resulting mixture was heated to reflux for 18 hours. The mixture was cooled to ambient temperature, and the solvent was evaporated in vacuo. The residue was dissolved in CH$_2$Cl$_2$ (150 mL), washed with water (2×100 mL), sat. sodium bicarbonate (100 mL), and brine (100 mL), and dried (MgSO$_4$). The solution was treated with Norite (~1 g), stirred for 10 minutes, and filtered through Celite. The yellow filtrate was evaporated in vacuo to give a yellow solid, which was purified by preparative HPLC, eluting with 7:3 water-acetonitrile, and providing 0.15 g as a yellow solid, 0.59 g of the product in 18% overall yield (final 3 steps): mp 267-268° C.; $^1$H NMR (DMSO-d$_6$) δ 2.03-2.09 (m, 1H), 2.51-2.64 (m, 2H), 2.84-2.97 (m, 1H), 4.19 (d, J=5.3 Hz, 2H), 5.10 (dd, J=12.5 Hz, J=5.1 Hz, 1H), 6.95-7.10 (m, 4H), 7.32 (t, J=7.7 Hz, 2H), 7.60 (d, J=7.4 Hz, 3H), 10.22 (s, 1H), 11.14 (s, 1H); $^{13}$C NMR (DMSO-d$_6$) δ 22.15, 30.98, 45.62, 48.59, 109.81, 111.03, 117.60, 119.18, 123.40, 128.78, 132.06, 136.22, 138.70, 145.95, 167.30, 167.49, 168.74, 170.05, 172.80; Anal. calcd. for $C_{21}H_{18}N_4O_5$: C, 61.52; H, 4.52; N, 13.66. Found: C, 61.35; H, 4.29; N, 13.40.

5.85 2-(2,6-DIOXOPIPERIDIN-3-YL)-4-[(PYRIDIN-2-YLMETHYL)AMINO]ISOINDOLE-1,3-DIONE HYDROCHLORIDE

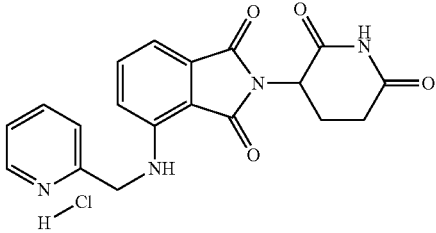

Step 1:
To a stirred solution of dimethyl 3-aminophthalate (0.84 g, 4.0 mmol) in CH$_2$Cl$_2$ (40 mL), were added 2-pyridinecarboxaldehyde (0.86 g, 8.0 mmol) and acetic acid (1.4 mL). The mixture was stirred for 5 minutes, followed by addition of sodium triacetoxyborohydride (2.5 g, 12 mmol). The mixture was stirred at ambient temperature overnight under an atmosphere of nitrogen. The reaction mixture was diluted with 50 mL of CH$_2$Cl$_2$, washed with water (3×100 mL), saturated aqueous sodium bicarbonate (2×100 mL), and brine (100 mL), and dried (MgSO$_4$). The solvent was evaporated under vacuum. The resulting yellow oil was dissolved in diethyl ether and extracted with 0.1N HCl (2×100 mL). The combined extracts were washed with diethyl ether (2×100 mL) and then basified with saturated aqueous sodium carbonate. The combined aqueous phases were then extracted with diethyl ether (3×100 mL), and the combined ethereal extracts were washed with brine (100 mL), and dried (MgSO$_4$). Upon evaporation of the solvent, 1.1 g (88%) of the sample was obtained.

Step 2:
A mixture of the product from step 1 and 5N NaOH (8 mL) in methanol (20 mL) was stirred overnight. The solvent was evaporated, and the resulting white solid was dissolved in water (20 mL), washed with diethyl ether (2×100 mL), and acidified to pH 2-3 (conc. HCl), and then evaporated once more, giving a white solid.

Step 3:
The product from step 2 and rac-α-aminoglutarimide hydrochloride (0.66 g, 4.0 mmol) were dissolved in pyridine (40 mL), and the resulting mixture was heated to reflux for 5 hours. The mixture was cooled to ambient temperature, and the solvent was evaporated in vacuo. The residue was dissolved in CH$_2$Cl$_2$ (100 mL), washed with water (3×100 mL) and brine (100 mL), and dried (MgSO$_4$). The solution was treated with Norite (~2 g), stirred for 30 minutes, and filtered through Celite. The yellow filtrate was evaporated in vacuo to give a yellow semi-solid. This material was purified by preparative HPLC, running with 25:75 ACN-H$_2$O, providing 0.72 g of the free base. This material was dissolved in 1:1 CH$_2$Cl$_2$-MeOH (30 mL) and treated with 4N HCl/dioxane (2 mL). After stirring for 10 minutes, the solvent was evaporated, and the resulting residue was recrystallized from ethanol (30 mL), providing 0.45 g of the product as a yellow solid, in 30% overall yield (3 steps): mp 254-256° C.; $^1$H NMR (DMSO-d$_6$) δ 2.04-2.08 (m, 1H), 2.51-2.64 (m, 2H), 2.84-2.97 (m, 1H), 4.97 (s, 2H), 5.11 (dd, J=12.4 Hz, J=5.2 Hz, 1H), 7.10 (t, J=6.7 Hz, 2H), 7.56 (t, J=7.8 Hz, 2H), 7.86-7.79 (m, 2H), 8.37 (t, J=7.7 Hz, 1H), 8.81 (d, J=5.1 Hz, 1H), 11.15 (s, 1H); $^{13}$C NMR (DMSO-d$_6$) δ 22.14, 30.97, 44.16, 48.61, 110.51, 111.62, 117.47, 124.27, 124.83, 132.28, 136.36, 143.39, 144.02, 145.29, 155.10, 167.18, 168.51, 170.04, 172.80; Anal. calcd. for C$_{19}$H$_{17}$ClN$_4$O$_4$·0.3H$_2$O: C, 56.32; H, 4.23; N, 13.64. Found: C, 56.18; H, 4.37; N, 13.79.

5.86 2-(2,6-DIOXOPIPERIDIN-3-YL)-4-[(PYRIDIN-4-YLMETHYL)AMINO]ISOINDOLE-1,3-DIONE HYDROCHLORIDE

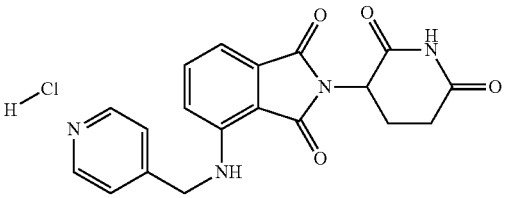

Step 1:
To a stirred solution of dimethyl 3-aminophthalate (0.84 g, 4.0 mmol) in CH$_2$Cl$_2$ (40 mL), were added 4-pyridinecarboxaldehyde (0.86 g, 8.0 mmol) and acetic acid (1.4 mL). The mixture was stirred for 5 minutes, followed by addition of sodium triacetoxyborohydride (2.5 g, 12 mmol). The mixture was stirred at ambient temperature overnight under an atmosphere of nitrogen. The reaction mixture was diluted with 60 mL of CH$_2$Cl$_2$, washed with water (3×100 mL), saturated aqueous sodium bicarbonate (3×100 mL), and brine (100 mL), and dried (MgSO$_4$). The solvent was evaporated under vacuum. The resulting yellow oil was dissolved 0.2N HCl (60 mL). The aqueous solution was washed with diethyl ether (2×100 mL) and then basified with saturated aqueous sodium carbonate. The combined aqueous phases were then extracted with diethyl ether (3×100 mL), and the combined ethereal extracts were washed with brine (100 mL) and dried (MgSO$_4$). Upon evaporation of the solvent, 0.58 g of the sample was obtained.

Step 2:
A mixture of the product from step 1 and 5N NaOH (8 mL) in methanol (20 mL) was stirred overnight. The solvent was evaporated, and the resulting white solid was dissolved in water (20 mL), washed with diethyl ether (2×100 mL), and acidified to pH 2-3 (conc. HCl), and then evaporated once more, and the resulting solid was dried under high vacuum overnight.

Step 3:
The product from step 2 and rac-α-aminoglutarimide hydrochloride (0.66 g, 4.0 mmol) were dissolved in pyridine (30 mL), and the resulting mixture was heated to reflux for 5 hours. The mixture was cooled to ambient temperature, and the solvent was evaporated in vacuo. The residue was dissolved in CH$_2$Cl$_2$ (125 mL), washed with water (3×100 mL) and brine (100 mL), and dried (MgSO$_4$). The solution was treated with Norite (~3 g), stirred for 10 minutes, and filtered through Celite. The yellow filtrate was evaporated in vacuo to give a yellow solid, which was triturated with methanol (15 mL), filtered and dried. This material was suspended in MeOH and treated with 2N HCl/diethyl ether. After stirring for 10 minutes, the solvent was evaporated, and the resulting residue was dissolved in water (100 mL) and washed with ethyl acetate. The aqueous phase was then neutralized (sat. aq. NaHCO$_3$) and extracted with ethyl acetate (3×100 mL). The combined organic extracts were washed with brine (100 mL), dried (MgSO$_4$) and then treated with 2N HCl/diethyl ether (2 mL). The mixture was stirred for 10 minutes, and the

5.87 4-[(FURAN-2-YLMETHYL)AMINO]-2-(3-METHYL-2,6-DIOXOPIPERIDIN-3-YL)ISOINDOLE-1,3-DIONE

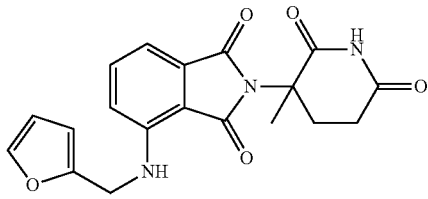 [SMILES: CC1(N2C(=O)c3cccc(NCc4ccco4)c3C2=O)CCC(=O)NC1=O]

Step 1:
To a stirred solution of dimethyl 3-aminophthalate (0.84 g, 4.0 mmol) in $CH_2Cl_2$ (40 mL), were added furfural (0.77 g, 8.0 mmol) and acetic acid (1.4 mL). The mixture was stirred for 5 minutes, followed by addition of sodium triacetoxyborohydride (2.5 g, 12 mmol). The mixture was stirred at ambient temperature overnight under an atmosphere of nitrogen. The reaction mixture was diluted with 60 mL of $CH_2Cl_2$ and washed with water (100 mL), saturated aqueous sodium bicarbonate (3×100 mL), and brine (100 mL), and dried ($MgSO_4$). The solvent was evaporated, providing 0.97 g of the sample as a yellow oil.

Step 2:
A mixture of the product from step 1 and 5N NaOH (8 mL) in methanol (20 mL) was stirred overnight. The solvent was evaporated and the resulting white solid was dissolved in water (50 mL), washed with diethyl ether (2×50 mL), and acidified to pH 2-3 (conc. HCl). The aqueous mixture was then extracted with ethyl acetate (3×75 mL). The combined organic extracts were washed with water (100 mL), brine (100 mL), and dried ($MgSO_4$) and evaporated, providing a light brown-yellow oil.

Step 3:
The product from step 2 and α-methyl-α-aminoglutarimide hydrochloride (0.71 g, 4.0 mmol) were dissolved in pyridine (30 mL), and the resulting mixture was heated to reflux for 20 hours. The mixture was cooled to ambient temperature, and the solvent was evaporated in vacuo. The residue was dissolved in $CH_2Cl_2$ (125 mL), washed with water (3×100 mL), 0.1N HCl (2×100 mL), and brine (100 mL), and dried ($MgSO_4$). The solvent was evaporated in vacuo, and the resulting yellow solid was chromatographed eluting with 9:1 ethyl acetate-methylene chloride, providing 0.61 g of the product in 42% overall yield (3 steps): mp 158-160° C.; $^1H$ NMR (DMSO-$d_6$) δ 1.88 (s, 3H), 1.96-2.09 (m, 1H), 2.51-2.77 (m, 3H), 4.53 (d, J=5.8 Hz, 2H), 6.35-6.40 (m, 2H), 6.97-7.17 (m, 3H), 7.52-7.59 (m, 2H), 11.01 (s, 1H); $^{13}C$ NMR (DMSO-$d_6$) δ 20.99, 28.62, 29.24, 58.39, 107.41, 109.46, 110.43, 110.59, 117.35, 131.92, 135.97, 142.43, 145.61, 151.97, 167.92, 169.73, 172.21, 172.42; Anal. calcd. for $C_{19}H_{17}N_3O_5$: C, 62.07; H, 4.70; N, 11.22. Found: C, 62.12; H, 4.66; N, 11.44.

solvent was removed under vacuum providing 0.25 g of the product as a yellow solid, in 16% overall yield (3 steps): mp 219-221° C.; $^1H$ NMR (DMSO-$d_6$) δ 2.05-2.09 (m, 1H), 2.51-2.65 (m, 2H), 2.87-2.98 (m, 1H), 4.88 (s, 2H), 5.11 (dd, J=12.2 Hz, J=4.9 Hz, 1H), 6.89 (d, J=8.4 Hz, 1H), 7.10 (d, J=7.0 Hz, 1H), 7.49-7.55 (m, 2H), 8.04 (s, 2H), 9.05 (s, 1H), 11.14 (s, 1H); $^{13}C$ NMR (DMSO-$d_6$) δ 22.14, 30.96, 45.00, 48.59, 110.29, 111.46, 117.45, 132.35, 136.31, 141.53, 145.23, 159.69, 167.17, 168.49, 170.05, 172.81; Anal. calcd. for $C_{19}H_{17}ClN_4O_4 \cdot 0.35H_2O \cdot 0.14EtOAc$: C, 56.01; H, 4.52; N, 13.36. Found: C, 55.65; H, 4.27; N, 13.36.

5.88 1-ETHYL-3-[2-(3-METHYL-2,6-DIOXO-PIPERIDIN-3-YL)-1,3-DIOXO-2,3-DIHYDRO-1H-ISOINDOL-4-YLMETHYL]-UREA

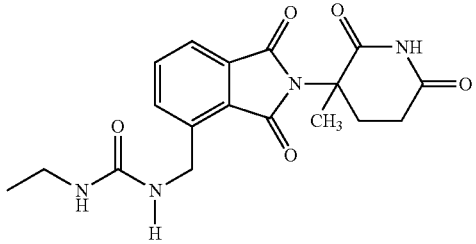 [SMILES: CCNC(=O)NCc1cccc2c1C(=O)N(C1(C)CCC(=O)NC1=O)C2=O]

Step 1:
A mixture of 3-(t-butoxycarbonylamino-methyl)-phthalic acid (3.3 g, 11.2 mmol) and 3-amino-3-methyl-piperidine-2,6-dione hydrochloride (2.0 g, 11.2 mmol) in pyridine (40 mL) was refluxed for 17 hours. The mixture was cooled and concentrated. The residue was dissolved in EtOAc (200 mL) and water (50 mL). The organic layer was washed with water (40 mL), Sat. $NaHCO_3$ (40 mL), water (40 mL), and brine (40 mL), and dried ($MgSO_4$). Solvent was removed, and the residue was purified by chromatography (Silica gel) to give [2-(3-methyl-2,6-dioxo-piperidin-3-yl)-1,3-dioxo-2,3-dihydro-1H-isoindol-4-ylmethyl]-carbamic acid t-butyl ester (2.3 g, 51%): $^1H$ NMR (CDCl$_3$) δ 1.43 (s, 9H, 3(CH$_3$)), 2.08 (s, 3H, CH$_3$), 2.10-2.15 (m, 1H), 2.69-2.84 (m, 3H), 4.62 (d, J=6.5 Hz, 2H, CH$_2$), 5.46 (m, 1H, NH), 7.64-7.76 (m, 3H, Ar), 8.15 (s, 1H, NH).

Step 2:
2N HCl/ether solution (8.5 mL) was added to a stirred solution of [2-(3-methyl-2,6-dioxo-piperidin-3-yl)-1,3-dioxo-2,3-dihydro-1H-isoindol-4-ylmethyl]-carbamic acid t-butyl ester (2.3 g, 5.7 mmol) in ethyl acetate (20 mL). The mixture was stirred at room temperature overnight. The mixture was filtered, and the solid was dried to gave 4-aminomethyl-2-(3-methyl-2,6-dioxo-piperidin-3-yl)-isoindole-1,3-dione hydrochloride (1.6 g, 80%) as a white solid: $^1H$ NMR (DMSO-$d_6$) δ 1.90 (s, 3H, CH$_3$), 2.08 (m, 1H), 2.61-2.71 (m, 3H), 4.44 (M, 2H, CH$_2$), 7.87-7.95 (m, 3H, Ar), 8.62 (s, 3H, NH$_3$), 11.05 (s, 1H, NH); $^{13}C$ NMR (DMSO-$d_6$) δ 20.97, 28.52, 29.04, 36.98, 58.77, 123.14, 128.38, 131.10, 132.28, 134.64, 135.58, 167.31, 168.00, 171.93, 172.09.

Step 3: 1,8-Diazabicyclo[5,4,0]undec-7-ene (0.2 g, 2.2 mmol) was added to a stirred suspension of 4-aminomethyl-2-(3-methyl-2,6-dioxo-piperidin-3-yl)-isoindole-1,3-dione hydrochloride (0.3 g, 1.0 mmol) in acetonitrile (40 mL). After stirring for 30 minutes, ethyl isocyanate (0.09 g, 1.3 mmol) was added, and the mixture was stirred at room temperature for 24 hours. The mixture was concentrated and the residue was dissolved in methylene chloride (60 mL). The methylene chloride solution was washed with water (2×30 mL) and brine (30 mL), and dried ($MgSO_4$). Solvent was removed and purified by chromatography (silica gel) to give 1-ethyl-3-[2-(3-methyl-2,6-dioxo-piperidin-3-yl)-1,3-dioxo-2,3-dihydro-1H-isoindol-4-ylmethyl]-urea (0.2 g, 55%) as a white solid: mp 220-222° C.; $^1H$ NMR (DMSO-$d_6$) δ 0.99 (t, J=7.1 Hz, 3H, CH$_3$), 1.90 (s, 3H, CH$_3$), 2.03-2.09 (m, 1H), 2.50-2.74 (m, 3H), 2.97-3.07 (m, 2H), 4.59 (d, J=5.8 Hz, 2H), 6.09 (t, J=5.0 Hz, 1H), 6.41 (t, J=5.6 Hz, 1H), 7.65-7.82 (e, 3H, Ar), 11.01 (s, 1H, NH); $^{13}C$ NMR (DMSO-$d_6$) δ 15.59, 21.01, 28.58, 29.11, 34.16, 38.65, 58.69, 121.25, 126.64, 131.37, 133.26, 134.46, 140.79, 157.92, 167.78, 168.41, 172.14, 172.22; Anal. calcd. for $C_{18}H_{20}N_4O_5$+0.08$H_2O$: C, 57.83; H, 5.44; N, 14.99. Found: C, 57.26; H, 5.21; N, 14.79.

5.89 1-[2-(2,6-DIOXO-PIPERIDIN-3-YL)-1,3-DIOXO-2,3-DIHYDRO-1H-ISOINDOL-4-YLMETHYL]-3-(3-METHOXY-PHENYL)-UREA

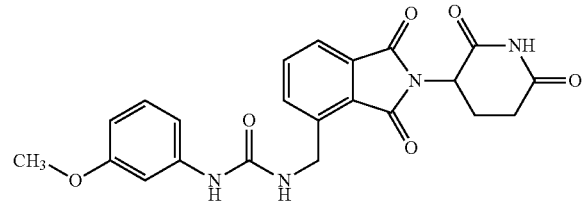 [SMILES: COc1cccc(NC(=O)NCc2cccc3c2C(=O)N(C2CCC(=O)NC2=O)C3=O)c1]

A suspension of 4-aminomethyl-2-(2,6-dioxo-piperidin-3-yl)-isoindole-1,3-dione hydrochloride (0.7 g, 2.0 mmol) and triethylamine (0.3 g, 2.6 mmol) in THF (30 mL) was cooled to 5° C. 3-Methoxyphenyl isocyanate (0.4 g, 2.6 mmol) was added, and the mixture was stirred at room temperature 5 hours. The mixture was concentrated, and the residue was dissolved in $CH_2Cl_2$ (80 mL). The $CH_2Cl_2$ solution was washed with 1N HCl (40 mL), water (40 mL), and brine (40 mL), and dried ($MgSO_4$). Solvent was removed, and the solid was slurried with ethanol (20 mL) to give 1-[2-(2,6-dioxo-piperidin-3-yl)-1,3-dioxo-2,3 dihydro-1H-isoindol-4-ylmethyl]-3-(3-methoxy-phenyl)-urea (0.7 g, 80%) as a white solid: mp 160-162° C.; $^1$H NMR (DMSO-$d_6$) δ 2.06-2.10 (m, 1H), 2.50-2.65 (m, 2H), 2.85-2.99 (m, 1H), 3.69 (s, 3H, $OCH_3$), 4.69 (d, J=5.2 Hz, 2H, $CH_2$), 5.14-5.20 (dd, J=4.6 and 12.1 Hz, 1H, CH), 6.49 (d, J=7.9 Hz, 1H, Ar), 6.76-6.86 (m, 2H, Ar), 7.08-7.14 (m, 2H), 7.76-7.85 (m, 3H, Ar), 8.81 (s, 1H, NH), 11.16 (s, 1H, NH); $^{13}$C NMR (DMSO-$d_6$) δ 21.99, 30.94, 38.72, 48.87, 54.82, 103.44, 106.70, 110.05, 121.86, 127.19, 129.36, 131.61, 133.62, 134.72, 140.23, 141.51, 155.15, 159.62, 167.01, 167.60, 169.82, 172.76; Anal. calcd. for $C_{22}H_{20}N_4O_6$: C, 60.55; H, 4.62; N, 12.84. Found: C, 60.18; H, 4.42; N, 12.63.

5.90 1-(3-CHLORO-PHENYL)-3-[2-(2,6-DIOXO-PIPERIDIN-3-YL)-1,3-DIOXO-2,3-DIHYDRO-1H-ISOINDOL-4-YLMETHYL]-UREA

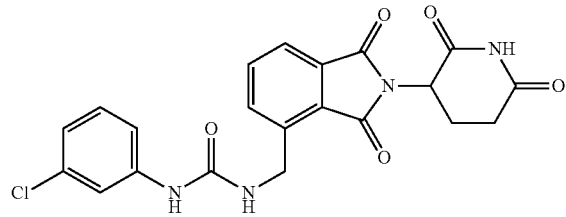 [SMILES: O=C1CCC(N2C(=O)c3cccc(CNC(=O)Nc4cccc(Cl)c4)c3C2=O)C(=O)N1]

A suspension of 4-aminomethyl-2-(2,6-dioxo-piperidin-3-yl)-sioindole-1,3-dione hydrochloride (0.7 g, 2.0 mmol) and teriethylamine (0.3 g, 2.6 mmol) in THF (30 mL) was cooled to 5° C. 3-Chloro-phenyl isocyanate (0.4 g, 2.6 mmol) was added, and the mixture was stirred at room temperature for 5 hours. The mixture was concentrated, and the residue was dissolved in $CH_2Cl_2$ (80 mL). The $CH_2Cl_2$ solution was washed with 1N HCl (40 mL), water (40 mL), and brine (40 mL), and dried ($MgSO_4$). Solvent was removed, and the residue was slurried with ethanol (10 mL) to give 1-(3-chloro-phenyl)-3-[2-(2,6-dioxo-piperidin-3-yl)-1,3-dioxo-2,3-dihydro-1H-isoindol-4-ylmethyl]-urea (0.6 g, 65%) as a white solid: mp 193-195° C.; $^1$H NMR (DMSO-$d_6$) δ 2.05-2.10 (m, 1H), 2.49-2.65 (m, 2H), 2.84-2.97 (m, 1H), 4.70 (d, J=5.8 Hz, 2H, $CH_2$), 5.13-5.20 (dd, J=5.3 and 12.5 Hz, 1H, CH), 6.84-6.96 (m, 2H), 7.16-7.27 (m, 2H), 7.66-7.68 (m, 1H), 7.75-7.88 (m, 3H), 9.04 (s, 1H, NH), 11.16 (s, 1H, NH); $^{13}$C NMR (DMSO-$d_6$) δ 21.98, 30.93, 48.86, 116.07, 117.05, 120.79, 121.90, 127.21, 130.22, 131.60, 133.08, 133.64, 134.73, 139.98, 141.83, 155.02, 166.99, 167.59, 169.81, 172.75; Anal. calcd. for $C_{21}H_{17}N_4O_5Cl$+0.3$C_2H_5OH$: C, 57.06; H, 4.17; N, 12.32; Cl, 7.80. Found: C, 56.82; H, 4.21; N, 11.93; Cl, 7.46.

5.91 1-(3-CYANO-PHENYL)-3-[2-(2,6-DIOXO-PIPERIDIN-3-YL)-1,3-DIOXO-2,3-DIHYDRO-1H-ISOINDOL-4-YLMETHYL]-UREA

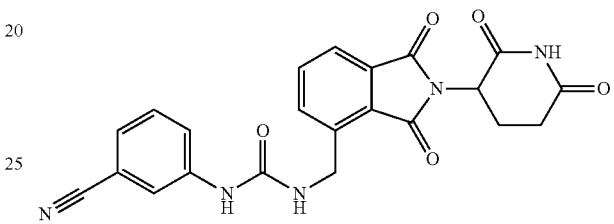

A suspension of 4-aminomethyl-2-(2,6-dioxo-piperidin-3-yl)-sioindole-1,3-dione hydrochloride (0.7 g, 2.0 mmol) and triethylamine (0.3 g, 2.6 mmol) in THF (30 mL) was cooled to 5° C. 3-Cyano-phenyl isocyanate (0.4 g, 2.6 mmol) was added, and the mixture was stirred at room temperature overnight. The mixture was concentrated, and the residue was dissolved in $CH_2Cl_2$ (80 mL). The $CH_2Cl_2$ solution was washed with 1N HCl (2×25 mL), H2O (2×30 mL), and brine (30 mL), and dried ($MgSO_4$). Solvent was removed, and the residue was slurried with ethanol (10 mL) to give 1-(3-cyano-phenyl)-3-[2-(2,6-dioxo-piperidin-3-yl)-1,3-dioxo-2,3-dihydro-1H-isoindol-4-ylmethyl]-urea (0.7 g, 80%) as a white solid: mp 228-230° C.; $^1$H NMR (DMSO-$d_6$) δ 2.06-2.10 (m, 1H), 2.50-2.65 (m, 2H), 2.84-2.97 (m, 1H), 4.74 (d, J=5.8 Hz, 2H, $CH_2$), 5.14-5.21 (dd, J=6.1 and 12.5 Hz, 1H, CH), 6.96 (t, J=5.9 Hz, 1H, NH), 7.36 (d, J=7.7 Hz, 1H, Ar), 7.43 (t, J=7.6 Hz, 1H, Ar), 7.57 (d, J=8.6 Hz, 1H, Ar), 7.76-7.94 (m, 4H, Ar), 9.20 (s, 1H, NH), 11.16 (s, 1H, NH); $^{13}$C NMR (DMSO-$d_6$) δ 21.97, 30.92, 48.86, 111.44, 118.88, 120.19, 121.92, 122.29, 124.67, 127.22, 130.02, 131.60, 133.63, 134.73, 139.84, 141.17, 155.02, 166.97, 167.57, 169.80, 172.73; Anal. calcd. for $C_{22}H_{17}N_5O_5$+0.15$H_2O$: C, 60.87; H, 4.02; N, 16.18. Found: C, 60.82; H, 3.94; N, 15.89.

5.92 1-[2-(2,6-DIOXO-PIPERIDIN-3-YL)-1,3-DIOXO-2,3-DIHYDRO-1H-ISOINDOL-4-YLMETHYL]-3-(4-METHOXY-PHENYL)-UREA

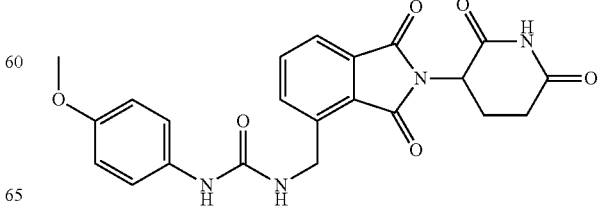

4-Methoxyphenyl isocyanate (0.4 g, 2.6 mmol) was added to a stirred suspension of 4-aminomethyl-2-(2,6-dioxo-piperidin-3-yl)-isoindole-1,3-dione hydrochloride (0.7 g, 2.0 mmol) and triethylamine (0.3 g, 2.8 mmol) in THF (30 mL) at 5-10° C. After 10 minutes, the mixture was stirred at room temperature overnight. The reaction was quenched with methanol (1 mL), and the mixture was concentrated. The residue was stirred with 1N HCl (30 mL) for one hour and then filtered. The solid was slurried with hot ethanol (20 mL) to give 1-[2-(2,6-dioxo-piperidin-3-yl)-1,3-dioxo-2,3-dihydro-1H-isoindol-4-ylmethyl]-3-(4-methoxy-phenyl)-urea (0.5 g, 59%) as a white solid: mp 205-207° C.; $^1$H NMR (DMSO-d$_6$) δ 2.05-2.09 (m, 1H), 2.49-2.65 (m, 2H), 2.84-2.97 (m, 1H), 3.68 (s, 3H, OCH$_3$), 4.70 (d, J=5.7 Hz, 2H, CH$_2$), 5.13-5.20 (dd, J=5.2 and 12.4 Hz, 1H, CH), 6.66 (t, J=5.7 Hz, 1H, NH), 6.79 (d, J=9.0 Hz, 2H, Ar), 7.27 (d, J=9.0 Hz, 2H, Ar), 7.75-7.88 (m, 3H, Ar), 8.59 (a, 1H, NH), 11.65 (s, 1H, NH); $^{13}$C NMR (DMSO-d$_6$) δ 21.99, 30.94, 48.86, 55.10, 113.86, 119.50, 121.82, 127.15, 131.59, 133.38, 133.62, 134.70, 140.46, 154.03, 155.45, 167.02, 167.60, 169.84, 172.22; Anal. calcd. for C$_{22}$H$_{20}$N$_4$O$_6$: C, 60.55; H, 4.62; N, 12.84. Found: C, 60.43; H, 4.42; N, 12.58.

5.93 1-[2-(2,6-DIOXO-PIPERIDIN-3-YL)-1,3-DIOXO-2,3-DIHYDRO-1H-ISOINDOL-4-YLMETHYL]-3-(2-METHOXY-PHENYL)-UREA

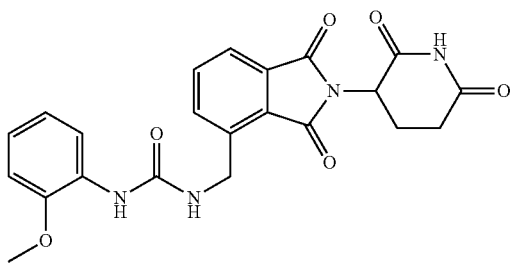 [SMILES: COc1ccccc1NC(=O)NCc1cccc2c1C(=O)N(C1CCC(=O)NC1=O)C2=O]

2-Methoxyphenyl isocyanate (0.4 g, 2.6 mmol) was added to a stirred suspension of 4-aminomethyl-2-(2,6-dioxo-piperidin-3-yl)-isoindole-1,3-dione hydrochloride (0.7 g, 2.0 mmol) and triethylamine (0.3 g, 2.8 mmol) in THF (30 mL) at 5-10° C. After stirring for 10 minutes at 5° C., the mixture was warmed to room temperature and stirred overnight. The mixture was concentrated, and the residue was stirred with 1N HCl (30 mL) for 30 minutes. The solid was collected and slurried with hot methanol (15 mL) to give 1-[2-(2,6-dioxo-piperidin-3-yl)-1,3-dioxo-2,3-dihydro-1H-isoindol-4-ylmethyl]-3-(2-methoxy-phenyl)-urea (0.7 g, 80%) as a white solid: mp 214-216° C.; $^1$H NMR (DMSO-d$^6$) δ 2.05-2.10 (m, 1H), 2.50-2.65 (m, 2H), 2.84-2.97 (m, 1H), 3.83 (s, 3H, OCH$_3$), 4.73 (d, J=5.7 Hz, 2H, CH$_2$), 5.13-5.20 (dd, J=5.3 and 12.5 Hz, 1H, CH), 6.79-6.98 (m, 3H, Ar), 7.49 (t, H=5.7 Hz, 1H, NH), 7.77-7.89 (m, 3H, Ar), 8.04-8.08 (dd, J=1.4 and 7.3 Hz, 1H, Ar), 8.19 (s, 1H, NH), 11.15 (s, 1H, NH); $^{13}$C NMR (DMSO-d$_6$) δ 21.99, 30.93, 48.86, 55.64, 110.59, 118.07, 120.42, 121.22, 121.88, 127.16, 129.20, 131.61, 133.65, 134.77, 140.112, 147.40, 155.24, 167.00, 167.50, 169.83, 172.76; Anal. calcd. for C$_{22}$H$_{20}$N$_4$O$_6$+0.66H$_2$O: C, 58.94; H, 4.79; N, 12.50. Found: C, 59.24; H, 4.86; N, 12.74.

5.94 1-(3,4-METHYLENEDIOXYPHENYL)-3-[2-(2,6-DIOXOPIPERIDIN-3-YL)-1,3-DIOXO-2,3-DIHYDRO-1H-ISOINDOL-4-YLMETHYL]UREA

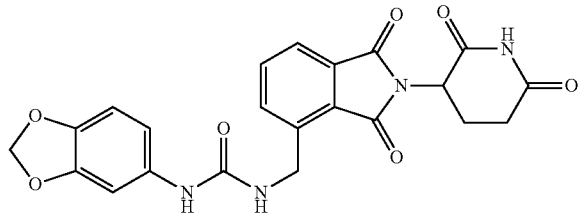 [SMILES: O=C1CCC(N2C(=O)c3cccc(CNC(=O)Nc4ccc5c(c4)OCO5)c3C2=O)C(=O)N1]

A mixture of 4-aminomethyl-2-(2,6-dioxopiperidin-3-yl) isoindole-1,3-dione hydrochloride (0.50 g, 1.6 mmol), 3,4-methylenedioxyphenyl isocyanate (0.25 g, 1.6 mmol), and diisopropylethylamine (0.40 g, 3.1 mmol) in 10 mL pyridine was warmed to 40° C. with stirring under N$_2$, and the resulting solution was stirred at the same temperature for 2 hours. The mixture was cooled, and the solvent was evaporated under vacuum. The residue was chromatographed, eluting with 95:5 methylene chloride-methanol, to provide 0.56 g of the product in 81% yield: mp 216-218° C.; $^1$H NMR (DMSO-d$_6$) δ 2.05-2.09 (m, 1H), 2.50-2.58 (m, 2H), 2.84-2.91 (m, 1H), 4.69 (d, J=5.8 Hz, 2H), 5.16 (dd, J=12.4 Hz, d=5.1 Hz, 1H), 5.93 (s, 2H), 6.67-6.70 (m, 2H), 6.77 (d, J=8.4 Hz, 1H), 7.16 (d, J=1.6 Hz, 1H), 7.75-7.88 (m, 3H), 8.67 (s, 1H), 11.15 (s, 1H); $^{13}$C NMR (DMSO-d$_6$) δ 22.0, 30.9, 38.7, 48.9, 100.5, 100.6, 108.0, 110.4, 121.8, 127.2, 131.6, 133.6, 134.7, 134.8, 140.3, 141.5, 147.1, 155.3, 167.0, 167.6, 169.8, 172.8; Anal. calcd. for C$_{22}$H$_{18}$N$_4$O$_5$: C, 58.67; H, 4.03; N, 12.44. Found: C, 58.35; H, 3.95; N, 12.25.

5.95 1-(3-CHLORO-4-METHYLPHENYL)-3-[2-(2,6-DIOXOPIPERIDIN-3-YL)-1,3-DIOXO-2,3-DIHYDRO-1H-ISOINDOL-4-YLMETHYL]UREA

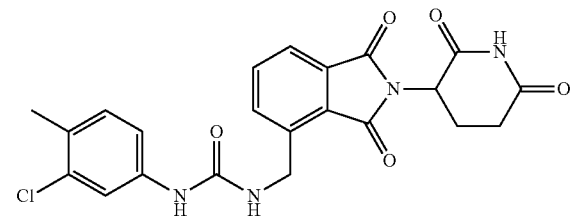 [SMILES: Cc1ccc(NC(=O)NCc2cccc3c2C(=O)N(C2CCC(=O)NC2=O)C3=O)cc1Cl]

A mixture of 4-aminomethyl-2-(2,6-dioxopiperidin-3-yl) isoindole-1,3-dione hydrochloride (0.50 g, 1.6 mmol), 3-chloro-4-methylphenyl isocyanate (0.26 g, 1.6 mmol), and diisopropylethylamine (0.40 g, 3.1 mmol) in 10 mL pyridine was warmed to 40° C. with stirring under N$_2$, and the resulting solution was stirred at the same temperature for 2 hours. The mixture was cooled, and the solvent was evaporated under vacuum. The residue was chromatographed, eluting with 95:5 methylene chloride-methanol, to provide 0.63 g of the product in 90% yield: mp 238-240° C.; $^1$H NMR (DMSO-d$_6$) δ 2.05-2.10 (m, 1H), 2.22 (s, 3H), 2.49-2.65 (m, 2H), 2.84-2.97 (m, 1H), 4.70 (d, J=6.0 Hz, 2H), 5.17 (dd, J=12.5 Hz, d=5.3 Hz, 1H), 6.81 (t, J=6.0 Hz, 1H), 7.10 (dd, J=8.3 Hz, J=2.0 Hz, 1H), 7.18 (d, J=8.3 Hz, 1H), 7.65 (d, J=2.0 Hz, 1H), 7.75-7.85 (m, 3H), 8.90 (s, 1H), 11.15 (s, 1H); $^{13}$C NMR (DMSO-d$_6$) δ 18.7, 22.0, 30.9, 38.7, 48.9, 116.4, 117.6, 121.9, 127.2, 127.5, 131.0, 131.6, 133.0, 133.7, 134.7, 139.5, 140.1, 155.1, 167.0, 167.6, 169.8, 172.8; Anal. calcd. for $C_{22}H_{19}ClN_4O_5 \cdot 0.25H_2O$: C, 57.52; H, 4.27; N, 12.19. Found: C, 57.80; H, 4.33; N, 11.83.

5.96 1-(3,4-DICHLOROPHENYL)-3-[2-(2,6-DIOXOPIPERIDIN-3-YL)-1,3-DIOXO-2,3-DIHYDRO-1H-ISOINDOL-4-YLMETHYL]UREA

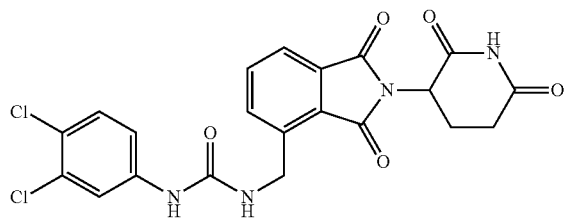 [SMILES: O=C1CCC(N2C(=O)c3cccc(CNC(=O)Nc4ccc(Cl)c(Cl)c4)c3C2=O)C(=O)N1]

A mixture of 4-aminomethyl-2-(2,6-dioxopiperidin-3-yl) isoindole-1,3-dione hydrochloride (0.50 g, 1.6 mmol), 3,4-dichlorophenyl isocyanate (0.29 g, 1.6 mmol), and diisopropylethylamine (0.40 g, 3.1 mmol) in 10 mL pyridine was warmed to 40° C. with stirring under $N_2$, and the resulting solution was stirred at the same temperature for 2 hours. The mixture was cooled, and the solvent was evaporated under vacuum. The residue was chromatographed using a methylene chloride-methanol gradient, eluting with 97:3 methylene chloride-methanol, to provide 0.60 g of the product in 82% yield: mp 241-243° C.; $^1$H NMR (DMSO-$d_6$) δ 2.05-2.10 (m, 1H), 2.54-2.64 (m, 2H), 2.84-2.97 (m, 1H), 4.71 (d, J=6.0 Hz, 2H), 5.17 (dd, J=12.5 Hz, d=5.4 Hz, 1H), 6.92 (t, J=6.0 Hz, 1H), 7.25 (dd, J=8.8 Hz, J=2.5 Hz, 1H), 7.45 (d, J=8.8 Hz, 1H), 7.75-7.88 (m, 4H), 9.15 (s, 1H), 11.15 (s, 1H); $^{13}$C NMR (DMSO-$d_6$) δ 22.0, 30.9, 38.8, 48.9, 117.8, 118.8, 121.9, 122.4, 127.2, 130.4, 130.9, 131.6, 133.7, 134.8, 139.9, 140.5, 154.9, 167.0, 167.6, 169.8, 172.8; Anal. calcd. for $C_{21}H_{16}Cl_2N_4O_5 \cdot 0.25H_2O$: C, 52.57; H, 3.47; N, 11.68. Found: C, 52.78; H, 3.41; N, 11.37.

5.97 1-[2-(2,6-DIOXOPIPERIDIN-3-YL)-1,3-DIOXO-2,3-DIHYDRO-1H-ISOINDOL-4-YLMETHYL]-3-NAPHTHALEN-1-YL-UREA

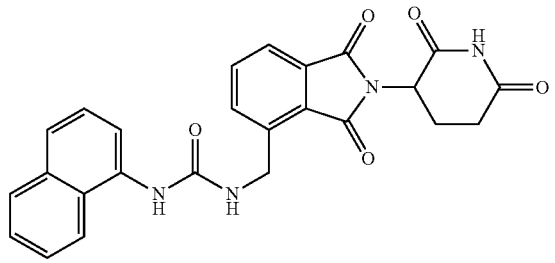 [SMILES: O=C1CCC(N2C(=O)c3cccc(CNC(=O)Nc4cccc5ccccc45)c3C2=O)C(=O)N1]

A mixture of 4-aminomethyl-2-(2,6-dioxopiperidin-3-yl) isoindole-1,3-dione hydrochloride (0.50 g, 1.6 mmol), 1-naphthyl isocyanate (0.26 g, 1.6 mmol), and diisopropylethylamine (0.40 g, 3.1 mmol) in 10 mL pyridine was warmed to 40° C. with stirring under $N_2$, and the resulting solution was stirred at the same temperature for 2 hours. The mixture was cooled, and the solvent was evaporated under vacuum. The residue was chromatographed, eluting with 95:5 methylene chloride-methanol, to provide 0.40 g of the product in 60% yield: mp 250-252° C.; $^1$H NMR (DMSO-$d_6$) δ 2.06-2.11 (m, 1H), 2.51-2.65 (m, 2H), 2.85-2.97 (m, 1H), 4.78 (d, J=6.0 Hz, 2H), 5.18 (dd, J=12.6 Hz, d=5.4 Hz, 1H), 7.23 (t, J=6.0, 1H), 7.41 (t, J=7.9 Hz, 1H), 7.49-7.58 (m, 3H), 7.80-7.91 (m, 4H), 7.98 (d, J=7.3, 1H), 8.12 (d, J=7.6 Hz, 1H), 8.81 (s, 1H), 11.20 (s, 1H); $^{13}$C NMR (DMSO-$d_6$) δ 22.0, 31.0, 38.9, 48.9, 116.8, 121.4, 121.9, 122.3, 125.4, 125.7, 125.8, 125.9, 127.3, 128.3, 131.7, 133.7, 133.8, 134.8, 134.9, 140.2, 155.7, 167.0, 167.6, 169.8, 172.8; Anal. calcd. for $C_{25}H_{20}N_4O_5 \cdot 0.25H_2O$: C, 65.14; H, 4.48; N, 12.15. Found: C, 65.08; H, 4.48; N, 11.96.

5.98 1-[2-(2,6-DIOXOPIPERIDIN-3-YL)-1,3-DIOXO-2,3-DIHYDRO-1H-ISOINDOL-4-YLMETHYL]-3-NAPHTHALEN-2-YL-UREA

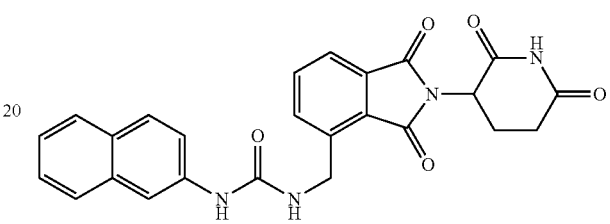

A mixture of 4-aminomethyl-2-(2,6-dioxopiperidin-3-yl) isoindole-1,3-dione hydrochloride (0.50 g, 1.6 mmol), 2-naphthyl isocyanate (0.26 g, 1.6 mmol), and diisopropylethylamine (0.40 g, 3.1 mmol) in 10 mL pyridine was warmed to 40° C. with stirring under $N_2$, and the resulting solution was stirred at the same temperature for 2 hours. The mixture was cooled, and the solvent was evaporated under vacuum. The residue was chromatographed, eluting with 96:4 methylene chloride-methanol, to provide 0.46 g of the product in 70% yield: mp 201-203° C.; $^1$H NMR (DMSO-$d_6$) δ 2.07-2.11 (m, 1H), 2.54-2.66 (m, 2H), 2.85-2.91 (m, 1H), 4.75 (d, J=6.0 Hz, 2H), 5.18 (dd, J=12.6 Hz, d=5.4 Hz, 1H), 6.88 (t, J=6.0 Hz, 1H), 7.28-7.34 (m, 1H), 7.38-7.45 (m, 2H), 7.70-7.88 (m, 6H), 8.05 (d, J=1.6 Hz, 1H), 9.05 (s, 1H), 11.20 (s, 1H); $^{13}$C NMR (DMSO-$d_6$) δ 22.0, 31.0, 38.8, 48.9, 112.7, 119.4, 121.9, 123.6, 126.2, 126.8, 127.2, 127.4, 128.3, 128.8, 131.7, 133.8, 134.8, 137.9, 140.2, 155.3, 167.0, 167.6, 169.8, 172.8; Anal. calcd. for $C_{25}H_{20}N_4O_5 \cdot 0.5H_2O$: C, 64.51; H, 4.54; N, 12.03. Found: C, 64.87; H, 4.88; N, 11.59.

5.99 1-(3,4-DIMETHYL-PHENYL)-3-[2-(2,6-DIOXO-PIPERIDIN-3-YL)-1,3-DIOXO-2,3-DIHYDRO-1H-ISOINDOL-4-YLMETHYL]-UREA

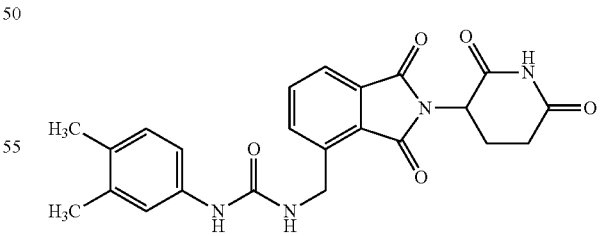

3,4-Dimethylphenyl isocyanate (0.4 g, 3.0 mmol) was added to a stirred suspension of 4-aminomethyl-2-(2,6-dioxo-piperidin-3-yl)-isoindole-1,3-dione hydrochloride (0.8 g, 2.3 mmol) and triethylamine (0.3 g, 3.2 mmol) in THF (40 mL) at 5° C. After stirring for 10 minutes at 5° C., the mixture was warmed to room temperature and stirred overnight. The mixture was concentrated, and the residue was stirred with 1N HCl (30 mL) for 30 minutes. The solid was collected and slurried with acetone (20 mL) to give 1-(3,4-dimethyl-phenyl)-3-[2-(2,6-dioxo-piperidin-3-yl)-1,3-dioxo-2,3-dihydro-1H-isoindol-4-ylmethyl]-urea (0.8 g, 82%) as a white solid: mp 222-224° C.; $^1$H NMR (DMSO-$d_6$) δ 2.05-2.08 (m, 1H), 2.12 (s, 3H), 2.14 (s, 3H), 2.50-2.65 (m, 2H), 2.84-2.97 (m, 1H), 4.70 (d, J=5.8 Hz, 2H), 5.13-5.20 (dd, J=5.3 and 12.6 Hz, 1H), 6.69 (t, J=5.9 Hz, 1H), 6.97 (d, J=8.2 Hz, 1H), 7.08 (d, J=8.2 Hz, 1H), 7.17 (s, 1H), 7.75-7.88 (m, 3H), 8.57 (s, 1H), 11.14 (s, 1H); $^{13}$C NMR (DMSO-$d_6$) δ 18.60, 19.61, 21.99, 30.94, 38.72, 48.86, 115.33, 119.13, 121.84, 127.18, 128.75, 129.51, 131.60, 133.68, 134.71, 136.11, 137.96, 140.40, 155.29, 167.03, 167.61, 169.84, 172.78; Anal. calcd. for $C_{23}H_{22}N_4O_5$: C, 63.59; H, 5.10; N, 12.90. Found: C, 63.21; H, 5.09; N, 12.74.

5.100 1-[2-(2,6-DIOXO-PIPERIDIN-3-YL)-1,3-DIOXO-2,3-DIHYDRO-1H-ISOINDOL-4-YLMETHYL]-3-M-TOLYL-UREA

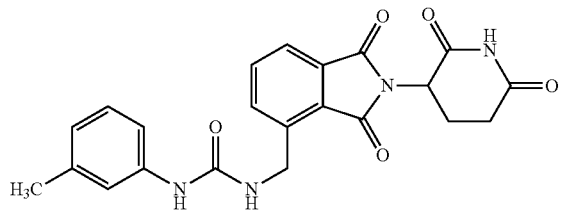 [SMILES: Cc1cccc(NC(=O)NCc2cccc3c2C(=O)N(C2CCC(=O)NC2=O)C3=O)c1]

m-Tolyl isocyanate (0.4 g, 3.0 mmol) was added to a stirred suspension of 4-aminomethyl-2-(2,6-dioxo-piperidin-3-yl)-isoindole-1,3-dione hydrochloride (0.8 g, 2.3 mmol) and triethylamine (0.3 g, 3.2 mmol) in THF (40 mL) at 5° C. After stirring for 10 minutes at 5° C., the mixture was warmed to room temperature and stirred overnight. The mixture was concentrated, and the residue was stirred with 1N HCl (30 mL) for 30 minutes. The solid was collected and slurried with ether (20 mL) to give 1-[2-(2,6-dioxo-piperidin-3-yl)-1,3-dioxo-2,3-dihydro-1H-isoindol-4-ylmethyl]-3-m-tolyl-urea (0.7 g, 76%) as a white solid: mp>260° C.; $^1$H NMR (DMSO-$d_6$) δ 2.05-2.10 (m, 1H), 2.23 (s, 3H), 2.50-2.65 (m, 2H), 2.84-2.97 (m, 1H), 4.71 (d, J=6.0 Hz, 2H), 5.13-5.20 (dd, J=5.4 and 12.6 Hz, 1H), 6.70-6.77 (m, 2H), 7.05-7.17 (m, 2H), 7.25 (s, 1H), 7.75-7.88 (m, 3H), 8.70 (s, 1H), 11.16 (s, 1H); $^{13}$C NMR (DMSO-$d_6$) δ 21.19, 21.99, 30.93, 38.71, 48.86, 114.90, 118.25, 121.85, 121.95, 127.18, 128.46, 131.60, 133.66, 134.71, 137.73, 140.18, 140.30, 155.22, 167.01, 167.59, 169.82, 172.76; Anal. calcd. for $C_{22}H_{20}N_4O_5$+0.5$H_2O$: C, 61.53; H, 4.93; N, 13.05. Found: C, 61.87; H, 4.72; N, 12.92.

5.101 1-[2-(2,6-DIOXO-PIPERIDIN-3-YL)-1,3-DIOXO-2,3-DIHYDRO-1H-ISOINDOL-4-YLMETHYL]-3-PYRIDIN-2-YL-UREA

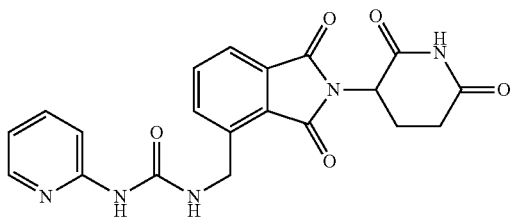 [SMILES: O=C1CCC(N2C(=O)c3cccc(CNC(=O)Nc4ccccn4)c3C2=O)C(=O)N1]

Step 1:

A solution of 2-aminopyridine (2.0 g, 21.3 mmol) in acetonitrile (20 mL) was added to a stirred suspension of N,N-disuccinimidyl carbonate (5.4 g, 21.3 mmol) in acetonitrile (150 mL). The mixture was stirred at room temperature overnight. The mixture was concentrated, and the residue was dissolved in methylene chloride (120 mL). The methylene chloride solution was washed with sat. NaHCO$_3$ (40 mL), water (2×40 mL), brine (40 mL) and dried (MgSO$_4$). Solvent was removed, and the residue was slurried with ether (30 mL) to give pyridin-2-yl-carbamic acid 2,5-dioxo-pyrrolidin-1-yl ester (2.5 g).

Step 2: 1,8-Diazabicyclo[5.4.0]undec-7-ene (0.4 g, 2.4 mmol) was added to a stirred suspension of 4-aminomethyl-2-(2,6-dioxo-piperidin-3-yl)-isoindole-1,3-dione hydrochloride (0.7 g, 2.0 mmol) in acetonitrile (50 mL). After stirring for 30 minutes, pyridin-2-yl-carbamic acid 2,5-dioxo-pyrrolidin-1-yl ester (0.7 g, 3.0 mmol) was added, and the mixture was stirred at room temperature overnight. The solid was collected and slurried with hot acetone (20 mL) to give 1-[2-(2,6-dioxo-piperidin-3-yl)-1,3-dioxo-2,3-dihydro-1H-isoindol-4-ylmethyl]-3-pyridin-2-yl-urea (0.5 g, 64%) as a white solid: mp>260° C.; $^1$H NMR (DMSO-$d_6$) δ 2.05-2.09 (m, 1H), 2.49-2.65 (m, 2H), 2.84-2.79 (m, 1H), 4.83 (d, J=6.1 Hz, 2H), 5.14-5.21 (dd, J=5.5 and 12.7 Hz, 1H), 6.91-6.96 (m, 1H), 7.33 (d, J=8.5 Hz, 1H), 7.64-7.88 (m, 4H), 8.17-8.20 (dd, J=1.3 and 5.0 Hz, 1H), 8.90 (t, J=5.7 Hz, 1H), 9.44 (s, 1H), 11.16 (s, 1H); $^{13}$C NMR (DMSO-$d_6$) δ 21.96, 30.92, 38.67, 48.85, 93.31, 111.57, 116.91, 121.90, 127.20, 131.67, 133.43, 134.80, 138.23, 139.82, 146.69, 153.27, 154.93, 166.97, 167.49, 169.81, 172.75; Anal. calcd. for $C_{20}H_{17}N_5O_5$: C, 58.97; H, 4.21; N, 17.19. Found: C, 58.69; H, 4.10; N, 17.05.

5.102 1-[2-(2,6-DIOXO-PIPERIDIN-3-YL)-1,3-DIOXO-2,3-DIHYDRO-1H-ISOINDOL-4-YLMETHYL]-3-P-TOLYL-UREA

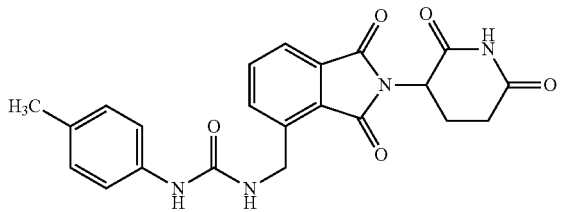 [SMILES: Cc1ccc(NC(=O)NCc2cccc3c2C(=O)N(C2CCC(=O)NC2=O)C3=O)cc1]

p-Tolyl isocyanate (0.4 g, 3.0 mmol) was added to a stirred suspension of 4-aminomethyl-2-(2,6-dioxo-piperidin-3-yl)-isoindole-1,3-dione hydrochloride (0.8 g, 2.3 mmol) and triethylamine (0.3 g, 3.2 mmol) in THF (40 mL) at 5° C. After stirring for 10 minutes at 5° C., the mixture was warmed to room temperature and stirred overnight. The mixture was concentrated, and the residue was stirred with 1N HCl (30 mL) for 30 minutes. The solid was collected and slurried with hot ethanol (20 mL) to give 1-[2-(2,6-didoxo-piperidin-3-yl)-1,3-dioxo-2,3-dihydro-1H-isoindol-4-ylmethyl]-3-p-tolyl-urea (0.8 g, 78%) as a white solid: mp 227-229° C.; $^1$H NMR (DMSO-$d_6$) δ 2.05-2.09 (m, 1H), 2.20 (s, 3H), 2.49-2.65 (m, 2H), 2.84-2.98 (m, 1H), 4.70 (d, J=6.0 Hz, 2H), 5.13-5.20 (dd, J=5.4 and 12.6 Hz, 1H), 6.71 (t, J=6.0 Hz, 1H), 7.03 (d, J=8.3 Hz, 2H), 7.25 (d, J=8.4 Hz, 2H), 7.75-7.88 (m, 3H), 8.66 (s, 1H), 11.15 (s, 1H); $^{13}$C NMR (DMSO-$d_6$) δ 20.26, 21.98, 30.93, 38.72, 48.85, 117.82, 121.83, 127.17, 129.01, 129.92, 131.60, 133.65, 134.70, 137.71, 140.34, 155.28, 167.02, 167.60, 169.83, 172.76; Anal. calcd. for $C_{22}H_{20}N_4O_5$: C, 62.85; H, 4.79; N, 13.33. Found: C, 62.61; H, 4.63; N, 13.26.

5.103 1-[2-(2,6-DIOXO-PIPERIDIN-3-YL)-1,3-DIOXO-2,3-DIHYDRO-1H-ISOINDOL-4-YLM-ETHYL]-3-O-TOLYL-UREA

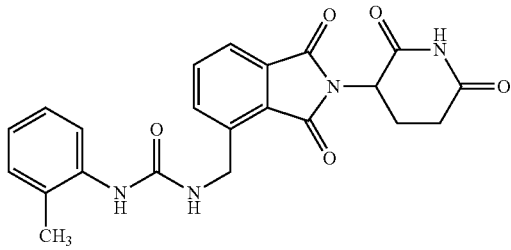 [SMILES: Cc1ccccc1NC(=O)NCc1cccc2c1C(=O)N(C1CCC(=O)NC1=O)C2=O]

o-Tolyl isocyanate (0.4 g, 3.0 mmol) was added to a stirred suspension of 4-aminomethyl-2-(2,6-dioxo-piperidin-3-yl)-isoindole-1,3-dione hydrochloride (0.8 g, 2.3 mmol) and triethylamine (0.3 g, 3.2 mmol) in THF (40 mL) at 5° C. After stirring for 10 minutes at 5° C., the mixture was warmed to room temperature and stirred overnight. The mixture was concentrated, and the residue was stirred with 1N HCl (30 mL) for 30 minutes. The solid was collected and slurried with hot acetone (15 mL) to give 1-[2-(2,6-dioxo-piperidin-3-yl)-1,3-dioxo-2,3-dihydro-1H-isoindol-4-ylmethyl]-3-o-tolyl-urea (0.7 g, 72%) as a white solid: mp>260° C.; $^1$H NMR (DMSO-d$_6$) δ 2.05-2.09 (m, 1H), 2.19 (s, 3H), 2.49-2.65 (m, 2H), 2.84-2.98 (m, 1H), 4.73 (d, J=5.9 Hz, 2H), 5.13-5.20 (dd, J=5.4 and 12.7 Hz, 1H), 6.85-7.19 (m, 4H), 7.77-7.92 (m, 5H), 11.15 (s, 1H); $^{13}$C NMR (DMSO-d$_6$) δ 13.90, 17.99, 26.93, 34.68, 44.86, 116.73, 117.88, 118.14, 122.03, 123.05, 123.18, 126.06, 127.61, 129.69, 130.75, 133.93, '36.25, 151.47, 163.00, 163.56, 165.83, 168.76; Anal. calcd. for $C_{22}H_{20}N_4O_5$: C, 62.85; H, 4.79; N, 13.33. Found: C, 62.76; H, 4.75; N, 13.12.

5.104 [2-(2,6-DIOXO-PIPERIDIN-3-YL)-1,3-DIOXO-2,3-DIHYDRO-1H-ISOINDOL-4-YLM-ETHYL]-UREA

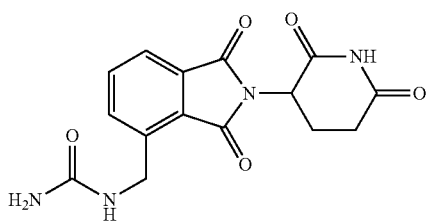 [SMILES: NC(=O)NCc1cccc2c1C(=O)N(C1CCC(=O)NC1=O)C2=O]

Step 1:
Potassium cyanate (1.9 g, 22.93 mmol) was added portionwise over 2 hours to a stirred solution of 3-aminomethyl-phthalic acid dimethyl ester hydrochloride (2.0 g, 7.7 mmol) in water (60 mL). After stirred for another 2 hours, the mixture was acidified to pH 4. The mixture was filtered to give 3-ureidomethyl-phthalic acid dimethyl ester (1.4 g, 70%): $^1$H NMR (DMSO-d$_6$) δ 3.82 (s, 6H), 4.19 d, J=6.0 Hz, 2H), 5.63 (s, 2H), 6.38 (t, J=5.8 Hz, 1H), 7.54-7.62 (m, 2H), 7.78-7.81 (dd, J=2.2 and 6.4 Hz, 1H).
Step 2:
A solution of sodium hydroxide (0.4 g, 10.5 mmol) in water (10 mL) was added to a stirred suspension of 3-ureidomethyl-phthalic acid dimethyl ester (1.4 g, 5.3 mmol) in ethanol (30 mL). The mixture was refluxed for one hour and then cooled to room temperature. The mixture was concentrated, and the residue was dissolved in water (30 mL). The mixture was acidified with 4N HCl to pH 1. The mixture was filtered to give 3-ureidomethyl-phthalic acid (1.0 g, 76%): $^1$H NMR (DMSO-d$_6$) δ 4.22 (d, J=5.9 Hz, 2H, CH$_2$), 5.68 (s, 2H, NH$_2$), 6.40 (t, J=6.0 Hz, 1H, NH), 7.46-7.56 (m, 2H, Ar), 7.73 (d, J=6.9 Hz, 1H, Ar), 13.23 (b, 2H).
Step 3:
A mixture of 3-ureidomethyl-phthalic acid (1.5 g, 6.1 mmol) and α-amino-glutarimide hydrochloride (1.0 g, 6.1 mmol) in pyridine (15 mL) was refluxed for 5 hours. The mixture was concentrated and the residue was stirred with water (20 mL). The solid was slurried with hot methanol to give [2-(2,6-dioxo-piperidin-3-yl)-1,3-dioxo-2,3-dihydro-1H-isoindol-4-ylmethyl]-urea (0.7 g, 36%): mp 292-294° C.; $^1$H NMR (DMSO-d$_6$) δ 2.04-2.08 (m, 1H), 2.50-2.63 (m, 2H), 2.83-2.98 (m, 1H), 4.61 (d, J=6.1 Hz, 2H, CH$_2$), 5.11-5.18 (m, dd, J=5.3 and 12.5 Hz, 1H, CH), 5.71 (s, 2H, NH$_2$), 6.57 (t, J=6.0 Hz, 1H, NH), 7.70-7.87 (m, 3H, Ar), 11.15 (s, 1H, NH); $^{13}$C NMR (DMSO-d$_6$) δ 21.98, 30.92, 38.66, 48.82, 121.63, 126.95, 131.50, 133.32, 134.61, 141.06, 158.65, 167.04, 167.57, 169.82, 172.76; Anal. calcd. for $C_{15}H_{14}N_4O_5$: C, 54.44; H, 4.27; N, 16.96. Found: C, 54.47; H, 4.17; N, 16.76.

5.105 3-[2-(2,6-DIOXO-PIPERIDIN-3-YL)-1,3-DIOXO-2,3-DIHYDRO-1H-ISOINDOL-4-YLM-ETHYL]-1,1-DIMETHYL-UREA

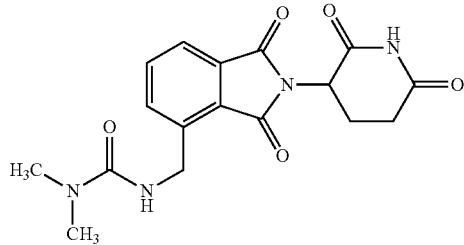 [SMILES: CN(C)C(=O)NCc1cccc2c1C(=O)N(C1CCC(=O)NC1=O)C2=O]

1,8-Diazabicyclo[5,4,0]undec-7-ene (1.0 g, 6.8 mmol) was added to a stirred suspension of 4-aminomethyl-2-(2,6-dioxo-piperidin-3-yl)-isoindole-1,3-dione hydrochloride (1.0 g, 3.1 mmol) in acetonitrile (50 mL). The mixture was stirred for 30 minutes, then added slowly to a stirred solution of triphosgen (0.3 g, 1.1 mmol) in acetonitrile (20 mL) over 20 minutes. After stirring for another 10 minutes, a solution of dimethylamine/THF (2.0 M, 1.6 mL, 3.1 mmol) and diidopropylethylamine (0.5 g, 3.7 mmol) was added in one portion. The mixture was stirred at room temperature overnight. The mixture was concentrated, and the residue was dissolved in methylene chloride (80 mL). The methylene chloride solution was washed with 1N HCl (40 mL), water (40 mL), and brine (40 mL), and dried (MgSO$_4$). Solvent was removed and purified by chromatography (silica gel) to give 3-[2-(2,6-dioxo-piperidin-3-yl)-1,3-dioxo-2,3-dihydro-1H-isoindol-4-ylmethyl]-1,1-dimethyl-urea (0.4 g, 36%) as a white solid: mp 143-145° C.; $^1$H NMR (DMSO-d$_6$) δ 2.04-2.08 (m, 1H), 2.50-2.63 (m, 2H), 2.84 (s, 6H, 2CH$_3$), 2.84-2.96 (m, m, 1H), 4.68 (d, J=5.6 Hz, 2H, CH$_2$), 5.11-5.18 (dd, J=5.2 and 121.5 Hz, 1H, CH), 6.98 (t, J=5.6 Hz, 1H, NH), 7.69-7.85 (m, 3H, Ar), 11.13 (s, 1H, NH); $^{13}$C NMR (DMSO-d$_6$) δ 21.98, 30.93, 35.88, 39.30, 48.82, 121.45, 126.75, 131.38, 132.92, 134.56, 141.44, 148.14, 167.06, 167.63, 169.84, 172.75; Anal. calcd. for $C_{17}H_{18}N_4O_5$: C, 56.98; H, 5.06; N, 15.63. Found: C, 56.87; H, 5.16; N, 15.16.

5.106 N-[2-(2,6-DIOXO-PIPERIDIN-3-YL)-1,3-DIOXO-2,3-DIHYDRO-1H-ISOINDOL-4-YLMETHYL]-4-METHOXY-BENZAMIDE

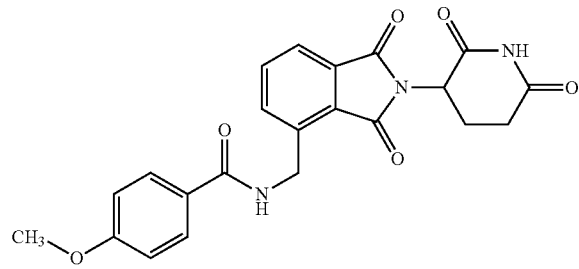 [SMILES: COc1ccc(C(=O)NCc2cccc3c2C(=O)N(C2CCC(=O)NC2=O)C3=O)cc1]

Triethylamine (0.5 g, 5.0 mmol) was added slowly to a stirred suspension of 4-aminomethyl-2-(2,6-dioxo-piperidin-3-yl)-isoindole-1,3-dione hydrochloride (0.7 g, 2.0 mmol) and p-anisoyl chloride (0.5 g, 2.8 mmol) in THF (30 mL) at 5-10° C. After 10 minutes, the mixture was stirred at room temperature overnight. The reaction was quenched with methanol (1 mL), and the mixture was concentrated. The residue was stirred with 1N HCl (30 mL) for 1 hour then filtered. The solid was slurried with hot ethanol (15 mL) to give N-[2-(2,6-dioxo-piperidin-3-yl)-1,3-dioxo-2,3-dihydro-1H-isoindol-4-ylmethyl]-4-methoxy-benzamide (0.6 g, 71%) as a white solid: mp 193-195° C.; $^1$H NMR (DMSO-d$_6$) δ 2.06-2.10 (m, 1H), 2.50-2.65 (m, 2H), 2.84-2.97 (m, 1H), 3.83 (s, 3H, OCH$_3$), 4.93 (d, J=5.7 Hz, 2H, CH$_2$), 5.14-5.21 (dd, J=5.4 and 12.7 Hz, 1H, CH), 7.04 (d, J=8.8 Hz, 2H, Ar), 7.69-7.86 (m, 3H, Ar), 7.89 (d, J=8.7 Hz, 2H, Ar), 9.01 (t, J=5.7 Hz, 1H, NH), 11.15 (s, 1H, NH); $^{13}$C NMR (DMSO-d$_6$) δ 21.99, 30.94, 38.25, 48.87, 55.36, 113.57, 121.80, 126.10, 127.06, 129.15, 131.51, 133.00, 134.77, 139.63, 161.75, 166.08, 166.99, 167.56, 169.85, 172.77; Anal. calcd. for $C_{22}H_{19}N_3O_6+0.34H_2O$: C, 61.81; H, 4.64; N, 9.83. Found: C, 61.77; H, 4.54; N, 9.63.

5.107 N-[2-(2,6-DIOXO-PIPERIDIN-3-YL)-1,3-DIOXO-2,3-DIHYDRO-1H-ISOINDOL-4-YLMETHYL]-3-METHYL-BENZAMIDE

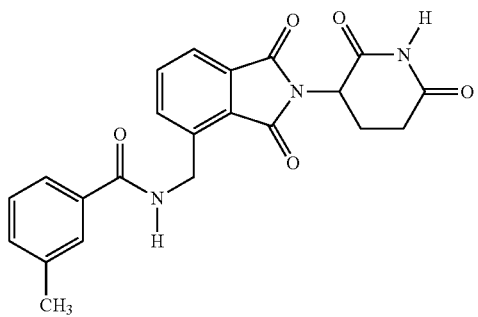 [SMILES: Cc1cccc(C(=O)NCc2cccc3c2C(=O)N(C2CCC(=O)NC2=O)C3=O)c1]

Triethylamine (0.5 g, 5.0 mmol) was added to a stirred suspension of 4-aminomethyl-2-(2,6-dioxo-piperidin-3-yl)-isoindole-1,3-dione hydrochloride (0.7 g, 2.0 mmol) and m-toluoyl chloride (0.4 g, 2.8 mmol) in THF (30 mL) at 5-10° C. After stirring at 5° C. for 10 minutes, the mixture was stirred at room temperature overnight. The mixture was concentrated, and the residue was stirred with 1N HCl (20 mL). The residue was dissolved in CH$_2$Cl$_2$ (80 mL), washed with H$_2$O (30 mL) and brine (30 mL), and dried (MgSO$_4$). Solvent was removed and the residue was purified by chromatography (silica gel) to N-[2-(2,6-dioxo-piperidin-3-yl)-1,3-dioxo-2,3 dihydro-1H-isoindol-4-ylmethyl]-3-methyl-benzamide (0.5 g, 66%) as a white solid: mp 218-220° C.; $^1$H NMR (DMSO-d$_6$) δ 2.06-2.10 (m, 1H), 2.37 (s, 3H, CH$_3$), 2.50-2.65 (m, 2H), 2.84-2.97 (m, 1H), 4.94 (d, J=5.7 Hz, 2H, CH$_2$), 5.14-5.21 (dd, J=5.4 and 12.7 Hz, 1H, CH), 7.37-7.41 (m, 2H, Ar), 7.72-7.86 (m, 5H, Ar), 9.10 (t, J=5.6 Hz, 1H, NH), 11.14 (s, 1H, NH); $^{13}$C NMR (DMSO-d$_6$) δ 20.91, 21.98, 30.93, 38.30, 48.87, 121.82, 124.42, 127.10, 127.83, 128.24, 131.52, 131.98, 132.99, 133.92, 134.77, 137.64, 139.39, 166.71, 166.96, 167.53, 169.81, 172.73; Anal. calcd. for $C_{22}H_{19}N_3O_5+0.04H_2O$: C, 65.06; H, 4.74; N, 10.35. Found: C, 64.75; H, 4.68; N, 10.02.

5.108 3,4-DICHLORO-N-[2-(2,6-DIOXOPIPERIDIN-3-YL)-1,3-DIOXO-2,3-DIHYDRO-1H-ISOINDOL-4-YLMETHYL]BENZAMIDE

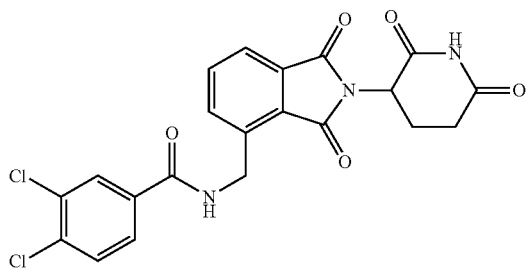 [SMILES: O=C1CCC(N2C(=O)c3cccc(CNC(=O)c4ccc(Cl)c(Cl)c4)c3C2=O)C(=O)N1]

3,4-Dichlorobenzoic acid (0.30 g, 1.6 mmol) was dissolved in 10 mL DMF and CDI (0.30 g, 1.9 mmol) was added. The mixture was stirred at 40° C. for 1 hour, and then 4-aminomethyl-2-(2,6-dioxopiperidin-3-yl)isoindole-1,3-dione hydrochloride (0.50 g, 1.6 mmol) and triethylamine (0.31 g, 3.1 mmol) were added. After an additional 90 minutes stirring at 40° C., the mixture was cooled. The solvent was evaporated, and the residue was dissolved in 60 mL CH$_2$Cl$_2$, and this solution was washed with water (2×60 mL), dried (MgSO$_4$), and evaporated. The residue was chromatographed using a methylene chloride-methanol gradient, eluting 0.49 g of the product with 98:2 methylene chloride-methanol, in 70% yield: mp 161-163° C.; $^1$H NMR (DMSO-d$_6$) δ 2.06-2.09 (m, 1H), 2.51-2.58 (m, 2H), 2.84-2.91 (m, 1H), 4.94 (d, J=5.7 Hz, 2H), 5.17 (dd, J=12.6 Hz, d=5.3 Hz, 1H), 7.74-7.95 (m, 5H), 8.17 (d, J=1.9 Hz, 1H), 9.33 (t, J=5.7 Hz, 1H), 11.10 (s, 1H); $^{13}$C NMR (DMSO-d$_6$) δ 22.0, 30.9, 38.5, 48.9, 122.0, 127.2, 127.7, 129.3, 130.8, 131.3, 131.6, 133.3, 134.3, 134.9, 138.8, 164.4, 167.0, 167.5, 169.8, 172.8; Anal. calcd for $C_{21}H_{15}Cl_2N_3O_5$: C, 54.80; H, 3.28; N, 9.13. Found: C, 54.85; H, 3.36; N, 8.95.

5.109 ISOQUINOLINE-3-CARBOXYLIC ACID [2-(2,6-DIOXOPIPERIDIN-3-YL)-1,3-DIOXO-2,3-DIHYDRO-1H-ISOINDOL-4-YLMETHYL]AMIDE

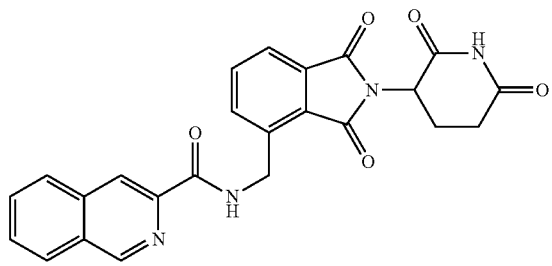 [SMILES: O=C1CCC(N2C(=O)c3cccc(CNC(=O)c4cc5ccccc5cn4)c3C2=O)C(=O)N1]

A mixture of isoquinoline 3-carboxylic acid (0.39 g, 2.0 mmol) and thionyl chloride (10 mL) was heated to reflux for 1 hour. Excess thionyl chloride was removed under vacuum. To the acid chloride, was then added 4-aminomethyl-2-(2,6-dioxopiperidin-3-yl)isoindole-1,3-dione hydrochloride (0.65 g, 2.0 mmol), THF (30 mL) and triethylamine (0.61 g, 6.0 mmol), and the resulting mixture was stirred at reflux for 90 minutes. The solvent was evaporated and the crude residue was chromatographed using a methylene chloride-methanol gradient, eluting 0.67 g of the product with 96:4 methylene chloride-methanol, in 76% yield: mp 198-200° C.; $^1$H NMR (DMSO-$d_6$) δ 2.07-2.11 (m, 1H), 2.53-2.66 (m, 2H), 2.85-2.97 (m, 1H), 5.02 (d, J=6.3 Hz, 2H), 5.19 (dd, J=12.6 Hz, d=5.3 Hz, 1H), 7.71-7.92 (m, 5H), 8.21 (d, J=7.8 Hz, 1H), 8.28 (d, J=7.8 Hz, 1H) 8.59 (s, 1H), 9.43 (s, 1H), 9.65 (t, J=6.3 Hz, 1H), 11.17 (s, 1H); $^{13}$C NMR (DMSO-$d_6$) δ 22.0, 31.0, 38.5, 48.9, 120.0, 121.9, 127.2, 127.8, 128.0, 129.2, 129.3, 131.4, 131.6, 133.0, 134.8, 135.4, 139.2, 143.4, 151.7, 164.7, 167.0, 167.6, 169.9, 172.8; Anal. calcd for $C_{24}H_{18}N_4O_5 \cdot 0.5H_2O$: C, 63.85; H, 4.24; N, 12.41. Found: C, 63.85; H, 3.93; N, 12.31.

5.110 5-BUTYLPYRIDINE-2-CARBOXYLIC ACID [2-(2,6-DIOXO PIPERIDIN-3-YL)-1,3-DIOXO-2,3-DIHYDRO-1H-ISOINDOL-4-YLMETHYL]AMIDE

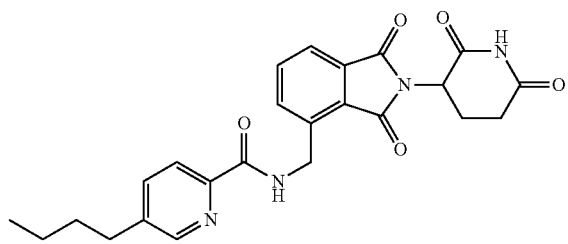 [SMILES: CCCCc1ccc(C(=O)NCc2cccc3c2C(=O)N(C2CCC(=O)NC2=O)C3=O)nc1]

A mixture of fusaric acid (0.36 g, 2.0 mmol) and thionyl chloride (10 mL) was heated to reflux for 1 hour. Excess thionyl chloride was removed under vacuum. To the acid chloride, was then added 4-aminomethyl-2-(2,6-dioxopiperidin-3-yl)isoindole-1,3-dione hydrochloride (0.65 g, 2.0 mmol), THF (30 mL) and triethylamine (0.61 g, 6.0 mmol), and the resulting mixture was stirred at room temperature for 16 hours. The solvent was evaporated, and the crude residue was chromatographed using a methylene chloride-methanol gradient, eluting the product with 95:5 methylene chloride-methanol. This material was further purified by preparative HPLC, eluting with 1:1 acetonitrile-water, providing 0.58 g of the purified product in 64% yield: mp 137-139° C.; $^1$H NMR (DMSO-$d_6$) δ 0.91 (t, J=7.3 Hz, 3H), 1.24-1.39 (m, 2H), 1.54-1.65 (m, 2H), 2.06-2.10 (m, 2H), 2.51-2.72 (m, 4H), 2.84-2.97 (m, 1H), 4.94 (d, J=6.4 Hz, 2H), 5.17 (dd, J=12.6 Hz, d=5.4 Hz, 1H), 7.66-7.71 (m, 1H), 7.77-7.86 (m, 3H), 7.97 (d, J=8.0 Hz, 1H), 8.54 (d, J=1.7 Hz, 1H), 9.43 (t, J=6.4 Hz, 1H), 11.16 (s, 1H); $^{13}$C NMR (DMSO-$d_6$) δ 13.7, 21.6, 22.0, 31.0, 31.7, 32.6, 38.5, 48.9, 121.8, 121.9, 127.2, 131.6, 133.0, 134.8, 137.3, 139.2, 141.2, 147.5, 148.5, 164.5, 167.0, 167.6, 169.9, 172.8; Anal. calcd for $C_{24}H_{24}N_4O_5 \cdot 0.3H_2O$: C, 63.51; H, 5.46; N, 12.34. Found: C, 63.52; H, 5.55; N, 12.05.

5.111 6-BROMOPYRIDINE-2-CARBOXYLIC ACID [2-(2,6-DIOXO PIPERIDIN-3-YL)-1,3-DIOXO-2,3-DIHYDRO-1H-ISOINDOL-4-YLMETHYL]AMIDE

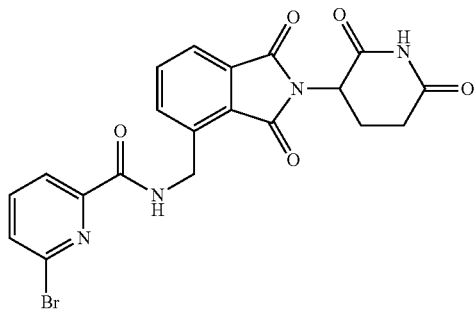 [SMILES: O=C1CCC(N2C(=O)c3cccc(CNC(=O)c4cccc(Br)n4)c3C2=O)C(=O)N1]

A mixture of 6-bromopicolinic acid (0.40 g, 2.0 mmol) and CDI (0.39 g, 2.4 mmol) in DMF (25 mL) was stirred at ambient temperature under nitrogen for 2 hours. 4-Aminomethyl-2-(2,6-dioxopiperidin-3-yl)isoindole-1,3-dione hydrochloride (0.65 g, 2.0 mmol) and triethylamine (0.61 g, 6.0 mmol) were added, and the mixture was allowed to stir for 16 hours. The solvent was evaporated under vacuum, and the residue was chromatographed using a methylene chloride-methanol gradient, eluting the product with 97:3 methylene chloride-methanol. This material was further purified by preparative HPLC, eluting with 1:1 acetonitrile-water, providing 0.50 g of the purified product in 53% yield: mp 181-183° C.; $^1$H NMR (DMSO-$d_6$) δ 2.06-2.10 (m, 1H), 2.52-2.65 (m, 2H), 2.84-2.93 (m, 1H), 4.96 (d, J=6.3 Hz, 2H), 5.17 (dd, J=12.6 Hz, d=5.4 Hz, 1H), 7.67-7.72 (m, 1H), 7.80-7.82 (m, 2H), 7.90 (dd, J=7.8 Hz, J=1.0 Hz, 1H), 7.97 (t, J=7.6 Hz, 1H), 8.07 (dd, J=7.3 Hz, J=1.1 Hz, 1H), 9.39 (t, J=6.3 Hz, 1H), 11.15 (s, 1H); $^{13}$C NMR (DMSO-$d_6$) δ 22.0, 30.9, 38.5, 48.9, 121.7, 121.9, 127.1, 131.2, 131.6, 133.0, 134.8, 138.9, 140.3, 141.0, 151.0, 163.1, 167.0, 167.6, 169.8, 172.8; Anal. calcd for $C_{20}H_{15}BrN_4O_5 \cdot 0.5H_2O$: C, 50.01; H, 3.35; N, 11.66. Found: C, 49.97; H, 3.21; N, 11.56.

5.112 6-METHYLPYRIDINE-2-CARBOXYLIC ACID [2-(2,6-DIOXO PIPERIDIN-3-YL)-1,3-DIOXO-2,3-DIHYDRO-1H-ISOINDOL-4-YLMETHYL]AMIDE

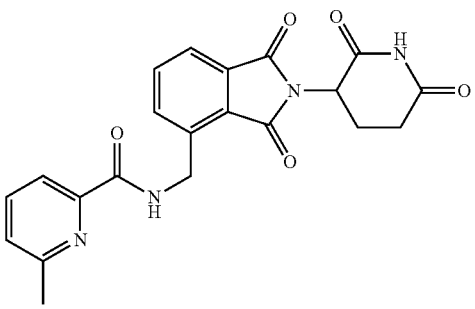 [SMILES: Cc1cccc(C(=O)NCc2cccc3c2C(=O)N(C2CCC(=O)NC2=O)C3=O)n1]

A mixture of 6-methylpicolinic acid (0.27 g, 2.0 mmol) and CDI (0.39 g, 2.4 mmol) in DMF (25 mL) was stirred at ambient temperature under nitrogen for 1 hour. 4-Aminomethyl-2-(2,6-dioxopiperidin-3-yl)isoindole-1,3-dione hydrochloride (0.65 g, 2.0 mmol) and triethylamine (0.61 g, 6.0 mmol) were added, and the mixture was allowed to stir for 16 hours. The solvent was evaporated under vacuum, and the residue was purified by preparative HPLC, eluting with 45:55 acetonitrile-water, providing 0.34 g of the product in 54% yield: mp 197-199° C.; $^1$H NMR (DMSO-d$_6$) δ 2.06-2.11 (m, 1H), 2.53-2.65 (m, 2H), 2.58 (s, 3H), 2.84-2.94 (m, 1H), 4.96 (d, J=6.3 Hz, 2H), 5.18 (dd, J=12.6 Hz, d=5.4 Hz, 1H), 7.49 (dd, J=6.8 Hz, J=1.9 Hz, 1H), 7.69 (dd, J=8.5 Hz, J=4.1 Hz, 1H), 7.79-7.93 (m, 4H), 9.36 (t, J=6.3 Hz, 1H), 11.15 (s, 1H); $^{13}$C NMR (DMSO-d$_6$) δ 22.0, 23.9, 30.9, 38.3, 48.9, 119.2, 121.9, 126.3, 127.2, 131.6, 133.0, 134.8, 137.9, 139.2, 149.0, 157.3, 164.5, 167.0, 167.6, 169.8, 172.8; Anal. calcd for $C_{21}H_{18}N_4O_5 \cdot 0.6H_2O$: C, 60.45; H, 4.63; N, 13.42. Found: C, 60.47; H, 4.53; N, 13.36.

5.113 PYRAZINE-2-CARBOXYLIC ACID [2-(2,6-DIOXOPIPERIDIN-3-YL)-1,3-DIOXO-2,3-DIHYDRO-1H-ISOINDOL-4-YLMETHYL]AMIDE

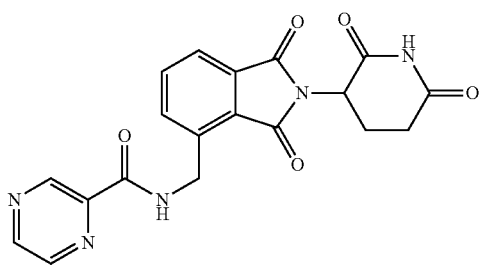 [SMILES: O=C1CCC(N2C(=O)c3cccc(CNC(=O)c4cnccn4)c3C2=O)C(=O)N1]

A mixture of 4-aminomethyl-2-(2,6-dioxopiperidin-3-yl)isoindole-1,3-dione hydrochloride (0.63 g, 1.9 mmol), 2-pyrazinecarbonylchloride (0.25 g, 1.9 mmol) and triethylamine (0.61 g, 6.0 mmol) in THF (30 mL) was stirred at ambient temperature under nitrogen for 18 hours. The mixture was evaporated, and the residue was chromatographed using a methylene chloride-methanol gradient, eluting the product with 95:5 methylene chloride-methanol. This material dissolved in 4 mL acetonitrile, and this solution was poured into 50 mL of water, resulting in precipitation of the product, which was filtered, washed with additional water (20 mL), and dried, providing 0.46 g (61% yield): mp>260° C.; $^1$H NMR (DMSO-d$_6$) δ 2.06-2.10 (m, 1H), 2.54-2.65 (m, 2H), 2.84-2.91 (m, 1H), 4.97 (d, J=6.3 Hz, 2H), 5.18 (dd, J=12.0 Hz, d=5.4 Hz, 1H), 7.69-7.83 (m, 3H), 8.29 (t, J=1.9 Hz, 1H), 8.91 (d, J=2.5 Hz, 1H), 9.21 (d, J=1.4 Hz, 1H), 9.61 (t, J=6.3 Hz, 1H), 11.15 (s, 1H); $^{13}$C NMR (DMSO-d$_6$) δ 22.0, 30.9, 38.3, 48.9, 121.9, 127.2, 131.2, 131.6, 133.0, 134.7, 143.5, 143.6, 144.5, 147.7, 163.4, 167.0, 167.6, 169.8, 172.8; Anal. calcd for $C_{19}H_{15}N_5O_5 \cdot 0.5H_2O$: C, 56.71; H, 4.01; N, 17.41. Found: C, 56.64; H, 3.75; N, 17.28.

5.114 QUINOXALINE-2-CARBOXYLIC ACID [2-(2,6-DIOXOPIPERIDIN-3-YL)-1,3-DIOXO-2,3-DIHYDRO-1H-ISOINDOL-4-YLMETHYL] AMIDE

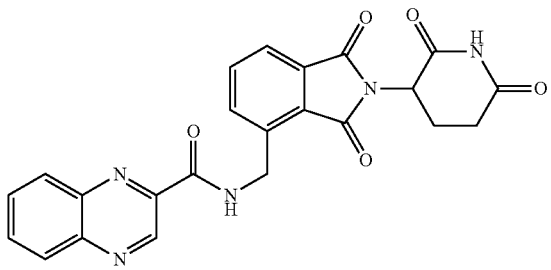 [SMILES: O=C1CCC(N2C(=O)c3cccc(CNC(=O)c4cnc5ccccc5n4)c3C2=O)C(=O)N1]

A mixture of 2-quinoxalinecarboxylic acid (0.35 g, 2.0 mmol) and CDI (0.39 g, 2.4 mmol) in DMF (25 mL) was stirred at ambient temperature under nitrogen for 90 minutes. 4-Aminomethyl-2-(2,6-dioxopiperidin-3-yl)isoindole-1,3-dione hydrochloride (0.65 g, 2.0 mmol) and triethylamine (0.61 g, 6.0 mmol) were added, and the mixture was allowed to stir for 16 hours. The mixture was poured into water, resulting in precipitation of the product, which was filtered, washed with additional water (40 mL) and dried, providing 0.61 g, in 69% yield: mp>260° C.; $^1$H NMR (DMSO-d$_6$) δ 2.07-2.12 (m, 1H), 2.56-2.65 (m, 2H), 2.85-2.98 (m, 1H), 5.05 (d, J=6.3 Hz, 2H), 5.19 (dd, J=12.6 Hz, d=5.4 Hz, 1H), 7.78-7.83 (m, 3H), 7.98-8.04 (m, 2H), 8.19-8.24 (m, 2H), 9.50 (s, 1H), 9.76 (t, J=6.3 Hz, 1H), 11.16 (s, 1H); $^{13}$C NMR (DMSO-d$_6$) δ 22.0, 30.9, 38.4, 48.9, 121.9, 127.2, 129.1, 129.4, 131.3, 131.6, 132.0, 133.1, 134.8, 138.7, 139.8, 143.0, 143.8, 144.1, 163.7, 167.0, 167.6, 169.8, 172.8; Anal. calcd for $C_{23}H_{17}N_5O_5 \cdot 0.5H_2O$: C, 61.06; H, 4.01; N, 15.47. Found: C, 61.19; H, 3.95; N, 15.37.

5.115 PYRIMIDINE-5-CARBOXYLIC ACID [2-(2,6-DIOXOPIPERIDIN-3-YL)-1,3-DIOXO-2,3-DIHYDRO-1H-ISOINDOL-4-YLMETHYL]AMIDE

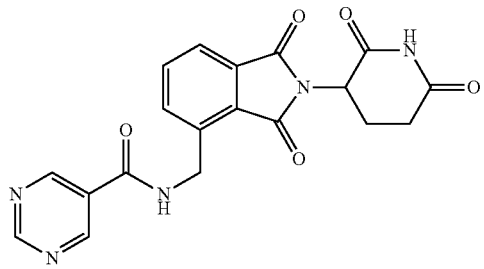 [SMILES: O=C1CCC(N2C(=O)c3cccc(CNC(=O)c4cncnc4)c3C2=O)C(=O)N1]

A mixture of pyrimidine-5-carboxylic acid (0.25 g, 2.0 mmol) and CDI (0.39 g, 2.4 mmol) in DMF (25 mL) was stirred at ambient temperature under nitrogen for 2 hours. 4-Aminomethyl-2-(2,6-dioxopiperidin-3-yl)isoindole-1,3-dione hydrochloride (0.65 g, 2.0 mmol) and triethylamine (0.61 g, 6.0 mmol) were added, and the mixture was allowed to stir for 16 hours. The solvent was evaporated under vacuum, and the residue was chromatographed using a methylene chloride-methanol gradient, eluting with 95:5 methylene chloride-methanol, providing 0.39 g of the product in 50% yield: mp>260° C.; $^1$H NMR (DMSO-$d_6$) δ 2.05-2.10 (m, 1H), 2.53-2.65 (m, 2H), 2.83-2.91 (m, 1H), 4.98 (d, J=5.7 Hz, 2H), 5.18 (dd, J=12.4 Hz, d=5.4 Hz, 3H), 7.84 (s, 3H), 9.24 (s, 2H), 9.35 (s, 1H), 9.52 (t, J=5.7 Hz, 1H), 11.16 (s, 1H); $^{13}$C NMR (DMSO-$d_6$) δ 22.0, 30.9, 38.3, 48.9, 122.1, 127.3, 127.5, 131.6, 133.4, 134.9, 138.4, 156.0, 160.1, 163.5, 167.0, 167.5, 169.8, 172.8; Anal. calcd for $C_{19}H_{15}N_5O_5 \cdot 0.3H_2O$: C, 57.23; H, 3.94; N, 17.56. Found: C, 57.27; H, 3.71; N, 17.27.

5.116 2,5-DICHLORO-N-[2-(2,6-DIOXOPIPERIDIN-3-YL)-1,3-DIOXO-2,3-DIHYDRO-1H-ISOINDOL-4-YLMETHYL]NICOTINAMIDE

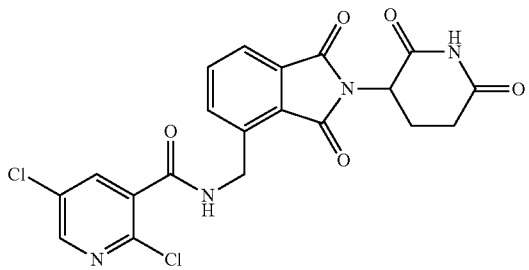 [SMILES: O=C1CCC(N2C(=O)c3cccc(CNC(=O)c4cc(Cl)cnc4Cl)c3C2=O)C(=O)N1]

A mixture of 4-aminomethyl-2-(2,6-dioxopiperidin-3-yl)isoindole-1,3-dione hydrochloride (0.65 g, 2.0 mmol), 2,5-dichloropyridine-3-carbonyl chloride (0.42 g, 2.0 mmol) and triethylamine (0.61 g, 6.0 mmol) in THF (30 mL) was stirred at ambient temperature under nitrogen for 18 hours. The mixture was evaporated, and the residue was chromatographed using a methylene chloride-methanol gradient, eluting with 95:5 methylene chloride-methanol, providing 0.50 g of the product (54% yield): mp>260° C.; $^1$H NMR (DMSO-$d_6$) δ 2.05-2.09 (m, 1H), 2.53-2.58 (m, 2H), 2.83-2.97 (m, 1H), 4.93 (d, J=5.7 Hz, 2H), 5.17 (dd, J=12.5 Hz, d=5.3 Hz, 1H), 7.82-7.91 (m, 3H), 8.28 (d, J=2.5 Hz, 1H), 8.61 (d, J=2.5 Hz, 1H), 9.35 (t, J=5.7 Hz, 1H), 11.15 (s, 1H); $^{13}$C NMR (DMSO-$d_6$) δ 22.0, 30.9, 38.3, 48.9, 122.1, 127.3, 130.3, 131.6, 133.4, 134.9, 137.8, 138.0, 145.0, 148.8, 164.1, 166.9, 167.5, 169.8, 172.8; Anal. calcd for $C_{20}H_{14}Cl_2N_4O_5 \cdot 0.2H_2O$: C, 51.68; H, 3.12; N, 12.05. Found: C, 51.64; H, 3.05; N, 11.98.

5.117 6-(3-ETHOXY-4-METHOXYPHENYL)PYRIDINE-2-CARBOXYLIC ACID [2-(2,6-DIOXOPIPERIDIN-3-YL)-1,3-DIOXO-2,3-DIHYDRO-1H-ISOINDOL-4-YLMETHYL]AMIDE

5.117.1 3-Ethoxy-4-Methoxyphenylboronic Acid

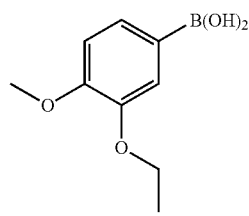

A mixture of 4-Bromo-2-ethoxy-1-methoxybenzene (4.00 g, 17.3 mmol) in THF (75 mL) was cooled to −78° C.; during cooling, a precipitate formed. t-BuLi (22.4 mL, 1.7 M in pentane, 38.1 mmol) was added dropwise, while maintaining the temperature at −78° C. The mixture was stirred at −78° C. for 1 hour following completion of the addition. B(Oi-Pr)$_3$ (9.76 g, 51.9 mmol) was added. The mixture was allowed to gradually warm to room temperature, and then stirred under nitrogen for 16 hours. 3N HCl (20 mL) was added, and the mixture stirred for 10 minutes. The mixture was poured into water (100 mL) and extracted with diethyl ether (3×75 mL), and the combined ethereal layers were washed with water (3×75 mL), dried (MgSO$_4$) and evaporated, providing 3.15 g of the product in 93% yield: $^1$H NMR (DMSO-$d_6$) δ 1.32 (t, J=7.0 Hz, 3H), 3.75 (s, 3H), 3.99 (q, J=7.0 Hz, 2H), 6.90 (d, J=8.3 Hz, 1H), 7.35-7.37 (m, 2H).

5.117.2 3'-Ethoxy-4'-Methoxybiphenyl-3-Carboxylic Acid

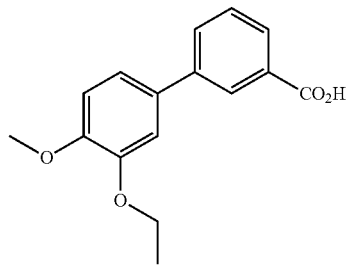 [SMILES: CCOc1cc(-c2cccc(C(=O)O)c2)ccc1OC]

6-Bromonicotinic acid (2.02 g, 10.0 mmol) was dissolved in DME (80 mL) under nitrogen. Pd(PPh$_3$)$_4$ (0.58 g, 0.5 mmol) was added, and the resulting mixture was stirred at ambient temperature for 15 minutes. 3-ethoxy-4-methoxyphenylboronic acid (2.4 g, 12.2 mmol) and 2N Na$_2$CO$_3$ (40 mL, 80 mmol) were added, and the resulting mixture was heated to reflux with stirring for 24 hours. The mixture was poured into 300 mL of water and extracted with ethyl acetate (3×200 mL), and the product precipitated upon standing, providing 2.05 g of the product in 76% yield: $^1$H NMR (CDCl$_3$) δ 1.53 (t, J=7.0 Hz, 3H), 3.96 (s, 3H), 4.22 (q, J=7.0 Hz, 2H), 7.00 (d, J=8.6 Hz, 1H), 7.53-7.58 (m, 2H), 7.91-8.02 (m, 2H), 8.12 (dd, J=6.9 Hz, J=1.5 Hz, 1H).

5.117.3 6-(3-Ethoxy-4-Methoxyphenyl)Pyridine-2-Carboxylic Acid [2-(2,6-Dioxopiperidin-3-yl)-1,3-Dioxo-2,3-Dihydro-1H-Isoindol-4-yl-Methyl]Amide

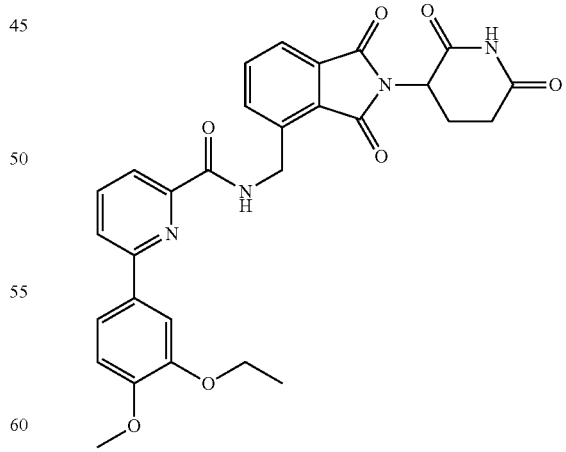

A mixture of 3'-ethoxy-4'-methoxybiphenyl-3-carboxylic acid (0.55 g, 2.0 mmol) and CDI (0.39 g, 2.4 mmol) in DMF (30 mL) was stirred at ambient temperature under nitrogen for 90 minutes. 4-aminomethyl-2-(2,6-dioxopiperidin-3-yl)isoindole-1,3-dione hydrochloride (0.65 g, 2.0 mmol) and triethylamine (0.61 g, 6.0 mmol) were added, and the mixture was allowed to stir for 3 hours. The mixture was poured into water (200 mL) and extracted with ethyl acetate (3×100 mL). The combined organic phases were washed with water (3×150 mL), dried (MgSO$_4$), and evaporated, providing 0.75 g of the product as a pale yellow solid (69% yield): mp 196-198° C.; $^1$H NMR (DMSO-d$_6$) δ 1.36 (t, J=6.9 Hz, 3H), 2.05-2.10 (m, 1H), 2.54-2.64 (m, 2H), 2.85-2.98 (m, 1H), 3.83 (s, 3H), 4.18 (q, J=6.3 Hz, 2H), 5.02 (d, J=6.3 Hz, 2H), 5.20 (dd, J=12.7 Hz, d=5.4 Hz, 1H), 7.06 (d, J=8.5 Hz, 1H), 7.74-7.83 (m, 4H), 7.87-7.94 (m, 2H), 8.03 (t, J=7.8 Hz, 1H), 8.16 (d, J=7.7 Hz, 1H), 9.56 (t, J=6.3 Hz, 1H), 11.18 (s, 1H); $^{13}$C NMR (DMSO-d$_6$) δ 14.8, 22.0, 31.0, 38.6, 49.0, 55.5, 64.0, 111.8, 119.8, 120.0, 122.0, 122.4, 127.3, 130.1, 131.7, 133.3, 134.9, 138.6, 139.1, 148.2, 149.2, 150.5, 155.1, 164.5, 167.0, 167.8, 169.8, 172.7; Anal. calcd for $C_{29}H_{26}N_4O_7 \cdot 0.5H_2O$: C, 63.15; H, 4.93; N, 10.16. Found: C, 63.36; H, 4.80; N, 10.19.

5.118 1H-INDOLE-2-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

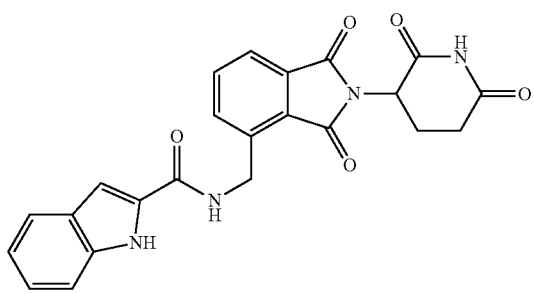 [SMILES: O=C1CCC(N2C(=O)c3cccc(CNC(=O)c4cc5ccccc5[nH]4)c3C2=O)C(=O)N1]

1,8-Diazabicyclo[5.4.0]undec-7-ene (0.8 g, 5.0 mmol) was added to a stirred suspension of 4-aminomethyl-2-(2,6-dioxo-piperidin-3-yl)-isoindole-1,3-dione hydrochloride (0.7 g, 2.0 mmol) in DMF (30 mL). After stirring for 10 minutes, 1-hydroxybenzenetriazole (0.3 g, 2.4 mmol) and indole-2-carboxylic acid (0.4 g, 2.2 mmol) were added. The reaction was initiated by adding 1-(3-dimethylaminopropyl)-3-ethylcarbodiimide hydrochloride (0.6 g, 3.0 mmol) and stirred at room temperature overnight. The mixture was poured into cold water (120 mL) and extracted with EtOAc (3×50 mL). The combined EtOAc solution was washed with water (3×40 mL) and brine (40 mL), and dried (MgSO$_4$). Solvent was removed, and the solid residue was slurried with hot acetone (20 mL) to give 1H-indole-2-carboxylic acid [2-(2,6-dioxo-piperidin-3-yl)-1,3-dioxo-2,3-dihydro-1H-isoindol-4-ylmethyl]-amide (0.6 g, 70%) as a white solid: mp>260° C.; $^1$H NMR (DMSO-d$_6$) δ 2.08-2.11 (m, 1H), 2.56-2.65 (m, 2H), 2.85-2.98 (m, 1H), 4.99 (d, J=5.5 Hz, 2H), 5.15-5.22 (dd, J=5.4 and 12.7 Hz, 1H), 7.05 (t, J=7.5 Hz, 1H), 7.16-7.22 (m, 3H), 7.42 (d, J=8.1 Hz, 1H), 7.62 (d, J=7.9 Hz, 1H), 7.75-7.83 (m, 3H), 9.15 (t, J=5.4 Hz, 1H), 11.15 (s, 1H), 11.64 (s, 1H); $^{13}$C NMR (DMSO-d$_6$) δ 22.00, 30.34, 37.92, 48.89, 102.95, 112.31, 119.78, 121.54, 121.92, 123.45, 127.04, 127.14, 131.18, 131.57, 133.06, 134.33, 136.54, 139.29, 161.52, 166.97, 167.55, 169.83, 172.75; Anal. calcd. for $C_{23}H_{18}N_4O_5 + 0.24H_2O$: C, 63.54; H, 4.28; N, 12.89. Found: C, 63.39; H, 4.38; N, 12.80.

5.119 1,5-DIMETHYL-1H-PYRAZOLE-3-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

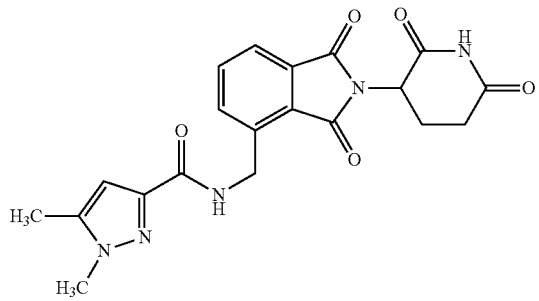 [SMILES: Cc1cc(C(=O)NCc2cccc3c2C(=O)N(C2CCC(=O)NC2=O)C3=O)nn1C]

1,8-Diazabicyclo[5.4.0]undec-7-ene (1.0 g, 6.6 mmol) was added to a stirred suspension of 4-aminomethyl-2-(2,6-dioxo-piperidin-3-yl)-isoindole-1,3-dione hydrochloride (0.7 g, 2.0 mmol) in acetonitrile (40 mL). After stirring for 10 minutes, 1,5-dimethyl-1H-pyrazole-3-carbonyl chloride (0.4 g, 2.6 mmol) was added. The mixture was stirred at room temperature overnight. The mixture was concentrated, and the residue was dissolved in CH$_2$Cl$_2$ (80 mL). The CH$_2$Cl$_2$ solution was washed with water (2×30 mL) and brine (30 mL), and dried (MgSO$_4$). Solvent was removed, and the residue was purified by chromatography (SiO$_2$, CH$_2$Cl$_2$:CH$_3$OH 97.5:2.5) to give 1,5-dimethyl-1H-pyrazole-3-carboxylic acid [2-(2,6-dioxo-piperidin-3-yl)-1,3-dioxo-2,3-dihydro-1H-isoindol-4-ylmethyl]-amide (0.3 g, 38%) as a white solid: mp 213-215° C.; $^1$H NMR (DMSO-d$_6$) δ 2.05-2.09 (m, 1H), 2.28 (s, 3H), 2.50-2.64 (m, 2H), 2.84-2.97 (m, 1H), 3.79 (s, 3H), 4.86 (d, J=5.9 Hz, 2H), 5.13-5.20 (dd, J=5.1 and 12.4 Hz, 1H), 6.44 (s, 1H), 7.65-7.79 (m, 3H), 8.69 (t, J=5.9 Hz, 1H), 11.15 (s, 1H); $^{13}$C NMR (DMSO-d$_6$) δ 10.66, 21.97, 30.93, 36.39, 37.80, 48.86, 105.53, 121.71, 127.01, 131.51, 132.78, 134.70, 139.60, 140.35, 144.26, 161.91, 167.00, 167.56, 169.83, 172.75; Anal. calcd. for $C_{20}H_{19}N_5O_5 + 0.4H_2O$: C, 57.66; H, 4.79; N, 16.81. Found: C, 57.85; H, 4.80; N, 16.64.

5.120 5-METHYL-ISOXAZOLE-3-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

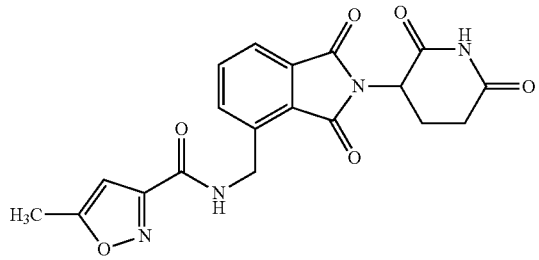 [SMILES: Cc1cc(C(=O)NCc2cccc3c2C(=O)N(C2CCC(=O)NC2=O)C3=O)no1]

1,8-Diazabicyclo[5.4.0]undec-7-ene (1.0 g, 6.6 mmol) was added to a stirred suspension of 4-aminlmethyl-2-(2,6-dioxo-piperidin-3-yl)-isoindole-1,3-dione hydrochloride (0.7 g, 2.0 mmol) in acetonitrile (40 mL). After stirring for 10 minutes, 5-methylisoxazole-3-carbonyl chloride (0.4 g, 2.6 mmol) was added. The mixture was stirred at room temperature overnight. The mixture was concentrated, and the residue was dissolved in $CH_2Cl_2$ (80 mL). The $CH_2Cl_2$ solution was washed with water (2×40 mL) and brine (40 mL), and dried ($MgSO_4$). Solvent was removed, and the residue was purified by chromatography ($SiO_2$, $CH_2Cl_2$: $CH_3OH$ 97.5:2.5) to give 5-methyl-isoxazole-3-carboxylic acid [2-(2,6-dioxo-piperidin-3-yl)-1,3-dioxo-2,3-dihydro-1H-isoindol-4-ylmethyl]-amide (0.4 g, 44%) as a light brown solid: mp 207-209° C.; $^1$H NMR (DMSO-$d_6$) δ 2.05-2.09 (m, 1H), 2.48 (s, 3H), 2.50-2.64 (m, 2H), 2.84-2.98 (m, 1H), 4.91 (d, J=6.0 Hz, 2H), 5.13-5.20 (dd, J=5.4 and 12.6 Hz, 1H), 6.58 (s, 1H), 7.69-7.87 (m, 3H), 9.35 (t, J=6.0 Hz, 1H), 11.15 (s, 1H); $^{13}$C NMR (DMSO-$d_6$) δ 11.82, 21.97, 30.92, 38.00, 48.88, 101.35, 121.99, 127.18, 131.55, 132.87, 134.84, 138.39, 158.61, 159.15, 166.93, 167.47, 169.81, 171.36, 172.84; Anal. calcd. for $C_{19}H_{16}N_4O_6$+0.2$H_2O$: C, 57.03; H, 4.14; N, 14.00. Found: C, 57.34; H, 3.99; N, 13.70.

5.121 1-METHYL-1H-PYRROLE-2-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

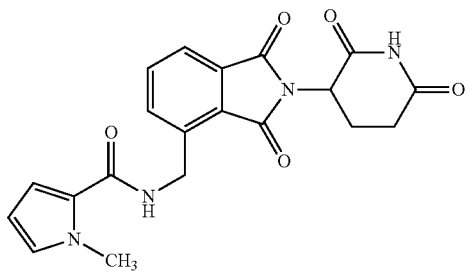 [SMILES: Cn1cccc1C(=O)NCc1cccc2c1C(=O)N(C1CCC(=O)NC1=O)C2=O]

A mixture of 1-methyl-1H-pyrrole-2-carboxylic acid (0.3 g, 2.6 mmol) and carbonyl diimidazole (0.5 g, 3.0 mmol) in DMF (30 mL) was stirred for 2 hours. Triethylamine (0.8 g, 6.0 mmol) was added, followed by 4-aminomethyl-2-(2,6-dioxo-piperidin-3-yl)-isoindole-1,3-dione hydrochloride (0.7 g, 2.0 mmol). The mixture was stirred at 75° C. (oil bath) overnight. The mixture was cooled to room temperature and concentrated. The residue was stirred with EtOAc (80 mL) and water (30 mL). The EtOAc solution was washed with water (2×40 mL) and brine (40 mL), and dried ($MgSO_4$). Solvent was removed, and the residue was purified by chromatography ($SiO_2$, $CH_2Cl_2$: $CH_3OH$ 97.5:2.5) to give 1-methyl-1H-pyrrole-2-carboxylic acid [2-(2,6-dioxo-piperidin-3-yl)-1,3-dioxo-2,3-dihydro-1H-isoindol-4-ylmethyl]-amide (0.2 g, 25%) as a white solid: mp>260° C.; $^1$H NMR (DMSO-$d_6$) δ 2.06-2.10 (m, 1H), 2.50-2.65 (m, 2H), 2.84-2.97 (m, 1H), 3.83 (s, 3H), 4.86 (d, J=5.8 Hz, 2H), 5.13-5.20 (dd, J=5.5 and 12.7 Hz, 1H), 6.04 (t, J=3.4 Hz, 1H), 6.88-6.93 (m, 2H), 7.70-7.86 (m, 3H), 8.63 (t, J=5.8 Hz, 1H), 11.13 (s, 1H); $^{13}$C NMR (DMSO-$d_6$) δ 21.98, 30.93, 36.19, 37.47, 48.86, 106.75, 112.63, 121.73, 124.98, 126.95, 128.07, 131.49, 132.96, 134.76, 140.06, 161.56, 166.98, 167.58, 169.82, 172.74; Anal. calcd. for $C_{20}H_{18}N_4O_5$+0.18$H_2O$+0.1 ether: C, 60.49; H, 4.82; N, 13.83. Found: C, 60.54; H, 4.74; N, 13.50.

5.122 3-METHYL-3H-IMIDAZOLE-4-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

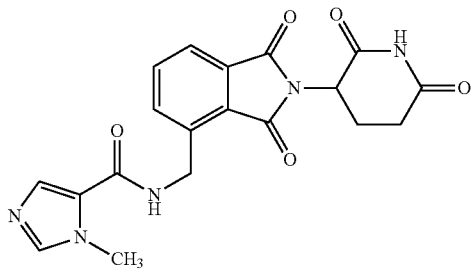 [SMILES: Cn1cncc1C(=O)NCc1cccc2c1C(=O)N(C1CCC(=O)NC1=O)C2=O]

A mixture of 1-methyl-1H-imidazole-5-carboxylic acid (0.3 g, 2.6 mmol) and carbonyl diimidazole (0.5 g, 3.0 mmol) in DMF (30 mL) was stirred at room temperature for 3 hours. Triethylamine (0.8 g, 6.0 mmol) was added, followed by 4-aminomethyl-2-(2,6-dioxo-piperidin-3-yl)-isoindole-1,3-dione hydrochloride (0.7 g, 2.0 mmol). The mixture was stirred at 75° C. (oil bath) for 3 hours. The mixture was cooled to room temperature and concentrated. The residue was dissolved in EtOAc (100 mL) and washed with water (2×40 mL) and brine (40 mL), and dried ($MgSO_4$). Solvent was removed, and the residue was purified by chromatography ($SiO_2$, $CH_2Cl_2$: $CH_3OH$ 97.5:2.5) to give 3-methyl-3H-imidazole-4-carboxylic acid [2-(2,6-dioxo-piperidin-3-yl)-1,3-dioxo-2,3-dihydro-1H-isoindol-4-ylmethyl]-amide (0.2 g, 28%) as a white solid: mp>260° C.; $^1$H NMR (DMSO-$d_6$) δ 2.05-2.09 (m, 1H), 2.50-2.64 (m, 2H), 2.84-2.97 (m, 1H), 3.81 (s, 3H), 4.89 (d, J=5.6 Hz, 2H), 5.13-5.20 (dd, J=5.2 and 12.5 Hz, 1H), 7.68-7.84 (m, 5H), 8.94 (t, J=5.5 Hz, 1H), 11.15 (s, 1H); $^{13}$C NMR (DMSO-$d_6$) δ 21.98, 30.93, 33.51, 37.44, 48.88, 121.88, 125.45, 127.05, 131.52, 132.29, 133.09, 134.83, 139.42, 142.08, 160.25, 166.94, 167.53, 169.82, 172.74; Anal. calcd. for $C_{19}H_{17}N_5O_5$+0.13$H_2O$+0.1$Et_2O$: C, 57.52; H, 4.54; N, 17.29. Found: C, 57.23; H, 4.27; N, 16.95.

5.123 N-[2-(2,6-DIOXO-PIPERIDIN-3-YL)-1,3-DIOXO-2,3-DIHYDRO-1H-ISOINDOL-4-YLMETHYL]-4-TRIFLUOROMETHYL-BENZAMIDE

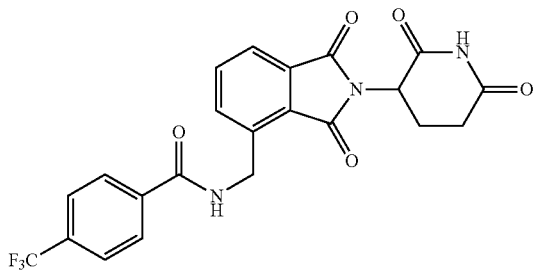 [SMILES: O=C1CCC(N2C(=O)c3cccc(CNC(=O)c4ccc(C(F)(F)F)cc4)c3C2=O)C(=O)N1]

A mixture of 4-Aminomethyl-2-(2,6-dioxo-piperidin-3-yl)-isoindole-1,3-dione hydrochloride (0.97 g, 3.0 mmol), 4-(trifluoromethyl)-benzoyl chloride (0.63 g, 3.0 mmol) and triethylamine (0.61 g, 6.00 mmol) in acetonitrile (20 mL) was stirred at room temperature for 13 hours. The reaction mixture was concentrated and the residue was purified by ISCO silica gel flash chromatography using a methanol-$CH_2Cl_2$ gradient, eluting the product at 5:95 methanol-$CH_2Cl_2$. The resulting solid was stirred in ether for 5 hours, filtered and dried to give the 0.66 g of the product as a white solid, in 48% yield: mp 238-240° C.; HPLC, Waters Symmetry C-18, 3.9× 150 mm, 5 µm, 1 mL/min, 240 nm, 50/50 $CH_3CN$/0.1% $H_3PO_4$, 3.90 (99.09%); $^1$H NMR (DMSO-$d_6$) δ 2.07-2.12 (m, 1H), 2.54-2.65 (m, 2H), 2.86-2.98 (m, 1H), 4.97 (d, J=5.7 Hz, 2H), 5.18 (dd, J=12.6 Hz, J=5.4 Hz, 1H), 7.74-7.91 (m, 5H), 8.13 (d, J=8.1 Hz, 2H), 9.39 (t, J=5.7 Hz, 1H), 11.16 (s, 1H); $^{13}$C NMR (DMSO-$d_6$) δ 22.0, 31.0, 38.5, 48.9, 122.0, 123.9 (q, J=270.8 Hz), 125.5 (q, J=3.75 Hz), 127.2, 128.3, 131.4 (q, J=31.5 Hz), 131.6, 133.2, 134.9, 137.7, 138.9, 165.5, 167.0, 167.5, 169.9, 172.8; Anal. Calcd for $C_{22}H_{16}N_3O_5F_3$: C, 57.52; H, 3.51; N, 9.15. Found: C, 57.35; H, 3.23; N, 8.97.

5.124 5-PHENYL-[1,3,4]OXADIAZOLE-2-CARBOXYLIC ACID [2-(2,6-DIOXO-PIPERIDIN-3-YL)-1,3-DIOXO-2,3-DIHYDRO-1H-ISOINDOL-4-YLMETHYLAMIDE

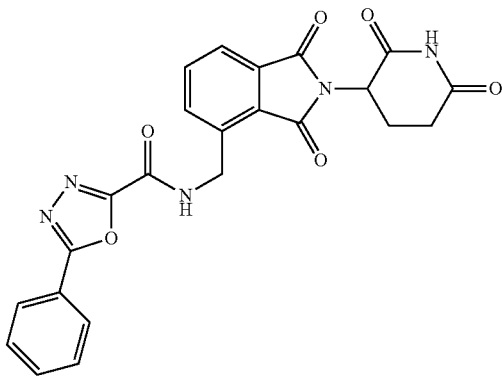 [SMILES: O=C1CCC(N2C(=O)c3cccc(CNC(=O)c4nnc(-c5ccccc5)o4)c3C2=O)C(=O)N1]

To a stirred suspension of 4-aminomethyl-2-(2,6-dioxo-piperidin-3-yl)-isoindole-1,3-dione hydrochloride (1.55 g, 4.8 mmol) in $CH_3CN$ (15 ml), was added triethyl amine (1.67 mL, 11.98 mmol) and 5-phenyl-1,3,4-oxadiazole-2-carbonyl-chloride (1.0 g, 4.8 mmol). The mixture was stirred at room temperature for 21 hours and a suspension was obtained. The reaction mixture was filtered, and the solid was rinsed with $CH_3CN$ (20 mL), water (2×20 mL), EtOAc (20 mL) and MeOH (20 mL) to afford 5-phenyl-[1,3,4]oxadiazole-2-carboxylic acid [2-(2,6-dioxo-piperidin-3-yl)-1,3-dioxo-2,3-dihydro-1H-isoindol-4-ylmethylamide as a white solid (1.34 g, 61%): mp, 279-281° C.; HPLC: Waters Symmetry C-18, 3.9×150 mm, 5 micro, 1 mL/min, 240 nm, 40/60 ($CH_3CN$/$H_2O$): $t_R$=4.90 min. (99%); $^1$H NMR (DMSO-$d_6$): δ 2.08-2.10 (m, 1H), 2.53-2.64 (m, 2H), 2.86-2.98 (m, 1H), 4.98 (d, J=5 Hz, 1H), 5.18 (dd, J=5, 13 Hz, 1H), 7.62-7.72 (m, 3H), 7.85 (broad, 3H), 8.09-8.12 (m, 2H). 9.97 (t, J=5 Hz, 1H), 11.15 (s, 1H). $^{13}$C NMR (DMSO-$d_6$) δ: 21.90, 30.85, 38.24, 48.82, 122.07, 122.70, 126.98, 127.16, 129.46, 131.49, 132.58, 133.03, 134.77, 137.63, 153.51, 158.29, 164.94, 166.84, 167.42, 169.74, 172.67. Anal Calcd for $C_{23}H_{17}N_5O_6$: C, 60.13; H, 3.73; N, 15.24. Found: C, 56.69; H, 3.34; N, 15.41.

5.125 N-[2-(2,6-DIOXO-PIPERIDIN-3-YL)-1,3-DIOXO-2,3-DIHYDRO-1H-ISOINDOL-4-YLMETHYL]-3-TRIFLUOROMETHYL-BENZAMIDE

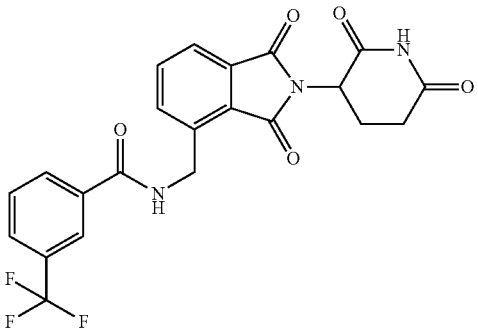 [SMILES: O=C1CCC(N2C(=O)c3cccc(CNC(=O)c4cccc(C(F)(F)F)c4)c3C2=O)C(=O)N1]

To a stirred suspension of 4-aminomethyl-2-(2,6-dioxo-piperidin-3-yl)-isoindole-1,3-dione hydrochloride (0.7 g, 2.16 mmol) in $CH_2Cl_2$ (80 ml), was added diisopropylethylamine (0.94 mL, 5.4 mmol) and 3-trifluoromethylbenzoyl chloride (0.42 mL, 2.8 mmol). The mixture was stirred at room temperature overnight and a suspension was obtained. The reaction mixture was filtered, and the solid was rinsed with $CH_2Cl_2$ (15 mL) and acetone (15 mL). The solid was then recrystallized with MeOH to afford N-[2-(2,6-dioxo-piperidin-3-yl)-1,3-dioxo-2,3-dihydro-1H-isoindol-4-ylmethyl]-3-trifluoromethyl-benzamide as a white solid (0.5 g, 54%): mp, 241-243° C.; HPLC: Waters Symmetry C-18, 3.9×150 mm, 5 micro, 1 mL/min, 240 nm, 40/60 ($CH_3CN$/$H_2O$): $t_R$=4.4 min. (99%); $^1$H NMR (DMSO-$d_6$): δ 2.06-2.11 (m, 1H), 2.53-2.65 (m, 2H), 2.85-2.93 (m, 1H), 4.96 (d, J=5.8 Hz, 2H), 5.15-5.21 (dd, J=5, 12 Hz, 1H), 7.46-7.84 (m, 6H), 9.33 (t, J=6 Hz, 1H), 11.15 (s, 1H). $^{13}$C NMR (DMSO-$d_6$) δ: 21.96, 30.92, 38.49, 48.86, 106.93, 110.58, 110.69, 110.82, 110.93, 121.99, 127.21, 131.54, 133.20, 134.83, 137.42, 138.62, 160.51, 160.67, 163.78, 163.95, 164.10, 166.92, 167.48, 169.81, 172.73. Anal Calcd for $C_{21}H_{15}FN_3O_5$: C, 59.02; H, 3.54; N, 9.83; F, 8.89. Found: C, 58.90; H, 3.15; N, 9.73; F, 9.08.

5.126 N-[2-(2,6-DIOXO-PIPERIDIN-3-YL)-1,3-DIOXO-2,3-DIHYDRO-1H-ISOINDOL-4-YLMETHYL]-3,4-DIFLUORO-BENZAMIDE

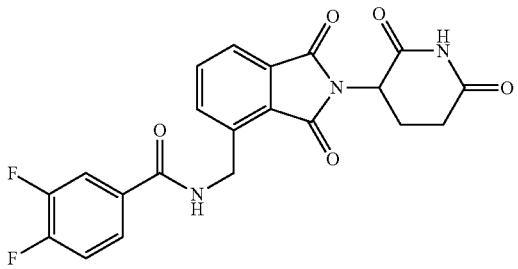 [SMILES: O=C1CCC(N2C(=O)c3cccc(CNC(=O)c4ccc(F)c(F)c4)c3C2=O)C(=O)N1]

To a stirred suspension of 4-aminomethyl-2-(2,6-dioxo-piperidin-3-yl)-isoindole-1,3-dione hydrochloride (0.7 g, 2.16 mmol) in $CH_2Cl_2$ (60 ml), was added diisopropylethylamine (0.94 mL, 5.4 mmol) and 3,4-difluorobenzoyl chloride (0.5 g, 2.8 mmol). The mixture was stirred at room

5.127 N-[2-(2,6-DIOXO-PIPERIDIN-3-YL)-1,3-DIOXO-2,3-DIHYDRO-1H-ISOINDOL-4-YLMETHYL]-3-FLUORO-BENZAMIDE

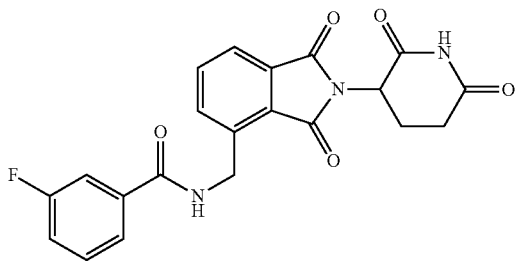 [SMILES: O=C1CCC(N2C(=O)c3cccc(CNC(=O)c4cccc(F)c4)c3C2=O)C(=O)N1]

To a stirred suspension of 4-aminomethyl-2-(2,6-dioxo-piperidin-3-yl)-isoindole-1,3-dione hydrochloride (0.7 g, 2.16 mmol) in $CH_2Cl_2$ (60 ml), was added diisopropylethylamine (0.94 mL, 5.4 mmol) and 3-fluorobenzoyl chloride (0.45 g, 2.8 mmol). The mixture was stirred at room temperature overnight and a suspension was obtained. The reaction mixture was quenched with MeOH (1 mL) and concentrated in vacuo. The resulting oil was purified by ISCO silica gel flash chromatography (eluent: 3% MeOH in $CH_2Cl_2$ for 10 min, then 5% MeOH in $CH_2Cl_2$ for 10 min) to afford N-[2-(2,6-dioxo-piperidin-3-yl)-1,3-dioxo-2,3-dihydro-1H-isoindol-4-ylmethyl]-3-fluoro-benzamide as a white solid (0.7 g, 77%): mp, 215-217° C.; HPLC: Waters Symmetry C-18, 3.9×150 mm, 5 micro, 1 mL/min, 240 nm, 40/60 ($CH_3CN/H_2O$): $t_R$=3.2 min. (99%); $^1H$ NMR (DMSO-$d_6$): δ 2.07-2.12 (m, 1H), 2.54-2.65 (m, 2H), 2.87-2.93 (m, 1H), 4.96 (d, J=5.8 Hz, 2H), 5.15-5.21 (dd, J=5, 12 Hz, 1H), 7.39-7.84 (m, 7H), 9.26 (t, J=6 Hz, 1H), 11.15 (s, 1H). $^{13}C$ NMR (DMSO-$d_6$) δ: 21.97, 30.92, 38.40, 48.86, 114.29, 118.49, 121.92, 123.50, 127.15, 130.62, 131.52, 133.09, 134.82, 136.31, 138.97, 163.69, 165.31, 166.94, 167.51, 169.83, 172.74. Anal Calcd for $C_{21}H_{16}FN_3O_5$: C, 61.61; H, 3.94; N, 10.26; F, 4.64. Found: C, 61.36; H, 3.84; N, 10.00; F, 4.74.

5.128 N-[2-(2,6-DIOXO-PIPERIDIN-3-YL)-1,3-DIOXO-2,3-DIHYDRO-1H-ISOINDOL-4-YLMETHYL]-4-METHYL-BENZAMIDE

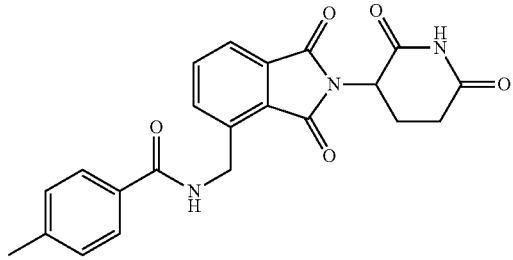 [SMILES: Cc1ccc(C(=O)NCc2cccc3c2C(=O)N(C2CCC(=O)NC2=O)C3=O)cc1]

To a stirred suspension of 4-aminomethyl-2-(2,6-dioxo-piperidin-3-yl)-isoindole-1,3-dione hydrochloride (0.7 g, 2.16 mmol) in $CH_2Cl_2$ (60 ml), was added diisopropylethylamine (0.94 mL, 5.4 mmol) and p-toluoyl chloride (0.43 g, 2.8 mmol). The mixture was then stirred at room temperature overnight and a suspension was obtained. The reaction mixture was quenched with MeOH (1 mL) and washed with $H_2O$ (40 mL), 1N HCl (40 mL) and brine (40 mL). The organic layer was dried over $MgSO_4$ and concentrated in vacuo. The resulting mixture was purified by ISCO silica gel flash chromatography (eluent: 3% MeOH in $CH_2Cl_2$) to afford N-[2-(2,6-dioxo-piperidin-3-yl)-1,3-dioxo-2,3-dihydro-1H-isoindol-4-ylmethyl]-4-methyl-benzamide as a white solid (0.5 g, 61%): mp, 218-220° C.; HPLC: Waters Symmetry C-18, 3.9×150 mm, 5 micro, 1 mL/min, 240 nm, 40/60 ($CH_3CN/H_2O$): $t_R$=3.3 (97%); $^1H$ NMR (DMSO-$d_6$): δ 2.06-2.11 (m, 1H), 2.36 (s, 3H), 2.54-2.64 (m, 2H), 2.85-2.93 (m, 1H), 4.94 (d, J=5.7 Hz, 2H), 5.15-5.21 (dd, J=5, 12 Hz, 1H), 7.31 (d, J=8.0 Hz, 2H), 9.07 (t, J=6 Hz, 1H), 11.15 (s, 1H). $^{13}C$ NMR (DMSO-$d_6$) δ: 20.93, 31.97, 30.92, 38.26, 48.85, 121.81, 127.08, 127.30, 128.87, 131.11, 131.51, 132.98, 134.77, 139.47, 141.35, 166.47, 166.97, 167.54, 169.83, 172.74. Anal Calcd for $C_{22}H_{19}N_3O_5$: C, 65.18; H, 4.72; N, 10.36. Found: C, 64.78; H, 4.72; N, 10.07.

5.129 3,5-DICHLORO-N-[2-(2,6-DIOXO-PIPERIDIN-3-YL)-1,3-DIOXO-2,3-DIHYDRO-1H-ISOINDOL-4-YLMETHYL]-BENZAMIDE

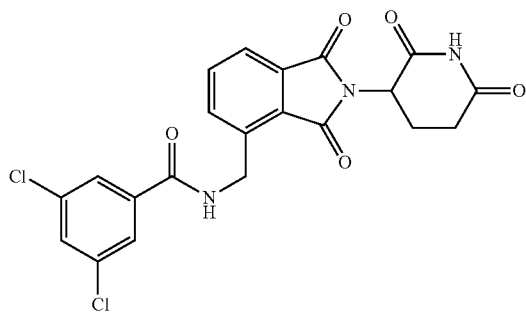 [SMILES: O=C1CCC(N2C(=O)c3cccc(CNC(=O)c4cc(Cl)cc(Cl)c4)c3C2=O)C(=O)N1]

To a stirred suspension of 4-aminomethyl-2-(2,6-dioxo-piperidin-3-yl)-isoindole-1,3-dione hydrochloride (0.7 g, 2.16 mmol) in $CH_2Cl_2$ (60 ml), was added diisopropylethylamine (0.94 mL, 5.4 mmol) and 3,5-difluorobenzoyl chloride (0.59 g, 2.8 mmol). This mixture was stirred at room temperature overnight and a suspension was obtained. The reaction mixture was then quenched with MeOH (1 mL) and washed with H$_2$O (40 mL), 1N HCl (40 mL) and brine (40 mL). The organic layer was dried over MgSO$_4$ and concentrated in vacuo, and the resulting mixture was stirred with acetone (10 mL). The resulting suspension was filtered, and the solid was washed with acetone and dried in vacuum oven to afford 3,5-dichloro-N-[2-(2,6-dioxo-piperidin-3-yl)-1,3-dioxo-2,3-dihydro-1H-isoindol-4-ylmethyl]-benzamide as a white solid (0.8 g, 76%): mp, 250-252° C.; HPLC: Waters Symmetry C-18, 3.9×150 mm, 5 micro, 1 mL/min, 240 nm, 50/50 (CH$_3$CN/H$_2$O): t$_R$=4.3 min (96%); $^1$H NMR (DMSO-d$_6$): δ 2.05-2.11 (m, 1H), 2.53-2.64 (m, 2H), 2.85-2.93 (m, 1H), 4.95 (d, J=5.7 Hz, 2H), 5.15-5.21 (dd, J=5, 12 Hz, 1H), 7.76-7.94 (m, 6H), 9.37 (t, J=6 Hz, 1H), 11.15 (s, 1H). $^{13}$C NMR (DMSO-d$_6$) δ: 21.97, 30.92, 38.54, 48.86, 121.99, 126.20, 127.21, 130.82, 131.52, 133.27, 134.32, 134.83, 137.11, 138.54, 163.94, 166.92, 167.47, 169.81, 172.74. Anal Calcd for C$_{21}$H$_{15}$Cl$_2$N$_3$O$_5$: C, 54.80; H, 3.28; N, 9.13; Cl, 15.41. Found: C, 54.93; H, 2.96; N, 9.01; Cl, 15.62.

5.130 N-[2-(2,6-DIOXO-PIPERIDIN-3-YL)-1,3-DIOXO-2,3-DIHYDRO-1H-ISOINDOL-4-YLMETHYL]-3,5-DIFLUORO-BENZAMIDE

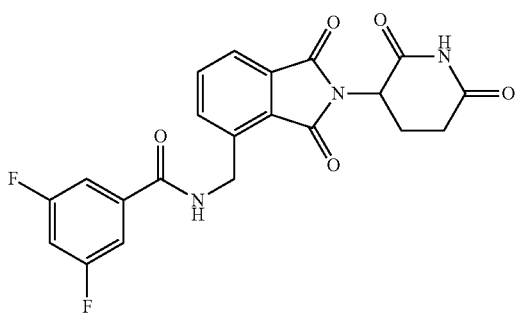

To a stirred suspension of 4-aminomethyl-2-(2,6-dioxo-piperidin-3-yl)-isoindole-1,3-dione hydrochloride (0.7 g, 2.16 mmol) in CH$_2$Cl$_2$ (60 ml) was added diisopropylethylamine (0.94 mL, 5.4 mmol) and 3,5-difluorobenzoyl chloride (0.5 g, 2.8 mmol). The reaction mixture was stirred at room temperature overnight and a suspension was obtained. The reaction mixture was then quenched with MeOH (1 mL) and washed with H$_2$O (40 mL), 1N HCl (40 mL) and brine (40 mL). The organic layer was dried over MgSO$_4$ and concentrated in vacuo, and the resulting mixture was purified by ISCO silica gel flash chromatography (eluent: 3% MeOH in CH$_2$Cl$_2$ for 10 min, then 5% MeOH in CH$_2$Cl$_2$ for 10 min) to afford N-[2-(2,6-Dioxo-piperidin-3-yl)-1,3-dioxo-2,3-dihydro-1H-isoindol-4-ylmethyl]-3,5-difluoro-benzamide as a white solid (0.5 g, 54%): mp, 218-220° C.; HPLC: Waters Symmetry C-18, 3.9×150 mm, 5 micro, 1 mL/min, 240 nm, 40/60 (CH$_3$CN/H$_2$O): t$_R$=4.4 min. (99%); $^1$H NMR (DMSO-d$_6$): δ 2.06-2.11 (m, 1H), 2.53-2.65 (m, 2H), 2.85-2.93 (m, 1H), 4.96 (d, J=5.8 Hz, 2H), 5.15-5.21 (dd, J=5, 12 Hz, 1H), 7.46-7.84 (m, 6H), 9.33 (t, J=6 Hz, 1H), 11.15 (s, 1H). $^{13}$C NMR (DMSO-d$_6$) δ: 21.96, 30.92, 38.49, 48.86, 106.93, 110.58, 110.69, 110.82, 110.93, 121.99, 127.21, 131.54, 133.20, 134.83, 137.42, 138.62, 160.51, 160.67, 163.78, 163.95, 164.10, 166.92, 167.48, 169.81, 172.73. Anal Calcd for C$_{21}$H$_{15}$F$_2$N$_3$O$_5$: C, 59.02; H, 3.54; N, 9.83. Found: C, 58.90; H, 3.15; N, 9.73.

5.131 4-CHLORO-N-[2-(2,6-DIOXO-PIPERIDIN-3-YL)-1,3-DIOXO-2,3-DIHYDRO-1H-ISOINDOL-4-YLMETHYL]-BENZAMIDE

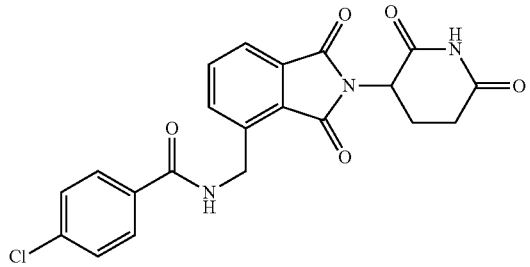 [SMILES: O=C1CCC(N2C(=O)c3cccc(CNC(=O)c4ccc(Cl)cc4)c3C2=O)C(=O)N1]

To a stirred suspension of 4-aminomethyl-2-(2,6-dioxo-piperidin-3-yl)-isoindole-1,3-dione hydrochloride (0.7 g, 2.16 mmol) in CH$_2$Cl$_2$ (60 ml), was added diisopropylethylamine (0.94 mL, 5.4 mmol) and 4-chlorobenzoyl chloride (0.5 g, 2.8 mmol). The mixture was stirred at room temperature overnight and a suspension was obtained. The reaction mixture was quenched with MeOH (1 mL). The suspension was then filtered, and the solid was rinsed with CH$_2$Cl$_2$ (10 mL) to afford 4-chloro-N-[2-(2,6-dioxo-piperidin-3-yl)-1,3-dioxo-2,3-dihydro-1H-isoindol-4-ylmethyl]-benzamide as a white solid (0.5 g, 52%): mp, 233-235° C.; HPLC: Waters Symmetry C-18, 3.9×150 mm, 5 micro, 1 mL/min, 240 nm, 40/60 (CH$_3$CN/H$_2$O): t$_R$=4.7 min. (99%); $^1$H NMR (DMSO-d$_6$): δ 2.06-2.11 (m, 1H), 2.53-2.64 (m, 2H), 2.84-2.93 (m, 1H), 4.95 (d, J=5.8 Hz, 2H), 5.15-5.20 (dd, J=5, 12 Hz, 1H), 7.56-7.59 (dd, J=1.7, 6.8 Hz, 2H), 7.72-7.83 (m, 3H), 7.93-7.96 (dd, J=1.8, 6.8 Hz, 2H), 9.23 (t, J=6 Hz, 1H), 11.15 (s, 1H). $^{13}$C NMR (DMSO-d$_6$) δ: 21.97, 30.92, 38.38, 48.86, 121.90, 127.15, 128.45, 129.25, 131.53, 132.65, 133.09, 134.80, 136.28, 139.08, 165.57, 166.94, 167.51, 169.81, 172.74. Anal Calcd for C$_{21}$H$_{16}$ClN$_3$O$_5$: C, 59.23; H, 3.79; N, 9.87; Cl, 8.33. Found: C, 59.27; H, 3.42; N, 9.75; Cl, 8.57.

5.132 2-CHLORO-N-[2-(2,6-DIOXO-PIPERIDIN-3-YL)-1,3-DIOXO-2,3-DIHYDRO-1H-ISOINDOL-4-YLMETHYL]-BENZAMIDE

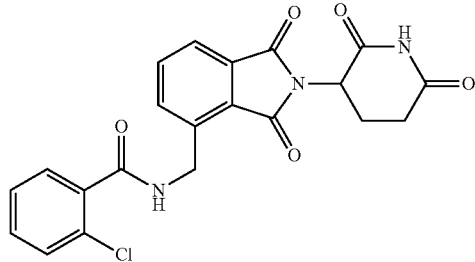 [SMILES: O=C1CCC(N2C(=O)c3cccc(CNC(=O)c4ccccc4Cl)c3C2=O)C(=O)N1]

To a stirred suspension of 4-aminomethyl-2-(2,6-dioxo-piperidin-3-yl)-isoindole-1,3-dione hydrochloride (0.7 g, 2.16 mmol) in CH$_2$Cl$_2$ (60 ml), was added diisopropylethylamine (0.94 mL, 5.4 mmol) and 2-chlorobenzoyl chloride (0.5 g, 2.8 mmol). The mixture was stirred at room temperature overnight. The reaction mixture was quenched with MeOH (1 mL) and then washed with H$_2$O (40 mL), 1N HCl (40 mL), brine (40 mL), and dried over MgSO$_4$. The organic layer was concentrated in vacuo, and the resulting oil was purified by ISCO silica gel flash chromatography (eluent: 3% MeOH in CH$_2$Cl$_2$ for 10 min, then 5% MeOH in CH$_2$Cl$_2$ for 10 min):) to afford 2-chloro-N-[2-(2,6-dioxo-piperidin-3-yl)-1,3-dioxo-2,3-dihydro-1H-isoindol-4-ylmethyl]-benzamide as a white solid (0.55 g, 60%): mp, 209-211° C.; HPLC: Waters Symmetry C-18, 3.9×150 mm, 5 micro, 1 mL/min, 240 nm, 40/60 (CH$_3$CN/H$_2$O): t$_R$=3.0 min (99%); $^1$H NMR (DMSO-d$_6$): δ 2.06-2.11 (m, 1H), 2.53-2.64 (m, 2H), 2.87-2.93 (m, 1H), 4.92 (d, J=5.9 Hz, 2H), 5.14-5.20 (dd, J=5, 12 Hz, 1H), 7.39-7.57 (m, 4H), 7.82-7.89 (m, 3H), 9.12 (t, J=6 Hz, 1H), 11.15 (s, 1H). $^{13}$C NMR (DMSO-d$_6$) δ: 21.96, 30.91, 38.10, 48.86, 121.95, 127.15, 128.97, 129.62, 129.83, 130.94, 131.54, 133.10, 134.80, 136.49, 138.74, 166.77, 166.93, 167.48, 169.80, 172.74. Anal Calcd for C$_{21}$H$_{16}$ClN$_3$O$_5$: C, 59.23; H, 3.79; N, 9.87; Cl, 8.33. Found: C, 59.24; H, 3.45; N, 9.71; Cl, 8.32.

5.133 3-CHLORO-N-[2-(2,6-DIOXO-PIPERIDIN-3-YL)-1,3-DIOXO-2,3-DIHYDRO-1H-ISOINDOL-4-YLMETHYL]-4-METHYL-BENZAMIDE

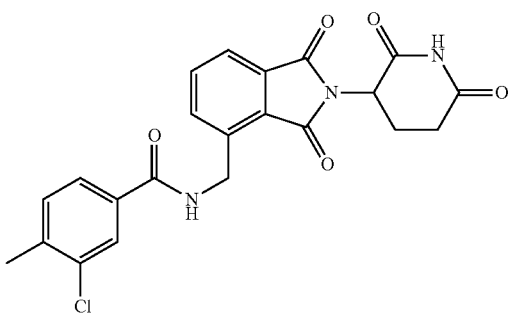 [SMILES: Cc1ccc(C(=O)NCc2cccc3c2C(=O)N(C2CCC(=O)NC2=O)C3=O)cc1Cl]

To a stirred suspension of 4-aminomethyl-2-(2,6-dioxo-piperidin-3-yl)-isoindole-1,3-dione hydrochloride (0.7 g, 2.2 mmol) in CH$_3$CN (60 ml), was added 1,8-diazabicyclo[5.4.0]undec-7-ene (0.8 g, 5.4 mmol). After stirring for 10 minutes, 1-hydroxybenzenetriazole (0.35 g, 2.6 mmol) and 3-chloro-4-methyl-benzoic acid (0.4 g, 2.4 mmol) were added. To the reaction mixture, was then added 1-(3-dimethylaminopropyl)-3-ethylcarbodiimide hydrochloride (0.62 g, 3.2 mmol), and the mixture was stirred at room temperature overnight. The reaction mixture was then concentrated in vacuo, and the residue was stirred in H$_2$O (50 mL). A suspension formed and after filtration the solid was reslurried in acetone (20 mL). The suspension was filtered to afford 3-chloro-N-[2-(2,6-dioxo-piperidin-3-yl)-1,3-dioxo-2,3-dihydro-1H-isoindol-4-ylmethyl]-4-methyl-benzamide as a white solid (0.75 g, 79%): mp, 249-251° C.; HPLC: Waters Symmetry C-18, 3.9×150 mm, 5 micro, 1 mL/min, 240 nm, 40/60 (CH$_3$CN/H$_2$O): t$_R$=6.8 min. (97%); $^1$H NMR (DMSO-d$_6$): δ 2.06-2.11 (m, 1H), 2.39 (s, 3H), 2.53-2.64 (m, 2H), 2.85-2.96 (m, 1H), 4.94 (d, J=5.8 Hz, 2H), 5.15-5.20 (dd, J=5, 12 Hz, 1H), 7.47-7.97 (m, 6H), 7.82-7.89 (m, 3H), 9.22 (t, J=6 Hz, 1H), 11.15 (s, 1H). $^{13}$C NMR (DMSO-d$_6$) δ: 19.55, 21.97, 30.92, 38.36, 48.86, 121.89, 126.07, 127.15, 127.60, 131.22, 131.52, 133.11, 133.33, 134.80, 139.06, 139.10, 165.13, 166.94, 167.50, 169.81, 172.74. Anal Calcd for C$_{22}$H$_{18}$ClN$_3$O$_5$: C, 60.08; H, 4.12; N, 9.55; Cl, 8.06. Found: C, 59.69; H, 4.15; N, 9.60; Cl, 8.08.

5.134 BENZOFURAN-2-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

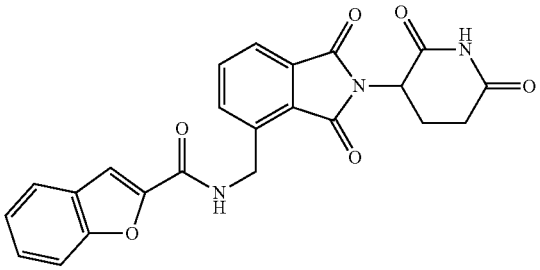 [SMILES: O=C1CCC(N2C(=O)c3cccc(CNC(=O)c4cc5ccccc5o4)c3C2=O)C(=O)N1]

To a stirred suspension of 4-aminomethyl-2-(2,6-dioxo-piperidin-3-yl)-isoindole-1,3-dione hydrochloride (0.7 g, 2.2 mmol) in CH$_3$CN (60 ml), was added 1,8-diazabicyclo[5.4.0]undec-7-ene (0.8 g, 5.4 mmol). After stirring for 10 minutes, 1-hydroxybenzenetriazole (0.35 g, 2.6 mmol) and 2-benzofuran carboxylic acid (0.39 g, 2.4 mmol) were added. To the reaction, was then added 1-(3-dimethylaminopropyl)-3-ethylcarbodiimide hydrochloride (0.62 g, 3.2 mmol), and the resulting mixture was stirred at room temperature overnight. The reaction mixture was then concentrated in vacuo, and the residue was dissolved in CH$_2$Cl$_2$ (50 mL). The CH$_2$Cl$_2$ solution was washed with water (2×30 mL) and brine (30 mL), and dried over MgSO$_4$. Solvent was removed in vacuo, and the resulting oil was purified by ISCO silica gel flash chromatography (eluent: 30% EtOAc in CH$_2$Cl$_2$ for 10 min, then 40% EtOAc in CH$_2$Cl$_2$ for 10 min) to afford benzofuran-2-carboxylic acid [2-(2,6-dioxo-piperidin-3-yl)-1,3-dioxo-2,3-dihydro-1H-isoindol-4-ylmethyl]-amide as a white solid (0.59 g, 63%): mp, 292-295° C.; HPLC: Waters Symmetry C-18, 3.9×150 mm, 5 micro, 1 mL/min, 240 nm, 40/60 (CH$_3$CN/H$_2$O): t$_R$=4.3 min. (98%); $^1$H NMR (DMSO-d$_6$): δ 2.09-2.10 (m, 1H), 2.55-2.65 (m, 2H), 2.84-2.93 (m, 1H), 4.97 (d, J=6.0 Hz, 2H), 5.15-5.21 (dd, J=5, 12 Hz, 1H), 7.33-7.84 (m, 8H), 9.40 (t, J=6 Hz, 1H), 11.15 (s, 1H). $^{13}$C NMR (DMSO-d$_6$) δ: 21.97, 30.92, 37.90, 48.87, 109.90, 111.79, 121.95, 122.81, 123.74, 126.96, 127.09, 127.15, 131.54, 133.02, 134.83, 138.71, 148.71, 154.27, 158.52, 166.94, 167.51, 169.82, 172.74. Anal Calcd for C$_{23}$H$_{17}$N$_3$O$_6$+0.2H$_2$O: C, 63.51; H, 4.03; N, 9.66. Found: C, 63.45; H, 3.76; N, 9.52.

5.135 2-(3,4-DICHLORO-PHENYL)-N-[2-(2,6-DIOXO-PIPERIDIN-3-YL)-1,3-DIOXO-2,3-DIHYDRO-1H-ISOINDOL-4-YLMETHYL]-ACETAMIDE

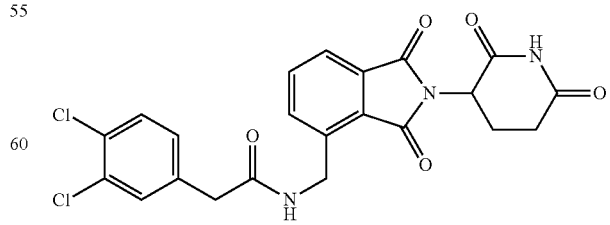

To a stirred suspension of 4-aminomethyl-2-(2,6-dioxo-piperidin-3-yl)-isoindole-1,3-dione hydrochloride (0.7 g, 2.2 mmol) in CH$_3$CN (60 ml), was added 1,8-diazabicyclo[5.4.0]

undec-7-ene (0.8 g, 5.4 mmol). After stirring for 10 minutes, 1-hydroxybenzenetriazole (0.35 g, 2.6 mmol) and 3,4-dichlorophenylacetic acid (0.49 g, 2.4 mmol) were added. The mixture was then added 1-(3-dimethylaminopropyl)-3-ethylcarbodiimide hydrochloride (0.62 g, 3.2 mmol) and stirred overnight at room temperature. The reaction mixture was concentrated in vacuo, and the residue was dissolved in $CH_2Cl_2$ (50 mL). The $CH_2Cl_2$ solution was washed with water (2×30 mL) and brine (30 mL), and dried over $MgSO_4$. Solvent was removed in vacuo. The resulting oil solidified on standing and the mixture was stirred in acetone (10 mL) then in MeOH (10 mL). The resulting solid was filtered and dried in vacuum oven to afford 2-(3,4-dichloro-phenyl)-N-[2-(2,6-dioxo-piperidin-3-yl)-1,3-dioxo-2,3-dihydro-1H-isoindol-4-ylmethyl]-acetamide as an off-white solid (0.69 g, 67%): mp, 163-165° C.; HPLC: Waters Symmetry C-18, 3.9×150 mm, 5 micro, 1 mL/min, 240 nm, 40/60 ($CH_3CN/H_2O$): $t_R$=6.5 min. (98%); $^1H$ NMR (DMSO-$d_6$): δ 2.03-2.08 (m, 1H), 2.52-2.63 (m, 2H), 2.84-2.92 (m, 1H), 3.58 (s, 2H), 4.73 (d, J=6.0 Hz, 2H), 5.12-5.18 (dd, J=5, 12 Hz, 1H), 7.26-7.82 (m, 6H), 8.69 (t, J=6 Hz, 1H), 11.14 (s, 1H). $^{13}C$ NMR (DMSO-$d_6$) δ: 21.95, 30.90, 37.92, 40.80, 48.83, 121.95, 127.16, 129.13, 129.58, 130.29, 130.65, 131.15, 131.52, 133.31, 134.68, 137.19, 138.92, 166.88, 167.39, 169.77, 172.72. Anal Calcd for $C_{22}H_{17}Cl_2N_3O_5+0.2H_2O$: C, 55.29; H, 3.67; N, 8.79; Cl, 14.84. Found: C, 55.19; H, 3.33; N, 8.83; Cl, 14.71.

5.136 2-(3-CHLORO-PHENYL)-N-[2-(2,6-DIOXO-PIPERIDIN-3-YL)-1,3-DIOXO-2,3-DIHYDRO-1H-ISOINDOL-4-YLMETHYL]-ACETAMIDE

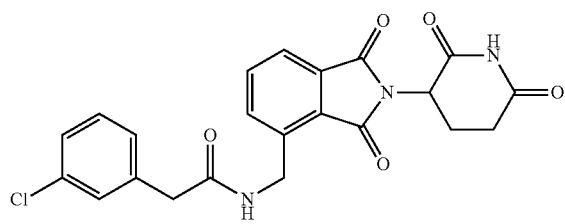 [SMILES: O=C(Cc1cccc(Cl)c1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in $CH_3CN$ (60 ml), was added 1,8-diazabicyclo[5.4.0] undec-7-ene (0.8 g, 5.4 mmol). After stirring for 10 minutes, 1-hydroxybenzenetriazole (0.35 g, 2.6 mmol) and 3-chlorophenylacetic acid (0.41 g, 2.4 mmol) were added. The reaction was then added 1-(3-dimethylaminopropyl)-3-ethylcarbodiimide hydrochloride (0.62 g, 3.2 mmol) and was stirred at room temperature overnight. The reaction mixture was then concentrated in vacuo, and the residue was dissolved in $CH_2Cl_2$ (50 mL). The $CH_2Cl_2$ solution was washed with water (2×30 mL) and brine (30 mL), and dried over $MgSO_4$. Solvent was removed in vacuo, and the resulting oil was purified by ISCO silica gel flash chromatography (eluent: 30% EtOAc in $CH_2Cl_2$ for 10 min, then increase to 60% EtOAc in $CH_2Cl_2$ over 20 min) to afford 2-(3-chloro-phenyl)-N-[2-(2,6-dioxo-piperidin-3-yl)-1,3-dioxo-2,3-dihydro-1H-isoindol-4-ylmethyl]-acetamide as a white solid (0.73 g, 76%): mp, 185-187° C.; HPLC: Waters Symmetry C-18, 3.9×150 mm, 5 micro, 1 mL/min, 240 nm, 40/60 ($CH_3CN/H_2O$): $t_R$=4.2 min. (99%); $^1H$ NMR (DMSO-$d_6$): δ 2.03-2.08 (m, 1H), 2.52-2.63 (m, 2H), 2.86-2.91 (m, 1H), 3.56 (s, 2H), 4.73 (d, J=6.0 Hz, 2H), 5.12-5.18 (dd, J=5, 13 Hz, 1H), 7.23-7.82 (m, 7H), 8.70 (t, J=6 Hz, 1H), 11.13 (s, 1H). $^{13}C$ NMR (DMSO-$d_6$) δ: 21.95, 30.90, 37.87, 41.53, 48.83, 121.93, 126.40, 127.15, 127.82, 128.94, 130.04, 131.52, 132.74, 133.25, 134.66, 138.54, 139.01, 166.88, 167.41, 169.77, 170.03, 172.73. Anal Calcd for $C_{22}H_{18}ClN_3O_5$: C, 60.08; H, 4.12; N, 9.55; Cl, 8.06. Found: C, 59.92; H, 3.85; N, 9.55; Cl, 8.37.

5.137 BENZO[1,3]DIOXOLE-5-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

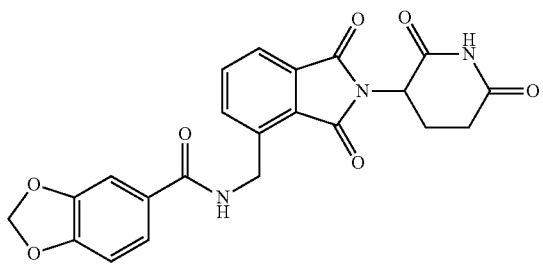 [SMILES: O=C1CCC(N2C(=O)c3cccc(CNC(=O)c4ccc5c(c4)OCO5)c3C2=O)C(=O)N1]

To a stirred suspension of 4-aminomethyl-2-(2,6-dioxo-piperidin-3-yl)-isoindole-1,3-dione hydrochloride (0.7 g, 2.16 mmol) in $CH_2Cl_2$ (60 ml), was added diisopropylethylamine (0.94 mL, 5.4 mmol) and piperonyloyl chloride (0.5 g, 2.8 mmol). The mixture was stirred at room temperature overnight and a suspension was obtained. The reaction mixture was quenched by the addition of MeOH (1 mL). The suspension was filtered, and the solid was rinsed with $CH_2Cl_2$ (10 mL) to afford benzo[1,3]dioxole-5-carboxylic acid [2-(2,6-dioxo-piperidin-3-yl)-1,3-dioxo-2,3-dihydro-1H-isoindol-4-ylmethyl]-amide as a white solid (0.8 g, 85%): mp, 231-233° C.; HPLC: Waters Symmetry C-18, 3.9×150 mm, 5 micro, 1 mL/min, 240 nm, 40/60 ($CH_3CN/H_2O$): $t_R$=2.7 (99%); $^1H$ NMR (DMSO-$d_6$): δ 2.06-2.10 (m, 1H), 2.53-2.64 (m, 2H), 2.86-2.97 (m, 1H), 4.92 (d, J=5.6 Hz, 2H), 5.14-5.20 (dd, J=5, 12 Hz, 1H), 6.11 (s, 2H), 7.03 (d, J=8.1 Hz, 1H), 7.45-7.85 (m, 5H), 9.00 (t, J=6 Hz, 1H), 11.15 (s, 1H). $^{13}C$ NMR (DMSO-$d_6$) δ: 21.97, 30.92, 38.33, 48.85, 101.68, 107.34, 107.90, 121.81, 122.35, 127.08, 127.88, 131.50, 133.01, 134.77, 139.44, 147.36, 149.87, 165.70, 166.96, 167.52, 169.82, 172.74. Anal Calcd for $C_{22}H_{17}N_3O_7+0.2H_2O$: C, 60.19; H, 4.00; N, 9.57. Found: C, 60.15; H, 3.71; N, 9.46.

5.138 N-[2-(2,6-DIOXO-PIPERIDIN-3-YL)-1,3-DIOXO-2,3-DIHYDRO-1H-ISOINDOL-4-YL-METHYL]-3,4-DIMETHOXY-BENZAMIDE

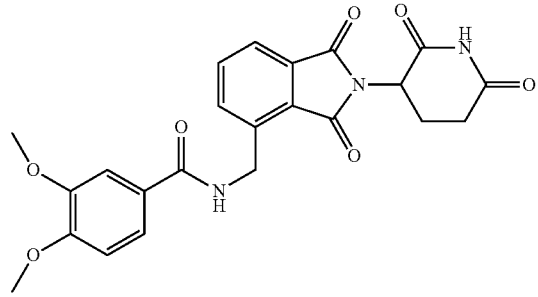 [SMILES: COc1ccc(C(=O)NCc2cccc3c2C(=O)N(C2CCC(=O)NC2=O)C3=O)cc1OC]

To a stirred suspension of 4-aminomethyl-2-(2,6-dioxo-piperidin-3-yl)-isoindole-1,3-dione hydrochloride (0.7 g, 2.16 mmol) in $CH_2Cl_2$ (60 ml), was added diisopropylethylamine (0.94 mL, 5.4 mmol) and 3,4-dimethyoxybenzoyl chloride (0.6 g, 2.8 mmol). The mixture was stirred at room temperature overnight followed by the addition of MeOH (1 mL). The reaction mixture was then washed with water (40 mL), 1N HCl (2×40 mL), and brine (40 mL), dried over MgSO$_4$, and concentrated in vacuo. The resulting oil was purified by ISCO silica gel flash chromatography (eluent: 0% MeOH in CH$_2$Cl$_2$ to 5% MeOH in 10 min then stay at this ratio for 15 min) to afford N-[2-(2,6-dioxo-piperidin-3-yl)-1,3-dioxo-2,3-dihydro-1H-isoindol-4-yl-methyl]-3,4-dimethoxy-benzamide as a white solid (0.8 g, 79%): mp, 198-200° C.; HPLC: Waters Symmetry C-18, 3.9×150 mm, 5 micro, 1 mL/min, 240 nm, 40/60 (CH$_3$CN/H$_2$O): t$_R$=2.2 min. (99%); $^1$H NMR (DMSO-d$_6$): δ 2.06-2.10 (m, 1H), 2.51-2.59 (m, 2H), 2.64 (m, 1H), 3.81 (s, 6H), 4.94 (d, J=5.9 Hz, 2H), 5.14-5.20 (dd, J=5, 12 Hz, 1H), 7.06 (d, J=8.5 Hz, 1H), 7.51-7.58 (m, 2H), 7.83-7.70 (m, 3H), 9.02 (t, J=6 Hz, 1H), 11.15 (s, 1H). $^{13}$C NMR (DMSO-d$_6$) δ: 21.97, 30.92, 38.22, 48.86, 55.53, 55.60, 110.67, 110.92, 120.56, 121.80, 126.10, 127.05, 131.50, 133.06, 134.77, 139.66, 148.28, 151.44, 166.09, 166.96, 167.57, 169.83, 172.74. Anal Calcd for C$_{23}$H$_{21}$N$_3$O$_7$+0.2H$_2$O: C, 60.71; H, 4.74; N, 9.23. Found: C, 60.39; H, 4.51; N, 8.99.

5.139 N-[2-(2,6-DIOXO-PIPERIDIN-3-YL)-1,3-DIOXO-2,3-DIHYDRO-1H-ISOINDOL-4-YLMETHYL]-4-TRIFLUOROMETHOXY-BENZAMIDE

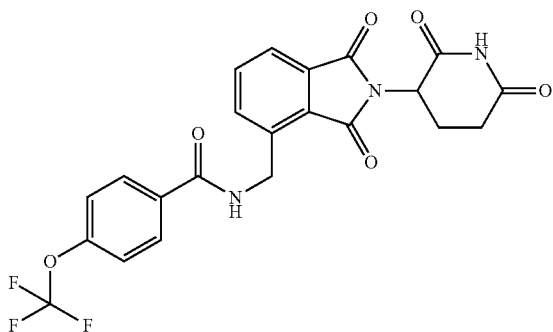 [SMILES: O=C1CCC(N2C(=O)c3cccc(CNC(=O)c4ccc(OC(F)(F)F)cc4)c3C2=O)C(=O)N1]

To a stirred suspension of 4-aminomethyl-2-(2,6-dioxo-piperidin-3-yl)-isoindole-1,3-dione hydrochloride (0.7 g, 2.16 mmol) in CH$_2$Cl$_2$ (60 ml), was added diisopropylethylamine (0.94 mL, 5.4 mmol) and 4-trifluoromethoxybenzoyl chloride (0.6 g, 2.8 mmol). The mixture was then stirred at room temperature overnight. The reaction mixture was quenched with MeOH (1 mL), washed with water (40 mL), 1N HCl (2×40 mL), and brine (40 mL), dried over MgSO$_4$, and concentrated in vacuo. The resulting oil was purified by ISCO silica gel flash chromatography (eluent: 0% MeOH in CH$_2$Cl$_2$ to 5% MeOH in 10 min then stay at this ratio for 15 min) to afford N-[2-(2,6-dioxo-piperidin-3-yl)-1,3-dioxo-2,3-dihydro-1H-isoindol-4-ylmethyl]-4-trifluoromethoxy-benzamide as an off-white solid (0.8 g, 78%): mp, 163-165° C.; HPLC: Waters Symmetry C-18, 3.9×150 mm, 5 micro, 1 mL/min, 240 nm, 40/60 (CH$_3$CN/H$_2$O): t$_R$=7.3 min. (99%); $^1$H NMR (DMSO-d$_6$): δ 2.07-2.10 (m, 1H), 2.51-2.64 (m, 2H), 2.91-2.92 (m, 1H), 4.96 (d, J=5.7 Hz, 2H), 5.15-5.21 (dd, J=5, 12 Hz, 1H), 7.52 (d, J=8.0 Hz, 2H), 7.74-7.84 (m, 3H), 8.04-8.07 (dd, J=6.8, 1.9 Hz, 2H), 9.28 (t, J=6 Hz, 1H), 11.15 (s, 1H). $^{13}$C NMR (DMSO-d$_6$) δ: 21.97, 30.92, 38.44, 118.23, 120.68, 121.64, 121.90, 127.15, 129.30, 129.67, 131.53, 133.01, 133.07, 134.80, 139.03, 150.39, 150.42, 165.39, 166.94, 167.51, 169.81, 172.74. Anal Calcd for C$_{22}$H$_{16}$F$_3$N$_3$O$_6$: C, 55.59; H, 3.39; N, 8.84; F, 11.99. Found: C, 55.43; H, 3.00; N, 8.76; F, 11.77.

5.140 N-[2-(2,6-DIOXO-PIPERIDIN-3-YL)-1,3-DIOXO-2,3-DIHYDRO-1H-ISOINDOL-4-YLMETHYL]-3-TRIFLUOROMETHOXY-BENZAMIDE

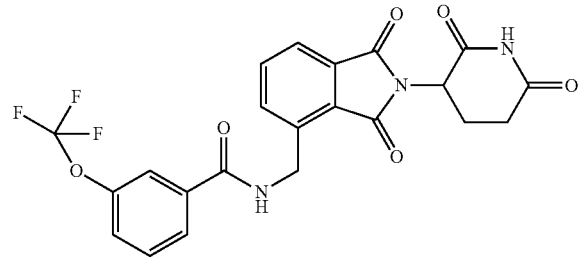 [SMILES: O=C1CCC(N2C(=O)c3cccc(CNC(=O)c4cccc(OC(F)(F)F)c4)c3C2=O)C(=O)N1]

To a stirred suspension of 4-aminomethyl-2-(2,6-dioxo-piperidin-3-yl)-isoindole-1,3-dione hydrochloride (0.70 g, 2.2 mmol) in CH$_3$CN (60 ml), was added 1,8-diazabicyclo[5.4.0]undec-7-ene (0.80 g, 5.4 mmol). After stirring for 10 minutes, 1-hydroxybenzenetriazole (0.35 g, 2.6 mmol) and 2-benzofuran carboxylic acid (0.39 g, 2.4 mmol) were added, followed by 1-(3-dimethylaminopropyl)-3-ethylcarbodiimide hydrochloride (0.62 g, 3.2 mmol). After stirring at room temperature overnight, the reaction mixture was concentrated in vacuo, and the residue was stirred with water and filtered. The resulting solid was dissolved in CH$_2$Cl$_2$ (50 mL) and purified by ISCO silica gel flash chromatography (eluent: 0% MeOH in CH$_2$Cl$_2$ to 5% MeOH in 10 min then stay at this ratio for 15 min) to afford N-[2-(2,6-dioxo-piperidin-3-yl)-1,3-dioxo-2,3-dihydro-1H-isoindol-4-ylmethyl]-3-trifluoromethoxy-benzamide as an off-white solid (0.75 g, 73%): mp, 162-164° C.; HPLC: Waters Symmetry C-18, 3.9×150 mm, 5 micro, 1 mL/min, 240 nm, 40/60 (CH$_3$CN/H$_2$O): t$_R$=7.2 min (99%); $^1$H NMR (DMSO-d$_6$): δ 2.06-2.10 (m, 1H), 2.50-2.64 (m, 2H), 2.86-2.93 (m, 1H), 4.97 (d, J=5.7 Hz, 2H), 5.15-5.21 (dd, J=5, 12 Hz, 1H), 7.57-7.99 (m, 7H), 9.34 (t, J=5.7 Hz, 1H), 11.15 (s, 1H). $^{13}$C NMR (DMSO-d$_6$) δ: 21.91, 30.86, 38.37, 48.81, 118.26, 119.78, 121.67, 121.89, 123.95, 126.37, 127.12, 130.57, 131.48, 133.12, 134.78, 136.02, 138.83, 148.27, 148.30, 164.93, 166.83, 167.45, 169.76, 172.68. Anal Calcd for C$_{22}$H$_{16}$F$_3$N$_3$O$_6$: C, 55.59; H, 3.39; N, 8.84; F, 11.99. Found: C, 55.53; H, 3.01; N, 8.70; F, 11.94.

5.141 4-DIFLUOROMETHOXY-N-[2-(2,6-DIOXO-PIPERIDIN-3-YL)-1,3-DIOXO-2,3-DIHYDRO-1H-ISOINDOL-4-YLMETHYL]-BENZAMIDE

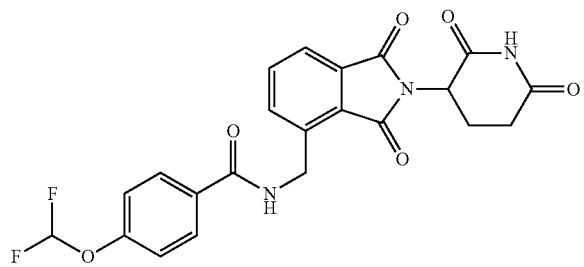 [SMILES: O=C1CCC(N2C(=O)c3cccc(CNC(=O)c4ccc(OC(F)F)cc4)c3C2=O)C(=O)N1]

To a stirred suspension of 4-aminomethyl-2-(2,6-dioxo-piperidin-3-yl)-isoindole-1,3-dione hydrochloride (0.70 g, 2.2 mmol) in CH$_3$CN (60 ml), was added 1,8-diazabicyclo

[5.4.0]undec-7-ene (0.82 g, 5.4 mmol). After stirring for 10 minutes, 1-hydroxybenzenetriazole (0.35 g, 2.6 mmol) and 4-difluoromethoxy benzoic acid (0.45 g, 2.4 mmol) were added followed by 1-(3-dimethylaminopropyl)-3-ethylcarbodiimide hydrochloride (0.62 g, 3.2 mmol). After stirring at room temperature overnight, the reaction mixture was concentrated in vacuo, and the residue was dissolved in $CH_2Cl_2$ (50 mL). The $CH_2Cl_2$ solution was washed with water (2×30 mL) and brine (30 mL) and dried over $MgSO_4$. Solvent was removed in vacuo, and the resulting oil was purified by ISCO silica gel flash chromatography (eluent: 0% MeOH in $CH_2Cl_2$ to 5% MeOH in 10 min then stay at this ratio for 15 min) to afford 4-difluoromethoxy-N-[2-(2,6-dioxo-piperidin-3-yl)-1,3-dioxo-2,3-dihydro-1H-isoindol-4-ylmethyl]-benzamide as a yellow solid (0.63 g, 64%): mp, 155-157° C.; HPLC: Waters Symmetry C-18, 3.9×150 mm, 5 micro, 1 mL/min, 240 nm, 40/60 ($CH_3CN/H_2O$): $t_R$=4.2 min. (97%); $^1$H NMR (DMSO-$d_6$): δ 2.06-2.11 (m, 1H), 2.50-2.65 (m, 2H), 2.85-2.92 (m, 1H), 4.95 (d, J=5.8 Hz, 2H), 5.16-5.21 (dd, J=5, 12 Hz, 1H), 7.28-7.30 (m, 2H), 7.36 (t, J=73.5 Hz, 1H), 7.72-7.86 (m, 3H), 7.98-8.02 (m, 2H), 9.18 (t, J=5.8 Hz, 1H), 11.15 (s, 1H). $^{13}$C NMR (DMSO-$d_6$) δ: 21.97, 30.92, 38.34, 48.86, 112.61, 116.03, 117.97, 119.45, 121.87, 127.13, 129.45, 130.55, 131.52, 133.05, 134.79, 139.22, 153.30, 165.60, 166.95, 167.52, 169.81, 172.74. Anal Calcd for $C_{22}H_{17}F_2N_3O_6$: C, 57.77; H, 3.75; N, 9.19; F, 8.31. Found: C, 57.67; H, 3.59; N, 9.01; F, 8.22.

5.142 3-DIFLUOROMETHOXY-N-[2-(2,6-DIOXO-PIPERIDIN-3-YL)-1,3-DIOXO-2,3-DIHYDRO-1H-ISOINDOL-4-YLMETHYL]-BENZAMIDE

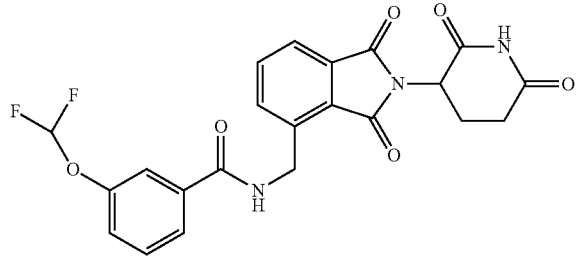 [SMILES: O=C1CCC(N2C(=O)c3cccc(CNC(=O)c4cccc(OC(F)F)c4)c3C2=O)C(=O)N1]

To a stirred suspension of 4-aminomethyl-2-(2,6-dioxo-piperidin-3-yl)-isoindole-1,3-dione hydrochloride (0.70 g, 2.2 mmol) in $CH_3CN$ (60 ml), was added 1,8-diazabicyclo[5.4.0]undec-7-ene (0.82 g, 5.4 mmol). After stirring for 10 minutes, 1-hydroxybenzenetriazole (0.35 g, 2.6 mmol) and 3-difluoromethoxy benzoic acid (0.45 g, 2.4 mmol) were added, followed by 1-(3-dimethylaminopropyl)-3-ethylcarbodiimide hydrochloride (0.62 g, 3.2 mmol). After stirring at room temperature overnight, the reaction mixture was concentrated in vacuo, and the residue was dissolved in $CH_2Cl_2$ (50 mL). The $CH_2Cl_2$ solution was then washed with water (2×30 mL) and brine (30 mL), and dried over $MgSO_4$. Solvent was removed in vacuo, and the resulting oil was purified by ISCO silica gel flash chromatography (eluent: 0% MeOH in $CH_2Cl_2$ to 5% MeOH in 10 min then stay at this ratio for 15 min) to afford 3-difluoromethoxy-N-[2-(2,6-dioxo-piperidin-3-yl)-1,3-dioxo-2,3-dihydro-1H-isoindol-4-ylmethyl]-benzamide as a white solid (0.64 g, 65%): mp, 164-166° C.; HPLC: Waters Symmetry C-18, 3.9×150 mm, 5 micro, 1 mL/min, 240 nm, 40/60 ($CH_3CN/H_2O$): $t_R$=3.6 min (99%); $^1$H NMR (DMSO-$d_6$): δ 2.04-2.09 (m, 1H), 2.53-2.64 (m, 2H), 2.85-2.93 (m, 1H), 4.92 (d, J=6.0 Hz, 2H), 5.14-5.20 (dd, J=5, 12 Hz, 1H), 6.97-7.86 (m, 8H), 8.97 (t, J=6.0 Hz, 1H), 11.15 (s, 1H). $^{13}$C NMR (DMSO-$d_6$) δ: 21.95, 30.91, 38.29, 48.86, 113.18, 116.60, 119.08, 120.02, 121.91, 125.34, 127.12, 128.74, 129.58, 131.48, 131.54, 113.18, 116.60, 119.08, 120.02, 121.91, 125.34, 127.12, 127.74, 128.58, 131.48, 131.54, 132.96, 134.64, 138.89, 147.66, 165.60, 166.94, 167.51, 169.81, 172.73. Anal Calcd for $C_{22}H_{17}F_2N_3O_6$: C, 57.77; H, 3.75; N, 9.19; F, 8.31. Found: C, 57.62; H, 3.60; N, 8.99; F, 8.32.

5.143 2-DIFLUOROMETHOXY-N-[2-(2,6-DIOXO-PIPERIDIN-3-YL)-1,3-DIOXO-2,3-DIHYDRO-1H-ISOINDOL-4-YLMETHYL]-BENZAMIDE

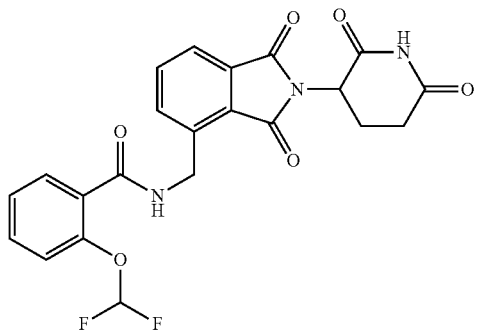 [SMILES: O=C1CCC(N2C(=O)c3cccc(CNC(=O)c4ccccc4OC(F)F)c3C2=O)C(=O)N1]

To a stirred suspension of 4-aminomethyl-2-(2,6-dioxo-piperidin-3-yl)-isoindole-1,3-dione hydrochloride (0.70 g, 2.2 mmol) in $CH_3CN$ (60 ml), was added 1,8-diazabicyclo[5.4.0]undec-7-ene (0.82 g, 5.4 mmol). After stirring for 10 minutes, 1-hydroxybenzenetriazole (0.35 g, 2.6 mmol) and 2-difluoromethoxy benzoic acid (0.45 g, 2.4 mmol) were added, followed by 1-(3-dimethylaminopropyl)-3-ethylcarbodiimide hydrochloride (0.62 g, 3.2 mmol). After stirring at room temperature overnight, the reaction mixture was concentrated in vacuo, and the residue was dissolved in $CH_2Cl_2$ (50 mL). The $CH_2Cl_2$ solution was then washed with water (2×30 mL) and brine (30 mL), and dried over $MgSO_4$. Solvent was removed in vacuo, and the resulting oil was purified by ISCO silica gel flash chromatography (eluent: 0% MeOH in $CH_2Cl_2$ to 5% MeOH in 10 min then stay at this ratio for 15 min) to afford 4-difluoromethoxy-N-[2-(2,6-dioxo-piperidin-3-yl)-1,3-dioxo-2,3-dihydro-1H-isoindol-4-ylmethyl]-benzamide as a solid (0.64 g, 65%): mp, 164-166° C.; HPLC: Waters Symmetry C-18, 3.9×150 mm, 5 micro, 1 mL/min, 240 nm, 40/60 ($CH_3CN/H_2O$): $t_R$=3.6 (99%); $^1$H NMR (DMSO-$d_6$): δ 2.04-2.09 (m, 1H), 2.53-2.64 (m, 2H), 2.85-2.93 (m, 1H), 4.92 (d, J=6.0 Hz, 2H), 5.14-5.20 (dd, J=5, 12 Hz, 1H), 6.97-7.86 (m, 8H), 8.97 (t, J=5.8 Hz, 1H), 11.15 (s, 1H). $^{13}$C NMR (DMSO-$d_6$) δ: 21.95, 30.91, 38.29, 48.86, 113.18, 116.60, 119.08, 120.02, 121.91, 125.34, 127.12, 128.74, 129.58, 131.48, 131.54, 132.96, 134.64, 138.89, 147.66, 165.60, 166.94, 167.51, 169.80, 172.73. Anal Calcd for $C_{22}H_{17}F_2N_3O_6$: C, 57.77; H, 3.75; N, 9.19; F, 8.31. Found: C, 57.62; H, 3.60; N, 8.99; F, 8.32.

5.144 N-[2-(2,6-DIOXO-PIPERIDIN-3-YL)-1,3-DIOXO-2,3-DIHYDRO-1H-ISOINDOL-4-YLM-ETHYL]-4-FLUORO-BENZAMIDE

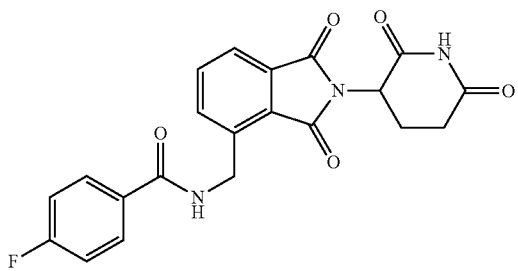

To a stirred suspension of 4-aminomethyl-2-(2,6-dioxo-piperidin-3-yl)-isoindole-1,3-dione hydrochloride (0.7 g, 2.16 mmol) in $CH_2Cl_2$ (60 ml), was added diisopropylethylamine (0.94 mL, 5.4 mmol) and 4-fluorobenzoyl chloride (0.45 g, 2.8 mmol). The mixture was stirred at room temperature overnight followed by addition of MeOH (1 mL). After filtration, the resulting solid was washed with $CH_2Cl_2$ then recrystallized in $CH_3OH$ to afford N-[2-(2,6-dioxo-piperidin-3-yl)-1,3-dioxo-2,3-dihydro-1H-isoindol-4-ylmethyl]-4-fluoro-benzamide as a white solid (0.5 g, 59%): mp, 233-235° C.; HPLC: Waters Symmetry C-18, 3.9×150 mm, 5 micro, 1 mL/min, 240 nm, 40/60 ($CH_3CN/H_2O$): $t_R$=3.6 (96%); $^1$H NMR (DMSO-$d_6$): δ 2.06-2.11 (m, 1H), 2.53-2.64 (m, 2H), 2.86-2.98 (m, 1H), 4.95 (d, J=5.7 Hz, 2H), 5.15-5.21 (dd, J=5, 12 Hz, 1H), 7.30-7.38 (m, 2H), 7.72-7.86 (m, 3H), 7.96-8.03 (m2H), 9.18 (t, J=6 Hz, 1H), 11.15 (s, 1H). $^{13}$C NMR (DMSO-$d_6$) δ: 21.97, 30.92, 38.35, 48.86, 115.15, 115.44, 121.87, 127.12, 129.91, 130.03, 130.37, 131.52, 133.05, 134.80, 139.21, 162.35, 165.54, 165.64, 166.95, 167.52, 169.82, 172.74. Anal Calcd for $C_{21}H_{16}FN_3O_5$: C, 66.61; H, 3.94; N, 10.26; F, 4.64. Found: C, 61.53; H, 3.82; N, 10.20; F, 4.72.

5.145 N-[2-(2,6-DIOXO-PIPERIDIN-3-YL)-1,3-DIOXO-2,3-DIHYDRO-1H-ISOINDOL-4-YLM-ETHYL]-2-(4-FLUORO-PHENYL)-ACETAMIDE

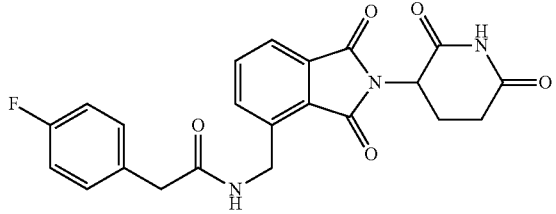 [SMILES: O=C(Cc1ccc(F)cc1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.70 g, 2.2 mmol) in $CH_3CN$ (60 ml), was added 1,8-diazabicyclo[5.4.0]undec-7-ene (0.82 g, 5.4 mmol). After stirring for 10 minutes, 1-hydroxybenzenetriazole (0.35 g, 2.6 mmol) and 4-fluorophenylacetic acid (0.37 g, 2.4 mmol) were added, followed by 1-(3-dimethylaminopropyl)-3-ethylcarbodiimide hydrochloride (0.62 g, 3.2 mmol). After stirring at room temperature overnight and was then concentrated in vacuo, and the residue was dissolved in $CH_2Cl_2$ (50 mL). The $CH_2Cl_2$ solution was washed with water (2×30 mL) and brine (30 mL), and dried over $MgSO_4$. The organic solvent was removed in vacuo, and the resulting oil was purified by ISCO silica gel flash chromatography (eluent: 0% MeOH in $CH_2Cl_2$ to 5% MeOH in 10 min then stay at this ratio for 15 min) to afford N-[2-(2,6-dioxo-piperidin-3-yl)-1,3-dioxo-2,3-dihydro-1H-isoindol-4-ylmethyl]-2-(4-fluoro-phenyl)-acetamide as a white solid (0.64 g, 65%): mp, 214-216° C.; HPLC: Waters Symmetry C-18, 3.9×150 mm, 5 micro, 1 mL/min, 240 nm, 40/60 ($CH_3CN/H_2O$): $t_R$=3.0 min (99%); $^1$H NMR (DMSO-$d_6$): δ 2.03-2.08 (m, 1H), 2.51-2.63 (m, 2H), 2.86-2.91 (m, 1H), 3.53 (s, 2H), 4.72 (d, J=6.0 Hz, 2H), 5.12-5.18 (dd, J=5, 12 Hz, 1H), 7.10-7.16 (m, 2H), 7.29-7.34 (m, 2H), 7.62-7.65 (m, 1H), 7.78-7.81 (m, 2H), 8.67 (t, J=5.9 Hz, 1H), 11.14 (s, 1H). $^{13}$C NMR (DMSO-$d_6$) δ: 21.95, 30.90, 37.83, 41.17, 48.82, 114.77, 115.05, 121.89, 127.12, 130.81, 130.92, 131.51, 132.24, 132.28, 133.19, 134.67, 139.09, 159.42, 162.62, 166.90, 167.42, 169.78, 170.51, 172.73. Anal Calcd for $C_{22}H_{18}FN_3O_5$: C, 62.41; H, 4.29; N, 9.92; F, 4.49. Found: C, 62.05; H, 4.18; N, 9.85; F, 4.48.

5.146 N-[2-(2,6-DIOXO-PIPERIDIN-3-YL)-1,3-DIOXO-2,3-DIHYDRO-1H-ISOINDOL-4-YLM-ETHYL]-2-(3-FLUORO-PHENYL)-ACETAMIDE

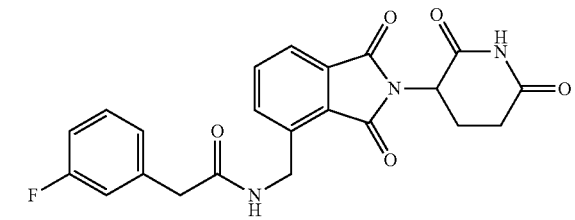

To a stirred suspension of 4-aminomethyl-2-(2,6-dioxo-piperidin-3-yl)-isoindole-1,3-dione hydrochloride (0.70 g, 2.2 mmol) in $CH_3CN$ (60 ml), was added 1,8-diazabicyclo[5.4.0]undec-7-ene (0.82 g, 5.4 mmol). After stirring for 10 minutes, 1-hydroxybenzenetriazole (0.35 g, 2.6 mmol) and 3-fluorophenylacetic acid (0.37 g, 2.4 mmol) were added, followed by 1-(3-dimethylaminopropyl)-3-ethylcarbodiimide hydrochloride (0.62 g, 3.2 mmol). After stirring at room temperature overnight, the mixture was concentrated in vacuo, and the residue was dissolved in $CH_2Cl_2$ (50 mL). The $CH_2Cl_2$ solution was then washed with water (2×30 mL) and brine (30 mL), and dried over $MgSO_4$. Solvent was removed in vacuo, and the resulting oil was purified by ISCO silica gel flash chromatography (eluent: 40% EtOAc in $CH_2Cl_2$ for 5 min then increase to 80% EtOAc in $CH_2Cl_2$ over 20 min.) to afford N-[2-(2,6-dioxo-piperidin-3-yl)-1,3-dioxo-2,3-dihydro-1H-isoindol-4-ylmethyl]-2-(3-fluoro-phenyl)-acetamide as a white solid (0.63 g, 69%): mp, 192-194° C.; HPLC: Waters Symmetry C-18, 3.9×150 mm, 5 micro, 1 mL/min, 240 nm, 40/60 ($CH_3CN/H_2O$): $t_R$=3.0 min (98%); $^1$H NMR (DMSO-$d_6$): δ 2.03-2.08 (m, 1H), 2.52-2.63 (m, 2H), 2.84-2.91 (m, 1H), 3.57 (s, 2H), 4.73 (d, J=5.9 Hz, 2H), 5.12-5.18 (dd, J=5, 12 Hz, 1H), 7.03-7.14 (m, 3H), 7.31-7.39 (m, 1H), 7.63-7.67 (m, 1H), 7.78-7.81 (m, 2H), 8.69 (t, J=6.0 Hz, 1H), 11.14 (s, 1H). $^{13}$C NMR (DMSO-$d_6$) δ: 21.94, 30.90, 37.86, 41.17, 48.82, 113.08, 113.35, 115.69, 115.98, 121.91, 125.19, 125.22, 127.13, 129.98, 130.09, 131.51, 133.22, 134.67, 138.77, 138.87, 139.03, 160.38, 163.60, 166.88, 167.41, 169.78, 170.06, 172.73. Anal Calcd for $C_{22}H_{18}FN_3O_5$: C, 62.41; H, 4.29; N, 9.92; F, 4.49. Found: C, 62.55; H, 4.04; N, 9.80; F, 4.36.

5.147 N-[2-(2,6-DIOXO-PIPERIDIN-3-YL)-1,3-DIOXO-2,3-DIHYDRO-1H-ISOINDOL-4-YLMETHYL]-2-(2-FLUORO-PHENYL)-ACETAMIDE

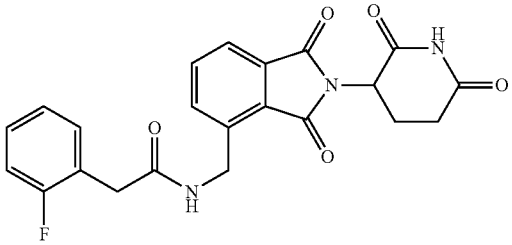 [SMILES: O=C(Cc1ccccc1F)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5.4.0]undec-7-ene (0.82 g, 5.4 mmol). After stirring for 10 minutes, 1-hydroxybenzotriazole (0.4 g, 2.6 mmol) and 2-fluorophenylacetic acid (0.4 g, 2.4 mmol) were added, followed by 1-(3-dimethylaminopropyl)-3-ethylcarbodiimide hydrochloride (0.6 g, 3.2 mmol). The reaction mixture was stirred at room temperature overnight and was then concentrated in vacuo. The residue was dissolved in $CH_2Cl_2$ (80 mL), and the solution was washed with water (40 mL), 1N HCl (2×30 mL), water (40 mL) and brine (40 mL), and dried over $MgSO_4$. Solvent was removed in vacuo, and the residue was purified by ISCO silica gel flash chromatography (eluent: EtOAc: $CH_2Cl_2$=4:6) to afford N-[2-(2,6-dioxo-piperidin-3-yl)-1,3-dioxo-2,3-dihydro-1H-isoindol-4-ylmethyl]-2-(2-fluoro-phenyl)-acetamide (0.7 g, 79%) as a white solid: mp 172-174° C.; HPLC: Waters Symmetry C-18, 3.9×150 mm, 5 micro, 1 mL/min, 240 nm, 40/60 ($CH_3CN/H_2O$): $t_R$=2.87 min. (98%); $^1H$ NMR (DMSO-$d_6$) δ 2.04-2.09 (m, 1H), 2.51-2.63 (m, 2H), 2.84-2.94 (m, 1H), 3.61 (s, 2H), 4.75 (d, J=5.9 Hz, 2H), 5.12-5.18 (dd, J=5.3 and 12.7 Hz, 1H), 7.12-7.38 (m, 4H), 7.68-7.86 (m, 3H), 8.70 (t, J=6.0 Hz, 1H), 11.14 (s, 1H); $^{13}C$ NMR (DMSO-$d_6$) δ 21.95, 30.90, 35.20, 37.87, 48.83, 114.83 (115.12), 121.88, 122.95 (123.17), 124.14 (124.19), 127.10, 128.60 (128.71), 131.51, 131.85 (131.91), 133.11, 134.68, 139.15, 158.96 (162.20), 166.90, 167.44, 169.59, 169.78, 172.73; Anal. Calcd. for $C_{22}H_{18}N_3O_5F$: C, 62.41; H, 4.29; N, 9.92; F, 4.49. Found: C, 62.65; H, 4.25; N, 9.95; F, 4.62.

5.148 2-(3,5-DIFLUORO-PHENYL)-N-[2-(2,6-DIOXO-PIPERIDIN-3-YL)-1,3-DIOXO-2,3-DIHYDRO-1H-ISINDOL-4-YLMETHYL]-ACETAMIDE

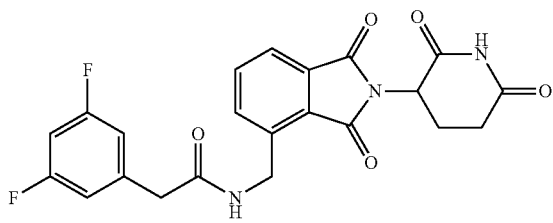

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 3,5-difluorophenylacetic acid (0.4 g, 2.4 mmol) were added followed by 1-(3-dimethylaminopropyl)-3-ethylcarbodiimide hydrochloride (0.6 g, 3.2 mmol). The mixture was stirred at room temperature overnight. The resulting suspension was filtered, and the solid was reslurried in hot acetone (15 mL) to afford 2-(3,5-difluoro-phenyl)-N-[2-(2,6-dioxo-piperidin-3-yl)-1,3-dioxo-2,3-dihydro-1H-isoindol-4-ylmethyl]-acetamide (0.5 g, 56%) as a white solid: mp, 238-240° C.; HPLC: Waters Symmetry C-18, 3.9×150 mm, 5 micro, 1 mL/min, 240 nm, 40/60 ($CH_3CN/H_2O$): $t_R$=3.63 min. (97%); $^1H$ NMR (DMSO-$d_6$) δ 2.02-2.07 (m, 1H), 2.51-2.63 (m, 2H), 2.84-2.96 (m, 1H), 3.60 (s, 2H), 4.73 (d, J=5.8 Hz, 2H), 5.12-5.18 (dd, J=5.3 and 12.7 Hz, 1H), 6.89-7.14 (m, 3H), 7.65-7.84 (m, 3H), 8.70 (t, J=5.8 Hz, 1H), 11.14 (s, 1H); $^{13}C$ NMR (DMSO-$d_6$) δ 21.94, 30.90, 37.91, 41.41, 48.83, 101.62 (101.95, 102.30), 112.18 (112.28, 112.41, 112.51), 121.95, 127.16, 131.52, 133.29, 134.68, 138.91, 140.24 (140.37, 140.50), 160.39 (160.57, 163.64, 163.82), 166.88, 167.41, 169.53, 169.77, 172.72; Anal. Calcd. for $C_{22}H_{17}N_3O_5F_2$: C, 59.87; H, 3.88; N, 9.52; F, 8.61. Found: C, 59.66; H, 3.83; N, 9.77; F, 8.47.

5.149 N-[2-(2,6-DIOXO-PIPERIDIN-3-YL)-1,3-DIOXO-2,3-DIHYDRO-1H-ISOINDOL-4-YLMETHYL]-2-(4-TRIFLUOROMETHOXY-PHENYL)-ACETAMIDE

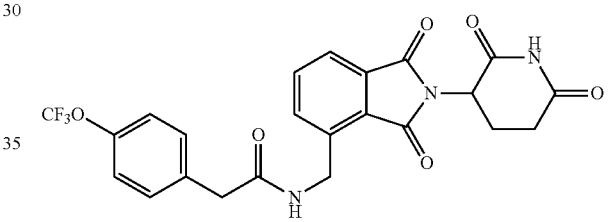

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 4-trifluoromethoxyphenylacetic acid (0.5 g, 2.4 mmol) were added, followed by 1-(3-dimethylaminopropyl)-3-ethylcarbodiimide hydrochloride (0.6 g, 3.2 mmol). After stirring at room temperature overnight, the reaction mixture was concentrated in vacuo. The residue was dissolved in $CH_2Cl_2$ (80 mL), and the solution was washed with water (40 mL), 1N HCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$=4:6) to afford N-[2-(2,6-dioxo-piperidin-3-yl)-1,3-dioxo-2,3-dihydro-1H-isoindol-4-ylmethyl]-2-(4-trifluoromethoxy-phenyl)-acetamide (0.7 g, 64%) as a white solid: mp 134-136° C.; HPLC: Waters Symmetry C-18, 3.9×150 mm, 5 micro, 1 mL/min, 240 nm, 40/60 ($CH_3CN/H_2O$): $t_R$=6.41 min. (98%); $^1H$ NMR (DMSO-$d_6$) δ 2.03-2.08 (m, 1H), 2.52-2.63 (m, 2H), 2.84-2.91 (m, 1H), 3.59 (s, 2H), 4.73 (d, J=5.8 Hz, 2H), 5.12-5.18 (dd, J=5.3 and 12.7 Hz, 1H), 7.29-7.32 (d, J=8.6 Hz, 2H), 7.40-7.43 (d, J=8.7 Hz, 2H), 7.63-7.82 (m, 2H), 8.72 (t, J=5.9 Hz, 1H), 11.14 (s, 1H); $^{13}C$ NMR (DMSO-$d_6$) δ 21.94, 30.90, 37.85, 41.23, 48.83, 120.81, 118.37 (121.76, 125.15), 121.91, 127.14, 130.91, 131.52, 133.22, 134.65, 135.64, 139.02, 147.02, 166.88, 167.41, 169.78, 170.21, 172.72; Anal. Calcd. for $C_{23}H_{18}N_3O_6F_3$: C, 56.45; H, 3.71; N, 8.59; F, 11.65. Found: C, 56.20; H, 3.39; N, 8.44; F, 11.87.

5.150 2-(3,5-BIS-TRIFLUOROMETHYL-PHENYL)-N-[2-(2,6-DIOXO-PIPERIDIN-3-YL)-1,3-DIOXO-2,3-DIHYDRO-1H-ISOINDOL-4-YLMETHYL]-ACETAMIDE

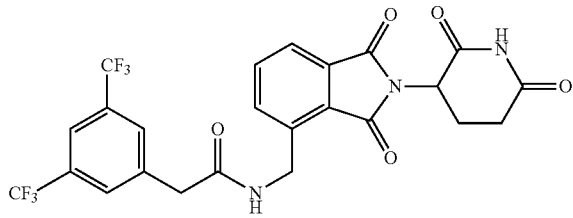 [SMILES: O=C(Cc1cc(C(F)(F)F)cc(C(F)(F)F)c1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 3,5-di-(trifluoromethyl)-phenylacetic acid (0.7 g, 2.4 mmol) were added, followed by 1-(3-dimethylaminopropyl)-3-ethylcarbodiimide hydrochloride (0.6 g, 3.2 mmol). The reaction mixture was stirred at room temperature overnight and was concentrated in vacuo. The residue was dissolved in $CH_2Cl_2$ (80 mL) and washed with water (40 mL), 1N HCl (2×30 mL), water (40 mL), and brine (40 mL), and dried over $MgSO_4$. Solvent was removed in vacuo, and the residue was purified by ISCO silica gel flash chromatography (eluent:EtOAc: $CH_2Cl_2$ 3:7) to afford 2-(3,5-bis-trifluoromethyl-phenyl)-N-[2-(2,6-dioxo-piperidin-3-yl)-1,3-dioxo-2,3-dihydro-1H-isoindol-4-ylmethyl]-acetamide (0.6 g, 54%) as a white solid: mp 202-204° C.; HPLC: Waters Symmetry C-18, 3.9×150 mm, 5 micro, 1 mL/min, 240 nm, 40/60 ($CH_3CN/H_2O$): $t_R$=13.69 min. (97%); $^1H$ NMR (DMSO-$d_6$) δ 2.03-2.08 (m, 1H), 2.51-2.63 (m, 2H), 2.84-2.92 (m, 1H), 3.82 (s, 2H), 4.75 (d, J=5.8 Hz, 2H), 5.12-5.18 (dd, J=5.3 and 12.7 Hz, 1H), 7.67-7.83 (m, 3H), 8.00 (s, 3H), 8.82 (t, J=5.8 Hz, 1H), 11.14 (s, 1H); $^{13}C$ NMR (DMSO-$d_6$) δ 21.93, 30.89, 37.91, 40.88, 48.83, 117.94, 120.21 (120.26, 120.31), 121.98, 117.94 (121.55, 125.17, 128.75), 127.19, 130.14, 129.28 (129.71, 130.57), 131.54, 133.27, 134.60, 138.86, 139.45, 166.87, 167.39, 169.43, 169.76, 172.71; Anal. Calcd. for $C_{24}H_{17}N_3O_5F_6$: C, 53.24; H, 3.16; N, 7.76; F, 21.05. Found: C, 53.16; H, 2.99; N, 7.73; F, 21.14.

5.151 (N-[2-(2,6-DIOXO-PIPERIDIN-3-YL)-1,3-DIOXO-2,3-DIHYDRO-1H-ISOINDOL-4-YLMETHYL]-2-(4-TRIFLUOROMETHYL-PHENYL)-ACETAMIDE

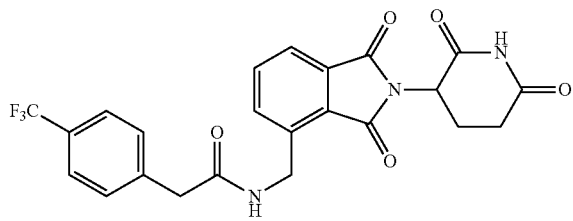 [SMILES: O=C(Cc1ccc(C(F)(F)F)cc1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 4-(trifluoromethyl)phenylacetic acid (0.6 g, 2.4 mmol) were added, followed by 1-(3-dimethylaminopropyl)-3-ethylcarbodiimide hydrochloride (0.6 g, 3.2 mmol). After stirring at room temperature overnight, the reaction mixture was concentrated in vacuo. The residue was dissolved in $CH_2Cl_2$ (80 mL) then washed with water (40 mL), 1N HCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$ 4:6) to afford N-[2-(2,6-dioxo-piperidin-3-yl)-1,3-dioxo-2,3-dihydro-1H-isoindol-4-ylmethyl]-2-(4-trifluoromethyl-phenyl)-acetamide (0.7 g, 71%) as a white solid: mp 144-146° C.; HPLC: Waters Symmetry C-18, 3.9×150 mm, 5 micro, 1 mL/min, 240 nm, 40/60 ($CH_3CN/H_2O$): $t_R$=5.58 min. (97%); $^1H$ NMR (DMSO-$d_6$) δ 2.03-2.08 (m, 1H), 2.51-2.63 (m, 2H), 2.84-2.91 (m, 1H), 3.66 (s, 2H), 4.74 (d, J=5.9 Hz, 2H), 5.12-5.18 (dd, J=5.3 and 12.7 Hz, 1H), 7.50-7.82 (m, 7H), 8.75 (t, J=5.8 Hz, 1H), 11.14 (s, 1H); $^{13}C$ NMR (DMSO-$d_6$) δ 21.94, 30.90, 37.89, 41.75, 48.83, 121.93, 124.95 (125.01, 125.05, 125.10), 122.56 (126.16), 126.96 (127.15, 127.38), 129.94, 131.52, 133.26, 134.69, 138.95, 140.95, 166.88, 167.41, 169.78, 169.87, 172.73; Anal. Calcd. for $C_{23}H_{18}N_3O_5F_3$: C, 58.35; H, 3.83; N, 8.88; F, 12.04. Found: C, 58.19; H, 3.53; N, 8.73; F, 12.07.

5.152 N-[2-(2,6-DIOXO-PIPERIDIN-3-YL)-1,3-DIOXO-2,3-DIHYDRO-1H-ISOINDOL-4-YLMETHYL]-2-(3-TRIFLUOROMETHYL-PHENYL)-ACETAMIDE

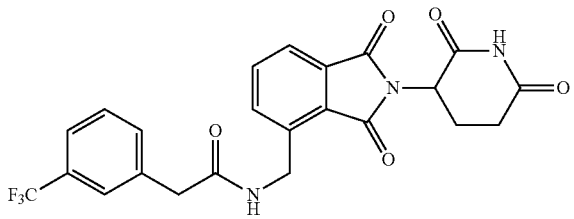 [SMILES: O=C(Cc1cccc(C(F)(F)F)c1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 3-(trifluoromethyl)phenylacetic acid (0.6 g, 2.4 mmol) were added, followed by 1-(3-dimethylaminopropyl)-3-ethylcarbodiimide hydrochloride (0.6 g, 3.2 mmol). The mixture was stirred at room temperature overnight then was concentrated in vacuo. The residue was dissolved in $CH_2Cl_2$ (80 mL) and washed with water (40 mL), 1N HCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$ 3:7) to afford N-[2-(2,6-dioxo-piperidin-3-yl)-1,3-dioxo-2,3-dihydro-1H-isoindol-4-ylmethyl]-2-(3-trifluoromethyl-phenyl)-acetamide (0.7 g, 70%) as a white solid: mp 156-158° C.; HPLC: Waters Symmetry C-18, 3.9×150 mm, 5 micro, 1 mL/min, 240 nm, 40/60 ($CH_3CN/H_2O$): $t_R$=5.36 min. (98%); $^1H$ NMR (DMSO-$d_6$) δ 2.03-2.09 (m, 1H), 2.51-2.63 (m, 2H), 2.84-2.91 (m, 1H), 3.67 (s, 2H), 4.74 (d, J=5.8 Hz, 2H), 5.12-5.18 (dd, J=5.3 and 12.7 Hz, 1H), 7.52-7.82 (m, 7H), 8.77 (t, J=5.9 Hz, 1H), 11.14 (s, 1H); $^{13}C$ NMR (DMSO-$d_6$) δ 21.94, 30.90, 37.84, 41.53, 48.83, 121.94, 123.12 (123.17, 123.22), 125.50 (125.56, 125.60, 125.66), 127.15, 128.68, 129.09, 129.23, 131.53, 133.19, 133.31, 134.61, 137.51, 138.99, 166.88, 167.40, 179.77, 170.00, 172.72; Anal. Calcd.

5.153 N-[2-(2,6-DIOXO-PIPERIDIN-3-YL)-1,3-DIOXO-2,3-DIHYDRO-1H-ISOINDOL-4-YLMETHYL]-2-(3-TRIFLUOROMETHOXY-PHENYL)-ACETAMIDE

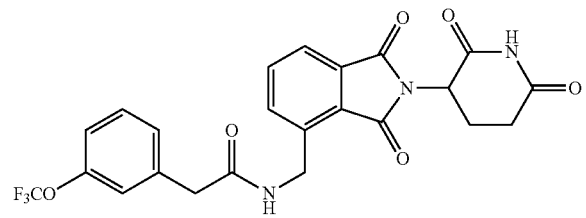 [SMILES: O=C(Cc1cccc(OC(F)(F)F)c1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 3-trifluoromethoxyphenylacetic acid (0.5 g, 2.4 mmol) were added, followed by 1-(3-dimethylaminopropyl)-3-ethylcarbodiimide hydrochloride (0.6 g, 3.2 mmol). The mixture was stirred at room temperature overnight then was concentrated in vacuo. The residue was dissolved in $CH_2Cl_2$ (80 mL) and washed with water (40 mL), 1NHCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$ 3:7) to afford N-[2-(2,6-dioxo-piperidin-3-yl)-1,3-dioxo-2,3-dihydro-1H-isoindol-4-ylmethyl]-2-(3-trifluoromethoxy-phenyl)-acetamide (0.8 g, 74%) as a white solid: mp 178-180° C.; HPLC: Waters Symmetry C-18, 3.9×150 mm, 5 micro, 1 mL/min, 240 nm, 40/60 ($CH_3CN/H_2O$): $t_R$=6.32 min. (97%); $^1H$ NMR (DMSO-$d_6$) δ 2.02-2.09 (m, 1H), 2.52-2.63 (m, 2H), 2.84-2.96 (m, 1H), 3.83 (s, 2H), 4.72 (d, J=5.8 Hz, 2H), 5.12-5.18 (dd, J=5.3 and 12.7 Hz, 1H), 7.23-8.10 (m, 7H), 8.74 (t, J=5.9 Hz, 1H), 11.14 (s, 1H); $^{13}C$ NMR (DMSO-$d_6$) δ 21.94, 30.90, 37.84, 48.83, 118.96, 121.43, 121.93, 127.15, 128.29, 130.07, 131.53, 133.15, 134.61, 138.80, 139.00, 148.24, 166.88, 167.41, 169.77, 169.96, 172.72; Anal. Calcd. for $C_{23}H_{18}N_3O_6F_3$: C, 56.45; H, 3.71; N, 8.59; F, 11.65. Found: C, 56.44; H, 3.44; N, 8.46; F, 11.89.

5.154 N-[2-(2,6-DIOXO-PIPERIDIN-3-YL)-1,3-DIOXO-2,3-DIHYDRO-1H-ISOINDOL-4-YLMETHYL]-2-(3-FLUORO-4-METHYL-PHENYL)-ACETAMIDE

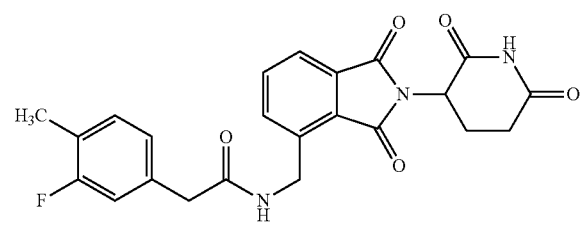 [SMILES: Cc1ccc(CC(=O)NCc2cccc3c2C(=O)N(C2CCC(=O)NC2=O)C3=O)cc1F]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotraiazole (0.4 g, 2.6 mmol) and 3-fluoro-4-methylphenylacetic acid (0.4 g, 2.4 mmol) were added, followed by 1-(3-dimethylaminopropyl)-3-ethylcarbodiimide hydrochloride (0.6 g, 3.2 mmol). The mixture was stirred at room temperature overnight then was concentrated in vacuo. The residue was dissolved in $CH_2Cl_2$ (80 mL) and washed with water (40 mL), 1NHCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$ 3:7) to afford N-[2-(2,6-dioxo-piperidin-3-yl)-1,3-dioxo-2,3-dihydro-1H-isoindol-4-ylmethyl]-2-(3-fluoro-4-methyl-phenyl)-acetamide (0.7 g, 70%) as a white solid: mp 148-150° C.; HPLC: Waters Symmetry C-18, 3.9×150 mm, 5 micro, 1 mL/min, 240 nm, 40/60 ($CH_3CN/H_2O$): $t_R$=4.06 min. (98%); $^1H$ NMR (DMSO-$d_6$) δ 2.04-2.07 (m, 1H), 2.20 (s, 3H), 2.52-2.63 (m, 2H), 2.84-2.96 (m, 1H), 3.52 (s, 2H), 4.70 (d, J=5.7 Hz, 2H), 5.12-5.18 (dd, J=5.1 and 12.7 Hz, 1H), 6.99-7.07 (dd, J=11.2 and 14.7 hz, 2H), 7.21 (t, J=8.0 Hz, 1H), 7.63-7.76 (dd, J=3.3 and 7.5 Hz, 1H), 7.77-7.83 (dd, J=7.6 and 11.9 Hz, 2H), 8.65 (t, J=5.8 Hz, 1H), 11.14 (s, 1H); $^{13}C$ NMR (DMSO-$d_6$) δ 13.74 (13.78), 21.95, 30.90, 37.84, 41.41, 48.83, 115.31, 115.60, 121.89, 124.84 (124.87), 127.12, 131.02 (131.28), 131.51, 133.20, 134.66, 135.87 (135.97), 139.09, 158.77 (161.98), 166.90, 167.42, 169.78, 170.26, 172.73; Anal. Calcd. for $C_{23}H_{20}N_3O_5F$: C, 63.15; H, 4.61; N, 9.61; F, 4.34. Found: C, 62.78; H, 4.45; N, 9.32; F, 4.47.

5.155 2-(3,5-DIMETHOXY-PHENYL)-N-[2-(2,6-DIOXO-PIPERIDIN-3-YL)-1,3-DIOXO-2,3-DIHYDRO-1H-ISOINDOL-4-YLMETHYL]-ACETAMIDE

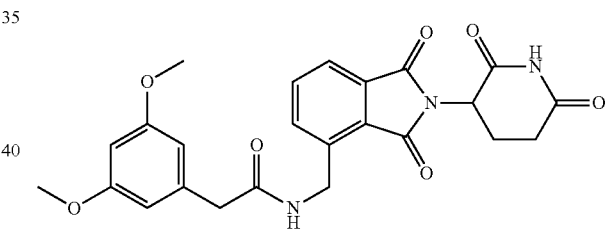

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 3,5-dimethoxyphenylacetic acid (0.5 g, 2.4 mmol) were added, followed by 1-(3-dimethylaminopropyl)-3-ethylcarbodiimide hydrochloride (0.6 g, 3.2 mmol). The mixture was stirred at room temperature overnight and was then concentrated in vacuo. The residue was dissolved in $CH_2Cl_2$ (80 mL) and washed with water (40 mL), 1NHCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$ 3:7) to afford 2-(3,5-dimethoxy-phenyl)-N-[2-(2,6-dioxo-piperidin-3-yl)-1,3-dioxo-2,3-dihydro-1H-isoindol-4-ylmethyl]-acetamide (0.8 g, 79%) as a white solid: mp 294-296° C.; HPLC: Waters Symmetry C-18, 3.9×150 mm, 5 micro, 1 mL/min, 240 nm, 40/60 ($CH_3CN/H_2O$): $t_R$=2.88 min. (98%); $^1H$ NMR (DMSO-$d_6$) δ 2.03-2.07 (m, 1H), 2.52-2.63 (m, 2H), 2.84-2.94 (m, 1H), 3.45 (s, 2H), 3.71 (s, 6H), 4.70 (d, J=5.9 Hz, 2H), 5.12-5.18 (dd, J=5.3 and 12.8 Hz, 1H), 6.37 (t, J=2.2 Hz, 1H), 6.46 (d, J=2.2 Hz, 2H), 7.51-7.67 (m, 1H), 7.72-7.81 (m, 2H), 8.61 (t, J=5.9 Hz, 1H), 11.13 (s, 1H); $^{13}C$ NMR (DMSO-d$_6$) δ 21.94, 30.90, 37.83, 42.51, 48.82, 55.05, 98.34, 107.08, 121.88, 127.12, 131.51, 133.17, 134.61, 138.20, 139.18, 160.28, 166.90, 167.42, 169.77, 170.34, 172.73; Anal. Calcd. for C$_{24}$H$_{23}$N$_3$O$_7$: C, 61.93; H, 4.98; N, 9.03. Found: C, 61.62; H, 4.61; N, 8.91.

5.156 2-(4-CHLORO-PHENYL)-N-[2-(2,6-DIOXO-PIPERIDIN-3-YL)-1,3-DIOXO-2,3-DIHYDRO-1H-ISOINDOL-4-YLMETHYL]-ACETAMIDE

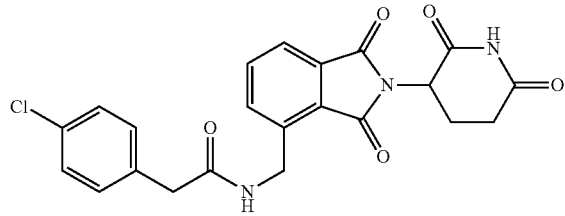 [SMILES: O=C(Cc1ccc(Cl)cc1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.4 mmol) and 4-chlorophenylacetic acid (0.4 g, 2.4 mmol) were added, followed by 1-(3-dimethylaminlpropyl)-3-ethylcarbodiimide hydrochloride (0.6 g, 3.2 mmol). The mixture was stirred at room temperature overnight then was filtered. The solid was slurried with hot acetone (15 mL) to afford 2-(4-chloro-phenyl)-N-[2-(2,6-dioxo-piperidin-3-yl)-1,3-dioxo-2,3-dihydro-1H-isoindol-4-ylmethyl]-acetamide (0.8 g, 82%) as a white solid: mp 243-245° C.; HPLC: Waters Symmetry C-18, 3.9×150 mm, 5 micro, 1 mL/min, 240 nm, 40/60 (CH$_3$CN/H$_2$O): t$_R$=4.04 min. (86%); $^1$H NMR (DMSO-d$_6$) δ 2.02-2.08 (m, 1H), 2.51-2.63 (m, 2H), 2.84-2.96 (m, 1H), 3.54 (s, 2H), 4.72 (d, J=5.9 Hz, 2H), 5.12-5.18 (dd, J=5.3 and 12.8 Hz, 1H), 7.29-7.38 (m, 4H), 7.61-7.67 (m, 1H), 7.71-7.83 (m, 2H), 8.68 (t, J=5.8 Hz, 1H), 11.14 (s, 1H); $^{13}$C NMR (DMSO-d$_6$) δ 21.95, 30.90, 37.86, 41.31, 48.83, 121.90, 127.13, 128.14, 130.94, 131.14, 131.52, 133.22, 134.69, 135.11, 139.95, 166.89, 167.42, 169.78, 170.24, 172.73; Anal. Calcd. for C$_{22}$H$_{18}$N$_3$O$_5$Cl: C, 60.08; H, 4.12; N, 9.55; Cl, 8.06. Found: C, 60.06; H, 3.85; N, 9.67; Cl, 8.07.

5.157 2-BENZO[1,3]DIOXO-5-YL-N-[2-(2,6-DIOXO-PIPERIDIN-3-YL)-1,3-DIOXO-2,3-DIHYDRO-1H-ISOINDOL-4-YLMETHYL]-ACETAMIDE

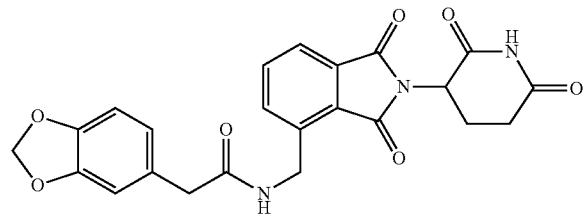 [SMILES: O=C(Cc1ccc2c(c1)OCO2)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.1 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 3,4-(methylenedioxy)-phenylacetic acid (0.4 g, 2.4 mmol) were added, followed by 1-(3-dimethylaminopropyl)-3-ethylcarbodiimide hydrochloride (0.6 g, 3.2 mmol). The mixture was stirred at room temperature overnight then was concentrated in vacuo. The residue was dissolved in CH$_2$Cl$_2$ (80 mL) and washed with water (40 mL), 1NHCl (2×30 mL), water (40 mL), and brine (40 mL), and dried over MgSO$_4$. Solvent was removed in vacuo, and the residue was purified by ISCO silica gel flash chromatography (Eluent: EtOAc: CH$_2$Cl$_2$ 3:7) to afford 2-benzo[1,3]dioxo-5-yl-N-[2-(2,6-dioxo-piperidin-3-yl)-1,3-dioxo-s,3-dihydro-1H-isoindol-4-ylmethyl]-acetamide (0.8 g, 77%) as a white solid: mp 196-198° C.; HPLC: Waters Symmetry C-18, 3.9×150 mm, 5 micro, 1 mL/min, 240 nm, 40/60 (CH$_3$CN/H$_2$O): t$_R$=2.59 min. (98%); $^1$H NMR (DMSO-d$_6$) δ 2.03-2.07 (m, 1H), 2.52-2.63 (m, 2H), 2.84-2.96 (m, 1H), 3.44 (s, 2H), 4.71 (d, J=5.7 Hz, 2H), 5.12-5.18 (dd, J=5.2 and 12.7 Hz, 1H), 5.97 (m, 2H), 6.73-6.75 (m, 1H), 6.83-6.85 (m, 2H), 7.61-7.66 (m, 1H), 7.79-7.83 (m, 2H), 8.56 (t, J=5.9 Hz, 1H), 11.13 (s, 1H); $^{13}$C NMR (DMSO-d$_6$) δ 21.95, 30.90, 37.84, 41.78, 48.83, 100.73, 108.01, 109.48, 121.87, 1222.04, 127.11, 129.70, 131.51, 133.18, 134.66, 139.18, 145.80, 147.07, 166.90, 167.42, 169.78, 170.73, 172.73; Anal. Calcd. for C$_{23}$H$_{19}$N$_3$O$_7$: C, 61.47; H, 4.26; N, 9.35. Found: C, 61.53; H, 3.94; N, 9.16.

5.158 N-[2-(2,6-DIOXO-PIPERIDIN-3-YL)-1,3-DIOXO-2,3-DIHYDRO-1H-ISOINDOL-4-YLMETHYL]-2-PYRIDINYL-2-YL-ACETAMIDE

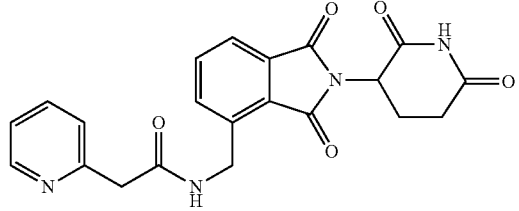 [SMILES: O=C(Cc1ccccn1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 2-pyridylacetic acid hydrochloride (0.4 g, 2.4 mmol) were added, followed by 1-(3-dimethylaminopropyl)-3-ethylcarbodiimide hydrochloride (0.6 g, 3.2 mmol). The mixture was stirred at room temperature overnight then was concentrated in vacuo. The residue was dissolved in CH$_2$Cl$_2$ (80 mL) and washed with water (3×40 mL) and brine (40 mL), and dried over MgSO$_4$. Solvent was removed in vacuo, and the residue was purified by ISCO silica gel flash chromatography (Eluent: CH$_3$OH/CH$_2$Cl$_2$ 3:97) to afford N-[2-(2,6-dioxo-piperidin-3-yl)-1,3-dioxo-2,3-dihydro-1H-isoindol-4-ylmethyl]-2-pyridinyl-2-yl-acetamide (0.7 g, 74%) as a white solid: mp 146-148° C.; HPLC: Waters Symmetry C-18, 3.9×150 mm, 5 micro, 1 mL/min, 240 nm, 40/60 (CH$_3$CN/H$_2$O): t$_R$=0.91 min. (96%); $^1$H NMR (DMSO-d$_6$) δ 2.02-2.09 (m, 1H), 2.53-2.63 (m, 2H), 2.84-2.96 (m, 1H), 3.74 (s, 2H), 4.75 (d, J=5.9 Hz, 2H), 5.12-5.18 (dd, J=5.2 and 12.7 Hz, 1H), 7.24-7.37 (m, 2H), 7.71-7.85 (m, 4H), 8.50-8.52 (d, J=0.8 and 4.9 Hz, 1H), 8.74 (t, J=5.9 Hz, 1H), 11.14 (s, 1H); $^{13}$C NMR (DMSO-d$_6$) δ 21.95, 30.91, 37.94, 44.77, 48.83, 121.81, 123.84, 127.07, 131.48, 133.23, 134.66, 136.52, 139.14, 148.92, 156.09,

5.159 N-[2-(2,6-DIOXO-PIPERIDIN-3-YL)-1,3-DIOXO-2,3-DIHYDRO-1H-ISOINDOL-4-YLMETHYL]-2-PYRIDINYL-3-YL-ACETAMIDE

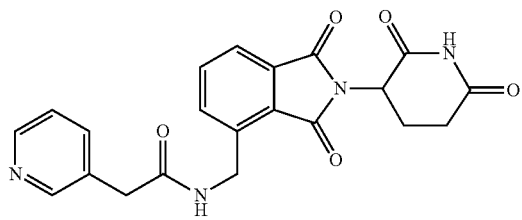 [SMILES: O=C(Cc1cccnc1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 3-pyridylacetic acid hydrochloride (0.4 g, 2.4 mmol) were added, followed by 1-(3-diemthylaminopropyl)-3-ethylcarbodiimide hydrochloride (0.6 g, 3.2 mmol). The mixture was stirred at room temperature overnight then was concentrated in vacuo. The residue was dissolved in CH$_2$Cl$_2$ (80 mL) and washed with water (3×40 mL) and brine (40 mL), and dried over MgSO$_4$. Solvent was removed in vacuo, and residue was purified by ISCO silica gel flash chromatography (Eluent: CH$_3$OH: CH$_2$Cl$_2$ 3:97) to afford N-[2-(2,6-dioxo-piperidin-3-yl)-1,3-dioxo-2,3-dihydro-1H-isoindol-4-ylmethyl]-2-pyridinyl-3-yl-acetamide (0.5 g, 57%) as a white solid: mp 292-294° C.; HPLC: Waters Symmetry C-18, 3.9×150 mm, 5 micro, 1 mL/min, 240 nm, 40/60 (CH$_3$CN/H$_2$O): t$_R$=0.87 min. (97%); $^1$H NMR (DMSO-d$_6$) δ 2.04-2.07 (m, 1H), 2.52-2.63 (m, 2H), 2.84-2.96 (m, 1H), 3.59 (s, 2H), 4.74 (d, J=5.8 Hz, 2H), 5.12-5.18 (dd, J=5.2 and 12.7 Hz, 1H), 7.32-7.36 (m, 1H), 7.65-7.71 (m, 2H), 7.80-7.84 (m, 2H), 8.43-8.49 (m, 2H), 8.75 (t, J=5.8 Hz, 1H), 11.14 (s, 1H); $^{13}$C NMR (DMSO-d$_6$) δ21.95, 30.90, 37.89, 39.03, 48.83, 121.93, 123.33, 127.15, 131.52, 131.79, 133.26, 134.70, 136.64, 138.97, 147.65, 150.01, 166.89, 167.41, 169.78, 170.03, 172.73; Anal. Calcd. for C$_{21}$H$_{18}$N$_4$O$_5$: C, 62.07; H, 4.46; N, 13.79. Found: C, 61.73; H, 4.46; N, 13.55.

5.160 N-[2-(2,6-DIOXO-PIPERIDIN-3-YL)-1,3-DIOXO-2,3-DIHYDRO-1H-ISOINDOL-4-YLMETHYL]-2-PYRIDIN-4-YL-ACETAMIDE

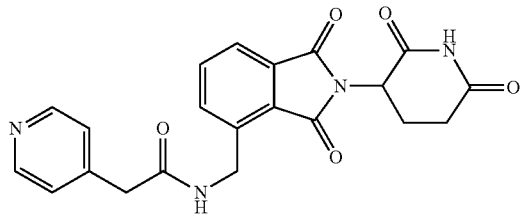 [SMILES: O=C(Cc1ccncc1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (1.2 g, 7.8 mmol). After stirring for 10 minutes, 1-hydroxybenzotriazole (0.4 g, 2.6 mmol) and 4-pyridylacetic acid hydrochloride (0.4 g, 2.4 mmol) were added, followed by 1-(3-dimethylaminopropyl)-3-ethylcarbodiimide hydrochloride (0.6 g, 3.2 mmol). The mixture was stirred at room temperature overnight. Solvent was removed in vacuo, and the residue was purified by ISCO silica gel flash chromatography (Eluent: CH$_3$OH: CH$_2$Cl$_2$ 3:97) to afford N-[2-(2,6-dioxo-piperidin-3-yl)-1,3-dioxo-2,3-dihydro-1H-isoindol-4-ylmethyl]-2-pyridin-4-yl-acetamide (0.4 g, 50%) as white solid: mp 294-296° C.; HPLC: Waters Symmetry C-18, 3.9×150 mm, 5 micro, 1 mL/min, 240 nm, 40/60 (CH$_3$CN/H$_2$O): t$_R$=0.87 min. (98%); $^1$H NMR (DMSO-d$_6$) δ 2.02-2.07 (m, 1H), 2.52-2.96 (m, 2H), 2.84-2.96 (m, 1H), 3.59 (s, 2H), 5.12-5.18 (dd, J=5.2 and 12.7 Hz, 1H), 7.31 (d, J=5.5 Hz, 2H), 7.64-7.70 (m, 1H), 7.79-7.84 (m, 2H), 8.50 (d, J=5.6 Hz, 2H), 8.77 (t, J=5.8 Hz, 1H), 11.14 (s, 1H); $^{13}$C NMR (DMSO-d$_6$) δ 21.95, 30.90, 37.91, 41.27, 48.83, 121.96, 124.54, 127.17, 131.53, 133.30, 134.71, 138.88, 144.92, 149.37, 166.88, 167.41, 169.33, 169.78, 172.73; Anal. Calcd. for C$_{21}$H$_{18}$N$_4$O$_5$: C, 62.07; H, 4.46; N, 13.79. Found: C, 61.77; H, 4.39; N, 13.59.

5.161 N-[2-(2,6-DIOXO-PIPERIDIN-3-YL)-1,3-DIOXO-2,3-DIHYDRO-1H-ISOINDOL-4-YLMETHYL]-2-NAPHTHALEN-1-YL-ACETAMIDE

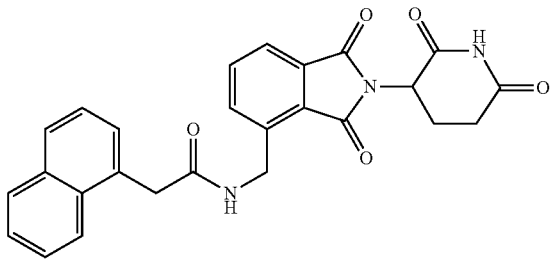 [SMILES: O=C(Cc1cccc2ccccc12)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 1-naphthylacetic acid (0.4 g, 2.4 mmol) were added, followed by 1-(3-dimethylaminopropyl)-3-ethylcarbodiimide hydrochloride (0.6 g, 3.2 mmol). The mixture was stirred at room temperature overnight then was concentrated in vacuo. The residue was dissolved in CH$_2$Cl$_2$ (80 mL), washed with water (40 mL), 1NHCl (2×30 mL), water (40 mL), and brine (40 mL), and dried over MgSO$_4$. Solvent was removed in vacuo, and the residue was purified by ISCO silica gel flash chromatography (Eluent: EtOAc: CH$_2$Cl$_2$ 3:7) to afford N-[2-(2,6-dioxo-piperidin-3-yl)-1,3-dioxo-2,3-dihydro-1H-isoindol-4-ylmethyl]-2-naphthalen-1-yl-acetamide (0.7 g, 74%) as a white solid: mp 187-189° C.; HPLC: Waters Symmetry C-18, 3.9×150 mm, 5 micro, 1 mL/min, 240 nm, 40/60 (CH$_3$CN/H$_2$O): t$_R$=4.70 min. (98%); $^1$H NMR (DMSO-d$_6$) δ 1.98-2.06 (m, 1H), 2.54-2.63 (m, 2H), 2.83-2.96 (m, 1H), 4.03 (s, 2H), 4.74 (d, J=5.8 Hz, 2H), 5.11-5.17 (dd, J=5.2 and 12.8 Hz, 1H), 7.43-8.11 (m, 10H), 8.71 (t, J=4.6 Hz, 1H), 11.13 (s, 1H); $^{13}$C NMR (DMSO-d$_6$) δ 21.95, 30.90, 37.89, 48.82, 121.86, 124.17, 125.52, 125.64, 125.95, 127.11, 127.15, 127.92, 128.37, 131.48, 131.90, 132.47, 133.23, 133.33, 134.56, 139.23, 166.89, 167.42, 169.77, 170.60, 172.72; Anal. Calcd. for C$_{26}$H$_{21}$N$_3$O$_5$: C, 68.56; H, 4.65; N, 9.23. Found: C, 68.24; H, 4.54; N, 9.19.

5.162 2-(4,5-DIMETHYL-FURAN-2-YL)-N-[2-(2, 6-DIOXO-PIPERIDIN-3-YL)-1,3-DIOXO-2,3-DI-HYDRO-1H-ISOINDOL-4-YLMETHYL]-ACETAMIDE

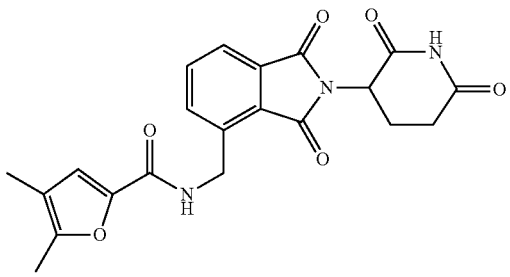 [SMILES: Cc1cc(C(=O)NCc2cccc3c2C(=O)N(C2CCC(=O)NC2=O)C3=O)oc1C]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo [5,4,0]undec-7-ene (0.8 g, 5.4 mmol). After stirring for 10 minutes, 1-hydroxybenzotriazole (0.4 g, 2.6 mmol) and 4,5-dimethyl-2-furoic acid (0.3 g, 2.4 mmol) were added, followed by 1-(3-dimethylaminopropyl)-3-ethylcarbodiimide hydrochloride (0.6 g, 3.2 mmol). The mixture was stirred at room temperature overnight and was concentrated in vacuo. The residue was dissolved in $CH_2Cl_2$ (80 mL), washed with water (40 mL), 1NHCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$ 3:7) to afford 2-(4, 5-dimethyl-furan-2-yl)-N-[2-(2,6-dioxo-piperidin-3-yl)-1,3-dioxo-2,3-dihydro-1H-isoindol-4-ylmethyl]-acetamide (0.6 g, 72%) as a white solid: mp 221-223° C.; HPLC: Waters Symmetry C-18, 3.9×150 mm, 5 micro, 1 mL/min, 240 nm, 40/60 ($CH_3CN/H_2O$): $t_R$=2.85 min. (99%); $^1H$ NMR (DMSO-$d_6$) δ 1.95 (s, 3H), 2.05-2.11 (m, 1H), 2.26 (s, 3H), 2.52-2.64 (m, 2H), 2.85-2.97 (m, 1H), 4.86 (d, J=6.0 Hz, 2H), 5.13-5.19 (dd, J=5.3 and 12.6 Hz, 1H), 6.95 (s, 1H), 7.65-7.85 (m, 3H), 8.81 (t, J=6.0 Hz, 1H), 11.14 (s, 1H); $^{13}C$ NMR (DMSO-$d_6$) δ 9.41, 11.41, 21.96, 30.91, 37.55, 48.84, 116.30, 117.01, 121.80, 127.01, 131.48, 132.88, 134.76, 139.33, 144.63, 150.08, 158.18, 166.95, 167.52, 169.81, 172.74; Anal. Calcd. for $C_{21}H_{19}N_3O_6$: C, 61.61; H, 4.68; N, 10.36. Found: C, 61.63; H, 4.43; N, 10.03.

5.163 2-(2,5-DIMETHYL-FURAN-3-YL)-N-[2-(2, 6-DIOXO-PIPERIDIN-3-YL)-1,3-DIOXO-2,3-DI-HYDRO-1H-ISOINDOL-4-YLMETHYL]-ACETAMIDE

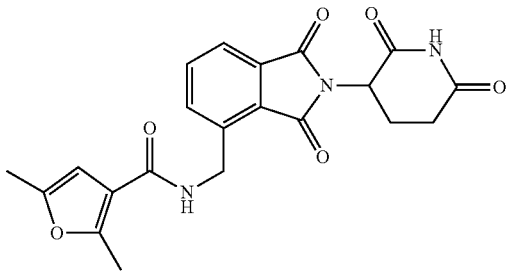 [SMILES: Cc1cc(C(=O)NCc2cccc3c2C(=O)N(C2CCC(=O)NC2=O)C3=O)c(C)o1]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo [5,4,0]undec-7-ene (0.8 g, 5.4 mmol). After stirring for 10 minutes, 1-hydroxybenzotriazole (0.4 g, 2.6 mmol) and 2,5-dimethyl-3-furoic acid (0.3 g, 2.4 mmol) were added, followed by 1-(3-dimethylaminopropyl)-3-ethylcarbodiimide hydrochloride (0.6 g, 3.2 mmol). The mixture was stirred at room temperature overnight and was concentrated in vacuo. The residue was dissolved in $CH_2Cl_2$ (80 mL) and washed with water (40 mL), 1NHCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$ 3:7) to afford 2-(2, 5-dimethyl-furan-3-yl)-N-[2-(2,6-dioxo-piperidin-3-yl)-1,3-dioxo-2,3-dihydro-1H-isoindol-4-ylmethyl]-acetamide (0.65 g, 73%) as a white solid: mp 193-195° C.; HPLC: Waters Symmetry C-18, 3.9×150 mm, 5 micro, 1 mL/min, 240 nm, 40/60 ($CH_3CN/H_2O$): $t_R$=3.45 min. (99%); $^1H$ NMR (DMSO-$d_6$) δ 2.06-2.11 (m, 1H), 2.23 (s, 3H), 2.46 (s, 3H), 2.54-2.63 (m, 2H), 2.85-2.97 (m, 1H), 4.85 (d, J=5.9 Hz, 2H), 5.14-5.20 (dd, J=5.3 and 12.6 Hz, 1H), 6.49 (s, 1H), 7.67-7.86 (m, 3H), 8.54 (t, J=5.9 Hz, 1H), 11.14 (s, 1H); $^{13}C$ NMR (DMSO-$d_6$) δ 12.98, 13.08, 21.96, 30.92, 37.53, 48.85, 104.86, 115.84, 121.77, 126.99, 131.48, 132.99, 134.76, 139.69, 149.11, 154.47, 163.32, 166.96, 167.54, 169.81, 172.74; Anal. Calcd. for $C_{21}H_{19}N_3O_6$: C, 61.61; H, 4.68; N, 10.26. Found: C, 61.66; H, 4.37; N, 9.99.

5.164 N-[2-(2,6-DIOXO-PIPERIDIN-3-YL)-1,3-DIOXO-2,3-DIHYDRO-1H-ISOINDOL-4-YLM-ETHYL]2-(6-METHOXY-BENZOFURAN-3-YL)-ACETAMIDE

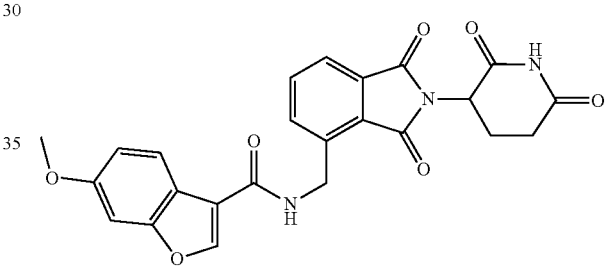

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo [5,4,0]undec-7-ene (0.8 g, 5.4 mmol). After stirring for 10 minutes, 1-hydroxybenzotriazole (0.4 g, 2.6 mmol) and 2-(6-methoxy-1-benzofuran-3-yl)-acetic acid were added, followed by 1-(3-dimethylaminopropyl)-3-ethylcarbodiimide hydrochloride (0.6 g, 3.2 mmol). After stirring at room temperature overnight, the mixture was concentrated in vacuo. The residue was dissolved in $CH_2Cl_2$ (80 mL) and washed with water (40 mL), 1NHCl (2×30 mL), water (40 mL), and brine (40 mL), and dried over $MgSO_4$. Solvent was removed in vacuo, and the residue was purified by ISCO silica gel flash chromatography (Eluent: EtOAc: $CH_2Cl_2$ 3:7) to afford N-[2-(2,6-dioxo-piperidin-3-yl)-1,3-dioxo-2,3-dihydro-1H-isoindol-4-ylmethyl]2-(6-methoxy-benzofuran-3-yl)-acetamide (0.76 g, 73%) as a white solid: mp 143-145° C.; HPLC: Waters Symmetry C-18, 3.9×150 mm, 5 micro, 1 mL/min, 240 nm, 40/60 ($CH_3CN/H_2O$): $t_R$=3.41 min. (98%); $^1H$ NMR (DMSO-$d_6$) δ 2.03-2.07 (m, 1H), 2.51-2.63 (m, 2H), 2.84-2.91 (m, 1H), 3.60 (s, 2H), 3.79 (s, 3H), 4.74 (d, J=5.9 Hz, 2H), 5.12-5.18 (dd, J=5.3 and 12.8 Hz, 1H), 6.85-6.89 (dd, J=2.2 and 8.6 Hz, 1H), 7.15 (d, J=2.2 Hz, 1H), 7.46 (d, J=8.6 Hz, 1H), 7.64-7.81 (m, 4H), 8.69 (t, J=5.9 Hz, 1H), 11.14 (s, 1H); $^{13}C$ NMR (DMSO-$d_6$) δ 21.95, 30.51, 30.90, 37.91, 48.83, 55.53, 95.93, 111.42, 114.55, 120.21, 120.91, 121.90, 127.12, 131.49, 133.29, 134.63, 139.06, 142.19, 155.57, 157.68, 166.90, 167.43, 169.78, 172.63, 172.73; Anal. Calcd. for $C_{25}H_{21}N_3O_7$: C, 63.16; H, 4.45; N, 8.84. Found: C, 62.90; H, 4.44; N, 8.74.

5.165 2-{2,5-DIMETHYL-1,3-THIAZOL-4-YL)-N-[2-(2,6-DIOXO-PIPERIDIN-3-YL)-1,3-DIOXO-2,3-DIHYDRO-1H-ISOINDOL-4-YLMETHYL]-ACETAMIDE

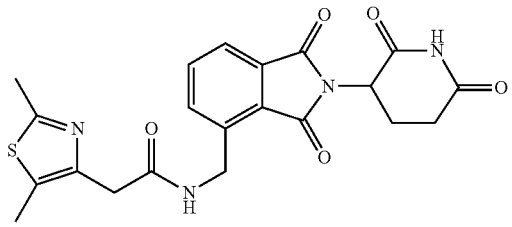 [SMILES: Cc1nc(CC(=O)NCc2cccc3c2C(=O)N(C2CCC(=O)NC2=O)C3=O)c(C)s1]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo [5,4,0]undec-7-ene (0.8 g, 5.4 mmol). After stirring for 10 minutes, 1-hydroxybenzotriazole (0.4 g, 2.6 mmol) and 2-(2,5-dimethyl-1,3-thiazol-4-yl)acetic acid (0.4 g, 2.4 mmol) were added, followed by 1-(3-dimethylaminopropyl)-3-ethylcarbodiimide hydrochloride (0.6 g, 3.2 mmol). The mixture was stirred at room temperature overnight and concentrated in vacuo. The residue was dissolved in $CH_2Cl_2$ (80 mL) and washed with water (3×40 mL) and brine (40 mL), and dried over $MgSO_4$. Solvent was removed in vacuo, and the residue was purified by ISCO silica gel flash chromatography (Eluent: CH3OH: CH2Cl2 3:97) to afford 2-(2,5-dimethyl-1,3-thiazol-4-yl)-N-[2-(2,6-dioxo-piperidin-3-yl)-1,3-dioxo-2,3-dihydro-1H-isoindol-4-ylmethyl]-acetamide (0.7 g, 76%) as a white solid: mp 140-142° C.; HPLC: Waters Symmetry C-18, 3.9×150 mm, 5 micro, 1 mL/min, 240 nm, 40/60 ($CH_3CN/H_2O$): $t_R$=1.39 min. (99%); $^1$H NMR (DMSO-$d_6$) δ 2.04-2.09 (m, 1H), 2.31 (s, 3H), 2.56 (s, 3H), 2.51-2.63 (m, 2H), 2.84-2.91 (m, 1H), 3.56 (s, 2H), 4.73 (d, J=5.9 Hz, 2H), 5.12-5.18 (dd, J=5.3 and 12.7 Hz, 1H), 7.76-7.85 (m, 3H), 8.58 (t, J=6.0 Hz, 1H), 11.13 (s, 1H); $^{13}$C NMR (DMSO-$d_6$) δ 10.84, 18.56, 21.95, 30.91, 35.85, 37.94, 48.82, 121.81, 127.03, 127.91, 131.46, 133.21, 134.60, 139.26, 145.51, 160.87, 166.94, 167.48, 169.51, 169.79, 172.73; Anal. Calcd. for $C_{21}H_{20}N_4O_5S$: C, 57.27; H, 4.58; N, 12.72; S, 7.28. Found: C, 57.13; H, 4.71; N, 12.45; S, 7.18.

5.166 N-[2-(2,6-DIOXO-PIPERIDIN-3-YL)-1,3-DIOXO-2,3-DIHYDRO-1H-ISOINDOL-4-YLMETHYL]-2-(3-METHYL-ISOXAZOL-5-YL)-ACETAMIDE

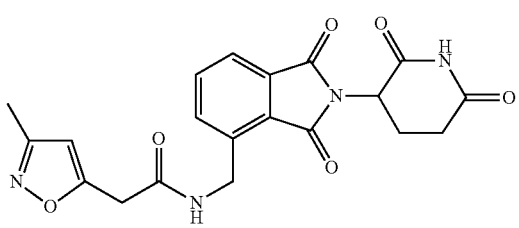 [SMILES: Cc1cc(CC(=O)NCc2cccc3c2C(=O)N(C2CCC(=O)NC2=O)C3=O)on1]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo [5,4,0]undec-7-ene (0.8 g, 5.4 mmol). After stirring for 10 minutes, 1-hydroxybenzotriazole (0.4 g, 2.6 mmol) and 3-methyl-5-isoxazoleacetic acid (0.3 g, 2.4 mmol) were added, followed by 1-(3-dimethylaminopropyl)-3-ethylcarbodiimide hydrochloride (0.6 g, 3.2 mmol). The mixture was stirred at room temperature overnight and was concentrated in vacuo. The residue was dissolved in $CH_2Cl_2$ (80 mL) and washed with water (3×40 mL) and brine (40 mL), and dried over $MgSO_4$. Solvent was removed in vacuo, and the residue was purified by ISCO silica gel flash chromatography (Eluent: $CH_3OH$: $CH_2Cl_2$ 5:95) to afford N-[2-(2,6-dioxo-piperidin-3-yl)-1,3-dioxo-2,3-dihydro-1H-isoindol-4-ylmethyl]-2-(3-methyl-isoxazol-5-yl)-acetamide (0.8 g, 84%) as a white solid: mp 179-181° C.; HPLC: Waters Symmetry C-18, 3.9×150 mm, 5 micro, 1 mL/min, 240 nm, 40/60 ($CH_3CN/H_2O$): $t_R$=1.71 min. (97%); $^1$H NMR (DMSO-$d_6$) δ 2.04-2.09 (m, 1H), 2.20 (s, 3H), 2.53-2.63 (m, 2H), 2.84-2.92 (m, 1H), 3.77 (s, 2H), 4.73 (d, J=5.8 Hz, 2H), 5.12-5.18 (dd, J=5.3 and 12.7 Hz, 1H), 6.21 (s, 1H), 7.69-7.87 (m, 3H), 8.80 (t, J=5.9 Hz, 1H), 11.13 (s, 1H); $^{13}$C NMR (DMSO-$d_6$) δ 10.91, 21.95, 30.90, 33.46, 38.00, 48.85, 103.79, 121.99, 127.18, 131.54, 133.27, 134.75, 138.66, 159.51, 166.85, 166.90, 167.41, 169.77, 172.72; Anal. Calcd. for $C_{20}H_{18}N_4O_6$: C, 58.54; H, 4.42; N, 13.65. Found: C, 58.18; H, 4.19; N, 13.52.

5.167 N-[2-(2,6-DIOXO-PIPERIDIN-3-YL)-1,3-DIOXO-2,3-DIHYDRO-1H-ISOINDOL-4-YLMETHYL]-2-(1-METHYL-1H-INDOL-3-YL)-ACETAMIDE

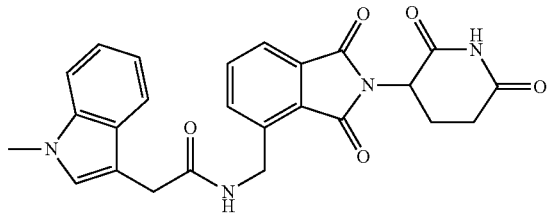 [SMILES: Cn1cc(CC(=O)NCc2cccc3c2C(=O)N(C2CCC(=O)NC2=O)C3=O)c2ccccc21]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo [5,4,0]undec-7-ene (0.8 g, 5.4 mmol). After stirring for 10 minutes, 1-hydroxybenzotriazole (0.4 g, 2.6 mmol) and 1-methyl-3-indoleacetic acid (0.5 g, 2.4 mmol) were added, followed by 1-(3-dimethylaminopropyl)-3-ethylcarbodiimide hydrochloride (0.6 g, 3.2 mmol). The mixture was stirred at room temperature overnight and concentrated in vacuo. The residue was dissolved in $CH_2Cl_2$ (80 mL) and washed with water (3×40 mL) and brine (40 mL), and dried over $MgSO_4$. Solvent was removed in vacuo, and the residue was purified by ISCO silica gel flash chromatography (Eluent: $CH_3OH$: $CH_2Cl_2$ 5:95) to afford N-[2-(2,6-dioxo-piperidin-3-yl)-1,3-dioxo-2,3-dihydro-1H-isoindol-4-ylmethyl]-2-(1-methyl-1H-indol-3-yl)-acetamide (0.8 g, 83%) as a yellow solid: mp 231-233° C.; HPLC: Waters Symmetry C-18, 3.9×150 mm, 5 micro, 1 mL/min, 240 nm, 40/60 ($CH_3CN/H_2O$): $t_R$=3.53 min. (98%); $^1$H NMR (DMSO-$d_6$) δ 2.02-2.07 (m, 1H), 2.54-2.63 (m, 2H), 2.83-2.91 (m, 1H), 3.62 (s, 2H), 3.73 (s, 3H), 4.70 (d, J=5.9 Hz, 2H), 5.10-5.16 (dd, J=5.2 and 12.7 Hz, 1H), 6.99-7.04 (dd, J=7.1 and 7.9 Hz, 1H), 7.12-7.17 (dd, J=7.1 and 7.9 Hz, 1H), 7.21 (s, 1H), 7.40 (d, J=8.2 Hz, 1H), 7.54-7.79 (m, 4H), 8.47 (t, J=5.9 Hz, 1H), 11.15 (s, 1H); $^{13}$C NMR (DMSO-$d_6$) δ 21.95, 30.90, 32.23, 32.34, 37.86, 48.83, 107.82, 109.50, 118.39, 118.78, 121.07, 121.79, 127.06, 127.47, 128.27, 131.46, 133.19, 134.54, 136.53, 139.38, 166.91, 167.45, 169.77, 171.15, 172.71; Anal. Calcd. for $C_{25}H_{22}N_4O_5$: C, 65.49; H, 4.84; N, 12.22. Found: C, 65.11; H, 4.54; N, 12.05.

5.168 N-[2-(2,6-DIOXO-PIPERIDIN-3-YL)-1,3-DIOXO-2,3-DIHYDRO-1H-ISOINDOL-4-YLMETHYL]-2-THIOPHEN-2-YL-ACETAMIDE

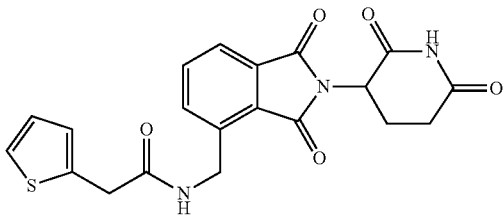 [SMILES: O=C(Cc1cccs1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 2-thiopheneacetic acid (0.3 g, 2.4 mmol) were added, followed by 1-(3-dimethylaminopropyo)-3-ethylcarbodiimide hydrochloride (0.6 g, 3.2 mmol). The mixture was stirred at room temperature overnight and was concentrated in vacuo. The residue was dissolved in $CH_2Cl_2$ (80 mL) and washed with water (3×40 mL) and brine (40 mL), and dried over $MgSO_4$. Solvent was removed in vacuo, and the residue was purified by ISCO silica gel flash chromatography (Eluent: EtOAc: $CH_2Cl_2$ 3:7) to afford N-[2-(2,6-dioxo-piperidin-3-yl)-1,3-dioxo-2,3-dihydro-1H-isoindol-4-ylmethyl]-2-thiophen-2-yl-acetamide (0.7 g, 78%) as a white solid: mp 171-173° C.; HPLC: Waters Symmetry C-18, 3.9×150 mm, 5 micro, 1 mL/min, 240 nm, 40/60 ($CH_3CN/H_2O$): $t_R$=2.24 min. (99%); $^1$H NMR (DMSO-$d_6$) δ 2.02-2.09 (m, 1H), 2.51-2.63 (m, 2H), 2.84-2.96 (m, 1H), 3.77 (s, 2H), 4.72 (d, J=5.9 Hz, 2H), 5.12-5.18 (dd, J=5.3 and 12.7 Hz, 1H), 6.95-6.97 (m, 2H), 7.35-7.38 (m, 1H), 7.65-7.69 (m, 1H), 7.78-7.84 (m, 2H), 8.70 (t, J=5.9 Hz, 1H), 11.13 (s, 1H); $^{13}$C NMR (DMSO-$d_6$) δ 21.95, 30.90, 36.35, 37.87, 48.84, 121.91, 124.90, 126.22, 126.60, 127.13, 131.52, 133.21, 134.68, 137.33, 138.97, 166.89, 167.42, 169.61, 169.78, 172.73; Anal. Calcd. for $C_{20}H_{17}N_3O_5S$: C, 58.39; H, 4.16; N, 10.21; S, 7.79. Found: C, 58.41; H, 4.01; N, 10.07; S, 7.62.

5.169 N-[2-(2,6-DIOXO-PIPERIDIN-3-YL)-1,3-DIOXO-2,3-DIHYDRO-1H-ISOINDOL-4-YLMETHYL]-2-THIOPHEN-3-YL-ACETAMIDE

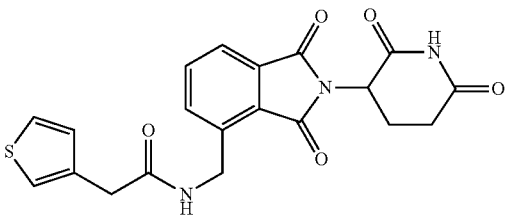 [SMILES: O=C(Cc1ccsc1)NCc1cccc2c1C(=O)N(C1CCC(=O)NC1=O)C2=O]

To a stirred suspension of 4-aminomethyl-2-(2,6-dioxo-piperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 3-thiopheneacetic acid (0.3 g, 2.4 mmol) were added, followed by 1-(3-dimethylaminopropyl)-3-ethylcarbodiimide hydrochloride (0.6 g, 3.2 mmol). The mixture was stirred at room temperature overnight then was concentrated in vacuo. The residue was dissolved in $CH_2Cl_2$ (80 mL) and washed with water (3×40 mL) and brine (40 mL), and dried over $MgSO_4$. Solvent was removed in vacuo, and the residue was purified by ISCO silica gel flash chromatography (Eluent: EtOAc: $CH_2Cl_2$ 3:7) to afford N-[2-(2,6-dioxo-piperidin-3-yl)-1,3-dioxo-2,3-dihydro-1H-isoindol-4-ylmethyl]-2-thiophen-3-yl-acetamide (0.7 g, 80%) as a white solid: mp 163-165° C.; HPLC: Waters Symmetry C-18, 3.9×150 mm, 5 micro, 1 mL/min, 240 nm, 40/60 ($CH_3CN/H_2O$): $t_R$=2.39 min. (99%); $^1$H NMR (DMSO-$d_6$) δ 2.02-2.09 (m, 1H), 2.52-2.63 (m, 2H), 2.84-2.96 (m, 1H), 3.55 (s, 2H), 4.71 (d, J=5.9 Hz, 2H), 5.12-5.18 (dd, J=5.3 and 12.7 Hz, 1H), 7.04-7.06 (m, 1H), 7.28-7.29 (m, 1H), 7.45-7.48 (m, 1H), 7.61-7.67 (m, 1H), 7.76-7.83 (m, 2H), 8.60 (t, J=5.9 Hz, 1H), 11.13 (s, 1H); $^{13}$C NMR (DMSO-$d_6$) δ21.95, 30.90, 36.88, 37.83, 48.83, 121.87, 122.35, 125.76, 127.11, 128.67, 131.51, 133.18, 134.67, 135.82, 139.17, 166.91, 167.44, 169.78, 170.23, 172.73; Anal. Calcd. for $C_{20}H_{17}N_3O_5S$: C, 58.39; H, 4.16; N, 10.21; S, 7.79. Found: C, 58.37; H, 3.98; N, 10.05; S, 7.83.

5.170 N-[2-(2,6-DIOXO-PIPERIDIN-3-YL)-1,3-DIOXO-2,3-DIHYDRO-1H-ISOINDOL-4-YLMETHYL]-3-FLUORO-4-TRIFLUOROMETHYL-BENZAMIDE

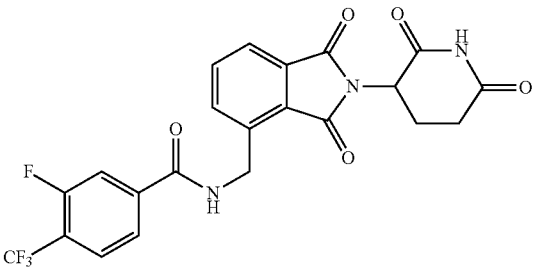 [SMILES: O=C1CCC(N2C(=O)c3cccc(CNC(=O)c4ccc(C(F)(F)F)c(F)c4)c3C2=O)C(=O)N1]

To the stirred suspension of 4-aminomethyl-2-(2,6-dioxo-piperidin-3-yl)-isoindole-1,3-dione hydrochloride (0.7 g, 2.2 mmol) and 3-fluoro-4-trifluoromethylbenzoyl chloride (0.6 g, 2.8 mmol) in dry methylene chloride (60 mL), was added diisopropylethylamine (0.7 g, 5.4 mmol). After stirring at room temperature overnight, the reaction mixture was quenched with methanol (1 mL) and washed with water (2×40 mL) and brine (40 mL), and dried over $MgSO_4$. Solvent was removed in vacuo, and the residue was purified by ISCO silica gel flash chromatography (Eluent: $CH_3OH$: $CH_2Cl_2$ 3:97) to afford N-[2-(2,6-dioxo-piperidin-3-yl)-1,3-dioxo-2,3-dihydro-1H-isoindol-4-ylmethyl]-3-fluoro-4-trifluoromethyl-benzamide (0.6 g, 53%) as a white solid: mp 165-167° C.; HPLC: Waters Symmetry C-18, 3.9×150 mm, 5 micro, 1 mL/min, 240 nm, 40/60 ($CH_3CN/H_2O$): $t_R$=8.20 min. (99%); $^1$H NMR (DMSO-$d_6$) δ 2.06-2.12 (m, 1H), 2.53-2.65 (m, 2H), 2.87-2.93 (m, 1H), 4.98 (d, J=5.7 Hz, 2H), 5.15-5.21 (dd, J=5.3 and 12.5 Hz, 1H), 7.76-7.84 (m, 3H), 7.95-8.01 (m, 3H), 9.45 (t, J=5.7 Hz, 1H), 11.15 (s, 1H); $^{13}$C NMR (DMSO-$d_6$) δ 21.97, 30.92, 38.54, 48.87, 115.88 (116.17), 118.56 (118.72, 119.00, 119.16), 122.30, 123.94 (123.98), 120.52 (124.13), 127.25, 127.74 (127.80), 131.55, 133.24, 134.83, 138.51, 140.42 (140.52), 157.04 (160.38), 164.19, 166.91, 167.48, 169.81, 172.74; Anal. Calcd. for $C_{22}H_{15}N_3O_5F_4$: C, 55.35; H, 3.17; N, 8.80; F, 15.92. Found: C, 55.00; H, 2.95; N, 8.80; F, 15.92.

5.171 N-[2-(2,6-DIOXO-PIPERIDIN-3-YL)-1,3-DIOXO-2,3-DIHYDRO-1H-ISOINDOL-4-YLMETHYL]-2-FLUORO-4-TRIFLUOROMETHYL-BENZAMIDE

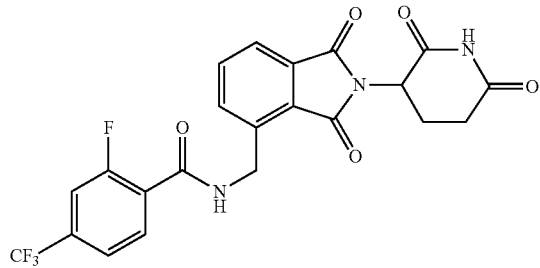 [SMILES: O=C1CCC(N2C(=O)c3cccc(CNC(=O)c4ccc(C(F)(F)F)cc4F)c3C2=O)C(=O)N1]

To the stirred suspension of 4-aminomethyl-2-(2,6-dioxo-piperidin-3-yl)-isoindole-1,3-dione hydrochloride (0.7 g, 2.2 mmol) and 2-fluoro-4-trifluoromethylbenzoyl chloride (0.6 g, 2.8 mmol) in dry methylene chloride (60 mL), was added diisopropylethylamine (0.7 g, 5.4 mmol). The mixture was stirred at room temperature overnight, quenched with methanol (1 mL), washed with water (2×40 mL) and brine (40 mL), and dried over $MgSO_4$. Solvent was removed in vacuo, and the residue was purified by ISCO silica gel flash chromatography (Eluent: $CH_3OH$: $CH_2Cl_2$ 3:97) to afford N-[2-(2,6-dioxo-piperidin-3-yl)-1,3-dioxo-2,3-dihydro-1H-isoindol-4-methyl]-2-fluoro-4-trifluoromethyl-benzamide (0.9 g, 83%) as a white solid: mp 238-240° C.; HPLC: Waters Symmetry C-18, 3.9×150 mm, 5 micro, 1 mL/min, 240 nm, 40/60 ($CH_3CN/H_2O$): $t_R$=7.16 min. (99%); $^1H$ NMR (DMSO-$d_6$) δ 2.06-2.09 (m, 1H), 2.53-2.64 (m, 2H), 2.85-2.93 (m, 1H), 4.96 (d, J=5.8 Hz, 2H), 5.15-5.21 (dd, J=5.3 and 12.6 Hz, 1H), 7.69-7.92 (m, 6H), 9.22 (t, J=5.4 Hz, 1H), 11.15 (s, 1H); $^{13}C$ NMR (DMSO-$d_6$) δ 21.96, 30.91, 38.46, 48.87, 113.68 (113.72, 114.02, 114.07), 121.45 (121.49, 121.54), 122.04, 124.17 (124.81), 127.24, 127.65 (127.85), 131.39 (131.43), 131.60, 132.18 (132.50, 132.62), 133.00, 134.86, 138.40, 157.20 (160.53), 163.05, 166.91, 167.46, 169.80, 172.74; Anal. Calcd. for $C_{22}H_{15}N_3O_5F_4$: C, 55.35; H, 3.17; N, 8.80; F, 15.92. Found: C, 55.12; H, 2.88; N, 7.74; F, 15.86.

5.172 N-[2-(2,6-DIOXO-PIPERIDIN-3-YL)-1,3-DIOXO-2,3-DIHYDRO-1H-ISOINDOL-4-YLMETHYL]-4-FLUORO-3-TRIFLUOROMETHYL-BENZAMIDE

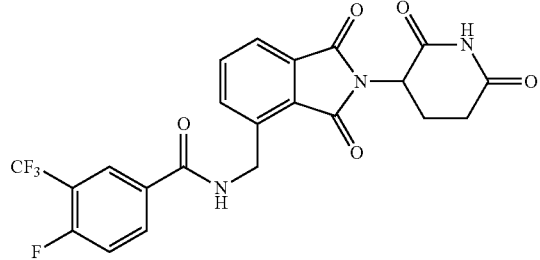 [SMILES: O=C1CCC(N2C(=O)c3cccc(CNC(=O)c4ccc(F)c(C(F)(F)F)c4)c3C2=O)C(=O)N1]

To a stirred suspension of 4-aminomethyl-2-(2,6-dioxo-piperidin-3-yl)-isoindole-1,3-dione hydrochloride (0.7 g, 2.2 mmol) and 4-fluoro-3-trifluoromethyl-benzoyl chloride (0.6 g, 2.8 mmol) in dry methylene chloride (60 mL), was added diisopropylethylamine (0.7 g, 5.4 mmol). After stirring at room temperature overnight, the reaction mixture was quenched with methanol (1 mL). The resulting suspension was filtered, and the solid was washed with methyene chloride to afford N-[2-(2,6-dioxo-piperidin-3-yl)-1,3-dioxo-2,3-dihydro-1H-isoindol-4-ylmethyl]-4-fluoro-3-trifluoromethyl-benzamide (0.8 g, 79%) as a white solid: mp 171-173° C.; HPLC: Waters Symmetry C-18, 3.9×150 mm, 5 micro, 1 mL/min, 240 nm, 40/60 ($CH_3CN/H_2O$): $t_R$=7.5 min. (99%); $^1H$ NMR (DMSO-$d_6$) δ 2.06-2.12 (m, 1H), 2.54-2.65 (m, 2H), 2.85-2.98 (m, 1H), 4.97 (d, J=5.7 Hz, 2H), 5.15-5.21 (dd, J=5.4 and 12.5 Hz, 1H), 7.68 (t, J=8.9 Hz, 1H), 7.76-7.84 (m, 3H), 8.28-8.35 (m, 2H), 9.43 (t, J=5.7 Hz, 1H), 11.15 (s, 1H); $^{13}C$ NMR (DMSO-$d_6$) δ 21.91, 30.86, 38.43, 48.82, 116.20 (116.37, 116.64, 116.80), 117.35 (117.63), 120.50 (124.10), 121.92, 126.51 (126.56), 127.14, 130.65 (130.70), 131.48, 133.22, 134.58, 134.71 (134.77), 138.70, 158.78 (162.21), 164.19, 166.87, 167.44, 169.75, 172.68; Anal. Calcd. for $C_{22}H_{15}N_3O_5F_4$+0.2$H_2O$: C, 54.94; H, 3.23; N, 8.74; F, 15.80. Found: C, 54.68; H, 3.17; N, 8.63; F, 15.72.

5.173 N-[2-(2,6-DIOXO-PIPERIDIN-3-YL)-1,3-DIOXO-2,3-DIHYDRO-1H-ISOINDOL-4-YLMETHYL]-2-FLUORO-3-TRIFLUOROMETHYL-BENZAMIDE

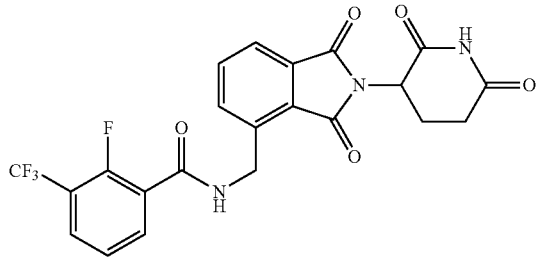 [SMILES: O=C1CCC(N2C(=O)c3cccc(CNC(=O)c4cccc(C(F)(F)F)c4F)c3C2=O)C(=O)N1]

To a stirred suspension of 4-aminomethyl-2-(2,6-dioxo-piperidin-3-yl)-isoindole-1,3-dione hydrochloride (0.7 g, 2.2 mmol) and 2-fluoro-3-trifluoromethyl-benzoyl chloride (0.6 g, 2.8 mmol) in dry methylene chloride (60 mL), was added diisopropylethylamine (0.7 g, 5.4 mmol). The mixture was stirred at room temperature overnight then quenched with methanol (1 mL). The resulting suspension was filtered and the solid was washed with methylene chloride to afford N-[2-(2,6-dioxo-piperidin-3-yl)-1,3-dioxo-2,3-dihydro-1H-isoindol-4-ylmethyl]-2-fluoro-3-trifluoromethyl-benzamide (0.8 g, 72%) as a white solid: mp 155-157° C.; HPLC: Waters Symmetry C-18, 3.9×150 mm, 5 micro, 1 mL/min, 240 nm, 40/60 ($CH_3CN/H_2O$): $t_R$=6.23 min. (99%); $^1H$ NMR (DMSO-$d_6$) δ 2.04-2.11 (s, 1H), 2.53-2.64 (m, 2H), 2.85-2.97 (m, 1H), 4.96 (d, J=5.8 Hz, 2H), 5.15-5.21 (dd, J=5.3 and 12.6 Hz, 1H), 7.52 (t, J=7.8 Hz, 1H), 7.79-8.01 (m, 5H), 9.26 (t, J=5.7 Hz, 1H), 11.15 (s, 1H); $^{13}C$ NMR (DMSO-$d_6$) δ 21.96, 30.91, 38.46, 48.87, 117.03 (117.29, 117.45), 120.65 (124.26), 122.03, 125.09 (125.15), 125.45 (125.64), 127.22, 129.24 (129.29), 131.58, 132.97, 134.89, 138.41, 154.37 (157.77), 162.90, 166.91, 167.45, 169.80, 172.73; Anal. Calcd. for $C_{22}H_{15}N_3O_5F_4$: C, 55.35; H, 3.17; N, 8.80; F, 15.92. Found: C, 55.13; H, 2.95; N, 8.73; F, 15.69.

5.174 BENZO[B]THIOPHENE-5-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

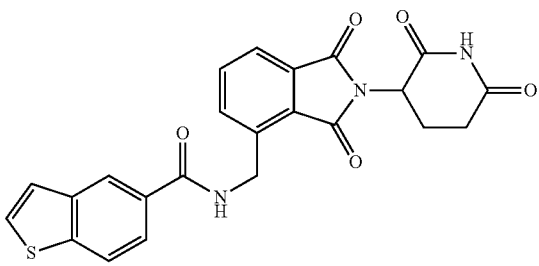 [SMILES: O=C1CCC(N2C(=O)c3cccc(CNC(=O)c4ccc5sccc5c4)c3C2=O)C(=O)N1]

To a stirred suspension of 4-aminomethyl-2-(2,6-dioxopiperidin-3-yl)-isoindole-1,3-dione hydrochloride (0.7 g, 2.2 mmol) in acetonitrile (60 mL), was added 1,8-diazabicyclo[5,4,0]undec-7-ene (0.8 g, 5.4 mmol). After stirring for 10 minutes, 1-hydroxybenzotriazole (0.4 g, 2.6 mmol) and 1-benzothiophene-5-carboxylic acid (0.4 g, 2.4 mmol) were added, followed by 1-(3-dimethylaminopropyl)-3-ethylcarbodiimide hydrochloride (0.6 g, 3.2 mmol). The mixture was stirred at room temperature overnight and was concentrated in vacuo. The residue was dissolved in $CH_2Cl_2$ (80 mL), washed with water (3×40 mL) and brine (40 mL), and dried over $MgSO_4$. Solvent was removed in vacuo, and the residue was purified by ISCO silica gel flash chromatography (Eluent: EtOAc: $CH_2Cl_2$ 3:7) to afford benzo[b]thiophene-5-carboxylic acid [2-(2,6-dioxo-piperidin-3-yl)-1,3-dioxo-2,3-dihydro-1H-isoindol-4-ylmethyl]-amide (0.5 g, 53%) as a white solid: mp 261-263° C.; HPLC: Waters Symmetry C-18, 3.9×150 mm, 5 micro, 1 mL/min, 240 nm, 40/60 ($CH_3CN/H_2O$): $t_R$=4.22 min. (99%); $^1H$ NMR (DMSO-$d_6$) δ 2.07-2.11 (m, 1H), 2.55-2.65 (m, 2H), 2.86-2.98 (m, 1H), 4.99 (d, J=5.6 Hz, 2H), 5.16-5.22 (dd, J=5.0 and 12.4 Hz, 1H), 7.59 (d, J=5.4 Hz, 1H), 7.79-7.92 (m, 5H), 8.11 (d, J=8.4 Hz, 1H), 8.48 (s, 1H), 9.24 (t, J=5.5 Hz, 1H), 11.16 (s, 1H); $^{13}C$ NMR (DMSO-$d_6$) δ 21.99, 30.93, 38.44, 48.88, 121.85, 122.50, 122.91, 122.95, 124.39, 127.14, 128.84, 130.39, 131.54, 133.07, 134.79, 139.18, 139.38, 141.92, 166.79, 166.97, 167.55, 169.83, 172.74; Anal. Calcd. for $C_{23}H_{17}N_3O_5S+0.2H_2O$: C, 61.24; H, 3.89; N, 9.32; S, 7.11. Found: C, 61.04; H, 3.57; N, 8.96; S, 7.19.

5.175 4-METHYL-OXAZOLE-5-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

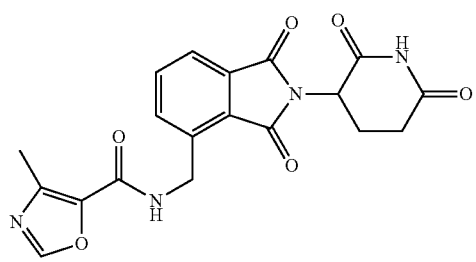 [SMILES: Cc1ncoc1C(=O)NCc1cccc2c1C(=O)N(C1CCC(=O)NC1=O)C2=O]

To a suspension of 4-aminomethyl-2-(2,6-dioxo-piperidin-3-yl)-isoindole-1,3-dione hydrochloride (1.90 g, 5.9 mmol) in $CH_3CN$ (25 ml), were added triethyl amine (2.05 mL, 14.7 mmol) and 4-methyl-oxazole-5-carbonyl-chloride (0.85 g, 5.9 mmol). The mixture was stirred at room temperature overnight and a suspension was obtained. The reaction mixture was filtered, and the solid was rinsed with $CH_3CN$ (20 mL), water (2×20 mL) and EtOAc (20 mL) to afford 4-methyl-oxazole-5-carboxylic acid [2-(2,6-dioxo-piperidin-3-yl)-1,3-dioxo-2,3-dihydro-1H-isoindol-4-ylmethyl]-amide as a white solid (1.82 g, 78%): mp, 308-310° C.; HPLC: Waters Symmetry C-18, 3.9×150 mm, 5 micro, 1 mL/min, 240 nm, gradient from 10/90 ($CH_3CN/H_2O$) to 95/5 ($CH_3CN/H_2O$) in 10 minutes: $t_R$=5.49 (98%); $^1H$ NMR (DMSO-$d_6$): δ 2.06-2.10 (m, 1H), 2.38 (s, 3H), 2.59-2.64 (m, 2H), 2.85-2.97 (m, 1H), 4.88 (d, J=5.9 Hz, 2H), 5.17 (dd, J=6, 12 Hz, 1H), 7.70-8.47 (m, 4H), 9.05 (t, J=5.9 Hz, 1H), 11.16 (s, 1H). $^{13}C$ NMR (DMSO-$d_6$) δ: 12.52, 21.96, 30.92, 37.57, 48.86, 121.91, 127.09, 131.51, 133.01, 134.81, 138.86, 138.89, 140.67, 151.42, 157.96, 166.94, 167.51, 169.82, 172.74. Anal Calcd for $C_{19}H_{16}N_4O_6$: C, 57.58; H, 4.07; N, 14.14. Found: C, 57.48; H, 4.04; N, 14.33.

5.176 4-METHYL-2-PHENYL-THIAZOLE-5-CARBOXYLIC ACID [2-(2,6-DIOXO-PIPERIDIN-3-YL)-1,3-DIOXO-2,3-DIHYDRO-1H-ISOINDOL-4-YLMETHYLAMIDE

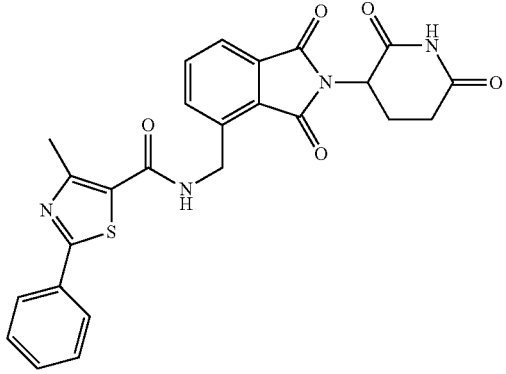 [SMILES: Cc1nc(-c2ccccc2)sc1C(=O)NCc1cccc2c1C(=O)N(C1CCC(=O)NC1=O)C2=O]

To a suspension of 4-aminomethyl-2-(2,6-dioxo-piperidin-3-yl)-isoindole-1,3-dione hydrochloride (1.45 g, 4.5 mmol) in $CH_3CN$ (25 ml), were added triethyl amine (1.56 mL, 11.22 mmol) and 4-methyl-2-phenyl-1,3-thiazole-5-carbonyl-chloride (1.07 g, 4.5 mmol). The mixture was stirred at room temperature overnight. The resulting suspension was filtered, and the solid was rinsed with $CH_3CN$ (20 mL), water (2×20 mL) and EtOAc (20 mL) to afford 4-methyl-2-phenyl-thiazole-5-carboxylic acid [2-(2,6-dioxo-piperidin-3-yl)-1,3-dioxo-2,3-dihydro-1H-isoindol-4-ylmethyl]-amide as a white solid (1.45 g, 66%): mp, 277-279° C.; HPLC: Waters Symmetry C-18, 3.9×150 mm, 5 micro, 1 mL/min, 240 nm, gradient from 10/90 ($CH_3CN/H_2O$) to 95/5($CH_3CN/H_2O$) in 10 minutes: $t_R$=6.96 min. (99%); $^1H$ NMR (DMSO-$d_6$): δ 2.08-2.10 (m, 1H), 2.55-2.59 (m, 2H), 2.66 (s, 3H), 2.86-2.98 (m, 1H), 4.91 (d, J=5.6 Hz, 2H), 5.18 (dd, J=6, 12 Hz, 1H), 7.53-7.98 (m, 8H), 8.91 (t, J=5.6 Hz, 1H), 11.16 (s, 1H). $^{13}C$ NMR (DMSO-$d_6$) δ: 17.20, 30.92, 38.56, 48.87, 121.98, 125.65, 126.65, 126.25, 127.18, 129.37, 130.95, 131.57, 132.36, 133.15, 134.85, 138.83, 155.65, 161.37, 166.14, 166.93, 167.51, 169.82, 172.75. Anal Calcd for $C_{25}H_{20}N_4O_5S$: C, 61.47; H, 4.13; N, 11.47; S: 6.56. Found: C, 61.44; H, 4.04; N, 11.63; S: 6.49.

5.177 ISOXAZOLE-5-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

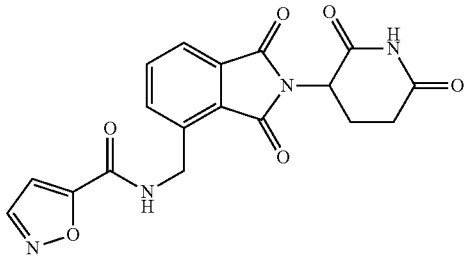 [SMILES: O=C1CCC(N2C(=O)c3cccc(CNC(=O)c4ccno4)c3C2=O)C(=O)N1]

To a suspension of 4-aminomethyl-2-(2,6-dioxo-piperidin-3-yl)-isoindole-1,3-dione hydrochloride (2.7 g, 8.4 mmol) in $CH_3CN$ (25 ml), were added triethyl amine (2.9 mL, 8.4 mmol) and isoxazole-5-carbonyl-chloride (1.07 g, 4.5 mmol). The mixture was stirred at room temperature overnight and a suspension was obtained. The reaction mixture was filtered, and the solid was rinsed with $CH_3CN$ (20 mL), water (2×20 mL) and EtOAc (20 mL). The solid was dissolved in $CH_2Cl_2$ (5 mL) and purified by ISCO silica gel flash chromatography (eluent: 2% MeOH in $CH_2Cl_2$) to afford isoxazole-5-carboxylic acid [2-(2,6-dioxo-piperidin-3-yl)-1,3-dioxo-2,3-dihydro-1H-isoindol-4-ylmethyl]-amide as a light yellow solid (0.87 g, 27%): mp, 257-259° C.; HPLC: Waters Symmetry C-18, 3.9×150 mm, 5 micro, 1 mL/min, 240 nm, gradient from 10/90 ($CH_3CN/H_2O$) to 95/5($CH_3CN/H_2O$) in 10 minutes: $t_R$=5.62 (99%); $^1$H NMR (DMSO-$d_6$): δ 2.04-2.11 (m, 1H), 2.53-2.64 (m, 2H), 2.85-2.97 (m, 1H), 4.93 (d, J=5.6 Hz, 2H), 5.17 (dd, J=6, 12 Hz, 1H), 7.14-8.78 (m, 5H), 9.60 (t, J=5.6 Hz, 1H), 11.15 (s, 1H). $^{13}$C NMR (DMSO-$d_6$) δ: 21.96, 30.92, 37.96, 48.87, 106.26, 122.11, 127.25, 131.56, 133.14, 134.89, 138.00, 151.75, 155.95, 162.35, 166.90, 167.44, 169.80, 172.73. Anal Calcd for $C_{18}H_{14}N_4O_6$: C, 56.55; H, 3.69; N, 14.65. Found: C, 56.20; H, 3.36; N, 14.47.

5.178 THIAZOLE-2-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

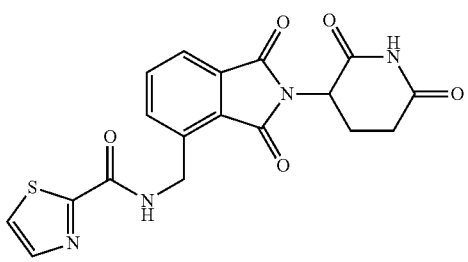 [SMILES: O=C1CCC(N2C(=O)c3cccc(CNC(=O)c4nccs4)c3C2=O)C(=O)N1]

To a suspension of 4-aminomethyl-2-(2,6-dioxo-piperidin-3-yl)-isoindole-1,3-dione hydrochloride (0.57 g, 1.75 mmol) in $CH_3CN$ (10 ml), were added triethyl amine (0.61 mL, 4.4 mmol) and 1,3-thiazole-2-carbonyl-chloride (1.07 g, 4.5 mmol). The mixture was stirred at room temperature overnight and a suspension was obtained. The reaction mixture was filtered, and the filtrate was concentrated in vacuo. The resulting oil was purified by ISCO silica gel flash chromatography (eluent: 3% MeOH in $CH_2Cl_2$) to afford thiazole-2-carboxylic acid [2-(2,6-dioxo-piperidin-3-yl)-1,3-dioxo-2,3-dihydro-1H-isoindol-4-ylmethyl]-amide as a white solid (0.52 g, 74%): mp, 189-191° C.; HPLC: Waters Symmetry C-18, 3.9×150 mm, 5 micro, 1 mL/min, 240 nm, gradient from 10/90 ($CH_3CN/H_2O$) to 95/5($CH_3CN/H_2O$) in 10 minutes: $t_R$=5.9 min (97%); $^1$H NMR (DMSO-$d_6$): δ 2.05-2.12 (m, 1H), 2.53-2.65 (m, 2H), 2.86-2.98 (m, 1H), 4.94 (d, J=6.2 Hz, 2H), 5.18 (dd, J=5, 11 Hz, 1H), 7.68-8.10 (m, 5H), 9.50 (t, J=6 Hz, 1H), 11.15 (s, 1H). $^{13}$C NMR (DMSO-$d_6$) δ: 21.96, 30.92, 38.32, 48.88, 121.98, 125.99, 127.17, 131.56, 132.92, 134.85, 138.43, 143.98, 159.59, 163.18, 166.93, 167.51, 169.81, 172.73. Anal Calcd for $C_{18}H_{14}N_4O_5S$: C, 54.27; H, 3.54; N, 14.06; S, 8.05. Found: C, 53.98; H, 3.49; N, 13.75; S, 8.22.

5.179 BENZO[C]ISOXAZOLE-3-CARBOXYLIC ACID [2-(2,6-DIOXO-PIPERIDIN-3-YL)-1,3-DIOXO-2,3-DIHYDRO-1H-ISOINDOL-4-YLMETHYL]-AMIDE

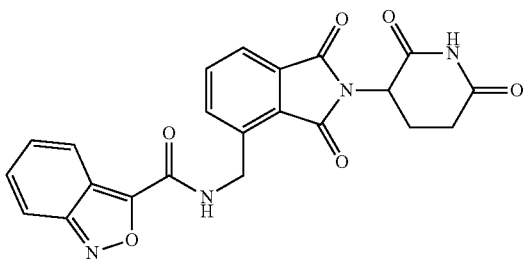 [SMILES: O=C1CCC(N2C(=O)c3cccc(CNC(=O)c4onc5ccccc45)c3C2=O)C(=O)N1]

To a stirred suspension of 4-aminomethyl-2-(2,6-dioxo-piperidin-3-yl)-isoindole-1,3-dione hydrochloride (1.8 g, 5.7 mmol) in DMF (20 ml), was added 1,8-diazabicyclo[5.4.0]undec-7-ene (0.9 g, 6.8 mmol). After stirring for 10 minutes, 1-hydroxybenzenetriazole (0.9 g, 6.8 mmol) and benzo[c]isoxazole-3-carboxylic acid (1.0 g, 6.3 mmol) were added, followed by 1-(3-dimethylaminopropyl)-3-ethylcarbodiimide hydrochloride (1.6 g, 8.5 mmol). The mixture was stirred at room temperature overnight and was concentrated in vacuo. The residue was dissolved in $CH_2Cl_2$ (50 mL), washed with water (2×30 mL) and brine (30 mL), and dried over $MgSO_4$. Solvent was removed in vacuo, and the resulting oil was purified by ISCO silica gel flash chromatography (eluent: 3% MeOH in $CH_2Cl_2$) to afford benzo[c]isoxazole-3-carboxylic acid [2-(2,6-dioxo-piperidin-3-yl)-1,3-dioxo-2,3-dihydro-1H-isoindol-4-ylmethyl]-amide as a yellow solid (1.93 g, 78%): mp, 253-255° C.; HPLC: Waters Symmetry C-18, 3.9×150 mm, 5 micro, 1 mL/min, 240 nm, gradient from 10/90 ($CH_3CN/H_2O$) to 95/5($CH_3CN/H_2O$) in 10 minutes: $t_R$=6.6 min (96%); $^1$H NMR (DMSO-$d_6$): δ 2.08-2.13 (m, 1H), 2.53-2.65 (m, 2H), 2.86-2.94 (m, 1H), 5.02 (d, J=6.0 Hz, 2H), 5.19 (dd, J=6, 12 Hz, 1H), 7.27-7.97 (m, 5H), 9.90 (t, J=6 Hz, 1H), 11.16 (s, 1H). $^{13}$C NMR (DMSO-$d_6$) δ: 21.98, 30.93, 40.33, 48.89, 115.15, 118.27, 120.74, 122.07, 127.24, 131.54, 131.96, 133.20, 134.88, 138.13, 156.43, 156.52, 156.97, 160.91, 166.93, 167.49, 169.82, 172.75. Anal Calcd for $C_{22}H_{16}N_4O_6$+0.2$H_2O$: C, 60.61; H, 3.79; N, 12.85. Found: C, 60.38; H, 3.50; N, 12.80.

5.180 CYCLOPROPANECARBOXYLIC ACID [2-((3S)-2,6-DIOXO-PIPERIDIN-3-YL)-1,3-DI-OXO-2,3-DIHYDRO-1H-ISOINDOL-4-YLM-ETHYL]-AMIDE

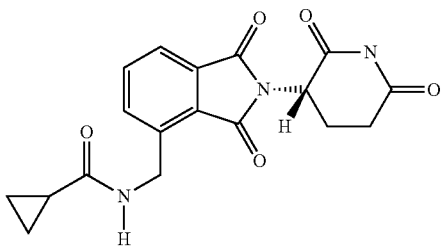

Step 1:

Triethylamine (1.2 g, 11.8 mmol) was added to a stirred suspension of (1,3-dioxo-1,3-dihydro-isobenzofuran-4-ylm-ethyl)carbamic acid t-butyl ester (2.1 g, 7.9 mmol) and L-glutamine t-butyl ester hydrochloride (2.1 g, 8.6 mmol) in toluene (90 mL). The mixture was refluxed under Dean-Stark water separator overnight. The mixture was cooled to room temperature and diluted with $CH_2Cl_2$ (60 mL). The solution was washed with $H_2O$ (2×40 mL) and brine (40 mL), and dried ($MgSO_4$). Solvent was removed, and the residue was purified by chromatography (silica gel) to give (2S)-2-[4-(t-butoxycarbonylamino-methyl)-1,3-dioxo-1,3-dihydro-isoindol-2-yl]-4-carbamoyl-butyric acid t-butylester (1.1 g, 29%): $^1$H NMR ($CDCl_3$) δ 1.41 (s, 9H), 1.43 (s, 9H), 2.25-3.60 (m, 4H), 4.65 (d, J=6.5 Hz, 2H), 4.76-4.82 (dd, J=4.9 and 9.8 Hz, 1H), 5.47-5.61 (m, 3H), 7.67-7.79 (m, 3H); Chiral HPLC: Daicel ChiralPak AD, 46×250 mm, 20/80 IPA/hexane, 1 mL/min, 240 nm, 8.87 min (98% ee).

Step 2:

2N HCl/ether (14 mL) was added to a stirred solution of (2S)-2-[4-(t-butoxycarbonylamino-methyl)-1,3-dioxo-1,3-dihydro-isoindol-2-yl]-4-carbamoyl-butyric acid t-butyl ester (2.5 g, 5.4 mmol) in $CH_2Cl_2$ (25 mL). The mixture was stirred for 5 hours. Solid was collected by filtration to give (2S)-2-(4-aminomethyl-1,3-dioxo-1,3-dihydro-isoindol-2-yl)-4-carbamoyl butyric acid t-butyl ester hydrochloride (2.1 g, 97%): $^1$H NMR (DMSO-$d_6$) δ 1.37 (s, 9H), 2.08-2.37 (m, 4H), 4.47-4.51 (m, 2H), 4.73-4.79 (dd, J=4.6 and 10.0 Hz, 1H), 6.73 (s, 1H), 7.25 (s, 1H), 7.92-8.03 (m, 3H), 8.68 (s, 3H).

Step 3:

Triethylamine (1.3 g, 12.6 mmol) was added to a stirred suspension of (2S)-2-(4-aminomethyl-1,3-dioxo-1,3-dihydro-isoindol-2-yl)-4-carbamoyl butyric acid t-butyl ester hydrochloride (2.1 g, 5.2 mmol) in acetonitrile (45 mL). The mixture was stirred for 10 minutes, and cyclopropanecarbonyl chloride (0.7 g, 6.8 mmol) was added slowly at 20° C. The mixture was stirred at room temperature for 3 hours. The mixture was concentrated, and the residue was dissolved in $CH_2Cl_2$ (100 mL). The $CH_2Cl_2$ solution was washed with $H_2O$ (2×30 mL) and brine (30 mL), and dried ($MgSO_4$). Solvent was removed, and the residue was purified by chromatography (silica gel) to (2S)-4-carbamoyl-2-{4-[(cyclo-propanecarbonyl-amino)-methyl]-1,3-dioxo-1,3-dihydro-isoindol-2-yl}-butyric acid t-butyl ester (1.4 g, 64%): $^1$H NMR ($CDCl_3$) δ 0.70-0.75 (m, 2H), 0.90-0.96 (m, 2H), 1.35-1.40 (m, 1H), 1.43 (s, 9H), 2.25-2.31 (m, 2H), 2.44-2.59 (m, 2H), 4.73 (d, J=6.5 Hz, 2H), 4.76-4.83 (dd, J=5.1 and 9.8 Hz, 1H), 5.45 (s, 1H), 5.60 (s, 1H), 6.92 (t, J=6.3 Hz, 1H), 7.63-7.78 (m, 3H).

Step 4:

HCl (gas) was bubbled into a stirred solution of (2S)-4-carbamoyl-2-{4-[cyclopropanecarbonyl-amino)-methyl]-1,3-dioxo-1,3-dihydro-isoindol-2-yl}-butyric acid t-butyl ester (1.4 g, 3.3 mmol) in $CH_2Cl_2$ (25 mL) for 1 hour. The mixture was stirred for another 1 hour then filtered to give (2S)-4-carbamoyl-2-{-4-[(cyclopropanecarbonyl-amino)-methyl]-1,3-dioxo-1,3-dihydro-isoindol-2-yl}-butyric acid (1.2 g, 96%) as a white solid: $^1$H NMR (DMSO-$d_6$) δ 0.69-0.72 (m, 4H), 1.65-1.69 (m, 1H), 2.06-2.38 (m, 4H), 4.72-4.77 (m, 3H), 6.73 (s, 1H), 7.22 (s, 1H), 7.66-7.87 (m, 3H), 8.73 (t, J=5.8 Hz, 1H); $^{13}$C NMR (DMSO-$d_6$) δ 6.42, 13.50, 23.97, 31.35, 37.70, 51.17, 121.76, 127.03, 131.51, 133.17, 134.65, 139.34, 167.16, 167.72, 170.37, 173.06, 173.12.

Step 5:

A suspension of (2S)-4-carbamoyl-2-{4-[(cyclopropan-ecarbonyl-amino)-methyl]-1,3-dioxo-1,3-dihydro-isoindol-2-yl}-butyric acid (1.4 g, 3.8 mmol) in dry $CH_2Cl_2$ (87 mL) was cooled to −40° C. with IPA/dry ice bath. Thionyl chloride (0.5 g, 4.1 mmol) was added dropwise, followed by pyridine (0.3 g, 4.1 mmol). The mixture was stirred at −40° C. for 30 minutes. Triethylamine (0.4 g, 4.2 mmol) was added dropwise, and the mixture was stirred at −30 to −40° C. for 3 hours. The mixture was filtered into ice water (150 mL). The aqueous layer was extracted with $CH_2Cl_2$ (40 mL), and the combined $CH_2Cl_2$ solution was washed with $H_2O$ (2×40 mL) and brine (40 mL), and dried ($MgSO_4$). Solvent was removed, and the solid was slurried with ethanol (20 mL) to give cyclopropanecarboxylic acid {2-((3S)-2,6-dioxo-piperidin-3-yl)-1,3-dioxo-2,3-dihydro-1H-isoindol-4-ylmethyl]-amide (1.0 g, 74%) as a white solid: mp 219-221° C.; Chiral HPLC: Daicel ChiralPak AD, 46×250 mm, 70/30 IPA/hexane, 0.6 mL/min, 19.76 min (98.5% ee); $^1$H NMR (DMSO-$d_6$) δ 0.69-0.72 (m, 4H), 1.61-1.71 (m, 1H), 2.04-2.08 (m, 1H), 2.50-2.63 (m, 2H), 2.83-2.97 (m, 1H), 4.74 (d, J=5.7 Hz, 2H, $CH_2$), 5.11-5.18 (dd, J=5.2 and 12.4 Hz, 1H, CH), 7.67-7.88 (m, 3H, Ar), 8.69 (t, J=5.6 Hz, 1H, NH), 11.13 (s, 1H, NH); $^{13}$C NMR (DMSO-$d_6$) δ 6.41, 13.50, 21.96, 30.91, 37.74, 48.84, 121.84, 127.08, 131.51, 133.31, 134.76, 139.39, 166.92, 167.44, 169.78, 172.72, 173.09; Anal. calcd. for $C_{18}H_{17}N_3O_5$: C, 60.84; H, 4.82; N, 11.82. Found: C, 60.49; H, 4.76; N, 11.51.

5.181 2-AMINO-N-[2-(3-METHYL-2,6-DIOXO-PIPERIDIN-3-YL)-1,3-DIOXO-2,3-DIHYDRO-1H-ISOINDOL-4-YL]-ACETAMIDE HYDROCHLORIDE

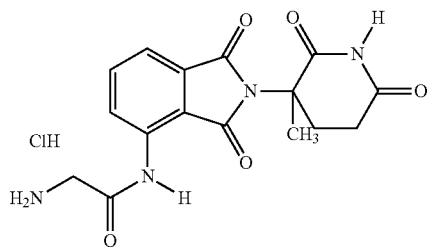 [SMILES: Cl ; CC1(N2C(=O)c3cccc(NC(=O)CN)c3C2=O)CCC(=O)NC1=O]

Step 1:

Chloroacetyl chloride (0.9 g, 7.8 mmol) was added to a stirred suspension of 4-amino-2-(3-methyl-2,6-dioxo-piperidin-3-yl)-isoindole-1,3-dione (1.5 g, 5.2 mmol) in THF (20 mL). The mixture was refluxed for 30 minutes. The mixture was cooled to room temperature and filtered to give 2-chloro-N-[2-(3-methyl-2,6-dioxo-piperidin-3-yl)-1,3-dioxo-2,3-dihydro-1H-isoindol-4-yl]-acetamide (1.6 g, 84%): $^1$H NMR (DSO-d$_6$) δ 1.89 (s, 3H, CH$_3$), 2.03-2.08 (m, 1H), 2.50-2.70 (m, 3H), 4.53 (s, 2H, CH$_2$), 7.60 (d, J=7.3 Hz, 1H, Ar), 7.84 (t, J=7.7 Hz, 1H, Ar), 8.51 (d, J=8.4 Hz, 1H, Ar), 10.26 (s, 1H, NH), 11.05 (s, 1H, NH); $^{13}$C NMR (DMSO-d$_6$) δ 20.98, 28.53, 29.04, 43.14, 58.89, 116.95, 118.54, 125.27, 131.30, 135.39, 136.16, 165.69, 167.31, 168.74, 171.98, 172.16.

Step 2:

A mixture of sodium azide (0.4 g, 6.2 mmol), sodium iodide (20 mg) and 2-chloro-N-[2-(3-methyl-2,6-dioxo-piperidin-3-yl)-1,3-dioxo-2,3-dihydro-1H-isoindol-4-yl]-acetamide (1.5 g, 4.1 mmol) in acetone (50 mL) was heated to reflux overnight. The mixture was cooled to room temperature and concentrated. The residue was stirred with H$_2$O (30 mL) for 30 minutes then filtered. The solid was slurried with ethanol (15 mL) to give 2-azido-N-[2-(3-methyl-2,6-dioxo-piperidin-3-yl)-1,3-dioxo-2,3-dihydro-1H-isoindo-4-yl]-acetamide (1.4 g, 91%): $^1$H NMR (DMSO-d$_6$) δ 1.90 (s, 3H, CH$_3$), 2.03-2.10 (m, 1H), 2.48-2.70 (m, 3H), 4.34 (s, 2H, CH$_2$), 7.59 (d, J=7.2 Hz, 1H, Ar), 7.80-7.86 (dd, J=7.4 and 8.3 Hz, 1H, Ar), 8.50 (d, J=8.4 Hz, 1H, Ar), 10.06 (s, 1H, NH), 11.05 (s, 1H, NH).

Step 3:

A mixture of 2-azido-N-[2-(3-methyl-2,6-dioxo-piperidin-3-yl)-1,3-dioxo-2,3-dihydro-1H-isoindol-4-yl]-acetamide (1.4 g, 3.8 mmol) and 10% Pd/C (0.2 g) in methanol (100 mL) and 4N HCl (20 mL) was hydrogenated in Parr Shaker for 5 hours. H$_2$O (10 mL) was added, and the mixture was filtered through celite. The filtrate was concentrated, and the residue was evaporated with ethanol (3×20 mL). The solid was slurried with hot methanol (30 mL) to give 2-amino-N-[2-(3-methyl-2,6-dioxo-piperidin-3-yl)-1,3-dioxo-2,3-dihydro-1H-isoindol-4-yl]-acetamide hydrochloride (0.5 g, 35%) as a yellow solid: mp 111-113° C.; $^1$H NMR (DMSO-d$_6$) δ 1.90 (s, 3H, CH$_3$), 2.04-2.09 (m, 1H), 2.50-2.72 (m, 3H), 3.97 (s, 2H, CH$_2$), 7.64 (d, J=7.2 Hz, 1H, Ar), 7.86 (t, J=7.7 Hz, 1H, Ar), 8.32 (d, J=8.2 Hz, 1H, Ar), 8.40 (s, 3H, NH$_3$), 10.30 (s, 1H, NH), 11.05 (s, 1H, NH); $^{13}$C NMR (DMSO-d$_6$) δ 21.05, 28.55, 29.10, 41.11, 58.83, 117.98, 118.92, 127.13, 131.76, 134.74, 135.99, 166.18, 167.22, 167.75, 172.04, 172.18; Anal. calcd. for C$_{16}$H$_{17}$N$_4$O$_5$Cl: C, 50.47; H, 4.50; N, 14.71; Cl, 9.31. Found: C, 50.35; H, 4.40; N, 14.54; Cl, 9.01.

5.181-1 (3'S)-2-AMINO-N-[2'-(3'-METHYL-2',6'-DIOXO-PIPERIDIN-3'-YL)-1",3"-DIOXO-2",3"-DIHYDRO-1"H-ISOINDOL-4"-YL]-ACETAMIDE HYDROCHLORIDE

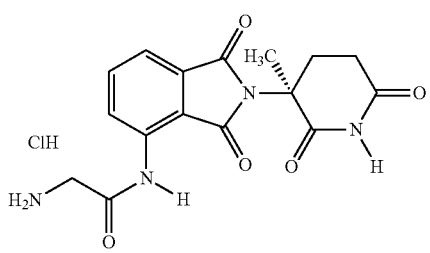 [SMILES: Cl ; C[C@]1(N2C(=O)c3cccc(NC(=O)CN)c3C2=O)CCC(=O)NC1=O]

Step 1:

Chloroacetyl chloride (0.9 g, 7.8 mmol) was added to a stirred suspension of (3' S)-4-amino-2-(3'-methyl-2',6'-dioxo-piperidin-3'-yl)-isoindole-1,3-dione (1.5 g, 5.2 mmol) in THF (40 mL). The resulting mixture was refluxed for 30 minutes then cooled to room temperature. The mixture was concentrated to half volume, and ether (30 mL) was added. The mixture was stirred for 30 minutes then filtered to give (3'S)-2-chloro-N-[2'-(3'-methyl-2',6'-dioxo-piperidin-3'-yl)-1",3"-dioxo-2",3"-dihydro-1"H-isoindol-4"-yl]-acetamide (1.9 g, 100%) as an off-white solid: $^1$H NMR (DMSO-d$_6$) δ 1.89 (s, 3H, CH$_3$), 2.03-2.10 (m, 1H), 2.49-2.68 (m, 3H), 4.53 (s, 2H, CH$_2$), 7.60 (d, J=7.3 Hz, 1H, Ar), 7.84 (t, J=7.8 Hz, 1H, Ar), 8.51 9d, J=8.3 Hz, 1H, Ar), 10.26 (s, 1H, NH), 11.05 (s, 1H, NH).

Step 2:

A mixture of (3'S)-2-chloro-N-[2'-(3'-methyl-2',6'-dioxo-piperidin-3'-yl)-1",3"-dioxo-2",3"-dihydro-1"H-isoindol-4"-yl]-acetamide (1.9 g, 4.1 mmol), sodium azide (0.5 g, 7.8 mmol), and sodium iodide (40 mg) in acetone (70 mL) was refluxed overnight. The mixture was cooled to room temperature and then concentrated. The residue was stirred with H$_2$O (30 mL) for 30 minutes then filtered. The solid was slurried with ethanol (20 mL) to give (3'S)-2-azido-N-[2"-(3'-methyl-2',6'-dioxo-piperidin-3'-yl)-1",3"-dioxo-2",3"-dihydro-1"H-isoindol-4"-yl]-acetamide (1.8 g, 94%) as a yellow solid: $^1$H NMR (DMSO-d$_6$) δ 1.90 (s, 3H, CH$_3$), 2.03-2.10 (m, 1H), 2.49-2.71 (m, 3H), 4.34 (s, 2H, CH$_2$), 7.59 (d, J=7.2 Hz, 1H, Ar), 7.83 (t, J=7.7 Hz, 1H, Ar), 8.50 (d, J=8.4 Hz, 1H, Ar), 10.05 (s, 1H, NH), 11.05 (s, 1H, NH).

Step 3:

A mixture of (3'S)-2-azido-N-[2'-(3'-methyl-2',6'-dioxo-piperidin-3'-yl)-1",3"-dioxo-2",3"-dihydro-1"H-isoindol-4"-yl]-acetamide (1.8 g, 4.9 mmol), 10% Pd/C (150 mg), and 4N HCl (20 mL) in methanol (200 mL) was hydrogenated at 60 psi of H$_2$ for 5 hours. H$_2$O (20 mL) was added, and the mixture was filtered through celite. The filtrate was concentrated and the residue was evaporated with ethanol (3×20 mL). The residue was slurried with hot methanol (30 mL) to give 1.4 g of crude product. The crude product was recrystallized from methanol (150 mL) to give (3'S)-2-amino-N-[2'-(3'-methyl-2',6'-dioxo-piperidin-3'-yl)-1",3"-dioxo-2",3"-dihydro-1"H-isoindol-4"-yl]-acetamide hydrochloride (0.9 g, 46%) as a yellow solid: mp>260° C.; $^1$H NMR (DMSO-d$_6$) δ 1.90 (s, 3H, CH$_3$), 2.04-2.09 (m, 1H), 2.51-2.72 (m, 3H), 3.97 (s, 2H, CH$_2$), 7.64 (d, J=7.2 Hz, 1H, Ar), 7.86 (t, J=7.5 Hz, 1H), 8.32 (d, J=8.4 Hz, 1H, Ar), 8.40 (b, 3H, NH$_3$), 10.30 (b, 1H, NH), 11.05 (s, 1H, NH); $^{13}$C NMR (DMSO-d$_6$) δ 21.06, 28.57, 29.11, 41.11, 58.83, 117.99, 118.94, 127.14, 131.77, 134.74, 136.00, 166.19, 167.24, 167.76, 172.06, 172.20; Anal. calcd. for C$_{16}$H$_{17}$N$_4$O$_5$Cl+0.46H$_2$O: C, 49.39; H, 4.64; N, 14.40; Cl, 9.11. Found: C, 49.07; H, 4.52; N, 14.11; Cl, 8.81.

5.182 3-{4-[(BENZOFURAN-2-YLMETHYL)-AMINO]-1-OXO-1,3-DIHYDRO-ISOINDOL-2-YL}-PIPERIDINE-2,6-DIONE

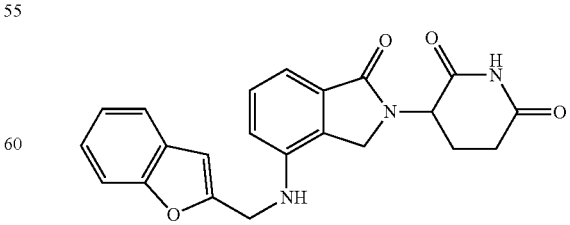

A mixture of 3-(4-amino-1-oxo-1,3-dihydro-isoindol-2-yl)-piperidine-1,3-dione (0.7 g, 2.7 mmol) and 2-benzofuran-carboxaldehyde (0.4 g, 3.0 mmol) in methanol (40 mL) was refluxed for 3 hours. Methanol was removed in vacuo, and the residue was dissolved in acetic acid (15 mL). The resulting mixture was treated with sodium triacetoxyborohydride (0.9 g, 4.1 mmol) and stirred overnight. The mixture was diluted with ethyl acetate (120 mL) and washed with water (2×45 mL), Sat. NaHCO$_3$ (2×45 mL), water (45 mL), and brine (45 mL), and dried over MgSO$_4$. Solvent was removed in vacuo, and the residue was slurried in hot acetone to give a crude product. The crude product was recrystallized from methanol to afford 3-{4-[(benzofuran-2-ylmethyl)-amino]-1-oxo-1,3-dihydro-isoindol-2-yl}-piperidine-2,6-dione (0.7 g, 64%) as a white solid: mp 253-255° C.; HPLC: Waters Symmetry C-18, 3.9×150 mm, 5 micro, 1 mL/min, 240 nm, 40/60 (CH$_3$CN/H$_2$O): t$_R$=5.42 min. (99%); $^1$H NMR (DMSO-d$_6$) δ 2.03-2.07 (m, 1H), 2.25-2.39 (m, 1H), 2.59-2.65 (m, 1H), 2.87-2.99 (m, 1H), 4.22 (d, J=17.3 Hz, 1H), 4.28 (d, J=17.1 Hz, 1H), 4.58 (d, J=5.5 Hz, 2H), 5.09-5.15 (dd, J=5.1 and 13.2 Hz, 1H), 6.40 (t, J=5.8 Hz, 1H), 6.79 (s, 1H), 6.90 (d, J=8.0 Hz, 1H), 6.98 (d, J=7.4 Hz, 1H), 7.17-7.29 (m, 3H), 7.50-7.57 (m, 2H), 11.02 (s, 1H); $^{13}$C NMR (DMSO-d$_6$) δ 22.76, 31.22, 45.74, 51.52, 103.67, 110.81, 110.87, 112.37, 120.76, 122.72, 123.76, 126.84, 128.08, 129.10, 132.17, 142.92, 154.15, 156.18, 168.67, 171.19, 172.86; Anal. Calcd. for C$_{22}$H$_{19}$N$_3$O$_4$: C, 67.86; H, 4.92; N, 10.79. Found: C, 67.82; H, 4.97; N, 10.76.

5.183 3-{4-[(4,5-DIMETHYL-FURAN-2-YLMETHYL)-AMINO]-1-OXO-1,3-DIHYDRO-ISOINDOL-2-YL}-PIPERIDINE-2,6-DIONE

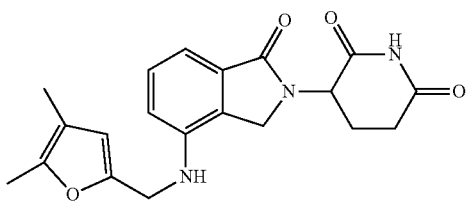 [SMILES: Cc1cc(CNc2cccc3c2CN(C2CCC(=O)NC2=O)C3=O)oc1C]

A mixture of 3-(4-amino-1-oxo-1,3-dihydro-isoindol-2-yl)-piperidine-1,3-dione (1.0 g, 3.9 mmol) and 4,5-dimethyl-furaldehyde (0.5 g, 4.2 mmol) in methanol (40 mL) was refluxed for 2 hours. Methanol was removed in vacuo, and the residue was dissolved in acetic acid (15 mL). Sodium triacetoxyborohydride (1.2 g, 5.8 mmol) was added, and the resulting mixture was stirred at room temperature overnight. The mixture was then diluted with CH$_2$Cl$_2$ (40 mL) and filtered to afford 1 g of crude product. The crude product was recrystallized from methanol (250 mL) to afford 3-{4-[(4,5-dimethyl-furan-2-ylmethyl)-amino]-1-oxo-1,3-dihydro-isoindol-2-yl}-piperidine-2,6-dione (0.7 g, 48%) as a white solid: mp 237-239° C.; HPLC: Waters Symmetry C-18, 3.9×150 mm, 5 micro, 1 mL/min, 240 nm, 40/60 (CH$_3$CN/H$_2$O): t$_R$=4.82 min. (99%); $^1$H NMR (DMSO-d$_6$) δ 1.84 (s, 3H), 2.01-2.05 (m, 1H), 2.12 (s, 3H), 2.24-2.35 (m, 1H), 2.59-2.64 (m, 1H), 2.86-2.98 (m, 1H), 4.10-4.28 (m, 4H), 5.07-5.14 (dd, J=5.1 and 13.2 Hz, 1H), 6.08 (s, 1H), 6.13 (t, J=6.6 Hz, 1H), 6.84 (d, J=8.0 Hz, 1H), 6.96 (d, J=7.4 Hz, 1H), 7.27 (t, J=7.7 Hz, 1H), 11.01 (s, 1H); $^{13}$C NMR (DMSO-d$_6$) δ 9.67, 11.22, 22.88, 31.34, 39.75, 45.86, 51.61, 110.38, 110.62, 112.42, 114.17, 126.83, 129.16, 132.19, 143.22, 145.81, 149.75, 168.86, 171.32, 172.99; Anal. Calcd. for C$_{20}$H$_{21}$N$_3$O$_4$: C, 65.38; H, 5.76; N, 11.44. Found: C, 65.30; H, 5.74; N, 11.36.

5.184 3-{4-[(5-METHYL-FURAN-2-YLMETHYL)-AMINO]-1-OXO-1,3-DIHYDRO-ISOINDOL-2-YL}-PIPERIDINE-2,6-DIONE

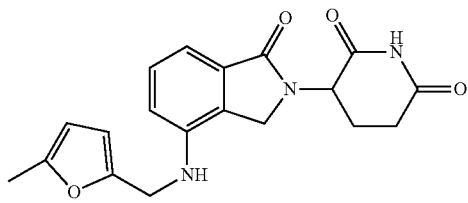 [SMILES: Cc1ccc(CNc2cccc3c2CN(C2CCC(=O)NC2=O)C3=O)o1]

A mixture of 3-(4-amino-1-oxo-1,3-dihydro-isoindol-2-yl)-piperidine-2,6-dinoe (1.0 g, 3.9 mmol) and 5-methylfurfural (0.5 g, 4.2 mmol) in methanol (40 mL) was refluxed for 2 hours. Methanol was removed in vacuo, and the residue was dissolved in acetic acid (15 mL). Sodium triacetoxyborohydride (1.2 g, 5.8 mmol) was added, and the resulting mixture was stirred at room temperature for 2 hours. The mixture was diluted with CH$_2$Cl$_2$ (40 mL) and filtered. The resulting solid was recrystallized from methanol (400 mL) to afford 3-{4-[(5-methyl-furan-2-ylmethyl)-amino]-1-oxo-1,3-dihydro-isoindol-2-yl}-piperidine-2,6-dione (0.8 g, 57%) as a white solid: mp 242-244° C.; HPLC: Waters Symmetry C-18, 3.9×150 mm, 5 micro, 1 mL/min, 240 nm, 40/60 (CH$_3$CN/H$_2$O): t$_R$=3.44 min. (99%); $^1$H NMR (DMSO-d$_6$) δ 2.00-2.06 (m, 1H), 2.21 (s, 3H), 2.27-2.35 (m, 1H), 2.58-2.64 (m, 1H), 2.86-2.98 (m, 1H), 4.11-4.30 (m, 4H), 5.07-5.14 (dd, J=5.1 and 13.2 Hz, 1H), 5.97 (d, J=1.9 Hz, 1H), 6.17-6.19 (m, 2H), 6.86 (d, J=8.0 Hz, 1H), 6.96 (d, J=7.3 Hz, 1H), 7.26 (t, J=7.7 Hz, 1H), 11.01 (s, 1H); $^{13}$C NMR (DMSO-d$_6$) δ 13.27, 22.75, 31.21, 39.65, 45.74, 51.48, 106.25, 107.93, 110.53, 112.32, 126.72, 129.02, 132.08, 143.09, 150.55, 150.87, 168.72, 171.19, 172.86; Anal. Calcd. for C$_{19}$H$_{19}$N$_3$O$_4$: C, 64.58; H, 5.42; N, 11.89. Found: C, 64.51; H, 5.70; N, 11.88.

5.185 Assays

5.185.1 TNFα Inhibition Assay in PMBC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/ml penicillin, and 100 µg/ml streptomycin (Life Technologies).

PBMC (2×10$^5$ cells) are plated in 96-well flat-bottom Costar tissue culture plates (Corning, N.Y., USA) in triplicate. Cells are stimulated with LPS (from Salmonella abortus equi, Sigma cat. no. L-1887, St. Louis, Mo., USA) at 1 ng/ml final in the absence or presence of compounds. Compounds of the invention are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% CO$_2$, and supernatants are then collected, diluted with culture medium and assayed for TNFα levels by ELISA (Endogen, Boston, Mass., USA). IC$_{50}$s are calculated using non-linear regression, sigmoidal dose-response, constraining the top to 100% and bottom to 0%, allowing variable slope (GraphPad Prism v3.02).

5.185.2 IL-2 and MIP-3α Production by T Cells

PBMC are depleted of adherent monocytes by placing 1×10$^8$ PBMC in 10 ml complete medium (RPMI 1640 supplemented with 10% heat-inactivated fetal bovine serum, 2 mM L-glutamine, 100 U/ml penicillin, and 100 μg/ml streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every $1 \times 10^8$ non-adherent PBMC: 0.3 ml Sheep anti-mouse IgG beads, 15 μl anti-CD16, 15 μl anti-CD33, 15 μl anti-CD56, 0.23 ml anti-CD19 beads, 0.23 ml anti-HLA class II beads, and 56 μl anti-CD14 beads. The cells and bead/antibody mixture is rotated end-over-end for 30-60 minutes at 4° C. Purified T cells are removed from beads using a Dynal magnet. Typical yield is about 50% T cells, 87-95% $CD3^+$ by flow cytometry.

Tissue culture 96-well flat-bottom plates are coated with anti-CD3 antibody OKT3 at 5 μg/ml in PBS, 100 μl per well, incubated at 37° C. for 3-6 hours, then washed four times with complete medium 100 μl/well just before T cells are added. Compounds are diluted to 20 times of final in a round bottom tissue culture 96-well plate. Final concentrations are about 10 μM to about 0.00064 μM. A 10 mM stock of compounds of the invention is diluted 1:50 in complete for the first 20× dilution of 200 μM in 2% DMSO and serially diluted 1:5 into 2% DMSO. Compound is added at 10 μl per 200 μl culture, to give a final DMSO concentration of 0.1%. Cultures are incubated at 37° C., 5% $CO_2$ for 2-3 days, and supernatants analyzed for IL-2 and MIP-3a by ELISA (R&D Systems). IL-2 and MIP-3a levels are normalized to the amount produced in the presence of an amount of a compound of the invention, and $EC_{50}$s calculated using non-linear regression, sigmoidal dose-response, constraining the top to 100% and bottom to 0%, allowing variable slope (GraphPad Prism v3.02).

5.185.3 Cell Proliferation Assay

Cell lines Namalwa, MUTZ-5, and UT-7 are obtained from the Deutsche Sammlung von Mikroorganismen und Zellkulturen GmbH (Braunschweig, Germany). The cell line KG-1 is obtained from the American Type Culture Collection (Manassas, Va., USA). Cell proliferation as indicated by $^3$H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 μM in a final concentration of about 0.25% DMSO in triplicate at 37° C. in a humidified incubator at 5% $CO_2$ for 72 hours. One microcurie of $^3$H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 μl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

5.185.4 Immunoprecipitation and Immunoblot

Namalwa cells are treated with DMSO or an amount of a compound of the invention for 1 hour, then stimulated with 10 U/ml of Epo (R&D Systems) for 30 minutes. Cell lysates are prepared and either immunoprecipitated with Epo receptor Ab or separated immediately by SDS-PAGE. Immunoblots are probed with Akt, phospho-Akt (Ser473 or Thr308), phospho-Gab1 (Y627), Gab1, IRS2, actin and IRF-1 Abs and analyzed on a Storm 860 Imager using ImageQuant software (Molecular Dynamics).

5.185.5 Cell Cycle Analysis

Cells are treated with DMSO or an amount of a compound of the invention overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

5.185.6 Apoptosis Analysis

Cells are treated with DMSO or an amount of a compound of the invention at various time points, then washed with annexin-V wash buffer (BD Biosciences). Cells are incubated with annexin-V binding protein and propidium iodide (BD Biosciences) for 10 minutes. Samples are analyzed using flow cytometry.

5.185.7 Luciferase Assay

Namalwa cells are transfected with 4 μg of AP1-luciferase (Stratagene) per $1 \times 10^6$ cells and 3 μl Lipofectamine 2000 (Invitrogen) reagent according to manufacturer's instructions. Six hours post-transfection, cells are treated with DMSO or an amount of a compound of the invention. Luciferase activity is assayed using luciferase lysis buffer and substrate (Promega) and measured using a luminometer (Turner Designs).

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

All of the patents, patent applications and publications referred to herein are incorporated herein in their entireties. Citation or identification of any reference in this application is not an admission that such reference is available as prior art to this invention. The full scope of the invention is better understood with reference to the appended claims.

What is claimed is:

1. A compound of formula I, or a pharmaceutically acceptable salt or stereoisomer thereof:

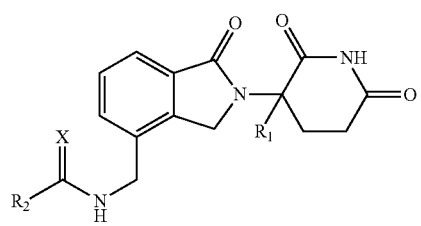

wherein:
X is O or S;
$R_1$ is H or methyl;
$R_2$ is $NHR_4$; and
$R_4$ is:
  $(C_3-C_6)$cycloalkyl; or
  phenyl substituted with $(C_1-C_4)$alkoxy.

2. The compound of claim 1, or a pharmaceutically acceptable salt or stereoisomer thereof, wherein X is S.

3. The compound of claim 1, which is:

| | | |
|---|---|---|
| 2 | 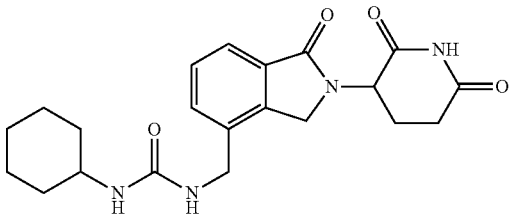 [SMILES: O=C1CCC(N2Cc3c(CNC(=O)NC4CCCCC4)cccc3C2=O)C(=O)N1] | 1-Cyclohexyl-3-[2-(2,6-dioxo-piperidin-3-yl)-1-oxo-2,3-dihydro-1H-isoindol-4-ylmethyl]-urea, |
| 15 | 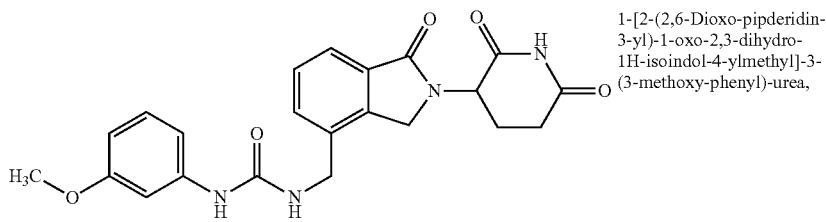 | 1-[2-(2,6-Dioxo-pipderidin-3-yl)-1-oxo-2,3-dihydro-1H-isoindol-4-ylmethyl]-3-(3-methoxy-phenyl)-urea, |
| 16 | 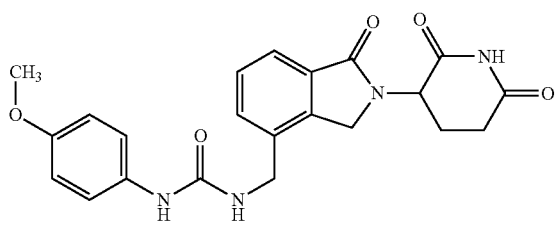 [SMILES: COc1ccc(NC(=O)NCc2cccc3c2CN(C2CCC(=O)NC2=O)C3=O)cc1] | 1-[2-(2,6-Dioxo-piperidin-3-yl)-1-oxo-2,3-dihydro-1H-isoindol-4-ylmethyl]-3-(4-methoxy-phenyl)-urea, |
| 17 | 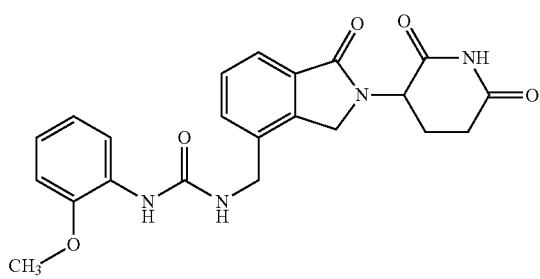 [SMILES: COc1ccccc1NC(=O)NCc1cccc2c1CN(C1CCC(=O)NC1=O)C2=O] | 1-[2-(2,6-Dioxo-piperidin-3-yl)-1-oxo-2,3-dihydro-1H-isoindol-4-ylmethyl]-3-(2-methoxy-phenyl)-urea, |
| 35 | 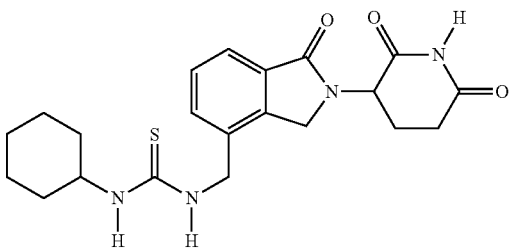 [SMILES: O=C1CCC(N2Cc3c(CNC(=S)NC4CCCCC4)cccc3C2=O)C(=O)N1] | 1-Cyclohexyl-3-[2-(2,6-dioxo-piperidin-3-yl)-1-oxo-2,3-dihydro-1H-isoindol-4-ylmethyl]-thiourea, |

4. A pharmaceutical composition comprising the compound of claim 1.

5. The compound of claim 1, or a pharmaceutically acceptable salt or stereoisomer thereof, wherein X is O.

* * * * *